United States Patent
Brebion et al.

(10) Patent No.: US 11,718,588 B2
(45) Date of Patent: Aug. 8, 2023

(54) 5-[(PIPERAZIN-1-YL)-3-OXO-PROPYL]-IMIDAZOLIDINE-2,4-DIONE DERIVATIVES AS ADAMTS INHIBITORS FOR THE TREATMENT OF OSTEOARTHRITIS

(71) Applicant: GALAPAGOS NV, Mechelen (BE)

(72) Inventors: Franck Laurent Brebion, Romainville (FR); Luke Jonathan Alvey, Romainville (FR); David Amantini, Romainville (FR); Frédéric André De Ceuninck, Paris (FR); Pierre Marc Marie Joseph Deprez, Romainville (FR); Romain Luc Marie Gosmini, Romainville (FR); Hélène Marie Jary, Romainville (FR); Christophe Peixoto, Romainville (FR); Iuliana Ecaterina Pop-Botez, Houilles (FR); Marie Laurence Claire Varin, Romainville (FR)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 17/141,902

(22) Filed: Jan. 5, 2021

(65) Prior Publication Data

US 2021/0309614 A1 Oct. 7, 2021

Related U.S. Application Data

(63) Continuation of application No. 16/653,668, filed on Oct. 15, 2019, now Pat. No. 10,941,117, which is a
(Continued)

(30) Foreign Application Priority Data

Dec. 22, 2014 (EP) .................................... 14307129

(51) Int. Cl.
| | | |
|---|---|---|
| *C07D 233/78* | (2006.01) | |
| *C07D 403/06* | (2006.01) | |
| *A61P 19/02* | (2006.01) | |
| *A61P 19/04* | (2006.01) | |
| *A61K 31/496* | (2006.01) | |
| *A61K 31/5377* | (2006.01) | |
| *C07D 401/04* | (2006.01) | |

(Continued)

(52) U.S. Cl.
CPC .......... *C07D 233/78* (2013.01); *A61K 31/496* (2013.01); *A61K 31/5377* (2013.01); *A61K 31/55* (2013.01); *A61P 19/02* (2018.01); *A61P 19/04* (2018.01); *C07D 401/04* (2013.01); *C07D 401/12* (2013.01); *C07D 401/14* (2013.01); *C07D 403/06* (2013.01); *C07D 403/14* (2013.01); *C07D 405/12* (2013.01); *C07D 417/12* (2013.01)

(58) Field of Classification Search
CPC .. C07D 233/78; C07D 401/04; C07D 401/12; C07D 401/14; C07D 403/06; C07D 403/14; C07D 405/12; C07D 417/12; A61P 19/04; A61P 19/02; A61K 31/496; A61K 31/5377; A61K 31/55
USPC ...................................................... 514/210.18
See application file for complete search history.

(56) References Cited

U.S. PATENT DOCUMENTS

| | | | | |
|---|---|---|---|---|
| 4,556,670 A | * | 12/1985 | Lipinski ............... | C07D 263/52 514/369 |
| 4,680,306 A | * | 7/1987 | Lipinski ............... | C07D 409/04 549/72 |

(Continued)

FOREIGN PATENT DOCUMENTS

| | | |
|---|---|---|
| WO | 92074751 A1 | 9/2002 |
| WO | 2002074767 A1 | 9/2002 |

(Continued)

OTHER PUBLICATIONS

Winstead et al., Relationship of Molecular Structure to in Vivo Scintigraphic Distribution Patterns of Carbon-11 Labeled Compounds. 3. [11C]Hydantoins, 1976, Journal of Medicinal Chemistry, vol. 19, No. 2, 279-286 (Year: 1976).*

(Continued)

*Primary Examiner* — Kristin A Vajda
(74) *Attorney, Agent, or Firm* — ArentFox Schiff LLP

(57) ABSTRACT

The present invention discloses compounds according to Formula I:

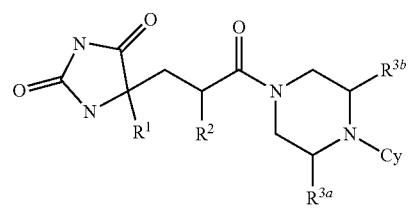

Wherein $R^1$, $R^2$, $R^{3a}$, $R^{3b}$, and Cy are as defined herein.
The present invention relates to compounds inhibiting ADAMTS, methods for their production, pharmaceutical compositions comprising the same, and methods of treatment using the same, for the prophylaxis and/or treatment of inflammatory conditions, and/or diseases involving degradation of cartilage and/or disruption of cartilage homeostasis by administering a compound of the invention.

16 Claims, No Drawings

Specification includes a Sequence Listing.

Related U.S. Application Data continuation of application No. 15/896,779, filed on Feb. 14, 2018, now Pat. No. 10,487,060, which is a continuation of application No. 15/538,393, filed as application No. PCT/EP2015/080430 on Dec. 18, 2015, now Pat. No. 9,926,281.

(51) Int. Cl.
*C07D 401/12* (2006.01)
*C07D 401/14* (2006.01)
*C07D 403/14* (2006.01)
*C07D 405/12* (2006.01)
*C07D 417/12* (2006.01)
*A61K 31/55* (2006.01)

(56) References Cited

U.S. PATENT DOCUMENTS 9,926,281 B2 3/2018 Brebion
10,487,060 B2 11/2019 Brebion et al.

FOREIGN PATENT DOCUMENTS

| WO | 02096426 A1 | 12/2002 |
| WO | 2005085232 A1 | 9/2005 |
| WO | 2007084415 A2 | 7/2007 |
| WO | 2013153189 A1 | 10/2013 |
| WO | 2014066151 A1 | 5/2014 |
| WO | 2014121884 A1 | 8/2014 |

OTHER PUBLICATIONS

P. Clement-Lacroix et al., "Pharmacological characterization of GLPG1972/S201086, a potent and selective small-molecule inhibitor of ADAMTS5," Osteoarthitis and Cartilage, Oct. 6, 2021, pp. 1-11.
Franck Brebion et al., "Discovery of GLPG1972/S201086, a Potent, Selective, and Orally Bioavailable ADAMTS-5 Inhibitor for the Treatment of Osteoarthritis," Journal of Medical Chemistry, 2021, vol. 64, pp. 2937-2952.
Durham et al., "A Highly Selective Hydantoin Inhibitor of Aggrecanase 1 and Aggrecanase 2 with a Low Projected Human Dose," Journal of Medicinal Chemistry, (2017), vol. 60, pp. 5933-5939.
Abbaszade et al., "Cloning and Characterization of ADAMTS11, an Aggrecanase from the ADAMTS Family," J. Biol. Chem., 1999, vol. 274, pp. 23443-23450.
Bendele, "Animal models of rheumatoid arthritis," J. Musculoskelet Neuronal Interact, 2001, vol. 1, pp. 377-385.
Botter et al., "ADAMTS5−/− miche have less subchondral bone changes after induction of ostearthritis through surgical instabiliity: implications for a link between cartilage and subchondral bone changes," Osteoarthritis and Cartilage, 2009, vol. 17, pp. 636-645.
Chockalingam et al., "Elevated aggrecanase activity in a rat model of joint injury is attenuated by an aggrecanase specific inhibitor," Osteoarthritis and Cartilage, 2011, vol. 19, pp. 315-323.
Clegg et al., "Glucosamine, Chondroitin Sulfate, and the Two in Combination for Painful Knee Osteoarthritis," 2006, vol. 354, pp. 795-808.
Dufour et al., "Missing the target: matrix metalloproteinase antitargets in inflammation and cancer," Trends Pharmacol Sci., 2013, vol. 34, pp. 233-242.
Durham et al., "A Highly Selective Hydantoin Inhibitor of Aggrecanase-1 and Aggrecanase-2 with a Low Projected Human Dose," J. Med. Chem., 2017, vol. 60, pp. 5933-5939.
Georgiadis et al., "Specific targeting of metzincin family members with small-molecule inhibitors: progress toward a multifarious challenge," Bioorg. Med Chem., 2008, vol. 16, pp. 8781-8794.
Glasson et al., Deletion of active ADAMTS5 prevents cartilage degradation in a murine model of osteoarthiritis, Nature, 2005, vol. 434, pp. 644-648.
International Search Report and Written Opinion issued in International Patent Application No. PCT/EP2015/080430, dated Feb. 19, 2016, pp. 1-12.
Janusz et al., "Induction of osteoarthritis in the rat by surgical tear of the meniscus: Inhibition of joint damage by a matrix metalloproteinase inhibitor," Osteoarthritis and Cartilage, 2002, vol. 10, pp. 785-791.
Kato et al., "Total Synthesis of Mappicine Ketone (Nothapodytine B) by Means of Sulfur-directed 5-exo-Selective Aryl Radical Cyclization onto Enamides," J. Org. Chem., 2003, vol. 68, ppl. 7983-7989.
Larsson et al., "An ARGS-aggrecan assay for analysis in blood and synovial fluid," Osteoarthritis and Cartilage, 2014, vol. 22, pp. 242-249.
Little et al., "Blocking aggrecanase cleavage in the aggrecan interglobular domain abrogates cartilage erosion and promotes cartilage repair," J. Clin. Invest., 2007, vol. 117, pp. 1627-1636.
Malfait et al., "ADAMTS-5 deficient mice do not develop mechanical allodynia associated with osteoarthritis following medial meniscal destabilization," Osteoathritis and Cartilage, 2010, vol. 18, pp. 572-580.
Mobasheri, "The Future of Osteoarthritis Therapeutics: Targeted Pharmacological Therapy," Curr. Rheumatol Rep. 2013, vol. 15, pp. 1-13.
Pond et al., "Experimentally-induced Osteoarthritis in the Dog," Ann Rheum Dis, 1973, vol. 32, pp. 387-388.
Pritzker et al., "Osteoarthritis cartilage histopathology: grading and staging," Osteoarthritis and Cartilage, 2006, vol. 14, pp. 13-29.
Shiomi et al., "Matrix metalloproteinases, a disintegrin and metalloproteinases, and a disintegrin and metalloproteinases with thrombospondin motifs in non-neoplastic diseases," Pathol Int, 2010, vol. 60, pp. 477-496.
Stanton et al., "ADAMTS5 is the major aggrecanase in mouse cartilage in vivo and in vitro," Nature, 2005, vol. 434, pp. 648-352.
Stanton et al., "Investigating ADAMTS-mediated aggrecanolysis in mouse cartilage," Nat. Protoc, 2011, vol. 6, pp. 388-404.
Tortorella et al., "Will the Real Aggrecanase(s) Step Up: Evaluating the Criteria that Define Aggrecanase Activity in Osteoarthritis," Curr Pharm Biotechnol, 2008, vol. 9, pp. 16-23.
Wieland et al., "Osteoarthritis—an Untreatable Disease?," Nat Rev Drug Discov. 2005, vol. 4, pp. 331-344.
Wiley et al., "Use of Osmotic Pumps to Establish the Pharmacokinetic-Pharmacodynamic Relationship and Define Desireable Human Performance Characteristics for Aggrecanase Inhibitors," J. Med. Chem., 2016, vol. 59, pp. 5810-5822.

\* cited by examiner

5-[(PIPERAZIN-1-YL)-3-OXO-PROPYL]-IMIDAZOLIDINE-2,4-DIONE DERIVATIVES AS ADAMTS INHIBITORS FOR THE TREATMENT OF OSTEOARTHRITIS

CROSS-REFERENCE TO RELATED APPLICATIONS

This application is a continuation of U.S. application Ser. No. 16/653,668, filed Oct. 15, 2019, which is a continuation of U.S. application Ser. No. 15/896,779, filed Feb. 14, 2018, which is a continuation of U.S. application Ser. No. 15/538,393, filed Jun. 21, 2017, which is a 371 National Stage Entry of PCT Application No. PCT/EP2015/080430, filed Dec. 18, 2015, which claims foreign priority to European Patent Application No. 14307129.8 filed Dec. 22, 2014, the disclosures of which are hereby incorporated by reference in their entireties.

FIELD OF THE INVENTION

The present invention relates to hydantoin compounds, and their use in the prophylaxis and/or treatment of inflammatory conditions, and/or diseases involving degradation of cartilage and/or disruption of cartilage homeostasis. In a particular aspect, the present compounds are ADAMTS inhibitors, and more particularly ADAMTS-5. The present invention also provides methods for the production of a compound of the invention, pharmaceutical compositions comprising a compound of the invention, methods for the prophylaxis and/or treatment of inflammatory conditions, and/or diseases involving degradation of cartilage and/or disruption of cartilage homeostasis by administering a compound of the invention.

BACKGROUND OF THE INVENTION

Cartilage is an avascular tissue of which chondrocytes are the main cellular component. One of the functional roles of cartilage in the joint is to allow bones to articulate on each other smoothly. Loss of articular cartilage, therefore, causes the bones to rub against each other leading to pain and loss of mobility, and is the hallmark of various diseases, among which rheumatoid arthritis and osteoarthritis are the most prominent.

The chondrocytes in normal articular cartilage occupy approximately 5% of the tissue volume, while the extracellular matrix makes up the remaining 95% of the tissue. The chondrocytes secrete the components of the matrix, mainly proteoglycans (including aggrecan) and collagens, which in turn supply the chondrocytes with an environment suitable for their survival under mechanical stress. Collagen type II, together with collagen type IX, is arranged in solid fibril-like structures, and provides cartilage with high mechanical strength properties, whereas aggrecan and other proteoglycans can absorb water and provide the resilient and shock-absorbing properties of the cartilage.

Under physiological conditions, cartilage homeostasis is maintained by a balance between the production (anabolism) and degradation (catabolism) of aggrecan and collagen. However, in OA and other joint disorders, this balance shifts toward catabolism. Loss of aggrecan occurs early in the onset of cartilage destruction, initially at the joint surface then spreading more deeply at more advanced stages (Pond and Nuki, 1973).

Osteoarthritis (also referred to as OA, or wear-and-tear arthritis) is the most common form of arthritis and is characterized by loss of articular cartilage, often associated with the subchondral bone remodelling and pain. The disease mainly affects hands, spine and weight-bearing joints such as knees, and hips. During the disease process, the cartilage progressively deteriorates, which can be graded. At more advanced stages, the deeper layers of cartilage are affected, leading to calcification and exposure of the subchondral bone (Wieland et al., 2005).

The clinical manifestations of the development of the osteoarthritis condition include: increased volume of the joint, pain, crepitation and functional disability that lead to pain and reduced mobility of the joints. When disease further develops, pain at rest emerges. If the condition persists without correction and/or therapy, the joint is destroyed leading to disability.

Osteoarthritis is difficult to treat. At present, no cure is available and treatment focuses on relieving pain and preventing the affected joint from becoming deformed. Common treatments are currently limited to steroidal and non-steroidal anti-inflammatory drugs (NSAIDS), which provide symptomatic relief for pain and inflammation but do not arrest or slow down the progression of the disease (Mobasheri, 2013).

Therapeutic methods for the correction of the articular cartilage lesions that appear during the osteoarthritic disease have been developed, but so far none of them have been able to slow down the disease progression or to promote the regeneration of articular cartilage in situ and in vivo.

Although some dietary supplements as chondroitin and glucosamine sulfate have been advocated as safe and effective options for the treatment of osteoarthritis, a clinical trial revealed that both treatments did not reduce pain associated to osteoarthritis (Clegg et al., 2006).

In severe cases, joint replacement may be necessary. This is especially true for hips and knees. If a joint is extremely painful and cannot be replaced, it may be fused. This procedure stops the pain, but results in the permanent loss of joint function, making walking and bending difficult.

Another possible treatment is the transplantation of cultured autologous chondrocytes. Here chondral cellular material is taken from the patient, sent to a laboratory where it is expanded. The material is then implanted in the damaged tissues to cover the tissue's defects.

Yet another treatment includes the intra-articular instillation of Hylan G-F 20 (Synvisc, Hyalgan, Artz etc.), a substance that improves temporarily the rheology of the synovial fluid, producing an almost immediate sensation of free movement and a marked reduction of pain.

Other methods include application of tendinous, periosteal, facial, muscular or perichondral grafts; implantation of fibrin or cultured chondrocytes; implantation of synthetic matrices, such as collagen, carbon fiber; and administration of electromagnetic fields. All of these have reported minimal and incomplete effects, resulting in a poor quality tissue that can neither support the weighted load nor allow the restoration of an articular function with normal movement.

The ADAMTS family of secreted zinc metalloproteinases includes nineteen members that are known to bind and degrade extra cartilage matrix (ECM) components (Shiomi et al., 2010). Several members of the ADAMTS family have been found to cleave aggrecan, the major proteoglycan component of cartilage: ADAMTS-1, -4, -5, -8, -9, -15, -16 and -18. Since the expression and/or aggrecanase degrading activity of ADAMTS-1, -8, -9, -15, -16 and -18 are quite low, ADAMTS-4 (aggrecanase-1) and ADAMTS-5 (aggrecanase-2) are believed to be the two major functional aggrecanases (Tortorella and Malfait, 2008).

ADAMTS-5 was identified in 1999 (Abbaszade et al., 1999). In 2005 two independent groups identified ADAMTS-5 as the principal aggrecanase in mouse cartilage (Glasson et al., 2005; Stanton et al., 2005). Proteolysis of aggrecan by ADAMTS-5 occurs at different sites: however cleavage at the Glu373-Ala374 bond (aggrecan IGD) is likely more important in the pathogenesis of osteoarthritis and inflammatory arthritis since a loss of integrity at this bond results in the loss of an entire aggrecan molecule, which is highly detrimental to cartilage integrity and function (Little et al., 2007).

Studies in genetically engineered mouse models (GeMMs) have demonstrated that ADAMTS-5 ablation protects against cartilage damage and aggrecan loss after osteoarthritis induction through surgical instability of the medial meniscus (DMM) (Glasson et al., 2005). Moreover in the DMM model ADAMTS-5 knock-out mice showed reduced subchondral bone changes (Botter et al., 2009) and did not develop osteoarthritis-associated mechanical allodynia (Malfait et al., 2010). Besides preclinical evidence, clinical evidence also indicates the importance of and interest in ADAMTS-5 as a target for osteoarthritis. Recently, studies with an antibody targeting ADAMTS-5 (Chiusaroli et al., 2013) have been reported. ELISA's have been developed allowing the measurement of aggrecanase-derived cartilage neo-epitope levels in the synovial fluid as well as blood from rodents to human. This method revealed increased levels of ADAMTS-5 derived neo-epitope levels in the joints of rats in which cartilage degradation was induced by meniscal tear as well as in joints of osteoarthritis patients, thereby providing further translational evidence for the importance of this protease in the development of osteoarthritis (Chockalingam et al., 2011; Larsson et al., 2014).

These findings provide strong evidence for a central role of ADAMTS-5 in osteoarthritis pathology as a key target and an ADAMTS-5 inhibitor capable to reach the joint cartilage at sufficient levels is expected to exert a protective effect on cartilage in osteoarthritic patients.

Matrix metalloproteinases (MMPs) constitute another family of 23 zinc metalloproteinases with many structural elements in common with ADAMTS family members (Georgiadis and Yiotakis, 2008). Clinical studies on broad spectrum MMP inhibitors in oncology revealed that inhibition of particular MMPs was associated with poorer prognosis and undesirable side effects. In particular, MMP8 and MMP12 have been categorized as antitargets based on in vivo animal studies (Dufour and Overall, 2013). Therefore, there is a need for selective ADAMTS, and in particular ADAMTS-5 inhibitors without affecting the activity of structurally related MMPs, and more particularly MMP-8 and -12.

Therefore the identification of novel inhibitors of ADAMTS, in particular ADAMTS-5, could provide desirable tools for the prophylaxis and/or treatment of diseases involving cartilage degradation, in particular osteoarthritis, and/or rheumatoid arthritis.

It is therefore an object of the present invention to provide compounds and their use in the prophylaxis and/or treatment of inflammatory conditions, and/or diseases involving degradation of cartilage and/or disruption of cartilage homeostasis. In particular the compounds of the present invention are inhibitors of ADAMTS, and more particularly ADAMTS-5.

SUMMARY OF THE INVENTION

The present invention is based on the identification of novel hydantoin compounds that may be useful for the prophylaxis and/or treatment of inflammatory conditions, and/or diseases involving degradation of cartilage and/or disruption of cartilage homeostasis. In a particular aspect, the compounds of the invention are inhibitors of ADAMTS-5. The present invention also provides methods for the production of these compounds, pharmaceutical compositions comprising these compounds and methods for treating inflammatory conditions, and/or diseases involving degradation of cartilage and/or disruption of cartilage homeostasis by administering the compounds of the invention.

Accordingly, in a first aspect of the invention, a compound of the invention is provided having a Formula (I):

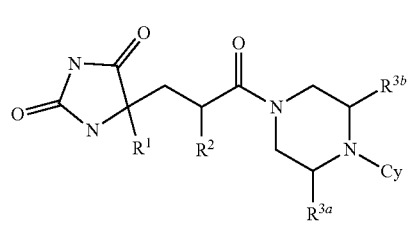

wherein
$R^1$ is:
  H,
  $C_{1-4}$ alkyl optionally substituted with one or more independently selected $R^4$ groups,
  $C_{3-7}$ monocyclic cycloalkyl optionally substituted with one or more independently selected $R^4$ groups,
  4-7 membered monocyclic heterocycloalkyl comprising 1 to 2 heteroatoms independently selected from N, O, and S, optionally substituted with one or more independently selected $C_{1-4}$ alkyl, —C(═O)$C_{1-4}$ alkyl, or —C(═O)O$C_{1-4}$ alkyl,
  phenyl optionally substituted with one or more independently selected $R^5$ groups,
  phenyl fused to a 5-6 membered monocyclic heterocycloalkyl comprising 1, 2 or 3 heteroatoms independently selected from N, O, and S, which heterocycloalkyl is optionally substituted with one or more ═O, or
  5-6 membered monocyclic heteroaryl comprising 1 or 2 heteroatoms independently selected from N, O, and S, optionally substituted with one or more independently selected $R^5$ groups;
$R^2$ is independently selected from:
  H,
  OH,
  $C_{1-4}$ alkoxy, and
  $C_{1-4}$ alkyl optionally substituted with one
    OH,
    CN,
    $C_{1-4}$ alkoxy optionally substituted with one phenyl, or
    5-6 membered monocyclic heteroaryl comprising 1 or 2 heteroatoms independently selected from N, O, and S, optionally substituted with one or more independently selected $C_{1-4}$ alkyl;
each $R^{3a}$, and $R^{3b}$ is independently selected from:
  H, and
  $C_{1-4}$ alkyl;

Cy is
- 6-10 membered monocyclic or fused bicyclic aryl optionally substituted with one or more independently selected $R^6$ groups,
- 5-10 membered monocyclic or fused bicyclic heteroaryl comprising 1, 2 or 3 heteroatoms independently selected from N, O, and S, optionally substituted with one or more independently selected $R^6$ groups;

$R^4$ is
- halo,
- OH,
- CN,
- $C_{1-4}$ alkyl,
- $C_{1-4}$ alkoxy optionally substituted with one $C_{1-4}$ alkoxy, or phenyl,
- $C_{1-4}$ thioalkoxy,
- 4-7-membered monocyclic heterocycloalkyl comprising one or more heteroatoms independently selected from N, S, and O, optionally substituted with one or more independently selected halo, or —C(=O)O$C_{1-4}$ alkyl,
- phenyl,
- —S(=O)$_2$$C_{1-4}$ alkyl,
- —C(=O)O$R^{7a}$,
- —C(=O)N$R^{7b}R^{7c}$,
- —NHC(=O)O$R^{7d}$,
- —NHC(=O)$R^{7e}$, or
- —N$R^{8a}R^{8b}$;

each $R^5$ is
- halo,
- OH,
- CN,
- $C_{1-4}$ alkyl optionally substituted with one or more independently selected halo, —N$R^{9a}R^{9b}$, or —C(=O)N$R^{9c}R^{9d}$,
- $C_{1-4}$ alkoxy optionally substituted with one —N$R^{9e}R^{9f}$, or —S(=O)$_2$$C_{1-4}$ alkyl;

each $R^6$ is
- halo,
- —CN,
- —NO$_2$,
- —CH$_3$,
- 5-10 membered monocyclic or fused bicyclic heteroaryl comprising 1, 2 or 3 heteroatoms independently selected from N, O, and S, optionally substituted with one or more independently selected halo, $C_{1-4}$ alkyl, or $C_{1-4}$ alkoxy, or
- —N$R^{9g}R^{9h}$;

each $R^{7a}$, $R^{7b}$, $R^{7c}$, $R^{7d}$, or $R^{7e}$ is
- H, or
- $C_{1-4}$ alkyl optionally substituted with one OH, $C_{1-4}$ alkoxy;

each $R^{8a}$, or $R^{8b}$ is independently selected from
- H, and
- $C_{1-4}$ alkyl optionally substituted with one or more independently selected OH, $C_{1-4}$ alkoxy, or phenyl;

each $R^{9a}$, $R^{9b}$, $R^{9c}$, $R^{9d}$, $R^{9e}$, $R^{9f}$, $R^{9g}$, and $R^{9h}$ is independently selected from H, and $C_{1-4}$ alkyl;

or a pharmaceutically acceptable salt, or a solvate, or a pharmaceutically acceptable salt of a solvate thereof;

provided that:
$R^1$ and $R^2$ are not simultaneously H, and
when $R^1$ is Me, then Cy is not

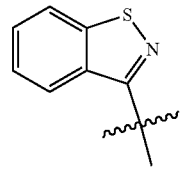

In a particular aspect, the compounds of the invention may exhibit selectivity towards the ADAMTS protease family, in particular towards the ADAMTS-5. In a further particular aspect, the compounds of the invention may show low activity on MMP family members, in particular MMP8 and/or MMP12. Such selectivity may result in improved drug safety and/or reduce off-target associated risks. In another more particular embodiment, the compounds of the invention surprisingly exhibit activity against ADAMTS-5 compared to structurally related close analogues.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the prophylaxis and/or treatment of inflammatory conditions, and/or diseases involving degradation of cartilage and/or disruption of cartilage homeostasis.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory conditions, and/or diseases involving degradation of cartilage and/or disruption of cartilage homeostasis, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory conditions, and/or diseases involving degradation of cartilage and/or disruption of cartilage homeostasis.

In a particular aspect, the compounds of the invention are provided for use in the prophylaxis and/or treatment of osteoarthritis.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —OR$^{20}$ where R$^{20}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$) and the like.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, and naphthyl.

'Cycloalkyl' refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1, 2 or 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl. Particular examples of bicyclic heteroaryl groups containing a five membered ring fused to another five-membered ring include but are not limited to imidazothiazolyl and imidazoimidazolyl. Particular examples of bicyclic heteroaryl groups containing a six membered ring fused to a five membered ring include but are not limited to benzfuranyl, benzthiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups. Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

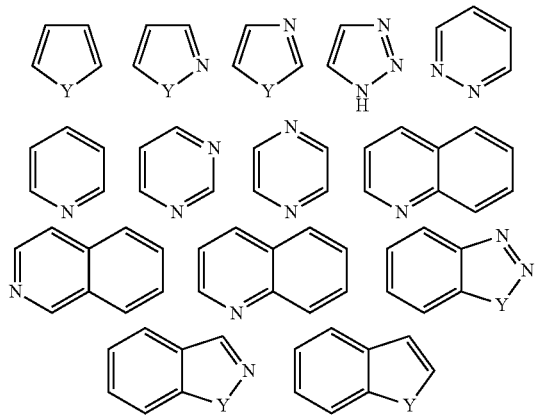

wherein each Y is selected from >C(=O), NH, O and S.

As used herein, the term 'heterocycloalkyl' means a stable non-aromatic ring structure, monocyclic or polycyclic, that includes one or more heteroatoms independently selected from O, N and S and the number of ring atoms specified. The non-aromatic ring structure may have from 4 to 10 ring members, and in particular from 4 to 7 ring members. A fused heterocyclic ring system may include carbocyclic rings and need only to include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

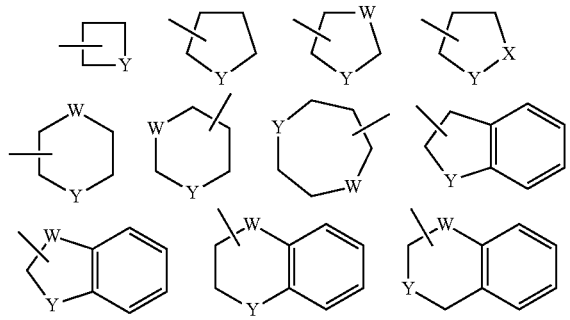

wherein each W is selected from $CH_2$, NH, O and S; and each Y is selected from NH, O, C(=O), $SO_2$, and S.

As used herein, the term 'heterocycloalkenyl' means a 'heterocycloalkyl, wherein one bond of the ring is reduced, thus the ring comprises a double bond. Particular examples of heterocycloalkenyl groups are shown in the following illustrative examples:

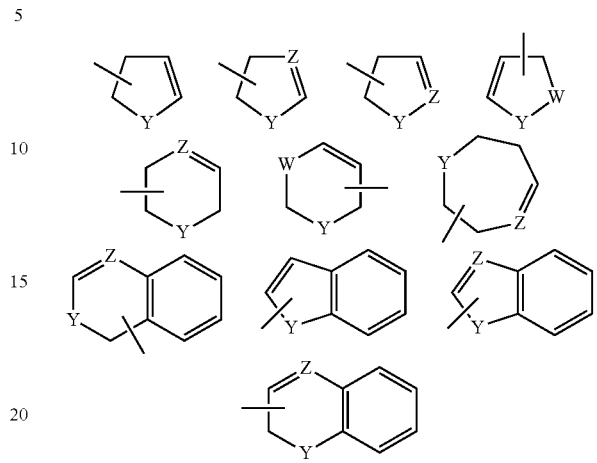

wherein each Z is =CH— or =N—; W is selected from —$CH_2$—, —NH—, —O— and —S—; and each Y is selected from —NH—, —O—, —C(=O)—, —$SO_2$—, and —S—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —$SO_3H$.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —$SR^{20}$ where $R^{20}$ has the number of carbon atoms specified and particularly $C_1$-$C_8$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzene sulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cine a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory diseases' refers to the group of conditions including rheumatoid arthritis, osteoarthritis, juvenile idiopathic arthritis, psoriasis, psoriatic arthritis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, and osteoarthritis (OA). Most particularly the term refers to osteoarthritis (OA).

As used herein the term 'diseases involving degradation of cartilage and/or disruption of cartilage homeostasis' includes conditions such as osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis (OA).

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention is based on the identification of novel hydantoin compounds that may be useful for the prophylaxis and/or treatment of inflammatory conditions, and/or diseases involving degradation of cartilage and/or disruption of cartilage homeostasis. In a particular aspect, the compounds of the invention are inhibitors of ADAMTS-5.

The present invention also provides methods for the production of these compounds, pharmaceutical compositions comprising these compounds and methods for inflammatory conditions, and/or diseases involving degradation of cartilage and/or disruption of cartilage homeostasis by administering the compounds of the invention.

Accordingly, in a first aspect of the invention, a compound of the invention is provided having a Formula (I):

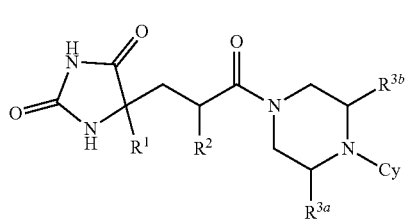

wherein
R$^1$ is:
  H,
  $C_{1-4}$ alkyl optionally substituted with one or more independently selected R$^4$ groups,
  $C_{3-7}$ monocyclic cycloalkyl optionally substituted with one or more independently selected R$^4$ groups, 4-7 membered monocyclic heterocycloalkyl comprising 1 to 2 heteroatoms independently selected from N, O, and S, optionally substituted with one or more independently selected $C_{1-4}$ alkyl, —C(=O)$C_{1-4}$ alkyl, or —C(=O)O$C_{1-4}$ alkyl, phenyl optionally substituted with one or more independently selected $R^5$ groups, phenyl fused to a 5-6 membered monocyclic heterocycloalkyl comprising 1, 2 or 3 heteroatoms independently selected from N, O, and S, which heterocycloalkyl is optionally substituted with one or more =O, or 5-6 membered monocyclic heteroaryl comprising 1 or 2 heteroatoms independently selected from N, O, and S, optionally substituted with one or more independently selected $R^5$ groups;

$R^2$ is independently selected from:
H,
OH,
$C_{1-4}$ alkoxy, and
$C_{1-4}$ alkyl optionally substituted with one
  OH,
  CN,
  $C_{1-4}$ alkoxy optionally substituted with one phenyl, or
  5-6 membered monocyclic heteroaryl comprising 1 or 2 heteroatoms independently selected from N, O, and S, optionally substituted with one or more independently selected $C_{1-4}$ alkyl;

each $R^{3a}$, and $R^{3b}$ is independently selected from:
H, and
$C_{1-4}$ alkyl;

Cy is
  6-10 membered monocyclic or fused bicyclic aryl optionally substituted with one or more independently selected $R^6$ groups,
  5-10 membered monocyclic or fused bicyclic heteroaryl comprising 1, 2 or 3 heteroatoms independently selected from N, O, and S, optionally substituted with one or more independently selected $R^6$ groups;

$R^4$ is
halo,
OH,
CN,
$C_{1-4}$ alkyl,
$C_{1-4}$ alkoxy optionally substituted with one $C_{1-4}$ alkoxy or phenyl,
$C_{1-4}$ thioalkoxy,
4-7-membered monocyclic heterocycloalkyl comprising one or more heteroatoms independently selected from N, S, and O, optionally substituted with one or more independently selected halo or —C(=O)O$C_{1-4}$ alkyl,
phenyl,
—S(=O)$_2$$C_{1-4}$ alkyl,
—C(=O)O$R^{7a}$,
—C(=O)N$R^{7b}R^{7c}$,
—NHC(=O)O$R^{7d}$,
—NHC(=O)$R^{7e}$, or
—N$R^{8a}R^{8b}$;

each $R^5$ is
halo,
OH,
CN,
$C_{1-4}$ alkyl optionally substituted with one or more independently selected halo, —N$R^{9a}R^{9b}$, or —C(=O)N$R^{9c}R^{9d}$,
$C_{1-4}$ alkoxy optionally substituted with one —N$R^{9e}R^{9f}$, or —S(=O)$_2$$C_{1-4}$ alkyl;

each $R^6$ is
halo,
—CN,
—NO$_2$,
—CH$_3$,
5-10 membered monocyclic or fused bicyclic heteroaryl comprising 1, 2 or 3 heteroatoms independently selected from N, O, and S, optionally substituted with one or more independently selected halo, $C_{1-4}$ alkyl, $C_{1-4}$ alkoxy, or
—N$R^{9g}R^{9h}$;

each $R^{7a}$, $R^{7b}$, $R^{7c}$, $R^{7d}$, or $R^{7e}$ is
H, or
$C_{1-4}$ alkyl optionally substituted with one OH, or $C_{1-4}$ alkoxy;

each $R^{8a}$ or $R^{8b}$ is independently selected from:
H, and
$C_{1-4}$ alkyl optionally substituted with one or more independently selected OH, $C_{1-4}$ alkoxy, or phenyl;

each $R^{9a}$, $R^{9b}$, $R^{9c}$, $R^{9d}$, $R^{9e}$, $R^{9f}$, $R^{9g}$, and $R^{9h}$ is independently selected from H, and $C_{1-4}$ alkyl; or a pharmaceutically acceptable salt, or a solvate, or a pharmaceutically acceptable salt of a solvate thereof; or a biologically active metabolite thereof;

provided that:
$R^1$, and $R^2$ are not simultaneously H, and
When $R^1$ is Me, then Cy is not

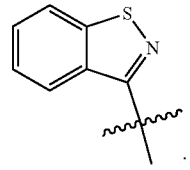

In one embodiment, a compound of the invention is according to Formula II:

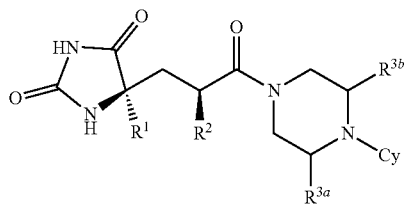

wherein $R^1$, $R^2$, $R^{3a}$, $R^{3b}$, and Cy are as defined above.

In one embodiment, a compound of the invention is according to Formula I or II, wherein $R^1$ is H.

In another embodiment, a compound of the invention is according to Formula I or II, wherein $R^1$ is $C_{1-4}$ alkyl. In a particular embodiment, $R^1$ is Me, Et, Pr, iPr, or tBu. In a more particular embodiment, $R^1$ is Me, or Et.

In another embodiment, a compound of the invention is according to Formula I or II, wherein $R^1$ is $C_{1-4}$ alkyl substituted with one or more independently selected $R^4$ groups. In another embodiment, $R^1$ is Me, or Et, each of which is substituted with one or more independently selected $R^4$ groups. In a particular embodiment, $R^1$ is $C_{1-4}$ alkyl substituted with one, two or three independently selected $R^4$ groups. In another particular embodiment, $R^1$ is Me, or Et, each of which is substituted with one, two or three independently selected $R^4$ groups. In a more particular embodiment, $R^1$ is $C_{1-4}$ alkyl substituted with one $R^4$ group. In another more particular embodiment, $R^1$ is Me, or Et, each of which is substituted with one $R^4$ group.

In one embodiment, a compound of the invention is according to Formula I or II, wherein $R^1$ is $C_{3-7}$ monocyclic cycloalkyl. In a particular embodiment, $R^1$ is cyclopropyl, cyclobutyl, cyclopentyl, or cyclohexyl. In a more particular embodiment, $R^1$ is cyclopropyl.

In another embodiment, a compound of the invention is according to Formula I or II, wherein $R^1$ is $C_{3-7}$ monocyclic cycloalkyl substituted with one or more independently selected $R^4$ groups. In another embodiment, $R^1$ is cyclopropyl, cyclobutyl, cyclopentyl, or cyclohexyl, each of which is substituted with one or more independently selected $R^4$ groups. In a particular embodiment, $R^1$ is $C_{3-7}$ monocyclic cycloalkyl substituted with one, two or three independently selected $R^4$ groups. In another particular embodiment, $R^1$ is cyclopropyl, cyclobutyl, cyclopentyl, or cyclohexyl, each of which is substituted with one, two or three independently selected $R^4$ groups. In a more particular embodiment, $R^1$ is $C_{3-7}$ monocyclic cycloalkyl substituted with one $R^4$ group. In another more particular embodiment, $R^1$ is cyclopropyl, cyclobutyl, cyclopentyl, or cyclohexyl, each of which is substituted with one $R^4$ group.

In one embodiment, a compound of the invention is according to Formula I or II, wherein $R^4$ is halo, OH, and CN. In a more particular embodiment, each $R^4$ is independently selected from F, Cl, OH, and CN.

In one embodiment, a compound of the invention is according to Formula I or II, wherein $R^4$ is $C_{1-4}$ alkyl. In a particular embodiment, $R^4$ is —$CH_3$, —$CH_2CH_3$, or —$CH(CH_3)_2$. In a more particular embodiment, $R^4$ is —$CH_3$.

In one embodiment, a compound of the invention is according to Formula I or II, wherein $R^4$ is $C_{1-4}$ alkoxy. In a particular embodiment, $R^4$ is OMe, OEt, or OiPr. In a more particular embodiment, $R^4$ is OMe.

In one embodiment, a compound of the invention is according to Formula I or II, wherein $R^4$ is $C_{1-4}$ alkoxy substituted with one $C_{1-4}$ alkoxy, or phenyl. In a particular embodiment, $R^4$ is OMe, OEt, or OiPr, each of which is substituted with one $C_{1-4}$ alkoxy, or phenyl. In a more particular embodiment, $R^4$ is $C_{1-4}$ alkoxy substituted with one OMe, OEt, or phenyl. In another more particular embodiment, $R^4$ is OMe, OEt, or OiPr, each of which is substituted with one OMe, OEt, or phenyl. In a most particular embodiment, $R^4$ is —$OCH_2$—$CH_2$—$OCH_3$, —$OCH_2$-Ph.

In one embodiment, a compound of the invention is according to Formula I or II, wherein $R^4$ is $C_{1-4}$ thioalkoxy. In a particular embodiment, $R^4$ is —$SCH_3$, or —$SCH_2CH_3$. In a more particular embodiment, $R^4$ is —$SCH_3$.

In one embodiment, a compound of the invention is according to Formula I or II, wherein $R^4$ is 4-7-membered monocyclic heterocycloalkyl comprising one or more heteroatoms independently selected from N, S, and O. In a particular embodiment, $R^4$ is azetidinyl, pyrrolidinyl, piperidinyl, piperazinyl, morpholinyl, tetrahydrofuranyl, tetrahydropyranyl, or dioxanyl. In a more particular embodiment, $R^4$ is azetidinyl, pyrrolidinyl, piperidinyl, or morpholinyl.

In one embodiment, a compound of the invention is according to Formula I or II, wherein $R^4$ is 4-7-membered monocyclic heterocycloalkyl comprising one or more heteroatoms independently selected from N, S, and O, substituted with one or more halo, —$C(=O)OC_{1-4}$ alkyl. In a particular embodiment, $R^4$ is 4-7-membered monocyclic heterocycloalkyl comprising one or more heteroatoms independently selected from N, S, and O, substituted with one, two or three independently selected F, Cl, —$C(=O)OCH_3$, —$C(=O)OCH_2CH_3$, or —$C(=O)OC(CH_3)_3$. In another particular embodiment, $R^4$ is azetidinyl, pyrrolidinyl, piperidinyl, piperazinyl, morpholinyl, tetrahydrofuranyl, tetrahydropyranyl, or dioxanyl, each of which is substituted with one, two or three independently selected F, Cl, —$C(=O)OCH_3$, —$C(=O)OCH_2CH_3$, or —$C(=O)OC(CH_3)_3$. In a more particular embodiment, $R^4$ is 4-7-membered monocyclic heterocycloalkyl comprising one or more heteroatoms independently selected from N, S, and O, substituted with one F, Cl, —$C(=O)OCH_3$, —$C(=O)OCH_2CH_3$, or —$C(=O)OC(CH_3)_3$. In another particular embodiment, $R^4$ is azetidinyl, pyrrolidinyl, piperidinyl, piperazinyl, morpholinyl, tetrahydrofuranyl, tetrahydropyranyl, or dioxanyl, each of which is substituted with one F, Cl, —$C(=O)OCH_3$, —$C(=O)OCH_2CH_3$, or —$C(=O)OC(CH_3)_3$. In a most particular embodiment, $R^4$ is azetidinyl, pyrrolidinyl, piperidinyl, or morpholinyl, each of which is substituted with one, two or three independently selected F, Cl. In another most particular embodiment, $R^4$ is azetidinyl, pyrrolidinyl, piperidinyl, or morpholinyl, each of which is substituted with one —$C(=O)OCH_3$, —$C(=O)OCH_2CH_3$, or —$C(=O)OC(CH_3)_3$.

In one embodiment, a compound of the invention is according to Formula I or II, wherein $R^4$ is phenyl.

In one embodiment, a compound of the invention is according to Formula I or II, wherein $R^4$ is —$S(=O)_2C_{1-4}$ alkyl. In a particular embodiment, $R^4$ is —$S(=O)_2CH_3$, or —$S(=O)_2CH_2CH_3$.

In one embodiment, a compound of the invention is according to Formula I or II, wherein $R^4$ is —$C(=O)OR^{7a}$, and $R^{7a}$ is as previously described. In a particular embodiment, $R^{7a}$ is H. In another particular embodiment, $R^{7a}$ is $C_{1-4}$ alkyl. In yet another particular embodiment, $R^{7a}$ is $C_{1-4}$ alkyl substituted with one OH, $C_{1-4}$ alkoxy. In a more particular embodiment, $R^{7a}$ is Me, Et, iPr or tBu. In another more particular embodiment, $R^{7a}$ is Me, Et, iPr or tBu, each of which is substituted with one OH, $C_{1-4}$ alkoxy. In yet another more particular embodiment, $R^{7a}$ is Me, Et, iPr or tBu, each of which is substituted with one OH, —$OCH_3$. In a most particular embodiment, $R^4$ is —$C(=O)OCH_3$, —$C(=O)OCH_2CH_3$, or —$C(=O)OC(CH_3)_3$.

In one embodiment, a compound of the invention is according to Formula I or II, wherein $R^4$ is —$C(=O)NR^{7b}R^{7c}$, and each $R^{7b}$ or $R^{7c}$ is as previously described. In a particular embodiment, $R^{7b}$ and $R^{7c}$ are H. In another particular embodiment, one of $R^{7b}$ or $R^{7c}$ is H, and the other is $C_{1-4}$ alkyl. In yet another particular embodiment, one of $R^{7b}$ or $R^{7c}$ is H, and the other is $C_{1-4}$ alkyl substituted with one OH, $C_{1-4}$ alkoxy. In a further particular embodiment, $R^{7b}$ and $R^{7c}$ are $C_{1-4}$ alkyl. In a more particular embodiment, one of $R^{7b}$ or $R^{7c}$ is H, and the other is Me, Et, iPr or tBu. In another more particular embodiment, one of $R^{7b}$ or $R^{7c}$ is H, and the other is Me, Et, iPr or tBu, each of which is substituted with one OH, $C_{1-4}$ alkoxy. In yet another more particular embodiment, one of $R^{7b}$ or $R^{7c}$ is H, and the other is Me, Et, iPr or tBu, each of which is substituted with one OH, —$OCH_3$. In a most particular embodiment, $R^4$ is —$C(=O)NHCH_3$, —$C(=O)N(CH_3)_2$, —$C(=O)NHCH_2CH_3$, —$C(=O)NHCH_2CH_2$—OH or —$C(=O)NHCH_2CH_2$—$OCH_3$.

In one embodiment, a compound of the invention is according to Formula I or II, wherein $R^4$ is —$NHC(=O)OR^{7d}$, and $R^{7d}$ is as previously described. In a particular embodiment, $R^{7d}$ is H. In another particular embodiment, $R^{7d}$ is $C_{1-4}$ alkyl. In yet another particular embodiment, $R^{7d}$ is $C_{1-4}$ alkyl substituted with one OH, $C_{1-4}$ alkoxy. In a more particular embodiment, $R^{7d}$ is Me, Et, iPr or tBu. In another more particular embodiment, $R^{7d}$ is Me, Et, iPr or tBu, each of which is substituted with one OH, $C_{1-4}$ alkoxy. In yet another more particular embodiment, $R^{7d}$ is Me, Et, iPr or tBu, each of which is substituted with one OH, —OCH$_3$. In a most particular embodiment, $R^4$ is —NHC(=O)OCH$_3$, —NHC(=O)OCH$_2$CH$_3$, or —NHC(=O)OC(CH$_3$)$_3$.

In one embodiment, a compound of the invention is according to Formula I or II, wherein $R^4$ is —NHC(=O)$R^{7e}$, and $R^{7e}$ is as previously described. In a particular embodiment, $R^{7e}$ is H. In another particular embodiment, $R^{7e}$ is $C_{1-4}$ alkyl. In yet another particular embodiment, $R^{7e}$ is $C_{1-4}$ alkyl substituted with one OH, $C_{1-4}$ alkoxy. In a more particular embodiment, $R^{7e}$ is Me, Et, iPr or tBu. In another more particular embodiment, $R^{7e}$ is Me, Et, iPr or tBu, each of which is substituted with one OH, $C_{1-4}$ alkoxy. In yet another more particular embodiment, $R^{7e}$ is Me, Et, iPr or tBu, each of which is substituted with one OH, —OCH$_3$. In a most particular embodiment, $R^4$ is —NHC(=O)CH$_3$, —NHC(=O)CH$_2$CH$_3$, or —NHC(=O)C(CH$_3$)$_3$.

In one embodiment, a compound of the invention is according to Formula I or II, wherein $R^4$ is —NR$^{8a}$R$^{8b}$, and each $R^{8a}$ or $R^{8b}$ is as previously described. In a particular embodiment, $R^{8a}$ and $R^{8b}$ are H. In another particular embodiment, one of $R^{8a}$ or $R^{8b}$ is H, and the other is $C_{1-4}$ alkyl. In yet another particular embodiment, one of $R^{8a}$ or $R^{8b}$ is H, and the other is $C_{1-4}$ alkyl substituted with one OH, $C_{1-4}$ alkoxy, or phenyl. In a further particular embodiment, $R^{8a}$ and $R^{8b}$ are $C_{1-4}$ alkyl. In a more particular embodiment, one of $R^{8a}$ or $R^{8b}$ is H, and the other is Me, Et, iPr or tBu. In another more particular embodiment, one of $R^{8a}$ or $R^{8b}$ is H, and the other is Me, Et, iPr or tBu, each of which is substituted with one OH, $C_{1-4}$ alkoxy, or phenyl. In yet another more particular embodiment, one of $R^{8a}$ or $R^{8b}$ is H, and the other is Me, Et, iPr or tBu, each of which is substituted with one OH, —OCH$_3$, or phenyl. In a most particular embodiment, $R^4$ is —NH$_2$, —NHCH$_3$, —N(CH$_3$)$_2$, —NHCH$_2$Phenyl, or —NHCH$_2$CH$_2$—OCH$_3$.

In another embodiment, a compound of the invention is according to Formula I or II, wherein $R^1$ is 4-7 membered monocyclic heterocycloalkyl comprising 1 to 2 heteroatoms independently selected from N, O, and S. In a particular embodiment, $R^1$ is azetidinyl, pyrrolidinyl, piperidinyl, piperazinyl, morpholinyl, tetrahydrofuranyl, tetrahydropyranyl, or dioxanyl. In a particular embodiment, $R^1$ is azetidinyl.

In one embodiment, a compound of the invention is according to Formula I or II, wherein $R^1$ is 4-7 membered monocyclic heterocycloalkyl comprising 1 to 2 heteroatoms independently selected from N, O, and S, substituted with one or more independently selected $C_{1-4}$ alkyl, —C(=O)$C_{1-4}$ alkyl, or —C(=O)OC$_{1-4}$ alkyl. In another embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one or more independently selected $C_{1-4}$ alkyl, —C(=O)$C_{1-4}$ alkyl, or —C(=O)OC$_{1-4}$ alkyl. In a particular embodiment, $R^1$ is 4-7 membered monocyclic heterocycloalkyl comprising 1 to 2 heteroatoms independently selected from N, O, and S, substituted with one $C_{1-4}$ alkyl, —C(=O)$C_{1-4}$ alkyl, or —C(=O)OC$_{1-4}$ alkyl. In another particular embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one $C_{1-4}$ alkyl, —C(=O)$C_{1-4}$ alkyl, or —C(=O)OC$_{1-4}$ alkyl. In a more particular embodiment, $R^1$ is 4-7 membered monocyclic heterocycloalkyl comprising 1 to 2 heteroatoms independently selected from N, O, and S, substituted with one or more independently selected —CH$_3$, —C(=O)CH$_3$, or —C(=O)OC(CH$_3$)$_3$. In another more particular embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one or more independently selected —CH$_3$, —C(=O)CH$_3$, —C(=O)OCH$_3$, or —C(=O)OC(CH$_3$)$_3$. In yet another more particular embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one —C(=O)CH$_3$, —C(=O)OCH$_3$, or —C(=O)OC(CH$_3$)$_3$.

In one embodiment, a compound of the invention is according to Formula I or II, wherein $R^1$ is phenyl.

In another embodiment, a compound of the invention is according to Formula I or II, wherein $R^1$ is phenyl substituted with one or more independently selected $R^5$ groups. In a particular embodiment, $R^1$ is phenyl substituted with one, two, or three independently selected $R^5$ groups. In another particular embodiment, $R^1$ is phenyl substituted with one $R^5$ group.

In one embodiment, a compound of the invention is according to Formula I or II, wherein $R^1$ is 5-6 membered monocyclic heteroaryl comprising 1 or 2 heteroatoms independently selected from N, O, and S. In a particular embodiment, $R^1$ is imidazolyl, pyrazolyl, thiazolyl, oxazolyl, pyridinyl, pyrimidinyl or pyrazinyl.

In another embodiment, a compound of the invention is according to Formula I or II, wherein $R^1$ is 5-6 membered monocyclic heteroaryl comprising 1, 2 or 3 heteroatoms independently selected from N, O, and S substituted with one or more independently selected $R^5$ groups. In another embodiment $R^1$ is imidazolyl, pyrazolyl, thiazolyl, oxazolyl, pyridinyl, pyrimidinyl or pyrazinyl, each of which is substituted with one or more independently selected $R^5$ groups. In a particular embodiment, $R^1$ is 5-6 membered monocyclic heteroaryl comprising 1, 2 or 3 heteroatoms independently selected from N, O, and S substituted with one, two, or three independently selected $R^5$ groups. In another particular embodiment, $R^1$ is imidazolyl, pyrazolyl, thiazolyl, oxazolyl, pyridinyl, pyrimidinyl or pyrazinyl, each of which is substituted with one, two, or three independently selected $R^5$ groups. In a more particular embodiment, $R^1$ is 5-6 membered monocyclic heteroaryl comprising 1, 2 or 3 heteroatoms independently selected from N, O, and S substituted with one $R^5$ group. In another more particular embodiment, $R^1$ is imidazolyl, pyrazolyl, thiazolyl, oxazolyl, pyridinyl, pyrimidinyl or pyrazinyl, each of which is substituted with one $R^5$ group.

In one embodiment, a compound of the invention is according to Formula I or II, wherein $R^5$ is halo, OH, or CN. In a particular embodiment, $R^5$ is F, Cl, OH, or CN.

In one embodiment, a compound of the invention is according to Formula I or II, wherein $R^5$ is $C_{1-4}$ alkyl. In a particular embodiment, $R^5$ is Me, Et, or iPr.

In another embodiment, a compound of the invention is according to Formula I or II, wherein $R^5$ is $C_{1-4}$ alkyl substituted with one or more independently selected halo, —NR$^{9a}$R$^{9b}$, —C(=O)NR$^{9c}$R$^{9d}$, wherein $R^{9a}$, $R^{9b}$, $R^{9c}$, or $R^{9d}$ is as previously described. In another embodiment, $R^5$ is Me, or Et, each of which is substituted with one or more independently selected halo, —NR$^{9a}$R$^{9b}$, —C(=O)NR$^{9c}$R$^{9d}$. In a particular embodiment, $R^5$ is $C_{1-4}$ alkyl substituted with one, two or three independently selected halo, —NR$^{9a}$R$^{9b}$, or —C(=O)NR$^{9c}$R$^{9d}$. In another particular embodiment, $R^5$ is Me, or Et, each of which is substituted with one, two, or three independently selected halo, —NR$^{9a}$R$^{9b}$, or —C(=O)NR$^{9c}$R$^{9d}$. In a more particular embodiment, R$^5$ is C$_{1-4}$ alkyl substituted with one halo, —NR$^{9a}$R$^{9b}$, or —C(=O)NR$^{9c}$R$^{9d}$. In another more particular embodiment, R$^5$ is Me, or Et, each of which is substituted with one halo, —NR$^{9a}$R$^{9b}$, or —C(=O)NR$^{9c}$R$^{9d}$. In one embodiment, each R$^{9a}$, R$^{9b}$, R$^{9c}$, or R$^{9d}$ is independently selected from H, Me, and Et. In a most particular embodiment, R$^5$ is —CF$_3$, —CH$_2$NH$_2$, —CH$_2$NHMe, —CH$_2$NMe$_2$, —CH$_2$C(=O)NH$_2$, —CH$_2$C(=O)NHMe, or —CH$_2$C(=O)NMe$_2$.

In one embodiment, a compound of the invention is according to Formula I or II, wherein R$^5$ is C$_{1-4}$ alkoxy. In a particular embodiment, R$^5$ is —OMe, -OEt, or -OiPr.

In another embodiment, a compound of the invention is according to Formula I or II, wherein R$^5$ is C$_{1-4}$ alkoxy substituted with one —NR$^{9e}$R$^{9f}$, wherein R$^{9e}$ are R$^{9f}$ as previously described. In another embodiment, R$^5$ is —OEt, substituted with one —NR$^{9e}$R$^{9f}$. In one embodiment, each R$^{9e}$, and R$^{9f}$, is independently selected from H, Me, and Et. In a most particular embodiment, R$^5$ is —OCH$_2$CH$_2$NH$_2$, —OCH$_2$CH$_2$NHMe, or —OCH$_2$CH$_2$NMe$_2$.

In another embodiment, a compound of the invention is according to Formula I or II, wherein R$^5$ is —S(=O)$_2$C$_{1-4}$ alkyl. In a particular embodiment, R$^5$ is —S(=O)$_2$CH$_3$.

In embodiment, a compound of the invention is according to Formula IIIa or IIIb:

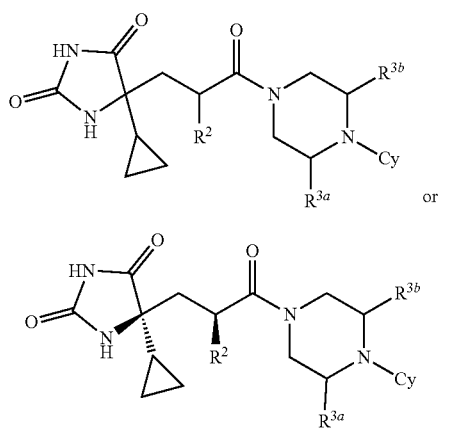

wherein R$^2$, R$^{3a}$, R$^{3b}$, and Cy are as described above.

In one embodiment, a compound of the invention is according to any one of Formulae I-IIIb, wherein R$^2$ is H.

In one embodiment, a compound of the invention is according to any one of Formulae I-IIIb, wherein R$^2$ is —OH.

In one embodiment, a compound of the invention is according to any one of Formulae I-IIIb, wherein R$^2$ is C$_{1-4}$ alkoxy. In a particular embodiment, R$^2$ is —OMe, -OEt, or -OiPr. In a more particular embodiment, R$^2$ is —OMe.

In one embodiment, a compound of the invention is according to any one of Formulae I-IIIb, wherein R$^2$ is C$_{1-4}$ alkyl. In a particular embodiment, R$^2$ is Me, Et, or iPr. In a more particular embodiment, R$^2$ is Me, or Et.

In one embodiment, a compound of the invention is according to any one of Formulae I-IIIb, wherein R$^2$ is C$_{1-4}$ alkyl substituted with one OH, or CN. In a particular embodiment, R$^2$ is Me, or Et, each of which is substituted with one OH, or CN. In a more particular embodiment, R$^2$ is —CH$_2$—OH, or —CH$_2$—CN.

In one embodiment, a compound of the invention is according to any one of Formulae I-IIIb, wherein R$^2$ is C$_{1-4}$ alkyl substituted with one C$_{1-4}$ alkoxy optionally substituted with one phenyl. In another embodiment, R$^2$ is Me, or Et, each of which is substituted with one C$_{1-4}$ alkoxy optionally substituted with one phenyl. In a particular embodiment, R$^2$ is C$_{1-4}$ alkyl substituted with one —OMe, -OEt, each of which is optionally substituted with one phenyl. In another particular embodiment, R$^2$ is Me, or Et, each of which is substituted with one —OMe, -OEt, each of which is optionally substituted with one phenyl. In a more particular embodiment, R$^2$ is —CH$_2$OCH$_3$, —CH$_2$OCH$_2$CH$_3$, —CH$_2$OCH$_2$CH$_2$OCH$_3$, or —CH$_2$OCH$_2$Phenyl.

In one embodiment, a compound of the invention is according to any one of Formulae I-IIIb, wherein R$^2$ is C$_{1-4}$ alkyl substituted with one 5-6 membered monocyclic heteroaryl comprising 1 or 2 heteroatoms independently selected from N, O, and S, optionally substituted with one or more independently selected C$_{1-4}$ alkyl. In another embodiment, R$^2$ is Me, or Et, each of which is substituted with one 5-6 membered monocyclic heteroaryl comprising 1 or 2 heteroatoms independently selected from N, O, and S, optionally substituted with one or more independently selected C$_{1-4}$ alkyl. In a particular embodiment, R$^2$ is C$_{1-4}$ alkyl substituted with one imidazolyl, pyrazolyl, oxazolyl, each of which is optionally substituted with one or more independently selected C$_{1-4}$ alkyl. In another particular embodiment, R$^2$ is Me or Et, each of which is substituted with one imidazolyl, pyrazolyl, oxazolyl, each of which is optionally substituted with one or more independently selected C$_{1-4}$ alkyl. In a more particular embodiment, R$^2$ is C$_{1-4}$ alkyl substituted with one imidazolyl, pyrazolyl, oxazolyl, each of which is optionally substituted with one or more independently selected Me, or Et. In another particular embodiment, R$^2$ is Me, or Et, each of which is substituted with one imidazolyl, pyrazolyl, oxazolyl, each of which is optionally substituted with one or more independently selected Me, or Et.

In one embodiment, a compound of the invention is according to Formula IVa or IVb:

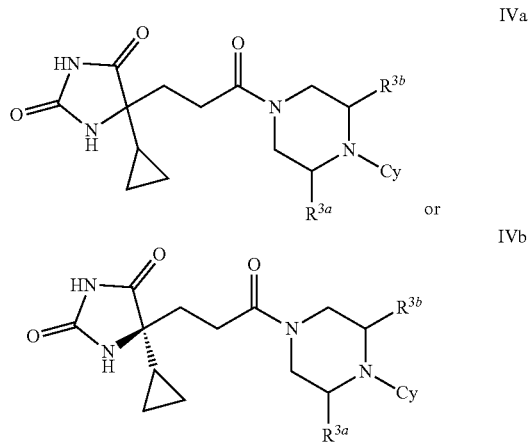

wherein R$^{3a}$, R$^{3b}$, X, and Cy are as described above.

In one embodiment, a compound of the invention is according to any one of Formulae I-IVb, wherein R$^{3a}$, and R$^{3b}$ are both H. In another embodiment, one of R$^{3a}$ and R$^{3b}$ is H, and the other is C$_{1-4}$ alkyl. In a particular embodiment, one of R$^{3a}$ and R$^{3b}$ is H, and the other is Me, or Et. In a more particular embodiment, one of $R^{3a}$ and $R^{3b}$ is H, and the other is Me, or Et. In a most particular embodiment, one of $R^{3a}$ and $R^{3b}$ is H, and the other is Me. In another most particular embodiment, $R^{3a}$ and $R^{3b}$ are both Me.

In one embodiment, a compound of the invention is according to Formula Va, or Vb:

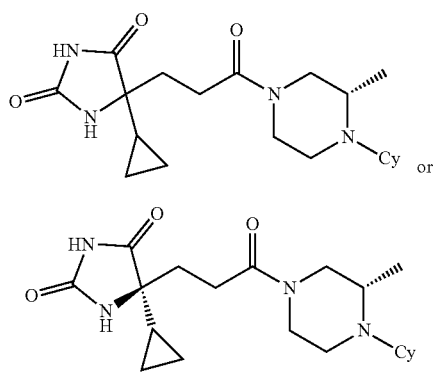

wherein Cy is as described above.

In one embodiment, a compound of the invention is according to any one of Formulae I-Vb, wherein Cy is 6-10 membered monocyclic or fused bicyclic aryl. In a particular embodiment, Cy is phenyl, or naphthyl. In a more particular embodiment, Cy is phenyl.

In one embodiment, a compound of the invention is according to any one of Formulae I-Vb, wherein Cy is 6-10 membered monocyclic or fused bicyclic aryl substituted with one or more independently selected $R^6$ groups. In another embodiment, Cy is phenyl, or naphthyl, each of which is substituted with one or more independently selected $R^6$ groups. In a particular embodiment, Cy is 6-10 membered monocyclic or fused bicyclic aryl substituted with one, two or three independently selected $R^6$ groups. In another embodiment, Cy is phenyl, or naphthyl, each of which is substituted with one, two or three independently selected $R^6$ groups. In a more particular embodiment, Cy is 6-10 membered monocyclic or fused bicyclic aryl substituted with one $R^6$ group. In another embodiment, Cy is phenyl, or naphthyl, each of which is substituted with one $R^6$ group.

In one embodiment, a compound of the invention is according to any one of Formulae I-Vb, wherein Cy is 5-10 membered monocyclic or fused bicyclic heteroaryl comprising 1, 2 or 3 heteroatoms independently selected from N, O, and S. In a particular embodiment, Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl. In a more particular embodiment, Cy is pyridinyl.

In one embodiment, a compound of the invention is according to any one of Formulae I-Vb, wherein Cy is 5-10 membered monocyclic or fused bicyclic heteroaryl comprising 1, 2 or 3 heteroatoms independently selected from N, O, and S substituted with one or more independently selected $R^6$ groups. In another embodiment, Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl, each of which is substituted with one or more independently selected $R^6$ groups. In a particular embodiment, Cy is 5-10 membered monocyclic or fused bicyclic heteroaryl comprising 1, 2 or 3 heteroatoms independently selected from N, O, and S substituted with one, two or three independently selected $R^6$ groups. In another embodiment, Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl, each of which is substituted with one, two or three independently selected $R^6$ groups. In a more particular embodiment, Cy is 5-10 membered monocyclic heteroaryl comprising 1, 2 or 3 heteroatoms independently selected from N, O, and S substituted with one $R^6$ group. In another embodiment, Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl, each of which is substituted with one $R^6$ group.

In one embodiment, a compound of the invention is according to any one of Formulae I-Vb, wherein $R^6$ is halo, —CN, or —$NO_2$. In a particular embodiment, $R^6$ is F, Cl, —CN, or —$NO_2$.

In one embodiment, a compound of the invention is according to any one of Formulae I-Vb, wherein $R^6$ is —$CH_3$.

In one embodiment, a compound of the invention is according to any one of Formulae I-Vb, wherein $R^6$ is 5-10 membered monocyclic or fused bicyclic heteroaryl comprising 1, 2 or 3 heteroatoms independently selected from N, O, and S, optionally substituted with one or more independently selected halo, $C_{1-4}$ alkyl, $C_{1-4}$ alkoxy. In another embodiment, $R^6$ is pyrazolyl, oxazolyl, oxadiazolyl, thiazolyl, pyridinyl, pyrazinyl, pyridazinyl, or pyrimidinyl, each of which is optionally substituted with one or more independently selected halo, $C_{1-4}$ alkyl, $C_{1-4}$ alkoxy. In a particular embodiment, $R^6$ is 5-10 membered monocyclic or fused bicyclic heteroaryl comprising 1, 2 or 3 heteroatoms independently selected from N, O, and S, optionally substituted with one, two, or three independently selected halo, $C_{1-4}$ alkyl, or $C_{1-4}$ alkoxy. In another particular embodiment, $R^6$ is pyrazolyl, oxazolyl, oxadiazolyl, thiazolyl, pyridinyl, pyrazinyl, pyridazinyl, or pyrimidinyl, each of which is optionally substituted with one, two, or three independently selected halo, $C_{1-4}$ alkyl, or $C_{1-4}$ alkoxy. In a more particular embodiment, $R^6$ is 5-10 membered monocyclic or fused bicyclic heteroaryl comprising 1, 2 or 3 heteroatoms independently selected from N, O, and S, optionally substituted with one halo, $C_{1-4}$ alkyl, $C_{1-4}$ alkoxy. In another more particular embodiment, $R^6$ is pyrazolyl, oxazolyl, oxadiazolyl, thiazolyl, pyridinyl, pyrazinyl, pyridazinyl, or pyrimidinyl, each of which is optionally substituted with one halo, $C_{1-4}$ alkyl, or $C_{1-4}$ alkoxy. In a most particular embodiment, $R^6$ is 5-10 membered monocyclic or fused bicyclic heteroaryl comprising 1, 2 or 3 heteroatoms independently selected from N, O, and S, optionally substituted with one, two, or three independently selected F, Cl, Me, Et, —OMe, or —OEt. In another more particular embodiment, $R^6$ is pyrazolyl, oxazolyl, oxadiazolyl, thiazolyl, pyridinyl, pyrazinyl, pyridazinyl, or pyrimidinyl, each of which is optionally substituted with one, two, or three independently selected F, Cl, Me, Et, —OMe, or —OEt.

In one embodiment, a compound of the invention is according to any one of Formulae I-Vb, wherein $R^6$ is —$NR^{9g}R^{9h}$, wherein $R^{9g}$ and $R^{9h}$ are as previously described. In a particular embodiment, $R^{9g}$ and $R^{9h}$ are both H. In another particular embodiment, $R^{9g}$ and $R^{9h}$ are both $C_{1-4}$ alkyl. In yet another particular embodiment, one of $R^{9g}$ and $R^{9h}$ is H, and the other is $C_{1-4}$ alkyl. In a more particular embodiment, $R^6$ is —$NH_2$, —NHMe, or —$NMe_2$.

In one embodiment, a compound of the invention is according to Formula VIa or VIb:

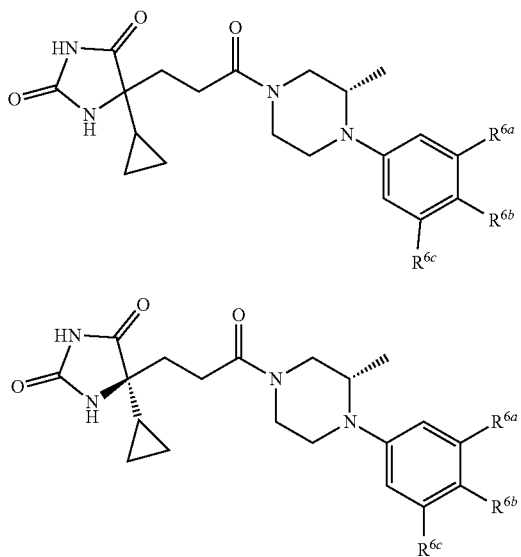

wherein each one of $R^{6a}$, $R^{6b}$ and $R^{6c}$ is independently selected from H, halo, —CN, and —CH$_3$.

In one embodiment, a compound of the invention is according to Formula VIa or VIb, wherein each one of $R^{6a}$, $R^{6b}$ and $R^{6c}$ is independently selected from H, halo, and —CH$_3$. In a more particular embodiment, each one of $R^{6a}$, $R^{6b}$ and $R^{6c}$ is independently selected from H, F, Cl, and —CH$_3$.

In another particular embodiment, a compound of the invention is according to Formula VIa or VIb, wherein $R^{6b}$ is H, and each one of $R^{6a}$, and $R^{6c}$ is independently selected from H, halo, and —CH$_3$. In a particular embodiment, $R^{6b}$ is H, and each one of $R^{6a}$, and $R^{6c}$ is independently selected from H, F, Cl, and —CH$_3$. In a more particular embodiment, $R^{6b}$ is H, and each one of $R^{6a}$, and $R^{6c}$ is independently selected from H, F, and Cl.

In another particular embodiment, a compound of the invention is according to Formula VIa or VIb, wherein $R^{6a}$ is H, and each one of $R^{6b}$, and $R^{6c}$ is independently selected from H, halo, and —CH$_3$. In a particular embodiment, $R^{6a}$ is H, and each one of $R^{6b}$, and $R^{6c}$ is independently selected from H, F, Cl, and —CH$_3$. In a more particular embodiment, $R^{6a}$ is H, and each one of $R^{6b}$, and $R^{6c}$ is independently selected from H, F, and Cl.

In one embodiment, a compound of the invention is selected from:

Cpd 1 5-methyl-5-[3-oxo-3-(4-phenylpiperazin-1-yl)propyl]imidazolidine-2,4-dione,
Cpd 2 5-[3-[4-(4-chlorophenyl)piperazin-1-yl]-3-oxo-propyl]-5-methyl-imidazolidine-2,4-dione,
Cpd 3 5-[3-[4-(3-chlorophenyl)piperazin-1-yl]-3-oxo-propyl]-5-methyl-imidazolidine-2,4-dione,
Cpd 4 5-[3-oxo-3-(4-phenylpiperazin-1-yl)propyl]-5-phenyl-imidazolidine-2,4-dione,
Cpd 5 5-[3-[4-(4-chlorophenyl)piperazin-1-yl]-3-oxo-propyl]-5-phenyl-imidazolidine-2,4-dione,
Cpd 6 5-[3-[4-(3-chlorophenyl)piperazin-1-yl]-3-oxo-propyl]-5-phenyl-imidazolidine-2,4-dione,
Cpd 7 5-[3-[4-(o-tolyl)piperazin-1-yl]-3-oxo-propyl]-5-phenyl-imidazolidine-2,4-dione,
Cpd 8 5-[3-[4-(2,3-dimethylphenyl)piperazin-1-yl]-3-oxo-propyl]-5-phenyl-imidazolidine-2,4-dione,
Cpd 9 5-[3-[4-(2-naphthyl)piperazin-1-yl]-3-oxo-propyl]-5-phenyl-imidazolidine-2,4-dione,
Cpd 10 5-[3-[4-(4-chloro-3-fluoro-phenyl)piperazin-1-yl]-3-oxo-propyl]-5-phenyl-imidazolidine-2,4-dione,
Cpd 11 5-[3-[4-(2,3-dimethylphenyl)piperazin-1-yl]-3-oxo-propyl]-5-methyl-imidazolidine-2,4-dione,
Cpd 12 5-methyl-5-[3-[4-(o-tolyl)piperazin-1-yl]-3-oxo-propyl]imidazolidine-2,4-dione,
Cpd 13 5-[3-[4-(4-chloro-2-methyl-phenyl)piperazin-1-yl]-3-oxo-propyl]-5-phenyl-imidazolidine-2,4-dione,
Cpd 14 5-[3-[4-(6-isoquinolyl)piperazin-1-yl]-3-oxo-propyl]-5-phenyl-imidazolidine-2,4-dione,
Cpd 15 5-[3-oxo-3-[4-(2-quinolyl)piperazin-1-yl]propyl]-5-phenyl-imidazolidine-2,4-dione,
Cpd 16 5-[3-[4-(5-chloro-2-methyl-phenyl)piperazin-1-yl]-3-oxo-propyl]-5-methyl-imidazolidine-2,4-dione,
Cpd 17 5-[3-[4-(4-chloro-2-methyl-phenyl)piperazin-1-yl]-3-oxo-propyl]-5-methyl-imidazolidine-2,4-dione,
Cpd 18 5-[3-[4-(3-chloro-2-methyl-phenyl)piperazin-1-yl]-3-oxo-propyl]-5-methyl-imidazolidine-2,4-dione,
Cpd 19 5-[3-[4-(2-chlorophenyl)piperazin-1-yl]-3-oxo-propyl]-5-methyl-imidazolidine-2,4-dione,
Cpd 20 5-[3-[4-(2-chlorophenyl)piperazin-1-yl]-3-oxo-propyl]-5-phenyl-imidazolidine-2,4-dione,
Cpd 21 5-[3-[4-(3-chloro-2-methyl-phenyl)piperazin-1-yl]-3-oxo-propyl]-5-phenyl-imidazolidine-2,4-dione,
Cpd 22 5-[3-[4-(2,6-dimethylphenyl)piperazin-1-yl]-3-oxo-propyl]-5-phenyl-imidazolidine-2,4-dione,
Cpd 23 5-[3-[4-(3-methyl-4-nitro-phenyl)piperazin-1-yl]-3-oxo-propyl]-5-phenyl-imidazolidine-2,4-dione,
Cpd 24 5-[3-[4-(5-chloro-2-methyl-phenyl)piperazin-1-yl]-3-oxo-propyl]-5-phenyl-imidazolidine-2,4-dione,
Cpd 25 5-[3-[4-(benzofuran-5-yl)piperazin-1-yl]-3-oxo-propyl]-5-phenyl-imidazolidine-2,4-dione,
Cpd 26 5-[3-[4-(1,3-benzothiazol-5-yl)piperazin-1-yl]-3-oxo-propyl]-5-phenyl-imidazolidine-2,4-dione,
Cpd 27 (5S)-5-[3-[4-(o-tolyl)piperazin-1-yl]-3-oxo-propyl]-5-phenyl-imidazolidine-2,4-dione,
Cpd 28 5-[3-[4-(4-bromophenyl)piperazin-1-yl]-3-oxo-propyl]-5-methyl-imidazolidine-2,4-dione,
Cpd 29 2-[4-[3-(4-methyl-2,5-dioxo-imidazolidin-4-yl)propanoyl]piperazin-1-yl]benzonitrile,
Cpd 30 5-[3-[4-(2-fluorophenyl)piperazin-1-yl]-3-oxo-propyl]-5-methyl-imidazolidine-2,4-dione,
Cpd 31 5-[3-[4-(2,4-dimethylphenyl)piperazin-1-yl]-3-oxo-propyl]-5-phenyl-imidazolidine-2,4-dione,
Cpd 32 5-isopropyl-5-[3-[4-(o-tolyl)piperazin-1-yl]-3-oxo-propyl]imidazolidine-2,4-dione,
Cpd 33 5-[3-[4-(5-chloro-2-methyl-phenyl)piperazin-1-yl]-3-oxo-propyl]-5-isopropyl-imidazolidine-2,4-dione,
Cpd 34 5-[3-[4-(3-chlorophenyl)piperazin-1-yl]-3-oxo-propyl]-5-cyclopropyl-imidazolidine-2,4-dione,
Cpd 35 5-cyclopropyl-5-[3-[4-(o-tolyl)piperazin-1-yl]-3-oxo-propyl]imidazolidine-2,4-dione,
Cpd 36 5-[3-[4-(5-chloro-2-methyl-phenyl)piperazin-1-yl]-3-oxo-propyl]-5-cyclopropyl-imidazolidine-2,4-dione,
Cpd 37 5-[3-[4-(3,4-difluorophenyl)piperazin-1-yl]-3-oxo-propyl]-5-methyl-imidazolidine-2,4-dione,
Cpd 38 5-[3-[4-(2,4-dimethylphenyl)piperazin-1-yl]-3-oxo-propyl]-5-methyl-imidazolidine-2,4-dione,
Cpd 39 5-[3-[4-(2,5-dimethylphenyl)piperazin-1-yl]-3-oxo-propyl]-5-methyl-imidazolidine-2,4-dione,
Cpd 40 5-[3-[4-(3,5-dichlorophenyl)piperazin-1-yl]-3-oxo-propyl]-5-methyl-imidazolidine-2,4-dione,
Cpd 41 5-[3-[4-(2,3-dichlorophenyl)piperazin-1-yl]-3-oxo-propyl]-5-methyl-imidazolidine-2,4-dione, Cpd 42 5-methyl-5-[3-oxo-3-[4-(2-pyridyl)piperazin-1-yl]propyl]imidazolidine-2,4-dione,
Cpd 43 5-methyl-5-[3-oxo-3-[4-(3-pyridyl)piperazin-1-yl]propyl]imidazolidine-2,4-dione,
Cpd 44 5-[3-[4-(3-chlorophenyl)piperazin-1-yl]-3-oxo-propyl]-5-(2-dimethylaminoethyl)imidazolidine-2,4-dione,
Cpd 45 5-[3-oxo-3-[4-(3-pyridyl)piperazin-1-yl]propyl]-5-phenyl-imidazolidine-2,4-dione,
Cpd 46 5-[3-[4-(5-chloro-2-methyl-phenyl)piperazin-1-yl]-3-oxo-propyl]-5-(3-pyridyl)imidazolidine-2,4-dione,
Cpd 47 5-[3-[4-(3-fluorophenyl)piperazin-1-yl]-3-oxo-propyl]-5-methyl-imidazolidine-2,4-dione,
Cpd 48 5-[3-[4-(3-bromophenyl)piperazin-1-yl]-3-oxo-propyl]-5-methyl-imidazolidine-2,4-dione,
Cpd 49 5-[3-[4-(4-chloro-3-fluoro-phenyl)piperazin-1-yl]-3-oxo-propyl]-5-methyl-imidazolidine-2,4-dione,
Cpd 50 5-[3-[4-[2-(dimethylamino)phenyl]piperazin-1-yl]-3-oxo-propyl]-5-methyl-imidazolidine-2,4-dione,
Cpd 51 5-[3-[4-(5-fluoro-2-methyl-phenyl)piperazin-1-yl]-3-oxo-propyl]-5-methyl-imidazolidine-2,4-dione,
Cpd 52 5-[3-[4-(3-chloro-4-fluoro-phenyl)piperazin-1-yl]-3-oxo-propyl]-5-methyl-imidazolidine-2,4-dione,
Cpd 53 5-[3-[4-(3-chlorophenyl)piperazin-1-yl]-3-oxo-propyl]-5-isopropyl-imidazolidine-2,4-dione,
Cpd 54 5-[3-[4-(3,5-dichlorophenyl)piperazin-1-yl]-3-oxo-propyl]-5-isopropyl-imidazolidine-2,4-dione,
Cpd 55 5-cyclopropyl-5-[3-[4-(3,5-dichlorophenyl)piperazin-1-yl]-3-oxo-propyl]imidazolidine-2,4-dione,
Cpd 56 5-[3-[4-(3-chlorophenyl)piperazin-1-yl]-3-oxo-propyl]-5-(3-pyridyl)imidazolidine-2,4-dione,
Cpd 57 5-cyclopropyl-5-[3-[4-(2,3-dimethylphenyl)piperazin-1-yl]-3-oxo-propyl]imidazolidine-2,4-dione,
Cpd 58 5-[3-[4-(3,5-dichlorophenyl)piperazin-1-yl]-3-oxo-propyl]-5-(2-dimethylaminoethyl)imidazolidine-2,4-dione,
Cpd 59 5-methyl-5-[3-oxo-3-(4-thiazol-2-ylpiperazin-1-yl)propyl]imidazolidine-2,4-dione,
Cpd 60 5-[3-[4-(3-fluoro-2-methyl-phenyl)piperazin-1-yl]-3-oxo-propyl]-5-methyl-imidazolidine-2,4-dione,
Cpd 61 5-[3-[4-(4-fluoro-2-methyl-phenyl)piperazin-1-yl]-3-oxo-propyl]-5-methyl-imidazolidine-2,4-dione,
Cpd 62 5-[3-(3-methyl-4-phenyl-piperazin-1-yl)-3-oxo-propyl]-5-phenyl-imidazolidine-2,4-dione,
Cpd 63 5-methyl-5-[3-(3-methyl-4-phenyl-piperazin-1-yl)-3-oxo-propyl]imidazolidine-2,4-dione,
Cpd 64 5-[3-[4-(o-tolyl)piperazin-1-yl]-3-oxo-propyl]-5-(3-pyridyl)imidazolidine-2,4-dione,
Cpd 65 5-[3-[4-(5-chloro-2-methyl-phenyl)piperazin-1-yl]-3-oxo-propyl]-5-(2-pyridyl)imidazolidine-2,4-dione,
Cpd 66 5-[3-[4-(4-fluorophenyl)piperazin-1-yl]-3-oxo-propyl]-5-methyl-imidazolidine-2,4-dione,
Cpd 67 5-[3-[4-(3,4-dichlorophenyl)piperazin-1-yl]-3-oxo-propyl]-5-methyl-imidazolidine-2,4-dione,
Cpd 68 5-[3-oxo-3-(4-phenylpiperazin-1-yl)propyl]-5-(3-pyridyl)imidazolidine-2,4-dione,
Cpd 69 5-[3-[4-(2,3-dimethylphenyl)piperazin-1-yl]-3-oxo-propyl]-5-(3-pyridyl)imidazolidine-2,4-dione,
Cpd 70 5-[3-[4-(3-chlorophenyl)piperazin-1-yl]-3-oxo-propyl]-5-cyclobutyl-imidazolidine-2,4-dione,
Cpd 71 5-[3-[4-(5-chloro-2-methyl-phenyl)piperazin-1-yl]-3-oxo-propyl]-5-cyclobutyl-imidazolidine-2,4-dione,
Cpd 72 5-[3-[4-(3-chlorophenyl)piperazin-1-yl]-3-oxo-propyl]-5-cyclohexyl-imidazolidine-2,4-dione,
Cpd 73 5-[3-[4-(5-chloro-2-methyl-phenyl)piperazin-1-yl]-3-oxo-propyl]-5-cyclohexyl-imidazolidine-2,4-dione,
Cpd 74 5-(4-chlorophenyl)-5-[3-[4-(3-chlorophenyl)piperazin-1-yl]-3-oxo-propyl]imidazolidine-2,4-dione,
Cpd 75 5-[3-[4-(5-chloro-2-methyl-phenyl)piperazin-1-yl]-3-oxo-propyl]-5-(4-chlorophenyl)imidazolidine-2,4-dione,
Cpd 76 5-[3-[4-(3-chlorophenyl)piperazin-1-yl]-3-oxo-propyl]-5-(p-tolyl)imidazolidine-2,4-dione,
Cpd 77 5-[3-[4-(5-chloro-2-methyl-phenyl)piperazin-1-yl]-3-oxo-propyl]-5-(p-tolyl)imidazolidine-2,4-dione,
Cpd 78 5-[3-[4-(3-chlorophenyl)piperazin-1-yl]-3-oxo-propyl]-5-(4-methoxyphenyl)imidazolidine-2,4-dione,
Cpd 79 5-[3-[4-(5-chloro-2-methyl-phenyl)piperazin-1-yl]-3-oxo-propyl]-5-(4-methoxyphenyl)imidazolidine-2,4-dione,
Cpd 80 5-[3-[4-(3-chlorophenyl)piperazin-1-yl]-3-oxo-propyl]-5-[4-(2-dimethylaminoethyloxy)phenyl]imidazolidine-2,4-dione,
Cpd 81 5-[4-(2-dimethylaminoethyloxy)phenyl]-5-[3-[4-(o-tolyl)piperazin-1-yl]-3-oxo-propyl]imidazolidine-2,4-dione,
Cpd 82 5-[4-(dimethylaminomethyl)phenyl]-5-[3-[4-(o-tolyl)piperazin-1-yl]-3-oxo-propyl]imidazolidine-2,4-dione,
Cpd 83 5-[3-[4-(3-chlorophenyl)piperazin-1-yl]-3-oxo-propyl]-5-[4-(dimethylaminomethyl)phenyl]imidazolidine-2,4-dione,
Cpd 84 5-[3-[4-(5-fluoro-3-pyridyl)piperazin-1-yl]-3-oxo-propyl]-5-methyl-imidazolidine-2,4-dione,
Cpd 85 5-[3-[4-(5-chloro-3-pyridyl)piperazin-1-yl]-3-oxo-propyl]-5-methyl-imidazolidine-2,4-dione,
Cpd 86 5-[3-[4-(5-bromo-3-pyridyl)piperazin-1-yl]-3-oxo-propyl]-5-methyl-imidazolidine-2,4-dione,
Cpd 87 5-[3-[4-(2,5-dimethylphenyl)piperazin-1-yl]-3-oxo-propyl]-5-(2-pyridyl)imidazolidine-2,4-dione,
Cpd 88 5-[3-[4-(2,5-dimethylphenyl)piperazin-1-yl]-3-oxo-propyl]-5-(3-pyridyl)imidazolidine-2,4-dione,
Cpd 89 5-cyclopropyl-5-[3-[4-(2,5-dimethylphenyl)piperazin-1-yl]-3-oxo-propyl]imidazolidine-2,4-dione,
Cpd 90 5-[3-[4-(3,4-difluorophenyl)piperazin-1-yl]-3-oxo-propyl]-5-(3-pyridyl)imidazolidine-2,4-dione,
Cpd 91 5-[3-[4-(3-chloro-4-fluoro-phenyl)piperazin-1-yl]-3-oxo-propyl]-5-(3-pyridyl)imidazolidine-2,4-dione,
Cpd 92 5-[3-[4-(5-fluoro-2-methyl-phenyl)piperazin-1-yl]-3-oxo-propyl]-5-(3-pyridyl)imidazolidine-2,4-dione,
Cpd 93 5-[3-[4-(4-chloro-5-fluoro-2-methyl-phenyl)piperazin-1-yl]-3-oxo-propyl]-5-methyl-imidazolidine-2,4-dione,
Cpd 94 5-[3-[4-(4,5-difluoro-2-methyl-phenyl)piperazin-1-yl]-3-oxo-propyl]-5-methyl-imidazolidine-2,4-dione,
Cpd 95 5-[3-[4-(3,4-difluorophenyl)piperazin-1-yl]-3-oxo-propyl]-5-(2-pyridyl)imidazolidine-2,4-dione,
Cpd 96 5-[3-[4-(3-chloro-4-fluoro-phenyl)piperazin-1-yl]-3-oxo-propyl]-5-(2-pyridyl)imidazolidine-2,4-dione,
Cpd 97 5-[3-[4-(3-fluoro-2-methyl-phenyl)piperazin-1-yl]-3-oxo-propyl]-5-(3-pyridyl)imidazolidine-2,4-dione,
Cpd 98 5-[3-[4-(3-chloro-2-methyl-phenyl)piperazin-1-yl]-3-oxo-propyl]-5-cyclopropyl-imidazolidine-2,4-dione,
Cpd 99 5-cyclopropyl-5-[3-[4-(3-fluoro-2-methyl-phenyl)piperazin-1-yl]-3-oxo-propyl]imidazolidine-2,4-dione,
Cpd 100 5-[3-[4-(3-fluoro-2-methyl-phenyl)piperazin-1-yl]-3-oxo-propyl]-5-(2-pyridyl)imidazolidine-2,4-dione,
Cpd 101 5-[3-[4-(2,3-dimethylphenyl)piperazin-1-yl]-3-oxo-propyl]-5-(2-pyridyl)imidazolidine-2,4-dione,
Cpd 102 5-[3-[4-(3-chloro-2-methyl-phenyl)piperazin-1-yl]-3-oxo-propyl]-5-(3-pyridyl)imidazolidine-2,4-dione,
Cpd 103 5-[3-[4-(3-fluorophenyl)piperazin-1-yl]-3-oxo-propyl]-5-(2-pyridyl)imidazolidine-2,4-dione,
Cpd 104 5-[3-[4-(5-fluoro-2-methyl-phenyl)piperazin-1-yl]-3-oxo-propyl]-5-(2-pyridyl)imidazolidine-2,4-dione, Cpd 105 5-[3-(3-methyl-4-phenyl-piperazin-1-yl)-3-oxo-propyl]-5-(3-pyridyl)imidazolidine-2,4-dione, Cpd 106 5-cyclopropyl-5-[3-(3-methyl-4-phenyl-piperazin-1-yl)-3-oxo-propyl]imidazolidine-2,4-dione, Cpd 107 5-tert-butyl-5-[3-[4-(3-chlorophenyl)piperazin-1-yl]-3-oxo-propyl]imidazolidine-2,4-dione, Cpd 108 5-tert-butyl-5-[3-[4-(5-chloro-2-methyl-phenyl)piperazin-1-yl]-3-oxo-propyl]imidazolidine-2,4-dione, Cpd 109 5-[3-[4-(3-chlorophenyl)piperazin-1-yl]-3-oxo-propyl]-5-cyclopentyl-imidazolidine-2,4-dione, Cpd 110 5-[3-[4-(5-chloro-2-methyl-phenyl)piperazin-1-yl]-3-oxo-propyl]-5-cyclopentyl-imidazolidine-2,4-dione, Cpd 111 5-[3-[4-(3,5-dichlorophenyl)piperazin-1-yl]-3-oxo-propyl]-5-(3-pyridyl)imidazolidine-2,4-dione, Cpd 112 5-[3-[4-(3-fluorophenyl)piperazin-1-yl]-3-oxo-propyl]-5-(3-pyridyl)imidazolidine-2,4-dione, Cpd 113 5-cyclopropyl-5-[3-[4-(3,4-difluorophenyl)piperazin-1-yl]-3-oxo-propyl]imidazolidine-2,4-dione, Cpd 114 5-[3-[4-(3-chloro-4-fluoro-phenyl)piperazin-1-yl]-3-oxo-propyl]-5-cyclopropyl-imidazolidine-2,4-dione, Cpd 115 5-cyclopropyl-5-[3-[4-(3-fluorophenyl)piperazin-1-yl]-3-oxo-propyl]imidazolidine-2,4-dione, Cpd 116 5-cyclopropyl-5-[3-[4-(5-fluoro-2-methyl-phenyl)piperazin-1-yl]-3-oxo-propyl]imidazolidine-2,4-dione, Cpd 117 5-[3-[4-(3-chloro-5-fluoro-phenyl)piperazin-1-yl]-3-oxo-propyl]-5-methyl-imidazolidine-2,4-dione, Cpd 118 5-[3-[4-(3-chlorophenyl)piperazin-1-yl]-3-oxo-propyl]-5-(dimethylaminomethyl)imidazolidine-2,4-dione, Cpd 119 5-(dimethylaminomethyl)-5-[3-[4-(o-tolyl)piperazin-1-yl]-3-oxo-propyl]imidazolidine-2,4-dione, Cpd 120 5-[3-[4-(5-chloro-2-methyl-phenyl)piperazin-1-yl]-3-oxo-propyl]-5-(dimethylaminomethyl)imidazolidine-2,4-dione, Cpd 121 5-[3-[4-(3-chlorophenyl)piperazin-1-yl]-2-methyl-3-oxo-propyl]-5-cyclopropyl-imidazolidine-2,4-dione, Cpd 122 5-[3-[4-(3-chlorophenyl)piperazin-1-yl]-3-oxo-propyl]-5-ethyl-imidazolidine-2,4-dione, Cpd 123 5-[3-[4-(3-chlorophenyl)piperazin-1-yl]-3-oxo-propyl]-5-(3-methoxyphenyl)imidazolidine-2,4-dione, Cpd 124 5-[3-[4-(3-chlorophenyl)piperazin-1-yl]-3-oxo-propyl]-5-(4-methylsulfonylphenyl)imidazolidine-2,4-dione, Cpd 125 4-[4-[3-[4-(3-chlorophenyl)piperazin-1-yl]-3-oxo-propyl]-2,5-dioxo-imidazolidin-4-yl]benzonitrile, Cpd 126 5-[3-[4-(4-chlorophenyl)-3-methyl-piperazin-1-yl]-3-oxo-propyl]-5-(3-pyridyl)imidazolidine-2,4-dione, Cpd 127 5-[3-[4-(3,5-dichlorophenyl)-3-methyl-piperazin-1-yl]-3-oxo-propyl]-5-(3-pyridyl)imidazolidine-2,4-dione, Cpd 128 5-cyclopropyl-5-[3-[(3R)-3-methyl-4-phenyl-piperazin-1-yl]-3-oxo-propyl]imidazolidine-2,4-dione, Cpd 129 5-cyclopropyl-5-[3-[4-(5-fluoro-2-methyl-phenyl)-3-methyl-piperazin-1-yl]-3-oxo-propyl]imidazolidine-2,4-dione, Cpd 130 5-cyclopropyl-5-[3-[4-(3,5-dichlorophenyl)-3-methyl-piperazin-1-yl]-3-oxo-propyl]imidazolidine-2,4-dione, Cpd 131 5-[3-[(3R)-3-methyl-4-phenyl-piperazin-1-yl]-3-oxo-propyl]-5-phenyl-imidazolidine-2,4-dione, Cpd 132 5-(5-chloro-2-methoxy-phenyl)-5-[3-[4-(3-chlorophenyl)piperazin-1-yl]-3-oxo-propyl]imidazolidine-2,4-dione, Cpd 133 5-(5-chloro-2-methoxy-phenyl)-5-[3-[4-(5-chloro-2-methyl-phenyl)piperazin-1-yl]-3-oxo-propyl]imidazolidine-2,4-dione, Cpd 134 5-[3-[(3R)-3-methyl-4-phenyl-piperazin-1-yl]-3-oxo-propyl]-5-(3-pyridyl)imidazolidine-2,4-dione, Cpd 135 5-cyclopropyl-5-[3-[(3S)-3-methyl-4-phenyl-piperazin-1-yl]-3-oxo-propyl]imidazolidine-2,4-dione, Cpd 136 5-[3-[(3S)-3-methyl-4-phenyl-piperazin-1-yl]-3-oxo-propyl]-5-(3-pyridyl)imidazolidine-2,4-dione, Cpd 137 5-[3-[(3S)-3-methyl-4-phenyl-piperazin-1-yl]-3-oxo-propyl]-5-phenyl-imidazolidine-2,4-dione, Cpd 138 5-cyclopropyl-5-[3-oxo-3-(4-phenylpiperazin-1-yl)propyl]imidazolidine-2,4-dione, Cpd 139 5-[3-[4-(3,5-dichloro-2-methyl-phenyl)piperazin-1-yl]-3-oxo-propyl]-5-methyl-imidazolidine-2,4-dione, Cpd 140 5-[3-[4-(3,5-difluorophenyl)piperazin-1-yl]-3-oxo-propyl]-5-methyl-imidazolidine-2,4-dione, Cpd 141 5-[3-[4-(3-chlorophenyl)piperazin-1-yl]-3-oxo-propyl]-5-(m-tolyl)imidazolidine-2,4-dione, Cpd 142 5-cyclopropyl-5-[3-[(3S)-4-(3,5-dichlorophenyl)-3-methyl-piperazin-1-yl]-3-oxo-propyl]imidazolidine-2,4-dione, Cpd 143 5-[3-[(3S)-4-(4-chlorophenyl)-3-methyl-piperazin-1-yl]-3-oxo-propyl]-5-methyl-imidazolidine-2,4-dione, Cpd 144 5-[3-[(3S)-4-(3,5-dichlorophenyl)-3-methyl-piperazin-1-yl]-3-oxo-propyl]-5-methyl-imidazolidine-2,4-dione, Cpd 145 5-[3-[(3S)-4-(5-fluoro-2-methyl-phenyl)-3-methyl-piperazin-1-yl]-3-oxo-propyl]-5-methyl-imidazolidine-2,4-dione, Cpd 146 5-[3-[4-(3-chlorophenyl)piperazin-1-yl]-3-oxo-propyl]-5-(2-methoxyphenyl)imidazolidine-2,4-dione, Cpd 147 5-[3-[(3S)-4-(4-chlorophenyl)-3-methyl-piperazin-1-yl]-3-oxo-propyl]-5-cyclopropyl-imidazolidine-2,4-dione, Cpd 148 5-cyclopropyl-5-[3-[(3S)-4-(5-fluoro-2-methyl-phenyl)-3-methyl-piperazin-1-yl]-3-oxo-propyl]imidazolidine-2,4-dione, Cpd 149 5-cyclopropyl-5-[3-[4-(3-fluorophenyl)-3-methyl-piperazin-1-yl]-3-oxo-propyl]imidazolidine-2,4-dione, Cpd 150 5-[3-[4-(3-chlorophenyl)-3-methyl-piperazin-1-yl]-3-oxo-propyl]-5-cyclopropyl-imidazolidine-2,4-dione, Cpd 151 5-cyclopropyl-5-[3-[(3S)-4-(3-fluorophenyl)-3-methyl-piperazin-1-yl]-3-oxo-propyl]imidazolidine-2,4-dione, Cpd 152 5-[3-[(3S)-4-(3-chlorophenyl)-3-methyl-piperazin-1-yl]-3-oxo-propyl]-5-cyclopropyl-imidazolidine-2,4-dione, Cpd 153 5-[3-[4-(3-chlorophenyl)piperazin-1-yl]-3-oxo-propyl]-5-(2-oxoindolin-5-yl)imidazolidine-2,4-dione, Cpd 154 5-[3-[4-(3-chlorophenyl)piperazin-1-yl]-3-oxo-propyl]-5-[[2-methoxyethyl(methyl)amino]methyl]imidazolidine-2,4-dione, Cpd 155 5-[3-[4-(3-chlorophenyl)piperazin-1-yl]-3-oxo-propyl]-5-(morpholinomethyl)imidazolidine-2,4-dione, Cpd 156 5-[3-[(3S)-4-(3,5-difluorophenyl)-3-methyl-piperazin-1-yl]-3-oxo-propyl]-5-methyl-imidazolidine-2,4-dione, Cpd 157 5-[3-[(3S)-4-(3-fluorophenyl)-3-methyl-piperazin-1-yl]-3-oxo-propyl]-5-methyl-imidazolidine-2,4-dione, Cpd 158 5-[3-[(3S)-4-(3-chlorophenyl)-3-methyl-piperazin-1-yl]-3-oxo-propyl]-5-methyl-imidazolidine-2,4-dione, Cpd 159 (5R)-5-[3-[4-(3,5-dichlorophenyl)piperazin-1-yl]-3-oxo-propyl]-5-methyl-imidazolidine-2,4-dione, Cpd 160 5-cyclopropyl-5-[3-[(3S)-4-(3,5-difluorophenyl)-3-methyl-piperazin-1-yl]-3-oxo-propyl]imidazolidine-2,4-dione, Cpd 161 5-cyclopropyl-5-[3-[(3S)-4-(3,4-difluorophenyl)-3-methyl-piperazin-1-yl]-3-oxo-propyl]imidazolidine-2,4-dione, Cpd 162 5-[3-[(3S)-4-(4-chloro-3-fluoro-phenyl)-3-methyl-piperazin-1-yl]-3-oxo-propyl]-5-cyclopropyl-imidazolidine-2,4-dione, Cpd 163 5-[3-[(3S)-4-(3-chloro-4-fluoro-phenyl)-3-methyl-piperazin-1-yl]-3-oxo-propyl]-5-cyclopropyl-imidazolidine-2,4-dione, Cpd 164 5-[3-[(3S)-4-(4-chloro-3-fluoro-phenyl)-3-methyl-piperazin-1-yl]-3-oxo-propyl]-5-methyl-imidazolidine-2,4-dione, Cpd 165 5-[3-[(3S)-4-(3,4-difluorophenyl)-3-methyl-piperazin-1-yl]-3-oxo-propyl]-5-methyl-imidazolidine-2,4-dione, Cpd 166 5-[3-[(3S)-4-(3-chloro-4-fluoro-phenyl)-3-methyl-piperazin-1-yl]-3-oxo-propyl]-5-methyl-imidazolidine-2,4-dione, Cpd 167 5-cyclopropyl-5-[3-[(3S)-4-(3,4-dichlorophenyl)-3-methyl-piperazin-1-yl]-3-oxo-propyl]imidazolidine-2,4-dione, Cpd 168 5-[3-[(3S)-4-(3,4-dichlorophenyl)-3-methyl-piperazin-1-yl]-3-oxo-propyl]-5-methyl-imidazolidine-2,4-dione, Cpd 169 5-[3-[(3S)-4-(3-chloro-5-fluoro-phenyl)-3-methyl-piperazin-1-yl]-3-oxo-propyl]-5-cyclopropyl-imidazolidine-2,4-dione, Cpd 170 5-[3-[(3S)-4-(3-chloro-5-fluoro-phenyl)-3-methyl-piperazin-1-yl]-3-oxo-propyl]-5-methyl-imidazolidine-2,4-dione, Cpd 171 5-(aminomethyl)-5-[3-[4-(3-chlorophenyl)piperazin-1-yl]-3-oxo-propyl]imidazolidine-2,4-dione, Cpd 172 5-cyclopropyl-5-[3-[4-(3,5-dichlorophenyl)piperazin-1-yl]-2-methyl-3-oxo-propyl]imidazolidine-2,4-dione, Cpd 173 (5S)-5-cyclopropyl-5-[3-[4-(3,5-dichlorophenyl)piperazin-1-yl]-3-oxo-propyl]imidazolidine-2,4-dione, Cpd 174 5-cyclopropyl-5-[3-[4-(5-fluoro-2-methyl-phenyl)piperazin-1-yl]-2-methyl-3-oxo-propyl]imidazolidine-2,4-dione, Cpd 175 5-[3-[4-(5-fluoro-2-methyl-phenyl)piperazin-1-yl]-2-methyl-3-oxo-propyl]-5-methyl-imidazolidine-2,4-dione, Cpd 176 5-[3-[4-(3-chloro-2-methyl-phenyl)piperazin-1-yl]-2-methyl-3-oxo-propyl]-5-cyclopropyl-imidazolidine-2,4-dione, Cpd 177 5-cyclopropyl-5-[3-[(3S)-4-(3,5-dichloro-2-methyl-phenyl)-3-methyl-piperazin-1-yl]-3-oxo-propyl]imidazolidine-2,4-dione, Cpd 178 5-[3-[(3S)-4-(3,5-dichloro-2-methyl-phenyl)-3-methyl-piperazin-1-yl]-3-oxo-propyl]-5-methyl-imidazolidine-2,4-dione, Cpd 179 5-[3-[4-(3-chloro-2-methyl-phenyl)piperazin-1-yl]-2-methyl-3-oxo-propyl]-5-methyl-imidazolidine-2,4-dione, Cpd 180 5-(aminomethyl)-5-[3-[4-(3,5-dichlorophenyl)piperazin-1-yl]-3-oxo-propyl]imidazolidine-2,4-dione, Cpd 181 5-[(benzylamino)methyl]-5-[3-[4-(3,5-dichlorophenyl)piperazin-1-yl]-3-oxo-propyl]imidazolidine-2,4-dione, Cpd 182 methyl 2-[4-[3-[4-(3,5-dichlorophenyl)piperazin-1-yl]-3-oxo-propyl]-2,5-dioxo-imidazolidin-4-yl]acetate, Cpd 183 2-[4-[3-[4-(3,5-dichlorophenyl)piperazin-1-yl]-3-oxo-propyl]-2,5-dioxo-imidazolidin-4-yl]acetic acid, Cpd 184 5-[(benzylamino)methyl]-5-[3-[4-(3-chlorophenyl)piperazin-1-yl]-3-oxo-propyl]imidazolidine-2,4-dione, Cpd 185 5-cyclopropyl-5-[3-[4-[2-(methylamino)phenyl]piperazin-1-yl]-3-oxo-propyl]imidazolidine-2,4-dione, Cpd 186 5-[3-[4-(3,5-dichlorophenyl)piperazin-1-yl]-3-oxo-propyl]-5-(methoxymethyl)imidazolidine-2,4-dione, Cpd 187 2-[4-[3-[4-(3,5-dichlorophenyl)piperazin-1-yl]-3-oxo-propyl]-2,5-dioxo-imidazolidin-4-yl]-N-(2-methoxyethyl)acetamide, Cpd 188 tert-butyl 2-[4-[3-[4-(3,5-dichlorophenyl)piperazin-1-yl]-3-oxo-propyl]-2,5-dioxo-imidazolidin-4-yl]acetate, Cpd 189 2-[4-[3-[4-(3,5-dichlorophenyl)piperazin-1-yl]-3-oxo-propyl]-2,5-dioxo-imidazolidin-4-yl]-N-(2-hydroxyethyl)acetamide, Cpd 190 5-cyclopropyl-5-[3-[(3S)-4-(3-fluorophenyl)-3-methyl-piperazin-1-yl]-2-methyl-3-oxo-propyl]imidazolidine-2,4-dione, Cpd 191 5-cyclopropyl-5-[3-[(3S)-4-(3,4-difluorophenyl)-3-methyl-piperazin-1-yl]-2-methyl-3-oxo-propyl]imidazolidine-2,4-dione, Cpd 192 5-[3-[(3S)-4-(3-chloro-4-fluoro-phenyl)-3-methyl-piperazin-1-yl]-2-methyl-3-oxo-propyl]-5-cyclopropyl-imidazolidine-2,4-dione, Cpd 193 5-[3-[(3S)-4-(4-chlorophenyl)-3-methyl-piperazin-1-yl]-2-methyl-3-oxo-propyl]-5-cyclopropyl-imidazolidine-2,4-dione, Cpd 194 5-[3-[(3S)-4-(3-chloro-5-fluoro-phenyl)-3-methyl-piperazin-1-yl]-2-methyl-3-oxo-propyl]-5-cyclopropyl-imidazolidine-2,4-dione, Cpd 195 3-[4-[3-(4-cyclopropyl-2,5-dioxo-imidazolidin-4-yl)propanoyl]piperazin-1-yl]benzonitrile, Cpd 196 5-(azetidin-3-yl)-5-[3-[4-(3,5-dichlorophenyl)piperazin-1-yl]-2-methyl-3-oxo-propyl]imidazolidine-2,4-dione, Cpd 197 5-[3-[4-(3,5-dichlorophenyl)piperazin-1-yl]-2-methyl-3-oxo-propyl]-5-(2-methylsulfanylethyl)imidazolidine-2,4-dione, Cpd 198 tert-butyl 4-[[4-[3-[4-(3,5-dichlorophenyl)piperazin-1-yl]-2-methyl-3-oxo-propyl]-2,5-dioxo-imidazolidin-4-yl]methyl]piperidine-1-carboxylate, Cpd 199 5-[3-[4-(3,5-dichlorophenyl)piperazin-1-yl]-2-methyl-3-oxo-propyl]-5-tetrahydropyran-4-yl-imidazolidine-2,4-dione, Cpd 200 5-[3-[4-(3,5-dichlorophenyl)piperazin-1-yl]-2-methyl-3-oxo-propyl]imidazolidine-2,4-dione, Cpd 201 5-cyclopropyl-5-[3-[4-(3,5-dichlorophenyl)piperazin-1-yl]-2-hydroxy-3-oxo-propyl]imidazolidine-2,4-dione, Cpd 202 5-[3-[(3S)-4-(4-chloro-5-fluoro-2-methyl-phenyl)-3-methyl-piperazin-1-yl]-3-oxo-propyl]-5-methyl-imidazolidine-2,4-dione, Cpd 203 (5S)-5-cyclopropyl-5-[3-[(3S)-4-(3-fluorophenyl)-3-methyl-piperazin-1-yl]-3-oxo-propyl]imidazolidine-2,4-dione, Cpd 204 (5S)-5-cyclopropyl-5-[3-[(3S)-4-(3,5-dichlorophenyl)-3-methyl-piperazin-1-yl]-3-oxo-propyl]imidazolidine-2,4-dione, Cpd 205 (5S)-5-cyclopropyl-5-[3-[(3S)-4-(3,4-difluorophenyl)-3-methyl-piperazin-1-yl]-3-oxo-propyl]imidazolidine-2,4-dione, Cpd 206 5-cyclopropyl-5-[3-[4-(3,5-dichlorophenyl)piperazin-1-yl]-2-methoxy-3-oxo-propyl]imidazolidine-2,4-dione, Cpd 207 (5S)-5-cyclopropyl-5-[3-[(3S)-4-(3,4-dichlorophenyl)-3-methyl-piperazin-1-yl]-3-oxo-propyl]imidazolidine-2,4-dione, Cpd 208 5-[3-[4-(3,5-dichlorophenyl)piperazin-1-yl]-2-methyl-3-oxo-propyl]-5-(4-piperidylmethyl)imidazolidine-2,4-dione, Cpd 209 5-cyclopropyl-5-[3-[4-[3-(dimethylamino)phenyl]piperazin-1-yl]-3-oxo-propyl]imidazolidine-2,4-dione, Cpd 210 5-(2-aminoethyl)-5-[3-[4-(3,5-dichlorophenyl)piperazin-1-yl]-2-methyl-3-oxo-propyl]imidazolidine-2,4-dione, Cpd 211 5-[3-[4-(3,4-difluorophenyl)piperazin-1-yl]-2-methyl-3-oxo-propyl]-5-methyl-imidazolidine-2,4-dione, Cpd 212 (5S)-5-cyclopropyl-5-[(2S)-3-[(3S)-4-(3,4-difluorophenyl)-3-methyl-piperazin-1-yl]-2-methyl-3-oxo-propyl]imidazolidine-2,4-dione, Cpd 213 5-[3-[(3S)-4-(3,5-difluorophenyl)-3-methyl-piperazin-1-yl]-2-methyl-3-oxo-propyl]-5-methyl-imidazolidine-2,4-dione, Cpd 214 5-[3-[(3S)-4-(3-chlorophenyl)-3-methyl-piperazin-1-yl]-2-methyl-3-oxo-propyl]-5-methyl-imidazolidine-2,4-dione, Cpd 215 5-[3-[(3S)-4-(3-fluorophenyl)-3-methyl-piperazin-1-yl]-2-methyl-3-oxo-propyl]-5-methyl-imidazolidine-2,4-dione, Cpd 216 5-[3-[(3S)-4-(5-fluoro-2-methyl-phenyl)-3-methyl-piperazin-1-yl]-2-methyl-3-oxo-propyl]-5-methyl-imidazolidine-2,4-dione, Cpd 217 5-methyl-5-[2-methyl-3-[(3S)-3-methyl-4-phenyl-piperazin-1-yl]-3-oxo-propyl]imidazolidine-2,4-dione, Cpd 218 5-[3-[4-(3,5-dichlorophenyl)piperazin-1-yl]-2-methyl-3-oxo-propyl]-5-(2-methylsulfonylethyl)imidazolidine-2,4-dione, Cpd 219 5-[3-[4-(3,5-dichlorophenyl)piperazin-1-yl]-2-methyl-3-oxo-propyl]imidazolidine-2,4-dione, Cpd 220 5-[3-[4-(3,5-dichlorophenyl)piperazin-1-yl]-2-(hydroxymethyl)-3-oxo-propyl]-5-methyl-imidazolidine-2,4-dione, Cpd 221 5-[3-[(3S)-4-(3,5-dichlorophenyl)-3-methyl-piperazin-1-yl]-2-methyl-3-oxo-propyl]-5-(2-methoxyethoxymethyl)imidazolidine-2,4-dione, Cpd 222 5-[3-[4-(3,5-dichlorophenyl)piperazin-1-yl]-2-methyl-3-oxo-propyl]-5-(methoxymethyl)imidazolidine-2,4-dione, Cpd 223 N-[[4-[3-[4-(3,5-dichlorophenyl)piperazin-1-yl]-3-oxo-propyl]-2,5-dioxo-imidazolidin-4-yl]methyl]acetamide, Cpd 224 5-[3-[4-(3,4-difluorophenyl)piperazin-1-yl]-2-methyl-3-oxo-propyl]-5-(methoxymethyl)imidazolidine-2,4-dione, Cpd 225 5-[3-[(3S)-4-(3,5-difluorophenyl)-3-methyl-piperazin-1-yl]-2-methyl-3-oxo-propyl]-5-(methoxymethyl)imidazolidine-2,4-dione, Cpd 226 5-[3-[(S)-4-(3,4-difluorophenyl)-3-methyl-piperazin-1-yl]-2-methyl-3-oxo-propyl]-5-(methoxymethyl)imidazolidine-2,4-dione, Cpd 227 5-[3-[(3S)-4-(3,5-dichloro-2-methyl-phenyl)-3-methyl-piperazin-1-yl]-2-methyl-3-oxo-propyl]-5-(methoxymethyl)imidazolidine-2,4-dione, Cpd 228 5-[3-[(3S)-4-(5-fluoro-2-methyl-phenyl)-3-methyl-piperazin-1-yl]-2-methyl-3-oxo-propyl]-5-(methoxymethyl)imidazolidine-2,4-dione, Cpd 229 5-[3-[(3S)-4-(3-fluorophenyl)-3-methyl-piperazin-1-yl]-2-methyl-3-oxo-propyl]-5-(methoxymethyl)imidazolidine-2,4-dione, Cpd 230 5-[3-[4-(5-fluoro-2-methyl-phenyl)piperazin-1-yl]-2-methyl-3-oxo-propyl]-5-(methoxymethyl)imidazolidine-2,4-dione, Cpd 231 5-[3-[4-(3,5-dichlorophenyl)piperazin-1-yl]-2-methyl-3-oxo-propyl]-5-(2-pyridyl)imidazolidine-2,4-dione, Cpd 232 5-[3-[(3S)-4-(3-chloro-2-methyl-phenyl)-3-methyl-piperazin-1-yl]-2-methyl-3-oxo-propyl]-5-(methoxymethyl)imidazolidine-2,4-dione, Cpd 233 5-[3-[(3S)-4-(3-chlorophenyl)-3-methyl-piperazin-1-yl]-2-methyl-3-oxo-propyl]-5-(methoxymethyl)imidazolidine-2,4-dione, Cpd 234 tert-butyl 3-[4-[3-[4-(3,4-difluorophenyl)piperazin-1-yl]-2-methyl-3-oxo-propyl]-2,5-dioxo-imidazolidin-4-yl]azetidine-1-carboxylate, Cpd 235 tert-butyl N-[2-[4-[3-[4-(3,4-difluorophenyl)piperazin-1-yl]-2-methyl-3-oxo-propyl]-2,5-dioxo-imidazolidin-4-yl]ethyl]carbamate, Cpd 236 5-[2-[4-(3,5-dichlorophenyl)piperazine-1-carbonyl]butyl]-5-methyl-imidazolidine-2,4-dione, Cpd 237 5-[3-[(3S)-4-(3-chloro-2-methyl-phenyl)-3-methyl-piperazin-1-yl]-2-methyl-3-oxo-propyl]-5-methyl-imidazolidine-2,4-dione, Cpd 238 5-[3-[4-(3,5-dichlorophenyl)piperazin-1-yl]-2-[(2,5-dimethylpyrazol-3-yl)methyl]-3-oxo-propyl]-5-methyl-imidazolidine-2,4-dione, Cpd 239 tert-butyl 3-[4-[3-[(3S)-4-(3,4-difluorophenyl)-3-methyl-piperazin-1-yl]-2-methyl-3-oxo-propyl]-2,5-dioxo-imidazolidin-4-yl]azetidine-1-carboxylate, Cpd 240 5-(azetidin-3-yl)-5-[3-[4-(3,4-difluorophenyl)piperazin-1-yl]-2-methyl-3-oxo-propyl]imidazolidine-2,4-dione, Cpd 241 5-(2-aminoethyl)-5-[3-[4-(3,4-difluorophenyl)piperazin-1-yl]-2-methyl-3-oxo-propyl]imidazolidine-2,4-dione, Cpd 242 5-[3-[4-(3,5-dichlorophenyl)piperazin-1-yl]-2-methyl-3-oxo-propyl]-5-(morpholinomethyl)imidazolidine-2,4-dione, Cpd 243 5-[3-[(3R,5S)-4-(3,5-dichlorophenyl)-3,5-dimethyl-piperazin-1-yl]-2-methyl-3-oxo-propyl]-5-methyl-imidazolidine-2,4-dione, Cpd 244 5-[3-[(3R,5S)-4-(3,5-dichlorophenyl)-3,5-dimethyl-piperazin-1-yl]-2-methyl-3-oxo-propyl]-5-(methoxymethyl)imidazolidine-2,4-dione, Cpd 245 5-[3-[(3S)-4-(3-chloro-4-fluoro-phenyl)-3-methyl-piperazin-1-yl]-2-methyl-3-oxo-propyl]-5-(2-pyridyl)imidazolidine-2,4-dione, Cpd 246 5-[3-[(3S)-4-(3,5-dichlorophenyl)-3-methyl-piperazin-1-yl]-2-methyl-3-oxo-propyl]-5-(morpholinomethyl)imidazolidine-2,4-dione, Cpd 247 5-(azetidin-3-yl)-5-[3-[(3S)-4-(3,4-difluorophenyl)-3-methyl-piperazin-1-yl]-2-methyl-3-oxo-propyl]imidazolidine-2,4-dione, Cpd 248 5-(1-acetylazetidin-3-yl)-5-[3-[4-(3,4-difluorophenyl)piperazin-1-yl]-2-methyl-3-oxo-propyl]imidazolidine-2,4-dione, Cpd 249 5-(1-acetylazetidin-3-yl)-5-[3-[(3S)-4-(3,4-difluorophenyl)-3-methyl-piperazin-1-yl]-2-methyl-3-oxo-propyl]imidazolidine-2,4-dione, Cpd 250 5-[3-[4-(4,5-dichloro-2-methyl-phenyl)piperazin-1-yl]-3-oxo-propyl]-5-methyl-imidazolidine-2,4-dione, Cpd 251 5-[3-[(3S)-4-(3,4-difluorophenyl)-3-methyl-piperazin-1-yl]-2-methyl-3-oxo-propyl]imidazolidine-2,4-dione, Cpd 252 5-[3-[4-(3,5-dichlorophenyl)piperazin-1-yl]-2-methyl-3-oxo-propyl]-5-[(3,3-difluoropyrrolidin-1-yl)methyl]imidazolidine-2,4-dione, Cpd 253 5-[3-[(3S)-4-(3-chloro-4-fluoro-phenyl)-3-methyl-piperazin-1-yl]-2-methyl-3-oxo-propyl]-5-[(3,3-difluoropyrrolidin-1-yl)methyl]imidazolidine-2,4-dione, Cpd 254 4-[4-(3,5-dichlorophenyl)piperazin-1-yl]-3-[(4-methyl-2,5-dioxo-imidazolidin-4-yl)methyl]-4-oxo-butanenitrile, Cpd 255 (5S)-cyclopropyl-5-[3-[(3S)-4-(3,5-difluorophenyl)-3-methyl-piperazin-1-yl]-3-oxo-propyl]imidazolidine-2,4-dione, Cpd 25 6 5-[3-[(3S)-4-(6-chloropyrimidin-4-yl)-3-methyl-piperazin-1-yl]-3-oxo-propyl]-5-cyclopropyl-imidazolidine-2,4-dione, Cpd 257 5-cyclopropyl-5-[3-[(3S)-4-(4,6-dichloro-2-pyridyl)-3-methyl-piperazin-1-yl]-3-oxo-propyl]imidazolidine-2,4-dione, Cpd 258 5-cyclopropyl-5-[3-[(3S)-4-(2,6-dichloro-4-pyridyl)-3-methyl-piperazin-1-yl]-3-oxo-propyl]imidazolidine-2,4-dione, Cpd 259 5-cyclopropyl-5-[3-[(3S)-3-methyl-4-(3-pyridyl)piperazin-1-yl]-3-oxo-propyl]imidazolidine-2,4-dione, Cpd 260 5-[3-[(3S)-4-(5-chloro-3-pyridyl)-3-methyl-piperazin-1-yl]-3-oxo-propyl]-5-cyclopropyl-imidazolidine-2,4-dione, Cpd 261 5-cyclopropyl-5-[3-[(3S)-4-(5-fluoro-3-pyridyl)-3-methyl-piperazin-1-yl]-3-oxo-propyl]imidazolidine-2,4-dione, Cpd 262 5-[3-[(3S)-4-(4,5-dichloro-2-methyl-phenyl)-3-methyl-piperazin-1-yl]-3-oxo-propyl]-5-methyl-imidazolidine-2,4-dione, Cpd 263 5-[3-[(3S)-4-(3-fluorophenyl)-3-methyl-piperazin-1-yl]-2-methyl-3-oxo-propyl]-5-(2-pyridyl)imidazolidine-2,4-dione, Cpd 264 5-[3-[(3S)-4-(3,4-difluorophenyl)-3-methyl-piperazin-1-yl]-2-methyl-3-oxo-propyl]-5-(2-pyridyl)imidazolidine-2,4-dione, Cpd 265 (5R)-5-[(2S)-3-[(3S)-4-(3-chloro-4-fluoro-phenyl)-3-methyl-piperazin-1-yl]-2-methyl-3-oxo-propyl]-5-methyl-imidazolidine-2,4-dione, Cpd 266 5-ethyl-5-[3-[(3S)-4-(3-fluorophenyl)-3-methyl-piperazin-1-yl]-2-methyl-3-oxo-propyl]imidazolidine-2,4-dione, Cpd 267 5-[3-[4-(4-chloro-2-fluoro-5-methyl-phenyl)piperazin-1-yl]-3-oxo-propyl]-5-methyl-imidazolidine-2,4-dione, Cpd 268 5-[3-[(3S)-4-(3-fluorophenyl)-3-methyl-piperazin-1-yl]-2-(hydroxymethyl)-3-oxo-propyl]-5-methyl-imidazolidine-2,4-dione, Cpd 269 5-[3-[(3S)-4-(3-chlorophenyl)-3-methyl-piperazin-1-yl]-2-methyl-3-oxo-propyl]-5-(2-pyridyl)imidazolidine-2,4-dione, Cpd 270 5-[3-[(3S)-4-(3-bromophenyl)-3-methyl-piperazin-1-yl]-3-oxo-propyl]-5-cyclopropyl-imidazolidine-2,4-dione, Cpd 271 5-[3-[(3S,5S)-4-(3,5-dichlorophenyl)-3,5-dimethyl-piperazin-1-yl]-2-methyl-3-oxo-propyl]-5-methyl-imidazolidine-2,4-dione, Cpd 272 5-[3-[(3S,5S)-4-(3,5-dichlorophenyl)-3,5-dimethyl-piperazin-1-yl]-2-methyl-3-oxo-propyl]-5-(methoxymethyl)imidazolidine-2,4-dione, Cpd 273 5-cyclopropyl-5-[3-[(3S)-3-methyl-4-[3-(3-pyridyl)phenyl]piperazin-1-yl]-3-oxo-propyl]imidazolidine-2,4-dione, Cpd 274 5-cyclopropyl-5-[3-[(3S)-4-(1H-indol-5-yl)-3-methyl-piperazin-1-yl]-3-oxo-propyl]imidazolidine-2,4-dione, Cpd 275 5-methyl-5-[2-methyl-3-[(3S)-3-methyl-4-(3-pyridyl)piperazin-1-yl]-3-oxo-propyl]imidazolidine-2,4-dione, Cpd 276 5-[3-[(3S)-4-(5-chloro-3-pyridyl)-3-methyl-piperazin-1-yl]-2-methyl-3-oxo-propyl]-5-methyl-imidazolidine-2,4-dione, Cpd 277 5-[3-[(3S)-4-(5-fluoro-3-pyridyl)-3-methyl-piperazin-1-yl]-2-methyl-3-oxo-propyl]-5-methyl-imidazolidine-2,4-dione, Cpd 278 5-cyclopropyl-5-[3-oxo-3-[4-(4-pyridyl)piperazin-1-yl]propyl]imidazolidine-2,4-dione, Cpd 279 5-[3-[4-(4-chloro-3,5-difluoro-phenyl)piperazin-1-yl]-2-methyl-3-oxo-propyl]-5-(methoxymethyl)imidazolidine-2,4-dione, Cpd 280 5-[3-[(3S)-4-(benzofuran-7-yl)-3-methyl-piperazin-1-yl]-3-oxo-propyl]-5-cyclopropyl-imidazolidine-2,4-dione, Cpd 281 5-cyclopropyl-5-[3-[(3S)-3-methyl-4-[3-(4-pyridyl)phenyl]piperazin-1-yl]-3-oxo-propyl]imidazolidine-2,4-dione, Cpd 282 5-cyclopropyl-5-[3-[(3S)-3-methyl-4-[3-(1H-pyrazol-4-yl)phenyl]piperazin-1-yl]-3-oxo-propyl]imidazolidine-2,4-dione, Cpd 283 5-cyclopropyl-5-[3-[(3S)-3-methyl-4-[3-(1-methylpyrazol-4-yl)phenyl]piperazin-1-yl]-3-oxo-propyl]imidazolidine-2,4-dione, Cpd 284 5-[3-[(3S)-4-(4-chloropyrimidin-2-yl)-3-methyl-piperazin-1-yl]-3-oxo-propyl]-5-cyclopropyl-imidazolidine-2,4-dione, Cpd 285 5-[3-[(3S)-4-(6-chloropyridazin-3-yl)-3-methyl-piperazin-1-yl]-3-oxo-propyl]-5-cyclopropyl-imidazolidine-2,4-dione, Cpd 286 5-cyclopropyl-5-[3-[(3S)-3-methyl-4-pyrazin-2-yl-piperazin-1-yl]-3-oxo-propyl]imidazolidine-2,4-dione, Cpd 287 5-[3-[(3S)-4-(3-chloro-4-fluoro-phenyl)-3-methyl-piperazin-1-yl]-3-oxo-propyl]-5-(6-methyl-3-pyridyl)imidazolidine-2,4-dione, Cpd 288 5-[3-[(3S)-4-(3-chloro-4-fluoro-phenyl)-3-methyl-piperazin-1-yl]-3-oxo-propyl]-5-(4-pyridyl)imidazolidine-2,4-dione, Cpd 289 5-cyclopropyl-5-[3-[(3S)-3-methyl-4-(3-quinolyl)piperazin-1-yl]-3-oxo-propyl]imidazolidine-2,4-dione, Cpd 290 5-cyclopropyl-5-[3-[(3S)-3-methyl-4-(1-methylindol-5-yl)piperazin-1-yl]-3-oxo-propyl]imidazolidine-2,4-dione, Cpd 291 5-cyclopropyl-5-[3-[(3S)-3-methyl-4-(1-methylindol-6-yl)piperazin-1-yl]-3-oxo-propyl]imidazolidine-2,4-dione, Cpd 292 5-[3-[(3S)-4-(3-fluorophenyl)-3-methyl-piperazin-1-yl]-2-(methoxymethyl)-3-oxo-propyl]-5-methyl-imidazolidine-2,4-dione, Cpd 293 5-[3-[4-(3-chloro-5-fluoro-2-methyl-phenyl)piperazin-1-yl]-3-oxo-propyl]-5-methyl-imidazolidine-2,4-dione, Cpd 294 5-[3-[(3S)-4-(3-fluorophenyl)-3-methyl-piperazin-1-yl]-2-methoxy-3-oxo-propyl]-5-methyl-imidazolidine-2,4-dione, Cpd 295 5-[3-[(3S)-4-(3-chloro-5-fluoro-phenyl)-3-methyl-piperazin-1-yl]-2-methoxy-3-oxo-propyl]-5-methyl-imidazolidine-2,4-dione, Cpd 296 5-cyclopropyl-5-[3-[(3S)-4-(1H-indazol-5-yl)-3-methyl-piperazin-1-yl]-3-oxo-propyl]imidazolidine-2,4-dione, Cpd 297 5-cyclopropyl-5-[3-[(3S)-3-methyl-4-(1-methylindazol-5-yl)piperazin-1-yl]-3-oxo-propyl]imidazolidine-2,4-dione, Cpd 298 5-cyclopropyl-5-[3-[(3S)-4-(4-fluoro-3-methyl-phenyl)-3-methyl-piperazin-1-yl]-3-oxo-propyl]imidazolidine-2,4-dione, Cpd 299 5-cyclopropyl-5-[3-[(3S)-4-(3-fluoro-4-methyl-phenyl)-3-methyl-piperazin-1-yl]-3-oxo-propyl]imidazolidine-2,4-dione, Cpd 300 5-cyclopropyl-5-[3-[(3S)-4-(4-fluorophenyl)-3-methyl-piperazin-1-yl]-3-oxo-propyl]imidazolidine-2,4-dione, Cpd 301 5-[3-[(3S)-4-(2-chloropyrimidin-4-yl)-3-methyl-piperazin-1-yl]-3-oxo-propyl]-5-cyclopropyl-imidazolidine-2,4-dione, Cpd 302 5-cyclopropyl-5-[3-[(3S)-3-methyl-4-pyridazin-3-yl-piperazin-1-yl]-3-oxo-propyl]imidazolidine-2,4-dione, Cpd 303 5-cyclopropyl-5-[3-[(3S)-3-methyl-4-(5-methyl-3-pyridyl)piperazin-1-yl]-3-oxo-propyl]imidazolidine-2,4-dione, Cpd 304 5-cyclopropyl-5-[3-[(3S)-3-methyl-4-pyrimidin-5-yl-piperazin-1-yl]-3-oxo-propyl]imidazolidine-2,4-dione, Cpd 305 5-[3-[(3S)-4-(1,3-benzothiazol-6-yl)-3-methyl-piperazin-1-yl]-3-oxo-propyl]-5-cyclopropyl-imidazolidine-2,4-dione, Cpd 306 5-[3-[(3S)-4-(3-chloro-4-methyl-phenyl)-3-methyl-piperazin-1-yl]-3-oxo-propyl]-5-cyclopropyl-imidazolidine-2,4-dione, Cpd 307 5-[3-[(3S)-4-(3-chloro-5-fluoro-phenyl)-3-methyl-piperazin-1-yl]-3-oxo-propyl]-5-(6-methyl-2-pyridyl)imidazolidine-2,4-dione, Cpd 308 5-[3-[(3S)-4-(3-fluorophenyl)-3-methyl-piperazin-1-yl]-3-oxo-propyl]-5-(6-methyl-2-pyridyl)imidazolidine-2,4-dione, Cpd 309 5-[3-[(3S)-4-(3,5-difluorophenyl)-3-methyl-piperazin-1-yl]-3-oxo-propyl]-5-(6-methyl-2-pyridyl)imidazolidine-2,4-dione, Cpd 310 5-[3-[(3S)-4-(3,5-dichlorophenyl)-3-methyl-piperazin-1-yl]-3-oxo-propyl]-5-(6-methyl-2-pyridyl)imidazolidine-2,4-dione, Cpd 311 5-[3-[(3S)-4-(3-chlorophenyl)-3-methyl-piperazin-1-yl]-3-oxo-propyl]-5-(6-methyl-2-pyridyl)imidazolidine-2,4-dione, Cpd 312 5-[3-[(3S)-4-(4-chlorophenyl)-3-methyl-piperazin-1-yl]-3-oxo-propyl]-5-(6-methyl-2-pyridyl)imidazolidine-2,4-dione, Cpd 313 5-cyclopropyl-5-[3-[(3S)-4-(5-fluoro-3-pyridyl)-3-methyl-piperazin-1-yl]-2-methyl-3-oxo-propyl]imidazolidine-2,4-dione, Cpd 314 5-[3-[(3S)-4-(5-chloro-3-pyridyl)-3-methyl-piperazin-1-yl]-2-methyl-3-oxo-propyl]-5-cyclopropyl-imidazolidine-2,4-dione, Cpd 315 5-[3-[(3S)-4-(4-chloro-3-fluoro-phenyl)-3-methyl-piperazin-1-yl]-3-oxo-propyl]-5-(3-pyridyl)imidazolidine-2,4-dione, Cpd 316 5-[3-[(3S)-4-(3-chloro-4-fluoro-phenyl)-3-methyl-piperazin-1-yl]-3-oxo-propyl]-5-(3-pyridyl)imidazolidine-2,4-dione, Cpd 317 5-[3-[(3S)-4-(3-chloro-5-fluoro-phenyl)-3-methyl-piperazin-1-yl]-3-oxo-propyl]-5-(3-pyridyl)imidazolidine-2,4-dione, Cpd 318 5-[3-[(3S)-4-(3,5-dichlorophenyl)-3-methyl-piperazin-1-yl]-3-oxo-propyl]-5-(3-pyridyl)imidazolidine-2,4-dione, Cpd 319 5-[3-[(3S)-4-(3-fluorophenyl)-3-methyl-piperazin-1-yl]-3-oxo-propyl]-5-(3-pyridyl)imidazolidine-2,4-dione, Cpd 320 5-[3-[(3S)-4-(3,5-difluorophenyl)-3-methyl-piperazin-1-yl]-3-oxo-propyl]-5-(3-pyridyl)imidazolidine-2,4-dione, Cpd 321 5-cyclopropyl-5-[3-[(3S)-4-[3-(2-methoxy-4-pyridyl)phenyl]-3-methyl-piperazin-1-yl]-3-oxo-propyl]imidazolidine-2,4-dione, Cpd 322 5-[3-[(3S)-4-[3-(5-chloro-3-pyridyl)phenyl]-3-methyl-piperazin-1-yl]-3-oxo-propyl]-5-cyclopropyl-imidazolidine-2,4-dione, Cpd 323 5-cyclopropyl-5-[3-[(3S)-3-methyl-4-[3-(2-methyl-3-pyridyl)phenyl]piperazin-1-yl]-3-oxo-propyl]imidazolidine-2,4-dione, Cpd 324 5-cyclopropyl-5-[3-[(3S)-3-methyl-4-[3-(6-methyl-3-pyridyl)phenyl]piperazin-1-yl]-3-oxo-propyl]imidazolidine-2,4-dione, Cpd 325 5-[3-[(3S)-4-(4-chloro-2-pyridyl)-3-methyl-piperazin-1-yl]-3-oxo-propyl]-5-cyclopropyl-imidazolidine-2,4-dione, Cpd 326 5-[3-[(3S)-4-(3-chloro-5-fluoro-phenyl)-3-methyl-piperazin-1-yl]-3-oxo-propyl]-5-pyrazin-2-yl-imidazolidine-2,4-dione, Cpd 327 5-[3-[(3S)-4-(3,5-difluorophenyl)-3-methyl-piperazin-1-yl]-3-oxo-propyl]-5-pyrazin-2-yl-imidazolidine-2,4-dione, Cpd 328 5-cyclopropyl-5-[3-[(3S)-3-methyl-4-(1-methylindol-4-yl)piperazin-1-yl]-3-oxo-propyl]imidazolidine-2,4-dione, Cpd 329 5-cyclopropyl-5-[3-[(3S)-3-methyl-4-[3-(2-methyl-4-pyridyl)phenyl]piperazin-1-yl]-3-oxo-propyl]imidazolidine-2,4-dione, Cpd 330 5-[(2S)-4-[3-(4-cyclopropyl-2,5-dioxo-imidazolidin-4-yl)propanoyl]-2-methyl-piperazin-1-yl]pyridine-3-carbonitrile, Cpd 331 (S)-5-((S)-3-((S)-4-(3-chloro-4-fluorophenyl)-3-methylpiperazin-1-yl)-2-methyl-3-oxopropyl)-5-(methoxymethyl)imidazolidine-2,4-dione, Cpd 332 5-[3-[(3S)-4-(3,5-difluorophenyl)-3-methyl-piperazin-1-yl]-3-oxo-propyl]-5-pyrimidin-5-yl-imidazolidine-2,4-dione, Cpd 333 5-cyclopropyl-5-[3-[(3S)-3-methyl-4-(1-methylindazol-4-yl)piperazin-1-yl]-3-oxo-propyl]imidazolidine-2,4-dione, Cpd 334 3-[(2S)-4-[3-(4-cyclopropyl-2,5-dioxo-imidazolidin-4-yl)propanoyl]-2-methyl-piperazin-1-yl]-5-fluoro-benzonitrile, Cpd 335 5-[3-[(3S)-4-(3,5-difluorophenyl)-3-methyl-piperazin-1-yl]-3-oxo-propyl]-5-[6-(trifluoromethyl)-3-pyridyl]imidazolidine-2,4-dione, Cpd 336 5-[3-[(3S)-4-(3,5-difluorophenyl)-3-methyl-piperazin-1-yl]-3-oxo-propyl]-5-(6-methoxy-2-pyridyl)imidazolidine-2,4-dione, Cpd 337 5-cyclopropyl-5-[3-[(3S)-3-methyl-4-(1-methylpyrrolo[3,2-b]pyridin-6-yl)piperazin-1-yl]-3-oxo-propyl]imidazolidine-2,4-dione, Cpd 338 5-cyclopropyl-5-[3-[(3S)-4-[3-fluoro-5-(1H-pyrazol-4-yl)phenyl]-3-methyl-piperazin-1-yl]-3-oxo-propyl]imidazolidine-2,4-dione, Cpd 339 5-cyclopropyl-5-[(2S)-2-methyl-3-[(3S)-3-methyl-4-[3-(1H-pyrazol-4-yl)phenyl]piperazin-1-yl]-3-oxo-propyl]imidazolidine-2,4-dione, Cpd 340 5-cyclopropyl-5-[3-[(3S)-4-[4-fluoro-3-(1H-pyrazol-4-yl)phenyl]-3-methyl-piperazin-1-yl]-3-oxo-propyl]imidazolidine-2,4-dione, Cpd 341 5-cyclopropyl-5-[3-[(3S)-3-methyl-4-(1-methylindazol-6-yl)piperazin-1-yl]-3-oxo-propyl]imidazolidine-2,4-dione, Cpd 342 5-cyclopropyl-5-[2-methyl-3-[(3S)-3-methyl-4-(5-methyl-3-pyridyl)piperazin-1-yl]-3-oxo-propyl]imidazolidine-2,4-dione, Cpd 343 5-cyclopropyl-5-[3-[(3S)-4-(4-fluorophenyl)-3-methyl-piperazin-1-yl]-2-methyl-3-oxo-propyl]imidazolidine-2,4-dione, Cpd 344 5-cyclopropyl-5-[3-[(3S)-3-methyl-4-(5-methyl-1,2,4-oxadiazol-3-yl)piperazin-1-yl]-3-oxo-propyl]imidazolidine-2,4-dione, Cpd 345 5-[3-[(3S)-4-(3-fluorophenyl)-3-methyl-piperazin-1-yl]-3-oxo-propyl]-5-(2-pyridyl)imidazolidine-2,4-dione, Cpd 346 5-[3-[(3S)-4-(3-chloro-5-fluoro-phenyl)-3-methyl-piperazin-1-yl]-3-oxo-propyl]-5-(2-pyridyl)imidazolidine-2,4-dione, Cpd 347 5-[3-[(3S)-4-(3,4-dichlorophenyl)-3-methyl-piperazin-1-yl]-3-oxo-propyl]-5-(2-pyridyl)imidazolidine-2,4-dione, Cpd 348 5-[3-[(3S)-4-(3,5-difluorophenyl)-3-methyl-piperazin-1-yl]-3-oxo-propyl]-5-(2-pyridyl)imidazolidine-2,4-dione, Cpd 349 5-[3-[(3S)-4-(3-chloro-4-fluoro-phenyl)-3-methyl-piperazin-1-yl]-3-oxo-propyl]-5-pyrazin-2-yl-imidazolidine-2,4-dione, Cpd 350 5-[3-[(3S)-4-(3-fluorophenyl)-3-methyl-piperazin-1-yl]-3-oxo-propyl]-5-pyrazin-2-yl-imidazolidine-2,4-dione, Cpd 351 5-cyclopropyl-5-[2-methyl-3-[(3S)-3-methyl-4-(3-pyridyl)piperazin-1-yl]-3-oxo-propyl]imidazolidine-2,4-dione, Cpd 352 5-cyclopropyl-5-[3-[(3S)-3-methyl-4-(3-methyl-1,2,4-oxadiazol-5-yl)piperazin-1-yl]-3-oxo-propyl]imidazolidine-2,4-dione, Cpd 353 5-cyclopropyl-5-[3-[(3S)-4-[3-(3,5-dimethyl-1H-pyrazol-4-yl)phenyl]-3-methyl-piperazin-1-yl]-3-oxo-propyl]imidazolidine-2,4-dione, Cpd 354 5-[3-[(3S)-4-(3,5-difluorophenyl)-3-methyl-piperazin-1-yl]-3-oxo-propyl]-5-(2-methyl-1H-imidazol-4-yl)imidazolidine-2,4-dione, Cpd 355 5-cyclopropyl-5-[3-[(3S)-3-methyl-4-[3-(3-methyl-1H-pyrazol-4-yl)phenyl]piperazin-1-yl]-3-oxo-propyl]imidazolidine-2,4-dione, Cpd 356 5-[3-[(3S)-4-(3,5-difluorophenyl)-3-methyl-piperazin-1-yl]-3-oxo-propyl]-5-(6-methoxy-3-pyridyl)imidazolidine-2,4-dione, Cpd 357 (5S)-5-cyclopropyl-5-[3-[(3S)-4-[3-fluoro-5-(1H-pyrazol-4-yl)phenyl]-3-methyl-piperazin-1-yl]-3-oxo-propyl]imidazolidine-2,4-dione, Cpd 358 5-cyclopropyl-5-[3-[(3S)-3-methyl-4-[3-(1H-pyrazol-4-yl)phenyl]piperazin-1-yl]-3-oxo-propyl]imidazolidine-2,4-dione, Cpd 359 5-[(2S)-3-[4-(5-chloro-3-pyridyl)-3-methyl-piperazin-1-yl]-2-methyl-3-oxo-propyl]-5-ethyl-imidazolidine-2,4-dione, Cpd 360 5-ethyl-5-[3-[(3S)-4-(5-fluoro-3-pyridyl)-3-methyl-piperazin-1-yl]-2-methyl-3-oxo-propyl]imidazolidine-2,4-dione, Cpd 361 5-[3-[(3S)-4-(3,5-difluorophenyl)-3-methyl-piperazin-1-yl]-3-oxo-propyl]-5-(1-methylimidazol-4-yl)imidazolidine-2,4-dione, Cpd 362 5-[3-[(3S)-4-(3,5-difluorophenyl)-3-methyl-piperazin-1-yl]-3-oxo-propyl]-5-oxazol-4-yl-imidazolidine-2,4-dione, Cpd 363 5-[3-[(3S)-4-(5-chloro-3-pyridyl)-3-methyl-piperazin-1-yl]-2-methyl-3-oxo-propyl]-5-(methoxymethyl)imidazolidine-2,4-dione, Cpd 364 5-[3-[(3S)-4-(5-fluoro-3-pyridyl)-3-methyl-piperazin-1-yl]-2-methyl-3-oxo-propyl]-5-(methoxymethyl)imidazolidine-2,4-dione, Cpd 365 5-[3-[(3S)-4-(4-fluorophenyl)-3-methyl-piperazin-1-yl]-2-methyl-3-oxo-propyl]-5-methyl-imidazolidine-2,4-dione, Cpd 366 5-[3-[(3S)-4-(4-fluorophenyl)-3-methyl-piperazin-1-yl]-2-methyl-3-oxo-propyl]-5-(methoxymethyl)imidazolidine-2,4-dione, Cpd 367 5-[3-[(3S)-4-(3,5-difluorophenyl)-3-methyl-piperazin-1-yl]-3-oxo-propyl]-5-(2-methyl-4-pyridyl)imidazolidine-2,4-dione, Cpd 368 5-cyclopropyl-5-[3-[(3S)-3-methyl-4-[3-(2-methylpyrazol-3-yl)phenyl]piperazin-1-yl]-3-oxo-propyl]imidazolidine-2,4-dione, Cpd 369 5-cyclopropyl-5-[3-[(3S)-4-[3-(3,5-dimethylisoxazol-4-yl)phenyl]-3-methyl-piperazin-1-yl]-3-oxo-propyl]imidazolidine-2,4-dione, Cpd 370 5-cyclopropyl-5-[3-[(3S)-4-[3-(1-isopropylpyrazol-4-yl)phenyl]-3-methyl-piperazin-1-yl]-3-oxo-propyl]imidazolidine-2,4-dione, Cpd 371 5-methyl-5-[(2-methyl-3-[(3S)-3-methyl-4-[3-(1H-pyrazol-4-yl)phenyl]piperazin-1-yl]-3-oxo-propyl]imidazolidine-2,4-dione, Cpd 372 5-cyclopropyl-5-[3-[(3S)-3-methyl-4-(3-pyrazin-2-ylphenyl)piperazin-1-yl]-3-oxo-propyl]imidazolidine-2,4-dione, Cpd 373 5-[3-[(3S)-4-(6-chloropyridazin-4-yl)-3-methyl-piperazin-1-yl]-3-oxo-propyl]-5-cyclopropyl-imidazolidine-2,4-dione, Cpd 374 5-cyclopropyl-5-[3-[(3S)-3-methyl-4-(1-methylpyrazol-3-yl)piperazin-1-yl]-3-oxo-propyl]imidazolidine-2,4-dione, Cpd 375 5-[3-[(3S)-4-[3-fluoro-5-(1H-pyrazol-4-yl)phenyl]-3-methyl-piperazin-1-yl]-2-methyl-3-oxo-propyl]-5-methyl-imidazolidine-2,4-dione, Cpd 376 5-[3-[(3S)-4-[3-fluoro-5-(1H-pyrazol-4-yl)phenyl]-3-methyl-piperazin-1-yl]-2-methyl-3-oxo-propyl]-5-(methoxymethyl)imidazolidine-2,4-dione, Cpd 377 5-cyclopropyl-5-[3-[(3S)-3-methyl-4-(3-pyrimidin-5-ylphenyl)piperazin-1-yl]-3-oxo-propyl]imidazolidine-2,4-dione, Cpd 378 5-cyclopropyl-5-[3-[(3S)-4-[4-fluoro-3-(1H-pyrazol-4-yl)phenyl]-3-methyl-piperazin-1-yl]-2-methyl-3-oxo-propyl]imidazolidine-2,4-dione, Cpd 379 5-cyclopropyl-5-[3-[(3S)-4-[3-fluoro-5-(1H-pyrazol-4-yl)phenyl]-3-methyl-piperazin-1-yl]-2-methyl-3-oxo-propyl]imidazolidine-2,4-dione, Cpd 380 5-(methoxymethyl)-5-[2-methyl-3-[(3S)-3-methyl-4-[3-(1H-pyrazol-4-yl)phenyl]piperazin-1-yl]-3-oxo-propyl]imidazolidine-2,4-dione, Cpd 381 5-[3-[(3S)-4-[3-(6-chloropyridazin-3-yl)phenyl]-3-methyl-piperazin-1-yl]-3-oxo-propyl]-5-cyclopropyl-imidazolidine-2,4-dione, Cpd 382 5-[3-[(3S)-4-(3,5-difluorophenyl)-3-methyl-piperazin-1-yl]-3-oxo-propyl]-5-pyrimidin-2-yl-imidazolidine-2,4-dione, Cpd 383 5-[3-[(3S)-4-(3-chloro-5-fluoro-phenyl)-3-methyl-piperazin-1-yl]-3-oxo-propyl]-5-(6-methyl-3-pyridyl)imidazolidine-2,4-dione, Cpd 384 5-[3-[(3S)-4-(3,5-dichlorophenyl)-3-methyl-piperazin-1-yl]-3-oxo-propyl]-5-(6-methyl-3-pyridyl)imidazolidine-2,4-dione, Cpd 385 5-[3-[(3S)-4-(3-fluorophenyl)-3-methyl-piperazin-1-yl]-3-oxo-propyl]-5-(6-methyl-3-pyridyl)imidazolidine-2,4-dione, Cpd 386 5-[3-[(3S)-4-(3,5-difluorophenyl)-3-methyl-piperazin-1-yl]-3-oxo-propyl]-5-(6-methyl-3-pyridyl)imidazolidine-2,4-dione, Cpd 387 5-[3-[(3S)-4-(3,5-difluorophenyl)-3-methyl-piperazin-1-yl]-3-oxo-propyl]-5-(5-methylisoxazol-3-yl)imidazolidine-2,4-dione, Cpd 388 5-[3-[(3S)-4-(3-chloro-5-fluoro-phenyl)-3-methyl-piperazin-1-yl]-3-oxo-propyl]-5-oxazol-4-yl-imidazolidine-2,4-dione, Cpd 389 5-[3-[(3S)-4-(3-chloro-5-fluoro-phenyl)-3-methyl-piperazin-1-yl]-3-oxo-propyl]-5-(1-methylimidazol-4-yl)imidazolidine-2,4-dione, Cpd 390 (5R)-5-[3-[4-(4-chloro-3-methyl-phenyl)piperazin-1-yl]-3-oxo-propyl]-5-methyl-imidazolidine-2,4-dione, Cpd 391 (5R)-5-[3-[(3S)-4-[4-chloro-3-(dimethylamino)phenyl]-3-methyl-piperazin-1-yl]-3-oxo-propyl]-5-methyl-imidazolidine-2,4-dione, Cpd 392 (5R)-5-[3-[(3S)-4-[4-chloro-3-(methylamino)phenyl]-3-methyl-piperazin-1-yl]-3-oxo-propyl]-5-methyl-imidazolidine-2,4-dione, Cpd 393 (5R)-5-methyl-5-[3-[4-(m-tolyl)piperazin-1-yl]-3-oxo-propyl]imidazolidine-2,4-dione, Cpd 394 5-[3-[(3S)-4-(3,5-difluorophenyl)-3-methyl-piperazin-1-yl]-3-oxo-propyl]-5-(1-methylpyrazol-3-yl)imidazolidine-2,4-dione, Cpd 395 5-[3-[(3S)-4-(3,5-difluorophenyl)-3-methyl-piperazin-1-yl]-3-oxo-propyl]-5-(2-methyloxazol-4-yl)imidazolidine-2,4-dione, Cpd 396 5-[3-[(3S)-4-(3,5-difluorophenyl)-3-methyl-piperazin-1-yl]-3-oxo-propyl]-5-(2,5-dimethyloxazol-4-yl)imidazolidine-2,4-dione, Cpd 397 5-[3-[(3S)-4-(3,5-difluorophenyl)-3-methyl-piperazin-1-yl]-3-oxo-propyl]-5-(1-methylpyrazol-4-yl)imidazolidine-2,4-dione, Cpd 398 (5R)-5-[3-[(3S)-4-(2,5-dimethylphenyl)-3-methyl-piperazin-1-yl]-3-oxo-propyl]-5-methyl-imidazolidine-2,4-dione, Cpd 399 5-[3-[(3S)-4-(3,4-difluorophenyl)-3-methyl-piperazin-1-yl]-2-methyl-3-oxo-propyl]-5-(1-methylazetidin-3-yl)imidazolidine-2,4-dione, Cpd 400 (5R)-5-[3-[(3S)-4-(4-chloro-3,5-dimethyl-phenyl)-3-methyl-piperazin-1-yl]-3-oxo-propyl]-5-methyl-imidazolidine-2,4-dione, Cpd 401 (5R)-5-[3-[4-(4-chloro-3,5-dimethyl-phenyl)piperazin-1-yl]-3-oxo-propyl]-5-methyl-imidazolidine-2,4-dione, Cpd 402 2-[4-[3-[4-(4-chloro-3-methyl-phenyl)piperazin-1-yl]-3-oxo-propyl]-2,5-dioxo-imidazolidin-4-yl]-N-(2-hydroxyethyl)acetamide, Cpd 403 (5S)-5-cyclopropyl-5-[3-[(3R)-4-(3,5-difluorophenyl)-3-methyl-piperazin-1-yl]-3-oxo-propyl]imidazolidine-2,4-dione, Cpd 404 5-[3-[(3S)-4-(4-chloro-3,5-difluoro-phenyl)-3-methyl-piperazin-1-yl]-2-methyl-3-oxo-propyl]-5-methyl-imidazolidine-2,4-dione, Cpd 405 5-{3-[(S)-4-(3-Chloro-4-fluoro-phenyl)-3-methyl-piperazin-1-yl]-2-methyl-3-oxo-propyl}-5-methyl-imidazolidine-2,4-dione, and Cpd 406 5-{3-[(S)-4-(3-Chloro-4-fluoro-phenyl)-3-methyl-piperazin-1-yl]-2-methyl-3-oxo-propyl}-5-methoxymethyl-imidazolidine-2,4-dione.

In another embodiment, a compound of the invention is selected from:

Cpd 407 5-(3-(4-(3,5-dichlorophenyl)piperazin-1-yl)-3-oxopropyl)-5-(pyridin-2-yl)imidazolidine-2,4-dione, Cpd 408 5-cyclopropyl-5-(3-((S)-4-(3,4-dichlorophenyl)-3-methylpiperazin-1-yl)-3-oxopropyl)imidazolidine-2,4-dione, Cpd 409 5-cyclopropyl-5-(3-(4-(3,5-dichlorophenyl)piperazin-1-yl)-2-methyl-3-oxopropyl)imidazolidine-2,4-dione, Cpd 410 5-(3-(4-(3,5-dichlorophenyl)piperazin-1-yl)-2-methyl-3-oxopropyl)-5-methylimidazolidine-2,4-dione, Cpd 411 5-(3-((S)-4-(3-chloro-4-fluorophenyl)-3-methylpiperazin-1-yl)-2-methyl-3-oxopropyl)-5-cyclopropylimidazolidine-2,4-dione, Cpd 412 5-(3-((S)-4-(4-chlorophenyl)-3-methylpiperazin-1-yl)-2-methyl-3-oxopropyl)-5-cyclopropylimidazolidine-2,4-dione, Cpd 413 5-(3-((S)-4-(3-chloro-5-fluorophenyl)-3-methylpiperazin-1-yl)-2-methyl-3-oxopropyl)-5-cyclopropylimidazolidine-2,4-dione, Cpd 414 (R)-5-(3-((S)-4-(3,4-dichlorophenyl)-3-methylpiperazin-1-yl)-3-oxopropyl)-5-methylimidazolidine-2,4-dione, Cpd 415 5-(benzyloxymethyl)-5-(3-(4-(3,5-dichlorophenyl)piperazin-1-yl)-2-methyl-3-oxopropyl)imidazolidine-2,4-dione, Cpd 416 5-cyclopropyl-5-(3-((S)-4-(3,4-dichlorophenyl)-3-methylpiperazin-1-yl)-3-oxopropyl)imidazolidine-2,4-dione, Cpd 417 5-(3-(4-(3,5-dichlorophenyl)piperazin-1-yl)-2-methyl-3-oxopropyl)-5-(hydroxymethyl)imidazolidine-2,4-dione, Cpd 418 5-(3-((S)-4-(3-chloro-5-fluorophenyl)-3-methylpiperazin-1-yl)-2-methyl-3-oxopropyl)-5-methylimidazolidine-2,4-dione, Cpd 419 (R)-5-((S)-3-((S)-4-(3,4-dichlorophenyl)-3-methylpiperazin-1-yl)-2-methyl-3-oxopropyl)-5-methylimidazolidine-2,4-dione, Cpd 420 5-(3-((S)-4-(3,5-dichlorophenyl)-3-methylpiperazin-1-yl)-2-methyl-3-oxopropyl)-5-methylimidazolidine-2,4-dione, Cpd 421 5-(3-((S)-4-(3,4-difluorophenyl)-3-methylpiperazin-1-yl)-2-methyl-3-oxopropyl)-5-methylimidazolidine-2,4-dione, Cpd 422 5-(3-((S)-4-(3-chloro-4-fluorophenyl)-3-methylpiperazin-1-yl)-2-methyl-3-oxopropyl)-5-methylimidazolidine-2,4-dione, Cpd 423 5-(3-((S)-4-(3,5-dichloro-2-methylphenyl)-3-methylpiperazin-1-yl)-2-methyl-3-oxopropyl)-5-methylimidazolidine-2,4-dione, Cpd 424 5-(2-(benzyloxymethyl)-3-(4-(3,5-dichlorophenyl)piperazin-1-yl)-3-oxopropyl)-5-methylimidazolidine-2,4-dione, Cpd 425 5-(3-(4-(3,5-dichlorophenyl)piperazin-1-yl)-2-(hydroxymethyl)-3-oxopropyl)-5-methylimidazolidine-2,4-dione, Cpd 426 5-(3-((S)-4-(3,5-dichlorophenyl)-3-methylpiperazin-1-yl)-2-methyl-3-oxopropyl)-5-((2-methoxyethoxy)methyl)imidazolidine-2,4-dione, Cpd 427 5-(3-(4-(3,5-dichlorophenyl)piperazin-1-yl)-2-methyl-3-oxopropyl)-5-(methoxymethyl)imidazolidine-2,4-dione, Cpd 428 5-(3-(4-(3,4-difluorophenyl)piperazin-1-yl)-2-methyl-3-oxopropyl)-5-(methoxymethyl)imidazolidine-2,4-dione, Cpd 429 5-(3-((S)-4-(3,5-dichlorophenyl)-3-methylpiperazin-1-yl)-2-methyl-3-oxopropyl)-5-(methoxymethyl)imidazolidine-2,4-dione, Cpd 430 5-(3-((S)-4-(3,5-dichloro-2-methylphenyl)-3-methylpiperazin-1-yl)-2-methyl-3-oxopropyl)-5-(methoxymethyl)imidazolidine-2,4-dione, Cpd 431 5-(3-((S)-4-(3-chloro-5-fluorophenyl)-3-methylpiperazin-1-yl)-2-methyl-3-oxopropyl)-5-(methoxymethyl)imidazolidine-2,4-dione, Cpd 432 5-(3-((S)-4-(3-chloro-4-fluorophenyl)-3-methylpiperazin-1-yl)-2-methyl-3-oxopropyl)-5-(methoxymethyl)imidazolidine-2,4-dione, Cpd 433 5-(3-(4-(3-chloro-2-methylphenyl)piperazin-1-yl)-2-methyl-3-oxopropyl)-5-(methoxymethyl)imidazolidine-2,4-dione, Cpd 434 5-(3-(4-(3,5-dichlorophenyl)piperazin-1-yl)-2-methyl-3-oxopropyl)-5-(pyridin-2-yl)imidazolidine-2,4-dione, Cpd 435 5-(2-(4-(3,5-dichlorophenyl)piperazine-1-carbonyl)butyl)-5-methylimidazolidine-2,4-dione, Cpd 436 5-(3-(4-(3,5-dichlorophenyl)piperazin-1-yl)-2-(methoxymethyl)-3-oxopropyl)-5-methylimidazolidine-2,4-dione, Cpd 43 7 5-(3-((S)-4-(3-chloro-4-fluorophenyl)-3-methylpiperazin-1-yl)-2-methyl-3-oxopropyl)-5-(pyridin-2-yl)imidazolidine-2,4-dione, Cpd 438 5-(2-(4-(3,5-dichlorophenyl)piperazine-1-carbonyl)-3-methylbutyl)-5-methylimidazolidine-2,4-dione, Cpd 439 5-(3-(4-(3,5-dichlorophenyl)piperazin-1-yl)-2-methoxy-3-oxopropyl)-5-methylimidazolidine-2,4-dione, Cpd 440 5-(3-(4-(4,5-dichloro-2-methylphenyl)piperazin-1-yl)-3-oxopropyl)-5-methylimidazolidine-2,4-dione, Cpd 441 5-(3-((S)-4-(3-chloro-4-fluorophenyl)-3-methylpiperazin-1-yl)-2-methyl-3-oxopropyl)imidazolidine-2,4-dione, Cpd 442 5-(3-((S)-4-(3,5-dichlorophenyl)-3-methylpiperazin-1-yl)-2-methyl-3-oxopropyl)-5-(pyridin-2-yl)imidazolidine-2,4-dione, Cpd 443 5-(3-((S)-4-(3-chloro-4-fluorophenyl)-3-methylpiperazin-1-yl)-2-(hydroxymethyl)-3-oxopropyl)-5-methylimidazolidine-2,4-dione, Cpd 444 5-(3-((S)-4-(3-chloro-4-fluorophenyl)-3-methylpiperazin-1-yl)-2-methyl-3-oxopropyl)-5-ethylimidazolidine-2,4-dione, Cpd 445 5-(3-((S)-4-(3-chloro-5-fluorophenyl)-3-methylpiperazin-1-yl)-2-methyl-3-oxopropyl)-5-ethylimidazolidine-2,4-dione, Cpd 446 5-(3-((S)-4-(3-chlorophenyl)-3-methylpiperazin-1-yl)-2-methyl-3-oxopropyl)-5-(pyridin-2-yl)imidazolidine-2,4-dione, Cpd 447 5-[3-[(3S)-4-(3-chloro-4-fluoro-phenyl)-3-methyl-piperazin-1-yl]-3-oxo-propyl]-5-(6-methyl-2-pyridyl)imidazolidine-2,4-dione, Cpd 448 5-(3-(4-(4-chloro-3,5-difluorophenyl)piperazin-1-yl)-2-methyl-3-oxopropyl)-5-(methoxymethyl)imidazolidine-2,4-dione, Cpd 449 5-(3-((S)-4-(3-chloro-4-fluorophenyl)-3-methylpiperazin-1-yl)-2-(methoxymethyl)-3-oxopropyl)-5-methylimidazolidine-2,4-dione, Cpd 450 5-(3-((S)-4-(3-chloro-4-fluorophenyl)-3-methylpiperazin-1-yl)-2-methoxy-3-oxopropyl)-5-methylimidazolidine-2,4-dione, Cpd 451 5-(3-((S)-4-(3-chloro-5-fluorophenyl)-3-methylpiperazin-1-yl)-2-(methoxymethyl)-3-oxopropyl)-5-methylimidazolidine-2,4-dione, Cpd 452 5-[3-[(3S)-4-(3,4-dichlorophenyl)-3-methyl-piperazin-1-yl]-3-oxo-propyl]-5-(6-methyl-2-pyridyl)imidazolidine-2,4-dione, Cpd 453 5-[3-[(3S)-4-(3,4-dichlorophenyl)-3-methyl-piperazin-1-yl]-3-oxo-propyl]-5-(3-pyridyl)imidazolidine-2,4-dione, Cpd 454 5-[3-[(3S)-4-(3-chloro-4-fluoro-phenyl)-3-methyl-piperazin-1-yl]-3-oxo-propyl]-5-(6-methyl-2-pyridyl)imidazolidine-2,4-dione, Cpd 455 (S)-5-{(S)-3-[(S)-4-(3-Chloro-4-fluoro-phenyl)-3-methyl-piperazin-1-yl]-2-methyl-3-oxo-propyl}-5-methoxymethyl-imidazolidine-2,4-dione, Cpd 456 5-cyclopropyl-5-(3-((S)-4-(4-fluoro-3-methylphenyl)-3-methylpiperazin-1-yl)-2-methyl-3-oxopropyl)imidazolidine-2,4-dione, Cpd 457 5-[3-[(3S)-4-(3-chloro-4-fluoro-phenyl)-3-methyl-piperazin-1-yl]-3-oxo-propyl]-5-(2-pyridyl)imidazolidine-2,4-dione, Cpd 458 5-[3-[(3S)-4-(3,4-dichlorophenyl)-3-methyl-piperazin-1-yl]-3-oxo-propyl]-5-(2-pyridyl)imidazolidine-2,4-dione, Cpd 459 5-[3-[(3S)-4-(3,5-dichlorophenyl)-3-methyl-piperazin-1-yl]-3-oxo-propyl]-5-(2-pyridyl)imidazolidine-2,4-dione, Cpd 460 5-[3-[(3S)-4-(3,4-dichlorophenyl)-3-methyl-piperazin-1-yl]-3-oxo-propyl]-5-pyrazin-2-yl-imidazolidine-2,4-dione, Cpd 461 5-[3-[(3S)-4-(3,5-dichlorophenyl)-3-methyl-piperazin-1-yl]-3-oxo-propyl]-5-pyrazin-2-yl-imidazolidine-2,4-dione, Cpd 462 5-[3-[(3S)-4-(3,4-dichlorophenyl)-3-methyl-piperazin-1-yl]-3-oxo-propyl]-5-pyrimidin-2-yl-imidazolidine-2,4-dione, Cpd 463 5-[3-[(3S)-4-(3-chloro-5-fluoro-phenyl)-3-methyl-piperazin-1-yl]-3-oxo-propyl]-5-pyrimidin-2-yl-imidazolidine-2,4-dione, Cpd 464 5-[3-[(3S)-4-(3,4-dichlorophenyl)-3-methyl-piperazin-1-yl]-3-oxo-propyl]-5-(6-methyl-3-pyridyl)imidazolidine-2,4-dione, Cpd 465 5-[3-[(3S)-4-(3,5-dichlorophenyl)-3-methyl-piperazin-1-yl]-3-oxo-propyl]-5-oxazol-4-yl-imidazolidine-2,4-dione, Cpd 466 5-[3-[(3S)-4-(3,5-dichlorophenyl)-3-methyl-piperazin-1-yl]-3-oxo-propyl]-5-(1-methylimidazol-4-yl)imidazolidine-2,4-dione, Cpd 467 5-[3-[(3S)-4-(3-chloro-4-fluoro-phenyl)-3-methyl-piperazin-1-yl]-3-oxo-propyl]-5-(1-methylimidazol-4-yl)imidazolidine-2,4-dione, Cpd 468 (5R)-5-[3-[(3S)-4-(4-chloro-3-isopropyl-phenyl)-3-methyl-piperazin-1-yl]-3-oxo-propyl]-5-methyl-imidazolidine-2,4-dione, Cpd 469 (5R)-5-[3-[(3S)-4-(4-chloro-3-methyl-phenyl)-3-methyl-piperazin-1-yl]-3-oxo-propyl]-5-methyl-imidazolidine-2,4-dione, Cpd 470 (5R)-5-[3-[(3S)-4-(4-chloro-3,5-dimethyl-phenyl)-3-methyl-piperazin-1-yl]-3-oxo-propyl]-5-methyl-imidazolidine-2,4-dione, Cpd 471 2-[4-[3-[(3S)-4-(4-chloro-3-ethyl-phenyl)-3-methyl-piperazin-1-yl]-3-oxo-propyl]-2,5-dioxo-imidazolidin-4-yl]acetic acid, Cpd 472 (5R)-5-[3-[(3S)-4-[4-chloro-3-(trifluoromethyl)phenyl]-3-methyl-piperazin-1-yl]-3-oxo-propyl]-5-methyl-imidazolidine-2,4-dione, Cpd 473 5-[3-[(3S)-4-(4-chloro-3-ethyl-phenyl)-3-methyl-piperazin-1-yl]-3-oxo-propyl]-5-(6-methyl-2-pyridyl)imidazolidine-2,4-dione, Cpd 474 (5R)-5-[3-[(3S)-4-[4-chloro-3-(difluoromethyl)phenyl]-3-methyl-piperazin-1-yl]-3-oxo-propyl]-5-methyl-imidazolidine-2,4-dione, Cpd 475 tert-butyl 3-[4-[3-[(3S)-4-(4-chloro-3-ethyl-phenyl)-3-methyl-piperazin-1-yl]-3-oxo-propyl]-2,5-dioxo-imidazolidin-4-yl]propanoate, Cpd 476 (5R)-5-[3-[(3S)-4-[4-chloro-3-(fluoromethyl)phenyl]-3-methyl-piperazin-1-yl]-3-oxo-propyl]-5-methyl-imidazolidine-2,4-dione, Cpd 477 3-[4-[3-[(3S)-4-(4-chloro-3-ethyl-phenyl)-3-methyl-piperazin-1-yl]-3-oxo-propyl]-2,5-dioxo-imidazolidin-4-yl]propanoic acid, Cpd 478 5-{3-[(S)-4-(4-Chloro-3-trifluoromethyl-phenyl)-3-methyl-piperazin-1-yl]-2-methyl-3-oxo-propyl}-5-methoxymethyl-imidazolidine-2,4-dione, Cpd 479 5-[3-[(3S)-4-(4-chloro-3,5-difluoro-phenyl)-3-methyl-piperazin-1-yl]-2-methyl-3-oxo-propyl]-5-methyl-imidazolidine-2,4-dione, Cpd 480 5-[3-[(3S)-4-(4-chloro-3,5-difluoro-phenyl)-3-methyl-piperazin-1-yl]-2-methyl-3-oxo-propyl]-5-(methoxymethyl)imidazolidine-2,4-dione, and Cpd 481 5-[3-[(3S)-4-(4-chloro-3-ethyl-phenyl)-3-methyl-piperazin-1-yl]-2-methyl-3-oxo-propyl]-5-(methoxymethyl)imidazolidine-2,4-dione.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Clauses

1. A compound according to Formula I:

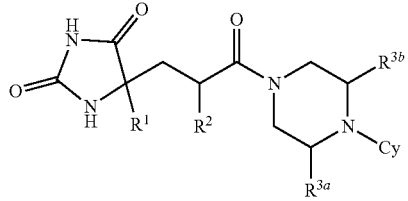

wherein $R^1$ is:
  H,
  $C_{1-4}$ alkyl optionally substituted with one or more independently selected $R^4$ groups,
  $C_{3-7}$ monocyclic cycloalkyl optionally substituted with one or more independently selected $R^4$ groups,
  4-7 membered monocyclic heterocycloalkyl comprising 1 to 2 heteroatoms independently selected from N, O, and S, optionally substituted with one or more independently selected $C_{1-4}$ alkyl, —C(=O)$C_{1-4}$ alkyl, or —C(=O)O$C_{1-4}$ alkyl,
  phenyl optionally substituted with one or more independently selected $R^5$ groups,
  phenyl fused to a 5-6 membered monocyclic heterocycloalkyl comprising 1, 2 or 3 heteroatoms independently selected from N, O, and S, which heterocycloalkyl is optionally substituted with one or more =O, or
  5-6 membered monocyclic heteroaryl comprising 1 or 2 heteroatoms independently selected from N, O, and S, optionally substituted with one or more independently selected $R^5$ groups;

$R^2$ is independently selected from:
  H,
  OH,
  $C_{1-4}$ alkoxy, and
  $C_{1-4}$ alkyl optionally substituted with one
    OH,
    CN,
    $C_{1-4}$ alkoxy optionally substituted with one phenyl, or
    5-6 membered monocyclic heteroaryl comprising 1 or 2 heteroatoms independently selected from N, O, and S, optionally substituted with one or more independently selected $C_{1-4}$ alkyl;

each $R^{3a}$, and $R^{3b}$ is independently selected from:
  H, and
  $C_{1-4}$ alkyl;

Cy is
  6-10 membered monocyclic or fused bicyclic aryl optionally substituted with one or more independently selected $R^6$ groups,
  5-10 membered monocyclic or fused bicyclic heteroaryl comprising 1, 2 or 3 heteroatoms independently selected from N, O, and S, optionally substituted with one or more independently selected $R^6$ groups;

$R^4$ is
halo,
OH,
CN,
$C_{1-4}$ alkyl,
$C_{1-4}$ alkoxy optionally substituted with one $C_{1-4}$ alkoxy, or phenyl,
$C_{1-4}$ thioalkoxy,
4-7-membered monocyclic heterocycloalkyl comprising one or more heteroatoms independently selected from N, S, and O, optionally substituted with one or more halo, or —C(=O)O$C_{1-4}$ alkyl,
Phenyl,
—S(=O)$_2$$C_{1-4}$ alkyl,
—C(=O)O$R^{7a}$,
—C(=O)N$R^{7b}R^{7c}$,
—NHC(=O)O$R^{7d}$,
—NHC(=O)$R^{7e}$, or
—N$R^{8a}R^{8b}$;
each $R^5$ is
halo,
OH,
CN,
$C_{1-4}$ alkyl optionally substituted with one or more independently selected halo, —N$R^{9a}R^{9b}$, —C(=O)N$R^{9c}R^{9d}$,
$C_{1-4}$ alkoxy optionally substituted with one —N$R^{9e}R^{9f}$, or —S(=O)$_2$$C_{1-4}$ alkyl;
each $R^6$ is
halo,
—CN,
—NO$_2$,
—CH$_3$,
5-10 membered monocyclic or fused bicyclic heteroaryl comprising 1, 2 or 3 heteroatoms independently selected from N, O, and S, optionally substituted with one or more independently selected halo, $C_{1-4}$ alkyl, $C_{1-4}$ alkoxy, or —N$R^{9g}R^{9h}$;
each $R^{7a}$, $R^{7b}$, $R^{7c}$, $R^{7d}$, or $R^{7e}$, is
H, or
$C_{1-4}$ alkyl optionally substituted with one OH, or $C_{1-4}$ alkoxy;
each $R^{8a}$, or $R^{8b}$ is independently selected from
H, and
$C_{1-4}$ alkyl optionally substituted with OH, $C_{1-4}$ alkoxy, or phenyl;
each $R^{9a}$, $R^{9b}$, $R^{9c}$, $R^{9d}$, $R^{9e}$, $R^{9f}$, $R^{9g}$, and $R^{9h}$ is independently selected from H, and $C_{1-4}$ alkyl; or a pharmaceutically acceptable salt, or a solvate, or a pharmaceutically acceptable salt of a solvate thereof; or a biologically active metabolite thereof;
provided that:
$R^1$, and $R^2$ are not simultaneously H, and
When $R^1$ is Me, X is N, then Cy is not

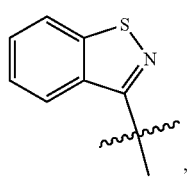 [SMILES: *c1nsc2ccccc12]

,
or a pharmaceutically acceptable salt, or a solvate, or the salt of the solvate thereof.

2. A compound or pharmaceutically acceptable salt thereof, according to clause 1, wherein the compound is according to Formula II:

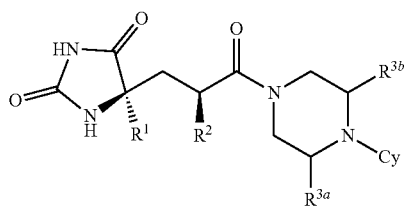

3. A compound or pharmaceutically acceptable salt thereof, according to clause 1 or 2, wherein $R^1$ is H.
4. A compound or pharmaceutically acceptable salt thereof, according to clause 1 or 2, wherein $R^1$ is $C_{1-4}$ alkyl.
5. A compound or pharmaceutically acceptable salt thereof, according to clause 1 or 2, wherein $R^1$ is Me, Et, Pr, iPr, or tBu.
6. A compound or pharmaceutically acceptable salt thereof, according to clause 1 or 2, wherein $R^1$ is $C_{1-4}$ alkyl substituted with one or more independently selected $R^4$ groups.
7. A compound or pharmaceutically acceptable salt thereof, according to clause 1 or 2, wherein $R^1$ is Me, Et, Pr, iPr, or tBu substituted with one or more independently selected $R^4$ groups.
8. A compound or pharmaceutically acceptable salt thereof, according to clause 1 or 2, wherein $R^1$ is $C_{1-4}$ alkyl substituted with one $R^4$ group.
9. A compound or pharmaceutically acceptable salt thereof, according to clause 1 or 2, wherein $R^1$ is Me, Et, Pr, iPr, or tBu substituted with one $R^4$ group.
10. A compound or pharmaceutically acceptable salt thereof, according to clause 1 or 2, wherein $R^1$ is $C_{3-7}$ monocyclic cycloalkyl.
11. A compound or pharmaceutically acceptable salt thereof, according to clause 1 or 2, wherein $R^1$ is cyclopropyl, cyclobutyl, cyclopentyl, or cyclohexyl.
12. A compound or pharmaceutically acceptable salt thereof, according to clause 1 or 2, wherein $R^1$ is cyclopropyl.
13. A compound or pharmaceutically acceptable salt thereof, according to any one of clauses 6-9, wherein $R^4$ is selected from F, Cl, OH, and CN.
14. A compound or pharmaceutically acceptable salt thereof, according to any one of clauses 6-9, wherein $R^4$ is $C_{1-4}$ alkoxy.
15. A compound or pharmaceutically acceptable salt thereof, according to any one of clauses 6-9, wherein $R^4$ is OMe, OEt, or OiPr.
16. A compound or pharmaceutically acceptable salt thereof, according to any one of clauses 6-9, wherein $R^4$ is $C_{1-4}$ alkoxy substituted with one $C_{1-4}$ alkoxy, or phenyl.
17. A compound or pharmaceutically acceptable salt thereof, according to any one of clauses 6-9, wherein $R^4$ is OMe, OEt, or OiPr, each of which is substituted with one $C_{1-4}$ alkoxy, or phenyl.
18. A compound or pharmaceutically acceptable salt thereof, according to any one of clauses 6-9, wherein $R^4$ is OMe, OEt, or OiPr, each of which is substituted with one OMe, OEt, or phenyl.
19. A compound or pharmaceutically acceptable salt thereof, according to any one of clauses 6-9, wherein $R^4$ is $C_{1-4}$ thioalkoxy.

20. A compound or pharmaceutically acceptable salt thereof, according to any one of clauses 6-9, wherein $R^4$ is —SMe.

21. A compound or pharmaceutically acceptable salt thereof, according to any one of clauses 6-9, wherein $R^4$ is 4-7-membered monocyclic heterocycloalkyl comprising one or more heteroatoms independently selected from N, S, and O.

22. A compound or pharmaceutically acceptable salt thereof, according to any one of clauses 6-9, wherein $R^4$ is azetidinyl, pyrrolidinyl, piperidinyl, piperazinyl, morpholinyl, tetrahydrofuranyl, tetrahydropyranyl, or dioxanyl.

23. A compound or pharmaceutically acceptable salt thereof, according to any one of clauses 6-9, wherein $R^4$ is 4-7-membered monocyclic heterocycloalkyl comprising one or more heteroatoms independently selected from N, S, and O, substituted with one or more halo, or —C(=O)OC$_{1-4}$ alkyl.

24. A compound or pharmaceutically acceptable salt thereof, according to any one of clauses 6-9, wherein $R^4$ is azetidinyl, pyrrolidinyl, piperidinyl, piperazinyl, morpholinyl, tetrahydrofuranyl, tetrahydropyranyl, or dioxanyl, each of which is substituted with one or more halo, or —C(=O)OC$_{1-4}$ alkyl.

25. A compound or pharmaceutically acceptable salt thereof, according to any one of clauses 6-9, wherein $R^4$ is phenyl.

26. A compound or pharmaceutically acceptable salt thereof, according to any one of clauses 6-9, wherein $R^4$ is —S(=O)$_2$C$_{1-4}$ alkyl.

27. A compound or pharmaceutically acceptable salt thereof, according to any one of clauses 6-9, wherein $R^4$ is —S(=O)$_2$Me, or —S(=O)$_2$Et.

28. A compound or pharmaceutically acceptable salt thereof, according to any one of clauses 6-9, wherein $R^4$ is —C(=O)OR$^{7a}$.

29. A compound or pharmaceutically acceptable salt thereof, according to clause 28, wherein $R^{7a}$ is H.

30. A compound or pharmaceutically acceptable salt thereof, according to clause 28, wherein $R^{7a}$ is C$_{1-4}$ alkyl.

31. A compound or pharmaceutically acceptable salt thereof, according to clause 28, wherein $R^{7a}$ is Me, Et, iPr or tBu.

32. A compound or pharmaceutically acceptable salt thereof, according to clause 28, wherein $R^{7a}$ is C$_{1-4}$ alkyl substituted with one OH, or C$_{1-4}$ alkoxy.

33. A compound or pharmaceutically acceptable salt thereof, according to clause 28, wherein $R^{7a}$ is Me, Et, iPr or tBu, each of which is substituted with one OH, or C$_{1-4}$ alkoxy.

34. A compound or pharmaceutically acceptable salt thereof, according to any one of clauses 6-9, wherein $R^4$ is —C(=O)NR$^{7b}$R$^{7c}$.

35. A compound or pharmaceutically acceptable salt thereof, according to clause 34, wherein each $R^{7b}$ or $R^{7c}$ is independently selected from H, Me, and Et.

36. A compound or pharmaceutically acceptable salt thereof, according to any one of clauses 6-9, wherein $R^4$ is —NHC(=O)OR$^{7d}$.

37. A compound or pharmaceutically acceptable salt thereof, according to clause 36, wherein $R^{7d}$ is selected from H, Me, Et, iPr and tBu.

38. A compound or pharmaceutically acceptable salt thereof, according to any one of clauses 6-9, wherein $R^4$ is —NHC(=O)R$^{7e}$.

39. A compound or pharmaceutically acceptable salt thereof, according to clause 38, wherein $R^{7e}$ is selected from H, Me, Et, iPr and tBu.

40. A compound or pharmaceutically acceptable salt thereof, according to any one of clauses 6-9, wherein $R^4$ is —NR$^{8a}$R$^{8b}$.

41. A compound or pharmaceutically acceptable salt thereof, according to clause 40, wherein each $R^{8a}$ or $R^{8b}$ is independently selected from H, Me, Et, iPr and tBu.

42. A compound or pharmaceutically acceptable salt thereof, according to clause 1 or 2, wherein $R^1$ is 4-7 membered monocyclic heterocycloalkyl comprising 1 to 2 heteroatoms independently selected from N, O, and S.

43. A compound or pharmaceutically acceptable salt thereof, according to clause 1 or 2, wherein $R^1$ is azetidinyl, pyrrolidinyl, piperidinyl, piperazinyl, morpholinyl, tetrahydrofuranyl, tetrahydropyranyl, or dioxanyl.

44. A compound or pharmaceutically acceptable salt thereof, according to clause 1 or 2, wherein $R^1$ is 4-7 membered monocyclic heterocycloalkyl comprising 1 to 2 heteroatoms independently selected from N, O, and S, substituted with one or more independently selected C$_{1-4}$ alkyl, —C(=O)C$_{1-4}$ alkyl, or —C(=O)OC$_{1-4}$ alkyl.

45. A compound or pharmaceutically acceptable salt thereof, according to clause 1 or 2, wherein $R^1$ is azetidinyl, pyrrolidinyl, piperidinyl, piperazinyl, morpholinyl, tetrahydrofuranyl, tetrahydropyranyl, or dioxanyl, each of which is substituted with one or more independently selected F, Cl, —CH$_3$, —C(=O)Me, —C(=O)OMe, or —C(=O)OEt.

46. A compound or pharmaceutically acceptable salt thereof, according to clause 1 or 2, wherein $R^1$ is phenyl.

47. A compound or pharmaceutically acceptable salt thereof, according to clause 1 or 2, wherein $R^1$ is phenyl substituted with one or more independently selected $R^5$ groups.

48. A compound or pharmaceutically acceptable salt thereof, according to clause 1 or 2, wherein $R^1$ is phenyl substituted with one $R^5$ group.

49. A compound or pharmaceutically acceptable salt thereof, according to clause 1 or 2, wherein $R^1$ is 5-6 membered monocyclic heteroaryl comprising 1 or 2 heteroatoms independently selected from N, O, and S.

50. A compound or pharmaceutically acceptable salt thereof, according to clause 1 or 2, wherein $R^1$ is imidazolyl, pyrazolyl, thiazolyl, oxazolyl, pyridinyl, pyrimidinyl or pyrazinyl.

51. A compound or pharmaceutically acceptable salt thereof, according to clause 1 or 2, wherein $R^1$ is 5-6 membered monocyclic heteroaryl comprising 1 or 2 heteroatoms independently selected from N, O, and S, substituted with one or more independently selected $R^5$ groups.

52. A compound or pharmaceutically acceptable salt thereof, according to clause 1 or 2, wherein $R^1$ is imidazolyl, pyrazolyl, thiazolyl, oxazolyl, pyridinyl, pyrimidinyl or pyrazinyl, each of which is substituted with one or more independently selected $R^5$ groups.

53. A compound or pharmaceutically acceptable salt thereof, according to clause 47, 48, 51 or 52, wherein $R^5$ is F, Cl, OH, or CN.

54. A compound or pharmaceutically acceptable salt thereof, according to clause 47, 48, 51 or 52, wherein $R^5$ is C$_{1-4}$ alkyl.

55. A compound or pharmaceutically acceptable salt thereof, according to clause 47, 48, 51 or 52, wherein $R^5$ is Me, or Et.

56. A compound or pharmaceutically acceptable salt thereof, according to clause 47, 48, 51 or 52, wherein $R^5$ is C$_{1-4}$ alkyl substituted with one or more independently selected halo.

57. A compound or pharmaceutically acceptable salt thereof, according to clause 47, 48, 51 or 52, wherein $R^5$ is Me, or Et, each of which is substituted with one or more independently selected F, or Cl.

58. A compound or pharmaceutically acceptable salt thereof, according to clause 47, 48, 51 or 52, wherein $R^5$ is C$_{1-4}$ alkyl substituted with one —NR$^{9a}$R$^{9b}$.

59. A compound or pharmaceutically acceptable salt thereof, according to clause 47, 48, 51 or 52, wherein $R^5$ is Me, or Et, each of which is substituted with one $-NR^{9a}R^{9b}$.

60. A compound or pharmaceutically acceptable salt thereof, according to clause 58 or 59, wherein each $R^{9a}$ or $R^{9b}$ is independently selected from H, Me, and Et.

61. A compound or pharmaceutically acceptable salt thereof, according to clause 47, 48, 51 or 52, wherein $R^5$ is $C_{1-4}$ alkyl substituted with one $-C(=O)NR^{9c}R^{9d}$.

62. A compound or pharmaceutically acceptable salt thereof, according to clause 47, 48, 51 or 52, wherein $R^5$ is Me, or Et, each of which is substituted with one $-C(=O)NR^{9c}R^{9d}$.

63. A compound or pharmaceutically acceptable salt thereof, according to clause 61 or 62, wherein each $R^{9c}$ or $R^{9d}$ is independently selected from H, Me, and Et.

64. A compound or pharmaceutically acceptable salt thereof, according to clause 47, 48, 51 or 52, wherein $R^5$ is $C_{1-4}$ alkoxy.

65. A compound or pharmaceutically acceptable salt thereof, according to clause 47, 48, 51 or 52, wherein $R^5$ is OMe, or OEt.

66. A compound or pharmaceutically acceptable salt thereof, according to clause 47, 48, 51 or 52, wherein $R^5$ is $C_{1-4}$ alkoxy substituted with one $-NR^{9e}R^{9f}$.

67. A compound or pharmaceutically acceptable salt thereof, according to clause 47, 48, 51 or 52, wherein $R^5$ is OMe, or OEt, each of which is substituted with one $-NR^{9e}R^{9f}$.

68. A compound or pharmaceutically acceptable salt thereof, according to clause 66 or 67, wherein each $R^{9e}$ or $R^{9f}$ is independently selected from H, Me, and Et.

69. A compound or pharmaceutically acceptable salt thereof, according to clause 47, 48, 51 or 52, wherein $R^5$ is $-S(=O)_2 C_{1-4}$ alkyl.

70. A compound or pharmaceutically acceptable salt thereof, according to clause 47, 48, 51 or 52, wherein $R^5$ is $-S(=O)_2 CH_3$.

71. A compound or pharmaceutically acceptable salt thereof, according to any one of clauses 1-70, wherein the compound is according to Formula IIIa or IIIb:

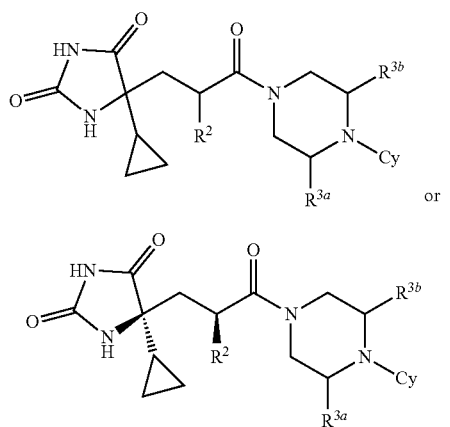

72. A compound or pharmaceutically acceptable salt thereof, according to any one of clauses 1-71, wherein $R^2$ is H.

73. A compound or pharmaceutically acceptable salt thereof, according to any one of clauses 1-71, wherein $R^2$ is $-OH$.

74. A compound or pharmaceutically acceptable salt thereof, according to any one of clauses 1-71, wherein $R^2$ is $C_{1-4}$ alkoxy.

75. A compound or pharmaceutically acceptable salt thereof, according to any one of clauses 1-71, wherein $R^2$ is $-OMe$, $-OEt$, or $-OiPr$.

76. A compound or pharmaceutically acceptable salt thereof, according to any one of clauses 1-71, wherein $R^2$ is $C_{1-4}$ alkyl.

77. A compound or pharmaceutically acceptable salt thereof, according to any one of clauses 1-71, wherein $R^2$ is Me, Et, or iPr.

78. A compound or pharmaceutically acceptable salt thereof, according to any one of clauses 1-71, wherein $R^2$ is $C_{1-4}$ alkyl substituted with one OH, or CN.

79. A compound or pharmaceutically acceptable salt thereof, according to any one of clauses 1-71, wherein $R^2$ is $-CH_2-OH$, or $-CH_2-CN$.

80. A compound or pharmaceutically acceptable salt thereof, according to any one of clauses 1-71, wherein $R^2$ is $C_{1-4}$ alkyl substituted with one $C_{1-4}$ alkoxy optionally substituted with one phenyl.

81. A compound or pharmaceutically acceptable salt thereof, according to any one of clauses 1-71, wherein $R^2$ is Me, or Et, each of which is substituted with one $C_{1-4}$ alkoxy optionally substituted with one phenyl.

82. A compound or pharmaceutically acceptable salt thereof, according to any one of clauses 1-71, wherein $R^2$ is $C_{1-4}$ alkyl substituted with one $-OMe$, $-OEt$, or $-OCH_2$-Phenyl.

83. A compound or pharmaceutically acceptable salt thereof, according to any one of clauses 1-71, wherein $R^2$ is $-CH_2-OMe$, $-CH_2-OEt$, or $-CH_2-OCH_2$-Phenyl.

84. A compound or pharmaceutically acceptable salt thereof, according to any one of clauses 1-71, wherein $R^2$ is $C_{1-4}$ alkyl substituted with one 5-6 membered monocyclic heteroaryl comprising 1 or 2 heteroatoms independently selected from N, O, and S.

85. A compound or pharmaceutically acceptable salt thereof, according to any one of clauses 1-71, wherein $R^2$ is $C_{1-4}$ alkyl substituted with one imidazolyl, pyrazolyl, oxazolyl.

86. A compound or pharmaceutically acceptable salt thereof, according to any one of clauses 1-71, wherein $R^2$ is Me, or Et, each of which is substituted with one imidazolyl, pyrazolyl, oxazolyl.

87. A compound or pharmaceutically acceptable salt thereof, according to any one of clauses 1-71, wherein $R^2$ is $C_{1-4}$ alkyl substituted with one 5-6 membered monocyclic heteroaryl comprising 1 or 2 heteroatoms independently selected from N, O, and S, substituted with one or more independently selected $C_{1-4}$ alkyl.

88. A compound or pharmaceutically acceptable salt thereof, according to any one of clauses 1-71, wherein $R^2$ is $C_{1-4}$ alkyl substituted with one imidazolyl, pyrazolyl, oxazolyl, each of which is substituted with one or more independently selected Me, or Et.

89. A compound or pharmaceutically acceptable salt thereof, according to any one of clauses 1-71, wherein $R^2$ is Me, or Et, each of which is substituted with one imidazolyl, pyrazolyl, oxazolyl, each of which is substituted with one or more independently selected Me, or Et.

90. A compound or pharmaceutically acceptable salt thereof, according to any one of clauses 1-89, wherein the compound is according to Formula IVa or IVb:

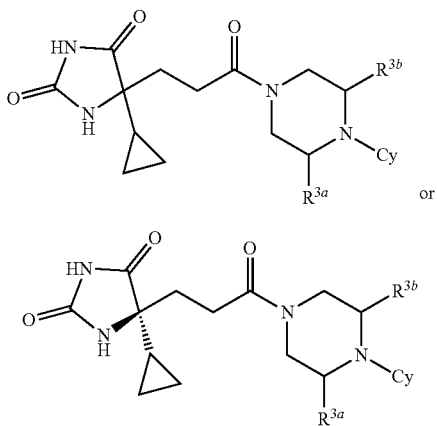

IVa or IVb

91. A compound or pharmaceutically acceptable salt thereof, according to any one of clauses 1-90, wherein each $R^{3a}$, and $R^{3b}$ is independently selected from H, and $CH_3$.

92. A compound or pharmaceutically acceptable salt thereof, according to any one of clauses 1-90, wherein $R^{3a}$ is H and $R^{3b}$ is selected from $CH_3$, and $CF_3$.

93. A compound or pharmaceutically acceptable salt thereof, according to any one of clauses 1-90, wherein $R^{3a}$ and $R^{3b}$ are H.

94. A compound or pharmaceutically acceptable salt thereof, according to any one of clauses 1-89, wherein the compound is according to Formula Va or Vb:

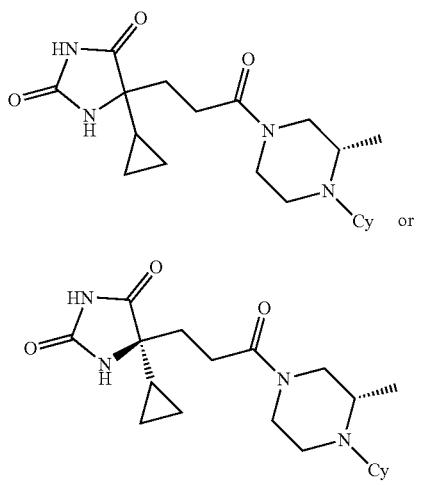

Va or Vb

95. A compound or pharmaceutically acceptable salt thereof, according to any one of clauses 1-94, wherein Cy is 6-10 membered monocyclic or fused bicyclic aryl.

96. A compound or pharmaceutically acceptable salt thereof, according to any one of clauses 1-94, wherein Cy is phenyl, or naphthyl.

97. A compound or pharmaceutically acceptable salt thereof, according to any one of clauses 1-94, wherein Cy is 6-10 membered monocyclic or fused bicyclic aryl, substituted with one or more $R^6$ groups.

98. A compound or pharmaceutically acceptable salt thereof, according to any one of clauses 1-94, wherein Cy is phenyl, substituted with one or more $R^6$ groups.

99. A compound or pharmaceutically acceptable salt thereof, according to any one of clauses 1-94, wherein Cy is phenyl, substituted with one, two, or three $R^6$ groups.

100. A compound or pharmaceutically acceptable salt thereof, according to any one of clauses 1-94, wherein Cy is 5-10 membered monocyclic or fused bicyclic heteroaryl comprising 1, 2 or 3 heteroatoms independently selected from N, O, and S.

101. A compound or pharmaceutically acceptable salt thereof, according to any one of clauses 1-94, wherein Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl.

102. A compound or pharmaceutically acceptable salt thereof, according to any one of clauses 1-94, wherein Cy is 5-10 membered monocyclic or fused bicyclic heteroaryl comprising 1, 2 or 3 heteroatoms independently selected from N, O, and S, substituted with one or more $R^6$ groups.

103. A compound or pharmaceutically acceptable salt thereof, according to any one of clauses 1-94, wherein Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl, each of which is substituted with one or more $R^6$ groups.

104. A compound or pharmaceutically acceptable salt thereof, according to any one of clauses 1-94, wherein Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl, each of which is substituted with one, two, or three $R^6$ groups.

105. A compound or pharmaceutically acceptable salt thereof, according to any one of clauses 97-99, 102-104, wherein $R^6$ is F, Cl, CN, or $NO_2$.

106. A compound or pharmaceutically acceptable salt thereof, according to any one of clauses 97-99, 102-104, wherein $R^6$ is —$CH_3$.

107. A compound or pharmaceutically acceptable salt thereof, according to any one of clauses 97-99, 102-104, wherein $R^6$ is 5-10 membered monocyclic or fused bicyclic heteroaryl comprising 1, 2 or 3 heteroatoms independently selected from N, O, and S.

108. A compound or pharmaceutically acceptable salt thereof, according to any one of clauses 97-99, 102-104, wherein $R^6$ is pyrazolyl, oxazolyl, oxadiazolyl, thiazolyl, pyridinyl, pyrazinyl, pyridazinyl, or pyrimidinyl.

109. A compound or pharmaceutically acceptable salt thereof, according to any one of clauses 97-99, 102-104, wherein $R^6$ is 5-10 membered monocyclic or fused bicyclic heteroaryl comprising 1, 2 or 3 heteroatoms independently selected from N, O, and S, substituted with one or more independently selected halo, $C_{1-4}$ alkyl, or $C_{1-4}$ alkoxy.

110. A compound or pharmaceutically acceptable salt thereof, according to any one of clauses 97-99, 102-104, wherein $R^6$ is pyrazolyl, oxazolyl, oxadiazolyl, thiazolyl, pyridinyl, pyrazinyl, pyridazinyl, or pyrimidinyl, each of which is substituted with one or more independently selected halo, $C_{1-4}$ alkyl, or $C_{1-4}$ alkoxy.

111. A compound or pharmaceutically acceptable salt thereof, according to any one of clauses 97-99, 102-104, wherein $R^6$ is pyrazolyl, oxazolyl, oxadiazolyl, thiazolyl, pyridinyl, pyrazinyl, pyridazinyl, or pyrimidinyl, each of which is substituted with one or more independently selected F, Cl, Me, Et, OMe, or OEt.

112. A compound or pharmaceutically acceptable salt thereof, according to any one of clauses 97-99, 102-104, wherein $R^6$ is —$NR^{9g}R^{9h}$.

113. A compound or pharmaceutically acceptable salt thereof, according to clause 113, wherein each $R^{9g}$ or $R^{9h}$ is independently selected from H, Me, or Et.

114. A compound or pharmaceutically acceptable salt thereof, according to any one of clauses 1-89, wherein the compound is according to Formula VIa or VIb:

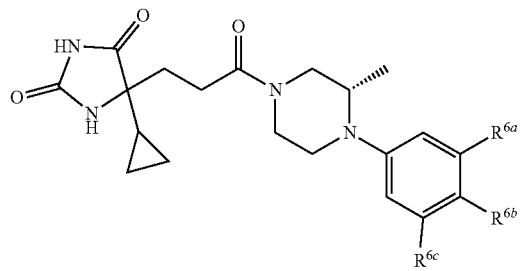

VIa or

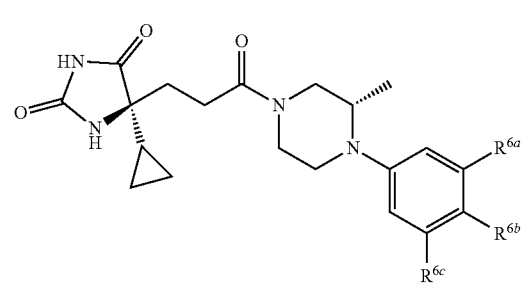

VIb wherein each one of $R^{6a}$, $R^{6b}$ and $R^{6c}$ is independently selected from H, F, Cl, and —CH$_3$.

115. A compound or pharmaceutically acceptable salt thereof, according to clause 115, wherein each $R^{9g}$ or $R^{9h}$ is independently selected from H, Me, and Et.

116. A compound or pharmaceutically acceptable salt thereof, according to clause 115, wherein $R^{6b}$ is H, and each one of $R^{6a}$, and $R^{6c}$ is independently selected from H, halo, and —CH$_3$.

117. A compound or pharmaceutically acceptable salt thereof, according to clause 115, wherein $R^{6b}$ is H, and each one of $R^{6a}$, and $R^{6c}$ is independently selected from H, F, Cl, and —CH$_3$.

118. A compound or pharmaceutically acceptable salt thereof, according to clause 115, wherein $R^{6b}$ is H, and each one of $R^{6a}$, and $R^{6c}$ is independently selected from H, F, and Cl.

119. A pharmaceutical composition comprising a pharmaceutically acceptable carrier and a pharmaceutically effective amount of a compound according to any one of clauses 1-119.

120. A pharmaceutical composition according to clause 120 comprising a further therapeutic agent.

121. A compound or pharmaceutically acceptable salt thereof, according to any one of clause 1-119, or a pharmaceutical composition according to clause 120 or 121 for use in medicine.

122. A compound or pharmaceutically acceptable salt thereof, according to any one of clause 1-119, or a pharmaceutical composition according to clause 120 or 121 for use in the prophylaxis and/or treatment of inflammatory conditions, and/or diseases involving degradation of cartilage and/or disruption of cartilage homeostasis.

123. A compound or pharmaceutically acceptable salt thereof, according to any one of clause 1-119, or a pharmaceutical composition according to clause 120 or 121 for use in the prophylaxis and/or treatment of osteoarthritis.

124. A compound or pharmaceutically acceptable salt thereof or a pharmaceutical composition for use according to clause 123 or 124, wherein said compound or pharmaceutical composition is administered in combination with a further therapeutic agent.

125. The pharmaceutical composition according to clause 121, or the use according to clause 125, wherein the further therapeutic agent is an agent for the prophylaxis and/or treatment of inflammatory conditions, and/or diseases involving degradation of cartilage and/or disruption of cartilage homeostasis.

126. The pharmaceutical composition according to clause 121, or the use according to clause 125, wherein the further therapeutic agent is an agent for the prophylaxis and/or treatment of osteoarthritis.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of inflammatory conditions, and/or diseases involving degradation of cartilage and/or disruption of cartilage homeostasis.

In another embodiment, the present invention provides compounds of the invention, or pharmaceutical compositions comprising a compound of the invention for use in the manufacture of a medicament for use in the prophylaxis and/or treatment of inflammatory conditions, and/or diseases involving degradation of cartilage and/or disruption of cartilage homeostasis.

In one embodiment, the present invention provides pharmaceutical compositions comprising a compound of the invention, and another therapeutic agent. In a particular embodiment, the other therapeutic agent is an agent for the prophylaxis and/or treatment of inflammatory conditions, and/or diseases involving degradation of cartilage and/or disruption of cartilage homeostasis.

In additional method of treatment aspects, this invention provides methods of prophylaxis and/or treatment of inflammatory conditions, and/or diseases involving degradation of cartilage and/or disruption of cartilage homeostasis, which methods comprise the administration of an effective amount of a compound of the invention or one or more of the pharmaceutical compositions herein described for the treatment or prophylaxis of said condition.

In additional method of treatment aspects, this invention provides methods of prophylaxis and/or treatment of a mammal afflicted with inflammatory conditions, and/or diseases involving degradation of cartilage and/or disruption of cartilage homeostasis, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of inflammatory diseases. In a particular embodiment, the inflammatory disease is selected from rheumatoid arthritis, and osteoarthritis. More particularly, the inflammatory disease is osteoarthritis.

In another embodiment, the present invention provides compounds of the invention, or pharmaceutical compositions comprising a compound of the invention for use in the manufacture of a medicament for use in the prophylaxis and/or treatment of inflammatory diseases. In a particular embodiment, the inflammatory disease is selected from rheumatoid arthritis, and osteoarthritis. More particularly, the inflammatory disease is osteoarthritis.

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In a particular embodiment, the inflammatory disease is selected from rheumatoid arthritis, and osteoarthritis. More particularly, the inflammatory disease is osteoarthritis.

In one embodiment, the present invention provides compounds of the invention or pharmaceutical compositions comprising a compound of the invention, for use in the prophylaxis and/or treatment of diseases involving degradation of cartilage and/or disruption of cartilage homeostasis. In a particular embodiment, the diseases involving degradation of cartilage and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the diseases involving degradation of cartilage and/or disruption of cartilage homeostasis is osteoarthritis (OA).

In another embodiment, the present invention provides compounds of the invention, or pharmaceutical compositions comprising a compound of the invention for use in the manufacture of a medicament for use in the prophylaxis and/or treatment of diseases involving degradation of cartilage and/or disruption of cartilage homeostasis. In a particular embodiment, the diseases involving degradation of cartilage and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the diseases involving degradation of cartilage and/or disruption of cartilage homeostasis is osteoarthritis (OA).

In additional method of treatment aspects, this invention provides methods of prophylaxis and/or treatment of a mammal afflicted with diseases involving degradation of cartilage and/or disruption of cartilage homeostasis, which methods comprise the administration of an effective amount of a compound of the invention or one or more of the pharmaceutical compositions herein described for the treatment or prophylaxis of said condition. In a particular embodiment, the diseases involving degradation of cartilage and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly the diseases involving degradation of cartilage and/or disruption of cartilage homeostasis is osteoarthritis (OA).

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, Auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologies such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts and Greene, 2012).

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 μm). Thin layer chromatography is carried out using pre-coated silica gel 60F-254 plates (thickness 0.25 mm). $^1$H NMR spectra are recorded on a 400 MHz Avance Bruker spectrometer or a 300 MHz DPX Bruker spectrometer. Chemical shifts (δ) for $^1$H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), quintuplet (quin), multiplet (m) and broad (br). Electrospray MS spectra are obtained on a Waters platform LC/MS spectrometer or with Waters Acquity UPLC with Waters Acquity PDA detector and SQD mass spectrometer. Columns used: UPLC BEH C18 1.7 μm 2.1×5 mm VanGuard Pre-column with Acquity UPLC BEH C18 1.7 μm 2.1×30 mm Column or Acquity UPLC BEH C18 1.7 μm 2.1×50 mm Column. All the methods are using MeCN/H$_2$O gradients. MeCN and H$_2$O contain either 0.1% Formic Acid or 0.05% NH$_3$. Preparative LCMS: column used, Waters XBridge Prep C18 5 μm ODB 30 mm ID×100 mm L (preparative column) and Waters XBridge C18 5 μm 4.6 mm ID×100 mm L (analytical column). All the methods are using MeCN/H$_2$O gradients. MeCN and H$_2$O contain either 0.1% Formic Acid or 0.1% Diethylamine. Chiral HPLC analysis are obtained from a Waters 2690 Alliance HPLC system. Microwave heating is performed with a Biotage Initiator. Optical rotation was determined on a Dr. Kernchen Propol digital automatic polarimeter.

TABLE I

List of abbreviations used in the experimental section:

| Abbreviation | Definition |
|---|---|
| μL | microliter |
| AUC | Area Under the Curve |
| BINAP | 2,2'-Bis(diphenylphosphino)-1,1'-binaphthalene |
| Bn | Benzyl |
| br. d | Broad doublet |
| Boc | tert-Butyloxy-carbonyl |
| BOP | (Benzotriazol-1-yloxy)tris(dimethylamino)phosphonium hexafluorophosphate |
| br. s | Broad singlet |
| br. t | Broad triplet |
| Cat. | Catalytic amount |
| CDI | 1,1'-Carbonyldiimidazole |
| COCl$_2$ | Phosgene |
| Cpd | Compound |
| d | doublet |
| DavePhos | 2-Dicyclohexylphosphino-2'-(N,N-dimethylamino)biphenyl |
| DCM | Dichloromethane |
| DEAD | Diethyl azodicarboxylate |
| DIPE | Diisopropylether |
| DIPEA | N,N-diisopropylethylamine |
| DMA | Dimethylacetamide |
| DMAP | 4-Dimethylaminopyridine |
| DME | Dimethoxyethane |
| DMF | N,N-dimethylformamide |
| DMPU | 1,3-Dimethyl-3,4,5,6-tetrahydro-2(1H)-pyrimidinone |
| DMSO | Dimethylsulfoxide |
| dppf | 1,1'-Bis(diphenylphosphino) ferrocene |
| EDC | 1-ethyl-3-(3-dimethylaminopropyl)carbodiimide |
| EDC•HCl | N-(3-Dimethylaminopropyl)-N'-ethylcarbodiimide hydrochloride |
| eq. | Equivalent |
| Et$_3$N | Triethylamine |
| Et$_2$O | Diethyl ether |
| EtOAc | Ethyl acetate |
| EtOH | Ethanol |
| FBS | Fetal bovine serum |
| g | gram |
| h | hour |
| HATU | O-(7-azabenzotriazol-1-yl)-N,N,N',N'-tetramethyluronium hexafluorophosphate |
| HOBt | Hydroxybenzotriazole |
| HPLC | High-performance liquid chromatography |
| HPLC/MS | High-performance liquid chromatography/mass-spectrometry |
| HRMS | High-resolution Mass Spectrometry |
| HRP | horseradish peroxydase |
| Int | Intermediate |
| JohnPhos | (2-Biphenyl)di-tert-butylphosphine |
| kg | kilogram |
| L | liter |
| LCMS | Liquid Chromatography- Mass Spectrometry |
| LDA | Lithium diisopropylamide |
| LiHMDS | Lithium bis(trimethylsilyl)amide |
| m | multiplet |

TABLE I-continued

List of abbreviations used in the experimental section:

| Abbreviation | Definition |
|---|---|
| m-CPBA | 3-Chloroperbenzoic acid |
| MeCN | Acetonitrile |
| MEK | Methyl ethyl ketone |
| Meldrum's acid | 2,2-dimethyl-1,3-dioxane-4,6-dione |
| MeOH | Methanol |
| mg | milligram |
| min | minute |
| mL | millilitre |
| mmol | millimoles |
| MMP | Matrix Metallo Proteinase |
| Ms'd | Mass measured by LCMS |
| Mtd | Method |
| Mukaiyama reagent | 2-Chloro-1-methylpyridinium iodide |
| MW | Molecular weight |
| N.A. | Not available |
| n/a | No measurable activity |
| iPrOH | Isopropyl alcohol |
| nBuOH | n-Butanol |
| NMR | Nuclear Magnetic Resonance |
| PBF | phosphate buffered formalin |
| PBS | Phosphate buffered salin |
| P(tBu)$_3$ | Tristertbutylphosphine |
| P(Bu)$_3$ | Tributylphosphine |
| Pd(PPh$_3$)$_4$ | Tetrakis(triphenylphosphine)palladium(0) |
| Pd/C | Palladium on Carbon 10% |
| Pd$_2$(dba)$_3$ | Tris(dibenzylideneacetone) dipalladium(0) |
| PdCl$_2$(dppf) | [1,1'-Bis(diphenylphosphino)ferrocene] dichloropalladium(II) |
| PdCl$_2$[P(o-Tol)$_3$]$_2$ | Dichlorobis(tri-o-tolylphosphine)palladium(II) |
| Pd(OAc)$_2$ | Palladium(II) acetate |
| Pd(OH)$_2$/C | Palladium hydroxide on carbon |
| PEG | Polyethylene glycol |
| PEPPSI™-IPr | [1,3-Bis(2,6-Diisopropylphenyl)imidazol-2-ylidene](3-chloropyridyl) palladium(II) dichloride |
| ppm | part-per-million |
| PS-CDI | Polymer supported 1,1'-Carbonyldiimidazole |
| PS-Mukaiyama reagent | Polymer supported Mukaiyama reagent |
| q | quadruplet |
| r.t. | room temperature |
| RNA | Ribonucleic acid |
| Rt | retention time |
| RuPhos | 2-Dicyclohexylphosphino-2',6'-diisopropoxybiphenyl |
| s | singlet |
| SCX | Biotage Isolute ® SCX(Biotage Part 530) |
| SCX-2 | Biotage Isolute ® SCX-2 (Biotage Part 532) |
| sept | septuplet |
| SFC | Supercritical fluid chromatography |
| SM | Starting Material |
| Ster | Stereochemistry |
| t | triplet |
| TBAF | Tetra-n-butylammonium fluoride |
| 5(6)-TAMRA | 5(6)-Carboxytetramethylrhodamine (CAS# 98181-63-6) |
| 5-FAM | 5-carboxyfluorescein (CAS# 76823-03-5) |
| t-BuOH | Tert-butanol |
| TBDPSCl | Tert-butyldiphenylsilyl chloride |
| TBSCl | Tert-butyldimethylsilyl chloride |
| TEA | Triethylamine |
| TFA | Trifluoroacetic acid |
| THF | Tetrahydrofuran |
| TLC | Thin-layer chromatography |
| TIPS | triisopropyl silyl |
| UPLC/MS | Ultra-performance liquid chromatography/mass-spectrometry |
| XantPhos | 4,5-Bis(diphenylphosphino)-9,9-dimethylxanthene |
| XPhos | 2-Dicyclohexylphosphino-2',4',6'-triisopropylbiphenyl |

Synthetic Preparation of the Compound of the Invention

Example 1. General Synthetic Methods 1.1. Synthetic Methods Overview

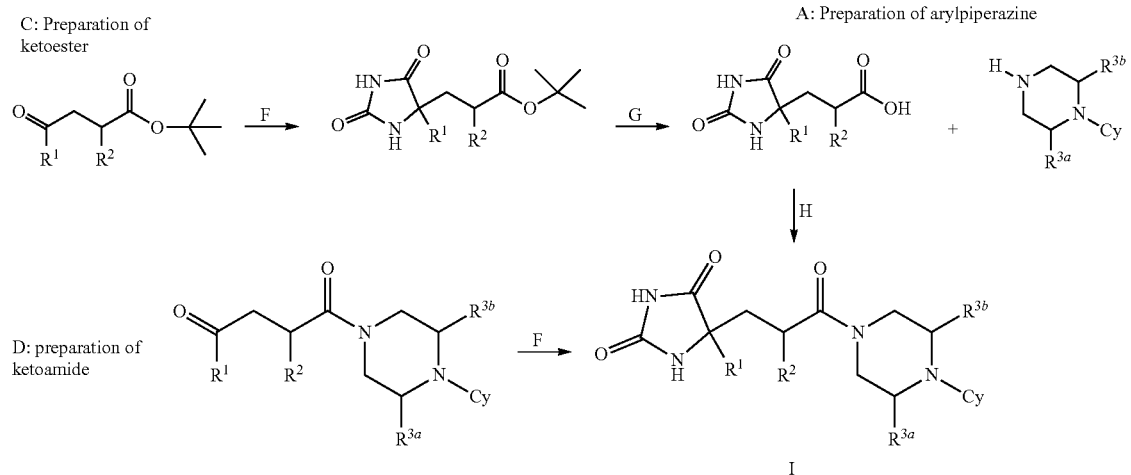

General Methods A: Preparation of Arylpiperazine
Method A1: NBoc protection
Method A2: Buchwald reaction with NBoc-piperazine
Method A3: Suzuki reaction
Method A4: SNAr with NBoc-piperazine
Method A5: NBoc deprotection
Method A6: with TIPS protecting group
Method A7: Buchwald reaction with NH-piperazine
Method A8: SNAr with NH-piperazine
General Methods C: Preparation of Ketoester
Method C1: from Meldrum's acid
Method C2: with tert-butyl bromoacetate
Method C3: esterification
Method C4: Stetter reaction
Method C5: via epoxide opening
General Method D: Preparation of Ketoamide
Method D1: preparation of acrylamide
Method D2: Stetter reaction
Method D4: Oxidative cleavage
Method D5: via furan oxidation
Method D6: via a-bromo ketone
Method D7: ketoamide functionalization by Suzuki coupling
General Method E: Functionalization of g-Ketoamide
General Method F: Bucherer Bergs Reaction
General Method G: Method for Preparation of Hydantoin Propionic Acids
General Method H: Amide Bond Formation
Method H1: EDC/HOBt
Method H2: HATU
Method H3: BOP
Method H4: CDI
Method H5: Mukaiyama reagent
General Method I: Functionalization of Final Compound
Method I1: acetylation
Method I2: N-Boc deprotection
Method I3: alkylation
Method I4: O-debenzylation
Method I5: Two-steps functionalization by Suzuki reaction
Method I6: Suzuki reaction 1.2. General Methods 1.2.1. General Methods A: Preparation of Arylpiperazine 1.2.1.1. Method A1: NBoc Protection

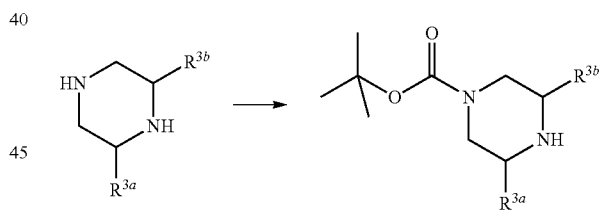

1.2.1.2. Illustrative synthesis of cis-3,5-dimethyl-piperazine-1-carboxylic acid tert-butyl ester

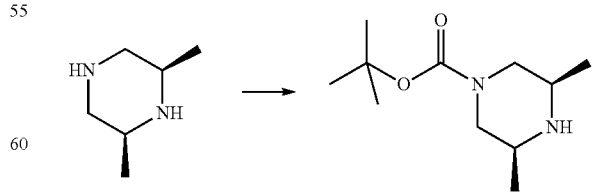

To a solution of the cis-2,6-dimethyl-piperazine (2 g, 17.515 mmol, 1 eq.) in DCM (200 mL) at 0° C. is added dropwise a solution of di-tert-butyl dicarbonate in DCM (20 mL). After 3.5 h, reaction mixture is quenched by a saturated $Na_2CO_3$ solution, the organic layer is separated, and the aqueous layer is extracted with DCM. The combined organic layers are washed with brine, dried over anhydrous Na₂SO₄, filtered and concentrated in vacuo. Purification by flash chromatography on silica gel (eluting with DCM/MeOH 100/0 to 90/10) affords the expected product.

1.2.2. Method A2: Buchwald Reaction with NBoc-Piperazine

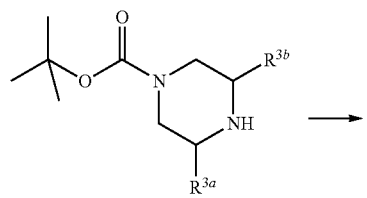

1.2.2.1. Method A2a (Pd₂(dba)₃/BINAP)

A flask is charged with N-Boc protected piperazine (1 eq.), bromoderivative (0.5-2 eq.), BINAP (0.042-0.12 eq.), NaOtBu (0.7-1.4 eq.) and toluene. The reaction mixture is degassed with N₂ and Pd₂(dba)₃ (0.021-0.06 eq.) is added. Reaction mixture is heated at 90-110° C. for 2 h-20 h. The reaction mixture is quenched by addition of water or saturated NaHCO₃ solution, extracted with DCM or EtOAc. The combined organic layers are washed with water and brine, dried (over anhydrous Na₂SO₄ or MgSO₄), filtered and concentrated in vacuo to afford the expected arylpiperazine (used as such or purified by flash chromatography on silica gel).

Illustrative Synthesis of (S)-3-Methyl-4-(5-methyl-pyridin-3-yl)-piperazine-1-carboxylic acid tert-butyl ester

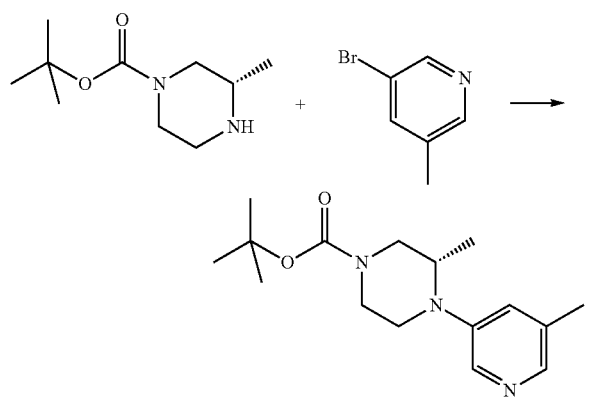

A flask is charged with (S)-3-methyl-piperazine-1-carboxylic acid tert-butyl ester (291 mg, 1.453 mmol, 1 eq.), 3-bromo-5-methyl-pyridine (300 mg, 1.744 mmol, 1.2 eq.), BINAP (45 mg, 0.073 mmol, 0.05 eq.), NaOtBu (196 mg, 2.034 mmol, 1.4 eq.) and toluene (2 mL). The reaction mixture is degassed with N₂ and Pd₂(dba)₃ (33 mg, 0.036 mmol, 0.025 eq.) is added. Reaction mixture is heated at 110° C. overnight, quenched with water, extracted with EtOAc. The combined organic layers are washed with water and brine, dried over anhydrous Na₂SO₄, filtered and concentrated in vacuo. Purification by flash chromatography on silica gel (eluting with DCM/MeOH 100/0 to 98/2) affords the expected product. LCMS: MW (calcd): 291; m/z MW (obsd): 292 (M+H).

Illustrative Synthesis of (S)-4-(3,5-Difluoro-phenyl)-3-methyl-piperazine-1-carboxylic acid tert-butyl ester

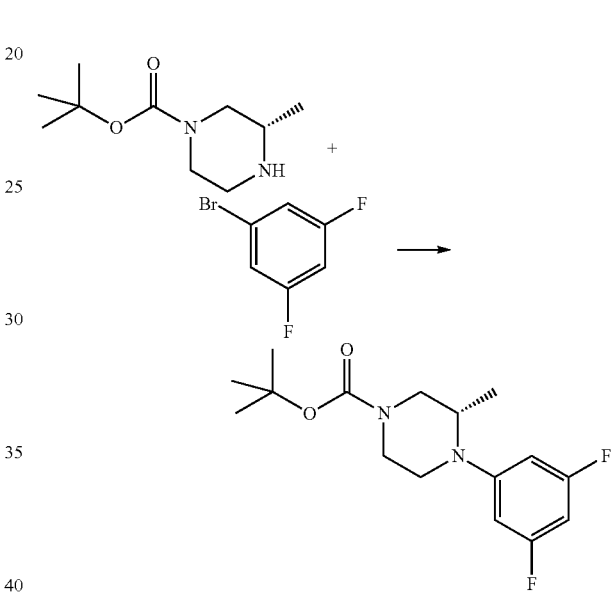

A flask is loaded with (S)-3-Methyl-piperazine-1-carboxylic acid tert-butyl ester (75 g, 0.374 mol, 1 eq.) and dry toluene (375 mL). The reaction mixture is degassed with N₂, 1-Bromo-3,5-difluoro-benzene (47.3 mL, 0.412 mol, 1.1 eq.), NaO^tBu (50.4 g, 0.524 mol, 1.4 eq.) and BINAP (11.66 g, 0.019 g, 0.05 eq.) are added. The reaction mixture is degassed with N₂ and Pd₂(dba)₃ (5.14 g, 0.006 mol, 0.015 eq.) is added. Reaction mixture is stirred at 110° C. for 2.5 h, quenched with water and EtOAc, extracted with EtOAc. The combined organic layers are washed with water and brine, dried over anhydrous Na₂SO₄, filtered and concentrated in vacuo to afford the expected N-Boc-arylpiperazine. LCMS: MW (calcd): 312; m/z MW (obsd): 313 (M+H).

1.2.2.1.1 Method A2b (Pd(OAc)₂/JohnPhos)

A flask is charged with N-Boc protected piperazine (1 eq.), halide derivative (1.1-1.2 eq.), JohnPhos (0.1-0.12 eq.), NaOtBu (1.2-1.4 eq.) and toluene. The reaction mixture is degassed with N₂ and Pd(OAc)₂ (0.06-0.1 eq.) is added. Reaction mixture is heated at 100° C. for 2 h-20 h, quenched by addition of water or saturated NaHCO₃ solution, extracted with DCM or EtOAc. The combined organic layers are washed with water and brine, dried (over anhydrous Na₂SO₄ or MgSO₄), filtered and concentrated in vacuo to afford the expected arylpiperazine after purification by flash chromatography on silica gel.

Illustrative Synthesis of (S)-4-(4-Chloro-pyridin-2-yl)-3-methyl-piperazine-1-carboxylic acid tert-butyl ester

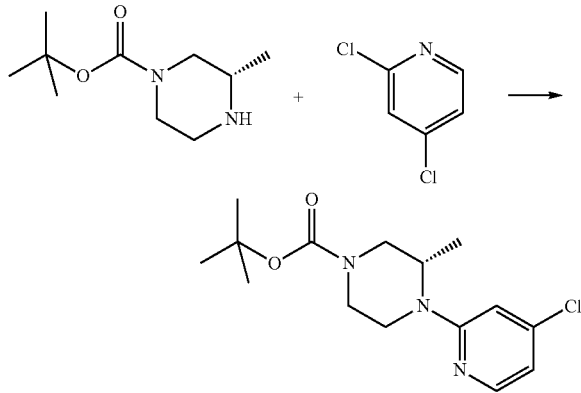

A flask is charged with (S)-3-methyl-piperazine-1-carboxylic acid tert-butyl ester (1 g, 4.993 mmol, 1 eq.), 2,4-dichloro-pyridine (887 mg, 5.992 mmol, 1.2 eq.), JohnPhos (149 mg, 0.499 mmol, 0.1 eq.), NaOtBu (672 mg, 6.990 mmol, 1.4 eq.) and toluene (5 mL). The reaction mixture is degassed with $N_2$ and Pd(OAc)$_2$ (112 mg, 0.499 mmol, 0.1 eq.) is added. Reaction mixture is heated at 100° C. overnight, quenched by addition of water, extracted with EtOAc. The combined organic layers are washed with brine, dried over anhydrous $Na_2SO_4$, filtered and concentrated in vacuo. Purification by flash chromatography on silica gel affords the expected product. LCMS: MW (calcd): 312; m/z MW (obsd): 312-314 (M+H).

1.2.2.1.2 Method A2c (PEPPSI)

Illustrative Synthesis of (S)-2-Methyl-2,3,5,6-tetrahydro-[1,2]bipyrazinyl-4-carboxylic acid tert-butyl ester

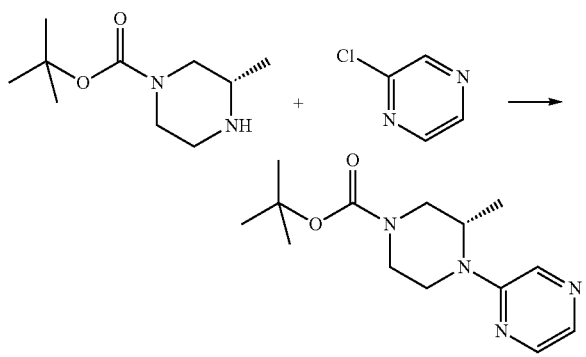

A flask is charged with (S)-3-methyl-piperazine-1-carboxylic acid tert-butyl ester (3 g, 14.979 mmol, 1 eq.), 2-chloropyrazine (1.71 g, 14.979 mmol, 1 eq.), $Cs_2CO_3$ (6.83 g, 20.97 mmol, 1.4 eq.) and DME (60 mL). The reaction mixture is degassed with $N_2$ and PEPPSI™-IPr (0.2 g, 0.3 mmol, 0.02 eq.) is added. Reaction mixture is heated at 110° C. overnight, quenched with water, extracted with $Et_2O$. The combined organic layers are washed with water and brine, dried over anhydrous $MgSO_4$, filtered and concentrated in vacuo. Purification by flash chromatography on silica gel (eluting with Heptane/EtOAc 80/20 to 30/70) affords the expected product. LCMS: MW (calcd): 278; m/z MW (obsd): 279 (M+H).

1.2.2.1.3 Method A2d (Pd(OAc)$_2$/P(tBu)$_3$)

A flask is charged with N-Boc protected piperazine (1 eq.), bromo derivative (1.1 eq.), Pd(OAc)$_2$ (0.06 eq.), NaOtBu (1.5 eq.) and toluene. The reaction mixture is degassed with $N_2$ and P(tBu)$_3$ (1M solution in toluene, 0.12 eq.) is added. Reaction mixture is heated at 105° C. for 4 h-20 h, filtered on celpure P65, washed with EtOAc and DCM. The filtrate is concentrated in vacuo to afford the expected arylpiperazine after purification by flash chromatography on silica gel.

Illustrative Synthesis of (S)-3-Methyl-4-(1-methyl-1H-indazol-5-yl)-piperazine-1-carboxylic acid tert-butyl ester

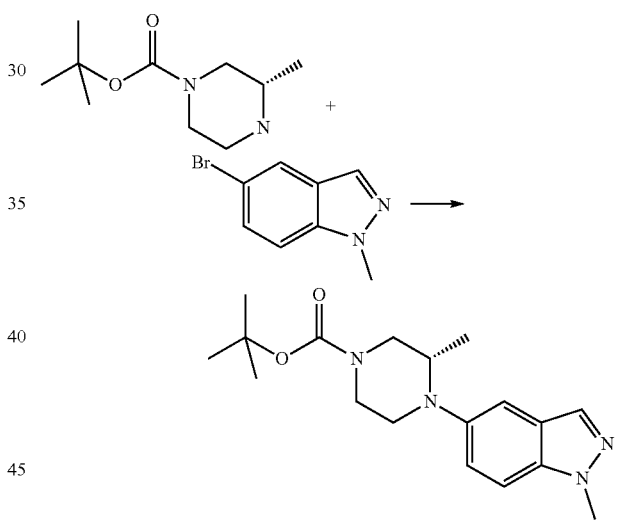

A flask is charged with (S)-3-methyl-piperazine-1-carboxylic acid tert-butyl ester (50 mg, 0.25 mmol, 1 eq.), 5-bromomethylindazole (58 mg, 0.27 mmol, 1.1 eq.), Pd(OAc)$_2$ (3 mg, 0.015 mmol, 0.06 eq.), NaOtBu (36 mg, 0.38 mmol, 1.5 eq.) and toluene. The reaction mixture is degassed with $N_2$ and P(tBu)$_3$ (1M solution in toluene, 30 µL, 0.03 mmol, 0.12 eq.) is added. Reaction mixture is heated at 105° C. overnight, filtered on celpure P65, washed with EtOAc and DCM. The filtrate is concentrated in vacuo and purified by flash chromatography on silica gel (eluting with Heptane/EtOAc 100/0 to 70/30) to afford the expected product. LCMS: MW (calcd): 330; m/z MW (obsd): 331 (M+H).

1.2.2.1.4 Method A2e (Pd$_2$(dba)$_3$/Xantphos)

A flask is charged with N-Boc protected piperazine (1 eq.), bromo derivative (0.67 eq. to 1.1 eq.), a base ($Cs_2CO_3$, 2eq. or NaOtBu, 1.4 eq.), Xantphos (0.12 eq.) and a solvent Illustrative Synthesis of (S)-4-(3-Cyano-5-fluoro-phenyl)-3-methyl-piperazine-1-carboxylic acid tert-butyl ester

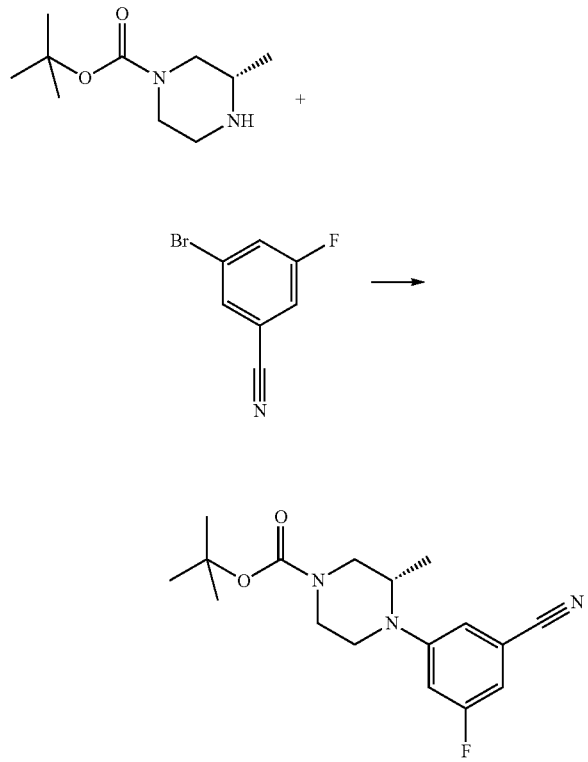

A flask is charged with (S)-3-methyl-piperazine-1-carboxylic acid tert-butyl ester (100 mg, 0.50 mmol, 1 eq.), 3-bromo-5-fluoro-benzonitrile (110 mg, 0.55 mmol, 1.1 eq.), NaOtBu (67 mg, 0.7 mmol, 1.4 eq.), Xantphos (35 mg, 0.06 mmol, 0.12 eq.) and toluene (2 mL). The reaction mixture is degassed with $N_2$ and $Pd_2(dba)_3$ (27 mg, 0.03 mmol, 0.06 eq.) is added. Reaction mixture is heated at 115° C. for 4.5 h and filtered on celpure P65. The filtrate is concentrated in vacuo and purified by flash chromatography on silica gel (eluting with Heptane/EtOAc 100/0 to 80/20) to afford the expected product. LCMS: MW (calcd): 319; m/z MW (obsd): 320 (M+H).

1.2.2.1.5 Method A2f ($Pd_2(dba)_3$/DavePhos)

A flask is charged with N-Boc protected piperazine (1 eq.), bromoderivative (1.1 eq.), DavePhos (0.12 eq.), NaOtBu (1.2 eq.) and toluene. The reaction mixture is degassed with $N_2$ and $Pd_2(dba)_3$ (0.06 eq.) is added. Reaction mixture heated at 90-110° C. for 2 h-20 h and filtered on celpure P65. The filtrate is concentrated in vacuo to afford the expected arylpiperazine after purification by flash chromatography on silica gel.

Illustrative Synthesis of (S)-3-Methyl-4-quinolin-3-yl-piperazine-1-carboxylic acid tert-butyl ester

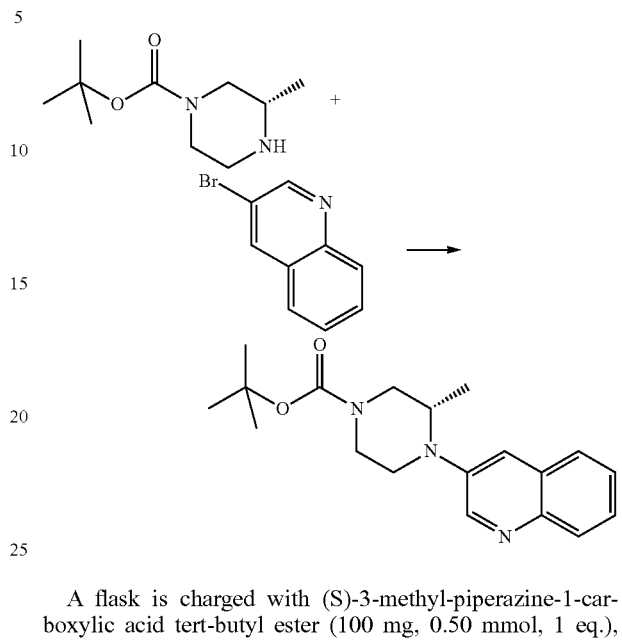

A flask is charged with (S)-3-methyl-piperazine-1-carboxylic acid tert-butyl ester (100 mg, 0.50 mmol, 1 eq.), 3-bromoquinoleine (114 mg, 0.55 mmol, 1.1 eq.), DavePhos (24 mg, 0.06 mmol, 0.12 eq.), NaOtBu (58 mg, 0.60 mmol, 1.2 eq.) and toluene (2 mL). The reaction mixture is degassed with $N_2$ and $Pd_2(dba)_3$ (27 mg, 0.03 mmol, 0.06 eq.) is added. Reaction mixture is heated at 95° C. overnight and filtered on celpure P65. The filtrate is concentrated in vacuo and purified by flash chromatography on silica gel (eluting with Heptane/EtOAc 100/0 to 70/30) to afford the expected product. LCMS: MW (calcd): 327; m/z MW (obsd): 328 (M+H).

1.2.2.1.6 Method A2 g ($Pd_2(dba)$/Xphos)

Illustrative Synthesis of (S)-3-Methyl-4-(1-methyl-1H-pyrazol-3-yl)-piperazine-1-carboxylic acid tert-butyl ester

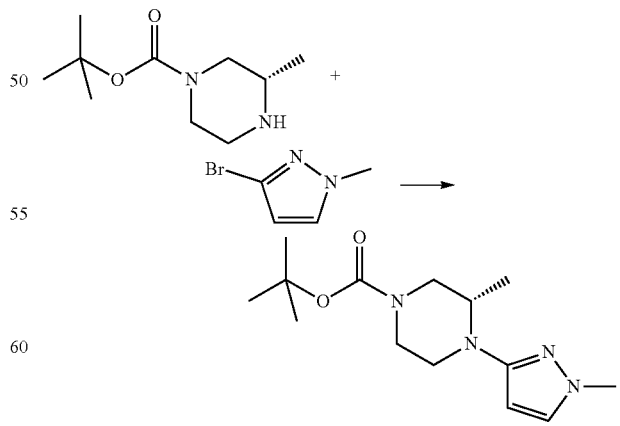

A flask is charged with (S)-3-methyl-piperazine-1-carboxylic acid tert-butyl ester (500 mg, 2.5 mmol, 1 eq.), 3-bromo-1-methyl-1H-pyrazole (442 mg, 2.75 mmol, 1.1 eq.), NaOtBu (288 mg, 3 mmol, 1.2 eq.), XPhos (143 mg, 0.3 mmol, 0.12 eq.) and toluene (15 mL). The reaction mixture is degassed with $N_2$ and $Pd_2(dba)_3$ (137 mg, 0.15 mmol, 0.06 eq.) is added. Reaction mixture is heated at 105° C. overnight, quenched with saturated $NaHCO_3$ solution, extracted with EtOAc. The combined organic layers are washed with brine, dried over anhydrous $Na_2SO_4$ and concentrated in vacuo. The residue is purified by flash chromatography on silica gel (eluting with Heptane/EtOAc 100/0 to 50/50) to afford the expected product. LCMS: MW (calcd): 280; m/z MW (obsd): 281 (M+H).

1.2.2.2. Method A3: Suzuki Reaction

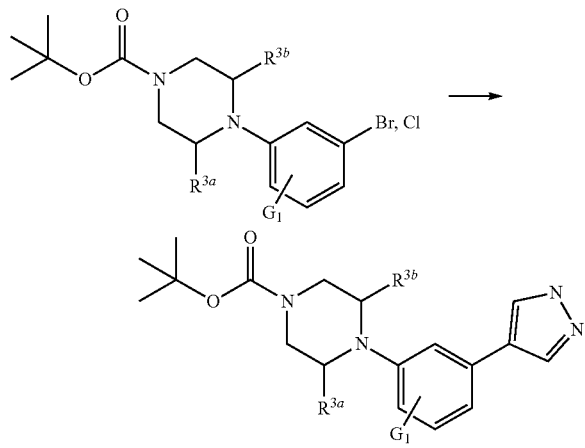

$G_1$=H, C or F

A solution of $Na_2CO_3$ (3 eq.) in water is added to a mixture of halogeno derivative (1 eq., obtained by any method A2), boronic ester (2 eq.) and dioxane degassed with argon. $PdCl_2(dppf)$ (0.2 eq.) is added, and the reaction is stirred at 140° C. in a microwave reactor for 30 min to 45 min. The reaction mixture is poured in water and DCM. The organic layer is washed with water and concentrated in vacuo to afford the expected arylpiperazine (used as such or purified by flash chromatography on silica gel).

Illustrative Synthesis of (S)-4-[3-Fluoro-5-(1H-pyrazol-4-yl)-phenyl]-3-methyl-piperazine-1-carboxylic acid tert-butyl ester

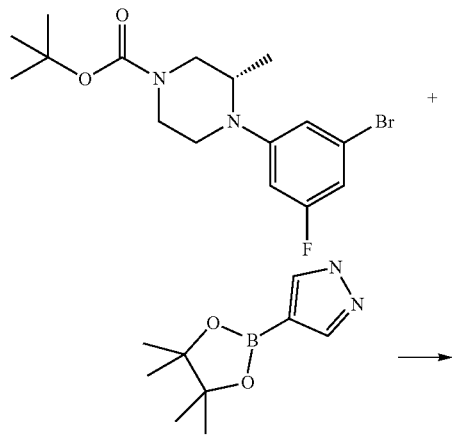

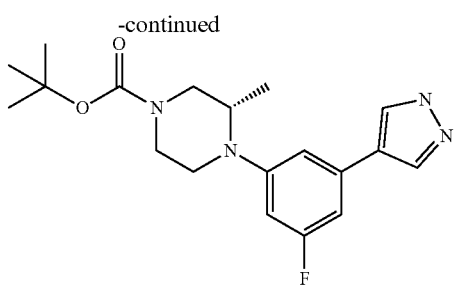

A solution of $Na_2CO_3$ (771 mg, 4.02 mmol, 3 eq.) in water (4 mL) is added to a mixture of ((S)-4-(3-Bromo-5-fluoro-phenyl)-3-methyl-piperazine-1-carboxylic acid tert-butyl ester (500 mg, 1.34 mmol, 1 eq.), 4-(4,4,5,5-Tetramethyl-[1,3,2]dioxaborolan-2-yl)-1H-pyrazole (520 mg, 2.68 mmol, 2 eq.) and dioxane (8 mL) degassed with argon. $PdCl_2(dppf)$ (219 mg, 0.27 mmol, 0.2 eq.) is added, and the reaction is stirred at 140° C. in a microwave reactor for 40 min. Reaction mixture is poured in 50 mL water and 50 mL DCM and extracted. The organic layer is washed with water and concentrated in vacuo to afford the expected product used in next reaction step without further purification. LCMS: MW (calcd): 360; m/z MW (obsd): 361 (M+H).

1.2.2.3. Method A4: SNAr with NBoc-piperazine

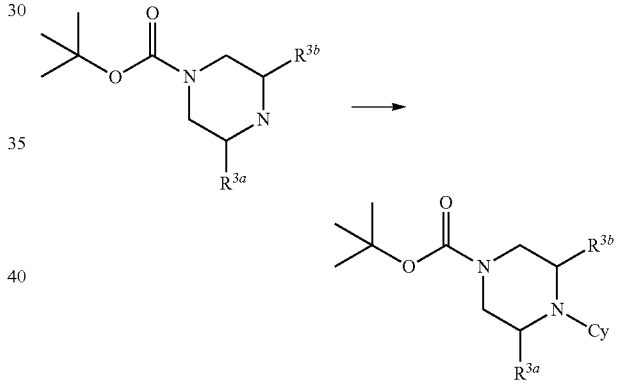

A vial is charged with arylchloride derivative (1 eq.), (S)-3-methyl-piperazine-1-carboxylic acid tert-butyl ester (1 to 1.6 eq.), a base ($Et_3N$ or DIPEA, 1 to 3 eq.) and a solvent (DCM, DMF, THF or MeCN). The reaction mixture is heated (60° C.-120° C.) for 1.5 h to 5 days. The appropriate work up (concentration in vacuo or aqueous work up extracting with EtOAc) followed by purification by flash chromatography on silica gel affords the expected arylpiperazine.

Illustrative Synthesis of (S)-4-(6-Chloro-pyrimidin-4-yl)-3-methyl-piperazine-1-carboxylic acid tert-butyl ester

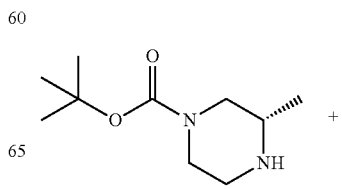

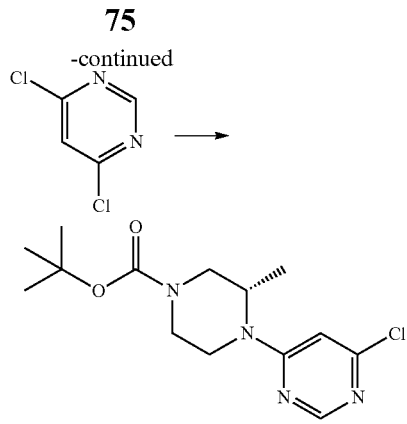

A vial is charged with 4,6-dichloropyrimidine (3.55 g, 23.83 mmol, 1 eq.), (S)-3-methyl-piperazine-1-carboxylic acid tert-butyl ester (5 g, 25.02 mmol, 1.05 eq.), Et₃N (3.35 mL, 23.83 mmol, 1 eq.) and CH₃CN (70 mL). The reaction mixture is heated at 120° C. for 1.5 h, concentrated in vacuo and the residue is taken up in EtOAC, washed with a saturated NH₄Cl solution, brine, dried over anhydrous MgSO₄, filtered and concentrated in vacuo. The residue is purified by flash chromatography on silica gel (eluting with Heptane/EtOAc 90/10 to 80/20) to afford the expected product. LCMS: MW (calcd): 323; m/z MW (obsd): 313-315 (M+H).

1.2.2.4. Method A5: NBoc Deprotection

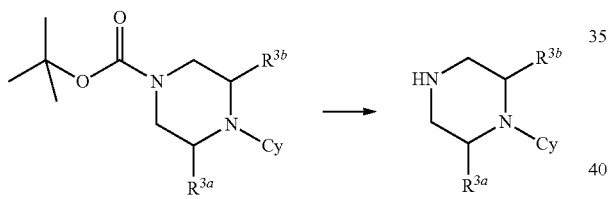

1.2.2.4.1 Method A5a (HCl)

A flask is charged with N-tert-butoxy carbonyl derivative (1 eq.), HCl 4N in dioxane (10 to 40 eq.) is added. The reaction mixture is stirred at r.t. for 1 h to 2 days. If a precipitate is formed, it is filtered and washed with Et₂O or CH₃CN, otherwise, the reaction mixture is concentrated in vacuo. Both work up afford the expected arylpiperazine as hydrochloride salt.

Illustrative Synthesis of Int 198

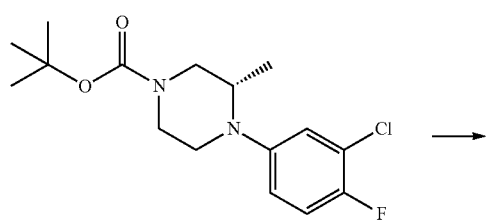

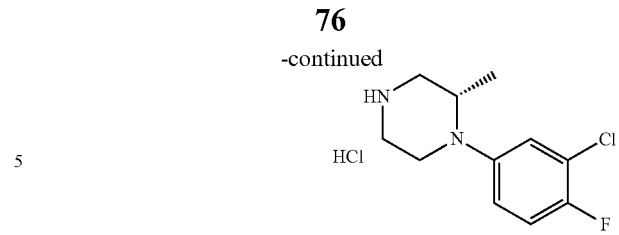

A flask is charged with N-tert-butoxycarbonyl derivative (4.06 g, 12.35 mmol, 1 eq.), HCl 4N in dioxane (100 mL, 400 mmol, 32 eq.) is added. The reaction mixture is stirred at r.t. overnight and concentrated in vacuo. The residue is triturated in Et₂O, filtered and dried in vacuo to afford the expected product as hydrochloride salt. LCMS: MW (calcd): 229; m/z MW (obsd): 229-231 (M+H).

Illustrative Synthesis of (2S)-1-(3,5-difluorophenyl)-2-methyl-piperazine (Int 207)

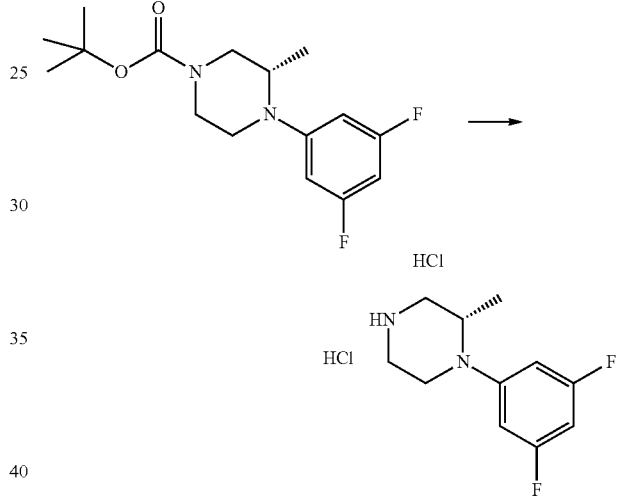

A flask is loaded with (S)-4-(3,5-Difluoro-phenyl)-3-methyl-piperazine-1-carboxylic acid tert-butyl ester (64 g, 0.204 mol, 1 eq.) and acetonitrile (191 mL). HCl 4N in dioxane (255 mL, 1.018 mol, 5 eq.) is added at 0° C. and the reaction mixture is stirred at 0° C. for 1.5 h then at r.t. for 3.5 h. The precipitate is filtered, washed with acetonitrile and Et₂O, suspended in a mixture acetonitrile/Et₂O (300 mL/100 mL) and stirred at r.t. overnight. The suspension is filtered; the precipitate is washed again with acetonitrile and Et₂O and dried in vacuo to afford the expected arylpiperazine hydrochloride salt. LCMS: MW (calcd): 212; m/z MW (obsd): 213 (M+H).

1.2.2.4.2 Method A5b (HCl+Basic Work Up)

To a solution of N-tert-butoxycarbonyl derivative (1 eq.) in acetonitrile or DCM is added HCl 4N in dioxane (10 to 40 eq.). The reaction mixture is stirred at r.t. for 1 h to 2 days, concentrated in vacuo and the residue is taken up in water and EtOAc or DCM. The aqueous layer is separated and basified (with either NaOH 1N solution or with a saturated Na₂CO₃ or NaHCO₃ solution) and extracted with EtOAc or DCM. The combined organic layers are dried over anhydrous Na₂SO₄ (or MgSO₄), filtered and concentrated in vacuo to afford the expected arylpiperazine.

Illustrative Synthesis of Int 278

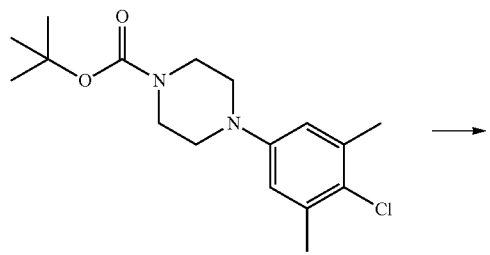

N-tert-butoxycarbonyl derivative (632 mg, 2.88 mmol, 1 eq.) is stirred in HCl 4N in dioxane (6 mL) at room temperature for 3 hours. The reaction mixture is diluted with water, a solution of saturated NaHCO₃ is added and the aqueous layer is extracted with DCM several times. The combined organic layers are dried over anhydrous Na₂SO₄, filtered and concentrated in vacuo to afford the expected product. LCMS: MW (calcd): 224; m/z MW (obsd): 225-227 (M+H).

1.2.2.4.3 Method A5c (TEA+Basic Work Up)

A flask is charged with N-tert-butoxycarbonyl derivative (1 eq.) and a mixture DCM/TFA (5/1). The reaction mixture is stirred at r.t. for 2 h to 3 h, concentrated in vacuo. The residue is taken up in a saturated Na₂CO₃ solution and extracted with EtOAc and/or EtOAc/n-BuOH. The combined organic layers are dried over anhydrous Na₂SO₄, filtered and concentrated in vacuo to afford the expected arylpiperazine.

Illustrative Synthesis of Int 259

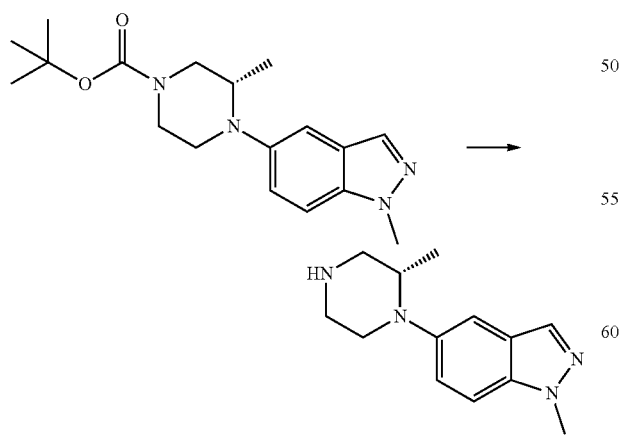

A flask is charged with N-tert-butoxy carbonyl derivative (320 mg, 0.97 mmol, 1 eq.), DCM (5 mL) and TFA (1 mL).

The reaction mixture is stirred at r.t. for 2 h, concentrated in vacuo. The residue is taken up in a saturated Na₂CO₃ solution and extracted with EtOAc and EtOAc/n-BuOH. The combined organic layers are dried over anhydrous Na₂SO₄, filtered and concentrated in vacuo to afford the expected product. LCMS: MW (calcd): 230; m/z MW (obsd): 231 (M+H).

1.2.2.4.4 Method A5e (H₂SO₄): Boc and Acetamide Deprotection

Illustrative Synthesis of Int 193

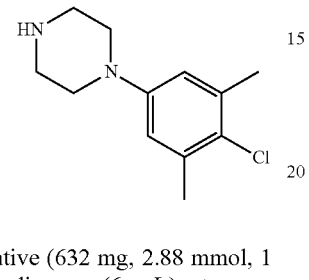

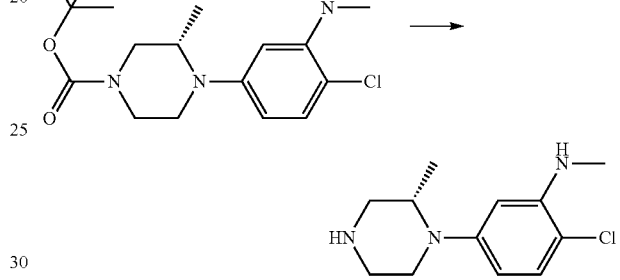

A flask is charged with N-tert-butoxycarbonyl derivative (60 mg, 0.16 mmol, 1.0 eq.) and water (1 mL), and concentrated sulfuric acid (0.2 mL) is added. The reaction mixture is stirred at 80° C. for 16 h. An aqueous NaOH 2N solution is added until pH reaches 13, and the aqueous phase is extracted 3 times with DCM. The combined organic phases are dried over anhydrous MgSO₄, filtered and concentrated in vacuo to afford the expected product. LCMS: MW (calcd): 239; m/z MW (obsd): 240 (M+H).

1.2.2.5. Method a 6: With TIPS Protecting Group

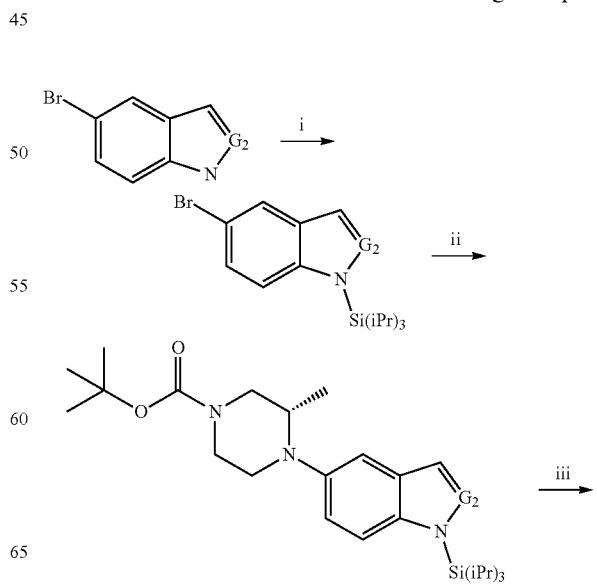

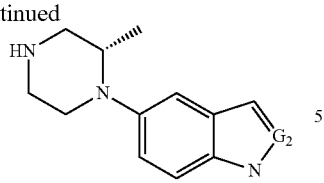

wherein $G_2$=C or N

Step i)

To a solution of the bromo heteroaryl derivative (1 eq.) in THF at 0° C. is added NaH portionwise (50% in oil, 2 eq.). Reaction mixture is stirred at r.t. for 1 h, cooled to 0° C. and a solution of triisopropylsilyl chloride (1.2 eq.) in THF is added dropwise. The reaction mixture is stirred at r.t. and concentrated in vacuo. The residue is partitioned between water and EtOAc, the organic layer is dried over anhydrous $Na_2SO_4$, filtered and concentrated in vacuo. Purification by flash chromatography on silica gel affords the expected triisopropylsilyl derivative.

Step ii)

A flask is charged with bromoderivative (1 eq.), (S)-3-methyl-piperazine-1-carboxylic acid tert-butyl ester (1.15 eq.), NaOtBu (1.7 eq.) and toluene. The reaction mixture is degassed with $N_2$ and $PdCl_2[P(o-Tol)_3]_2$ (0.05 eq.) is added. Reaction mixture is heated at 110° C. overnight, quenched by addition of water, extracted with EtOAc. The combined organic layers are washed with water and brine, dried over anhydrous $Na_2SO_4$, filtered and concentrated in vacuo. The residue is purified by flash chromatography on silica gel to afford the expected NBoc-arylpiperazine.

Step iii)

To a solution of the NBoc-arylpiperazine (1 eq.) in DCM is added TFA (50 eq.). Reaction mixture stirred at r.t. overnight and concentrated in vacuo. The residue is taken up in EtOAc and saturated $NaHCO_3$ solution and extracted with EtOAc. The combined organic layers are dried over anhydrous $Na_2SO_4$, filtered and concentrated in vacuo to afford the expected NH-arylpiperazine.

Illustrative Synthesis of Int 257

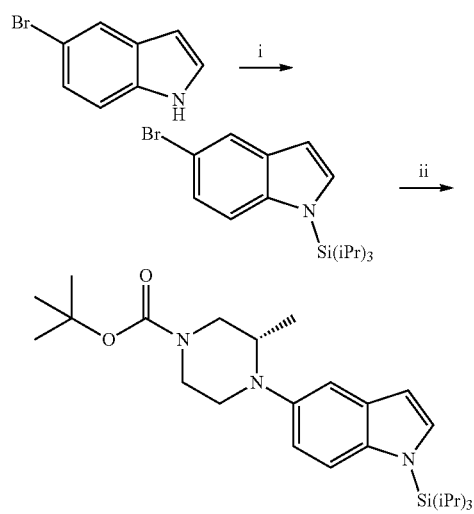

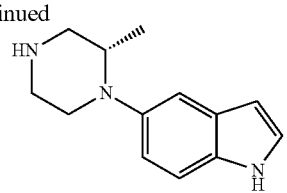

Step i) 5-Bromo-1-(triisopropylsilyl)-1H-indole

To a solution of 5-bromo-1H-indole (1.96 g, 10 mmol, 1 eq.) in THF (80 mL) at 0° C. is added NaH portionwise (50% in oil, 1 g, 20 mmol, 2 eq.). Reaction mixture is stirred at r.t. for 1 h, cooled to 0° C. and a solution of triisopropylsilyl chloride (2.3 g, 12 mmol, 1.2 eq.) in THF (10 mL) is added dropwise. The reaction mixture is stirred at r.t. and concentrated in vacuo. The residue is partitioned between water and EtOAc, the organic layer is dried over anhydrous $Na_2SO_4$, filtered and concentrated in vacuo. Purification by flash chromatography on silica gel (eluting with Heptane/EtOAc 100/0 to 50/50) affords the expected triisopropylsilyl derivative. LCMS: MW (calcd): 352; m/z MW (obsd): 352-354 (M+H).

Step ii) (S)-3-Methyl-4-(1-(triisopropylsilyl)-1H-indol-5-yl)-piperazine-1-carboxylic acid tert-butyl ester A flask is charged with bromo triisopropylsilyl derivative (1.4 g, 3.5 mmol, 1 eq.), (S)-3-methyl-piperazine-1-carboxylic acid tert-butyl ester (800 mg, 4 mmol, 1.15 eq.), NaOtBu (576 mg, 6 mmol, 1.7 eq.) and toluene (25 mL). The reaction mixture is degassed with $N_2$ and $PdCl_2[P(o-Tol)_3]_2$ (160 mg, 0.2 mmol, 0.05 eq.) is added. Reaction mixture is heated at 110° C. overnight, quenched by addition of water, extracted with EtOAc. The combined organic layers are washed with water and brine, dried over anhydrous $Na_2SO_4$, filtered and concentrated in vacuo. The residue is purified by flash chromatography on silica gel (eluting with Heptane/EtOAc 100/0 to 50/50) to afford the expected NBoc-arylpiperazine. LCMS: MW (calcd): 472; m/z MW (obsd): 473 (M+H).

Step iii) 5-((S)-2-Methyl-piperazin-1-yl)-1H-indole

To a solution of the NBoc-arylpiperazine (370 mg, 0.79 mmol, 1 eq.) in DCM (30 mL) is added TFA (3 mL). Reaction mixture stirred at r.t. overnight and concentrated in vacuo. The residue is taken up in EtOAc and saturated $NaHCO_3$ solution and extracted with EtOAc. The combined organic layers are dried over anhydrous $Na_2SO_4$, filtered and concentrated in vacuo to afford the expected product. LCMS: MW (calcd): 215; m/z MW (obsd): 216 (M+H).

1.2.2.6. Method a 7: Buchwald Reaction with NH-Piperazine

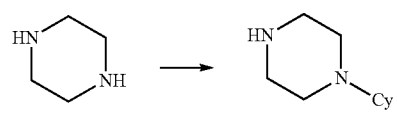

A flask is charged with bromoaryl derivative (1 eq.), piperazine (4-6 eq.), BINAP (0.06-0.22 eq.), NaOtBu (1.4-2.5 eq.) and toluene. The reaction mixture is degassed with $N_2$ and $Pd_2(dba)_3$ (0.03-0.11 eq.) is added. Reaction mixture is heated at 100-110° C. for 2 h-20 h. The reaction mixture is extracted with HCl 1N solution. The aqueous layer is basified with NaOH 2N solution and extracted with EtOAc or DCM. The combined organic layers are washed with water and brine, dried (over anhydrous $Na_2SO_4$ or $MgSO_4$), filtered and concentrated in vacuo to afford the expected arylpiperazine used without further purification.

Illustrative Synthesis of Int 266

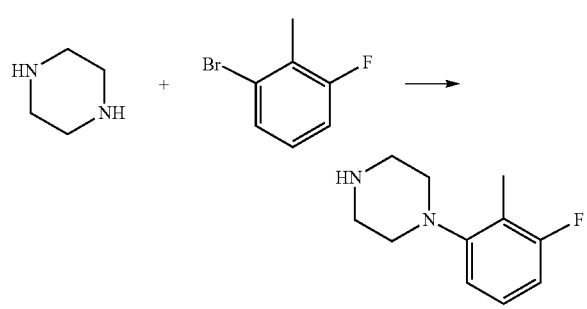

A flask is charged with 1-bromo-3-fluoro-2-methyl-benzene (189 mg, 1 mmol, 1 eq.), piperazine (517 mg, 6 mmol, 6 eq.), BINAP (37 mg, 0.06 mmol, 0.06 eq.), NaOtBu (135 mg, 1.4 mmol, 1.4 eq.) and toluene (2 mL). The reaction mixture is degassed with $N_2$ and $Pd_2(dba)_3$ (27 mg, 0.03 mmol, 0.03 eq.) is added. Reaction mixture is heated at 110° C. overnight. The reaction mixture is extracted with HCl 1N solution. The aqueous layer is basified with NaOH 2N solution and extracted with DCM. The combined organic layers are washed with water and brine, dried over anhydrous $MgSO_4$, filtered and concentrated in vacuo to afford the expected product. LCMS: MW (calcd): 194; m/z MW (obsd): 195 (M+H).

1.2.2.7. Method A8: SNAr with NH-Piperazine

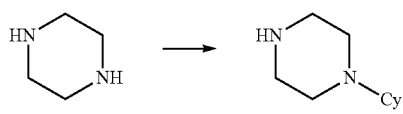

A vial is charged with arylfluoride derivative (1 eq.), piperazine (2-8 eq.), $K_2CO_3$ (1.5-2.6 eq.) and a solvent (dioxane, DMSO). The reaction mixture is heated at 100° C. for 1-3 days, diluted with water and extracted with EtOAc or DCM. The combined organic layers are washed with water and brine, dried (over anhydrous $Na_2SO_4$ or $MgSO_4$), filtered and concentrated in vacuo to afford the expected arylpiperazine used without further purification.

Illustrative Synthesis of Int 269

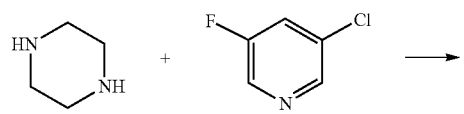

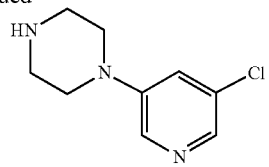

A vial is charged with 3-chloro-5-fluoro-pyridine (195 mg, 1.5 mmol, 1 eq.), piperazine (1.03 g, 12.0 mmol, 8 eq.), $K_2CO_3$ (553 mg, 4.0 mmol, 2.6 eq.) and a solvent dry dioxane (5 mL). The reaction mixture is heated at 100° C. for 3 days, diluted with water and extracted with DCM. The combined organic layers are washed with water and brine, dried over anhydrous $MgSO_4$, filtered and concentrated in vacuo to afford the expected product. LCMS: MW (calcd): 198; m/z MW (obsd): 198-200 (M+H).

1.2.3. General Methods C: Preparation of Ketoester 1.2.3.1. Method C1: From Meldrum's Acid

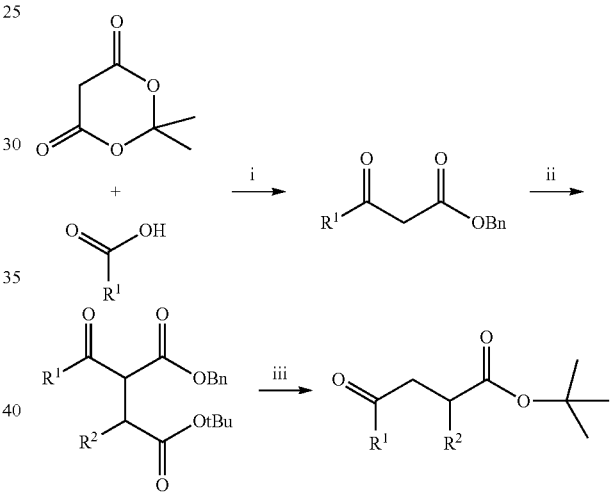

Step i)

To a solution of the carboxylic acid (1 eq.) in DCM at 0° C. under $N_2$ atmosphere is added portionwise DMAP (1.5 eq.) then 2,2-Dimethyl-[1,3]dioxane-4,6-dione (1.1 eq.) then EDC.HCl (1.2 eq.). After 10 min at 0° C., the reaction mixture is warmed to r.t. and stirred for 4 h. The reaction mixture is quenched with a solution of $KHSO_4$ 5%. The aqueous phase is extracted with DCM, the combined organic layers are washed with a solution of $KHSO_4$ 5%, water and brine, dried over anhydrous $Na_2SO_4$, filtered and concentrated in vacuo. This residue is taken up in anhydrous toluene and benzyl alcohol (1.1 eq.) is added. The reaction mixture is stirred at 120° C. for 16 h to 20 h, concentrated in vacuo and purified by flash chromatography on silica gel to afford the expected β-ketoester.

Step ii)

To a solution of the β-ketoester (1 eq.) in MEK are added $K_2CO_3$ (2 eq.), NaI (0.1 eq.) and bromoderivative (1 eq.). The reaction mixture is stirred at 90° C. for 6 h to 16 h and cooled to r.t. Water is added, reaction mixture acidified to pH 8 and extracted with EtOAc. The combined organic layers are washed with water and brine, dried over anhydrous Na$_2$SO$_4$, filtered and concentrated in vacuo. The residue is purified by flash chromatography on silica gel to afford the expected γ-ketoester.

Step iii)

To a solution of the γ-ketoester (1 eq.) in MeOH (or EtOH) are added Pd(OH)$_2$/C (0.01 eq.), and cyclohexene (10-50 eq.). The reaction mixture is stirred at 70-80° C. for 19 h. The reaction mixture is filtered on celpure P65 and the filtrate is concentrated in vacuo. The residue is used as such or is purified by flash chromatography on silica gel to afford the expected γ-ketoester.

Illustrative Synthesis of Int 158

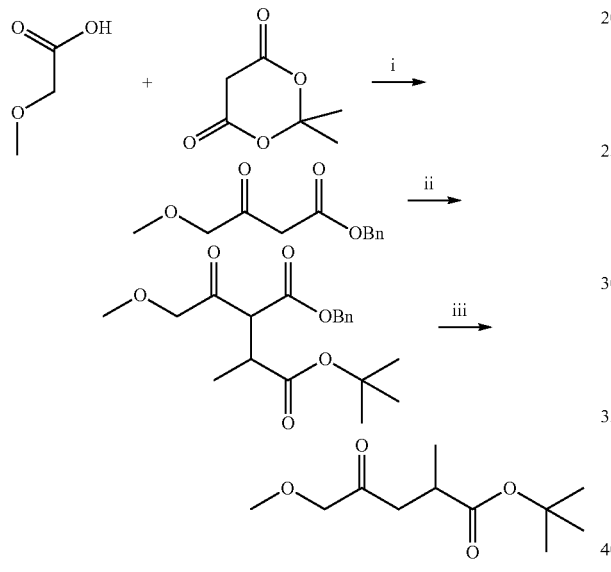

Step i) 4-Methoxy-3-oxo-butyric acid benzyl ester

To a solution of methoxy-acetic acid (5.11 mL, 0.067 mol, 1 eq.) in DCM (160 mL) at 0° C. under N$_2$ atmosphere is added portionwise DMAP (12.21 g, 0.100 mol, 1.5 eq.) then 2,2-Dimethyl-[1,3]dioxane-4,6-dione (10.56 g, 0.073 mol, 1.1 eq.) then EDC.HCl (15.32 g, 0.080 mol, 1.2 eq.). After 10 min at 0° C., the reaction mixture is warmed to r.t. and stirred for 4 h. The reaction mixture is quenched with a solution of KHSO$_4$ 5%. The aqueous phase is extracted with DCM, the combined organic layers are washed with a solution of KHSO$_4$ 5%, water and brine, dried over anhydrous Na$_2$SO$_4$, filtered and concentrated in vacuo. This residue is taken up in anhydrous toluene (220 mL) and benzyl alcohol (7.59 mL, 0.073 mol, 1.1 eq.) is added. The reaction mixture is stirred at 120° C. for 16 h, concentrated in vacuo and purified by flash chromatography on silica gel (eluting with DCM 100%) to afford the expected β-ketoester. LCMS: MW (calcd): 222; m/z MW (obsd): 245.3 (M+Na)

Step ii) 2-(2-Methoxy-acetyl)-3-benzyl-succinic acid 4-tert-butyl ester 1-methyl ester To a solution of the β-ketoester (8.96 g, 0.040 mol, 1 eq.) in MEK (120 mL) are added K$_2$CO$_3$ (11.14 g, 0.081 mol, 2 eq.), NaI (0.6 g, 0.004 mol, 0.1 eq.) and 2-Bromo-propionic acid tert-butyl ester (6.69 mL, 0.040 mol, 1 eq.). The reaction mixture is stirred at 90° C. for 6 h and cooled to r.t. Water is added, reaction mixture is acidified to pH 8 and extracted with EtOAc. The combined organic layers are washed with water and brine, dried over anhydrous Na$_2$SO$_4$, filtered and concentrated in vacuo. The residue is purified by flash chromatography on silica gel (eluting with Heptane/EtOAc 100/0 to 50/50) to afford the expected γ-ketoester. LCMS: MW (calcd): 350; m/z MW (obsd): 373.4 (M+Na)

Step iii) 5-Methoxy-2-methyl-4-oxo-pentanoic acid tert-butyl ester

To a solution of the γ-ketoester (6.42 g, 0.018 mol, 1 eq.) in MeOH are added Pd(OH)$_2$/C (0.642 g, 0.002 mol, 0.01 eq.), and cyclohexene (93 mL, 0.916 mol, 50 eq.). The reaction mixture is stirred at 70° C. for 19 h. The reaction mixture is filtered on celpure P65, washed with MeOH and the filtrate is concentrated in vacuo. The residue is purified by flash chromatography on silica gel (eluting with Heptane/EtOAc 100/0 to 70/30) to afford the expected product. LCMS: MW (calcd): 216; m/z MW (obsd): 239.3 (M+Na).

1.2.3.2. Method C2: with tert-butyl bromoacetate

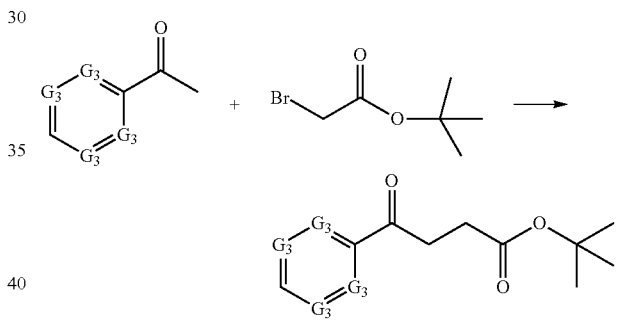

G$_3$=C or N

To a solution of the acetyl derivative (1 eq.) in THF and DMPU at 0° C. under N$_2$ atmosphere is added LiHMDS (1M solution in THF, 1.2 eq.) dropwise. After 15 min at 0° C., tert-butyl bromoacetate (1.5 eq.) is added dropwise and the reaction mixture is stirred at 0° C. for 3 h. The reaction mixture is quenched by a saturated NH$_4$Cl solution, the organic layer is separated, and the aqueous layer is extracted with EtOAc. The combined organic layers are washed with water and brine, dried over anhydrous MgSO$_4$, filtered and concentrated in vacuo. Purification by flash chromatography on silica gel affords the expected γ-ketoester.

Illustrative Synthesis of Int 141

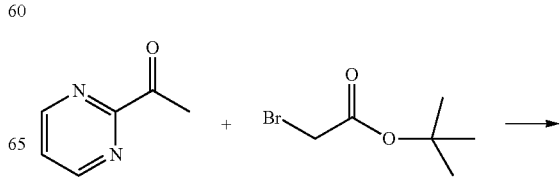

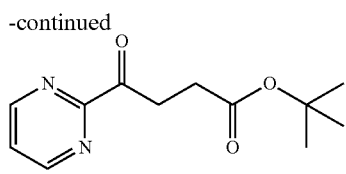

To a solution of the 2-acetyl pyrimidine (2 g, 16.38 mmol, 1 eq.) in THF and DMPU at 0° C. under $N_2$ atmosphere is added LiHMDS (1M solution in THF, 19.6 mL, 19.65 mmol, 1.2 eq.) dropwise. After 15 min at 0° C., tert-butyl bromoacetate (3.96 mL, 24.56 mmol, 1.5 eq.) is added dropwise and the reaction mixture is stirred at 0° C. for 3 h. The reaction mixture is quenched by a saturated $NH_4Cl$ solution, the organic layer is separated, and the aqueous layer is extracted with EtOAc. The combined organic layers are washed with water and brine, dried over anhydrous $MgSO_4$, filtered and concentrated in vacuo. Purification by flash chromatography on silica gel (eluting with Heptane/EtOAc 80/20 to 50/50) affords the expected product. LCMS: MW (calcd): 236; m/z MW (obsd): 237 (M+H).

1.2.3.3. Method C3: Esterification

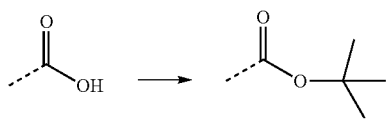

A glass pressure flask is charged with the carboxylic acid (1 eq.), DCM and concentrated $H_2SO_4$ (0.1 eq.). It is capped and weighted as such. It is then cooled to −45° C., the flask is opened and isobutene is bubbled through the cold reaction mixture for approximatively 5 min. The flask is capped and weighted. The process is repeated until the expected weigh of isobutene is obtained (5 eq.). The reaction mixture is stirred at r.t. for 4 days, then the flask is cooled to −45° C. prior to opening. A saturated $NaHCO_3$ solution is added portionwise, and the vigorous stirring kept for 30 min. The organic layer is separated; the aqueous layer is extracted with DCM. The combined organic layers are washed with brine, dried over anhydrous $MgSO_4$ and concentrated in vacuo (with a minimum vacuum of 50 mbar) to afford the expected γ-ketoester.

Illustrative Synthesis of Int 171

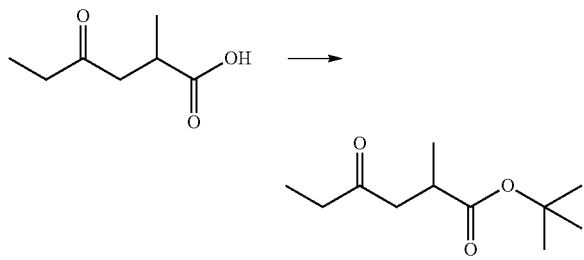

A glass pressure flask is charged with 2-Methyl-4-oxohexanoic acid (Kato et al., 2003) (7.3 g, 50.6 mmol, 1 eq.), DCM (40 mL) and concentrated $H_2SO_4$ (270 µL, 5.06 mmol, 0.1 eq.). The flask is capped and weighted as such. It is then cooled to −45° C., the flask is opened and isobutene is bubbled through the cold reaction mixture for approximatively 5 min. The flask is capped and weighted (11 g of isobutene is condensed). The process is repeated until the expected weight of isobutene is obtained (14.2 g, 253.2 mmol, 5 eq.). The reaction mixture is stirred at r.t. for 4 days, then the flask is cooled to −45° C. prior to opening. A saturated $NaHCO_3$ solution is added portionwise, and the vigorous stirring kept for 30 min. The organic layer is separated; the aqueous layer is extracted with DCM. The combined organic layers are washed with brine, dried over anhydrous $MgSO_4$ and concentrated in vacuo (with a minimum vacuum of 50 mbar) to afford the expected product.

1.2.3.4. Method C4: Stetter Reaction

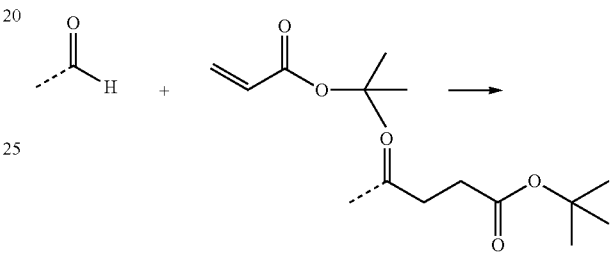

A vial is charged with aldehyde (1 eq.), tert-butyl ester acrylate (1 eq.), $P(Bu)_3$ (1 eq.) and dry THF. The vial is capped and heated at 70° C. for 2 h to 16 h. The reaction mixture is partitioned between EtOAc and water. The combined organic layers are washed with brine, dried over anhydrous $MgSO_4$, filtered and concentrated in vacuo to afford the expected γ-ketoester after purification by flash chromatography on silica gel.

Illustrative Synthesis of Int 181

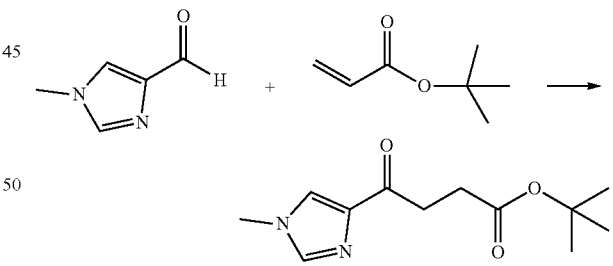

To a solution of 1-methyl-1H-imidazole-4-carbaldehyde (1 g, 9.1 mmol, 1.1 eq.) in THF (12 mL) is added $P(Bu)_3$ (2.16 mL, 8.7 mmol, 1.05 eq.) and the reaction mixture is heated at 50° C. for 5 min. tert-butyl ester acrylate (1.2 mL, 8.3 mmol, 1 eq.) is added and the reaction mixture is stirred at 80° C. for 3 h. tert-butyl ester acrylate (0.3 mL, 0.25 eq.) is added and this process (heating 3 h and addition of tert-butyl ester acrylate) is repeated until no evolution is observed by TLC (EtOAc) and UPLC/MS. The reaction mixture is concentrated in vacuo and the residue is purified by flash chromatography on silica gel (eluting with Heptane/EtOAc 100/0 to 0/100) to afford the expected product. LCMS: MW (calcd): 238; m/z MW (obsd): 239 (M+H).

1.2.3.5. Method C5: Via Epoxide Opening

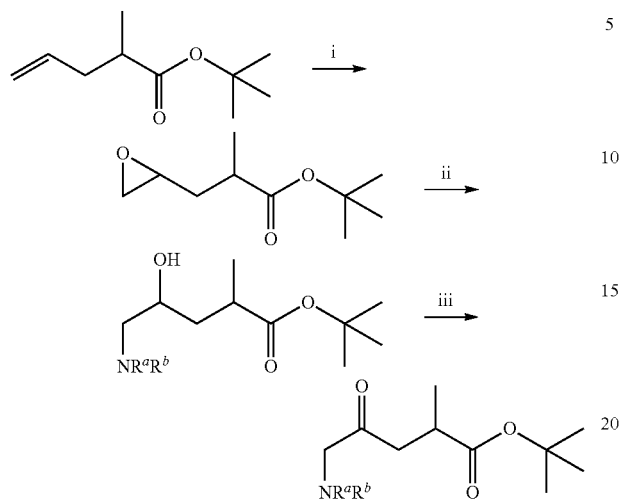

Step i)

To a solution of alkene (1 eq.) in DCM at 0° C., is added m-CPBA (1.5 eq.) and the reaction mixture is stirred at r.t. overnight. The white precipitate is filtered and washed with DCM. The filtrate is washed with a saturated NaHCO$_3$ solution, brine, dried over anhydrous MgSO$_4$ and concentrated in vacuo. The residue is purified by flash chromatography on silica gel to afford the expected epoxide.

Step ii)

A sealed tube is charged with the epoxide (1 eq.), EtOH and secondary amine (1.5 eq.). After heating at reflux for 3 h30, the reaction mixture is concentrated in vacuo. The residue is taken up in DCM, washed with a saturated NH$_4$Cl solution, dried over anhydrous MgSO$_4$, filtered and concentrated in vacuo to afford the expected aminoalcohol used in next step without further purification.

Step iii)

A two necked flask, under N$_2$ atmosphere, is charged with dry DCM and (COCl)$_2$ (1.1 eq.). The reaction mixture is cooled to −70° C., a solution of DMSO (2.4 eq.) in dry DCM is added dropwise and the reaction mixture is stirred at −70° C./−60° C. for 45 min. A solution of the aminoalcohol (1 eq.) in dry DCM is added dropwise and the reaction mixture is stirred for 1 h at −60° C. Et$_3$N (5 eq.) is added dropwise. Reaction mixture stirred at −40° C. for 30 min then warmed to r.t. and stirred overnight. Water is added, the organic layer is separated and washed with brine, dried over anhydrous MgSO$_4$ and concentrated in vacuo. The residue is purified by flash chromatography on silica gel to afford the expected γ-ketoester.

Illustrative Synthesis of Int 188

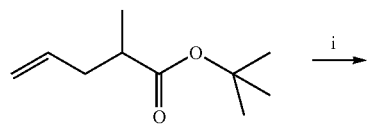

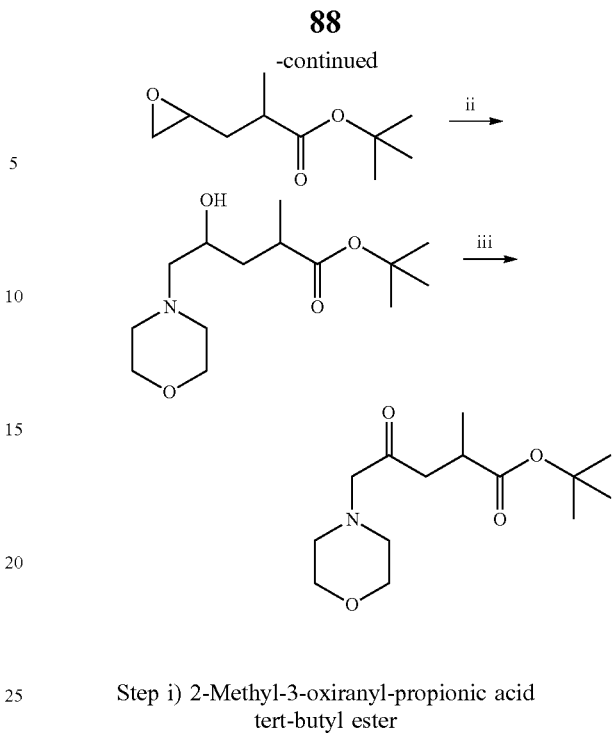

Step i) 2-Methyl-3-oxiranyl-propionic acid tert-butyl ester

To a solution of Int 148 (2 g, 11.8 mmol, 1 eq.) in DCM (20 mL) at 0° C., is added m-CPBA (3.05 g, 17.7 mmol, 1.5 eq.) and the reaction mixture is stirred at r.t. overnight. The white precipitate is filtered and washed with DCM. The filtrate is washed with a saturated NaHCO$_3$ solution, brine, dried over anhydrous MgSO$_4$ and concentrated in vacuo. The residue is purified by flash chromatography on silica gel (eluting with Heptane/EtOAc 100/0 to 80/20) to afford the expected epoxide.

Step ii) 4-Hydroxy-2-methyl-5-morpholin-4-yl-pentanoic acid tert-butyl ester A sealed tube is charged with the epoxide obtained in the previous step (0.19 g, 1.02 mmol, 1 eq.), EtOH (3 mL) and morpholine (0.134 mL, 1.53 mmol, 1.5 eq.). After heating at reflux for 3 h30, the reaction mixture is concentrated in vacuo. The residue is taken up in DCM, washed with a saturated NH$_4$Cl solution, dried over anhydrous MgSO$_4$, filtered and concentrated in vacuo to afford the expected aminoalcohol used in next step without further purification.

Step iii) 2-Methyl-5-morpholin-4-yl-4-oxo-pentanoic acid tert-butyl ester

A two necked flask, under N$_2$ atmosphere, is charged with dry DCM (5 mL) and (COCl)$_2$ (0.153 mL, 1.81 mmol, 1.1 eq.). The reaction mixture is cooled to −70° C., a solution of DMSO (0.281 mL, 3.96 mmol, 2.4 eq.) in dry DCM (0.5 mL) is added dropwise and the reaction mixture is stirred at −70° C./−60° C. for 45 min. A solution of the aminoalcohol obtained in the previous step (0.450 g, 1.65 mmol, 1 eq.) in dry DCM (2 mL) is added dropwise and the reaction mixture is stirred for 1 h at −60° C. Et$_3$N (1.19 mL, 8.24 mmol, 5 eq.) is added dropwise. Reaction mixture stirred at −40° C. for 30 min then warmed to r.t. and stirred overnight. Water is added, the organic layer is separated and washed with brine, dried over anhydrous MgSO$_4$ and concentrated in vacuo.

The residue is purified by flash chromatography on silica gel (eluting with DCM/acetone 90/10) to afford the expected product.

1.2.4. General Method D: Preparation of Ketoamide

1.2.4.1.1. Method D1: Preparation of Acrylamide

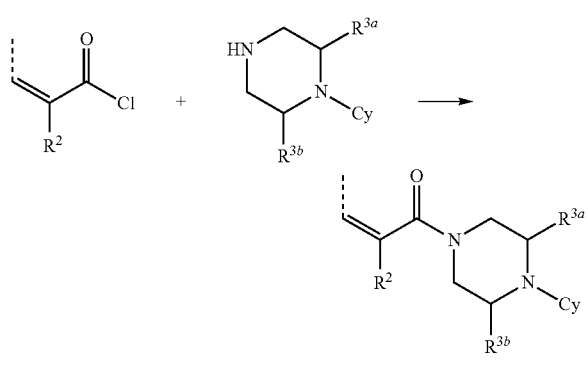

1.2.4.1. Method D1a

To a solution of piperazine (1 eq.) in EtOAc/NaHCO₃ sat. aq. (2/1 v/v) at 0° C. is added dropwise the acryloyl chloride derivative (1.1 eq.). Reaction mixture is stirred at 0° C. for 30 min then r.t. for 1 h. The organic layer is separated. The aqueous layer is extracted with EtOAc and the combined organic layers are washed with water, brine and dried over anhydrous MgSO₄, filtered and concentrated in vacuo to afford the expected acrylamide (used as such or purified by flash chromatography on silica gel).

Illustrative Synthesis of Int 006

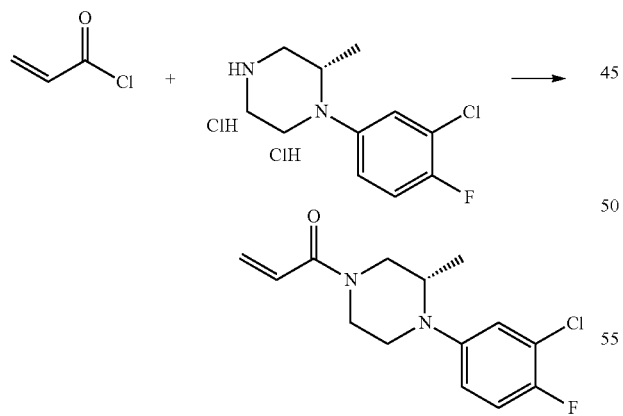

To a solution of (S)-1-(3-Chloro-4-fluoro-phenyl)-2-methyl-piperazine dihydrochloride (2 g, 6.63 mmol, 1 eq.) in EtOAc/NaHCO₃ sat. aq. (60 mL/30 mL) at 0° C. is added dropwise acryloyl chloride (0.595 mL, 7.29 mmol, 1.1 eq.). Reaction mixture is stirred at 0° C. for 30 min then r.t. for 1 h. The organic layer is separated. The aqueous layer is extracted with EtOAc and the combined organic layers are washed with water, brine and dried over anhydrous MgSO₄, filtered and concentrated in vacuo to afford the expected product. LCMS: MW (calcd): 283; m/z MW (obsd): 283-285 (M+H).

1.2.4.1.2 Method D1b

To a solution of piperazine (1 eq.) and Et3N (1.5 eq.) in DCM at 0° C. is added dropwise the acryloyl chloride derivative (1.5 eq.). Reaction mixture is stirred at 0° C. for 1 h and allowed to reach r.t. Water and DCM are added, the organic layer is separated. The aqueous layer is extracted with DCM, the combined organic layers are washed with brine and dried over anhydrous Na2SO4, filtered and concentrated in vacuo to afford the expected acrylamide after purification by flash chromatography on silica gel.

Illustrative Synthesis of Int 009

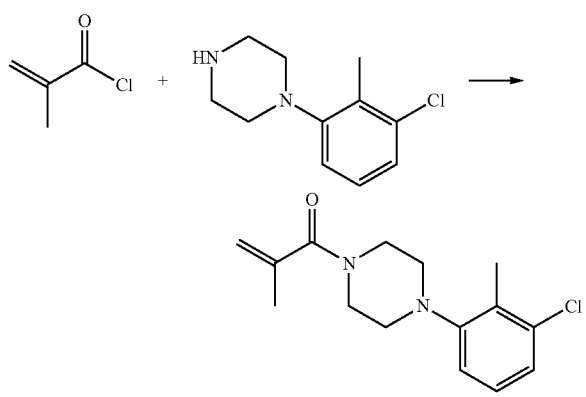

To a solution of 1-(3-Chloro-2-methyl-phenyl)-piperazine (2.06 g, 9.8 mmol, 1 eq.) and Et₃N (1.5 mL, 14.7 mmol, 1.5 eq.) in DCM at 0° C. is added dropwise 2-Methyl-acryloyl chloride (2.05 mL, 14.7 mmol, 1.5 eq.). Reaction mixture is stirred at 0° C. for 1 h and allowed to reach r.t. Water and DCM are added, the organic layer is separated. The aqueous layer is extracted with DCM, the combined organic layers are washed with brine and dried over anhydrous Na₂SO₄, filtered and concentrated in vacuo. The residue is purified by flash chromatography on silica gel (eluting with DCM/MeOH 100/0 to 90/10) to afford the expected product. LCMS: MW (calcd): 279; m/z MW (obsd): 279-281 (M+H).

1.2.4.2. Method D2: Stetter Reaction

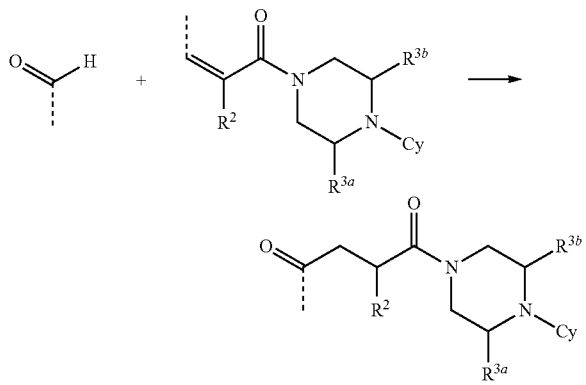

1.2.4.2.1 Method D2a (P(Bu)₃)

A vial is charged with aldehyde (1 eq.), acrylamide (0.95 eq.), P(Bu)₃ (1 eq.) and dry THF. The vial is capped and heated at 70° C. for 2 h to 3 h. The reaction mixture is partitioned between EtOAc and water. The combined organic layers are washed with brine, dried over anhydrous MgSO₄, filtered and concentrated in vacuo to afford the expected γ-ketoamide after purification by flash chromatography on silica gel.

Illustrative Synthesis of Int 095

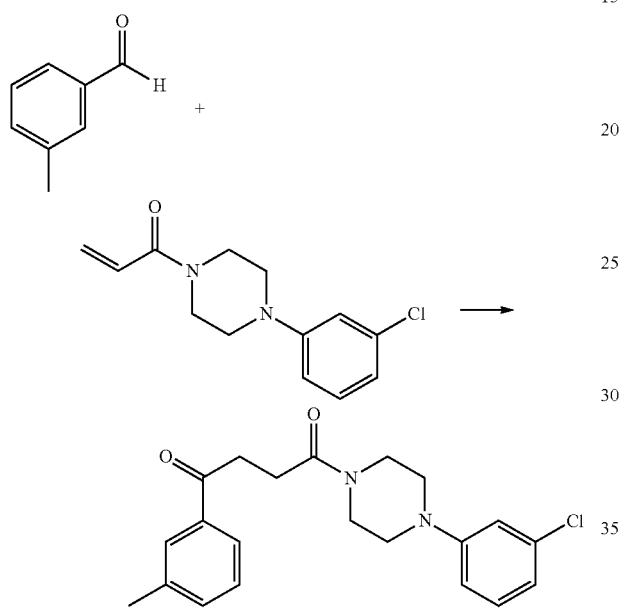

A vial is charged with 3-Methyl-benzaldehyde (0.141 mL, 0.1.2 mmol, 1 eq.), Int 005 (0.300 g, 1.2 mmol, 1 eq.), P(Bu)₃ (0.242 mL, 1.2 mmol, 1 eq.) and dry THF (2 mL). The vial is capped and heated at 70° C. for 2 h. Additional P(Bu)₃ (15 µL, 0.05eq.) and 3-Methyl-benzaldehyde (10 µL, 0.1 eq.) is added, and the vial is capped and heated at 80° C. for 2 h. The reaction mixture is partitioned between EtOAc and water. The combined organic layers are washed with brine, dried over anhydrous MgSO₄, filtered and concentrated in vacuo. The residue is purified by flash chromatography on silica gel (eluting with Heptane/EtOAc, from 100/0 to 0/100) to afford the expected product. LCMS: MW (calcd): 370; m/z MW (obsd): 371-373 (M+H).

1.2.4.2.2 Method D2b (Rh Catalyst)

A vial is charged with bis(1,5-cyclooctadiene)rhodium(I) tetrafluoroborate (0.10 eq.), 1,4-bis(diphenylphosphino)butane (0.10 eq.), dry DCM and sealed with a septum. The flask is evacuated and refilled with H₂ (3 times) and the reaction mixture is stirred under an atmosphere of H₂. After 3 h, volatiles are removed under a nitrogen stream. The residue is combined with acrylamide (1 eq.), aldehyde (1.5 equiv.) and 1,2-dichloroethane in a vial under a N₂ atmosphere. The vial is sealed with a cap and heated at 100° C. After 16 h, the mixture is concentrated in vacuo and purified by flash chromatography on silica gel to afford the expected γ-ketoamide.

Illustrative Synthesis of Int 021

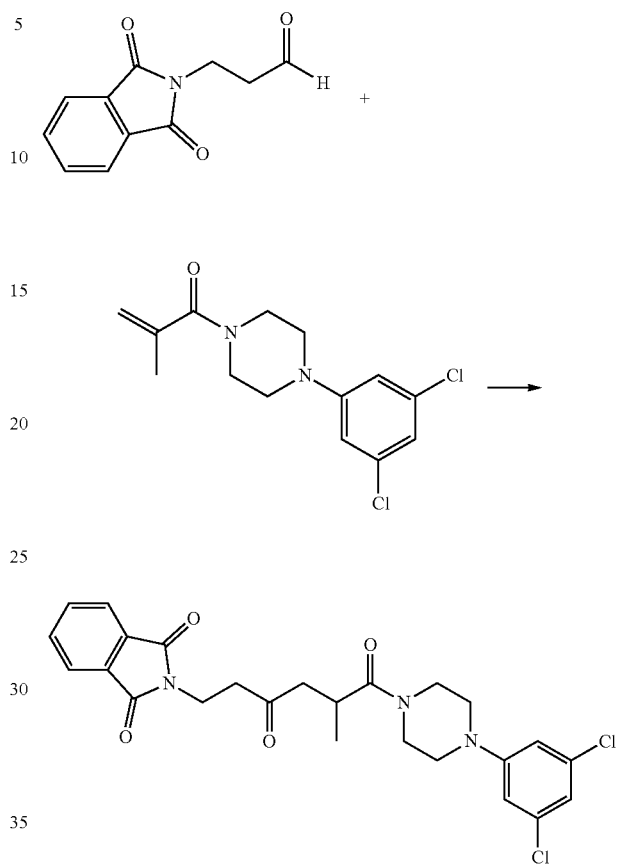

A vial is charged with bis(1,5-cyclooctadiene)rhodium(I) tetrafluoroborate (0.054 g, 0.132 mmol, 0.10 eq.), 1,4-bis(diphenylphosphino)butane (0.056 g, 0.132 mmol, 0.10 eq.), dry DCM (2 mL) and sealed with a septum. The flask is evacuated and refilled with H₂ (3 times) and the reaction mixture is stirred under an atmosphere of H₂. After 3 h, volatiles are removed under a nitrogen stream. The residue is combined with Int 001 (0.397 g, 1.328 mmol, 1 eq.), 3-(1,3-dioxo-1,3-dihydroisoindol-2-yl)-propionaldehyde (0.406 g, 2.00 mmol, 1.5 equiv.) and 1,2-dichloroethane (2 mL) in a vial under a N₂ atmosphere. The vial is sealed with a cap and heated at 100° C. After 2 days, the mixture is concentrated in vacuo. The residue is purified by flash chromatography on silica gel (eluting with Heptane/EtOAc 100/0 to 0/100, then DCM/MeOH 90/10) to afford Int 021. LCMS: MW (calcd): 502; m/z MW (obsd): 502-504 (M+H).

1.2.4.2.3 Method D2c (NaCN)

A vial is charged with aldehyde (3 eq.) and dry DMF. NaCN (1.5 eq) is added and the reaction mixture is stirred at r.t. for 5 min. A solution of acrylamide (1 eq.) in dry DMF is added, the vial is sealed and heated at 120° C. for 3 h30 and cooled to r.t. A saturated NaHCO₃ solution and water are added to the reaction mixture followed by extraction with EtOAc. The combined organic layer is washed with brine, dried over anhydrous MgSO₄, filtered, concentrated in vacuo and purified by flash chromatography on silica gel to afford the expected γ-ketoamide.

Illustrative Synthesis of Int 060

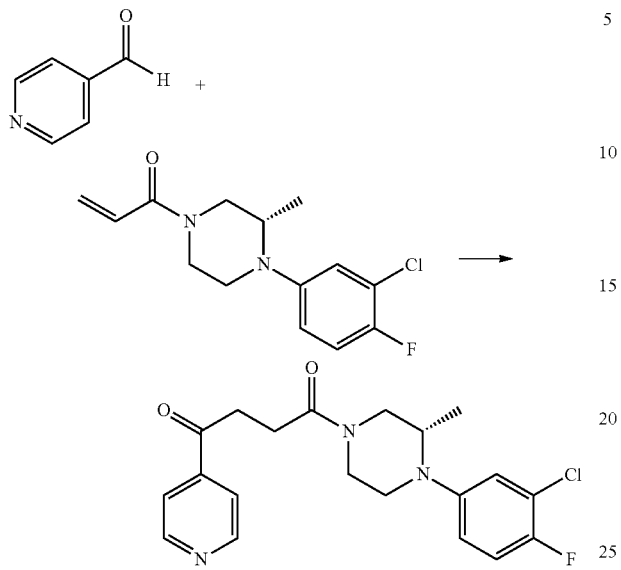

A vial is charged with pyridine-4-carbaldehyde (0.227 g, 2.12 mmol, 3 eq.) and dry DMF (4 mL). NaCN (0.052 g, 1.06 mmol, 1.5 eq) is added and the reaction mixture is stirred at r.t. for 5 min. A solution of Int 006 (0.200 g, 0.71 mmol, 1 eq.) in dry DMF (2 mL) is added, the vial is sealed and heated at 120° C. for 3 h30 and cooled to r.t. A saturated NaHCO$_3$ solution and water are added to the reaction mixture followed by extraction with EtOAc. The combined organic layers are washed with brine, dried over anhydrous MgSO$_4$, filtered, concentrated in vacuo. The residue is purified by flash chromatography on silica gel (eluting with DCM/MeOH 100/0 to 98/2) to afford the expected product. LCMS: MW (calcd): 390; m/z MW (obsd): 390-392 (M+H).

1.2.4.3. Method D4: Oxidative Cleavage

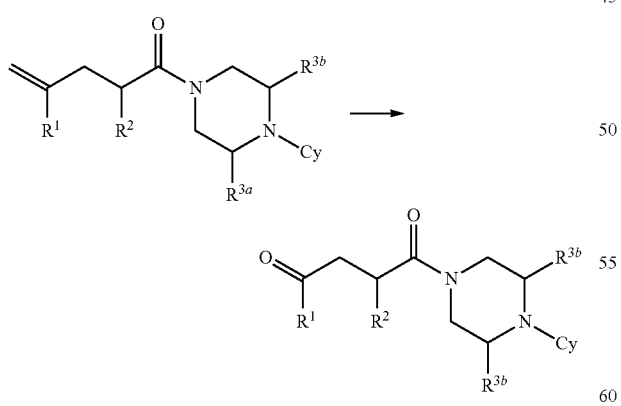

A vial is charged with alkene (1 eq.), a mixture of dioxane/water or THF/water and OsO$_4$ (0.01-0.06 eq.). After 15 min, NaIO$_4$ (2-4 eq.) is added and the reaction mixture is starred at r.t. for 2 h to 20 h, combined with water or a solution of NaHSO$_3$ and extracted with DCM. The combined organic layers are washed with brine, dried over anhydrous MgSO$_4$, filtered, concentrated in vacuo and purified by flash chromatography on silica gel to afford the expected γ-ketoamide.

Illustrative Synthesis of Int 055

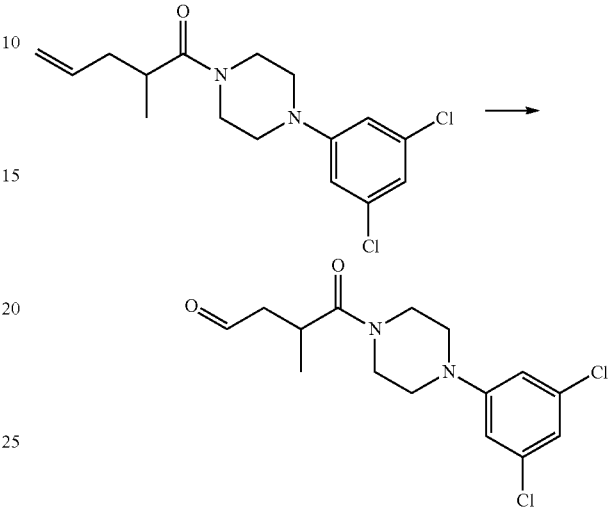

A vial is charged with alkene Int 124 (4.95 g, 15.1 mmol, 1 eq.), a mixture of dioxane (100 mL) and water (20 mL), and OsO$_4$ (2.5 wt % in t-BuOH, 2.8 mL, 223 mmol, 0.015 eq.). After 15 min, a solution of NaIO$_4$ (6.61 g, 30.9 mmol, 2 eq.) in water (150 mL) is added dropwise over 10 minutes, and the reaction mixture is starred at r.t. overnight, combined with water (600 mL) and extracted with CHCl$_3$ (250 mL). The organic layer is washed with brine, dried over anhydrous MgSO$_4$, filtered, concentrated in vacuo and purified by flash chromatography on silica gel (eluting with EtOAc/DCM 20/80) to afford the expected the expected product. LCMS: MW (calcd): 329; m/z MW (obsd): 329-331 (M+H).

1.2.4.4. Method D5: Via Furan Oxidation

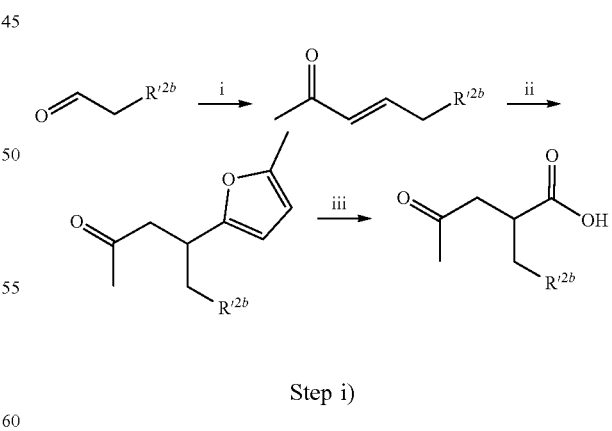

Step i)

To a solution of phosphonate (1.1 eq.) in EtOH is added K$_2$CO$_3$ (1.2 eq.). The reaction mixture is stirred at r.t. for 2 h prior to addition of the aldehyde (1 eq.). The reaction mixture is stirred at r.t. (1 h to 3 h), diluted with EtOAc and filtered on celpure P65. The filtrate is concentrated in vacuo. The residue is taken up in EtOAc and washed with a saturated NH$_4$Cl solution, a saturated NaHCO$_3$ solution, brine and dried over anhydrous MgSO₄, filtered, concentrated in vacuo and purified by flash chromatography on silica gel to afford the expected α,β-unsaturated ketone.

Step ii)

To a solution of the α,β-unsaturated ketone obtained in the previous step (1 eq.) in dry MeOH are added PdCl₂ (0.1 eq.) and 2-methylfuran (2 eq.). The reaction mixture is stirred at r.t. for 3 h to 24 h, diluted with EtOAc and filtered on celpure P65. The filtrate is concentrated in vacuo and purified by flash chromatography on silica gel to afford the expected ketone.

Step iii)

To a solution of ketone obtained in the previous step (1 eq.) in Heptane/EtOAc/water (1/3/4) is added NaIO₄ (7 eq.). The reaction mixture is stirred for 10 min then RuCl₃.3H₂O (0.02 eq.) is added. The reaction mixture is stirred for 30 min to 1 h30, filtered on celpure P65, washed with MeCN and the filtrate is concentrated in vacuo. The residue is purified by flash chromatography on silica gel to afford the expected γ-ketoacid.

Illustrative Synthesis of Int 138

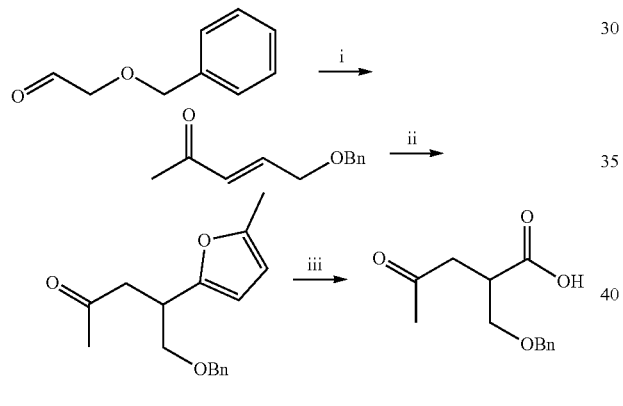

Step i)

To a solution of phosphonate (14.22 g, 73.24 mmol, 1.1 eq.) in EtOH (150 mL) is added K₂CO₃ (11 g, 79.90 mmol, 1.2 eq.). The reaction mixture is stirred at r.t. for 2 h prior to addition of benzyloxy-acetaldehyde (10 g, 66.59 mmol, 1 eq.). The reaction mixture is stirred at r.t. for 3 h, diluted with EtOAc and filtered on celpure P65. The filtrate is concentrated in vacuo. The residue is taken up in EtOAc and washed with a saturated NH₄Cl solution, a saturated NaHCO₃ solution, brine and dried over anhydrous MgSO₄, filtered, concentrated in vacuo and purified by flash chromatography on silica gel (eluting with Heptane/EtOAc 100/0 to 80/20) to afford the expected α,β-unsaturated ketone.

Step ii)

To a solution of the α,β-unsaturated ketone obtained in the previous step (8.7 g, 45.73 mmol, 1 eq.) in dry MeOH (183 mL) are added PdCl₂ (0.811 g, 0.457 mmol, 0.1 eq.) and 2-methylfuran (8.25 mL, 91.46 mmol, 2 eq.). The reaction mixture is stirred at r.t. for 3 h, diluted with EtOAc and filtered on celpure P65. The filtrate is concentrated in vacuo and purified by flash chromatography on silica gel eluting with Heptane/EtOAc 100/0 to 85/15) to afford the expected ketone.

Step iii)

To a solution of ketone obtained in the previous step (1 g, 3.67 mmol, 1 eq.) in Heptane/EtOAc/water (6 mL/18 mL/24 mL) is added NaIO₄ (5.48 g, 25.69 mmol, 7 eq.). The reaction mixture is stirred for 10 min then RuCl₃.3H₂O (0.019 g, 0.073 mmol, 0.02 eq.) is added. The reaction mixture is stirred for 1 h15, filtered on celpure P65, washed with MeCN and the filtrate is concentrated in vacuo. The residue is purified by flash chromatography on silica gel (eluting with DCM/MeOH 98/2 to 95/5) to afford the expected product (stored at 4° C.).

1.2.4.5. Method D6: Via α-Bromo Ketone

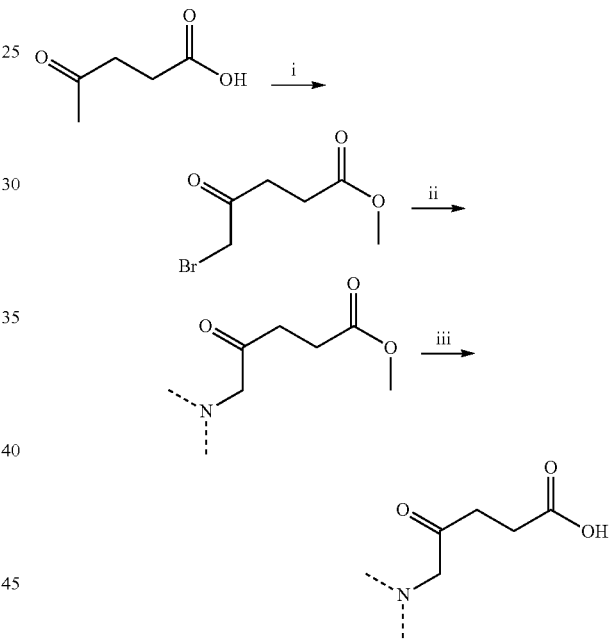

Step i)

To a solution of levulinic acid (1 eq.) in MeOH, bromine (1 eq.) is added dropwise. The reaction mixture is stirred at r.t. overnight and concentrated in vacuo. The residue is partitioned between water and Et₂O, the pH is adjusted to 8 using a saturated NaHCO₃ solution. After extraction with Et₂O, the combined organic layer are dried over anhydrous MgSO₄, filtered, concentrated in vacuo and purified by flash chromatography on silica gel to afford the expected bromo derivative as a methylester.

Step ii)

To a solution of the bromo derivative obtained in the previous step (1 eq.) in MeOH is added Et₃N (0 or 1 eq.) and secondary amine (1 to 2 eq.). Reaction mixture is stirred at r.t. for 30 to 120 min and concentrated in vacuo. The residue is used as such or purified by flash chromatography on silica gel to afford the expected amino ester derivative.

Step iii)

Amino ester obtained in the previous step (1 eq.) is heated at 80° C. with an excess of 1M solution of NaOH for 2 to 3 h. After complete hydrolysis (followed by HPLC/MS), the reaction mixture is acidified and evaporated to dryness and the crude amino acid is used as such in next step or triturated in DMF to remove salts.

Illustrative Synthesis of Int 130

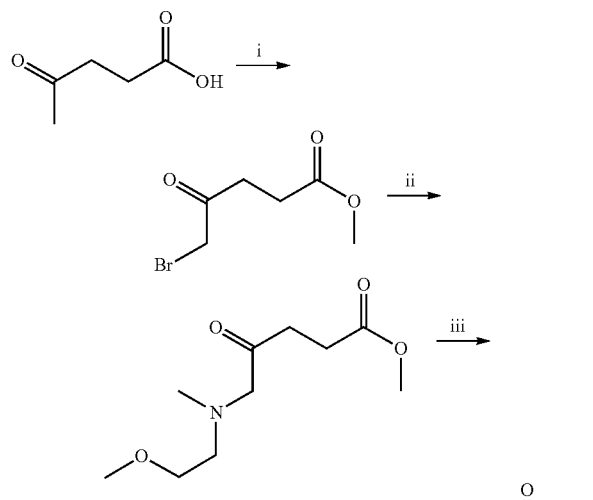

Step i) 5-Bromo-4-oxo-pentanoic acid methyl ester

To a solution of levulinic acid (5 g, 43.1 mmol, 1 eq.) in MeOH (103 mL) under $N_2$ atmosphere, bromine (2.2 mL, 43.1 mmol, 1 eq.) is added dropwise. The resultant solution is stirred at r.t. overnight and concentrated in vacuo. The residue is partitioned between water and $Et_2O$, the pH is adjusted to 8 using a saturated $NaHCO_3$ solution. After extraction with $Et_2O$, the combined organic layers are dried over anhydrous $MgSO_4$, filtered, concentrated in vacuo and purified by flash chromatography on silica gel (eluting with iso-Hexane/EtOAc 100/0 to 50/50) to afford the expected bromo derivative as a methylester.

Step ii) 5-[(2-Methoxy-ethyl)-methyl-amino]-4-oxo-pentanoic acid methyl ester To a solution of the bromo derivative obtained in the previous step (1 g, 4.78 mmol, 1 eq.) in MeOH (12.5 mL) is added $Et_3N$ (0.670 mL, 4.82 mmol, 1 eq.) and (2-methoxy-ethyl)-methyl-amine (0.420 mL, 4.83 mmol, 1 eq.). Reaction mixture is stirred at r.t. for 2 h and concentrated in vacuo. The expected amino ester derivative is used as such in next step.

Step iii) 5-[(2-Methoxy-ethyl)-methyl-amino]-4-oxo-pentanoic acid

Amino ester obtained in the previous step (1.75 g crude assumed as 4.78 mmol, 1 eq.) is heated at 80° C. with an excess of 1M solution of NaOH (15 mL, 15 mmol, 3eq.) for 2 h. After complete hydrolysis (followed by HPLC/MS), the reaction mixture is acidified and evaporated to dryness and the crude amino acid is used as such.

1.2.4.6. Method D7: Ketoamide Functionalization by Suzuki Coupling

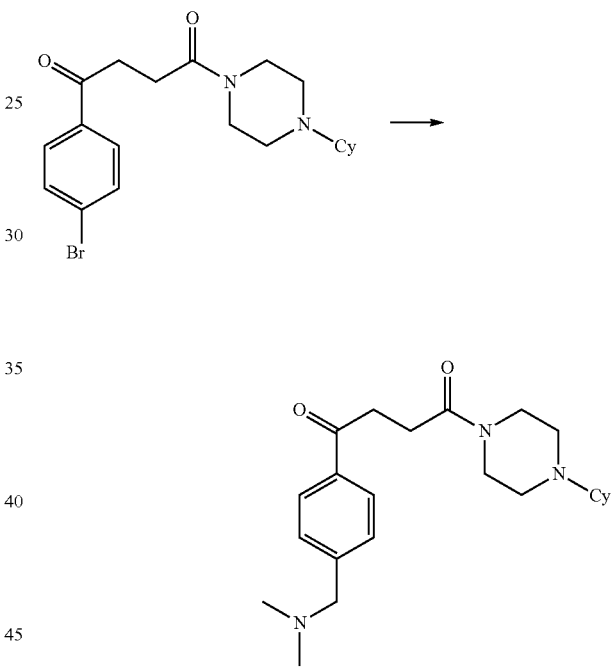

A vial is charged with bromide derivative (1 eq.), Xphos (0.06-0.018 eq.), $Pd(OAc)_2$ (0.03-0.09 eq.), $Cs_2CO_3$ (4-5 eq.), [(Dimethylammonium)methyl]trifluoroborate internal salt (3 eq.), THF and water. The reaction mixture is heated at 80° C. until completion is observed by UPLC/MS (6-8 days). Additions of Xphos, $Pd(OAc)_2$, $Cs_2CO_3$ and [(Dimethylammonium)methyl]trifluoroborate internal salt are performed every 24 h to reach a good level of conversion. A saturated $NaHCO_3$ solution is added to the reaction mixture followed by extraction with EtOAc. The combined organic layers are washed with water and brine, dried over anhydrous $MgSO_4$, filtered, concentrated in vacuo and purified by flash chromatography on silica gel to afford the expected functionalized γ-ketoamide.

Illustrative Synthesis of Int 090

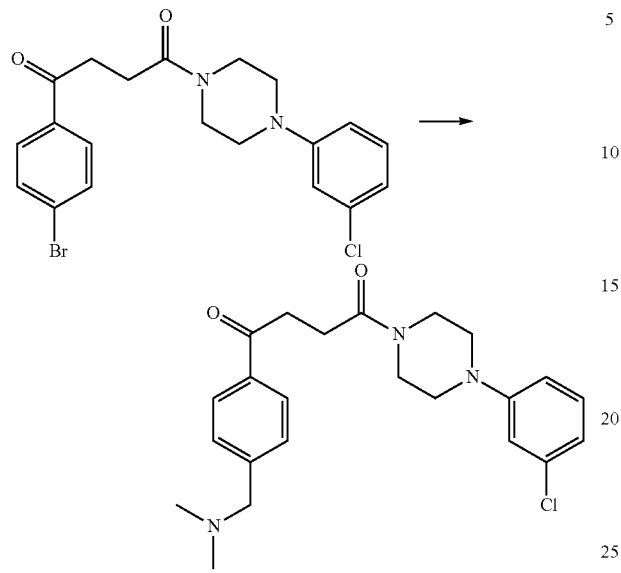

A vial is charged with Int 118 (300 mg, 0.69 mmol, 1 eq.), Xphos (59 mg, 0.0124 mmol, 0.018 eq.), Pd(OAc)$_2$ (14 mg, 0.062 mmol, 0.09 eq.), Cs$_2$CO$_3$ (1.12 g, 3.44 mmol, 5 eq.), [(Dimethylammonium)methyl]trifluoroborate internal salt (262 mg, 2.07 mmol, 3 eq.), THF (2.3 mL) and water (0.6 mL). The reaction mixture is heated at 80° C. for 2 days. Xphos (30 mg, 0.0062 mmol, 0.009 eq.), Pd(OAc)$_2$ (7 mg, 0.031 mmol, 0.045 eq.) and [(Dimethylammonium)methyl] trifluoroborate internal salt (66 mg, 0.52 mmol, 0.75 eq.) are added and the reaction mixture is heated at 80° C. for 24 h. Cs$_2$CO$_3$ (440 mg, 1.35 mmol, 2 eq.), and [(Dimethylammonium)methyl]trifluoroborate internal salt (80 mg, 0.63 mmol, 1 eq.) are added and the reaction mixture is heated at 80° C. for 2 days. Xphos (30 mg, 0.0062 mmol, 0.009 eq.) and Pd(OAc)$_2$ (7 mg, 0.031 mmol, 0.045 eq.) are added and the reaction mixture is stirred at r.t. for 3 days. A saturated NaHCO$_3$ solution is added to the reaction mixture followed by extraction with EtOAc. The combined organic layer are washed with water and brine, dried over anhydrous MgSO$_4$, filtered, concentrated in vacuo and purified by flash chromatography on silica gel (eluting with heptane/DCM 1/0 to 0/1 then DCM/MeOH 100/0 to 90/10) to afford the expected product. LCMS: MW (calcd): 414; m/z MW (obsd): 414-416 (M+H).

1.2.5. General Method E: Functionalization of γ-Ketoamide

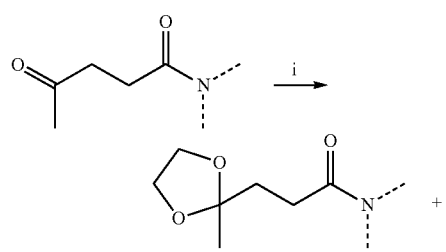

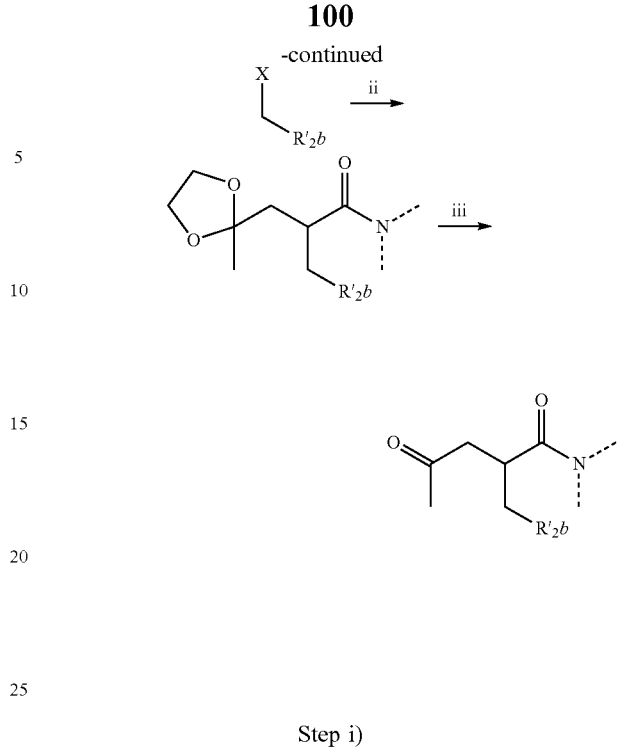

Step i)

A Dean-Starck apparatus is loaded with γ-ketoamide (1 eq.) in toluene, ethylene glycol (1.2 to 1.4 eq.) and p-toluenesulfonic acid (0.06 to 0.2 eq.). The reaction mixture is heated at reflux for 2 h to 4 h. A solution of NaOH 0.1N and EtOAc are added, the organic layer is separated, dried over anhydrous MgSO$_4$, filtered, concentrated in vacuo to afford the expected dioxolane. This residue is either purified by flash chromatography on silica gel or used as such in next step.

Step ii)

To a solution of the dioxolane obtained in the previous step (1 eq.) in dry THF at −78° C. is added dropwise LDA or LiHMDS (2M solution in THF, 1.1 eq.). The reaction mixture is stirred at −78° C. for 30 min, then 0° C. for 10 min then cooled to −78° C. for dropwise addition of a solution of alkyl halide (1.4 eq.) in dry THF. The reaction mixture is allowed to warm to r.t. and quenched with a saturated NH$_4$Cl solution. After evaporation of the THF, the aqueous layer is extracted with EtOAc, the combined organic layer are washed with water and brine, dried over anhydrous MgSO$_4$, filtered, concentrated in vacuo and purified by flash chromatography on silica gel to afford the expected functionalized dioxolane.

Step iii)

To a solution of the functionalized dioxolane obtained in the previous step (1 eq.) in MeOH is added an aqueous solution of HCl 6N (6 eq.). The reaction mixture is stirred at r.t. for 3 h, a saturated NaHCO$_3$ solution is added to the reaction mixture followed by extraction with EtOAc. The combined organic layers are washed with water and brine, dried over anhydrous MgSO$_4$, filtered, concentrated in vacuo and purified by flash chromatography on silica gel to afford the expected functionalized j-ketoamide.

101

Illustrative Synthesis of Int 066

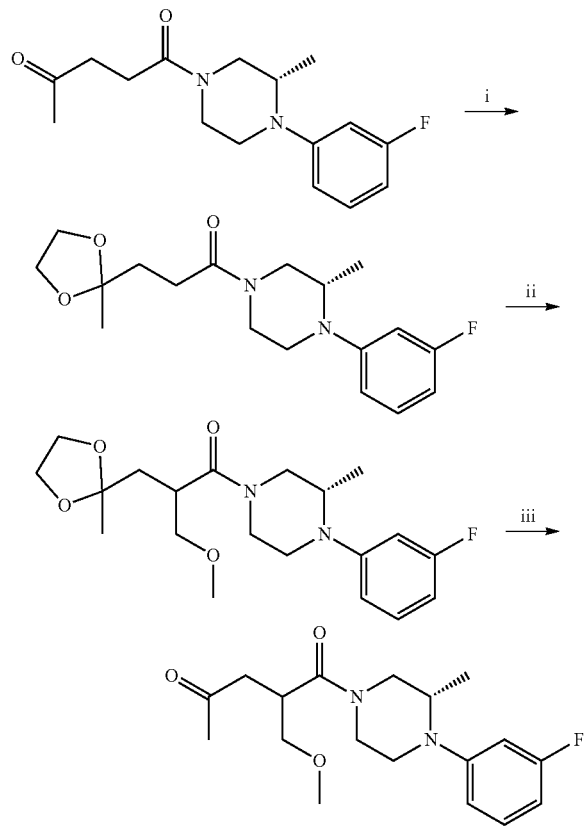

Step i) 1-[(S)-4-(3-Fluoro-phenyl)-3-methyl-piperazin-1-yl]-3-(2-methyl-[1,3]dioxolan-2-yl)-propan-1-one A Dean-Starck apparatus is loaded with Int 122 (1 g, 3.4 mmol, 1 eq.), toluene (50 mL), ethylene glycol (220 μL, 3.9 mmol, 1.2 eq.) and p-toluenesulfonic acid (100 mg, 0.58 mmol, 0.17 eq.). The reaction mixture is heated at reflux for 2 h. A solution of NaOH 0.1N and EtOAc are added, the organic layer is separated, dried over anhydrous MgSO₄, filtered, concentrated in vacuo to afford the expected dioxolane used as such in next step. LCMS: MW (calcd): 336; m/z MW (obsd): 337 (M+H).

Step ii) 1-[(S)-4-(3-Fluoro-phenyl)-3-methyl-piperazin-1-yl]-2-methoxymethyl-3-(2-methyl-[1,3]dioxolan-2-yl)-propan-1-one To a solution of the dioxolane obtained in the previous step (380 mg, 1.13 mmol, 1 eq.) in dry THF (30 mL) at −78° C. is added dropwise LDA (2M solution in THF, 0.6 mL, 1.2 mmol, 1.1 eq.). The reaction mixture is stirred at −78° C. for 30 min, then 0° C. for 10 min then cooled to −78° C. for dropwise addition of a solution of bromomethylether (137 μL, 1.5 mmol, 1.4 eq.) in dry THF (5 mL). The reaction mixture is allowed to warm to r.t. and quenched with a saturated NH₄Cl solution. After evaporation of the THF, the aqueous layer is extracted with EtOAc, the combined organic layer are washed with water and brine, dried over anhydrous MgSO₄, filtered, concentrated in vacuo and purified by flash chromatography on silica gel (eluting with Heptane/EtOAc 100/0 to 50/50) to afford the expected functionalized dioxolane. LCMS: MW (calcd): 380; m/z MW (obsd): 381 (M+H).

Step iii) 1-[(S)-4-(3-Fluoro-phenyl)-3-methyl-piperazin-1-yl]-2-methoxymethyl-pentane-1,4-dione To a solution of the functionalized dioxolane obtained in the previous step (190 mg, 0.5 mmol, 1 eq.) in MeOH (5 mL) is added an aqueous solution of HCl 6N (0.5 mL, 3 mmol, 6 eq.). The reaction mixture is stirred at r.t. for 3 h, a saturated NaHCO₃ solution is added to the reaction mixture followed by extraction with EtOAc. The combined organic layers are washed with water and brine, dried over anhydrous MgSO₄, filtered, concentrated in vacuo and purified by flash chromatography on silica gel (eluting with DCM/acetone 100/0 to 90/10) to afford the expected product. LCMS: MW (calcd): 336; m/z MW (obsd): 337 (M+H).

1.2.6. General Method F: Bucherer Bergs Reaction

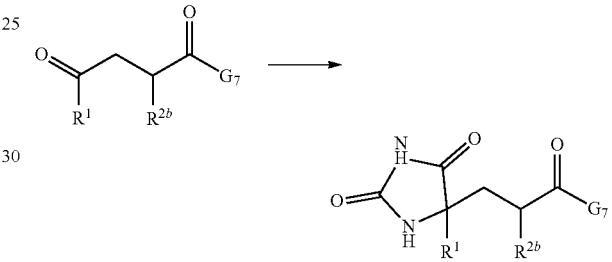

$G_7 = O\text{-}Alk_1, Alk_2\text{-}N\text{-}Alk_3$

A pressure reactor or an open round bottom flask equipped with a condenser is charged with a solution of (NH₄)₂CO₃ or (NH₄)HCO₃ (8-12 eq.) in water. KCN (2 to 4 eq.) is added portionwise then a solution of γ-ketoester or γ-ketoamide (1 eq.) in EtOH is added. The vessel is sealed and heated at 60-90° C. for 1 h to 2 days. The reaction mixture is cooled to r.t., combined with water and extracted with AcOEt or CHCl₃/nBuOH 10%. The combined organic layers are washed with water and brine, dried (over anhydrous Na₂SO₄ or MgSO₄), filtered and concentrated in vacuo. The residue is either recrystallized or purified by flash chromatography on silica gel to afford the expected hydantoin derivative.

Illustrative Synthesis of (R)-5-Methyl-5-((S)-2-methyl-3-oxo-butyl)-imidazolidine-2,4-dione+(S)-5-Methyl-5-((R)-2-methyl-3-oxo-butyl)-imidazolidine-2,4-dione

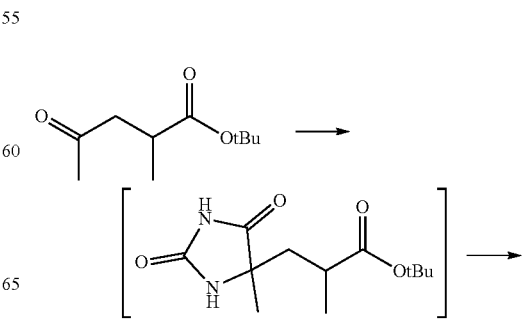

-continued

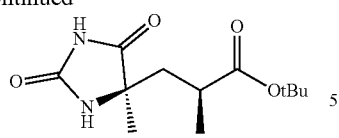

A pressure reactor is charged with a solution of (NH₄)₂CO₃ (79.4 g, 0.826 mol, 8 eq.) in water (400 mL). KCN (20 g, 0.307 mol, 3 eq.) is added portionwise then a solution of γ-ketoester (19.15 g, 0.103 mol, 1 eq.) in EtOH (400 mL) is added. The vessel is sealed and heated at 90° C. overnight. The reaction mixture is cooled to r.t., combined with water and extracted with CHCl₃/nBuOH 10%. The combined organic layers are washed with brine, dried over anhydrous MgSO₄, filtered, concentrated in vacuo.

The above reaction is performed twice and the two crude residues are gathered for recrystallization. A flask is charged with the two crude residues, EtOH (250 mL) is added and the reaction mixture is heated at reflux. Upon complete dissolution, the reaction mixture is allowed to cool to r.t. for 2 days, it is filtered and the crystalline solid is combined with EtOH (200 mL), heated to reflux, cooled to r.t. overnight and filtered to afford the expected hydantoin as a trans-Mc racemic mixture (LCMS: >99% de, MW (calcd): 256; m/z MW (obsd): 257 (M+H)).

Illustrative Synthesis of Cpd 172

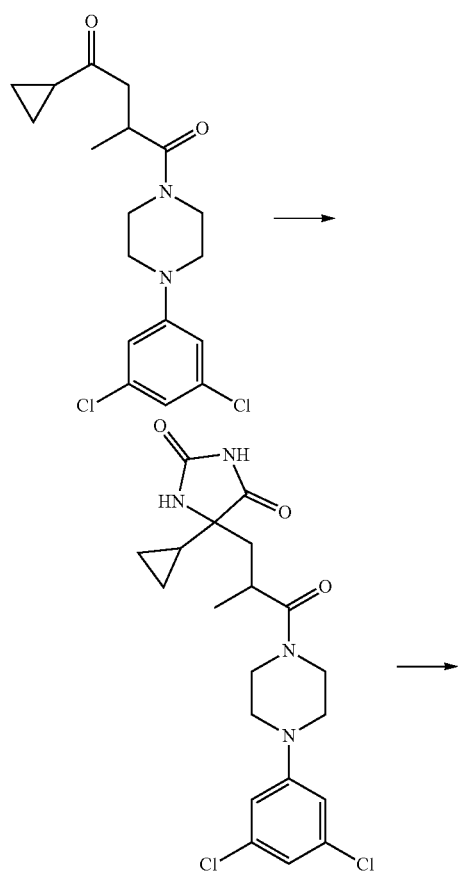

-continued

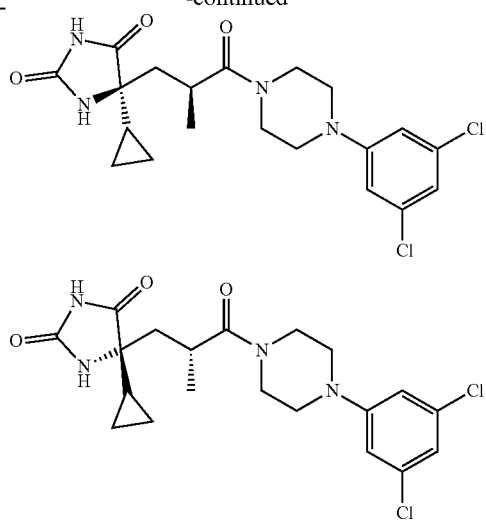

A pressure reactor is charged with (NH₄)₂CO₃ (0.645 g, 6.71 mmol, 10 eq.), KCN (0.175 g, 2.69 mmol, 4 eq.), Int 046 (0.248 g, 0.671 mmol, 1 eq.), EtOH (4 mL) and water (4 mL). The vessel is sealed and heated at 60° C. for 40 h. The reaction mixture is cooled to r.t., combined with water and extracted with DCM. The combined organic layers are washed with brine, dried over anhydrous MgSO₄, filtered, concentrated in vacuo. Purification by flash chromatography on silica gel (eluting with DCM/iPrOH 20/1) afforded the two diastereoisomers, of which the faster eluting compound is the expected product. (LCMS: MW (calcd): 439-441; m/z MW (obsd): 439-441 (M+H)).

1.2.7. General Method G: Method for Preparation of Hydantoin Propionic Acids

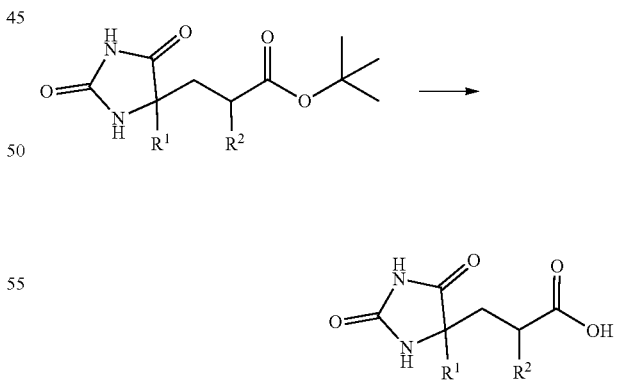

A flask is charged with tert-butyl ester (1 eq.) and HCl 4N in dioxane (5 to 40 eq.). In some cases, an additional solvent such as DCM, dioxane or water is added to increase solubility. The reaction mixture is stirred at r.t. for 1 h to 4 days until complete conversion. The reaction mixture is either concentrated in vacuo or filtered and washed with Et₂O to afford the expected carboxylic acid.

105
Illustrative Synthesis of Int 169

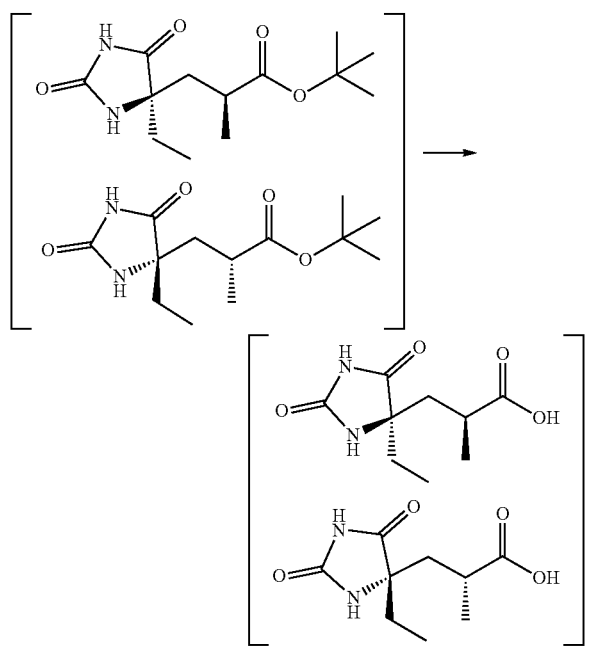

A flask is charged with Int 170 (3.6 g, 13.32 mmol, 1 eq.) and HCl 4N in dioxane (33.3 mL, 133 mmol, 10 eq.). The reaction mixture is stirred at r.t. for 2 days and concentrated in vacuo to afford the expected product.

1.2.8. General Method H: Amide Bond Formation

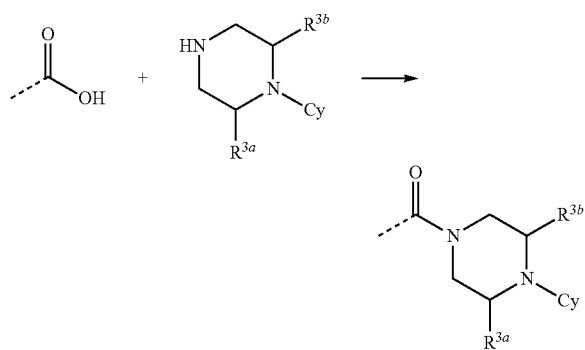

1.2.8.1. Method H1: EDC/HOBt

A solution of acid (1 eq.), Et$_3$N (3 to 4 eq.), HOBt (0.1 to 1.1 eq.) in DMF (or DCM) is stirred at r.t. EDC.HCl (1 to 1.2 eq.) is added, then amine (0.95 to 2 eq.) is added and the reaction mixture is stirred at r.t. for 5 h to 2 days. The reaction mixture is partitioned between DCM (or EtOAC) and water, extracted with DCM (or EtOAc). The combined organic layers are washed with water and brine, dried over anhydrous Na$_2$SO$_4$ (or MgSO$_4$), filtered, concentrated in vacuo and purified by flash chromatography on silica gel or preparative LCMS to afford the expected amide.

106
Illustrative Synthesis of Cpd 052

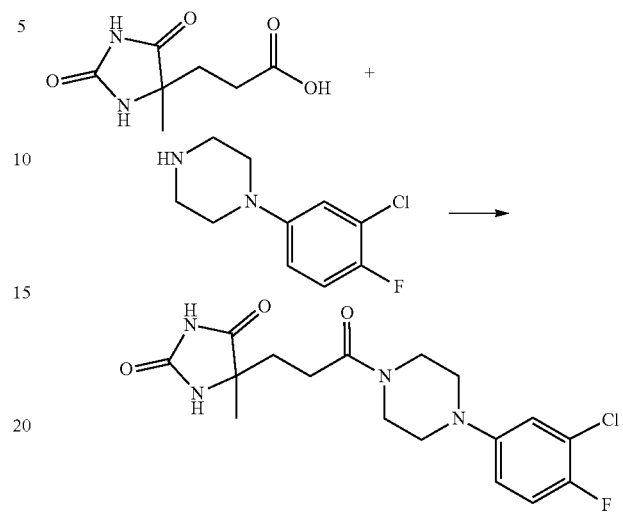

A solution of 3-(4-methyl-2,5-dioxo-imidazolidin-4-yl) propionic acid (64 mg, 0.34 mmol, 1 eq.), Et$_3$N (142 µL, 1.02 mmol, 3 eq.), HOBt (46 mg, 0.34 mmol, 1 eq.) in DMF (2 mL) is stirred at r.t. EDC.HCl (78 mg, 0.41 mmol, 1.2 eq.) is added, then 1-(3-chloro-4-fluorophenyl)piperazine dihydrochloride (150 mg, 0.52 mmol, 1.5 2 eq.) is added and the reaction mixture is stirred at r.t. overnight. The reaction mixture is partitioned between DCM and water, extracted with DCM. The combined organic layers are washed with water and brine, dried over anhydrous MgSO$_4$, filtered, concentrated in vacuo and purified by preparative LCMS to afford the expected product. LCMS: MW (calcd): 383; m/z MW (obsd): 383-385 (M+H).

1.2.8.2. Method H2: HATU

A flask is charged with acid (1 eq.), amine (0.85 to 1.1 eq.), HATU (0.85 to 1.1 eq.) and DMF (or THF). DIPEA (2 to 6 eq.) is added and the reaction mixture is stirred at r.t. for 5 h to 2 days. The reaction mixture is partitioned between EtOAc and water, extracted with EtOAc. The combined organic layers are washed with water and brine, dried (over anhydrous Na$_2$SO$_4$, MgSO$_4$, or hydrophobic column), filtered, concentrated in vacuo and purified by flash chromatography on silica gel or preparative LCMS to afford the expected amide.

Illustrative Synthesis of Cpd 237 (Mixture of Tram Isomers)

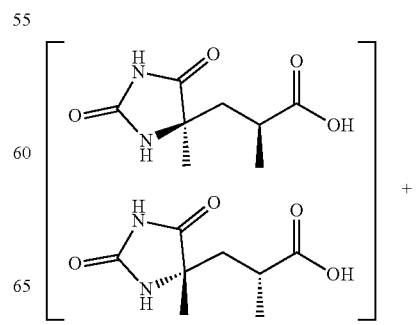

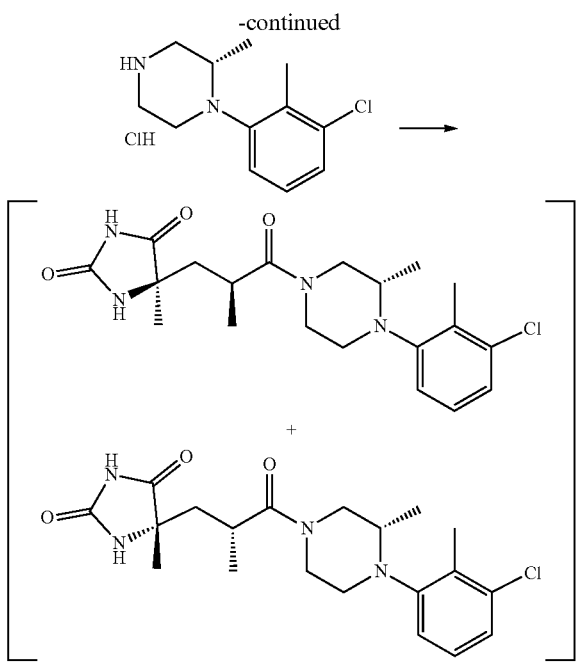

A flask is charged with Int 165 (70 mg, 0.35 mmol, 1.1 eq.), Int 216 (95 mg, 0.32 mmol, 1 eq.), HATU (127 mg, 0.34 mmol, 1.05 eq) and DMF (3 mL). DIPEA (167 µL, 0.96 mmol, 3 eq.) is added and the reaction mixture is stirred at r.t. overnight. The reaction mixture is partitioned between EtOAc and water, extracted with EtOAc. The combined organic layers are washed with water and brine, dried over hydrophobic column, filtered, concentrated in vacuo and purified by flash chromatography on silica gel (eluting with DCM/MeOH 100/0 to 96/4) to afford the expected product. LCMS: MW (calcd): 407; m/z MW (obsd): 407-409 (M+H).

1.2.8.3. Method H3: BOP

A flask is charged with acid (1 eq.), DMF (or DCM), DIPEA or Et₃N (2 to 6 eq.) and BOP (0.77 to 1.1 eq.). After 5-15 min, amine (0.77 to 1.5 eq.) is added and the reaction mixture is stirred at r.t. for 5 h to 2 days. The reaction mixture is partitioned between EtOAc (or DCM) and water, extracted with EtOAc (or DCM). The combined organic layers are washed with water and brine, dried (over anhydrous Na₂SO₄, MgSO₄, or hydrophobic column), filtered, concentrated in vacuo and purified by flash chromatography on silica gel or preparative LCMS to afford the expected amide.

Illustrative Synthesis of Int 034

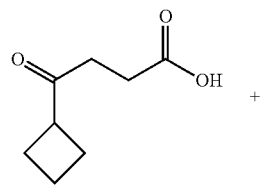

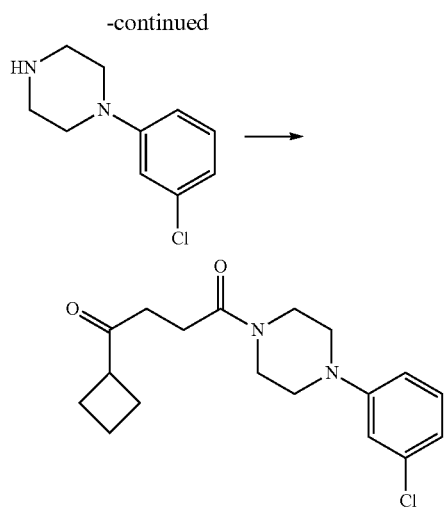

A flask is charged with 4-cyclobutyl-4-oxo-butyric acid (104 mg, 0.67 mmol, 1 eq.), DMF (2 mL), Et₃N (0.4 mL, 2.88 mmol, 4.3 eq.) and BOP (320 mg, 0.72 mmol, 1.1 eq.). After 5-15 min, 1-(3-chlorophenyl)piperazine (157 mg, 0.67 mmol, 1 eq.) is added and the reaction mixture is stirred at r.t. overnight. The reaction mixture is partitioned between DCM and water, extracted with DCM. The combined organic layers are washed with water and brine, concentrated in vacuo and purified by flash chromatography on silica gel (eluting with DCM/EtOAc 90/10) afford the expected product. LCMS: MW (calcd): 335; m/z MW (obsd): 335-337 (M+H).

1.2.8.4. Method H4: CDI

A flask is charged with acid (1 eq.), amine (1 eq.) and DMF. HOBt (0.8 eq.), DIPEA (1.5 eq.) and PS-CDI (load 1.25 mmol/g, 1.3 eq.) are added and the reaction mixture is stirred in a microwave reactor at 60° C. for 30-60 min. Reaction mixture is filtered to remove PS-CDI, washed with EtOAc and the filtrate is extracted with EtOAc and brine. The combined organic layers concentrated in vacuo and purified by flash chromatography on silica gel or preparative LCMS to afford the expected amide.

Illustrative Synthesis of Cpd 379

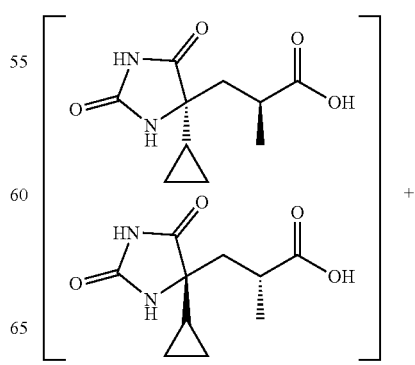

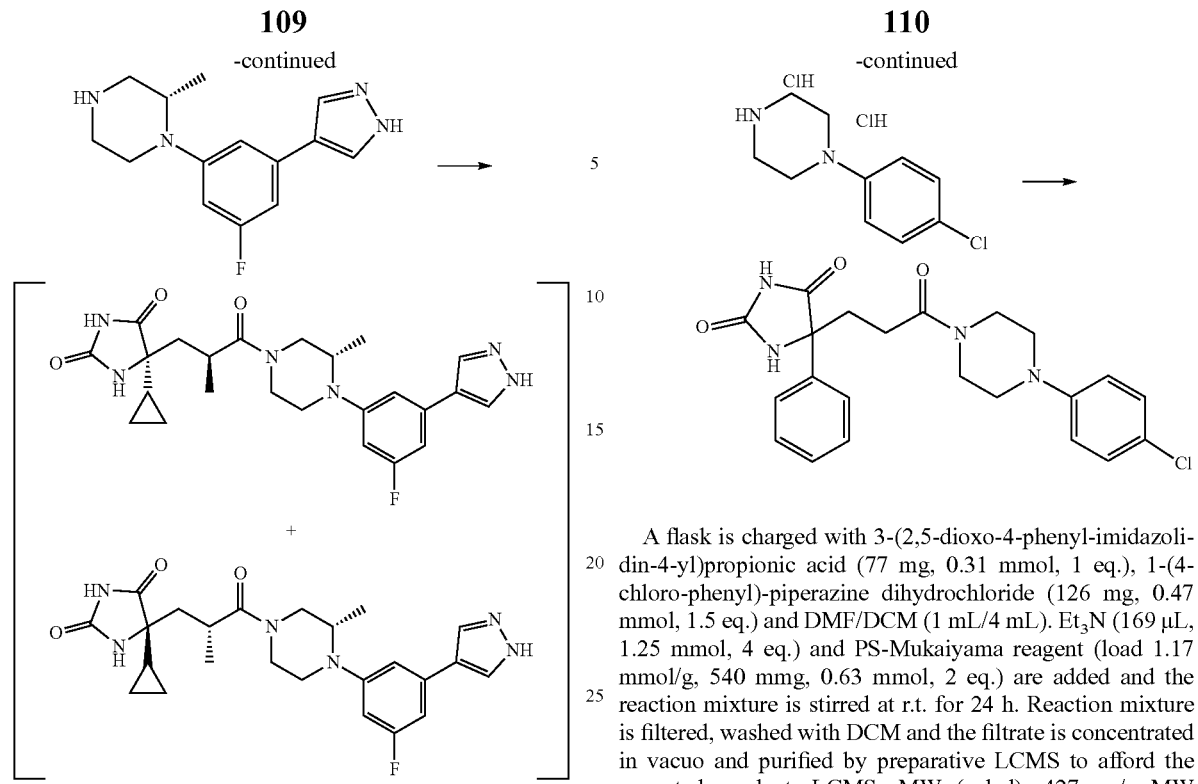

A flask is charged with Int 164 (41 mg, 0.23 mmol, 1 eq.), Int 232 (60 mg, 0.23 mmol, 1 eq.) and DMF (5 mL). HOBt (28 mg, 0.18 mmol, 0.8 eq.), DIPEA (60 µL, 0.34 mmol, 1.5 eq.) and PS-CDI (load 1.25 mmol/g, 237 mg, 0.29 mmol, 1.3 eq.) are added and the reaction mixture is stirred in a microwave reactor at 60° C. for 30 min. Reaction mixture is filtered to remove PS-CDI, washed with EtOAc and the filtrate is extracted with EtOAc and brine. The combined organic layers concentrated in vacuo and purified by flash chromatography (eluting with DCM/MeOH 100/0 to 90/10) to afford the expected product. LCMS: MW (calcd): 468; m/z MW (obsd): 469 (M+H).

1.2.8.5. Method H5: Mukaiyama Reagent

A flask is charged with acid (1 eq.), amine (1.5 eq.) and DMF/DCM. Et₃N (4 eq.) and PS-Mukaiyama reagent (load 1.17 mmol/g, 2 eq.) are added and the reaction mixture is stirred at r.t. for 24 h. Reaction mixture is filtered, washed with DCM and the filtrate is concentrated in vacuo and purified by preparative LCMS to afford the expected amide.

Illustrative Synthesis of Cpd 005

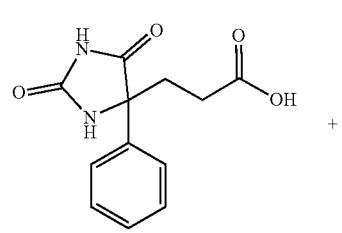

A flask is charged with 3-(2,5-dioxo-4-phenyl-imidazolidin-4-yl)propionic acid (77 mg, 0.31 mmol, 1 eq.), 1-(4-chloro-phenyl)-piperazine dihydrochloride (126 mg, 0.47 mmol, 1.5 eq.) and DMF/DCM (1 mL/4 mL). Et₃N (169 µL, 1.25 mmol, 4 eq.) and PS-Mukaiyama reagent (load 1.17 mmol/g, 540 mmg, 0.63 mmol, 2 eq.) are added and the reaction mixture is stirred at r.t. for 24 h. Reaction mixture is filtered, washed with DCM and the filtrate is concentrated in vacuo and purified by preparative LCMS to afford the expected product. LCMS: MW (calcd): 427; m/z MW (obsd): 427-429 (M+H).

1.2.9. General Method I: Functionalization of Final Compound 1.2.9.1. Method I1: Acetylation

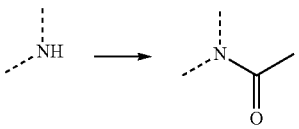

To a solution of amino derivative (1 eq.) in pyridine is added acetic anhydride (1.02 eq.). The reaction mixture is stirred at r.t. for 4 h to 16 h, concentrated in vacuo and purified by flash chromatography on silica gel to afford the expected acetamide.

Illustrative Synthesis of Cpd 223

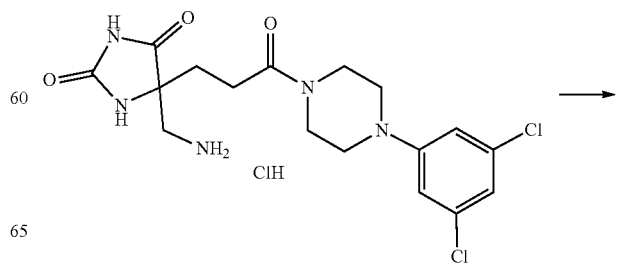

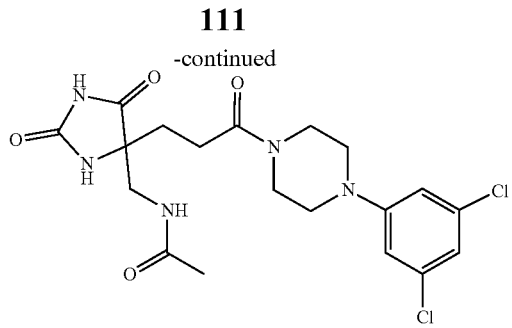

To a solution of Cpd 180 (150 mg, 0.33 mmol, 1 eq.) in pyridine (2 mL) is added acetic anhydride (32 μL, 0.34 mmol, 1.02 eq.). The reaction mixture is stirred at r.t. for 4 h, concentrated in vacuo and purified by flash chromatography on silica gel (eluting with DCM/MeOH 100/0 to 90/10) to afford the expected product. LCMS: MW (calcd): 456; m/z MW (obsd): 456-458 (M+H).

1.2.9.2. Method I2: NBoc Deprotection

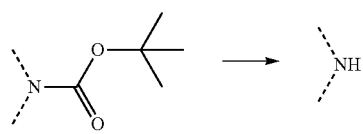

To a solution of N-tert-butoxycarbonyl derivative (1 eq.) in a mixture DCM/MeOH is added HCl 4N in dioxane (10 to 20 eq.). The reaction mixture is stirred at r.t. for 4 h to 2 days and concentrated in vacuo. The residue is either purified by preparative HPLC or dissolved in DCM/MeOH, neutralized by addition of a base (NH₃ in MeOH (7N) or NaHCO₃) and purified by SCX column or flash chromatography on silica gel to afford the expected amine.

Illustrative Synthesis of Cpd 241

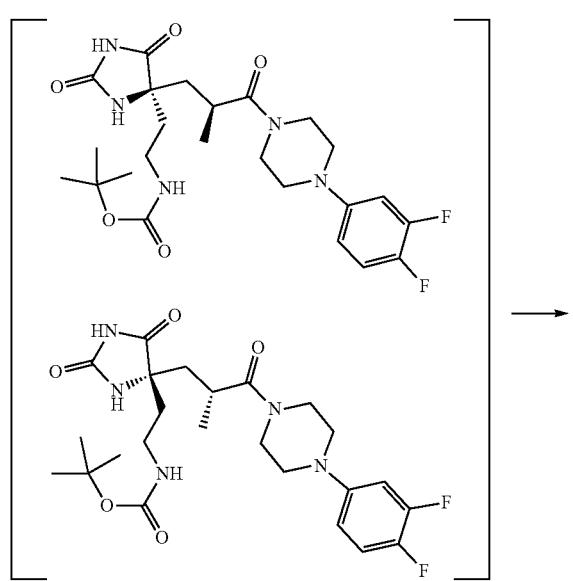

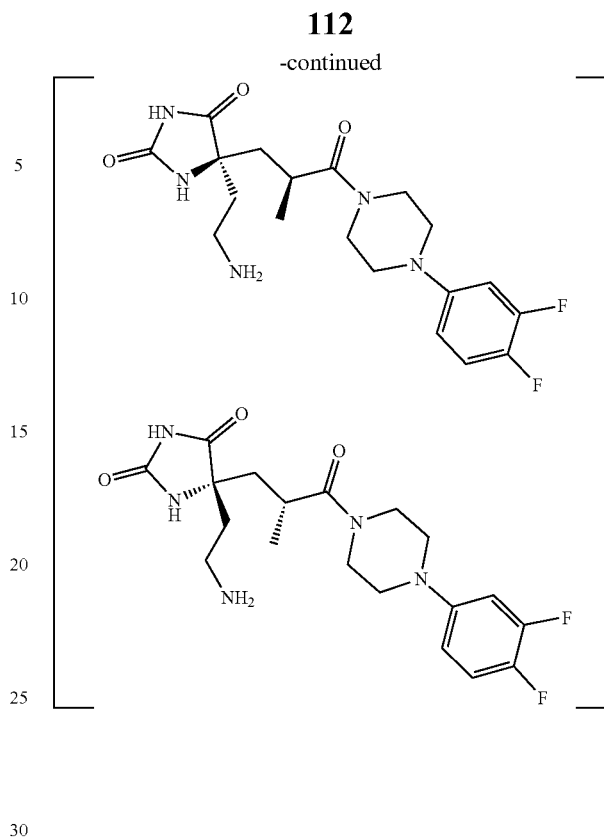

To a solution of Cpd 235 (39 mg, 0.076 mmol, 1 eq.) in a mixture DCM/MeOH (1.5 mL/1 mL) is added HCl 4N in dioxane (0.37 mL, 1.51 mmol, 20 eq.). The reaction mixture is stirred at r.t. for 16 h and concentrated in vacuo. The residue is dissolved in DCM/MeOH, neutralized by addition of NH₃ in MeOH (7N, 110 μL, 0.75 mmol, 10 eq.) and purified by SCX-2 column (eluting successively with DCM/MeOH/NH₃: 8/1/1, 6/3/1 and 0/9/1) to afford the expected product. LCMS: MW (calcd): 409; m/z MW (obsd): 410 (M+H).

1.2.9.3. Method I3: Alkylation

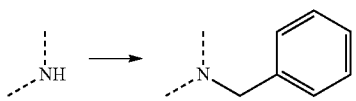

To a solution of amino derivative (1 eq.) in DMF is added K₂CO₃ (3 eq.) then benzyl bromide (1 eq.). The reaction mixture is stirred at r.t. for 16 h to 4 days, quenched by addition of water and extracted with EtOAc. The organic layers are combined, washed with brine, dried by filtration over hydrophobic column, concentrated in vacuo and purified by flash chromatography on silica gel to afford the expected benzylamine.

113
Illustrative Synthesis of Cpd 181

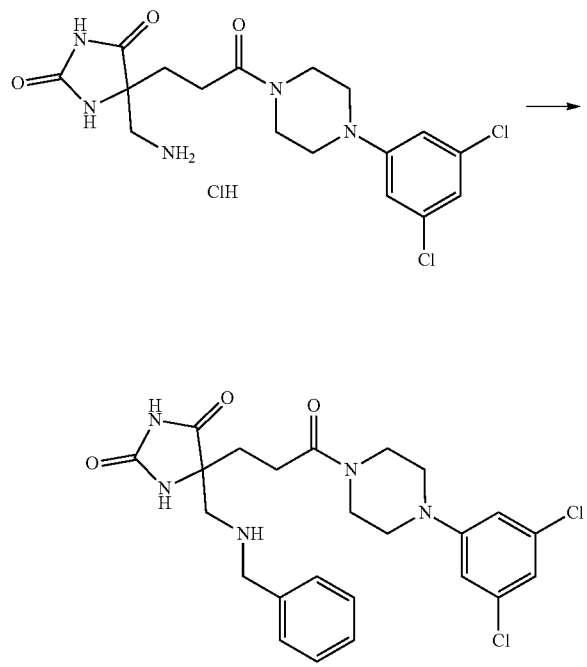

To a solution of Cpd 180 (200 mg, 0.444 mmol, 1 eq.) in DMF (2 mL) is added $K_2CO_3$ (184 mg, 1.331 mmol, 3 eq.) then benzyl bromide (76 mg, 0.444 mmol, 1 eq.). The reaction mixture is stirred at r.t. overnight, quenched by addition of water and extracted with EtOAc. The organic layers are combined, washed with brine, dried by filtration over hydrophobic column, concentrated in vacuo and purified by flash chromatography on silica gel (eluting with DCM/isopropyl alcohol 100/0 to 90/10) to afford the expected product. LCMS: MW (calcd): 504; m/z MW (obsd): 504-506 (M+H).

1.2.9.4. Method I4: O-Debenzylation

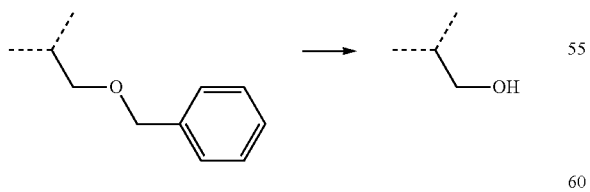

To a solution of benzyloxy derivative (1 eq.) in dry THF or MeOH under argon atmosphere is added $Pd(OH)_2/C$. The reaction mixture is stirred under $H_2$ atmosphere at r.t. for 5 h to 2 days then filtered on celpure P65. The filtrate is concentrated in vacuo and purified by flash chromatography on silica gel to afford the expected alcohol.

114
Illustrative Synthesis of Cpd 268 (Mixture of Trans Isomers)

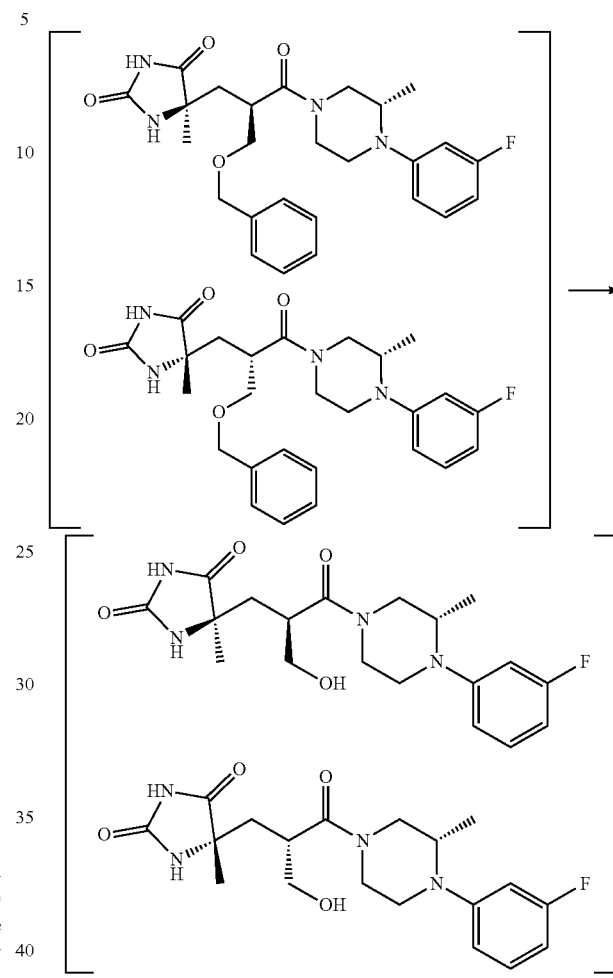

To a solution of Int 062 (70 mg, 0.15 mmol, 1 eq.) in dry THF (75 mL) under argon atmosphere is added $Pd(OH)_2/C$ (35 mg, 50% w/w). The reaction mixture is degassed by 3 vacuum/hydrogen filling cycles, and stirred under $H_2$ atmosphere at r.t. for 2 days then filtered on celpure P65. The filtrate is concentrated in vacuo and purified by flash chromatography on silica gel (eluting with DCM/MeOH 100/0 to 95/5) to afford the expected product. LCMS: MW (calcd): 392; m/z MW (obsd): 429-431 (M+H).

1.2.9.5. Method I5: Two-Steps Functionalization by Suzuki Reaction

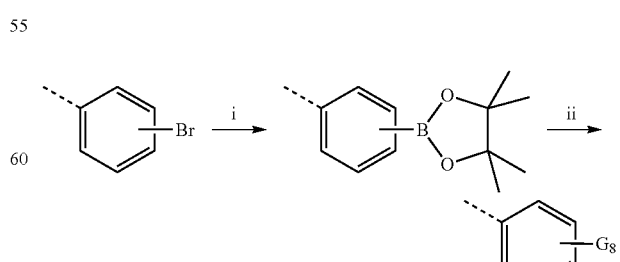

$G_8$=Ar, HetAr

Step i)

A vial is loaded with bromo derivative (1 eq.), bis(pinacolato)diboron (1.2 eq.), KOAc (3 eq.) and dioxane degassed with $N_2$. $PdCl_2(dppf)$ (0.05 eq.) is added, the vial is sealed and stirred at 90° C. overnight. The reaction mixture is filtered on celpure P65, washed with EtOAc. The filtrate is concentrated in vacuo and purified by flash chromatography on silica gel to afford the expected boronic ester.

Step ii)

A vial is loaded with the boronic ester obtained in the previous step (1 eq.), aryl halide (1.1 to 1.2 eq.), $Na_2CO_3$ (3 eq.) and a mixture dioxane/water (9/1) degassed with $N_2$. $PdCl_2(dppf)$ (0.05 to 0.2 eq.) is added, the vial is sealed and stirred at 90° C. overnight. The reaction mixture is filtered on celpure P65, washed with EtOAc. The filtrate is concentrated in vacuo and purified by flash chromatography on silica gel or preparative HPLC to afford the expected compound.

Illustrative Synthesis of Cpd 372

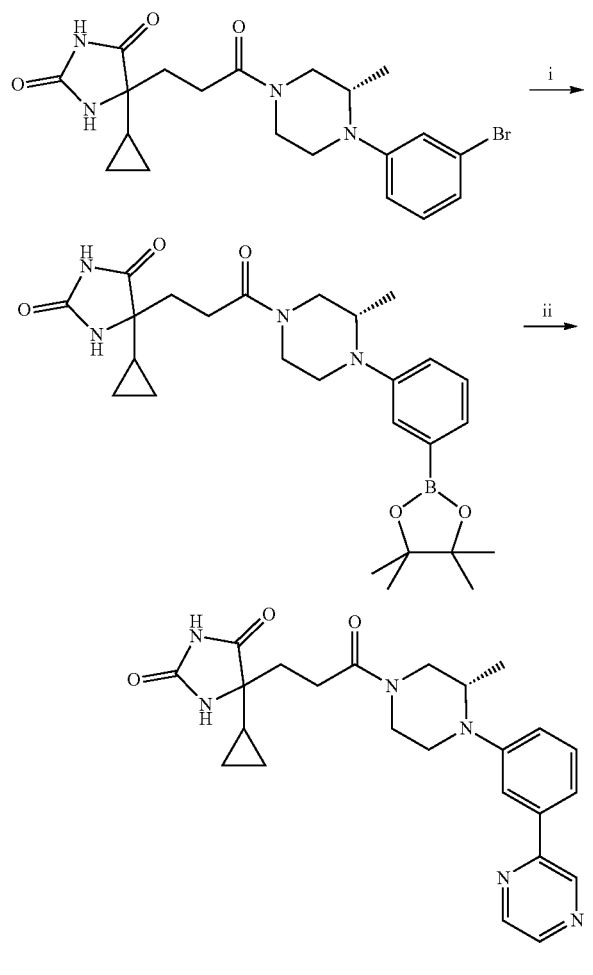

Step i) 5-Cyclopropyl-5-(3-{(S)-3-methyl-4-[3-(4,4,5,5-tetramethyl-[1,3,2]dioxaborolan-2-yl)-phenyl]-piperazin-1-yl}-3-oxo-propyl)-imidazolidine-2,4-dione A vial is loaded with Cpd 270 (90 mg, 0.200 mmol, 1 eq.), bis(pinacolato)diboron (61 mg, 0.240 mmol, 1.2 eq.), KOAc (59 mg, 0.601 mmol, 3 eq.) and dioxane (2 mL) degassed with $N_2$. $PdCl_2(dppf)$ (7 mg, 0.010 mmol, 0.05 eq.) is added, the vial is sealed and stirred at 90° C. overnight. The reaction mixture is filtered on celpure P65, washed with EtOAc. The filtrate is concentrated in vacuo and purified by flash chromatography on silica gel (eluting with DCM/MeOH 100/0 to 97/3) to afford the expected boronic ester. LCMS: MW (calcd): 496; m/z MW (obsd): 497 (M+H).

Step ii) 5-Cyclopropyl-5-{3-[(S)-3-methyl-4-(3-pyrazin-2-yl-phenyl)-piperazin-1-yl]-3-oxo-propyl}-imidazolidine-2,4-dione A vial is loaded with the boronic ester obtained in the previous step (86 mg, 0.173 mmol, 1 eq.), iodopyrazine (39 mg, 0.191 mmol, 1.1 eq.), $Na_2CO_3$ (100 mg, 0.520 mmol, 3 eq.) and a mixture dioxane/water (2.5 mL, 9/1) degassed with $N_2$. $PdCl_2(dppf)$ (7 mg, 0.009 mmol, 0.05 eq.) is added, the vial is sealed and stirred at 90° C. overnight. The reaction mixture is filtered on celpure P65, washed with EtOAc. The filtrate is concentrated in vacuo and purified by flash chromatography on silica gel (eluting with DCM/MeOH 100/0 to 95/5) to afford the expected product. LCMS: MW (calcd): 449; m/z MW (obsd): 450 (M+H).

1.2.9.6. Method I6: Suzuki Reaction

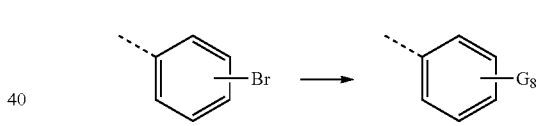

$G_8$=Ar, HetAr

A vial is loaded with bromo derivative (1 eq.), boronic acid or boronic ester (1.3 to 2 eq.), $Na_2CO_3$ (3 eq.) and a mixture dioxane/water (9/1) degassed with $N_2$. $PdCl_2(dppf)$ (0.05 to 0.2 eq.) is added, the vial is sealed and stirred at 90° C. for 3 h to 20 h. The reaction mixture is quenched with water and extracted with EtOAc. The combined organic layers are washed with brine, dried (filtration over hydrophobic column or anhydrous $MgSO_4$), concentrated in vacuo and purified by flash chromatography on silica gel or preparative HPLC to afford the expected compound.

Illustrative Synthesis of Cpd 281

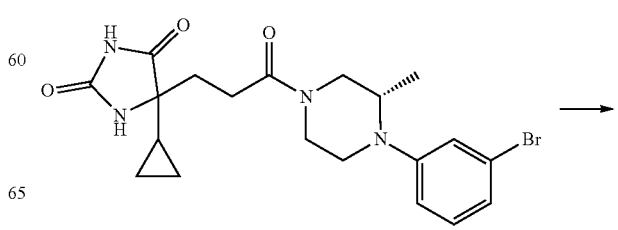

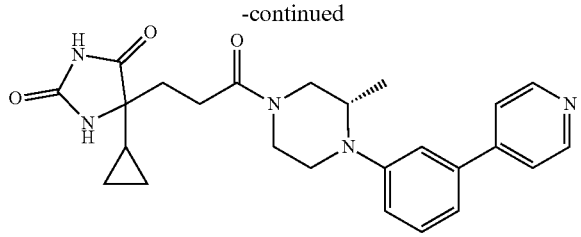

A vial is loaded with Cpd 270 (100 mg, 0.223 mmol, 1 eq.), pyridine-4-boronic acid (55 mg, 0.445 mmol, 2 eq.), Na₂CO₃ (128 mg, 0.668 mmol, 3 eq.) and a mixture dioxane/water (2 mL, 9/1) degassed with N₂. PdCl₂(dppf) (36 mg, 0.045 mmol, 0.2 eq.) is added, the vial is sealed and stirred at 90° C. for 3 h. The reaction mixture is quenched with water and extracted with EtOAc. The combined organic layers are washed with a saturated NaHCO₃ solution, brine, dried by filtration over hydrophobic column, concentrated in vacuo and purified by flash chromatography on silica gel (eluting with DCM/MeOH 100/0 to 94/6) to afford the expected product. LCMS: MW (calcd): 448; m/z MW (obsd): 449 (M+H).

Example 2. Preparation of the Compounds of the Invention 2.1. Methyl 2-[4-[3-[4-(3,5-dichlorophenyl)piperazin-1-yl]-3-oxo-propyl]-2,5-dioxo-imidazolidin-4-yl]acetate (Cpd 182) and 2-[4-[3-[4-(3,5-dichlorophenyl)piperazin-1-yl]-3-oxo-propyl]-2,5-dioxo-imidazolidin-4-yl]acetic acid (Cpd 183)

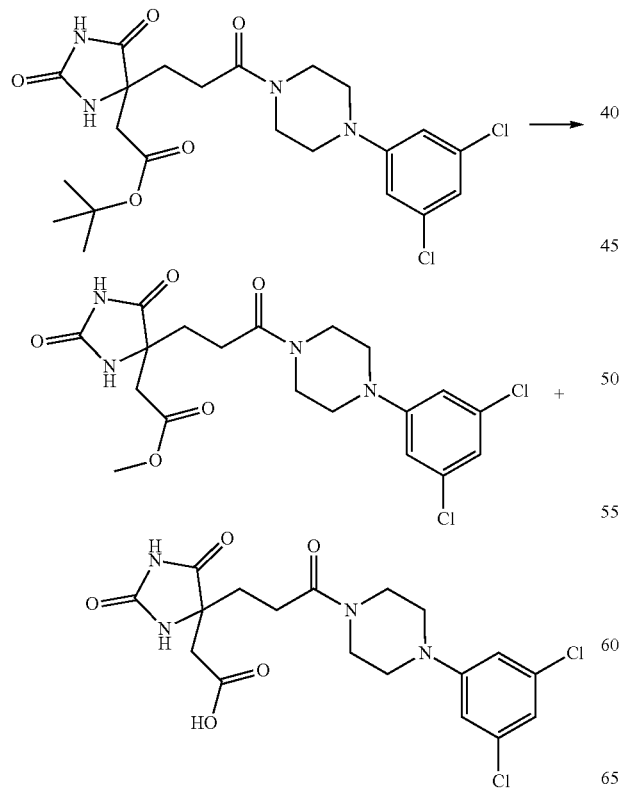

A vial is charged with Cpd 188 (1.61 g, 3.2 mmol, 1 eq.), dioxane (5 mL) and HCl 4N in dioxane (5 mL). The reaction is heated at 80° C. for 20 h, concentrated in vacuo and purified by flash chromatography on silica gel (eluting with DCM/EtOAc 60/40 to 10/90, then DCM/MeOH 90/10) to afford Cpd 182 (LCMS: MW (calcd): 457; m/z MW (obsd): 457-459 (M+H)) and Cpd 183 (LCMS: MW (calcd): 443; m/z MW (obsd): 443-445 (M+H)).

2.2. tert-butyl 2-[4-[3-[4-(3,5-dichlorophenyl)piperazin-1-yl]-3-oxo-propyl]-2,5-dioxo-imidazolidin-4-yl]acetate (Cpd 188)

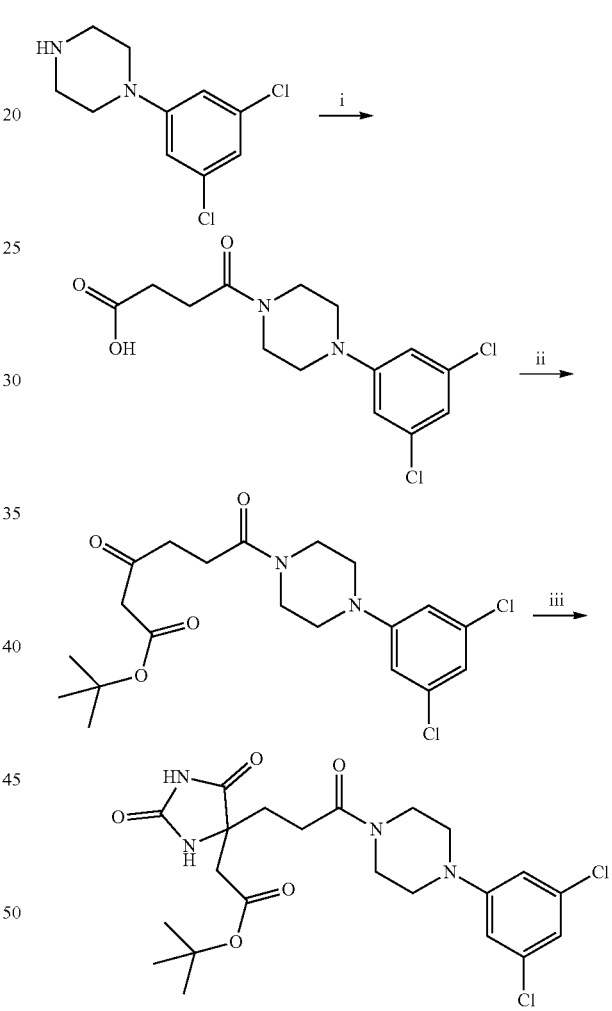

Step i) 4-[4-(3,5-Dichloro-phenyl)-piperazin-1-yl]-4-oxo-butyric acid

A flask is charged with succinic anhydride (2.38 g, 24 mmol, 1.1 eq.) and 1-(3,5-dichloro-phenyl)-piperazine (5 g, 22 mmol, 1 eq.) and toluene (100 mL). The reaction mixture is heated at reflux overnight, concentrated in vacuo and purified by flash chromatography on silica gel (eluting with DCM/MeOH 100/0 to 80/20) to afford the carboxylic acid derivative.

Step ii) 6-[4-(3,5-Dichloro-phenyl)-piperazin-1-yl]-3,6-dioxo-hexanoic acid tert-butyl ester To a solution of the carboxylic acid obtained in the previous step (7.29 g, 22 mmol, 1 eq.) in DCM (125 mL) are added DMAP (0.537 g, 4.4 mmol, 0.2 eq.), EDC.HCl (5.06 g, 26.4 mmol, 1.2 eq.) and Et₃N (9.2 mL, 66 mmol, 3 eq). The reaction mixture is stirred at r.t. for 15 min then a solution of 2,2-dimethyl-[1,3]dioxane-4,6-dione (3.8 g, 26.4 mmol, 1.2 eq.) in DCM (25 mL) is added and the reaction mixture is stirred at r.t. overnight. DMAP (1 g) and EDC.HCl (1.5 g) are added and the RM is stirred at 40° C. for 2 h, concentrated in vacuo and purified by flash chromatography on silica gel (eluting with DCM/MeOH 100/0 to 90/10). The residue is taken up in toluene (100 mL) and t-BuOH (5.8 mL, 61 mmol) is added. The reaction mixture is heated at reflux for 4 h, concentrated in vacuo and purified by flash chromatography on silica gel (eluting with Hexanes/EtOAc 70/30 to 30/70) to afford the expected β-ketoester.

Step iii) tert-butyl 2-[4-[3-[4-(3,5-dichlorophenyl)piperazin-1-yl]-3-oxo-propyl]-2,5-dioxo-imidazolidin-4-yl]acetate Starting from the above β-ketoester, the expected product is obtained according to Method F. LCMS: MW (calcd): 499; m/z MW (obsd): 499-501 (M+H).

2.3. 2-[4-[3-[4-(3,5-dichlorophenyl)piperazin-1-yl]-3-oxo-propyl]-2,5-dioxo-imidazolidin-4-yl]-N-(2-hydroxyethyl)acetamide (Cpd 189)

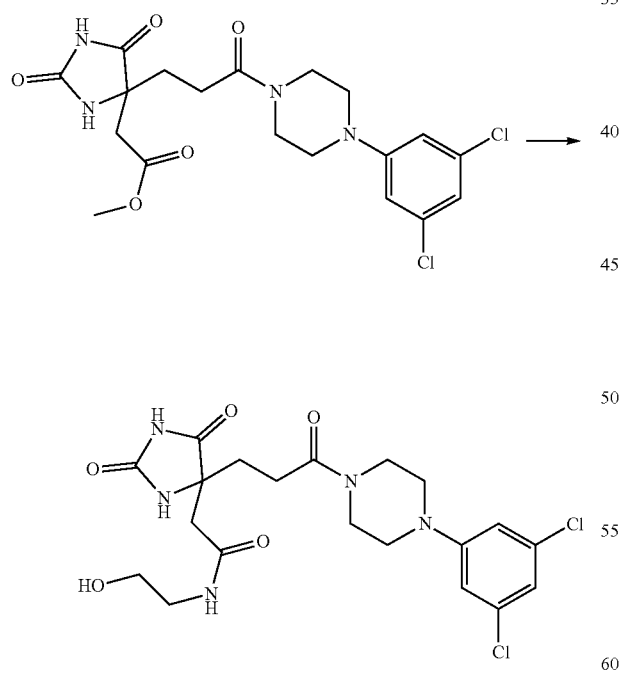

A vial is charged with Cpd 182 (150 mg, 0.32 mmol, 1 eq.), 2-amino-ethanol (193 µL, 3.2 mmol, 10 eq.) and EtOH (2 mL). The reaction mixture is heated at 160° C. for 1 h in microwave reactor, concentrated in vacuo and purified by preparative LCMS to afford the expected product. LCMS: MW (calcd): 486; m/z MW (obsd): 486-488 (M+H).

2.4. 5-[3-[4-(3,5-dichlorophenyl)piperazin-1-yl]-2-methyl-3-oxo-propyl]-5-(2-methylsulfonylethyl)imidazolidine-2,4-dione (Cpd 218)

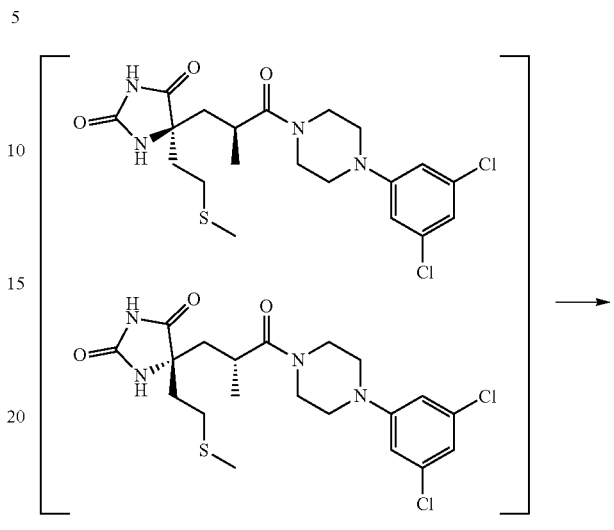

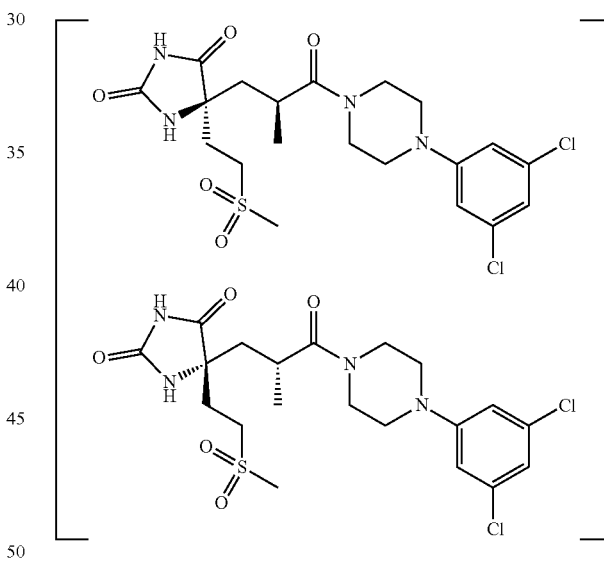

To a solution of Cpd 197 (40 mg, 0.084 mmol, 1 eq.) in DCM (2 mL) at 0° C. is added meta-chloroperoxybenzoic acid (32 mg, 0.186 mmol, 2.2 eq.). The reaction mixture is stirred at 0° C. for 45 min then at r.t. for 24 h, quenched with a saturated NaHCO₃ solution, extracted with DCM. The combined organic layers are washed with brine, dried by filtration over hydrophobic column and concentrated in vacuo. The residue is purified by flash chromatography on silica gel (eluting with DCM/MeOH 100/0 to 98/2) to afford the expected product. LCMS: MW (calcd): 505; m/z MW (obsd): 505-507 (M+H).

2.5. (5S)-cyclopropyl-5-[3-[(3S)-4-(3,5-difluorophenyl)-3-methyl-piperazin-1-yl]-3-oxo-propyl]imidazolidine-2,4-dione (Cpd 255)

2.7. 5-cyclopropyl-5-[3-[(3S)-3-methyl-4-pyridazin-3-yl-piperazin-1-yl]-3-oxo-propyl]imidazolidine-2,4-dione (Cpd 302)

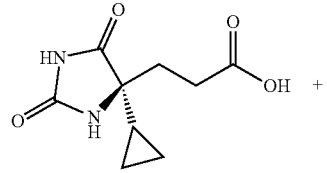 +

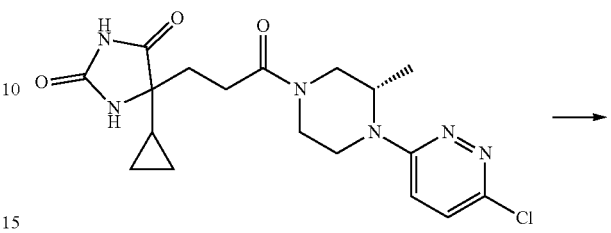

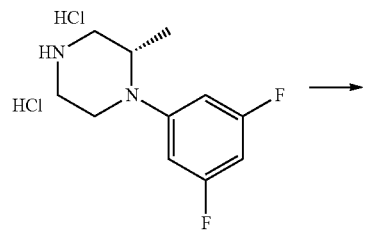

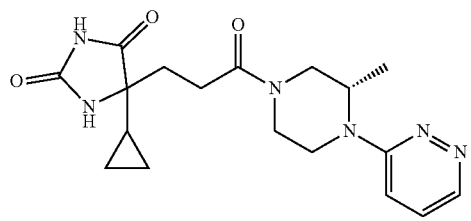

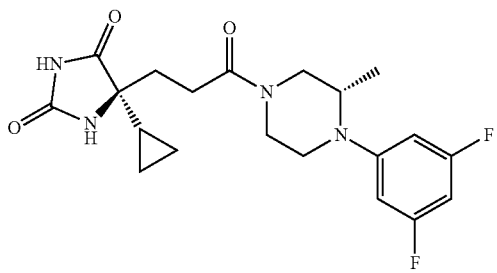

To a solution of Cpd 285 (72 mg, 0.177 mmol, 1 eq.) in EtOH (3.7 mL) and DMF (0.7 mL) is added Et₃N (0.2 mL, 1.44 mmol, 8 eq.) and the reaction mixture is heated at 40° C. to increase solubility. Pd/C 10% (14 mg) is added and the reaction mixture is stirred at r.t. overnight and filtered. The filtrate is concentrated in vacuo and purified by flash chromatography on silica gel (DCM/MeOH 100/0 to 94/6) to afford the expected product. LCMS: MW (calcd): 372; m/z MW (obsd): 373 (M+H).

(S)-Hydantoin propionic acid (Int 163, 50 g, 0.24 mol, 1.1 eq.) is dissolved in DMF (360 mL). Amine hydrochloride (61 g, 0.21 mol, 1 eq.), DIPEA (148 mL, 0.84 mol, 4 eq., added through glass funnel over 2 min), EDC.HCl (45 g, 0.24 mol, 1.1 eq.) and HOBt hydrate (4.95 g, 0.032 mol, 0.15 eq.) are added and reaction mixture is stirred at r.t. for 18 h. Reaction mixture is poured into cold stirring water (1.8 L) and stirred for 45 min. A small precipitate is formed, filtered off through black ribbon. Filtrate is extracted with EtOAc (2×650 mL and 300 mL). Combined organic layers are washed with sat. aq. NaHCO₃ (2×800 mL and 500 mL), brine (2×500 mL), dried over Na₂SO₄ and concentrated in vacuo. This residue is purified by flash chromatography on silica gel (eluting with DCM/MeOH/NH₃ 100/0/0 to 90/5/0.5) to afford the desired compound.

Chiral HPLC: ee≥99.4%; Condition used to determine the enantiomeric excess are the following:
- column: Chiralpak IC (250×4.6 mm), 5 μm, at room temperature
- mobile phase: Heptane/Ethanol/DEA (70/30/0.1, v/v/v)
- flow rate of 1 mL/min

2.8. 5-[3-[(3S)-4-(3,4-difluorophenyl)-3-methyl-piperazin-1-yl]-2-methyl-3-oxo-propyl]-5-(1-methyl-azetidin-3-yl)imidazolidine-2,4-dione (Cpd 399)

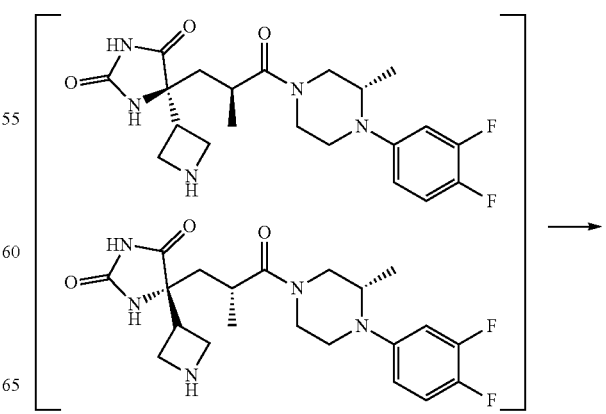

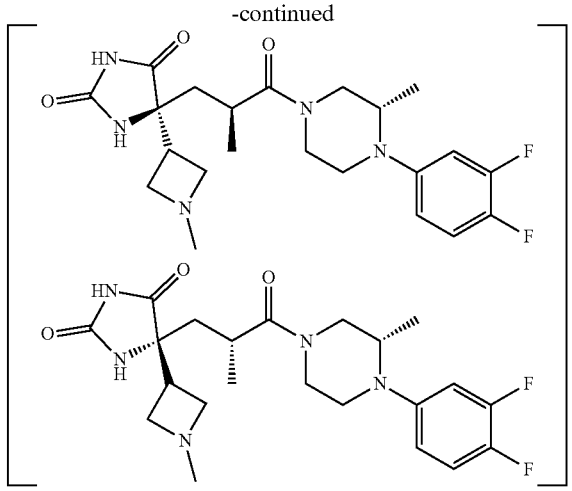

To a suspension of Cpd 247 (55 mg, 0.13 mmol, 1.0 eq.) in MeCN (1 mL) is added a formaldehyde in water solution (37% wt, 37 µL, 0.51 mmol, 4.0 eq.) and the mixture is stirred at r.t. for 10 min. Sodium cyanoborohydride is added (16 mg, 0.25 mmol, 2.0 eq.) and the reaction mixture is stirred at r.t. for 1 h. Sodium triacetoxyborohydride is added (53 mg, 0.25 mmol, 2.0 eq.) and the reaction mixture is stirred at r.t. for 2 h. An aqueous NaHCO₃ solution (1 mL) is added and the mixture is concentrated to dryness. The residue is purified by flash chromatography on KP-NH type silica gel (eluting with DCM/MeOH 100/0 to 95/5) to afford the expected product. LCMS: MW (calcd): 449; m/z MW (obsd): 450 (M+H).

2.9. 2-[4-[3-[4-(4-chloro-3-methyl-phenyl)piperazin-1-yl]-3-oxo-propyl]-2,5-dioxo-imidazolidin-4-yl]-N-(2-hydroxyethyl)acetamide (Cpd 402)

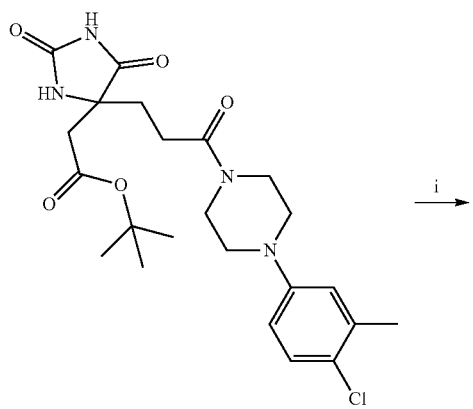

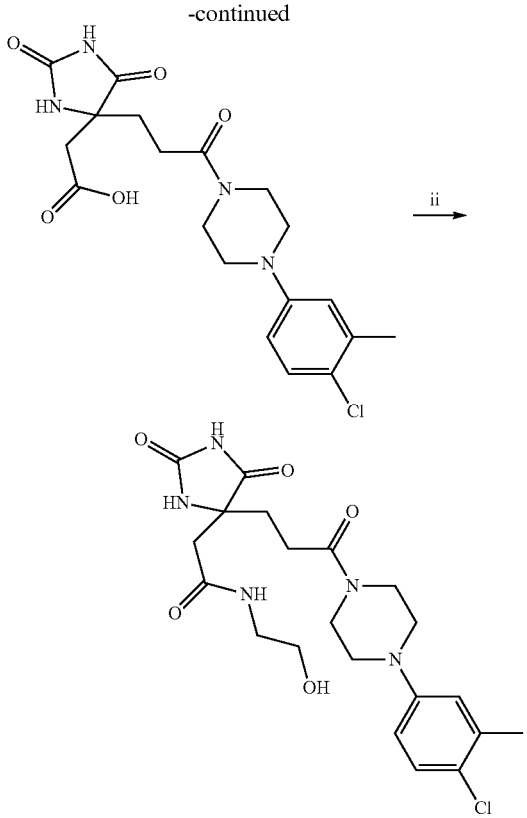

Step i) (4-{3-[4-(4-Chloro-3-methyl-phenyl)-piperazin-1-yl]-3-oxo-propyl}-2,5-dioxo-imidazolidin-4-yl)-acetic acid A flask is charged with Int 116 (30 mg, 0.06 mmol 1.0 eq.) and a solution of HCl in dioxane (4.0M, 630 µL, 40 mmol, 2.5 eq.). The reaction mixture is stirred at r.t. for 2 h, and then diluted with water and extracted 3 times with DCM. The combined organic layers are dried over anhydrous Na₂SO₄, filtered and concentrated in vacuo to afford the expected product. LCMS: MW (calcd): 422; m/z MW (obsd): 423 (M+H).

Step ii)

The carboxylic acid (18 mg, 0.04 mmol, 1.0 eq.) and 1-[bis(dimethylamino)methylene]-1H-1,2,3-triazolo-[4,5-b]pyridinium-3-oxide hexafluorophosphate (18 mg, 0.05 mmol, 1.1 eq.) are stirred in DMF (0.5 mL) at r.t. After 30 min, ethanolamine (2.6 µL, 0.04 mmol, 1.0 eq.) is added; the reaction mixture is stirred at r.t. for 2 h, then diluted with water and extracted 3 times with DCM. The combined organic layers are dried over anhydrous Na₂SO₄, filtered, concentrated in vacuo, and purified by preparative HPLC to afford the expected product. LCMS: MW (calcd): 465; m/z MW (obsd): 466 (M+H).

2.10. (5S)-5-[3-[4-(o-tolyl)piperazin-1-yl]-3-oxo-propyl]-5-phenyl-imidazolidine-2,4-dione (Cpd 027): Chiral Separation by Chiral HPLC

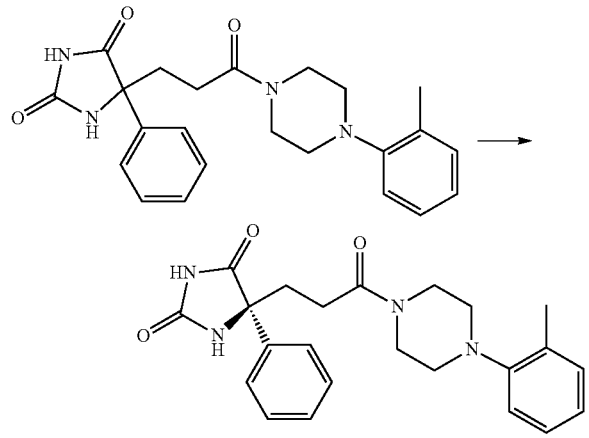

Cpd 007 is purified by chiral HPLC using the following conditions:
Column: Chiralpak AD 20 µm 250×21.7 mm,
Mobile phase: 100% EtOH,
Flow rate: 20 mL/min.
This purification affords the expected product as a single enantiomer.

2.11. (5S)-5-cyclopropyl-5-[(2S)-3-[(3S)-4-(3,4-difluorophenyl)-3-methyl-piperazin-1-yl]-2-methyl-3-oxo-propyl]imidazolidine-2,4-dione (Cpd 212): Chiral Separation by SFC

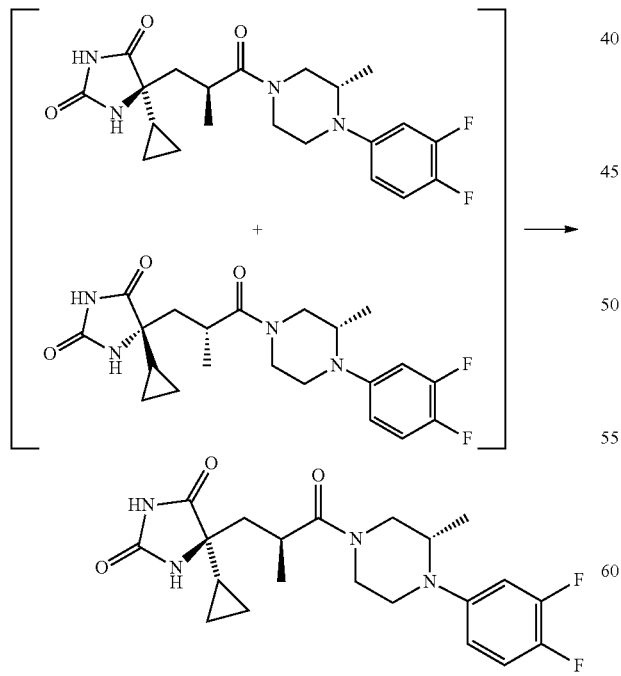

Cpd 191 is purified by SFC using the following conditions:

Instrument: Waters Thar SFC prep 100
Column: Chiralpak IA (30×250 mm), 5 µM
Mobile phase: Isocratic 25% iPrOH/DCM (80/20) and 75% $CO_2$.
Flow rate: 100 mL/min
Cpd 191 is dissolved in iPrOH (7 vol) and DCM (3 vol) (approximately 50 mg/mL), Injection volume 1500 µl which equates to loading of 75 mg on column per injection. This purification affords the expected product as a single enantiomer.

2.12. (5R)-5-[(2S)-3-[(3S)-4-(3-chloro-4-fluoro-phenyl)-3-methyl-piperazin-1-yl]-2-methyl-3-oxo-propyl]-5-methyl-imidazolidine-2,4-dione (Cpd 265): Chiral Separation by SFC Cpd 405 is purified by SFC the following conditions:
Instrument: Waters Thar SFC prep 100
Column: Chiralpak IA (30×250 mm), 5 uM
Mobile phase: Isocratic 20% iPrOH and 80% $CO_2$,
Flow rate: 100 mL/min
Cpd 405 is dissolved in iPrOH (2 vol) and acetonitrile (1 vol) (approximately 4.5 mg/mL), Injection volume 1500 µL which equates to loading of 6.75 mg on column per injection. This purification affords the expected product Cpd 265 as a single enantiomer.

2.13. (S)-5-((S)-3-((S)-4-(3-chloro-4-fluorophenyl)-3-methylpiperazin-1-yl)-2-methyl-3-oxopropyl)-5-(methoxymethyl)imidazolidine-2,4-dione (Cpd 331): Chiral Separation by SFC Cpd 406 is purified by SFC using the following conditions:
Instrument: Waters Thar SFC prep 100
Column: Chiralpak IA (20×250 mm), 5 uM
Mobile phase: Isocratic 35% EtOH and 65% $CO_2$.
Flowrate: 100 mL/min
Cpd 406 is dissolved in EtOH (70 mL) (approximately 20 mg/mL), Injection volume 1500 µL which equates to loading of 30 mg on column per injection, total number of stacks: 49. This purification affords the expected product Cpd 331 as a single enantiomer.

2.14. (S)-3-Methyl-4-(5-methyl-[1,2,4]oxadiazol-3-yl)-piperazine-1-carboxylic acid tert-butyl ester-Precursor of Int 237

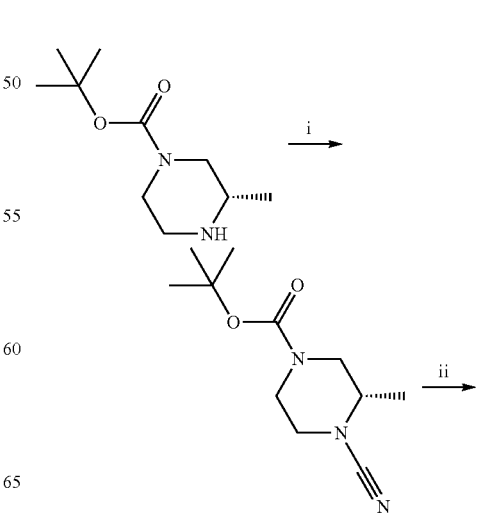

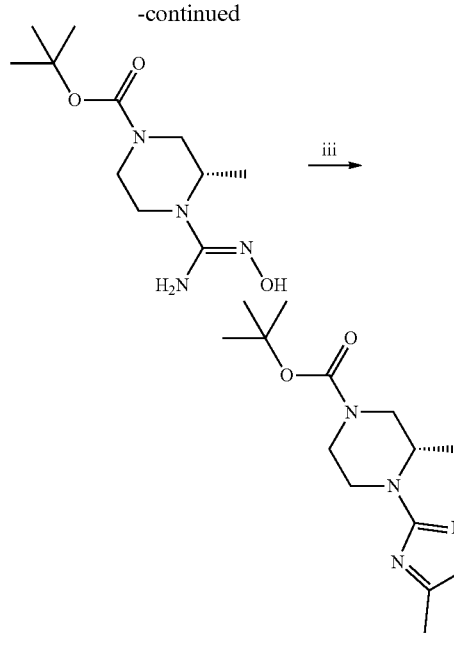

Step i) (S)-4-Cyano-3-methyl-piperazine-1-carboxylic acid tert-butyl ester (S)-3-Methyl-piperazine-1-carboxylic acid tert-butyl ester (1 g, 4.99 mmol, 1 eq.) is suspended in acetonitrile (20 mL), $K_2CO_3$ (1.851 g, 13.4 mmol, 2.7 eq.) is added and the suspension is stirred for 10 min before the addition of BrCN (5.0M in acetonitrile, 1.248 mL, 6.24 mmol, 1.25 eq.). The reaction is stirred at r.t. for 3 h and filtered; the solid is washed with EtOAc and the filtrate is concentrated in vacuo to afford the expected cyano derivative. LCMS: MW (calcd): 225; m/z MW (obsd): 226 (M+H).

Step ii) (S)-4-(N-Hydroxycarbamimidoyl)-3-methyl-piperazine-1-carboxylic acid tert-butyl ester To a solution of (S)-4-Cyano-3-methyl-piperazine-1-carboxylic acid tert-butyl ester (500 mg, 2.22 nmol, 1 eq.) in EtOH (10 mL), hydroxylamine hydrochloride (261 mg, 3.75 mmol, 1.5 eq.) and $Et_3N$ (869 µL, 6.25 mmol, 2.5 eq.) are added and reaction mixture is refluxed for 2 h concentrated in vacuo to afford the expected N-hydroxy amidine derivative used as such in the next reaction step.

Step iii) (S)-3-Methyl-4-(5-methyl-[1,2,4]oxadiazol-3-yl)-piperazine-1-carboxylic acid tert-butyl ester Crude N-hydroxy amidine derivative (2.22 mmol, 1 eq.) is dissolved in pyridine (10 mL) and acetylchloride (266 µL, 3.75 mmol, 1.5 eq.) is added. Reaction mixture is stirred at 120° C. for 1 h, poured into water, extracted with EtOAc. The combined organic layers are washed with brine, dried over anhydrous $Na_2SO_4$, filtered and concentrated in vacuo to afford the expected product (precursor of Int 237). LCMS: MW (calcd): 282; m/z MW (obsd): 283 (M+H).

2.15. 4-Cyclopropyl-1-[4-(3,5-dichlorophenyl)piperazin-1-yl]-2-hydroxy-butane-1,4-dione (Int 053) and benzyl 2-(cyclopropanecarbonyl)-4-[4-(3,5-dichlorophenyl)piperazin-1-yl]-3-ethoxy-4-oxo-butanoate (Int 054)

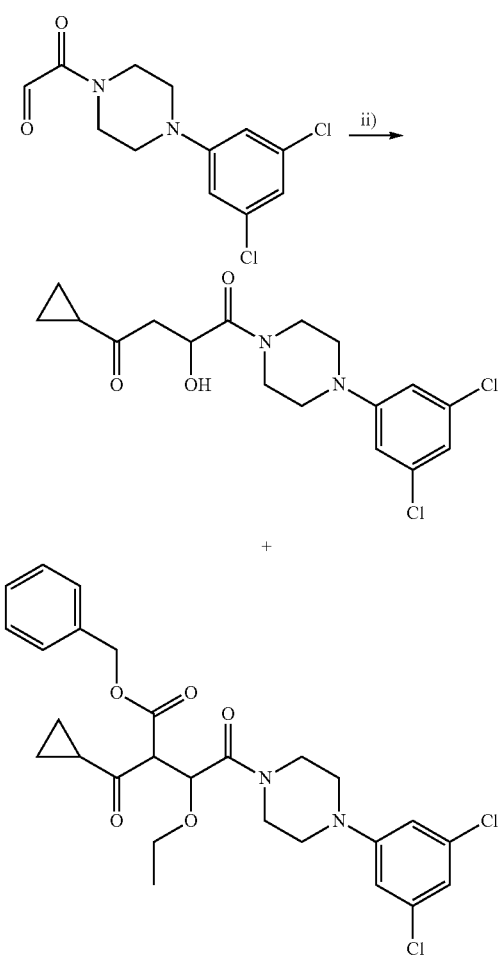

129

Step i) 3-Cyclopropyl-3-oxo-propionic acid benzyl ester and [4-(3,5-Dichloro-phenyl)-piperazin-1-yl]-oxo-acetaldehyde A flask is charged with Meldrum's acid (50.3 g, 349 mmol, 1.0 eq.), DCM (300 mL) and pyridine (90 mL, 1.1 mol, 3.2 eq), and cooled in an ice bath. To the resulting solution, is added dropwise cyclopropane carbonyl chloride (35.0 mL, 386 mmol, 1.1 eq). After 2 h, the cold bath is removed. After 16 h, the mixture is combined with aqueous HCl (2N, 700 mL) and DCM (200 mL) in a separatory funnel and agitated. The organic phase is collected and washed with aqueous HCl (2N) (500 mL), brine (500 mL), and dried over MgSO$_4$ and activated charcoal. After filtration, volatiles are removed via rotary evaporation. The residue is combined with toluene (100 mL) and benzyl alcohol (37 mL, 356 mmol, 1.02 eq) in a round bottomed flask equipped with a reflux condenser, and heated at reflux. After 16 h, the mixture is allowed to cool to room temperature. Volatiles are removed via rotary evaporation to give the crude product.

Step ii) 4-Cyclopropyl-1-[4-(3,5-dichloro-phenyl)-piperazin-1-yl]-2-hydroxy-butane-1,4-dione and 2-Cyclopropanecarbonyl-4-[4-(3,5-dichloro-phenyl)-piperazin-1-yl]-3-ethoxy-4-oxo-butyric acid benzyl ester A vial is charged with Int 149 (127 mg, 0.44 mmol, 1.0 eq), the β-keto ester from step i) (189 mg, 0.90 mmol, 2.0 eq), and DCM (2 mL). After 16 h, volatiles are removed via rotary evaporation. The residue is combined with Pd(OH)$_2$/C (20%) (81 mg, 0.12 mmol, 0.26 eq), ethanol (8 mL), and cyclohexene (2.0 mL, 20 mmol, 45eq.) in a round bottomed flask, and heated at reflux. After 1 h, the mixture is filtered through a plug of clarcel on a fritted funnel. Volatiles are removed via rotary evaporation. The residue is charged onto a column of silica gel and eluted with EtOAc/DCM (1:9), to afford compound Int 053.

By-product Int 054 is obtained when step iv) is done in higher scale and concentration:

A round bottom flask is charged with the aldehyde synthesized in step iii) (3.72 g, 12.9 mmol, 1.0 eq), the β-keto ester from step i) (7.10 g, 32.5 mmol, 2.5 eq) and DCM (10 mL) and left open to the air. After 16 h, volatiles were removed via rotary evaporation. The residue is combined with Pd(OH)$_2$/C (10%) (2.06 g, 1.47 mmol, 0.11 eq), ethanol (100 mL), and cyclohexene (25 mL, 250 mmol, 19 eq.) in a round bottomed flask, and heated at reflux for 16 h, and then allowed to cool to room temperature. The mixture is filtered through filter paper, and volatiles are removed via rotary evaporation. The residue is charged onto a column of silica gel and eluted with EtOAc/DCM (1/20), to afford Int 054 (3.55 g).

130

2.16. 4-Cyclopropyl-1-[4-(3,5-dichlorophenyl)piperazin-1-yl]-2-methoxy-butane-1,4-dione (Int 056)

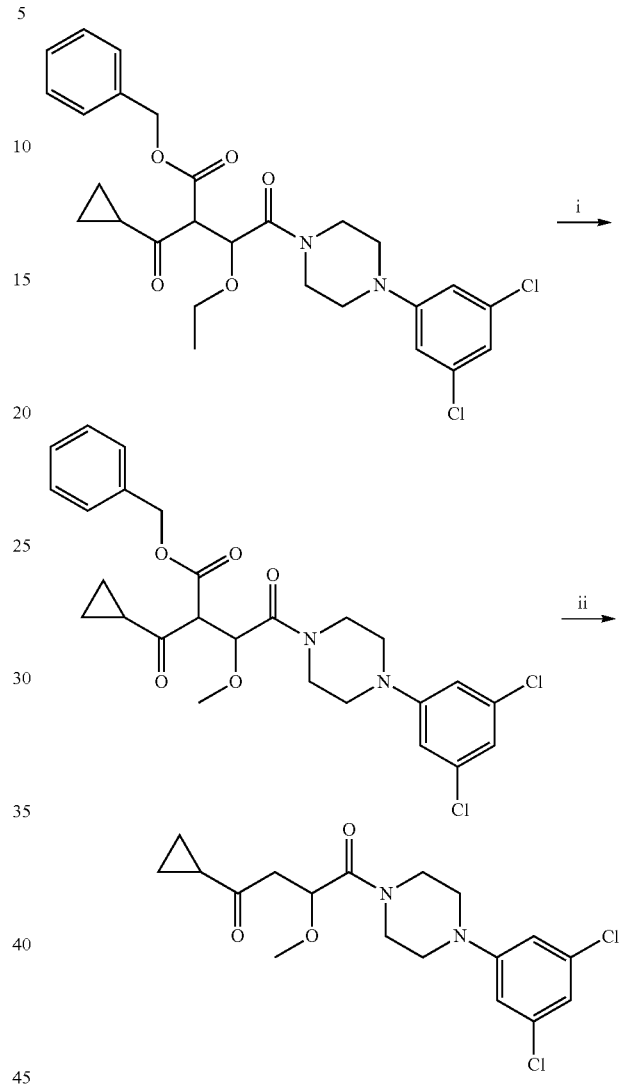

Step i) 2-Cyclopropanecarbonyl-4-[4-(3,5-dichlorophenyl)-piperazin-1-yl]-3-methoxy-4-oxo-butyric acid benzyl ester A flask is charged with Int 054 (289 mg, 0.54 mmol, 1.0 eq.), and MeOH (8 mL), and heated at 60° C. After 16 h, volatiles are removed from the filtrate via rotary evaporation. The residue is charged onto a column of silica gel, and eluted with EtOAc/DCM (1:20) to afford the expected intermediate.

Step ii) 4-Cyclopropyl-1-[4-(3,5-dichlorophenyl)piperazin-1-yl]-2-methoxy-butane-1,4-dione (Int 056)

The intermediate from step i) is stirred with MeOH (20 mL), Pd(OH)$_2$/C (10%) (45 mg, 0.032 mmol, 0.10 eq) and cyclohexene (4 mL, 39.5 mmol, 120 eq.) in a round flask, and heated to reflux. After 2 h, the mixture is filtered through filter paper. Volatiles are removed from the filtrate via rotary evaporation. The residue is charged onto a column of silica gel, and eluted with EtOAc/DCM (1:9) to afford Int 056.

2.17. 6-tert-butoxy-4,6-dioxo-hexanoic acid (Int 129)

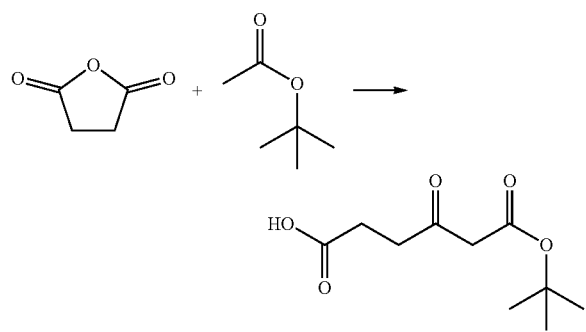

A solution of n-Butyl lithium (1.6M in hexane) (25 mL, 40 mmol, 2.0 eq) is added at 0° C. to a stirred solution of 1,1,1,3,3,3-hexamethyldisilazane (8.5 mL, 41 mmol, 2.04 eq) in anhydrous THF (17 mL). After cooling to −78° C., tertbutyl acetate (5.44 mL, 40 mmol, 2.0 eq) is added within 20 min to the solution and stirring is continued for 45 min. The resulting α-lithio acetic ester solution is added dropwise over 30 minutes to a solution of succinic anhydride (2 g, 20 mmol, 1.0 eq) in THF (24 mL). The resulting mixture is stirred for 3 h in a methanol/dry ice bath while the temperature is allowed to increase to −20° C.

The reaction mixture is warmed up to room temperature, then concentrated HCl (4 mL) and water (25 mL) are added. The organic solvent is evaporated, and the resulting aqueous solution is adjusted to pH=2, and extraction with ethyl acetate followed. Organic layers are combined, dried over Na$_2$SO$_4$, filtered, and concentrated under reduced pressure to give the expected product (used in the next step without further purification).

2.18. tert-butyl 2-(benzyloxymethyl)-4-oxo-pentanoate (Int 137)

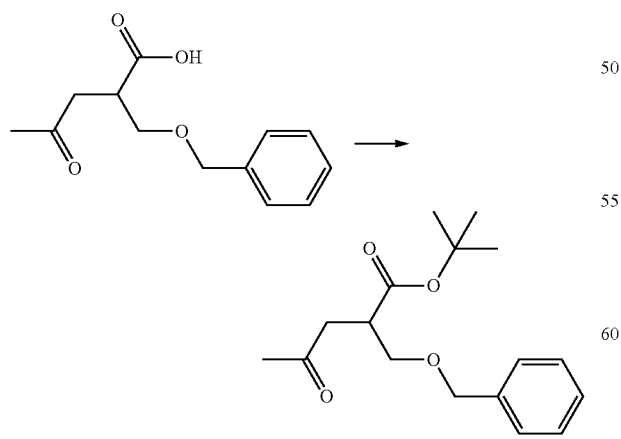

To a solution of Int 138 (530 mg, 2.24 mmol, 1 eq.) in toluene (7 mL) is added N,N-dimethylformamide di-tert-butyl acetal (2.69 mL, 11.2 mmol, 5 eq.). Reaction mixture is heated at 100° C. in a sealed tube for 4.5 h, quenched by addition of a saturated NaHCO$_3$ solution at 0° C., extracted with EtOAc. The combined organic layers are washed with saturated NaHCO$_3$ solution, brine, dried over anhydrous Na$_2$SO$_4$, filtered, concentrated in vacuo and purified by flash chromatography on silica gel (Heptane/EtOAc 100/0 to 60/40) to afford the expected product. LCMS: MW (calcd): 292; m/z MW (obsd): 315 (M+Na)

2.19. (S)-4-(3,5-Difluoro-phenyl)-3-methyl-piperazine-1-carboxylic acid tert-butyl ester (Int 110)

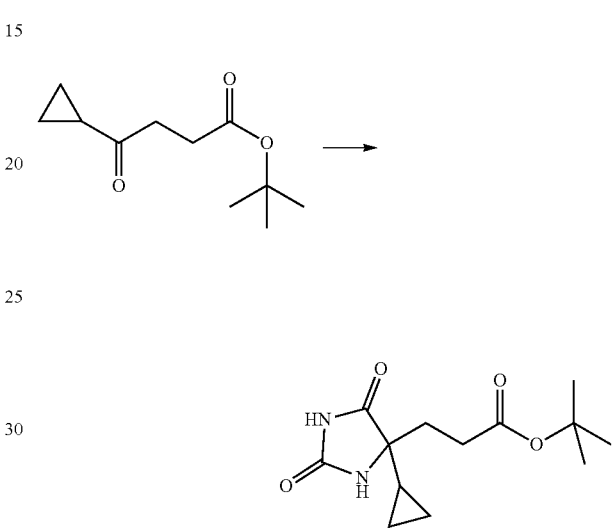

A mixture of γ-ketoester 4-Cyclopropyl-4-oxo-butyric acid tert-butyl ester (120 g, 605 mmol, 1 eq.), (NH$_4$)$_2$CO$_3$ (494 g, 5.15 mol, 8.5 eq.), NaCN (60 g, 1.45 mol, 2.4 eq.), H$_2$O (600 mL) and ethanol (600 mL) is heated at 60° C. for 18 h in the sealed reactor. The reaction mixture is poured in a mixture of EtOAc (900 mL) and water (900 mL), and the aqueous layer is additionally extracted with EtOAc (3×600 mL). The organic layer is concentrated until only about 100 mL EtOAc left, and added 500 mL petroleum ether dropwise to afford the expected hydantoin derivative Int 110.

2.20. tert-butyl N-[6-[4-(3,5-dichlorophenyl)piperazin-1-yl]-5-methyl-3,6-dioxo-hexyl]carbamate (Int 150)

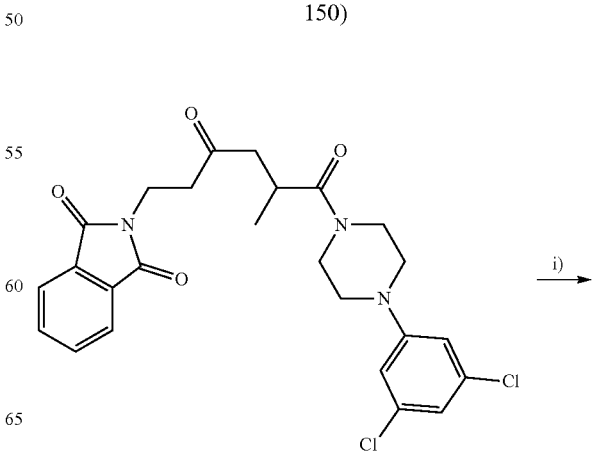

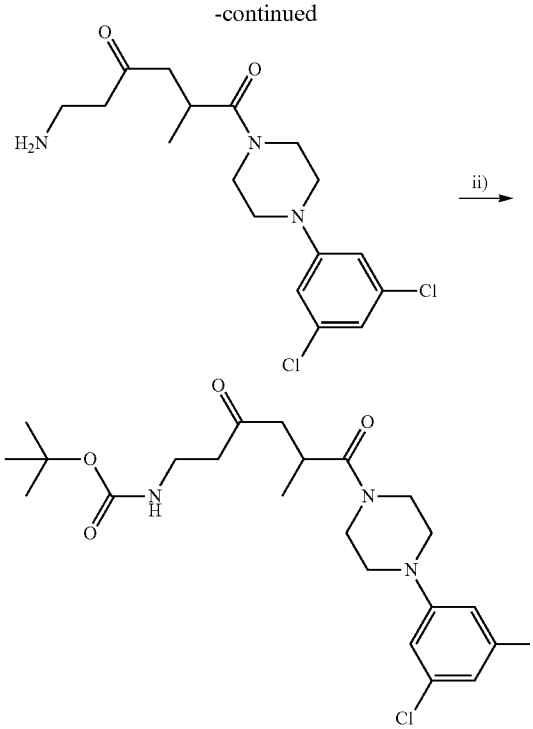

Step i) 6-Amino-1-[4-(3,5-dichloro-phenyl)-piperazin-1-yl]-2-methyl-hexane-1,4-dione To a solution of Int 021 (341 mg, 0.68 mmol, 1.0 eq) in ethanol (27 mL) is added methylamine (40% in water) (845 µL). Stirring is then kept at room temperature overnight. The organic solvent is then removed under reduced pressure, and the aqeuous residue is diluted with water and $K_2CO_3$ (10%), and extracted with ethyl acetate several times. The combined organic layer is washed with water and brine, before being dried, filtered, and concentrated under reduced pressure, to afford crude compound used directly in the next step.

Step ii) tert-butyl N-[6-[4-(3,5-dichlorophenyl)piperazin-1-yl]-5-methyl-3,6-dioxo-hexyl]carbamate (Int 150)

The crude from step i) is stirred in THF/MeOH (1/1) (14 mL). Di-tert-butyl dicarbonate (445 mg, 2.04 mmol, 3 eq) is added, and the mixture is stirred under reflux for 18 h. The organic solvents are removed, and the crude is purified by flash chromatography (DCM/Et$_2$O 100/0 to 0/100 and then DCM/MeOH 100/0 to 90/10) to afford the expected intermediate. LCMS: MW (calcd): 472; m/z MW (obsd): 472-474-476 (M+H).

2.21. tert-butyl 2-methyl-4-oxo-butanoate (Int 153)

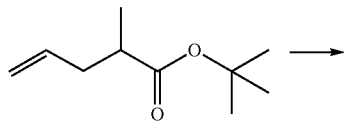

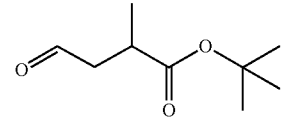

A three neck flask is charged with a solution of alkene Int 148 (6.3 g, 37 mmol, 1 eq.) and suddan III (cat.) in DCM and cooled at −78° C. $O_3$ is bubbled trough the reaction mixture until the color became deep blue. The reaction mixture is purged with $N_2$ for 30 min, $Me_2S$ is added and the reaction mixture is allowed to warm to r.t. overnight. The reaction mixture is washed with water and brine, dried over anhydrous $MgSO_4$, filtered and concentrated in vacuo. Purification by flash chromatography on silica gel (Heptane/EtOAc 100/0 to 80/20) affords the expected product.

2.22. 2-methoxy-4-methyl-pent-4-enoic acid (Int 154)

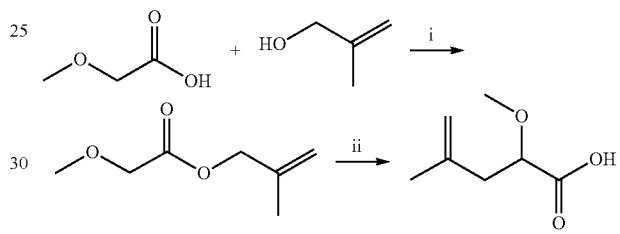

Step i) Methoxy-acetic acid 2-methyl-allyl ester

To a solution of methoxy-acetic acid (15.54 g, 173 mmol, 1.1 eq.) and 2-methyl-prop-2-en-1-ol (14.5 mL, 172 mmol, 1 eq.) in pyridine (100 mL) at 0° C., is added p-toluenesulfonyl chloride (33.08 g, 173 mmol, 1 eq.). After 1 h, the cold bath is removed and the reaction mixture is stirred at r.t. overnight. The reaction mixture is concentrated in vacuo and combined with a EtOAc and a saturated NaHCO$_3$ solution is added. The organic layer is collected, washed with a solution of HCl 1N, water, brine, dried over anhydrous MgSO$_4$, filtered and concentrated in vacuo to afford the expected ester used as such in next step. LCMS: MW (calcd): 144; m/z MW (obsd): 145 (M+H); 167 (M+Na)

Step ii) 2-methoxy-4-methyl-pent-4-enoic acid (Int 154)

To a solution of the ester (1 g, 6.94 mmol, 1 eq.) in dry Et$_2$O (10 mL) is added Et$_3$N (1 mL, 7.17 mmol, 1.03 eq.) and trimethylsilyl trifluoromethanesulfonate (1.3 mL, 7.18 mmol, 1.03 eq.). The reaction mixture is stirred at r.t. overnight, a solution of K$_2$CO$_3$ (5.45 g, 39.4 mmol, 5.68 eq.) in water (20 mL) is added. After 30 min, the reaction mixture is combined with Et$_2$O, the aqueous layer is collected, cooled in an ice bath and the pH adjusted to pH=2 with H$_3$PO$_4$ (85%). The solution is saturated with NaCl and extracted with Et$_2$O. The combined organic layers are dried over anhydrous MgSO$_4$, filtered, concentrated in vacuo to afford the expected product used as such in next step. LCMS: MW (calcd): 144; m/z MW (obsd): 143 (M−H).

2.23. 3-(4-cyclopropyl-2,5-dioxo-imidazolidin-4-yl)propanoic acid (Int 162), and 3-[(4S)-4-cyclopropyl-2,5-dioxo-imidazolidin-4-yl]propanoic acid (Int 163)

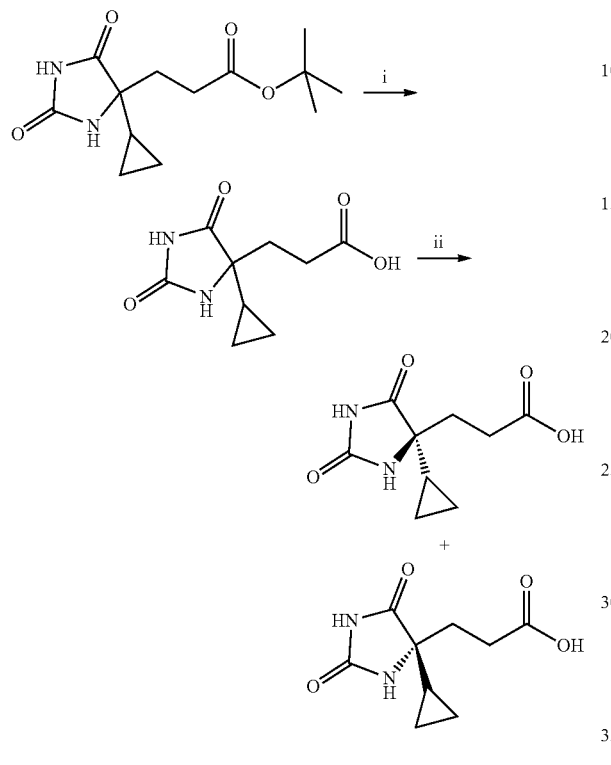

Step i) 3-(4-cyclopropyl-2,5-dioxo-imidazolidin-4-yl)propanoic acid (Int 162)

A flask is charged with a solution of hydantoin (200 g, 746 mmol, 1 eq.) in dioxane (100 mL) and is cooled in an ice bath, HCl 6N in dioxane (1 L) is added slowly. The reaction mixture is stirred at r.t. for 4 h and concentrated in vacuo. The resulting solid is suspended in 240 mL of acetonitrile, then stirred at reflux for 1 h, and allowed to cool down to r.t. under stirring. The resulting solid is separated by filtration, washed twice with acetonitrile (2×30 mL), and finally dried under vacuum at 45° C. to afford the expected carboxylic acid.

Step ii) 3-[(4S)-4-cyclopropyl-2,5-dioxo-imidazolidin-4-yl]propanoic acid (Int 163)

The racemic hydantoin propionic acid is separated by SFC to afford a fast eluting isomer ((R)-enantiomer) and a slow eluting isomer ((S)-enantiomer).

The purification is done in 2 stages.

Conditions of the first separation: preparative SFC, Column: ChiralPak AD-10 µm. 300×50 mmI.D., Mobile phase: A for $CO_2$ and B for Ethanol, Gradient: B 45%, Flow rate: 200 mL/min, Back pressure: 100 bar, Column temperature: 38° C., Wavelength: 220 nm, Cycletime: ~10.0 min. The compound is dissolved in methanol to ~120 mg/mL, and loaded on the column (16 mL per injection). After separation, the fractions are dried off via rotary evaporator to get the desired isomers.

Conditions of the second separation: Prep HPLC, Column: C18, 250×50 mm I.D., Mobile phase: A for $H_2O$ and B for Acetonitrile, Gradient: B 5%-20% in 15 min linearly, Flow rate: 80 mL/min, Wavelength: 220 nm. The compound is dissolved in methanol (~100 mg/mL) and loaded on the column (10 mL per injection). After separation, the fraction is concentrated via rotary evaporator and the remaining aqueous layer is lyophilized.

2.24. 4-cyclopropyl-2-methyl-4-oxo-butanoic acid (Int 155)

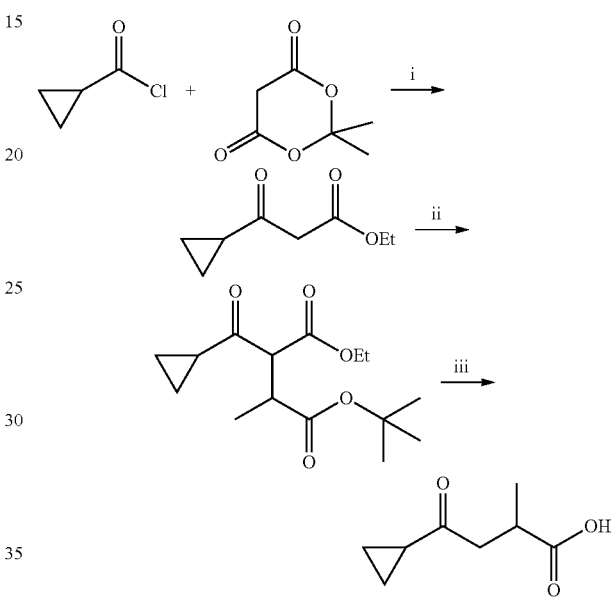

Step i) 3-Cyclopropyl-3-oxo-propionic acid ethyl ester

To a solution of Meldrum's acid (2,2-dimethyl-[1,3]dioxane-4,6-dione, 50.10 g, 0.347 mol, 1 eq.) in DCM (500 mL) and pyridine (90 mL, 1.11 mol, 3.2 eq.) at 0° C., cyclopropanecarbonyl chloride (35 mL, 0.386 mol, 1.1 eq.) is added dropwise. After 2 h, the cold bath is removed and the reaction mixture is stirred at r.t. overnight and combined with a solution of HCl 2N. The organic layer is collected, washed with brine, dried over anhydrous $MgSO_4$, filtered over activated charcoal and concentrated in vacuo. This residue is taken up in ethanol (300 mL) and stirred at reflux overnight, concentrated in vacuo and purified by flash chromatography on silica gel (Heptane/EtOAc 80/20) to afford the expected β-ketoester. LCMS: MW (calcd): 156; m/z MW (obsd): 157 (M+H); 179 (M+Na)

Step ii) 2-Cyclopropanecarbonyl-3-methyl-succinic acid 4-tert-butyl ester 1-ethyl ester To a solution of the β-ketoester (16.09 g, 0.103 mol, 1 eq.) in MEK (200 mL) are added $K_2CO_3$ (28.56 g, 0.207 mol, 2 eq.), NaI (1.65 g, 0.011 mol, 0.1 eq.) and 2-Bromo-propionic acid tert-butyl ester (18 mL, 0.108 mol, 1.04 eq.). The reaction mixture is heated at reflux for 40 h and cooled to r.t. Water is added, reaction mixture acidified to pH 8 and extracted with EtOAc. The combined organic layers are washed with water and brine, dried over anhydrous MgSO$_4$, filtered and concentrated in vacuo to afford the expected γ-ketoester used as such in next step. LCMS: MW (calcd): 284; m/z MW (obsd): 307 (M+Na)

Step iii) 4-cyclopropyl-2-methyl-4-oxo-butanoic acid (Int 155)

To a solution of the γ-ketoester (29.2 g, 0.103 mol, 1 eq.) in EtOH (100 mL) is added a solution of NaOH (12.6 g, 0.315 mol, 3 eq.) in water (100 mL). The reaction mixture is heated at reflux for 16 h, cooled to r.t., diluted with water (500 mL) and cooled in an ice bath. To this is added dropwise H$_3$PO$_4$ (85%, 4 mL, 0.059 mol) and conc. HCl (24 mL, 0.288 mol), the ice bath is removed and reaction mixture is stirred at r.t. for 30 min. The reaction mixture is cooled in an ice bath and a solution of NaOH (17 g, 0.425 mol) in water (50 mL) is added to adjust the pH to 8. The solution is combined with DCM, the aqueous layer is collected, cooled in an ice bath and the pH adjusted to pH=2 with conc. HCl. The solution is saturated with NaCl and extracted with DCM. The combined organic layers are dried over anhydrous MgSO$_4$, filtered, concentrated in vacuo to afford the expected product. LCMS: MW (calcd): 156; m/z MW (obsd): 157 (M+H); 179 (M+Na).

2.25. 3-[(4R)-4-methyl-2,5-dioxo-imidazolidin-4-yl] propanoic acid (Int 172)

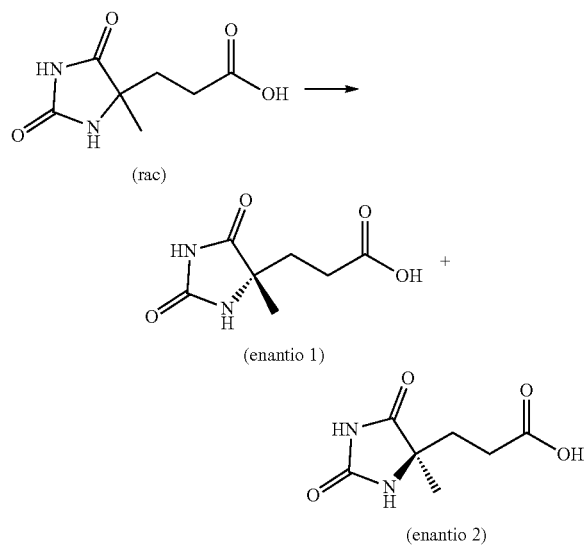

The racemic 3-(4-Methyl-2,5-dioxo-imidazolidin-4-yl) propionic acid (805 g) is separated by SFC to afford 384 g of the faster eluting isomer and 388 g of the slower eluting isomer. Conditions of the separation: Instrument: Thar350 preparative SFC, Column: ChiralPak AD-10 μm. 300×50 mmI.D., Mobile phase: A for CO$_2$ and B for iPrOH (0.1% TFA), Gradient: B 25%, Flow rate: 220 mL/min, Back pressure: 100 bar, Column temperature: 38° C., Wavelength: 210 nm, Cycletime: ~3.8 min, Sample preparation: Compound is dissolved in methanol to ~80 mg/mL, Injection: 1.0 mL per injection, Work up: After separation, the fractions are dried off via rotary evaporator at bath temperature 40° C. to get the desired isomers.

2.26. 5-(tert-butoxycarbonylamino)-4-oxo-pentanoic acid (Int 173)

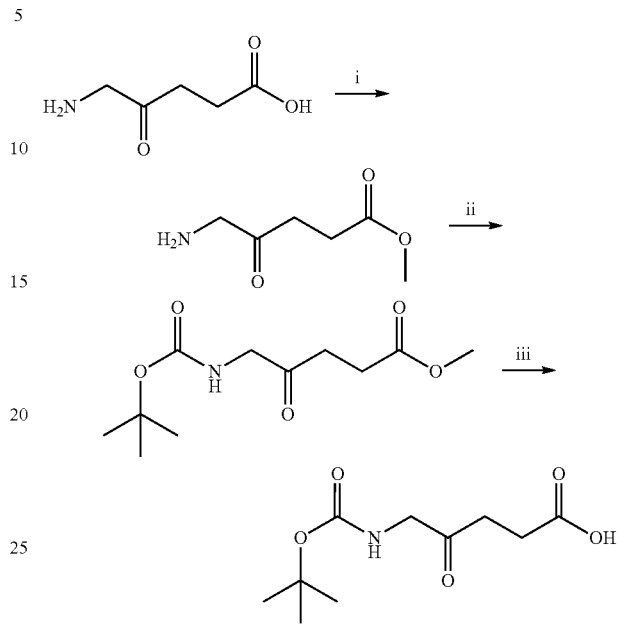

Step i) 5-Amino-4-oxo-pentanoic acid methyl ester

To a solution of 5-amino-4-oxo-pentanoic acid hydrochloride (0.5 g, 2.98 mmol, 1 eq.) in MeOH (3 mL) at 0° C. is added thionyl chloride (0.7 mL, 8.95 mmol, 3 eq.). The reaction mixture is stirred at r.t. overnight and concentrated in vacuo to afford the expected methyl ester (hydrochloride salt) used as such in next step.

Step ii) 5-tert-Butoxycarbonylamino-4-oxo-pentanoic acid methyl ester

To a solution of the methyl ester (0.54 g, 2.98 mmol, 1 eq.) and di-tert-butyl dicarbonate (1.3 g, 5.97 mmol, 2 eq.) in dry DMF (5 mL) at 0° C. is added Et$_3$N (0.8 mL, 5.97 mmol, 2 eq.). Reaction mixture is stirred at 0° C. for 2 h then at r.t. overnight, concentrated in vacuo. The residue is taken up in water, extracted with EtOAc. The combined organic layers are dried by filtration over hydrophobic column and concentrated in vacuo to afford the expected NBoc derivative.

Step iii) 5-(tert-butoxycarbonylamino)-4-oxo-pentanoic acid (Int 173)

To a solution of the methyl ester (0.495 g, 2.02 mmol, 1 eq.) in THF (4 mL) is added a solution of LiOH 1M (4 mL, 4 mmol, 2 eq.). Reaction mixture is stirred at r.t. for 3 h, neutralised to pH 5 and concentrated in vacuo (toluene azeotrope) to afford the expected product used as such in next step.

2.27. 5-methoxy-4-oxo-pentanoic acid (Int 177)

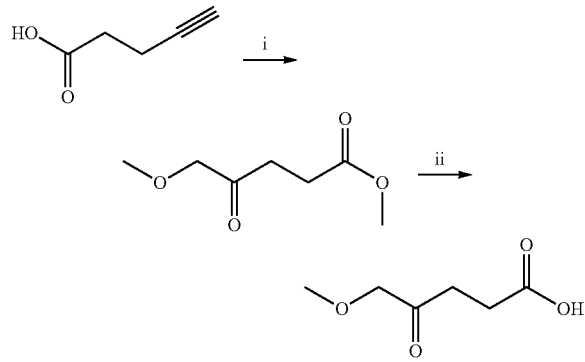

Step i) 5-Methoxy-4-oxo-pentanoic acid methyl ester

To a solution of iodosylbenzene (4.75 g, 21.6 mmol, 1.5 eq.) in DCM (200 mL) at 0° C. under N₂ atmosphere is added pent-4-ynoic acid (1.41 g, 14.4 mmol, 1 eq.) portion-wise. BF₃.OEt (3.65 mL, 28.8 mmol, 2 eq.) is added dropwise and the reaction mixture is stirred at r.t. for 30 min. The resulting precipitate is separated by filtration, and dried under N₂. MeOH (100 mL) is added, the reaction mixture is stirred at r.t. overnight, concentrated in vacuo and purified by flash chromatography on silica gel (Hexanes/EtOAc 700/30 to 400/60) to afford the expected methoxy methyl ester derivative used as such in the next step.

Step ii) 5-methoxy-4-oxo-pentanoic acid (Int 1 77)

A solution of the methyl ester (500 mg, 3.1 mmol, 1 eq.) and NaOH (625 mg, 15 mmol, 5 eq.) in THF (6.6 mL), water (4.4 mL) and MeOH (11 mL) is stirred at r.t. for 2 h. Then the pH is adjusted to 3.3 with conc. HCl. Reaction mixture is extracted with EtOAc, the combined organic layers are dried over anhydrous MgSO₄, filtered and concentrated in vacuo to afford the expected product used as such in next step.

2.28. 5-(2-methoxyethoxy)-2-methyl-4-oxo-pentanoic acid (Int 185)

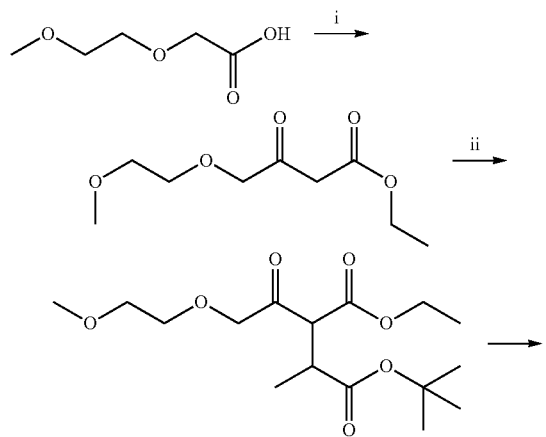

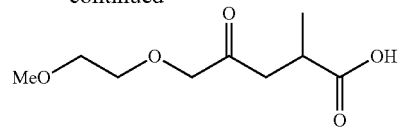

Step i) 4-(2-Methoxy-ethoxy)-3-oxo-butyric acid ethyl ester

To a solution of monoethyl malonic acid (5.9 mL, 50 mmol, 1.25 eq.) in dry THF (200 mL), is added magnesium ethoxide (2.86 g, 25 mmol, 0.625 eq.). The reaction mixture is stirred for 1.5 h and concentrated in vacuo. In another flask, CDI (7.13 g, 44 mmol, 1.1 eq.) is added to a solution of (2-methoxy-ethoxy)-acetic acid (4.6 mL, 40 mmol, 1 eq.) in THF (200 mL). After 4 h at r.t., this reaction mixture is added to the magnesium salt prepared above. This new mixture is heated at reflux for 4 h, stirred at r.t. for 2 days and concentrated in vacuo. The residue is taken up in water and EtOAc, a solution of HCl 0.5N is added, the organic layer is collected, dried over anhydrous MgSO₄, filtered and concentrated in vacuo. Purification by flash chromatography on silica gel (Heptane/EtOAc 100/0 to 50/50) affords the expected β-ketoester. LCMS: MW (calcd): 204; m/z MW (obsd): 205 (M+H); 227 (M+Na)

Step ii) 2-[2-(2-Methoxy-ethoxy)-acetyl]-3-methyl-succinic acid 4-tert-butyl ester 1-ethyl ester To a solution of the β-ketoester (3 g, 14.7 mmol, 1 eq.) in MEK (60 mL) are added K₂CO₃ (4.1 g, 29.5 mmol, 2 eq.), KI (0.32 g, 1.5 mmol, 0.1 eq.) and 2-bromo-propionic acid tert-butyl ester (2.4 mL, 14.7 mmol, 1 eq.). The reaction mixture is heated at reflux overnight and concentrated in vacuo. The residue is taken up in water and EtOAc, extracted with EtOAc. The combined organic layers are dried over anhydrous MgSO₄, filtered, concentrated in vacuo and purified by flash chromatography on silica gel (Heptane/EtOAc 100/0 to 0/100) to afford the expected γ-ketoester. LCMS: MW (calcd): 332; m/z MW (obsd): 333 (M+H), 355 (M+Na).

Step iii)

To a solution of the γ-ketoester (332 mg, 1 mmol, 1 eq.) in EtOH (1.5 mL) is added a solution of NaOH 2N (1.5 mL). Reaction mixture is heated at reflux for 16 h, cooled to r.t., diluted with water (2 mL) and cooled in an ice bath. To this is added dropwise H₃PO₄ (85%, 16 μL) and conc. HCl (180 μL), the ice bath is removed and reaction mixture is stirred at r.t. for 30 min. The reaction mixture is cooled in an ice bath, a solution of NaOH 2N is added to adjust the pH to 8. The solution is combined with DCM, the aqueous layer is collected, cooled in an ice bath and the pH adjusted to pH=2 with conc. HCl. The solution is saturated with NaCl and extracted with DCM. The combined organic layers are dried over anhydrous MgSO₄, filtered, concentrated in vacuo to afford the expected product. LCMS: MW (calcd): 248; m/z MW (obsd): 249 (M+H); 271 (M+Na).

2.29. 4-[4-(2-dimethylaminoethyloxy)phenyl]-4-oxo-butanoic acid (Int 189)

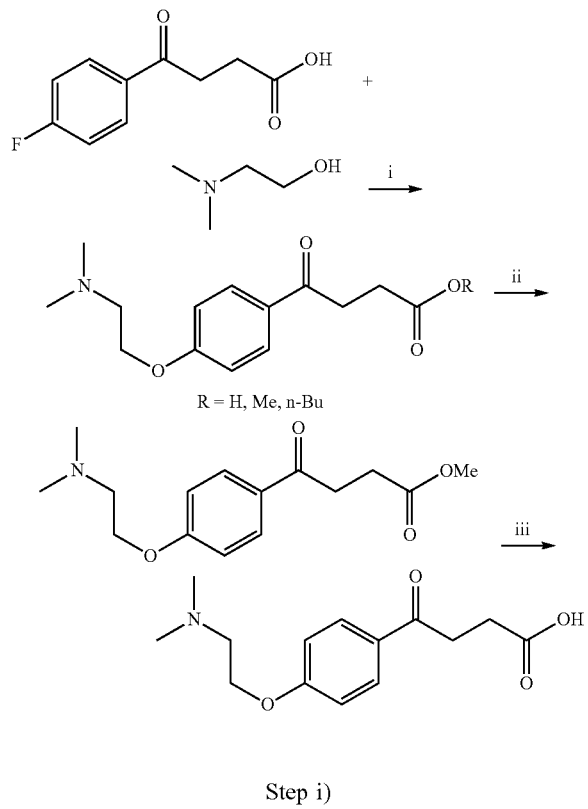

R = H, Me, n-Bu

Step i)

To a solution of 4-(4-fluoro-phenyl)-4-oxo-butyric acid (1 g, 5.1 mmol, 1 eq.) in DMA (20 mL) are added 2-dimethylamino-ethanol (1.02 mL, 10.2 mmol, 2 eq.) and KOH (1.43 g, 25.5 mmol, 5 eq.). Reaction mixture is heated at 120° C. for 1 h, 2-dimethylamino-ethanol (1.02 mL, 2 eq.) is added, heating is pursued for 2 h, 2-dimethylamino-ethanol (4.08 mL, 8 eq.) is added, heating is pursued for 3 h. A solution of 2N HCl is added and reaction mixture is extracted with EtOAc and n-BuOH. The combined organic layers are washed with brine, dried over anhydrous $Na_2SO_4$, filtered and concentrated in vacuo. The residue is taken up in MeOH and the precipitate is filtered. Analysis of the precipitate shows a mixture of expected carboxylic acid contaminated with methyl ester and n-butyl ester. The mixture is used as such for next step. LCMS: MW (calcd): 265 (R═H); 279 (R═Me); 321 (R═n-Bu); m/z MW (obsd): 266 (M+H, R═H), 280 (M+H, R═Me), 322 (M+H, R═n-Bu).

Step ii)

To a solution of the above mixture of carboxylic acid, methyl ester and n-butyl ester in MeOH (100 mL) is added conc. HCl (4 mL). Reaction mixture is heated at 70° C. overnight and concentrated in vacuo. The residue is taken up with saturated $NaHCO_3$ solution, extracted with EtOAc, the combined organic layers are washed with brine, dried over anhydrous $Na_2SO_4$, filtered and concentrated in vacuo. Purification by flash chromatography on silica gel (DCM/MeOH 100/0 to 80/20) affords the expected methyl ester derivative. LCMS: MW (calcd): 279; m/z MW (obsd): 280 (M+H).

Step iii)

To a solution of the methyl ester (535 mg, 1.92 mmol, 1 eq.) in MeOH (16 mL) is added a solution of NaOH 2N (1.15 mL, 2.3 mmol, 1.2 eq.). Reaction mixture is heated at 70° C. for 2 h and concentrated in vacuo to afford the expected product used as such in next step. LCMS: MW (calcd): 265; m/z MW (obsd): 266 (M+H).

2.30. 6-(tert-butoxycarbonylamino)-2-methyl-4-oxo-hexanoic acid (Int 191

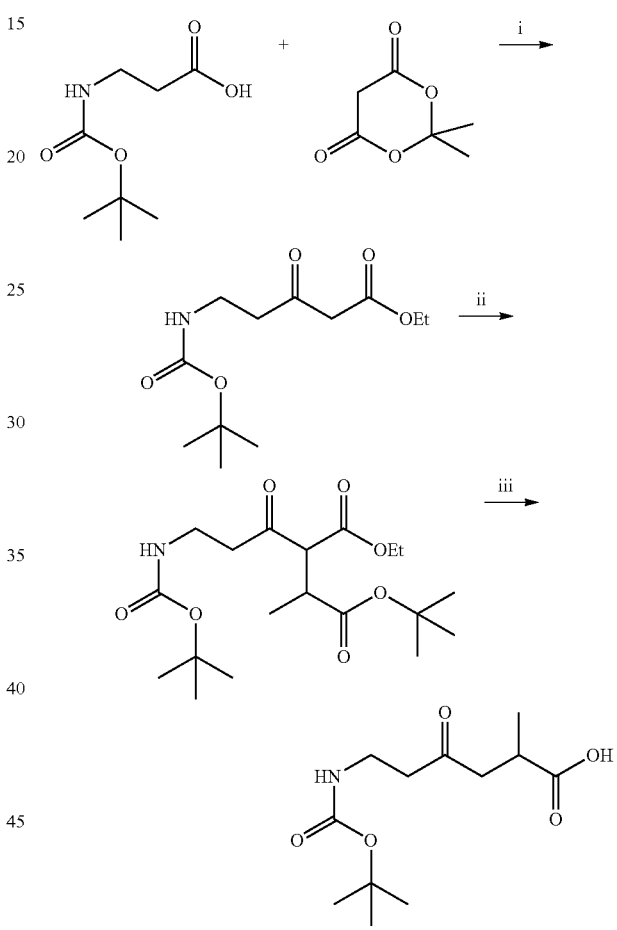

Step i)
5-tert-Butoxycarbonylamino-3-oxo-pentanoic acid ethyl ester

To a solution of 3-tert-butoxycarbonylamino-propionic acid (1 g, 5.29 mmol, 1 eq.) in DCM (30 mL) at 0° C. under $N_2$ atmosphere are added portionwise DMAP (969 mg, 7.93 mmol, 1.5 eq.) and 2,2-dimethyl-[1,3]dioxane-4,6-dione (838 mg, 5.81 mmol, 1.1 eq.) and finally EDC.HCl (1.22 g, 6.34 mmol, 1.2 eq.). The reaction mixture is stirred at r.t. overnight, diluted with DCM and washed with a solution of $KHSO_4$ 5%, brine, dried over anhydrous $Na_2SO_4$, filtered and concentrated in vacuo. This residue is taken up in dry Ethanol (20 mL) and the reaction mixture is stirred at reflux overnight, concentrated in vacuo and purified by flash chromatography on silica gel (eluting with DCM/EtOAc 100/0 to 50/50) to afford the expected β-ketoester. LCMS: MW (calcd): 259; m/z MW (obsd): 282 (M+Na).

Step ii) 2-(3-tert-Butoxycarbonylamino-propionyl)-3-methyl-succinic acid 4-tert-butyl ester 1-ethyl ester To a solution of the β-ketoester (919 mg, 3.54 mmol, 1 eq.) in MEK are added K$_2$CO$_3$ (980 mg, 7.09 mmol, 2 eq.), NaI (53 mg, 0.35 mmol, 0.1 eq.) and 2-bromo-propionic acid tert-butyl ester (588 μL, 3.54 mmol, 1 eq.). The reaction mixture is stirred at 95° C. for 24 h and cooled to r.t. Water is added, reaction mixture acidified to pH 8 and extracted with EtOAc. The combined organic layers are washed with water and brine, dried over anhydrous Na$_2$SO$_4$, filtered and concentrated in vacuo. The residue is purified by flash chromatography on silica gel (eluting with heptane/EtOAc 100/0 to 80/20) to afford the expected γ-ketoester. LCMS: MW (calcd): 387; m/z MW (obsd): 388 (M+H).

Step iii) 6-(tert-butoxycarbonylamino)-2-methyl-4-oxo-hexanoic acid (Int 191)

To a solution of the γ-ketoester (1.2 g, 3.1 mmol, 1 eq.) in EtOH (4.7 mL) is added a solution of NaOH 2N (4.65 mL, 9.29 mmol, 3 eq.). The reaction mixture is heated at reflux for 16 h, cooled to r.t, diluted with water (500 mL) and cooled in an ice bath. To this is added dropwise H$_3$PO$_4$ (85%, 48 μL) and conc. HCl (3.4 mL), the ice bath is removed and reaction mixture stirred at r.t. for 2 days. The reaction mixture is cooled in an ice bath, a solution of NaOH 2N is added to adjust the pH to 8. The solution is combined with DCM, the aqueous layer is collected, cooled in an ice bath and the pH adjusted to pH=3-4 with HCl 2N. The solution is extracted with DCM. The combined organic layers are dried over anhydrous MgSO$_4$, filtered, concentrated in vacuo to afford the expected product. LCMS: MW (calcd): 259; m/z MW (obsd): 260 (M+H).

2.31. 3-methyl-5-[(2S)-2-methylpiperazin-1-yl]-1,2,4-oxadiazole (Int 238)

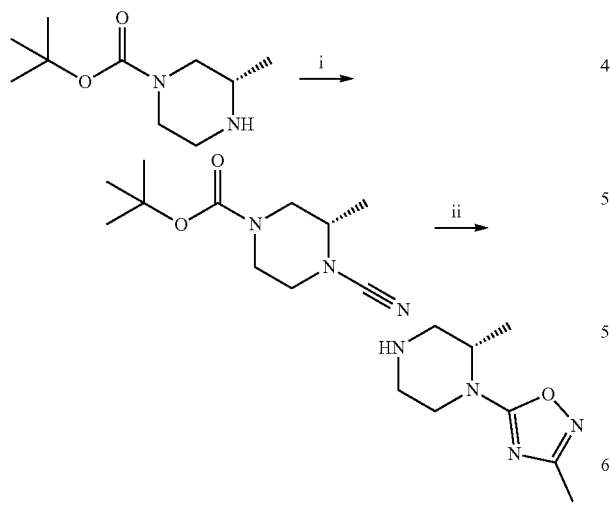

Step i) (S)-4-Cyano-3-methyl-piperazine-1-carboxylic acid tert-butyl ester

Same as 2.13, step i)

Step ii) 3-methyl-5-[(2S)-2-methylpiperazin-1-yl]-1,2,4-oxadiazole (Int 238)

To a solution of (S)-4-cyano-3-methyl-piperazine-1-carboxylic acid tert-butyl ester (617 mg, 2.74 nmol, 1 eq.) and N-hydroxy-acetamidine (304 mg, 4.11 mmol, 1.5 eq.) in THF (10 mL) and EtOAc (10 mL) under argon, is slowly added ZnCl$_2$ (1M in Et$_2$O, 6.85 mL, 6.85 mmol, 2.5eq.) and the reaction mixture is stirred at r.t. for 3 h and concentrated in vacuo. The residue is dissolved in ethanol (20 mL) and conc. HCl is added (2.5 mL). The resulting solution is stirred at 100° C. for 4 h, cooled and concentrated in vacuo. The residue is dissolved in water and pH adjusted to 12 with 2M NaOH. The white precipitate is filtered off and the water filtrate extracted with 10% MeOH in DCM. The combined organic layers are evaporated in vacuo to afford the expected product. LCMS: MW (calcd): 182; m/z MW (obsd): 183 (M+H).

2.32. 5-bromo-2-chloro-N,N-dimethyl-aniline (Int 285)

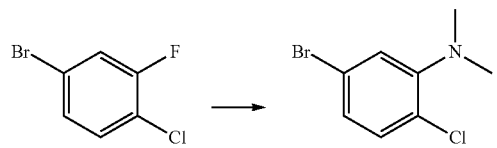

1-bromo-4-chloro-3-fluoro-benzene (367 μL, 3.0 mmol, 1.0 eq.), dimethylamine hydrochloride (489 mg, 6.0 mmol, 2.0 eq.) and DIPEA (1.6 mL, 9.0 mmol, 3.0 eq.) are heated in DMA (5 mL) in a sealed microwave vial at 115° C. for 18 h, then 125° C. for 2 days. Dimethylamine hydrochloride (400 mg, 4.9 mmol, 1.6 eq.) is added to the reaction mixture and the vial is heated at 130° C. for 2 days. The reaction mixture is then poured into water and brine. The aqueous layer is extracted 3 times with EtOAc. The combined organic phases are washed successively with water and brine, dried over anhydrous Na$_2$SO$_4$, filtered, concentrated in vacuo and purified by flash chromatography on silica gel to afford the expected product. LCMS: MW (calcd): 233; m/z MW (obsd): 234-236 (M+H).

2.33. N-(5-bromo-2-chloro-phenyl)-N-methyl-acetamide (Int 286)

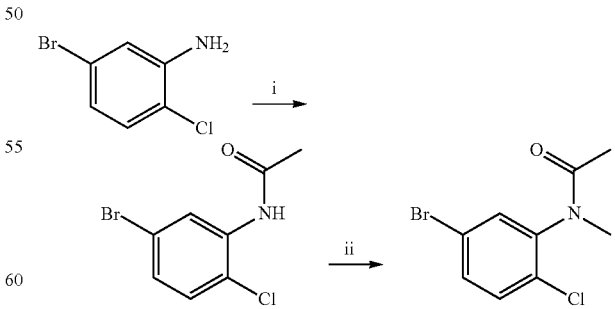

Step i) N-(5-Bromo-2-chloro-phenyl)-acetamide

To a solution of 3-bromo-6-chloroaniline (2.0 g, 9.7 mmol, 1.0 eq.) in DCM (30 mL) is added acetic anhydride (1.1 mL, 11.6 mmol, 1.2 eq.). The reaction mixture is stirred at r.t. for 22 h. The reaction mixture is washed successively with water and a saturated NaHCO₃ solution. The organic layer is dried over anhydrous Na₂SO₄, filtered and concentrated in vacuo. The crude residue is stirred in DCM and Et₂O is added. The resulting suspension is filtered and the solid is dried under suction to afford the expected acetamide. MW (calcd): 247; m/z MW (obsd): 248-250 (M+H).

Step ii) N-(5-bromo-2-chloro-phenyl)-N-methyl-acetamide (Int 286)

To a solution of 3-bromo-6-chloroacetanilide (1.53 g, 6.2 mmol, 1.0 eq.) in DMF (17 mL) is added sodium hydride (322 mg, 8.1 mmol, 1.3 eq.) under nitrogen atmosphere. After 10 min stirring at r.t., methyl iodide (502 µL, 8.1 mmol, 1.3 eq.) is added. The reaction mixture is allowed to stir at r.t. under nitrogen atmosphere for 18 h. The mixture is poured into water and brine and extracted 3 times with EtOAc. The combined organic phases are washed successively with water and brine, dried over anhydrous Na₂SO₄, filtered, concentrated in vacuo and purified by flash chromatography on silica gel to afford the expected product. LCMS: MW (calcd): 261; m/z MW (obsd): 262-264 (M+H).

2.34. 1-bromo-3-chloro-5-fluoro-2-methyl-benzene (Int 287)

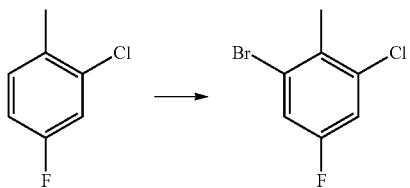

Sulfuric acid (0.9 mL) and NBS (1.0 g, 6.0 mmol, 1.2 eq.) are added to a solution of 2-chloro-4-fluorotoluene (604 µL, 5.0 mmol, 1.0 eq.) in TFA (3 mL). The reaction mixture is allowed to stir at r.t. for 18 h. The reaction is quenched with brine at 0° C., then extracted twice with DCM. The combined organic phases are washed with brine, dried over anhydrous Na₂SO₄, filtered, concentrated in vacuo and purified by flash chromatography on silica gel to afford the expected product as a mixture, which is used as such in the next step.

2.35. 4-Cyclo propyl-4-oxo-butyric acid tert-butyl ester (Int 290)

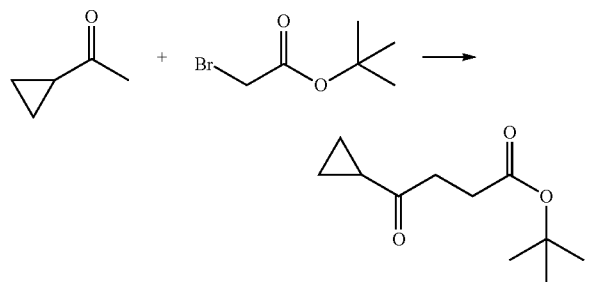

A solution of LDA (3.0 L, 5.98 mol, 1.17 eq.) in THF (2.5 L) is cooled to −78° C. A solution of 1-cyclopropylethanone (460 g, 5.11 mol, 1 eq.) in THF (0.5 L) is added dropwise, then warmed to −20° C. and stirred for 30 min. The reaction mixture is cooled to −78° C. and tert-butyl bromoacetate (997 g, 5.11 mol, 1 eq.) in THF (0.5 L) is added slowly. The reaction is stirred at 0° C. overnight, quenched with saturated NH₄Cl aq. (3.3 L), extracted with EtOAc (0.5 L×3), washed with water (0.5 L×2), saturated NH₄Cl aq. (1 L), and brine (1 L), dried over anhydrous Na₂SO₄. Purification by distillation under reduced pressure (5 mbar, 95° C.) affords the expected γ-ketoester.

2.36. 5-cyclopropyl-5-[3-[(3S)-3-methyl-4-pyridazin-3-yl-piperazin-1-yl]-3-oxo-propyl]imidazolidine-2,4-dione (Cpd 302)

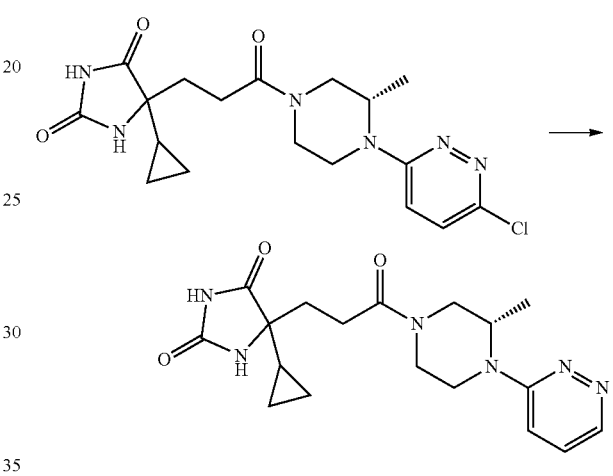

To a suspension of Cpd 285 (72 mg, 0.177 mmol, 1.0 eq.) in EtOH (1.7 mL) and DMF (0.7 mL) is added Et₃N (0.2 mL, 1.44 mmol, 8 eq.). The mixture is heated at 40-50° C. and Pd/C (14 mg) is added. The reaction mixture is stirred at room temperature for 21 hours. The mixture is filtered through diatonite and evaporated under vacuum. The crude residue is purified by flash chromatography on silica gel to afford the expected product.

2.37. Int 317

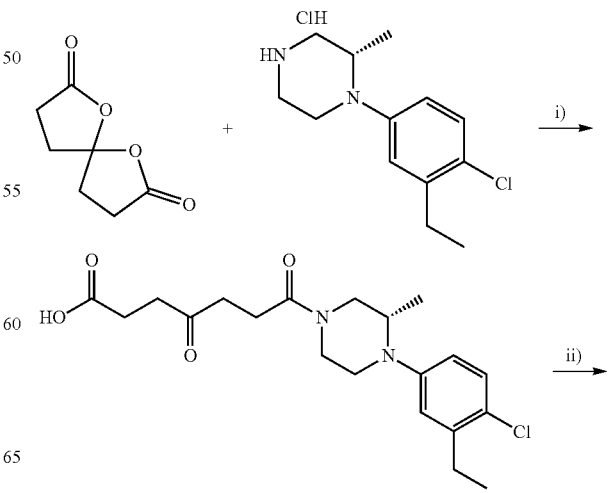

-continued

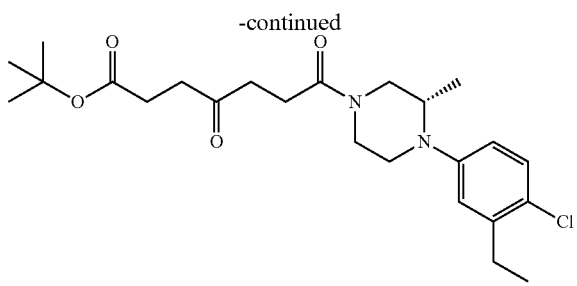

Step i)

A vial is charged with 1,6-dioxaspiro[4.4]nonane-2,7-dione (47.4 mg, 0.30 mmol, 1 eq), Int 313 (79 mg, 0.29 mmol, 0.95 eq), dry dioxane (2 mL), and triethyl amine (0.2 mL, 1.4 mmol, 4.7 eq). After 16 h, the mixture is combined with DCM (100 mL) and aqueous $H_3PO_4/NaH_2PO_4$ (1M, 100 mL) in a separation funnel. The organic phase is collected, washed with brine (100 mL), and dried over $MgSO_4$. After filtration, volatiles are removed via rotary evaporation to give the expected product which is used in the following step without further purification.

Step ii)

A pressure vessel is charged with the acid synthesized in step i) (0.92 mol), DCM (10 mL), and cooled in a NaCl/ice bath (−20° C.). Isobutene (3.06 g, 54.5 mmol, 59 eq) is condensed into the cold solution, and concentrated $H_2SO_4$ (0.1 mL, 1.8 mmol, 2.0 eq) is added. The vessel is hermetically sealed, and then the cold bath is removed. After 16 h, the vessel is cooled in a NaCl/ice bath (−20° C.), and opened. $Et_3N$ (1.0 mL, 7.2 mmol, 7.8 eq) is added, and the cold bath is removed. Once all volatiles had evaporated, the mixture is combined with $H_2O$ (100 mL) and DCM (100 mL) in a separatory funnel, and agitated. The organic phase is collected, washed with brine (100 mL) and dried over $MgSO_4$. After filtration, volatiles are removed from the filtrate via rotary evaporation. The residue is purified by flash chromatography on silica gel (EtOAc/DCM 1:4), to afford the expected compound Int 317.

2.38. Int 318

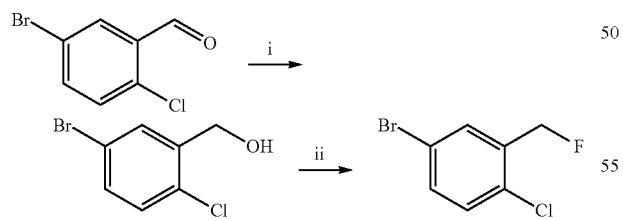

Step i)

Sodium tetraborohydride (345 mg, 9.1 mmol, 2.0 eq.) is added portionwise to a solution of 5-bromo-2-chloro-benz-aldehyde (1.0 g, 4.6 mmol, 1.0 eq.) in EtOH (12.5 mL). The reaction mixture is allowed to stir at r.t. for 40 min. Water and EtOAc are added and the reaction mixture is extracted 3 times with EtOAc. The organic phases are combined, dried over anhydrous $Na_2SO_4$, filtered and concentrated in vacuo to afford the expected intermediate.

Step ii)

Diethylaminosulfur trifluoride (393 µL, 2.7 mmol, 2.0 eq.) is added slowly to a solution of 5-bromo-2-chlorobenzyl alcohol (200 mg, 1.4 mmol, 1.0 eq.) in DCM (2 mL) at 0° C. The reaction mixture is allowed to warm to r.t. for 1 h45. The reaction mixture is concentrated to dryness and taken up in DCM. A saturated $NaHCO_3$ solution is cautiously added and the layers are separated. The combined organic layers are washed 3 times with water, dried over anhydrous $Na_2SO_4$, filtered, concentrated in vacuo to afford the expected product which is used as such in the next step.

2.39. Cpd 471

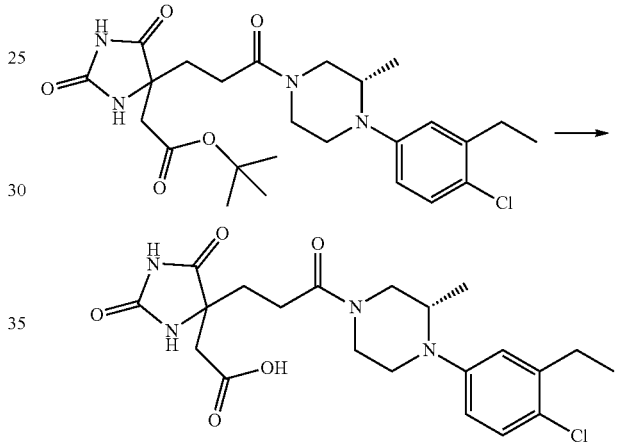

A flask is charged with Int 315 (28 mg, 0.06 mmol, 1.0 eq.) and a solution of HCl in dioxane (4N) (1 mL) is added, and stirring is kept at room temperature for 3 h. Reaction mixture is diluted with water, a solution of $NaHCO_3$ is added and extracted with DCM. Organic layers are combined and evaporated under reduced pressure to obtain crude product which is purified by flash chromatography on silica gel (DCM/MeOH 100/0 to 92/8) to afford the expected carboxylic acid. LCMS: MW (calcd): 450; m/z MW (obsd): 451-453 (M+H).

2.40. Cpd 477

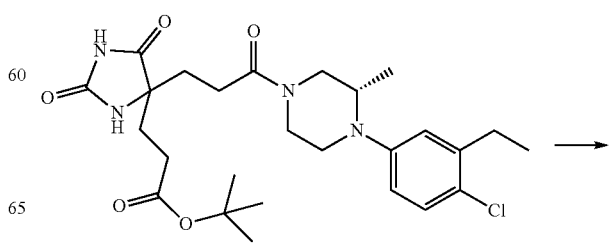

-continued

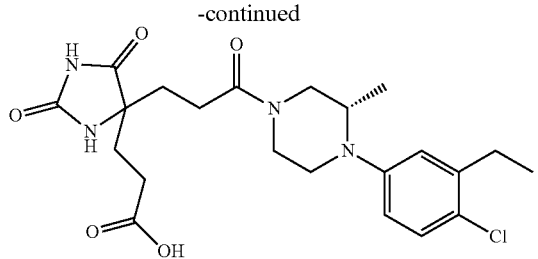

A flask is charged with Cpd 475 (68 mg, 0.013 mmol, 1.0 eq.) and a solution of HCl in dioxane (4.0M, 10 mL, 40 mmol, 300 eq.). The flask is capped with an oil bubbler and slowly flushed with a stream of $N_2$. After 64 h, volatiles are removed via rotary evaporation, and the residue is dissolved in a solution of HCl in dioxane (4.0M, 10 mL, 40 mmol, 300 eq.). The reaction mixture is allowed to stir at r.t. for 40 h. Volatiles are removed via rotary evaporation. The residue is dissolved in DMSO and purified by preparative LC-MS to afford the expected product. LCMS: MW (calcd): 464; m/z MW (obsd): 465 (M+H).

2.41. (5S)-5-[(2S)-3-[(3S)-4-(3-Chloro-4-fluoro-phenyl)-3-methyl-piperazin-1-yl]-2-methyl-3-oxo-propyl]-5-methoxymethyl-imidazolidine-2,4-dione (Cpd 455): Chiral Separation by SFC Cpd 432 is purified by SFC using the following conditions:
Instrument: Waters Thar SFC prep 100
Column: Chiralpak IA (20×250 mm), 5 uM
Mobile phase: Isocratic 35% EtOH and 65% $CO_2$.
Flow rate: 100 mL/min
Cpd 432 (1.372 g) is dissolved in EtOH (70 mL) (approximately 20 mg/mL), Injection volume 1500 μL which equates to loading of 30 mg on column per injection, total number of stacks: 49. This purification affords the expected product Cpd 455 as a single enantiomer.

TABLE II

Illustrative intermediate for the synthesis of illustrative compounds of the invention trans:

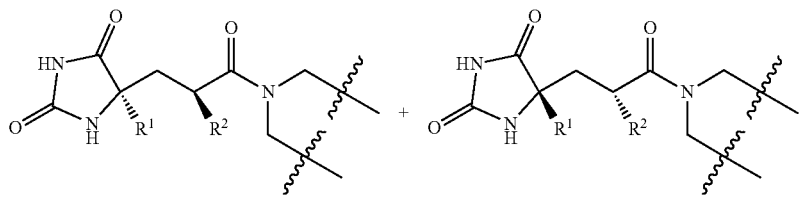

| Int | Structure | Name | Mtd | SM | MW | Ms'd |
|---|---|---|---|---|---|---|
| 001 | ![structure] | 1-[4-(3,5-dichlorophenyl)piperazin-1-yl]-2-methyl-prop-2-en-1-one | D1a | 2-Methyl-acryloyl chloride + 1-(3,5-dichlorophenyl)piperazine | 299 | 299-301 |
| 002 | ![structure] | 1-[4-(3,4-difluorophenyl)piperazin-1-yl]-2-methyl-prop-2-en-1-one | D1a | 2-Methyl-acryloyl chloride + 1-(3,4-difluorophenyl)piperazine | 266 | 267 |
| 003 | ![structure] | 1-[(3S)-4-(3,4-difluorophenyl)-3-methyl-piperazin-1-yl]-2-methyl-prop-2-en-1-one | D1a | 2-Methyl-acryloyl chloride + Int 199 | 280 | 281 |

TABLE II-continued

Illustrative intermediate for the synthesis of illustrative compounds of the invention trans:

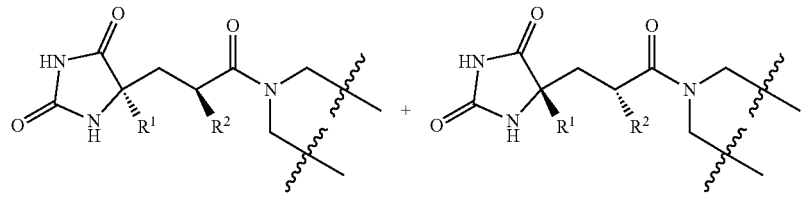

| Int | Structure | Name | Mtd | SM | MW | Ms'd |
|---|---|---|---|---|---|---|
| 004 | 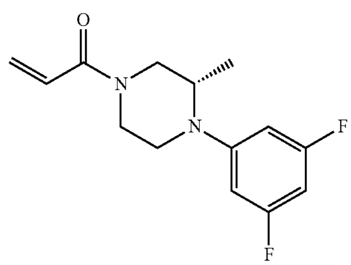 [SMILES: C=CC(=O)N1CCN(c2cc(F)cc(F)c2)[C@@H](C)C1] | 1-[(3S)-4-(3,5-difluorophenyl)-3-methyl-piperazin-1-yl]prop-2-en-1-one | D1a | Acryloyl chloride + Int 207 | 266 | 267 |
| 005 | 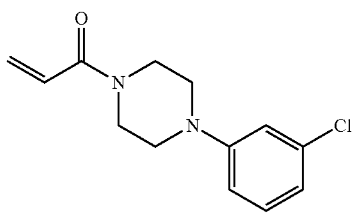 [SMILES: C=CC(=O)N1CCN(c2cccc(Cl)c2)CC1] | 1-[4-(3-chlorophenyl)piperazin-1-yl]prop-2-en-1-one | D1a | Acryloyl chloride + 1-(3-Chlorophenyl)piperazine | 251 | N.A. |
| 006 | 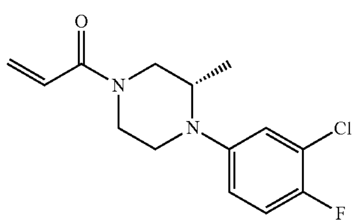 [SMILES: C=CC(=O)N1CCN(c2ccc(F)c(Cl)c2)[C@@H](C)C1] | 1-[(3S)-4-(3-chloro-4-fluoro-phenyl)-3-methyl-piperazin-1-yl]prop-2-en-1-one | D1a | Acryloyl chloride + Int 198 | 283 | 283-285 |
| 007 | 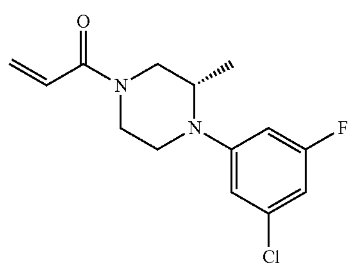 [SMILES: C=CC(=O)N1CCN(c2cc(F)cc(Cl)c2)[C@@H](C)C1] | 1-[(3S)-4-(3-chloro-5-fluoro-phenyl)-3-methyl-piperazin-1-yl]prop-2-en-1-one | D1a | Acryloyl chloride + Int 206 | 283 | 283-285 |
| 008 | 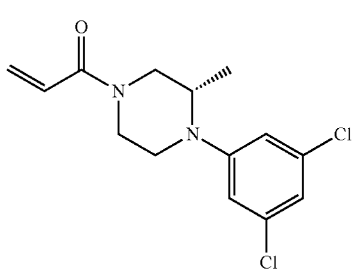 [SMILES: C=CC(=O)N1CCN(c2cc(Cl)cc(Cl)c2)[C@@H](C)C1] | 1-[(3S)-4-(3,5-dichlorophenyl)-3-methyl-piperazin-1-yl]prop-2-en-1-one | D1a | Acryloyl chloride + Int 197 | 299 | 299-301 |

TABLE II-continued

Illustrative intermediate for the synthesis of illustrative compounds of the invention trans:

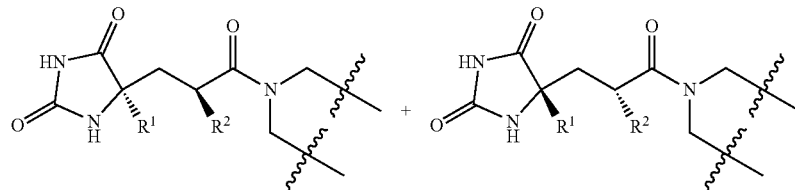

| Int | Structure | Name | Mtd | SM | MW | Ms'd |
|---|---|---|---|---|---|---|
| 009 | 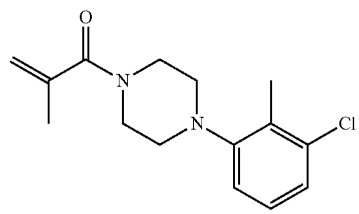 [SMILES: C=C(C)C(=O)N1CCN(c2cccc(Cl)c2C)CC1] | 1-[4-(3-chloro-2-methyl-phenyl)piperazin-1-yl]-2-methyl-prop-2-en-1-one | D1b | 2-Methyl-acryloyl chloride + Int 196 | 279 | 279-281 |
| 010 | 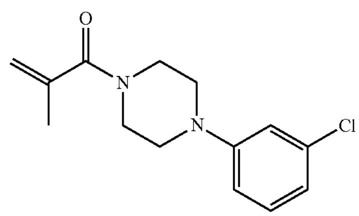 [SMILES: C=C(C)C(=O)N1CCN(c2cccc(Cl)c2)CC1] | 1-[4-(3-chlorophenyl)piperazin-1-yl]-2-methyl-prop-2-en-1-one | D1a | 2-Methyl-acryloyl chloride + 1-(3-Chlorophenyl)piperazine | 265 | N.A. |
| 011 | 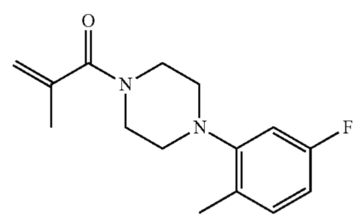 [SMILES: C=C(C)C(=O)N1CCN(c2cc(F)ccc2C)CC1] | 1-[4-(5-fluoro-2-methyl-phenyl)piperazin-1-yl]-2-methyl-prop-2-en-1-one | D1a | 2-Methyl-acryloyl chloride + Int 204 | 262 | N.A. |
| 012 | 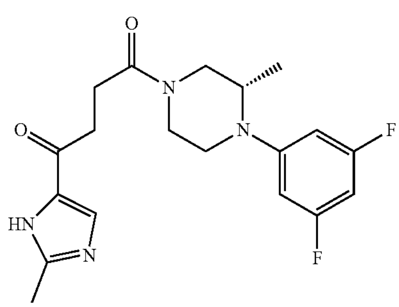 [SMILES: Cc1ncc(C(=O)CCC(=O)N2CCN(c3cc(F)cc(F)c3)[C@@H](C)C2)[nH]1] | 1-[(3S)-4-(3,5-difluorophenyl)-3-methyl-piperazin-1-yl]-4-(2-methyl-1H-imidazol-5-yl)butane-1,4-dione | D2a | 2-methyl-1H-imidazole-4-carbaldehyde + Int 004 | 376 | 377 |
| 013 | 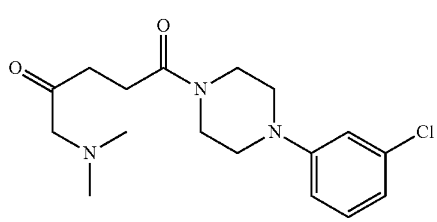 [SMILES: CN(C)CC(=O)CCC(=O)N1CCN(c2cccc(Cl)c2)CC1] | 1-[4-(3-chlorophenyl)piperazin-1-yl]-5-(dimethylamino)pentane-1,4-dione | H2 | Int 178 + 1-(3-chlorophenyl)piperazine | 338 | N.A. |

TABLE II-continued

Illustrative intermediate for the synthesis of illustrative compounds of the invention trans:

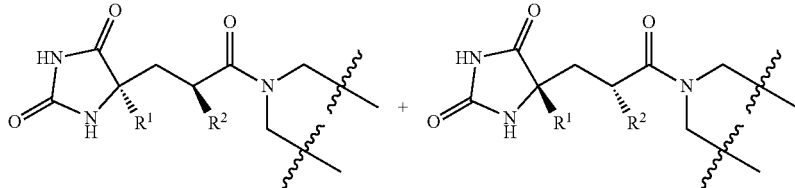

| Int | Structure | Name | Mtd | SM | MW | Ms'd |
|---|---|---|---|---|---|---|
| 014 | 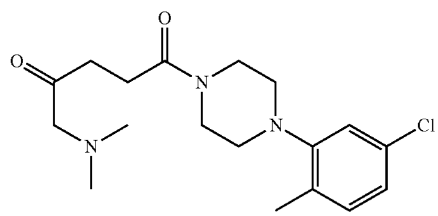 [SMILES: Cc1ccc(Cl)cc1N1CCN(C(=O)CCC(=O)CN(C)C)CC1] | 1-[4-(5-chloro-2-methyl-phenyl)piperazin-1-yl]-5-(dimethylamino)pentane-1,4-dione | H2 | Int 178+ 1-(5-chloro-2-methyl phenyl)-piperazine | 352 | N.A. |
| 015 | 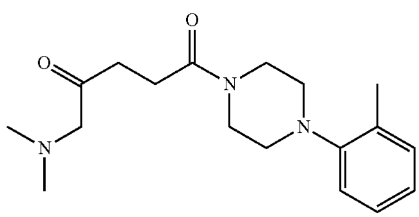 [SMILES: Cc1ccccc1N1CCN(C(=O)CCC(=O)CN(C)C)CC1] | 5-(dimethylamino)-1-[4-(o-tolyl)piperazin-1-yl]pentane-1,4-dione | H2 | Int 178 + 1-(o-tolyl) piperazine dihydrochloride | 317 | N.A. |
| 016 | 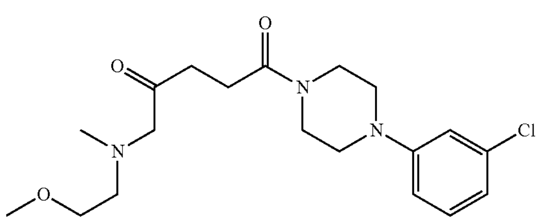 [SMILES: COCCN(C)CC(=O)CCC(=O)N1CCN(c2cccc(Cl)c2)CC1] | 1-[4-(3-chlorophenyl) piperazin-1-yl]-5-[2-methoxyethyl (methyl)amino] pentane-1,4-dione | H2 | Int 130 + 1-(3-chloro phenyl) piperazine | 382 | N.A. |
| 017 | 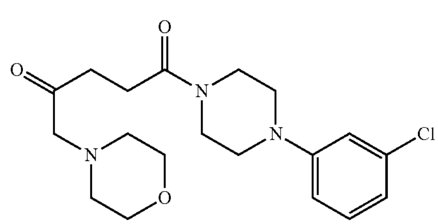 [SMILES: O=C(CCC(=O)N1CCN(c2cccc(Cl)c2)CC1)CN1CCOCC1] | 1-[4-(3-chlorophenyl) piperazin-1-yl]-5-morpholino-pentane-1,4-dione | H2 | Int 131 + 1-(3-chloro phenyl) piperazine | 380 | N.A. |
| 018 | 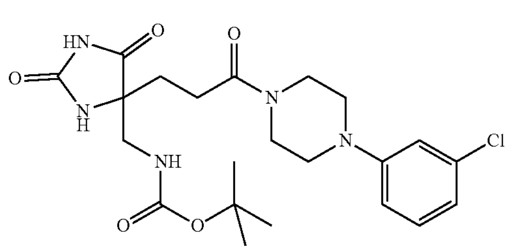 [SMILES: CC(C)(C)OC(=O)NCC1(CCC(=O)N2CCN(c3cccc(Cl)c3)CC2)NC(=O)NC1=O] | tert-butyl N-[[4-[3-[4-(3-chlorophenyl) piperazin-1-yl]-3-oxo-propyl]-2,5-dioxo-imidazolidin-4-yl]methyl]carbamate | F | Int 127 | 480 | N.A. |

TABLE II-continued

Illustrative intermediate for the synthesis of illustrative compounds of the invention trans:

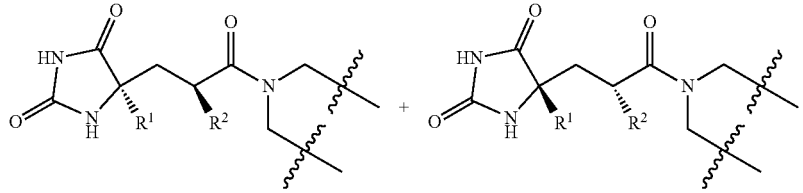

| Int | Structure | Name | Mtd | SM | MW | Ms'd |
|---|---|---|---|---|---|---|
| 019 | 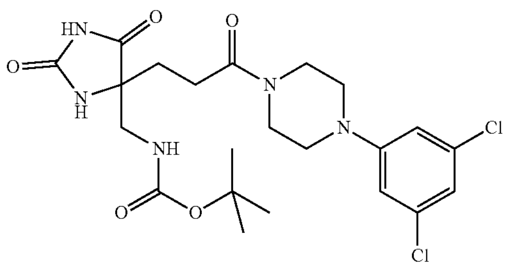 [SMILES: CC(C)(C)OC(=O)NCC1(CCC(=O)N2CCN(c3cc(Cl)cc(Cl)c3)CC2)NC(=O)NC1=O] | tert-butyl N-[[4-[3-[4-(3,5-dichlorophenyl)piperazin-1-yl]-3-oxo-propyl]-2,5-dioxo-imidazolidin-4-yl]methyl]carbamate | F | Int 128 | 514 | N.A. |
| 020 | 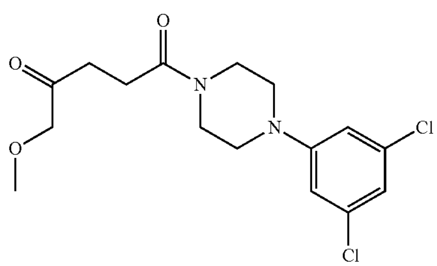 [SMILES: COCC(=O)CCC(=O)N1CCN(c2cc(Cl)cc(Cl)c2)CC1] | 1-[4-(3,5-dichlorophenyl)piperazin-1-yl]-5-methoxy-pentane-1,4-dione | H2 | Int 177 + 1-(3,5-dichlorophenyl)piperazine | 359 | 359-361 |
| 021 | 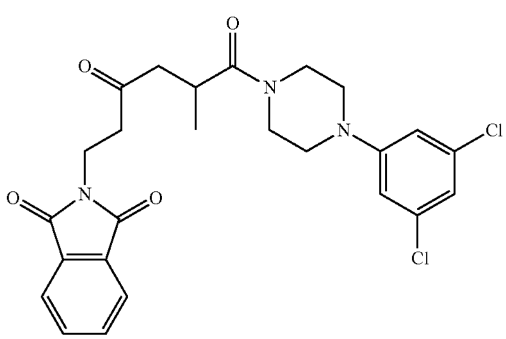 [SMILES: CC(CC(=O)CCN1C(=O)c2ccccc2C1=O)C(=O)N1CCN(c2cc(Cl)cc(Cl)c2)CC1] | 2-[6-[4-(3,5-dichlorophenyl)piperazin-1-yl]-5-methyl-3,6-dioxo-hexyl]isoindoline-1,3-dione | D2a | Int 001 + 3-(1,3-Dioxo-1,3-dihydroisoindol-2-yl)-propionaldehyde | 502 | 502-504-506 |
| 022 | 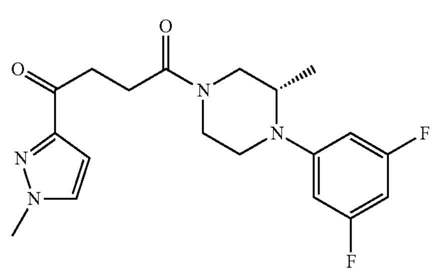 [SMILES: C[C@H]1CN(C(=O)CCC(=O)c2ccn(C)n2)CCN1c1cc(F)cc(F)c1] | 1-[(3S)-4-(3,5-difluorophenyl)-3-methyl-piperazin-1-yl]-4-(1-methylpyrazol-3-yl)butane-1,4-dione | D2a | Int 004+ 1-Methyl-1H-pyrazole-3-carbaldehyde | 376 | 377 |

TABLE II-continued

Illustrative intermediate for the synthesis of illustrative compounds of the invention trans:

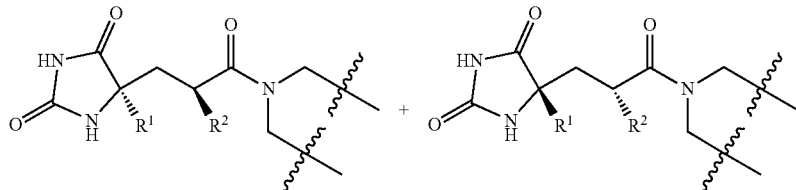

| Int | Structure | Name | Mtd | SM | MW | Ms'd |
|---|---|---|---|---|---|---|
| 023 | 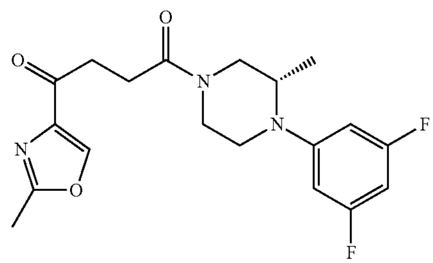 [SMILES: Cc1nc(C(=O)CCC(=O)N2CCN(c3cc(F)cc(F)c3)[C@@H](C)C2)co1] | 1-[(3S)-4-(3,5-difluorophenyl)-3-methyl-piperazin-1-yl]-4-(2-methyloxazol-4-yl)butane-1,4-dione | D2a | Int 004 + 2-Methyl-oxazole-4-carbaldehyde | 377 | 378 |
| 024 | 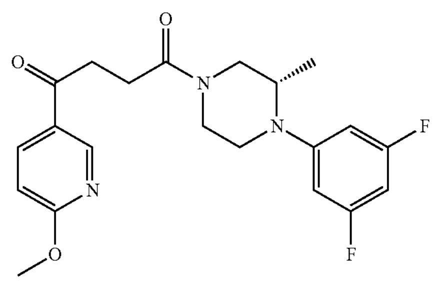 [SMILES: COc1ccc(C(=O)CCC(=O)N2CCN(c3cc(F)cc(F)c3)[C@@H](C)C2)cn1] | 1-[(3S)-4-(3,5-difluorophenyl)-3-methyl-piperazin-1-yl]-4-(6-methoxy-3-pyridyl)butane-1,4-dione | D2a | Int 004 + 6-Methoxy-pyridine-3-carbaldehyde | 403 | 404 |
| 025 | 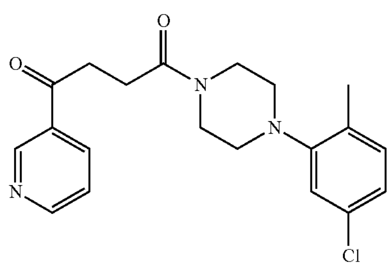 [SMILES: Cc1ccc(Cl)cc1N1CCN(C(=O)CCC(=O)c2cccnc2)CC1] | 1-[4-(5-chloro-2-methyl-phenyl)piperazin-1-yl]-4-(3-pyridyl)butane-1,4-dione | H1 | 4-Oxo-4-pyridin-3-yl-butyric acid + 1-(5-Chloro-2-methylphenyl)-piperazine | 372 | 372-374 |
| 026 | 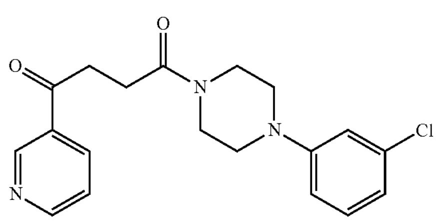 [SMILES: O=C(CCC(=O)N1CCN(c2cccc(Cl)c2)CC1)c1cccnc1] | 1-[4-(3-chlorophenyl)piperazin-1-yl]-4-(3-pyridyl)butane-1,4-dione | H1 | 4-Oxo-4-pyridin-3-yl-butyric acid + 1-(3-chlorophenyl)piperazine | 358 | 358-360 |
| 027 | 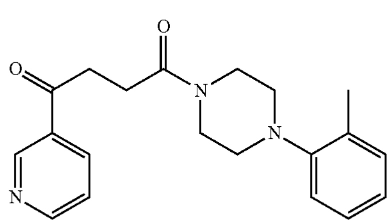 [SMILES: Cc1ccccc1N1CCN(C(=O)CCC(=O)c2cccnc2)CC1] | 1-[4-(o-tolyl)piperazin-1-yl]-4-(3-pyridyl)butane-1,4-dione | H1 | 4-Oxo-4-pyridin-3-yl-butyric acid + 1-(o-tolyl)piperazine dihydrochloride | 337 | 338 |

TABLE II-continued

Illustrative intermediate for the synthesis of illustrative compounds of the invention trans:

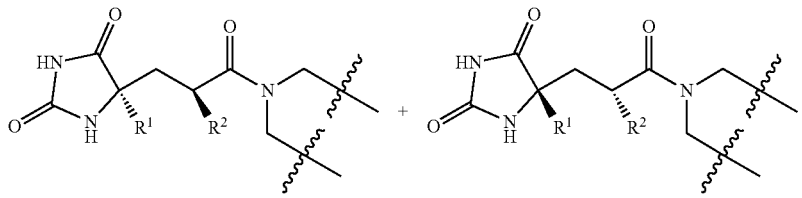

| Int | Structure | Name | Mtd | SM | MW | Ms'd |
|---|---|---|---|---|---|---|
| 028 | 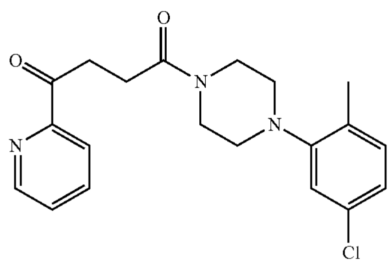 [SMILES: Cc1ccc(Cl)cc1N1CCN(C(=O)CCC(=O)c2ccccn2)CC1] | 1-[4-(5-chloro-2-methyl-phenyl)piperazin-1-yl]-4-(2-pyridyl)butane-1,4-dione | H1 | 4-Oxo-4-pyridin-2-yl-butyric acid + 1-(5-Chloro-2-methylphenyl)-piperazine | 372 | 372-374 |
| 029 | 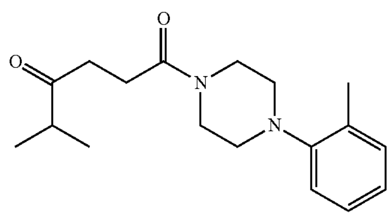 [SMILES: Cc1ccccc1N1CCN(C(=O)CCC(=O)C(C)C)CC1] | 5-methyl-1-[4-(o-tolyl)piperazin-1-yl]hexane-1,4-dione | H3 | 5-Methyl-4-oxohexanoic acid + 1-(o-tolyl)piperazine dihydrochloride | 302 | N.A. |
| 030 | 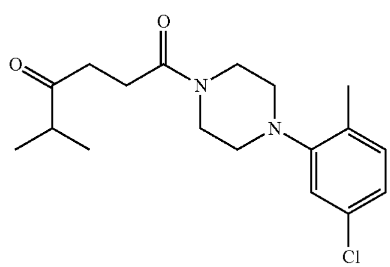 [SMILES: Cc1ccc(Cl)cc1N1CCN(C(=O)CCC(=O)C(C)C)CC1] | 1-[4-(5-chloro-2-methyl-phenyl)piperazin-1-yl]-5-methyl-hexane-1,4-dione | H3 | 5-Methyl-4-oxohexanoic acid + 1-(5-chloro-2-methylphenyl)-piperazine | 337 | N.A. |
| 031 | 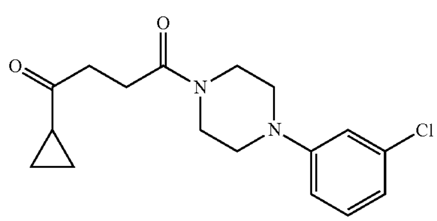 [SMILES: O=C(CCC(=O)N1CCN(c2cccc(Cl)c2)CC1)C1CC1] | 1-[4-(3-chlorophenyl)piperazin-1-yl]-4-cyclopropyl-butane-1,4-dione | H3 | 4-Cyclopropyl-4-oxobutyric acid + 1-(3-chlorophenyl)piperazine | 321 | N.A. |
| 032 | 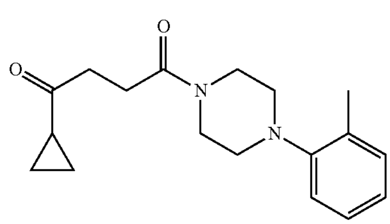 [SMILES: Cc1ccccc1N1CCN(C(=O)CCC(=O)C2CC2)CC1] | 1-cyclopropyl-4-[4-(o-tolyl)piperazin-1-yl]butane-1,4-dione | H3 | 4-Cyclopropyl-4-oxobutyric acid + 1-(o-tolyl)piperazine dihydrochloride | 300 | N.A. |

TABLE II-continued

Illustrative intermediate for the synthesis of illustrative compounds of the invention trans:

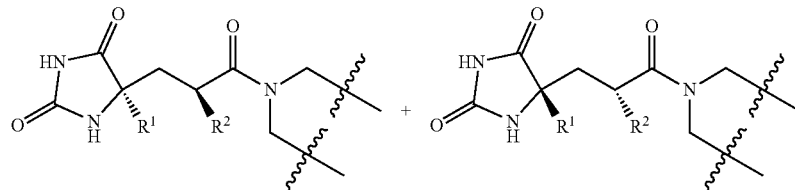

| Int | Structure | Name | Mtd | SM | MW | Ms'd |
|---|---|---|---|---|---|---|
| 033 | | 1-[4-(5-chloro-2-methyl-phenyl)piperazin-1-yl]-4-cyclopropyl-butane-1,4-dione | H3 | 4-Cyclopropyl-4-oxobutyric acid + 1-(5-chloro-2-methylphenyl)-piperazine | 335 | N.A. |
| 034 | | 1-[4-(3-chlorophenyl)piperazin-1-yl]-4-cyclobutyl-butane-1,4-dione | H3 | 4-Cyclobutyl-4-oxo-butyric acid + 1-(3-chlorophenyl)piperazine | 335 | 335-337 |
| 035 | | 1-[4-(5-chloro-2-methyl-phenyl)piperazin-1-yl]-4-cyclobutyl-butane-1,4-dione | H3 | 4-Cyclobutyl-4-oxo-butyric acid + 1-(5-chloro-2-methylphenyl)-piperazine | 349 | 349-351 |
| 036 | | 1-[4-(3-chloro-2-methyl-phenyl)piperazin-1-yl]-4-cyclopropyl-butane-1,4-dione | H3 | 4-Cyclopropyl-4-oxobutyric acid + 1-(3-chloro-2-methylphenyl)-piperazine | 335 | N.A. |
| 037 | | 1-cyclopropyl-4-[4-(3-fluoro-2-methyl-phenyl)piperazin-1-yl]butane-1,4-dione | H3 | 4-Cyclopropyl-4-oxobutyric acid + 1-(3-fluoro-2-methylphenyl)-piperazine | 318 | N.A. |

TABLE II-continued

Illustrative intermediate for the synthesis of illustrative compounds of the invention trans:

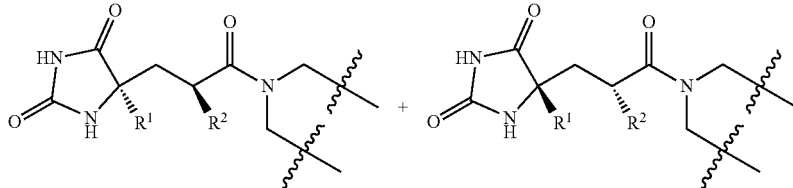

| Int | Structure | Name | Mtd | SM | MW | Ms'd |
|---|---|---|---|---|---|---|
| 038 | 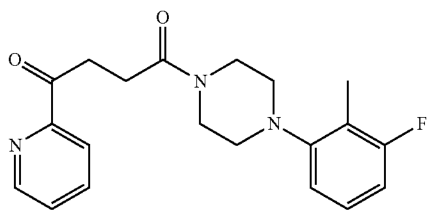 [SMILES: Cc1c(F)cccc1N1CCN(C(=O)CCC(=O)c2ccccn2)CC1] | 1-[4-(3-fluoro-2-methyl-phenyl)piperazin-1-yl]-4-(2-pyridyl)butane-1,4-dione | H3 | 4-Oxo-4-pyridin-2-yl-butyric acid + 1-(3-fluoro-2-methylphenyl)-piperazine | 355 | N.A. |
| 039 | 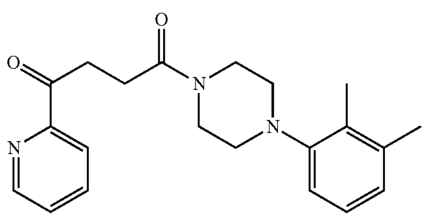 [SMILES: Cc1cccc(N2CCN(C(=O)CCC(=O)c3ccccn3)CC2)c1C] | 1-[4-(2,3-dimethylphenyl)piperazin-1-yl]-4-(2-pyridyl)butane-1,4-dione | H3 | 4-Oxo-4-pyridin-2-yl-butyric acid + 1-(2,3-Dimethyl-phenyl)-piperazine | 351 | N.A. |
| 040 | 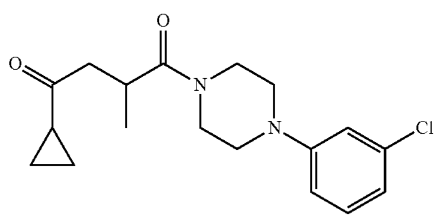 [SMILES: CC(CC(=O)C1CC1)C(=O)N1CCN(c2cccc(Cl)c2)CC1] | 1-[4-(3-chlorophenyl)piperazin-1-yl]-4-cyclopropyl-2-methyl-butane-1,4-dione | D2b | Int 010 + cyclopropane-carboxaldehyde | 335 | 335-337 |
| 041 | 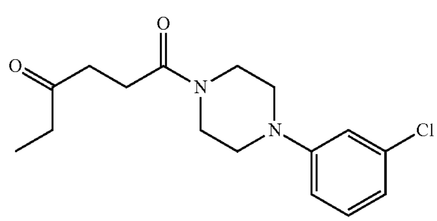 [SMILES: CCC(=O)CCC(=O)N1CCN(c2cccc(Cl)c2)CC1] | 1-[4-(3-chlorophenyl)piperazin-1-yl]hexane-1,4-dione | D2b | Int 005 + propanal | 309 | N.A. |
| 042 | 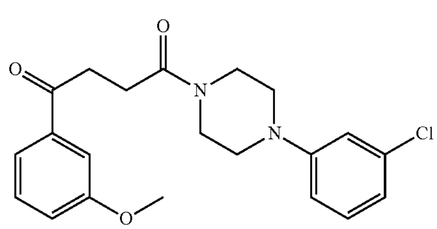 [SMILES: COc1cccc(C(=O)CCC(=O)N2CCN(c3cccc(Cl)c3)CC2)c1] | 1-[4-(3-chlorophenyl)piperazin-1-yl]-4-(3-methoxyphenyl)butane-1,4-dione | D2b | Int 005 + 3-Methoxy benzaldehyde | 387 | 387-389 |

TABLE II-continued

Illustrative intermediate for the synthesis of illustrative compounds of the invention trans:

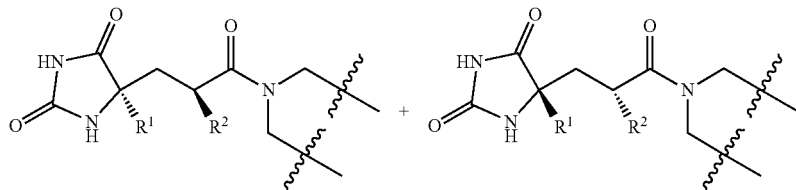

| Int | Structure | Name | Mtd | SM | MW | Ms'd |
|---|---|---|---|---|---|---|
| 043 | 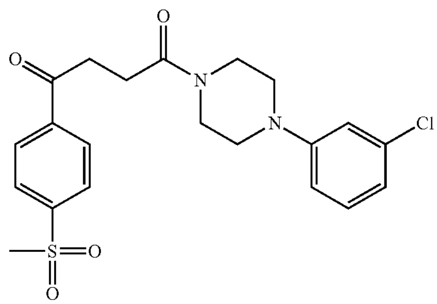 [SMILES: CS(=O)(=O)c1ccc(C(=O)CCC(=O)N2CCN(c3cccc(Cl)c3)CC2)cc1] | 1-[4-(3-chlorophenyl)piperazin-1-yl]-4-(4-methylsulfonyl-phenyl)butane-1,4-dione | D2b | Int 005 + 4-Methylsulphonyl benzaldehyde | 435 | 435-437 |
| 044 | 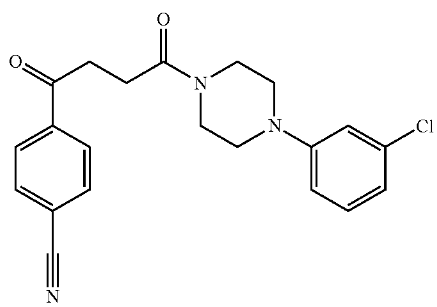 [SMILES: N#Cc1ccc(C(=O)CCC(=O)N2CCN(c3cccc(Cl)c3)CC2)cc1] | 4-[4-[4-(3-chlorophenyl)piperazin-1-yl]-4-oxo-butanoyl]benzonitrile | D2a | Int 005 + 4-cyano benzaldehyde | 382 | 382-384 |
| 045 | 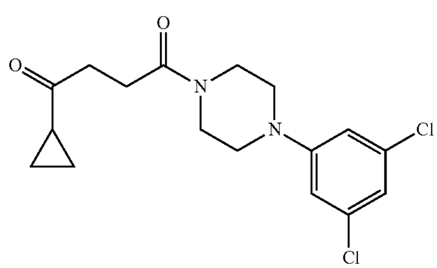 [SMILES: O=C(CCC(=O)N1CCN(c2cc(Cl)cc(Cl)c2)CC1)C1CC1] | 1-cyclopropyl-4-[4-(3,5-dichlorophenyl)piperazin-1-yl]butane-1,4-dione | H3 | 4-Cyclopropyl-4-oxobutyric acid + 1-(3,5-dichlorophenyl)piperazine | 355 | N.A. |
| 046 | 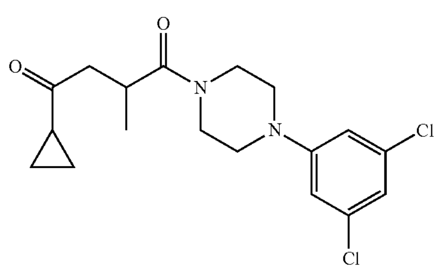 [SMILES: CC(CC(=O)C1CC1)C(=O)N1CCN(c2cc(Cl)cc(Cl)c2)CC1] | 4-cyclopropyl-1-[4-(3,5-dichlorophenyl)piperazin-1-yl]-2-methyl-butane-1,4-dione | D2b | Int 001 + cyclopropane-carboxaldehyde | 369 | 369-371 |

TABLE II-continued

Illustrative intermediate for the synthesis of illustrative compounds of the invention trans:

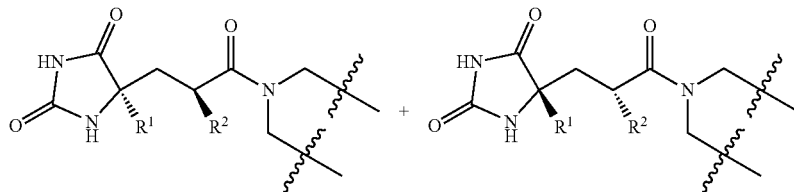

| Int | Structure | Name | Mtd | SM | MW | Ms'd |
|---|---|---|---|---|---|---|
| 047 | 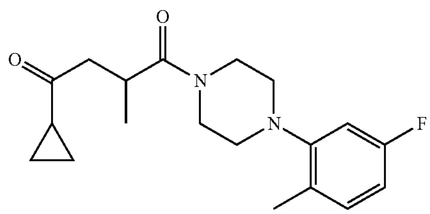 [SMILES: Cc1ccc(F)cc1N1CCN(C(=O)C(C)CC(=O)C2CC2)CC1] | 4-cyclopropyl-1-[4-(5-fluoro-2-methyl-phenyl)piperazin-1-yl]-2-methyl-butane-1,4-dione | D2b | Int 011 + cyclopropane-carboxaldehyde | 332 | 333 |
| 048 | 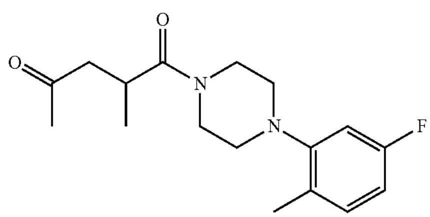 [SMILES: CC(=O)CC(C)C(=O)N1CCN(c2cc(F)ccc2C)CC1] | 1-[4-(5-fluoro-2-methyl-phenyl)piperazin-1-yl]-2-methyl-pentane-1,4-dione | D2b | Int 011 + acetaldehyde | 306 | 307 |
| 049 | 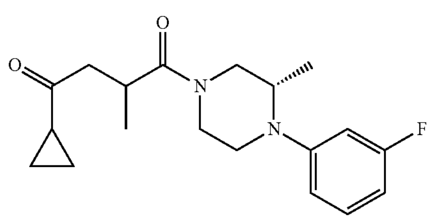 [SMILES: CC(CC(=O)C1CC1)C(=O)N1CCN(c2cccc(F)c2)[C@@H](C)C1] | 4-cyclopropyl-1-[(3S)-4-(3-fluorophenyl)-3-methyl-piperazin-1-yl]-2-methyl-butane-1,4-dione | H3 | Int 155 + Int 202 | 332 | 333 |
| 050 | 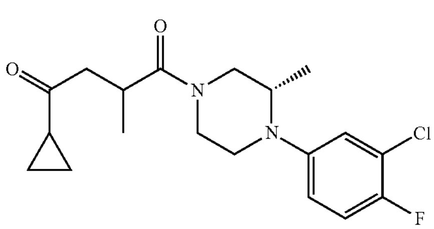 [SMILES: CC(CC(=O)C1CC1)C(=O)N1CCN(c2ccc(F)c(Cl)c2)[C@@H](C)C1] | 1-[(3S)-4-(3-chloro-4-fluoro-phenyl)-3-methyl-piperazin-1-yl]-4-cyclopropyl-2-methyl-butane-1,4-dione | H3 | Int 155 + Int 198 | 367 | 367-369 |
| 051 | 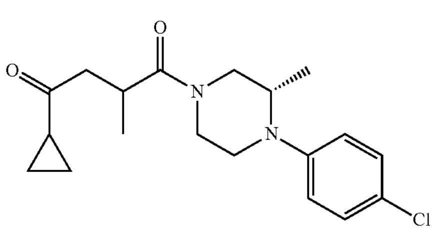 [SMILES: CC(CC(=O)C1CC1)C(=O)N1CCN(c2ccc(Cl)cc2)[C@@H](C)C1] | 1-[(3S)-4-(4-chlorophenyl)-3-methyl-piperazin-1-yl]-4-cyclopropyl-2-methyl-butane-1,4-dione | H3 | Int 155 + Int 205 | 349 | 349-351 |

TABLE II-continued

Illustrative intermediate for the synthesis of illustrative compounds of the invention trans:

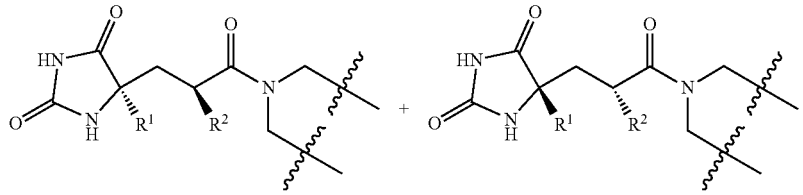

| Int | Structure | Name | Mtd | SM | MW | Ms'd |
|---|---|---|---|---|---|---|
| 052 | 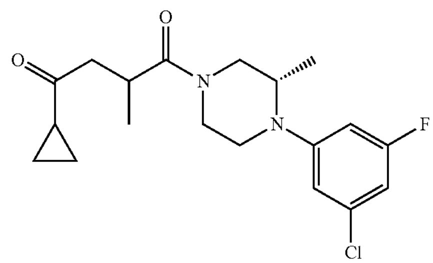 [SMILES: CC(CC(=O)C1CC1)C(=O)N1CCN(c2cc(F)cc(Cl)c2)[C@@H](C)C1] | 1-[(3S)-4-(3-chloro-5-fluoro-phenyl)-3-methyl-piperazin-1-yl]-4-cyclopropyl-2-methyl-butane-1,4-dione | H3 | Int 155 + Int 206 | 367 | 367-369 |
| 053 | 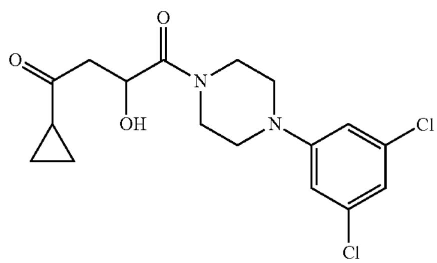 [SMILES: O=C(CC(O)C(=O)N1CCN(c2cc(Cl)cc(Cl)c2)CC1)C1CC1] | 4-cyclopropyl-1-[4-(3,5-dichlorophenyl)piperazin-1-yl]-2-hydroxy-butane-1,4-dione | 2.14 | Cyclopropane carbonyl chloride + Meldrum's acid + benzyl alcohol + crotonyl chloride + 3,5-dichlorophenyl piperazine | 371 | N.A. |
| 054 | 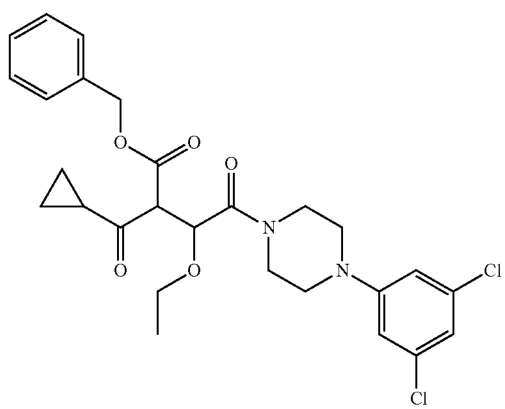 [SMILES: CCOC(C(=O)N1CCN(c2cc(Cl)cc(Cl)c2)CC1)C(C(=O)OCc1ccccc1)C(=O)C1CC1] | benzyl 2-(cyclopropanecarbonyl)-4-[4-(3,5-dichlorophenyl)piperazin-1-yl]-3-ethoxy-4-oxo-butanoate | 2.14 | Cyclopropane carbonyl chloride + Meldrum's acid + benzyl alcohol + crotonyl chloride + 3,5-dichlorophenyl piperazine | 533 | N.A. |
| 055 | 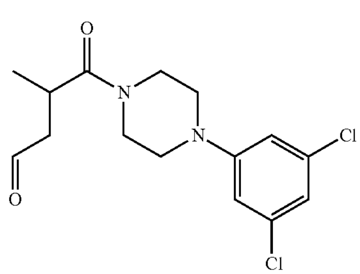 [SMILES: CC(CC=O)C(=O)N1CCN(c2cc(Cl)cc(Cl)c2)CC1] | 4-[4-(3,5-dichlorophenyl)piperazin-1-yl]-3-methyl-4-oxo-butanal | D4 | Int 124 | 329 | 329-331 |

TABLE II-continued

Illustrative intermediate for the synthesis of illustrative compounds of the invention trans:

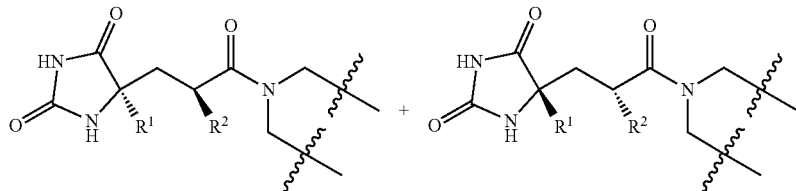

| Int | Structure | Name | Mtd | SM | MW | Ms'd |
|---|---|---|---|---|---|---|
| 056 | 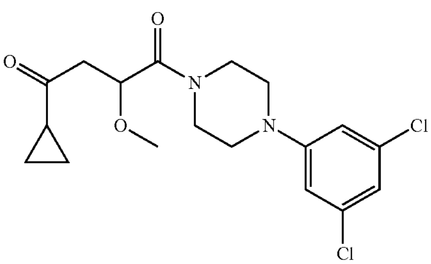 [SMILES: COC(CC(=O)C1CC1)C(=O)N1CCN(c2cc(Cl)cc(Cl)c2)CC1] | 4-cyclopropyl-1-[4-(3,5-dichlorophenyl)piperazin-1-yl]-2-methoxy-butane-1,4-dione | 2.15 | Int 054 | 385 | N.A. |
| 057 | 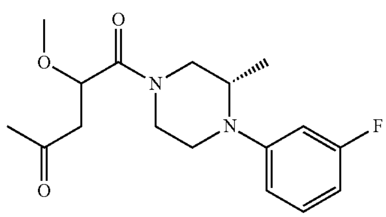 [SMILES: COC(CC(C)=O)C(=O)N1CCN(c2cccc(F)c2)[C@@H](C)C1] | 1-[(3S)-4-(3-fluorophenyl)-3-methyl-piperazin-1-yl]-2-methoxy-pentane-1,4-dione | D4 | Int 125 | 322 | N.A. |
| 058 | 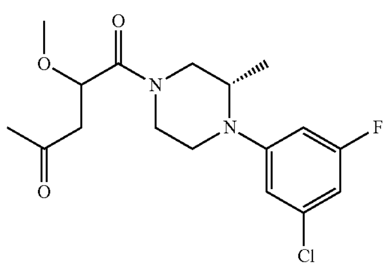 [SMILES: COC(CC(C)=O)C(=O)N1CCN(c2cc(F)cc(Cl)c2)[C@@H](C)C1] | 1-[(3S)-4-(3-chloro-5-fluoro-phenyl)-3-methyl-piperazin-1-yl]-2-methoxy-pentane-1,4-dione | D4 | Int 126 | 357 | N.A. |
| 059 | 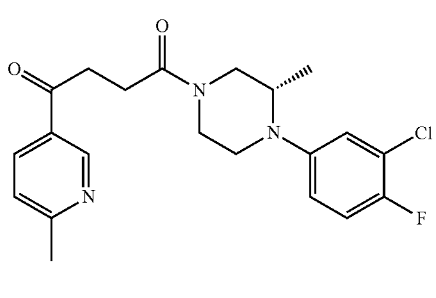 [SMILES: Cc1ccc(C(=O)CCC(=O)N2CCN(c3ccc(F)c(Cl)c3)[C@@H](C)C2)cn1] | 1-[(3S)-4-(3-chloro-4-fluoro-phenyl)-3-methyl-piperazin-1-yl]-4-(6-methyl-3-pyridyl)butane-1,4-dione | D2c | Int 006 + 6-Methyl-pyridine-3-carbaldehyde | 404 | 404-406 |
| 060 | 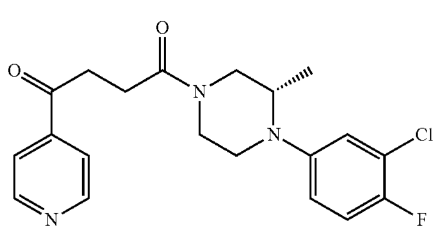 [SMILES: C[C@H]1CN(C(=O)CCC(=O)c2ccncc2)CCN1c1ccc(F)c(Cl)c1] | 1-[(3S)-4-(3-chloro-4-fluoro-phenyl)-3-methyl-piperazin-1-yl]-4-(4-pyridyl)butane-1,4-dione | D2c | Int 006 + Pyridine-4-carbaldehyde | 390 | 390-392 |

TABLE II-continued

Illustrative intermediate for the synthesis of illustrative compounds of the invention trans:

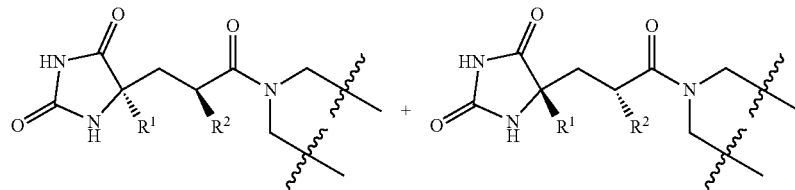

| Int | Structure | Name | Mtd | SM | MW | Ms'd |
|---|---|---|---|---|---|---|
| 061 | 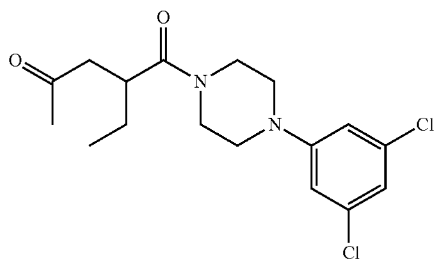 [SMILES: CCC(CC(C)=O)C(=O)N1CCN(c2cc(Cl)cc(Cl)c2)CC1] | 1-[4-(3,5-dichlorophenyl)piperazin-1-yl]-2-ethyl-pentane-1,4-dione | H2 | Int 190 + 1-(3,5-dichlorophenyl)piperazine | 357 | 357-359 |
| 062 | trans | 5-[2-(benzyloxymethyl)-3-[(3S)-4-(3-fluorophenyl)-3-methyl-piperazin-1-yl]-3-oxo-propyl]-5-methyl-imidazolidine-2,4-dione | H2 | Int 135 + Int 202 | 483 | N.A. |
| 063 | 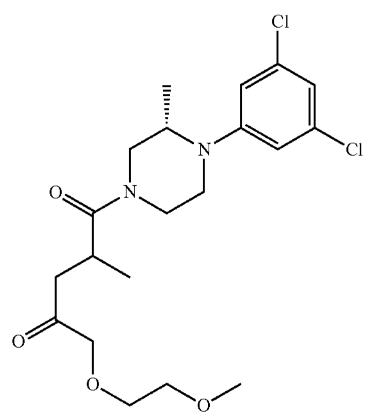 [SMILES: COCCOCC(=O)CC(C)C(=O)N1CCN(c2cc(Cl)cc(Cl)c2)[C@@H](C)C1] | 1-[(3S)-4-(3,5-dichlorophenyl)-3-methyl-piperazin-1-yl]-5-(2-methoxyethoxy)-2-methyl-pentane-1,4-dione | H2 | Int 185 + Int 197 | 431 | 431-433 |
| 064 | 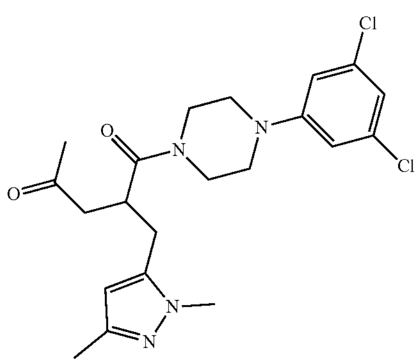 [SMILES: CC(=O)CC(Cc1cc(C)nn1C)C(=O)N1CCN(c2cc(Cl)cc(Cl)c2)CC1] | 1-[4-(3,5-dichlorophenyl)piperazin-1-yl]-2-[(2,5-dimethylpyrazol-3-yl)methyl]pentane-1,4-dione | E | Int 121 + 5-Chloromethyl-1,3-dimethyl-1H-pyrazole | 437 | 437-439 |

TABLE II-continued

Illustrative intermediate for the synthesis of illustrative compounds of the invention trans:

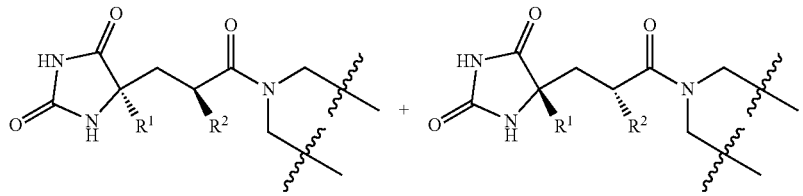

| Int | Structure | Name | Mtd | SM | MW | Ms'd |
|---|---|---|---|---|---|---|
| 065 | 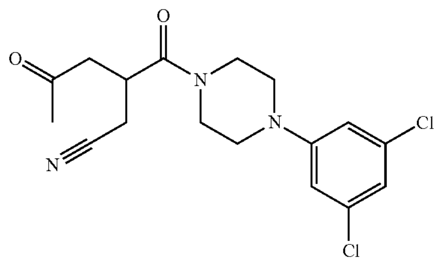 [SMILES: CC(=O)CC(CC#N)C(=O)N1CCN(c2cc(Cl)cc(Cl)c2)CC1] | 3-[4-(3,5-dichlorophenyl)piperazine-1-carbonyl]-5-oxo-hexanenitrile | E | Int 121 + Bromo-acetonitrile | 368 | 368-370 |
| 066 | 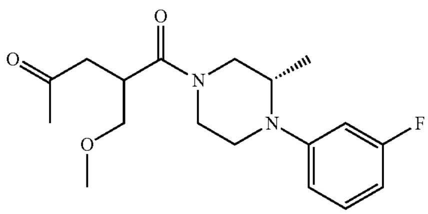 [SMILES: COCC(CC(C)=O)C(=O)N1CCN(c2cccc(F)c2)[C@@H](C)C1] | 1-[(3S)-4-(3-fluorophenyl)-3-methyl-piperazin-1-yl]-2-(methoxymethyl)pentane-1,4-dione | E | Int 122 + Bromo-methoxy-methane | 336 | 337 |
| 067 | 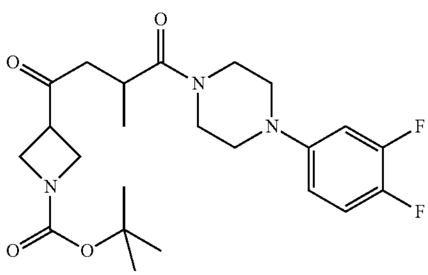 [SMILES: CC(CC(=O)C1CN(C(=O)OC(C)(C)C)C1)C(=O)N1CCN(c2ccc(F)c(F)c2)CC1] | tert-butyl 3-[4-[4-(3,4-difluorophenyl)piperazin-1-yl]-3-methyl-4-oxo-butanoyl]azetidine-1-carboxylate | D2b | Int 002 + 1-Boc-3-azetidinecarboxaldehyde | 452 | 453 |
| 068 | 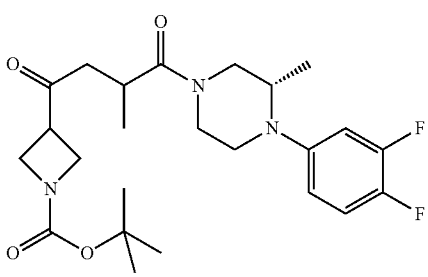 [SMILES: CC(CC(=O)C1CN(C(=O)OC(C)(C)C)C1)C(=O)N1CCN(c2ccc(F)c(F)c2)[C@@H](C)C1] | tert-butyl 3-[4-[(3S)-4-(3,4-difluorophenyl)-3-methyl-piperazin-1-yl]-3-methyl-4-oxo-butanoyl]azetidine-1-carboxylate | D2b | Int 003 + 1-Boc-3-azetidinecarboxaldehyde | 466 | 467 |
| 069 | 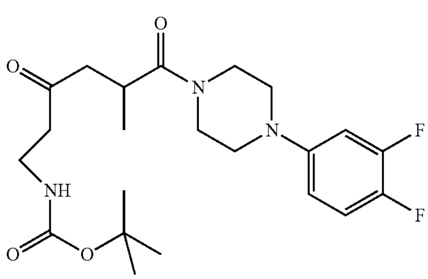 [SMILES: CC(CC(=O)CCNC(=O)OC(C)(C)C)C(=O)N1CCN(c2ccc(F)c(F)c2)CC1] | tert-butyl N-[6-[4-(3,4-difluorophenyl)piperazin-1-yl]-5-methyl-3,6-dioxo-hexyl]carbamate | H2 | Int 191 + 1-(3,4-difluorophenyl)piperazine | 440 | 441 |

TABLE II-continued

Illustrative intermediate for the synthesis of illustrative compounds of the invention trans:

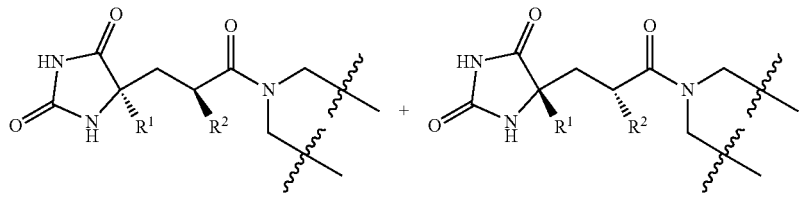

| Int | Structure | Name | Mtd | SM | MW | Ms'd |
|---|---|---|---|---|---|---|
| 070 | 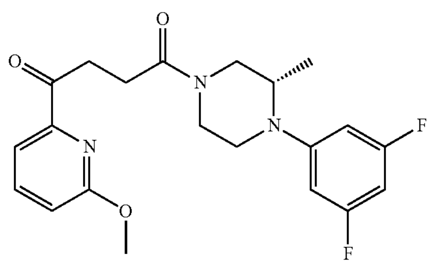 [SMILES: COc1cccc(C(=O)CCC(=O)N2CCN(c3cc(F)cc(F)c3)[C@@H](C)C2)n1] | 1-[(3S)-4-(3,5-difluorophenyl)-3-methyl-piperazin-1-yl]-4-(6-methoxy-2-pyridyl)butane-1,4-dione | D2a | Int 004 + 6-Methoxy-pyridine-2-carbaldehyde | 403 | 404 |
| 071 | 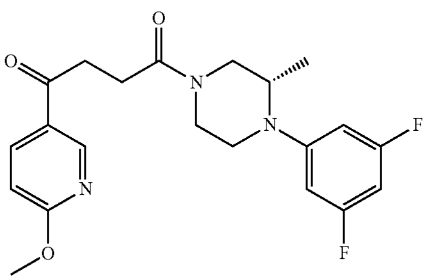 [SMILES: COc1ccc(C(=O)CCC(=O)N2CCN(c3cc(F)cc(F)c3)[C@@H](C)C2)cn1] | 1-[(3S)-4-(3,5-difluorophenyl)-3-methyl-piperazin-1-yl]-4-(6-methoxy-3-pyridyl)butane-1,4-dione | D2a | Int 004 + 6-Methoxy-pyridine-3-carbaldehyde | 403 | 404 |
| 072 | 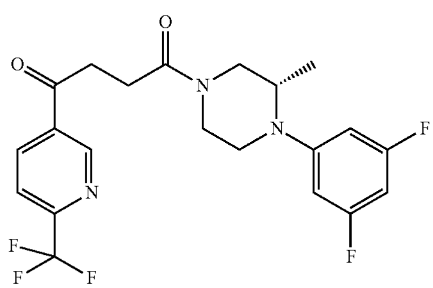 [SMILES: C[C@H]1CN(C(=O)CCC(=O)c2ccc(C(F)(F)F)nc2)CCN1c1cc(F)cc(F)c1] | 1-[(3S)-4-(3,5-difluorophenyl)-3-methyl-piperazin-1-yl]-4-[6-(trifluoromethyl)-3-pyridyl]butane-1,4-dione | D2a | Int 004 + 6-Trifluoromethyl-pyridine-3-carbaldehyde | 441 | 442 |
| 073 | 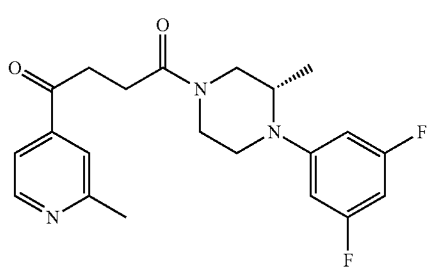 [SMILES: Cc1cc(C(=O)CCC(=O)N2CCN(c3cc(F)cc(F)c3)[C@@H](C)C2)ccn1] | 1-[(3S)-4-(3,5-difluorophenyl)-3-methyl-piperazin-1-yl]-4-(2-methyl-4-pyridyl)butane-1,4-dione | D2a | Int 004 + 2-Methyl-pyridine-4-carbaldehyde | 387 | 388 |
| 074 | 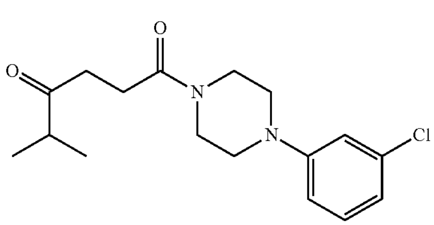 [SMILES: CC(C)C(=O)CCC(=O)N1CCN(c2cccc(Cl)c2)CC1] | 1-[4-(3-chlorophenyl)piperazin-1-yl]-5-methyl-hexane-1,4-dione | H3 | 5-Methyl-4-oxohexanoic acid + 1-(3-chlorophenyl)piperazine | 323 | 323-325 |

TABLE II-continued

Illustrative intermediate for the synthesis of illustrative compounds of the invention trans:

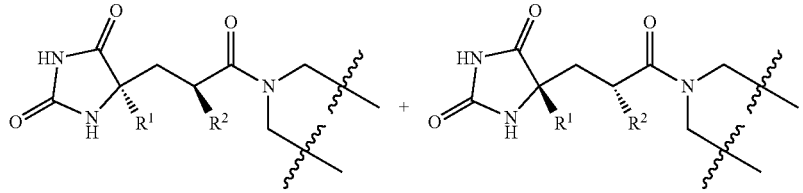

| Int | Structure | Name | Mtd | SM | MW | Ms'd |
|---|---|---|---|---|---|---|
| 075 | 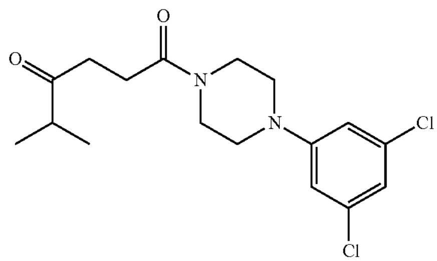 [SMILES: CC(C)C(=O)CCC(=O)N1CCN(c2cc(Cl)cc(Cl)c2)CC1] | 1-[4-(3,5-dichlorophenyl)piperazin-1-yl]-5-methyl-hexane-1,4-dione | H3 | 5-Methyl-4-oxohexanoic acid + 1-(3,5-dichlorophenyl)piperazine | 357 | 357-359 |
| 076 | 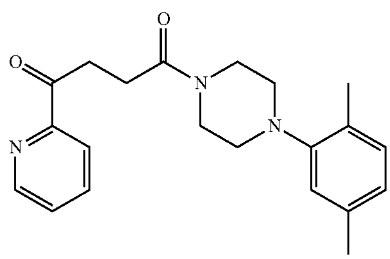 [SMILES: Cc1ccc(C)c(N2CCN(C(=O)CCC(=O)c3ccccn3)CC2)c1] | 1-[4-(2,5-dimethylphenyl)piperazin-1-yl]-4-(2-pyridyl)butane-1,4-dione | H1 | 4-Oxo-4-pyridin-2-yl-butyric acid + 1-(2,5-Dimethylphenyl)piperazine | 351 | 352 |
| 077 | 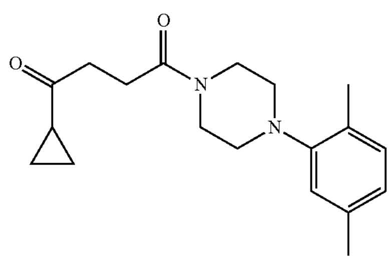 [SMILES: Cc1ccc(C)c(N2CCN(C(=O)CCC(=O)C3CC3)CC2)c1] | 1-cyclopropyl-4-4-(2,5-dimethylphenyl)piperazin-1-yl]butane-1,4-dione | H1 | 4-Cyclopropyl-4-oxo-butyric acid + 1-(2,5-Dimethylphenyl)piperazine | 314 | 315 |
| 078 | 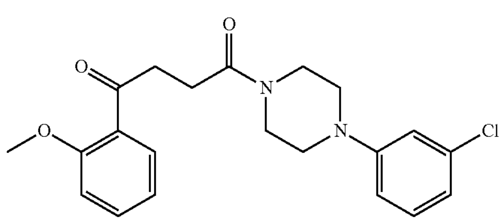 [SMILES: COc1ccccc1C(=O)CCC(=O)N1CCN(c2cccc(Cl)c2)CC1] | 1-[4-(3-chlorophenyl)piperazin-1-yl]-4-(2-methoxyphenyl)butane-1,4-dione | H2 | 4-(2-methoxyphenyl)-4-oxobutyric acid + 1-(3-chlorophenyl)piperazine | 387 | 387-389 |
| 079 | 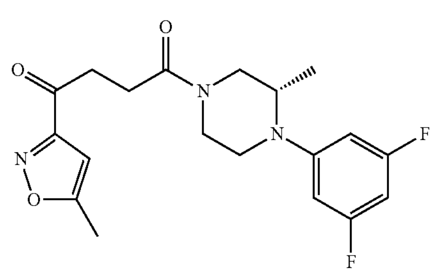 [SMILES: Cc1cc(C(=O)CCC(=O)N2CCN(c3cc(F)cc(F)c3)[C@@H](C)C2)no1] | 1-[(3S)-4-(3,5-difluorophenyl)-3-methyl-piperazin-1-yl]-4-(5-methylisoxazol-3-yl)butane-1,4-dione | D2a | Int 004 + 5-Methylisoxazole-3-carboxaldehyde | 377 | 378 |

TABLE II-continued

Illustrative intermediate for the synthesis of illustrative compounds of the invention trans:

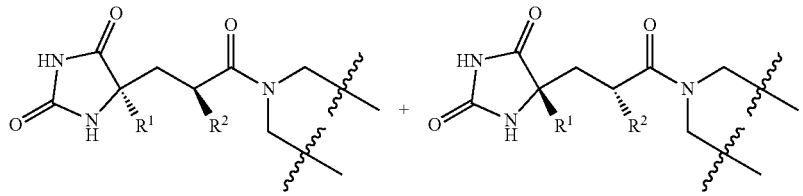

| Int | Structure | Name | Mtd | SM | MW | Ms'd |
|---|---|---|---|---|---|---|
| 080 | 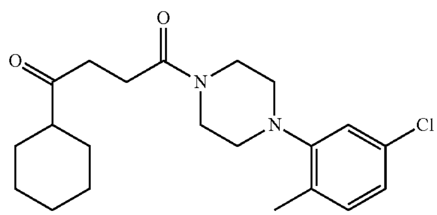 [SMILES: Cc1ccc(Cl)cc1N1CCN(C(=O)CCC(=O)C2CCCCC2)CC1] | 1-[4-(5-chloro-2-methyl-phenyl)piperazin-1-yl]-4-cyclohexyl-butane-1,4-dione | H3 | 4-cyclohexyl-4-oxobutyric acid + 1-(5-chloro-2-methylphenyl)-piperazine | 377 | 377-379 |
| 081 | 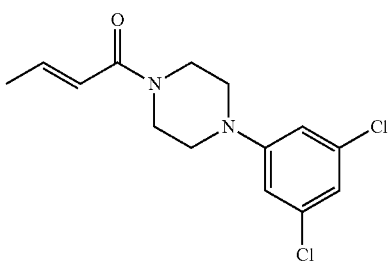 [SMILES: C/C=C/C(=O)N1CCN(c2cc(Cl)cc(Cl)c2)CC1] | (E)-1-[4-(3,5-dichlorophenyl)piperazin-1-yl]but-2-en-1-one | D1 | crotonyl chloride + 3,5-dichloro phenyl piperazine | 299 | N.A. |
| 082 | 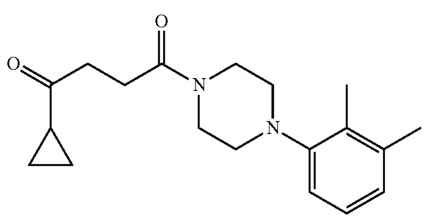 [SMILES: Cc1cccc(N2CCN(C(=O)CCC(=O)C3CC3)CC2)c1C] | 1-cyclopropyl-4-[4-(2,3-dimethyl-phenyl)piperazin-1-yl]butane-1,4-dione | H1 | 4-Cyclopropyl-4-oxo-butyric acid + 1-(2,3-Dimethylphenyl) piperazine | 314 | N.A. |
| 083 | 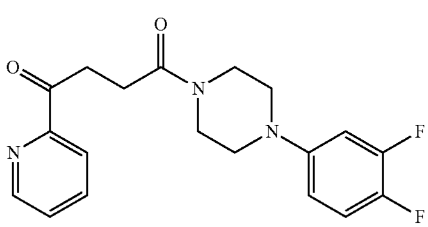 [SMILES: O=C(CCC(=O)N1CCN(c2ccc(F)c(F)c2)CC1)c1ccccn1] | 1-[4-(3,4-difluorophenyl) piperazin-1-yl]-4-(2-pyridyl)butane-1,4-dione | H1 | 4-Oxo-4-pyridin-2-yl-butyric acid + 1-(3,4-difluorophenyl) piperazine | 359 | 360 |
| 084 | 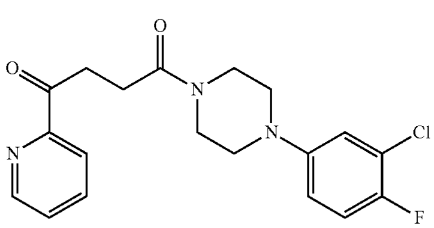 [SMILES: O=C(CCC(=O)N1CCN(c2ccc(F)c(Cl)c2)CC1)c1ccccn1] | 1-[4-(3-chloro-4-fluoro-phenyl) piperazin-1-yl]-4-(2-pyridyl)butane-1,4-dione | H1 | 4-Oxo-4-pyridin-2-yl-butyric acid + 1-(3-Chloro-4-fluorophenyl) piperazine dihydrochloride | 376 | 376-378 |

TABLE II-continued

Illustrative intermediate for the synthesis of illustrative compounds of the invention trans:

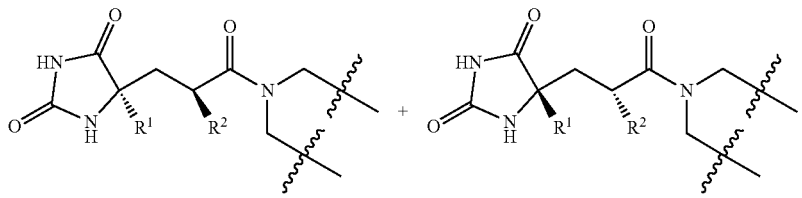

| Int | Structure | Name | Mtd | SM | MW | Ms'd |
|---|---|---|---|---|---|---|
| 085 | 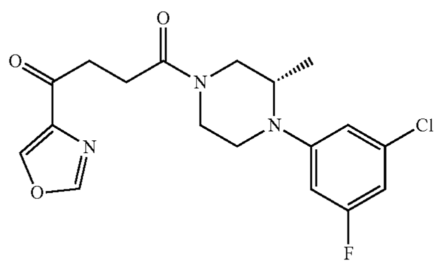 [SMILES: C[C@H]1CN(C(=O)CCC(=O)c2cocn2)CCN1c1cc(F)cc(Cl)c1] | 1-[(3S)-4-(3-chloro-5-fluoro-phenyl)-3-methyl-piperazin-1-yl]-4-oxazol-4-yl-butane-1,4-dione | D2a | Int 007 + Oxazole-4-carbaldehyde | 380 | 380-382 |
| 086 | 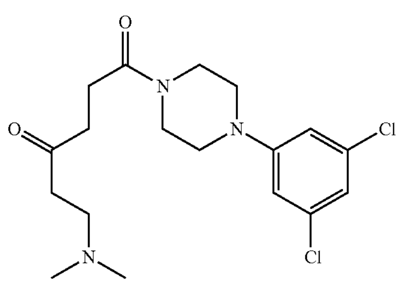 [SMILES: CN(C)CCC(=O)CCC(=O)N1CCN(c2cc(Cl)cc(Cl)c2)CC1] | 1-[4-(3,5-dichlorophenyl)piperazin-1-yl]-6-(dimethylamino)hexane-1,4-dione | H1 | 6-dimethylamino-4-ketohexanoic acid hydrochloride + 1-(3,5-dichlorophenyl)piperazine | 386 | 386-388-390 |
| 087 | 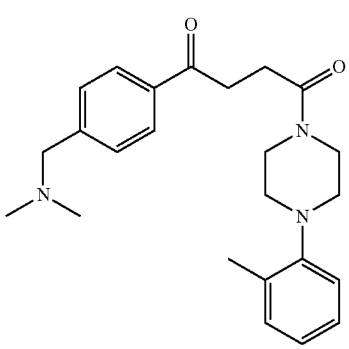 [SMILES: Cc1ccccc1N1CCN(C(=O)CCC(=O)c2ccc(CN(C)C)cc2)CC1] | 1-[4-(dimethylamino methyl)phenyl]-4-[4-(o-tolyl)piperazin-1-yl]butane-1,4-dione | D7 | Int 117 | 394 | 395 |
| 088 | 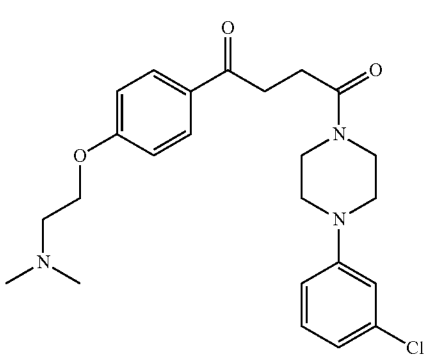 [SMILES: CN(C)CCOc1ccc(C(=O)CCC(=O)N2CCN(c3cccc(Cl)c3)CC2)cc1] | 1-[4-(3-chloro-phenyl)piperazin-1-yl]-4-[4-[2-dimethylamino-ethyloxy)phenyl]butane-1,4-dione | H1 | Int 189+ 1-(3-chlorophenyl)piperazine | 444 | 444-446 |

TABLE II-continued

Illustrative intermediate for the synthesis of illustrative compounds of the invention trans:

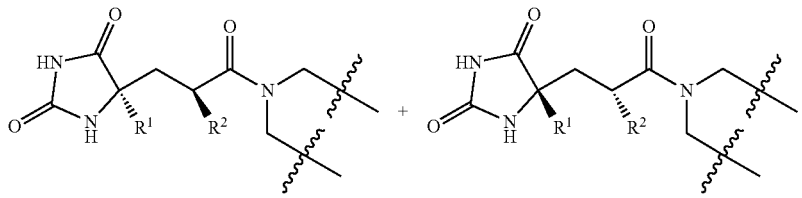

| Int | Structure | Name | Mtd | SM | MW | Ms'd |
|---|---|---|---|---|---|---|
| 089 | 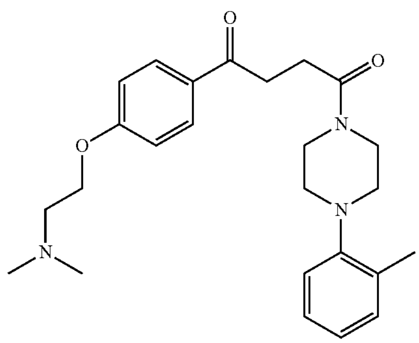 | 1-[4-2-dimethylamino-ethyloxy)phenyl]-4-[4-(o-tolyl)piperazin-1-yl]butane-1,4-dione | H1 | Int 189+ 1-(o-tolyl)piperazine dihydrochloride | 424 | 425 |
| 090 | 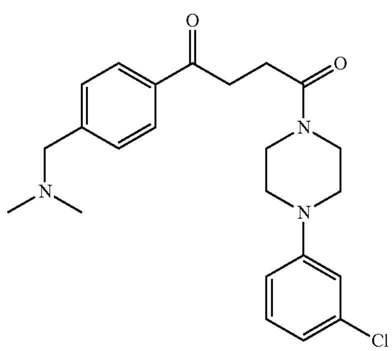 [SMILES: CN(C)Cc1ccc(C(=O)CCC(=O)N2CCN(c3cccc(Cl)c3)CC2)cc1] | 1-[4-(3-chlorophenyl)piperazin-1-yl]-4-[4-(dimethylamino-methyl)phenyl]butane-1,4-dione | D7 | Int 118 | 414 | 414-416 |
| 091 | 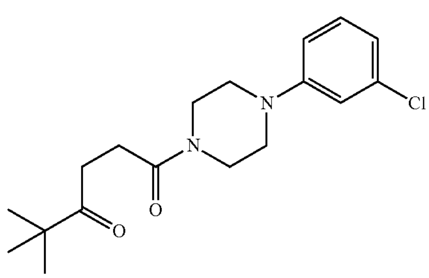 [SMILES: CC(C)(C)C(=O)CCC(=O)N1CCN(c2cccc(Cl)c2)CC1] | 1-[4-(3-chlorophenyl)piperazin-1-yl]-5,5-dimethyl-hexane-1,4-dione | H1 | 5,5-Dimethyl-4-oxo-hexanoic acid + 1-(3-chlorophenyl)piperazine | 337 | 337-339 |
| 092 | 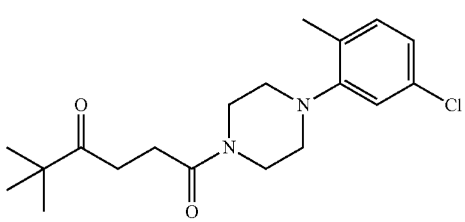 [SMILES: Cc1ccc(Cl)cc1N1CCN(C(=O)CCC(=O)C(C)(C)C)CC1] | 1-[4-(5-chloro-2-methyl-phenyl)piperazin-1-yl]-5,5-dimethyl-hexane-1,4-dione | H1 | 5,5-Dimethyl-4-oxo-hexanoic acid + 1-(5-chloro-2-methylphenyl)-piperazine | 351 | 351-353 |

TABLE II-continued

Illustrative intermediate for the synthesis of illustrative compounds of the invention trans:

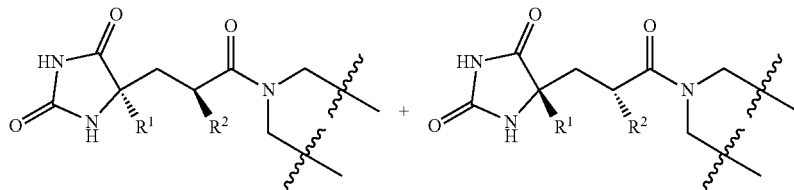

| Int | Structure | Name | Mtd | SM | MW | Ms'd |
|---|---|---|---|---|---|---|
| 093 | 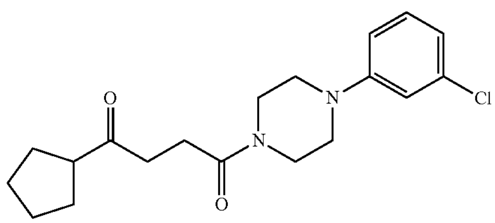 [SMILES: O=C(CCC(=O)N1CCN(c2cccc(Cl)c2)CC1)C1CCCC1] | 1-[4-(3-chlorophenyl)piperazin-1-yl]-4-cyclopentyl-butane-1,4-dione | H1 | 4-Cyclopentyl-4-oxo-butyric acid + 1-(3-chlorophenyl)piperazine | 349 | 349-351 |
| 094 | 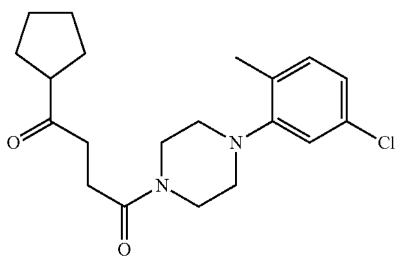 [SMILES: Cc1ccc(Cl)cc1N1CCN(C(=O)CCC(=O)C2CCCC2)CC1] | 1-[4-(5-chloro-2-methyl-phenyl)piperazin-1-yl]-4-cyclopentyl-butane-1,4-dione | H1 | 4-Cyclopentyl-4-oxo-butyric acid + 1-(5-chloro-2-methylphenyl)-piperazine | 363 | 363-365 |
| 095 | 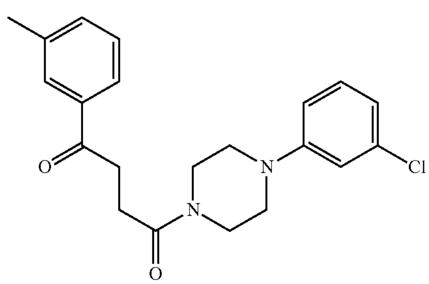 [SMILES: Cc1cccc(C(=O)CCC(=O)N2CCN(c3cccc(Cl)c3)CC2)c1] | 1-[4-(3-chlorophenyl)piperazin-1-yl]-4-(m-tolyl)butane-1,4-dione | D2a | Int 005 + 3-Methyl-benzaldehyde | 371 | 371-373 |
| 096 | 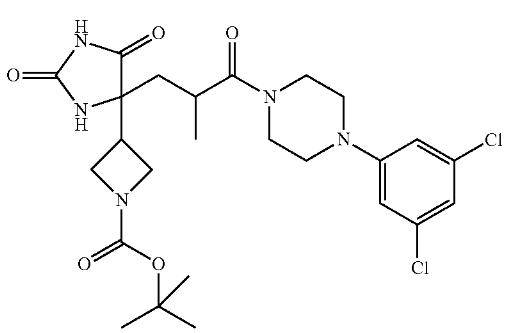 [SMILES: CC(CC1(C2CN(C(=O)OC(C)(C)C)C2)NC(=O)NC1=O)C(=O)N1CCN(c2cc(Cl)cc(Cl)c2)CC1] | tert-butyl 3-[4-[3-[4-(3,5-dichlorophenyl)piperazin-1-yl]-2-methyl-3-oxo-propyl]-2,5-dioxo-imidazolidin-4-yl]azetidine-1-carboxylate | F | Int 119 | 554 | 554-556 |

TABLE II-continued

Illustrative intermediate for the synthesis of illustrative compounds of the invention trans:

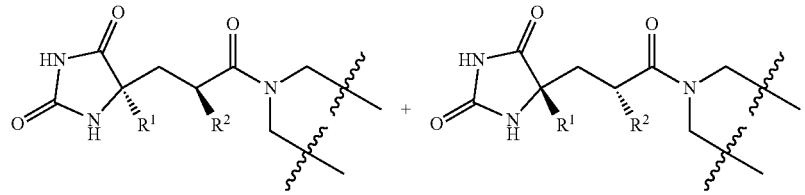

| Int | Structure | Name | Mtd | SM | MW | Ms'd |
|---|---|---|---|---|---|---|
| 097 | 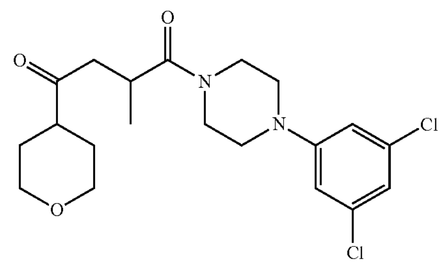 [SMILES: CC(CC(=O)C1CCOCC1)C(=O)N1CCN(c2cc(Cl)cc(Cl)c2)CC1] | 1-[4-(3,5-dichlorophenyl)piperazin-1-yl]-2-methyl-4-tetrahydropyran-4-yl-butane-1,4-dione | D2b | Int 001 + Tetrahydro-pyran-4-carbaldehyde | 413 | 413-415 |
| 098 | 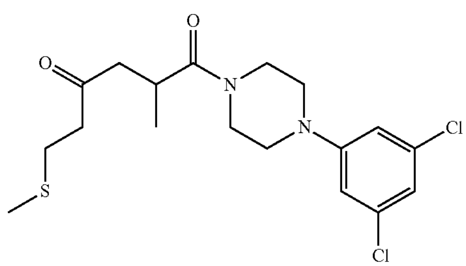 [SMILES: CSCCC(=O)CC(C)C(=O)N1CCN(c2cc(Cl)cc(Cl)c2)CC1] | 1-[4-(3,5-dichlorophenyl)piperazin-1-yl]-2-methyl-6-methylsulfanyl-hexane-1,4-dione | D2b | Int 001 + 3-(Methylthio)propionaldehyde | 403 | 403-405 |
| 099 | 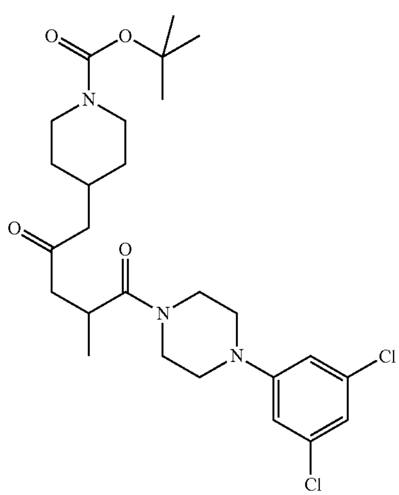 [SMILES: CC(CC(=O)CC1CCN(C(=O)OC(C)(C)C)CC1)C(=O)N1CCN(c2cc(Cl)cc(Cl)c2)CC1] | tert-butyl 4-[5-[4-(3,5-dichlorophenyl)piperazin-1-yl]-4-methyl-2,5-dioxo-pentyl]piperidine-1-carboxylate | D2b | Int 001 + 4-(2-Oxo-ethyl)-piperidine-1-carboxylic acid tert-butyl ester | 527 | 527-529 |

TABLE II-continued

Illustrative intermediate for the synthesis of illustrative compounds of the invention trans:

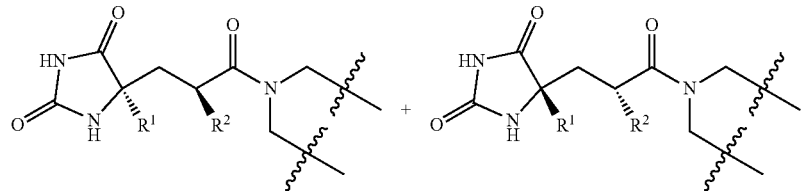

| Int | Structure | Name | Mtd | SM | MW | Ms'd |
|---|---|---|---|---|---|---|
| 100 | (trans) | tert-butyl N-[2-[4-[3-[4-(3,5-dichlorophenyl)piperazin-1-yl]-2-methyl-3-oxo-propyl]-2,5-dioxo-imidazolidin-4-yl]ethyl] carbamate | F | Int 150 | 542 | 542-544 |
| 101 | (trans) | 1-[4-(3-chloro-2-methylphenyl)piperazin-1-yl]-4-cyclopropyl-2-methyl-butane-1,4-dione | D2b | Int 009 + cyclopropane-carboxaldehyde | 349 | 349-351 |
| 102 | 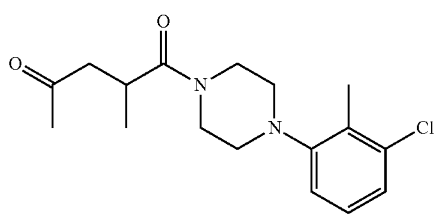 [SMILES: CC(=O)CC(C)C(=O)N1CCN(c2cccc(Cl)c2C)CC1] | 1-[4-(3-chloro-2-methylphenyl)piperazin-1-yl]-2-methyl-pentane-1,4-dione | D2b | Int 009 + Acetaldehyde | 323 | 323-325 |
| 103 | 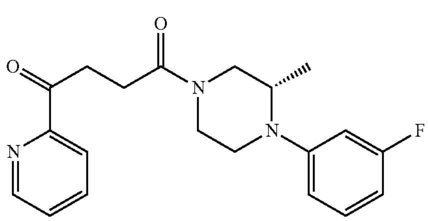 [SMILES: C[C@H]1CN(C(=O)CCC(=O)c2ccccn2)CCN1c1cccc(F)c1] | 1-[(3S)-4-(3-fluorophenyl)-3-methyl-piperazin-1-yl]-4-(2-pyridyl)butane-1,4-dione | H3 | 4-oxo-4-pyridin-2ylbutyric acid + Int 202 | 355 | 356 |
| 104 | 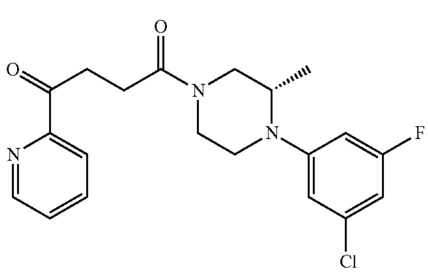 [SMILES: C[C@H]1CN(C(=O)CCC(=O)c2ccccn2)CCN1c1cc(F)cc(Cl)c1] | 1-[(3S)-4-(3-chloro-5-fluoro-phenyl)-3-methyl-piperazin-1-yl]-4-(2-pyridyl)butane-1,4-dione | H3 | 4-oxo-4-pyridin-2ylbutyric acid + Int 206 | 390 | 309-392 |

TABLE II-continued

Illustrative intermediate for the synthesis of illustrative compounds of the invention trans:

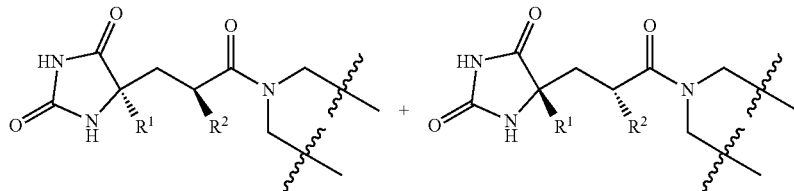

| Int | Structure | Name | Mtd | SM | MW | Ms'd |
|---|---|---|---|---|---|---|
| 105 | 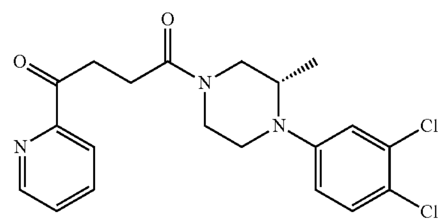 [SMILES: C[C@H]1CN(C(=O)CCC(=O)c2ccccn2)CCN1c1ccc(Cl)c(Cl)c1] | 1-[(3S)-4-(3,4-dichlorophenyl)-3-methyl-piperazin-1-yl]-4-(2-pyridyl)butane-1,4-dione | H3 | 4-oxo-4-pyridin-2ylbutyric acid + Int 201 | 406 | 406-408 |
| 106 | 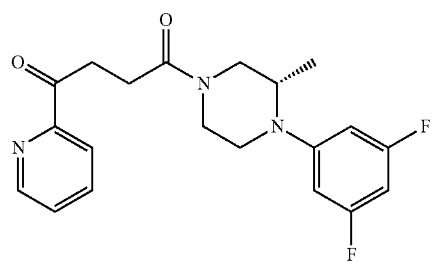 [SMILES: C[C@H]1CN(C(=O)CCC(=O)c2ccccn2)CCN1c1cc(F)cc(F)c1] | 1-[(3S)-4-(3,5-difluorophenyl)-3-methyl-piperazin-1-yl]-4-(2-pyridyl)bntane-1,4-dione | H3 | 4-oxo-4-pyridin-2ylbutyric acid + Int 207 | 373 | 374 |
| 107 | 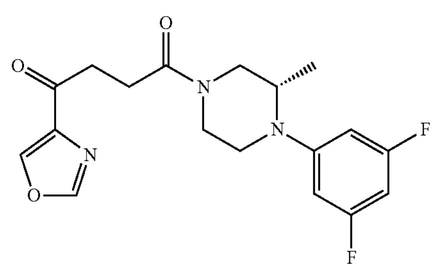 [SMILES: C[C@H]1CN(C(=O)CCC(=O)c2cocn2)CCN1c1cc(F)cc(F)c1] | 1-[(3S)-4-(3,5-difluorophenyl)-3-methyl-piperazin-1-yl]-4-oxazol-4-yl-butane-1,4-dione | D2a | Int 004 + Oxazole-4-carbaldehyde | 363 | 364 |
| 108 | 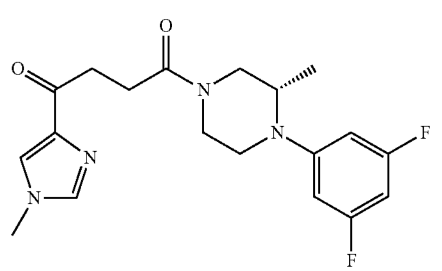 [SMILES: C[C@H]1CN(C(=O)CCC(=O)c2cn(C)cn2)CCN1c1cc(F)cc(F)c1] | 1-[(3S)-4-(3,5-difluorophenyl)-3-methyl-piperazin-1-yl]-4-(1-methylimidazol-4-yl)butane-1,4-dione | D2a | Int 004+ 1-Methyl-1H-imidazole-4-carbaldehyde | 376 | 377 |
| 109 | 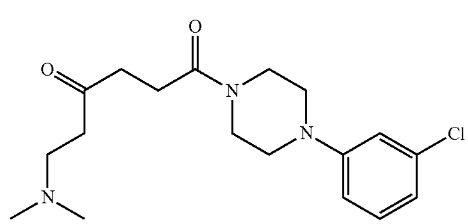 [SMILES: CN(C)CCC(=O)CCC(=O)N1CCN(c2cccc(Cl)c2)CC1] | 1-[4-(3-chlorophenyl)piperazin-1-yl]-6-(dimethylamino)hexane-1,4-dione | H1 | 6-dimethylamino-4-ketohexanoic acid hydrochloride + 1-(3-chlorophenyl)piperazine | 352 | 352-354 |

TABLE II-continued

Illustrative intermediate for the synthesis of illustrative compounds of the invention trans:

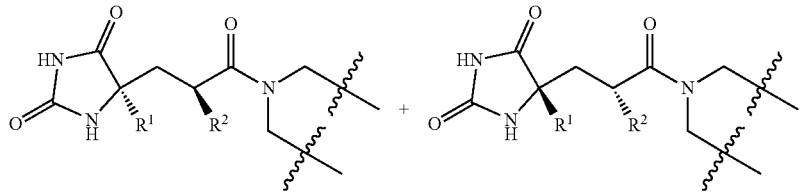

| Int | Structure | Name | Mtd | SM | MW | Ms'd |
|---|---|---|---|---|---|---|
| 110 | 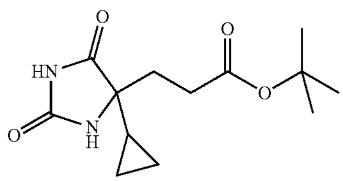 [SMILES: CC(C)(C)OC(=O)CCC1(C2CC2)NC(=O)NC1=O] | (S)-4-(3,5-Difluoro-phenyl)-3-methyl-piperazine-1-carboxylic acid tert-butyl ester | 2.18 | Int 290 | 268 | N.A. |
| 111 | 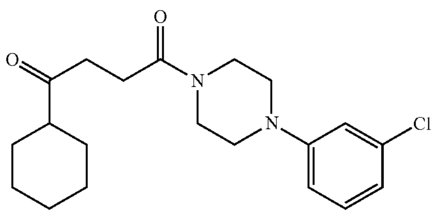 [SMILES: O=C(CCC(=O)N1CCN(c2cccc(Cl)c2)CC1)C1CCCCC1] | 1-[4-(3-chlorophenyl)piperazin-1-yl]-4-cyclohexyl-butane-1,4-dione | H3 | 4-cyclohexyl-4-oxobutyric acid + 1-(3-chlorophenyl)piperazine | 363 | 363-365 |
| 112 | 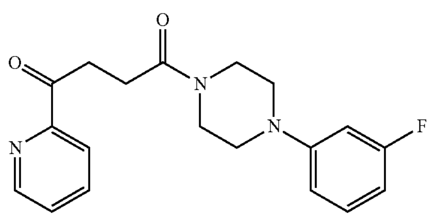 [SMILES: O=C(CCC(=O)N1CCN(c2cccc(F)c2)CC1)c1ccccn1] | 1-[4-(3-fluorophenyl)piperazin-1-yl]-4-(2-pyridyl)butane-1,4-dione | H1 | 4-oxo-4-pyridin-2ylbutyric acid + 1-(3-Fluorophenyl)piperazine | 341 | 342 |
| 113 | 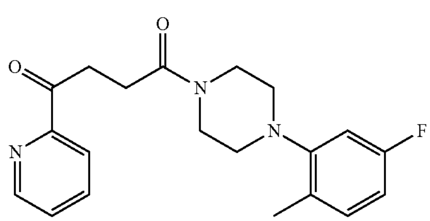 [SMILES: Cc1ccc(F)cc1N1CCN(C(=O)CCC(=O)c2ccccn2)CC1] | 1-[4-(5-fluoro-2-methyl-phenyl)piperazin-1-yl]-4-(2-pyridyl)butane-1,4-dione | H1 | 4-oxo-4-pyridin-2ylbutyric acid + Int 204 | 355 | 356 |
| 114 | 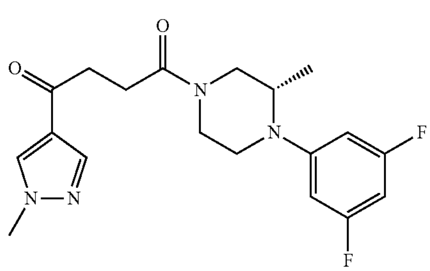 [SMILES: C[C@H]1CN(C(=O)CCC(=O)c2cnn(C)c2)CCN1c1cc(F)cc(F)c1] | 1-[(3S)-4-(3,5-difluorophenyl)-3-methyl-piperazin-1-yl]-4-(1-methylpyrazol-4-yl)butane-1,4-dione | D2a | Int 004+ 1-Methyl-1H-pyrazole-4-carbaldehyde | 376 | 377 |

TABLE II-continued

Illustrative intermediate for the synthesis of illustrative compounds of the invention trans:

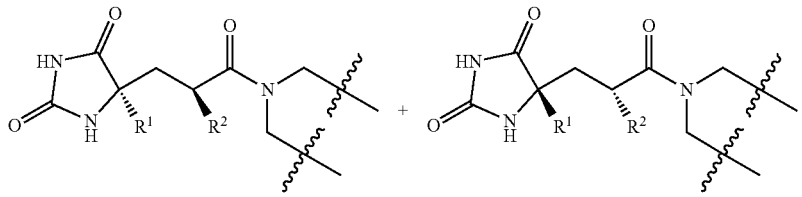

| Int | Structure | Name | Mtd | SM | MW | Ms'd |
|---|---|---|---|---|---|---|
| 115 | 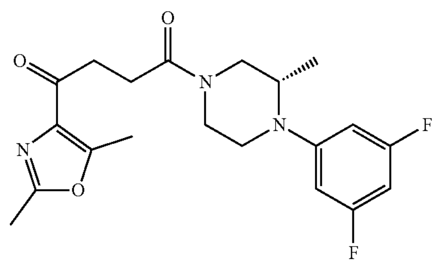 [SMILES: Cc1nc(C(=O)CCC(=O)N2CCN(c3cc(F)cc(F)c3)[C@@H](C)C2)c(C)o1] | 1-[(3S)-4-(3,5-difluorophenyl)-3-methyl-piperazin-1-yl]-4-(2,5-dimethyloxazol-4-yl)butane-1,4-dione | D2a | Int 004 + 2,5-Dimethyl-oxazole-4-carbaldehyde | 391 | 392 |
| 116 | 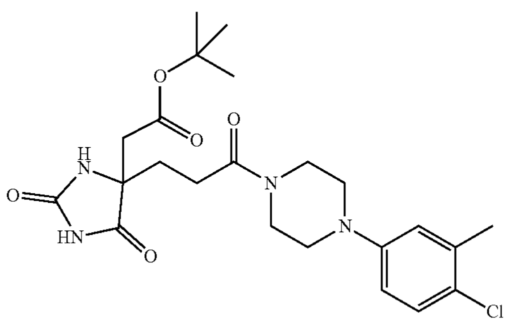 [SMILES: Cc1cc(N2CCN(C(=O)CCC3(CC(=O)OC(C)(C)C)NC(=O)NC3=O)CC2)ccc1Cl] | tert-butyl 2-[4-[3-[4-(4-chloro-3-methyl-phenyl)piperazin-1-yl]-3-oxo-propyl]-2,5-dioxo-imidazolidin-4-yl]acetate | F | Int 120 | 479 | 479 |
| 117 | 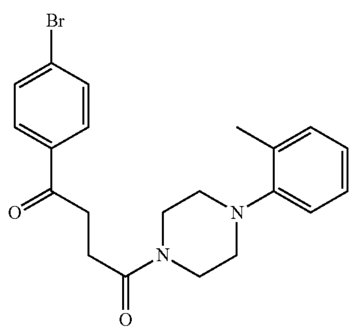 [SMILES: Cc1ccccc1N1CCN(C(=O)CCC(=O)c2ccc(Br)cc2)CC1] | 1-[4-bromophenyl)-4-[4-(o-tolyl)piperazin-1-yl]butane-1,4-dione | H1 | 4-(4-Bromo-phenyl)-4-oxo-butyric acid + 1-(o-tolyl)piperazine dihydrochloride | 415 | 415-417 |
| 118 | 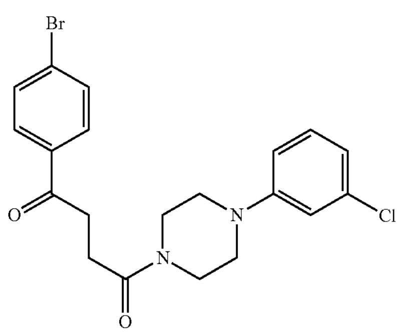 [SMILES: O=C(CCC(=O)N1CCN(c2cccc(Cl)c2)CC1)c1ccc(Br)cc1] | 1-[4-bromophenyl)-4-[4-(3-chlorophenyl)piperazin-1-yl]butane-1,4-dione | H1 | 4-(4-Bromo-phenyl)-4-oxo-butyric acid + 1-(3-chlorophenyl)piperazine | 436 | 435-437 |

TABLE II-continued

Illustrative intermediate for the synthesis of illustrative compounds of the invention trans:

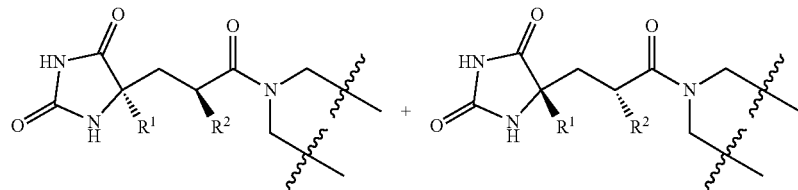

| Int | Structure | Name | Mtd | SM | MW | Ms'd |
|---|---|---|---|---|---|---|
| 119 | 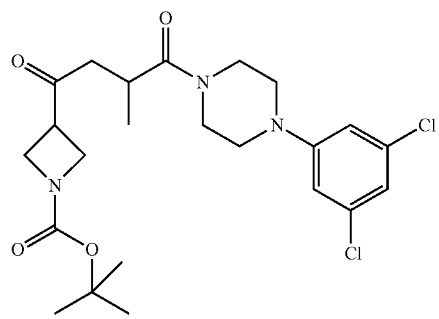 [SMILES: CC(CC(=O)C1CN(C(=O)OC(C)(C)C)C1)C(=O)N1CCN(c2cc(Cl)cc(Cl)c2)CC1] | tert-butyl 3-[4-[4-(3,5-dichlorophenyl)piperazin-1-yl]-3-methyl-4-oxo-butanoyl]azetidine-1-carboxylate | D2b | Int 001 + 3-Formyl-azetidine-1-carboxylic acid tert-butyl ester | 484 | 484-486 |
| 120 | 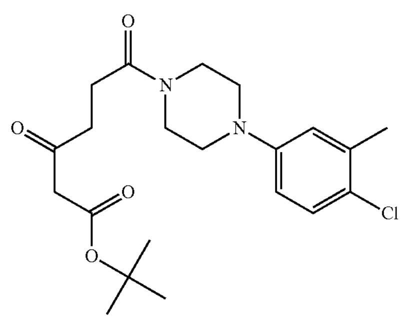 [SMILES: Cc1cc(N2CCN(C(=O)CCC(=O)CC(=O)OC(C)(C)C)CC2)ccc1Cl] | tert-butyl 6-[4-(4-chloro-3-methyl-phenyl)piperazin-1-yl]-3,6-dioxo-hexanoate | H2 | Int 129 + Int 284 | 409 | 409 |
| 121 | 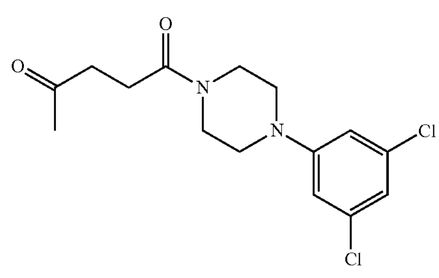 [SMILES: CC(=O)CCC(=O)N1CCN(c2cc(Cl)cc(Cl)c2)CC1] | 1-[4-(3,5-dichlorophenyl)piperazin-1-yl]pentane-1,4-dione | H2 | levulinic acid + 1-(3,5-dichlorophenyl)piperazine | 329 | 329-331 |
| 122 | 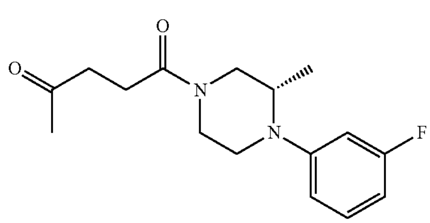 [SMILES: CC(=O)CCC(=O)N1CCN(c2cccc(F)c2)[C@@H](C)C1] | 1-[(3S)-4-(3-fluorophenyl)-3-methyl-piperazin-1-yl]pentane-1,4-dione | H2 | levulinic acid + Int 202 | 292 | 293 |

TABLE II-continued

Illustrative intermediate for the synthesis of illustrative compounds of the invention trans:

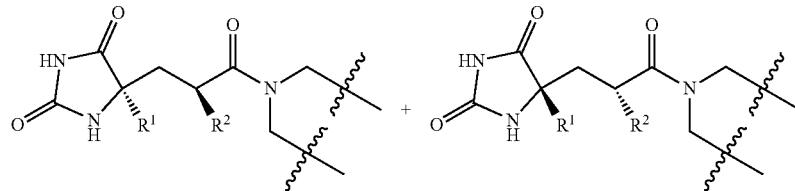

| Int | Structure | Name | Mtd | SM | MW | Ms'd |
|---|---|---|---|---|---|---|
| 123 | 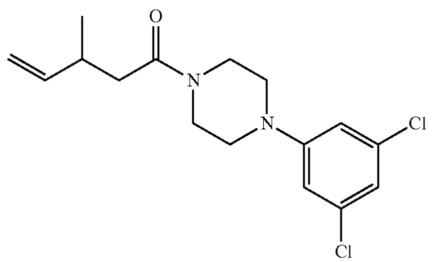 [SMILES: C=CC(C)CC(=O)N1CCN(c2cc(Cl)cc(Cl)c2)CC1] | 1-[4-(3,5-dichlorophenyl)piperazin-1-yl]-3-methyl-pent-4-en-1-one | H3 | 3-Methyl-4-pentenoic acid + 1-(3,5-dichlorophenyl)piperazine | 327 | N.A. |
| 124 | 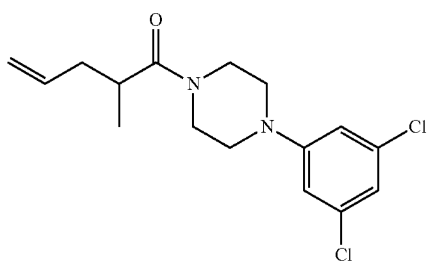 [SMILES: C=CCC(C)C(=O)N1CCN(c2cc(Cl)cc(Cl)c2)CC1] | 1-[4-(3,5-dichlorophenyl)piperazin-1-yl]-2-methyl-pent-4-en-1-one | H3 | 2-Methyl-4-pentenoic acid + 1-(3,5-dichlorophenyl)piperazine | 327 | 327-329 |
| 125 | 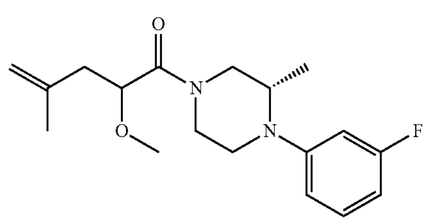 [SMILES: C=C(C)CC(OC)C(=O)N1CCN(c2cccc(F)c2)[C@@H](C)C1] | 1-[(3S)-4-(3-fluorophenyl)-3-methyl-piperazin-1-yl]-2-methoxy-4-methyl-pent-4-en-1-one | H3 | Int 154 + Int 202 | 320 | 321 |
| 126 | 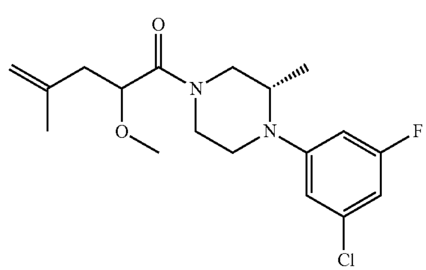 [SMILES: C=C(C)CC(OC)C(=O)N1CCN(c2cc(F)cc(Cl)c2)[C@@H](C)C1] | 1-[(3S)-4-(3-chloro-5-fluoro-phenyl)-3-methyl-piperazin-1-yl]-2-methoxy-4-methyl-pent-4-en-1-one | H3 | Int 154 + Int 206 | 355 | 355-357 |
| 127 | 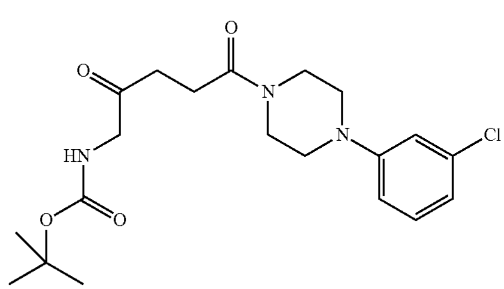 [SMILES: CC(C)(C)OC(=O)NCC(=O)CCC(=O)N1CCN(c2cccc(Cl)c2)CC1] | tert-butyl N-[5-[4-(3-chlorophenyl)piperazin-1-yl]-2,5-dioxo-pentyl]carbamate | H2 | Int 173 + 1-(3-chlorophenyl)piperazine | 410 | N.A. |

TABLE II-continued

Illustrative intermediate for the synthesis of illustrative compounds of the invention trans:

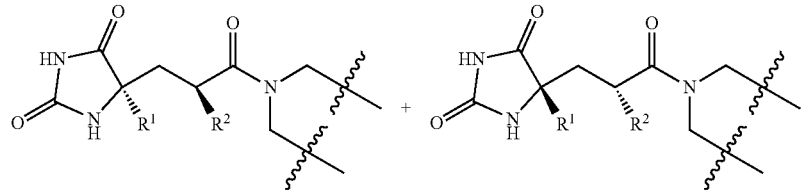

| Int | Structure | Name | Mtd | SM | MW | Ms'd |
|---|---|---|---|---|---|---|
| 128 | 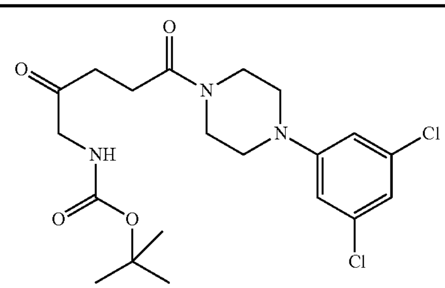 | tert-butyl N-[5-[4-(3,5-dichlorophenyl)piperazin-1-yl]-2,5-dioxo-pentyl]carbamate | H2 | Int 173 + 1-(3,5-dichlorophenyl)piperazine | 444 | N.A. |
| 129 | 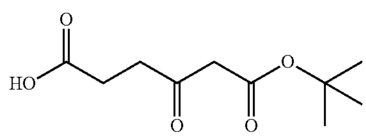 | 6-tert-butoxy-4,6-dioxo-hexanoic acid | 2.16 | Succinic anhydride + tertbutyl acetate | 216 | N.A. |
| 130 | 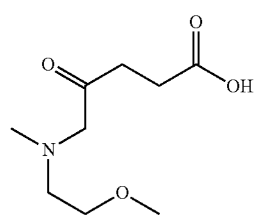 | 5-2-methoxyethyl(methyl)amino]-4-oxo-pentanoic acid | D6 | levulinic acid + (2-methoxy-ethyl)-methyl-amine | 203 | N.A. |
| 131 | 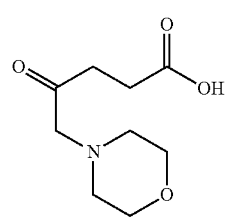 [SMILES: O=C(O)CCC(=O)CN1CCOCC1] | 5-morpholino-4-oxo-pentanoic acid | D6 | levulinic acid + morpholine | 201 | N.A. |
| 132 | 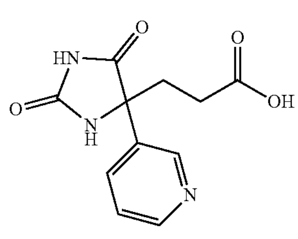 [SMILES: O=C(O)CCC1(c2cccnc2)NC(=O)NC1=O] | 3-[2,5-dioxo-4-(3-pyridyl)imidazolidin-4-yl]propanoic acid | G | Int 133 | 249 | N.A. |
| 133 | 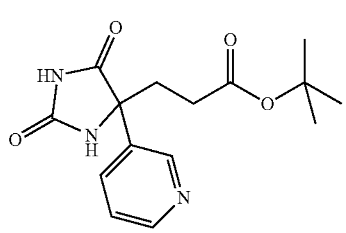 [SMILES: CC(C)(C)OC(=O)CCC1(c2cccnc2)NC(=O)NC1=O] | tert-butyl 3-[2,5-dioxo-4-(3-pyridyl)imidazolidin-4-yl]propanoate | F | Int 134 | 305 | 306 |

TABLE II-continued

Illustrative intermediate for the synthesis of illustrative compounds of the invention trans:

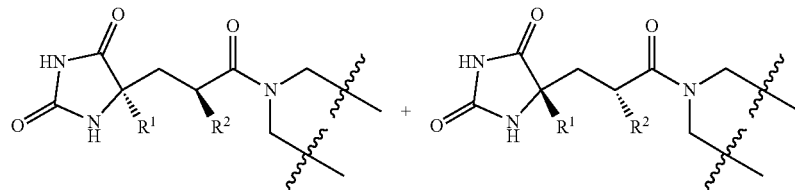

| Int | Structure | Name | Mtd | SM | MW | Ms'd |
|---|---|---|---|---|---|---|
| 134 | 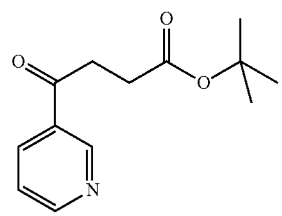 [SMILES: CC(C)(C)OC(=O)CCC(=O)c1cccnc1] | tert-butyl 4-oxo-4-(3-pyridyl)butanoate | C4 | Pyridine-3-carbaldehyde + Acrylic acid tert-butyl ester | 235 | 236 |
| 135 | trans | 2-(benzyloxymethyl)-3-(4-methyl-2,5-dioxo-imidazolidin-4-yl)propanoic acid | G | Int 136 | 306 | 307 |
| 136 | trans | tert-butyl 2-(benzyloxymethyl)-3-(4-methyl-2,5-dioxo-imidazolidin-4-yl)propanoate | F | Int 137 | 362 | N.A. |
| 137 | 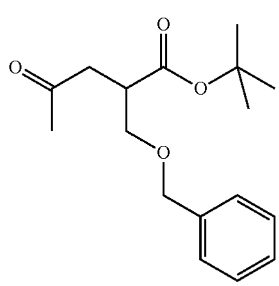 [SMILES: CC(=O)CC(COCc1ccccc1)C(=O)OC(C)(C)C] | tert-butyl 2-(benzyloxymethyl)-4-oxo-pentanoate | 2.17 | Int 138 | 292 | 315 (M + Na) |

TABLE II-continued

Illustrative intermediate for the synthesis of illustrative compounds of the invention trans:

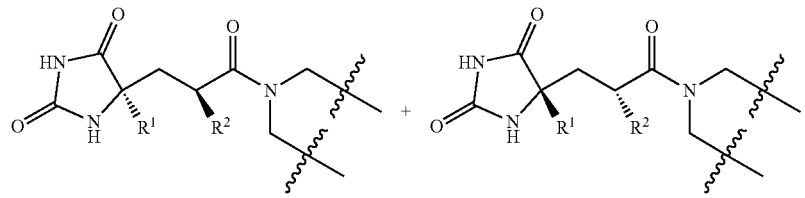

| Int | Structure | Name | Mtd | SM | MW | Ms'd |
|---|---|---|---|---|---|---|
| 138 | | 2-(benzyloxymethyl)-4-oxo-pentanoic acid | D5 | benzyloxy-acetaldehyde | 236 | N.A. |
| 139 | | 3-(2,5-dioxo-4-pyrimidin-2-yl-imidazolidin-4-yl)propanoic acid | G + $H_2O$ | Int 140 | 250 | 251 |
| 140 | | tert-butyl 3-(2,5-dioxo-4-pyrimidin-2-yl-imidazolidin-4-yl)propanoate | F | Int 141 | 306 | 307 |
| 141 | | tert-butyl 4-oxo-4-pyrimidin-2-yl-butanoate | C2 | 1-Pyrimidin-2-yl-ethanone + Bromo-acetic acid tert-butyl ester | 236 | 237 |
| 142 | | 3-(2,5-dioxo-4-pyrazin-2-yl-imidazolidin-4-yl)propanoic acid | G | Int 143 | 250 | 249 (M − H) |

TABLE II-continued

Illustrative intermediate for the synthesis of illustrative compounds of the invention trans:

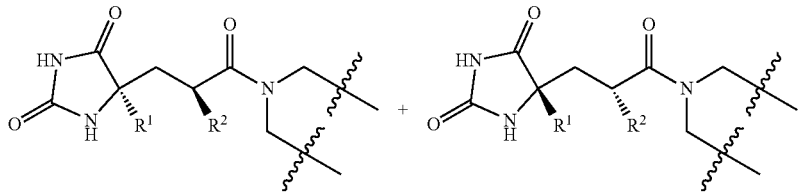

| Int | Structure | Name | Mtd | SM | MW | Ms'd |
|---|---|---|---|---|---|---|
| 143 | 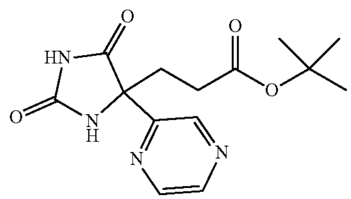 [SMILES: CC(C)(C)OC(=O)CCC1(c2cnccn2)NC(=O)NC1=O] | tert-butyl 3-(2,5-dioxo-4-pyrazin-2-yl-imidazolidin-4-yl)propanoate | F | Int 144 | 306 | 307 |
| 144 | 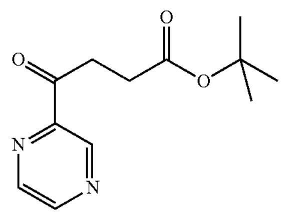 [SMILES: CC(C)(C)OC(=O)CCC(=O)c1cnccn1] | tert-butyl 4-oxo-4-pyrazin-2-yl-butanoate | C2 | 1-Pyrazin-2-yl-ethanone + Bromo-acetic acid tert-butyl ester | 236 | 237 |
| 145 | 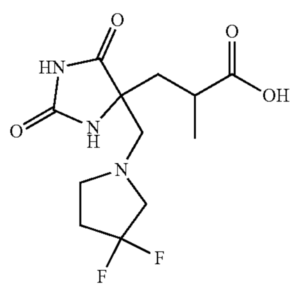 [SMILES: CC(CC1(CN2CCC(F)(F)C2)NC(=O)NC1=O)C(=O)O] | 3-[4-[(3,3-difluoropyrrolidin-1-yl)methyl]-2,5-dioxo-imidazolidin-4-yl]-2-methyl-propanoic acid | G | Int 146 | 305 | N.A. |
| 146 | 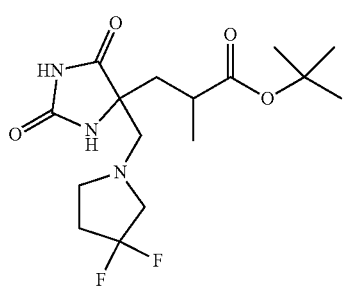 [SMILES: CC(CC1(CN2CCC(F)(F)C2)NC(=O)NC1=O)C(=O)OC(C)(C)C] | tert-butyl 3-[4-[(3,3-difluoropyrrolidin-1-yl)methyl]-2,5-dioxo-imidazolidin-4-yl]-2-methyl-propanoate | F | Int 147 | 361 | N.A. |
| 147 | 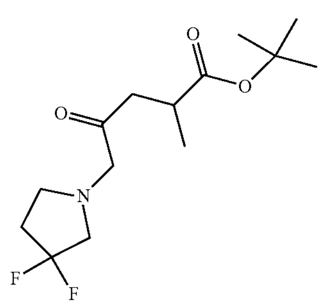 [SMILES: CC(CC(=O)CN1CCC(F)(F)C1)C(=O)OC(C)(C)C] | tert-butyl 5-(3,3-difluoropyrrolidin-1-yl)-2-methyl-4-oxo-pentanoate | C5 | Int 148 + 2,2-Difluoro-pyrrolidine hydrochloride | 291 | 292 |

TABLE II-continued

Illustrative intermediate for the synthesis of illustrative compounds of the invention trans:

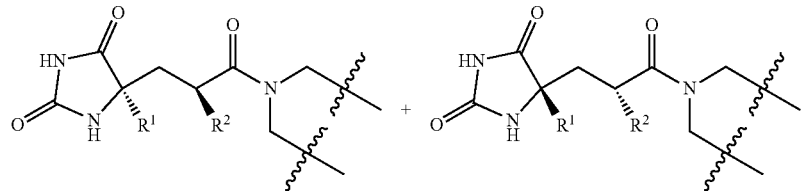

| Int | Structure | Name | Mtd | SM | MW | Ms'd |
|---|---|---|---|---|---|---|
| 148 | 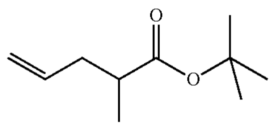 | tert-butyl 2-methylpent-4-enoate | 03 | 2-Methyl-pent-4-enoic acid | 170 | N.A. |
| 149 | 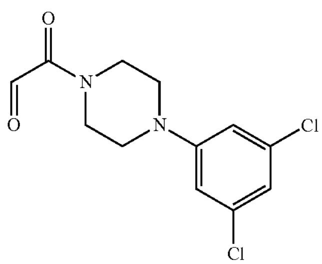 [SMILES: O=CC(=O)N1CCN(c2cc(Cl)cc(Cl)c2)CC1] | 2-[4-(3,5-dichlorophenyl)piperazin-1-yl]-2-oxo-acetaldehyde | D4 | Int 081 | 287 | N.A. |
| 150 | 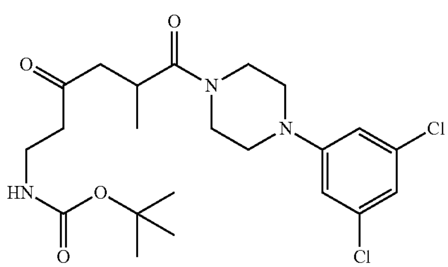 [SMILES: CC(CC(=O)CCNC(=O)OC(C)(C)C)C(=O)N1CCN(c2cc(Cl)cc(Cl)c2)CC1] | tert-butyl N-[6-[4-(3,5-dichlorophenyl)piperazin-1-yl]-5-methyl-3,6-dioxo-hexyl]carbamate | 2.19 | Int 021 | 472 | 472-474-476 |
| 151 | 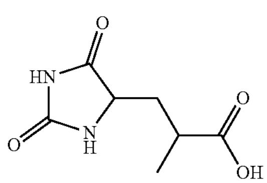 | 3-(2,5-dioxoimidazolidin-4-yl)-2-methyl-propanoic acid | G | Int 152 | 186 | N.A. |
| 152 | 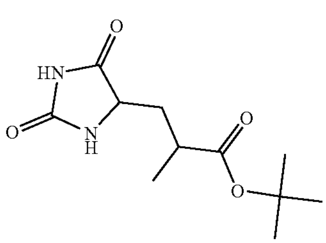 [SMILES: CC(CC1NC(=O)NC1=O)C(=O)OC(C)(C)C] | tert-butyl 3-(2,5-dioxoimidazolidin-4-yl)-2-methyl-propanoate | F | Int 153 | 242 | N.A. |
| 153 | 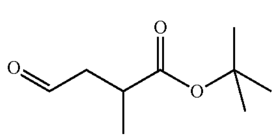 | tert-butyl 2-methyl-4-oxo-butanoate | 2.20 | Int 148 | 172 | N.A. |

TABLE II-continued

Illustrative intermediate for the synthesis of illustrative compounds of the invention trans:

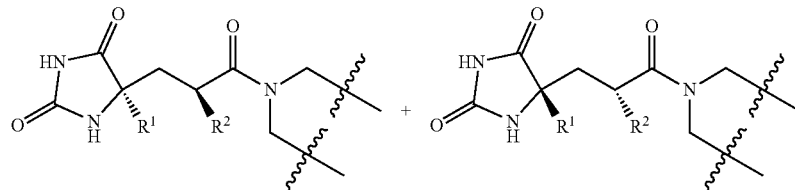

| Int | Structure | Name | Mtd | SM | MW | Ms'd |
|---|---|---|---|---|---|---|
| 154 | 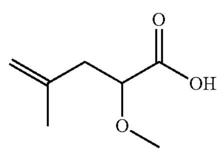 | 2-methoxy-4-methyl-pent-4-enoic acid | 2.21 | Methoxy-acetic acid + 2-Methyl-prop-2-en-1-ol | 144 | 143 (M − H) |
| 155 | 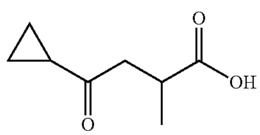 | 4-cyclopropyl-2-methyl-4-oxo-butanoic acid | 2.23 | cyclopropane-carbonyl chloride + 2,2-Dimethyl-[1,3]dioxane-4,6-dione | 156 | 155 (M − H) |
| 156 | 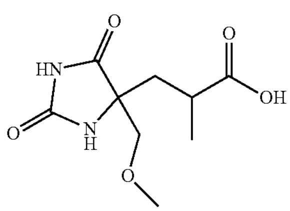 [SMILES: COCC1(CC(C)C(=O)O)NC(=O)NC1=O] | 3-[4-(methoxymethyl)-2,5-dioxo-imidazolidin-4-yl]-2-methyl-propanoic acid | G | Int 157 | 230 | 231 |
| 157 | 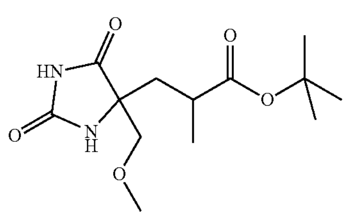 [SMILES: COCC1(CC(C)C(=O)OC(C)(C)C)NC(=O)NC1=O] | tert-butyl 3-[4-(methoxymethyl)-2,5-dioxo-imidazolidin-4-yl]-2-methyl-propanoate | F | Int 158 | 286 | 309 (M + Na) |
| 158 | 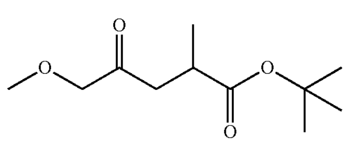 | tert-butyl 5-methoxy-2-methyl-4-oxo-pentanoate | C1 | Methoxy-acetic acid + 2,2-Dimethyl-[1,3]dioxane-4,6-dione | 216 | 239 (M+ Na) |
| 159 | 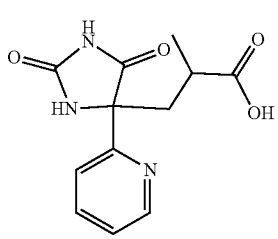 [SMILES: CC(CC1(c2ccccn2)NC(=O)NC1=O)C(=O)O] | 3-[2,5-dioxo-4-(2-pyridyl)imidazolidin-4-yl]-2-methyl-propanoic acid | G | Int 160 | 263 | 264 |

TABLE II-continued

Illustrative intermediate for the synthesis of illustrative compounds of the invention trans:
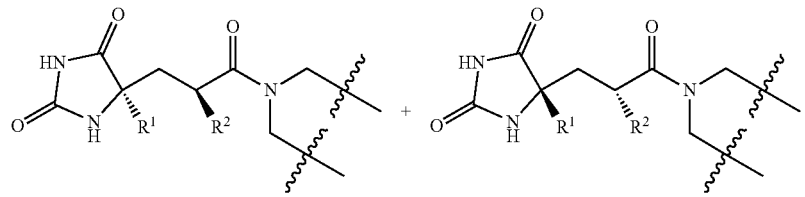

| Int | Structure | Name | Mtd | SM | MW | Ms'd |
|---|---|---|---|---|---|---|
| 160 | (structure, trans) | tert-butyl 3-[2,5-dioxo-4-(2-pyridyl)imidazolidin-4-yl]-2-methyl-propanoate | F | Int 161 | 319 | 320 |
| 161 | (structure) | tert-butyl 2-methyl-4-oxo-4-(2-pyridyl)butanoate | C1 step ii + step iii | 3-Oxo-3-pyridin-2-yl-propionic acid benzyl ester + Bromo-acetic acid tert-butyl ester | 249 | 272 (M + Na) |
| 162 | (structure) | 3-(4-cyclopropyl-2,5-dioxo-imidazolidin-4-yl)propanoic acid | 2.22 | Int 110 | 212 | 211 (M − H) |
| 163 | (structure) | 3-[(4S)-4-cyclopropyl-2,5-dioxo-imidazolidin-4-yl]propanoic acid | 2.22 | Int 162 | 212 | N.A. |
| 164 | (structure, trans) | 3-(4-cyclopropyl-2,5-dioxo-imidazolidin-4-yl)-2-methyl-propanoic acid | C3 + F + G | Int 155 | 226 | 225 (M − H) |
| 165 | (structure, trans) | 2-methyl-3-(4-methyl-2,5-dioxo-imidazolidin-4-yl)propanoic acid | G | Int 289 | 200 | 201 |

TABLE II-continued

Illustrative intermediate for the synthesis of illustrative compounds of the invention trans:

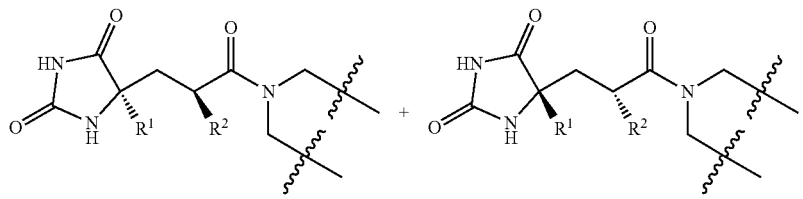

| Int | Structure | Name | Mtd | SM | MW | Ms'd |
|---|---|---|---|---|---|---|
| 166 | 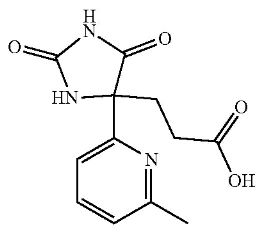 [SMILES: Cc1cccc(C2(CCC(=O)O)NC(=O)NC2=O)n1] | 3-[4-(6-methyl-2-pyridyl)-2,5-dioxo-imidazolidin-4-yl]propanoic acid | G | Int 167 | 263 | 264 |
| 167 | 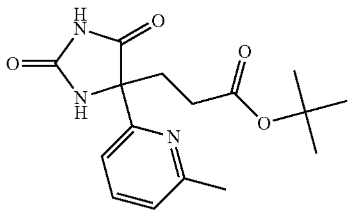 [SMILES: Cc1cccc(C2(CCC(=O)OC(C)(C)C)NC(=O)NC2=O)n1] | tert-butyl 3-[4-(6-methyl-2-pyridyl)-2,5-dioxo-imidazolidin-4-yl]propanoate | F | Int 168 | 319 | 320 |
| 168 | 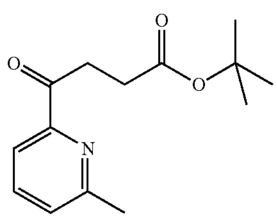 [SMILES: Cc1cccc(C(=O)CCC(=O)OC(C)(C)C)n1] | tert-butyl 4-(6-methyl-2-pyridyl)-4-oxo-butanoate | C4 | 6-Methyl-pyridine-2-carbaldehyde + Acrylic acid tert-butyl ester | 249 | 250 |
| 169 | 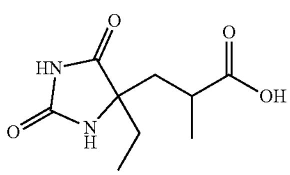 | 3-(4-ethyl-2,5-dioxo-imidazolidin-4-yl)-2-methyl-propanoic acid | G | Int 170 | 214 | 215 |
| 170 | 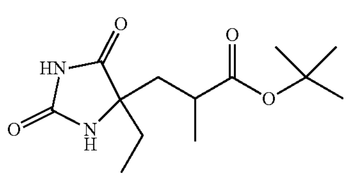 [SMILES: CCC1(CC(C)C(=O)OC(C)(C)C)NC(=O)NC1=O] | tert-butyl 3-(4-ethyl-2,5-dioxo-imidazolidin-4-yl)-2-methyl-propanoate | F | Int 171 | 270 | 271 |
| 171 | 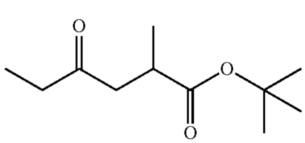 | tert-butyl 2-methyl-4-oxo-hexanoate | C3 | 2-Methyl-4-oxo-hexanoic acid [ref J. Org. Chem. 2003, 68, 7983-7989] | 200 | N.A. |

TABLE II-continued

Illustrative intermediate for the synthesis of illustrative compounds of the invention trans:

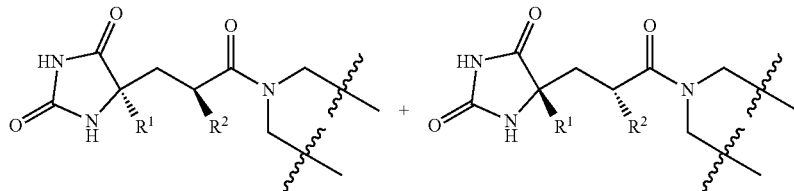

| Int | Structure | Name | Mtd | SM | MW | Ms'd |
|---|---|---|---|---|---|---|
| 172 | 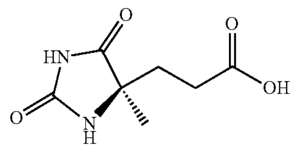 | 3-[(4R)-4-methyl-2,5-dioxo-imidazolidin-4-yl]propanoic acid | 2.24 | 3-(4-Methyl-2,5-dioxo-imidazolidin-4-yl)propionic acid | 186 | 373 (2M + H) |
| 173 | 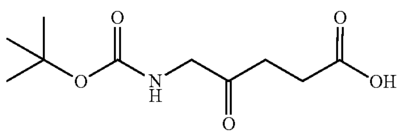 [SMILES: CC(C)(C)OC(=O)NCC(=O)CCC(=O)O] | 5-(tert-butoxycarbonyl-amino)-4-oxo-pentanoic acid | 2.25 | 5-Amino-4-oxo-pentanoic acid | 231 | N.A. |
| 174 | 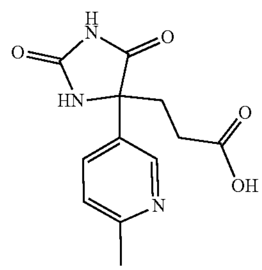 [SMILES: Cc1ccc(C2(CCC(=O)O)NC(=O)NC2=O)cn1] | 3-[4-(6-methyl-3-pyridyl)-2,5-dioxo-imidazolidin-4-yl]propanoic acid | G | Int 175 | 263 | 264 |
| 175 | 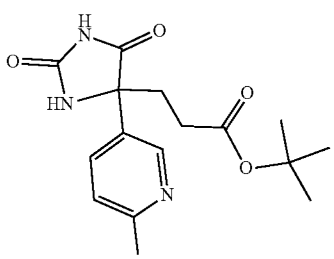 [SMILES: Cc1ccc(C2(CCC(=O)OC(C)(C)C)NC(=O)NC2=O)cn1] | tert-butyl 3-[4-(6-methyl-3-pyridyl)-2,5-dioxo-imidazolidin-4-yl]propanoate | F | Int 176 | 319 | 320 |
| 176 | 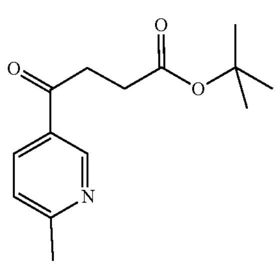 [SMILES: Cc1ccc(C(=O)CCC(=O)OC(C)(C)C)cn1] | tert-butyl 4-(6-methyl-3-pyridyl)-4-oxo-butanoate | D2c | 6-Methyl-pyridine-3-carbaldehyde + Acrylic acid tert-butyl ester | 249 | 250 |
| 177 | 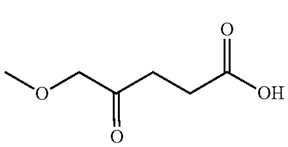 | 5-methoxy-4-oxo-pentanoic acid | 2.26 | pent-4-ynoic acid | 146 | N.A. |

TABLE II-continued

Illustrative intermediate for the synthesis of illustrative compounds of the invention trans:

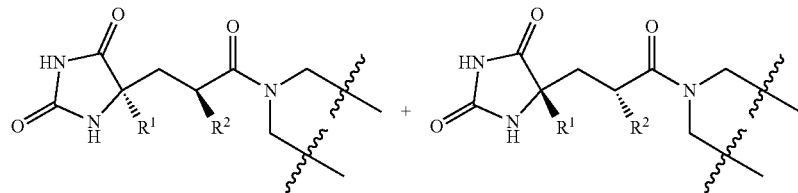

| Int | Structure | Name | Mtd | SM | MW | Ms'd |
|---|---|---|---|---|---|---|
| 178 | 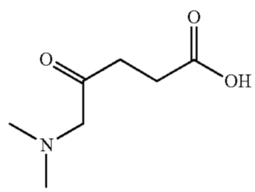 | 5-(dimethylamino)-4-oxo-pentanoic acid | D6 | levulinic acid + dimethylamine | 159 | N.A. |
| 179 | 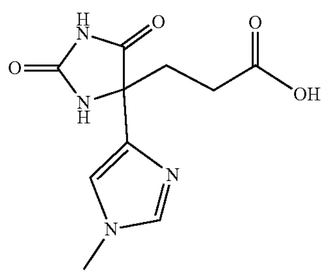 [SMILES: Cn1cnc(C2(CCC(=O)O)NC(=O)NC2=O)c1] | 3-[4-(1-methylimidazol-4-yl)-2,5-dioxo-imidazolidin-4-yl]propanoic acid | G | Int 180 | 252 | 253 |
| 180 | 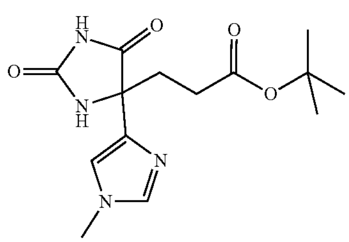 [SMILES: Cn1cnc(C2(CCC(=O)OC(C)(C)C)NC(=O)NC2=O)c1] | tert-butyl 3-[4-(1-methylimidazol-4-yl)-2,5-dioxo-imidazolidin-4-yl]propanoate | F | Int 181 | 308 | 309 |
| 181 | 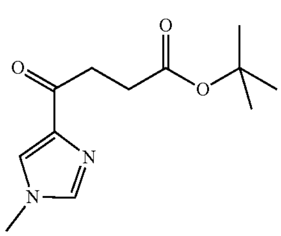 [SMILES: Cn1cnc(C(=O)CCC(=O)OC(C)(C)C)c1] | tert-butyl 4-(1-methylimidazol-4-yl)-4-oxo-butanoate | C4 | 1-Methyl-1H-imidazole-4-carbaldehyde + Acrylic acid tert-butyl ester | 238 | |
| 182 | 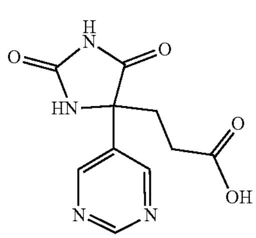 [SMILES: O=C(O)CCC1(c2cncnc2)NC(=O)NC1=O] | 3-(2,5-dioxo-4-pyrimidin-5-yl-imidazolidin-4-yl)propanoic acid | G | Int 183 | 250 | N.A. |

TABLE II-continued

Illustrative intermediate for the synthesis of illustrative compounds of the invention trans:

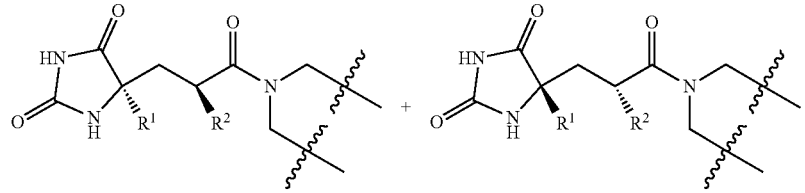

| Int | Structure | Name | Mtd | SM | MW | Ms'd |
|---|---|---|---|---|---|---|
| 183 | 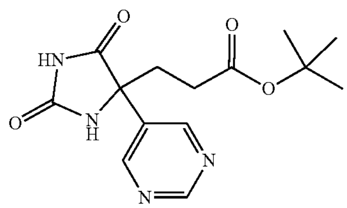 [SMILES: CC(C)(C)OC(=O)CCC1(c2cncnc2)NC(=O)NC1=O] | tert-butyl 3-(2,5-dioxo-4-pyrimidin-5-yl-imidazolidin-4-yl)propanoate | F | Int 184 | 306 | 307 |
| 184 | 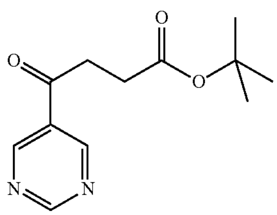 [SMILES: CC(C)(C)OC(=O)CCC(=O)c1cncnc1] | tert-butyl 4-oxo-4-pyrimidin-5-yl-butanoate | C2 | 1-Pyrimidin-5-yl-ethanone + Bromo-acetic acid tert-butyl ester | 236 | 237 |
| 185 | 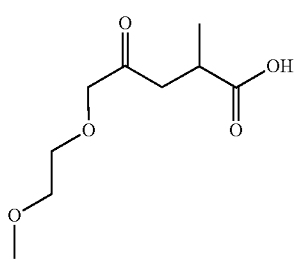 | 5-(2-methoxyethoxy)-2-methyl-4-oxo-pentanoic acid | 2.27 | (2-methoxy-ethoxy)-acetic acid | 204 | 203 (M − H) |
| 186 | 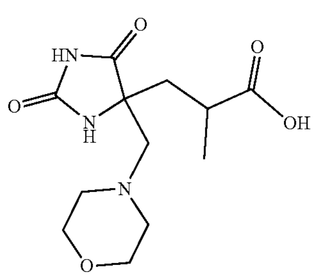 [SMILES: CC(CC1(CN2CCOCC2)NC(=O)NC1=O)C(=O)O] | 2-methyl-3-[4-(morpholinomethyl)-2,5-dioxo-imidazolidin-4-yl]propanoic acid | G | Int 187 | 285 | N.A. |
| 187 | 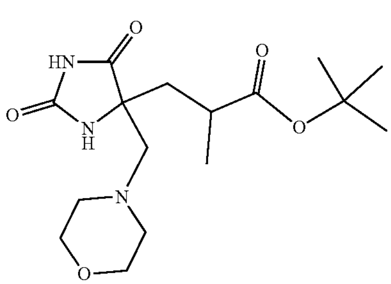 [SMILES: CC(CC1(CN2CCOCC2)NC(=O)NC1=O)C(=O)OC(C)(C)C] | tert-butyl 2-methyl-3-[4-(morpholinomethyl)-2,5-dioxo-imidazolidin-4-yl]propanoate | F | Int 188 | 341 | 342 |

TABLE II-continued

Illustrative intermediate for the synthesis of illustrative compounds of the invention trans:

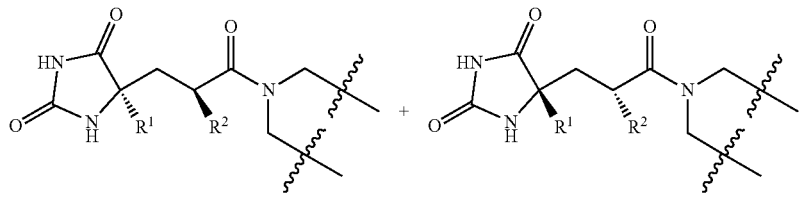

| Int | Structure | Name | Mtd | SM | MW | Ms'd |
|---|---|---|---|---|---|---|
| 188 | 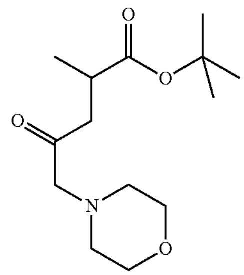 [SMILES: CC(CC(=O)CN1CCOCC1)C(=O)OC(C)(C)C] | tert-butyl 2-methyl-5-morpholino-4-oxo-pentanoate | 05 | Int 148 + morpholine | 271 | N.A. |
| 189 | 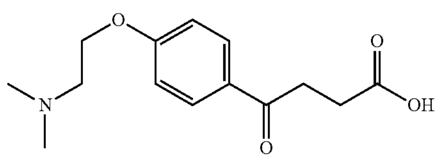 [SMILES: CN(C)CCOc1ccc(C(=O)CCC(=O)O)cc1] | 4-[4-(2-dimethylamino-ethyloxy)phenyl]-4-oxo-butanoic acid | 2.28 | 4-(4-fluoro-phenyl)-4-oxo-butyric acid + 2-dimethylamino-ethanol | 265 | 266 |
| 190 | 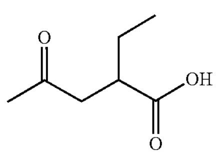 | 2-ethyl-4-oxo-pentanoic acid | D5 | propionaldehyde | 144 | N.A. |
| 191 | 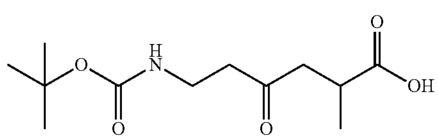 [SMILES: CC(CC(=O)CCNC(=O)OC(C)(C)C)C(=O)O] | 6-(tert-butoxycarbonyl-amino)-2-methyl-4-oxo-hexanoic acid | 2.29 | 3-tert-butoxycarbonyl-amino-propionic acid + Meldrum's acid | 259 | 260 |
| 192 | 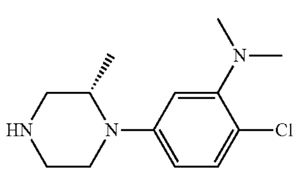 [SMILES: C[C@H]1CNCCN1c1ccc(Cl)c(N(C)C)c1] | 2-chloro-N,N-dimethyl-5-[(2S)-2-methylpiperazin-1-yl]aniline | A2a + A5a | (S)-3-Methyl-piperazine-1-carboxylic acid tert-butyl ester + Int 285 | 254 | 254 |
| 193 | 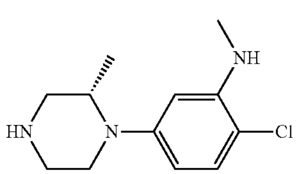 [SMILES: CNc1cc(N2CCNC[C@@H]2C)ccc1Cl] | 2-chloro-N-methyl-5-[(2S)-2-methylpiperazin-1-yl]aniline | A2a + A5e | (S)-3-Methyl-piperazine-1-carboxylic acid tert-butyl ester + Int 286 | 240 | 240 |
| 194 | 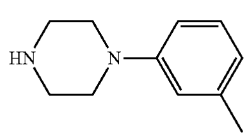 | 1-(m-tolyl)piperazine | A2a + A5a | Piperazine-1-carboxylic acid tert-butyl ester + 3-bromo toluene | 176 | 177 |

TABLE II-continued

Illustrative intermediate for the synthesis of illustrative compounds of the invention

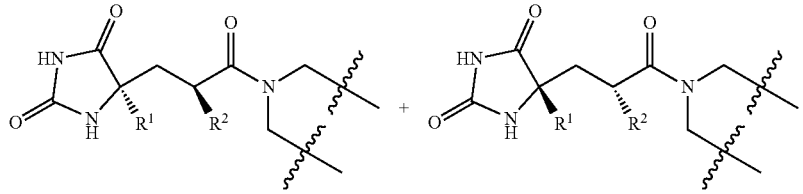

| Int | Structure | Name | Mtd | SM | MW | Ms'd |
|---|---|---|---|---|---|---|
| 195 | 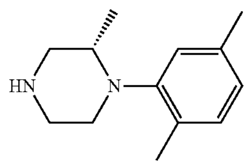 | (2S)-1-(2,5-dimethylphenyl)-2-methyl-piperazine | A2a + A5a | (S)-3-Methyl-piperazine-1-carboxylic acid tert-butyl ester + 2-bromo-1,4-dimethyl benzene | 204 | 205 |
| 196 | 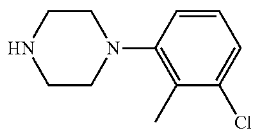 | 1-(3-chloro-2-methyl-phenyl)piperazine | A7 | Piperazine + 1-Bromo-3-chloro-2-methyl-benzene | 211 | 211 |
| 197 | 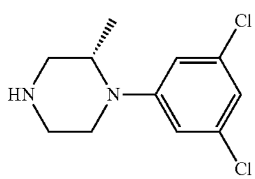 | (2S)-1-(3,5-dichlorophenyl)-2-methyl-piperazine | A2a + A5a | (S)-3-Methyl-piperazine-1-carboxylic acid tert-butyl ester + 1-Bromo-3,5-dichloro-benzene | 245 | 245–247 |
| 198 | 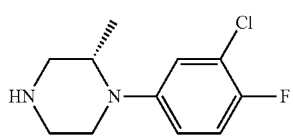 | (2S)-1-(3-chloro-4-fluoro-phenyl)-2-methyl-piperazine | A2a + A5a | (S)-3-Methyl-piperazine-1-carboxylic acid tert-butyl ester + 4-Bromo-2-chloro-1-fluoro-benzene | 229 | 229 |
| 199 | 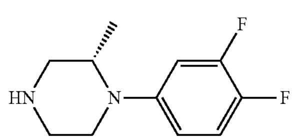 | (2S)-1-(3,4-difluorophenyl)-2-methyl-piperazine | A2a + A5b | (S)-3-Methyl-piperazine-1-carboxylic acid tert-butyl ester + 4-Bromo-1,2-difluoro-benzene | 212 | 214 |
| 200 | 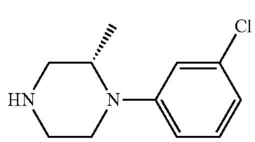 | (2S)-1-(3-chlorophenyl)-2-methyl-piperazine | A2a + A5a | (S)-3-Methyl-piperazine-1-carboxylic acid tert-butyl ester + 1-Bromo-3-chloro-benzene | 211 | 211 |
| 201 | 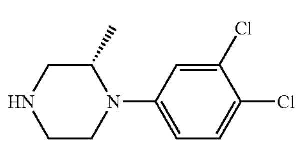 | (2S)-1-(3,4-dichlorophenyl)-2-methyl-piperazine | A2a + A5a | (S)-3-Methyl-piperazine-1-carboxylic acid tert-butyl ester + 1,2-Dichloro-4-iodo-benzene | 245 | 245 |
| 202 | 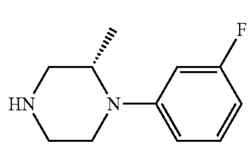 | (2S)-1-(3-fluorophenyl)-2-methyl-piperazine | A2a + A5b | (S)-3-Methyl-piperazine-1-carboxylic acid tert-butyl ester + 1-Bromo-3-fluoro-benzene | 194 | 195 |

TABLE II-continued

Illustrative intermediate for the synthesis of illustrative compounds of the invention trans:

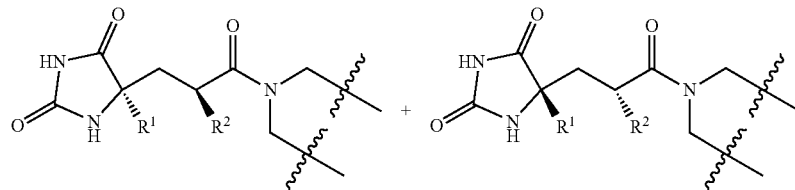

| Int | Structure | Name | Mtd | SM | MW | Ms'd |
|-----|-----------|------|-----|-----|-----|------|
| 203 | 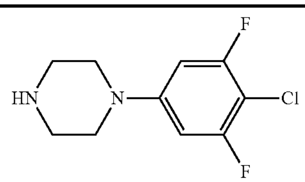 | 1-(4-chloro-3,5-difluoro-phenyl)piperazine | A7 | Piperazine + 5-Bromo-2-chloro-1,3-difluoro-benzene | 233 | 233 |
| 204 | 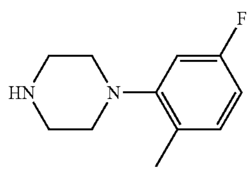 | 1-(5-fluoro-2-methyl-phenyl)piperazine | A7 | Piperazine + 4-Fluoro-2-bromo-1-methyl-benzene | 194 | 195 |
| 205 | 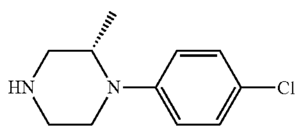 | (2S)-1-(4-chlorophenyl)-2-methyl-piperazine | A2a + A5a | (S)-3-Methyl-piperazine-1-carboxylic acid tert-butyl ester + 1-Bromo-4-chloro-benzene | 211 | 211 |
| 206 | 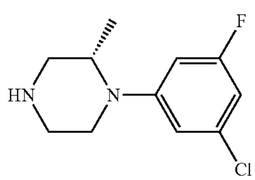 | (2S)-1-(3-chloro-5-fluoro-phenyl)-2-methyl-piperazine | A2a + A5a | (S)-3-Methyl-piperazine-1-carboxylic acid tert-butyl ester + 1-Bromo-3-chloro-5-fluoro-benzene | 229 | 229-231 |
| 207 | 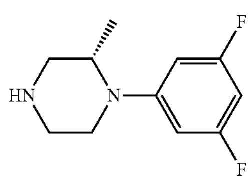 | (2S)-1-(3,5-difluorophenyl)-2-methyl-piperazine | A2a + A5a | (S)-3-Methyl-piperazine-1-carboxylic acid tert-butyl ester + 1-Bromo-3,5-difluoro-benzene | 212 | 213 |
| 208 | 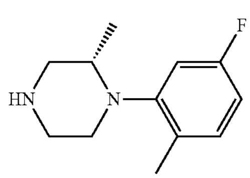 | (2S)-1-(5-fluoro-2-methyl-phenyl)-2-methyl-piperazine | A2a + A5a | (S)-3-Methyl-piperazine-1-carboxylic acid tert-butyl ester + 2-Bromo-4-fluoro-1-methyl-benzene | 208 | N.A. |
| 209 | 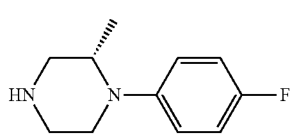 | (2S)-1-(4-fluorophenyl)-2-methyl-piperazine | A2a + A5b | (S)-3-Methyl-piperazine-1-carboxylic acid tert-butyl ester + 1-Bromo-4-fluoro-benzene | 194 | 195 |
| 210 | 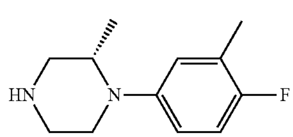 | (2S)-1-(4-fluoro-3-methyl-phenyl)-2-methyl-piperazine | A2a + A5b | (S)-3-Methyl-piperazine-1-carboxylic acid tert-butyl ester + 4-Bromo-1-fluoro-2-methyl-benzene | 208 | 209 |

TABLE II-continued

Illustrative intermediate for the synthesis of illustrative compounds of the invention trans:

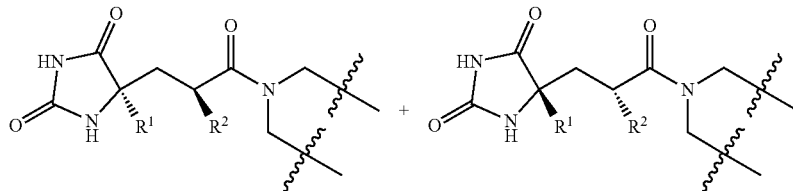

| Int | Structure | Name | Mtd | SM | MW | Ms'd |
|---|---|---|---|---|---|---|
| 211 | 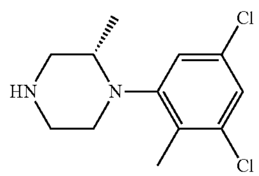 [SMILES: Cc1c(Cl)cc(Cl)cc1N1CCNC[C@@H]1C] | (2S)-1-(3,5-dichloro-2-methyl-phenyl)-2-methyl-piperazine | A2a + A5a | (S)-3-Methyl-piperazine-1-carboxylic acid tert-butyl ester + 1-Bromo-3,5-dichloro-2-methyl-benzene | 259 | 261 |
| 212 | 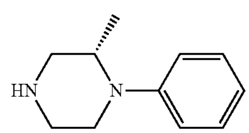 | (2S)-2-methyl-1-phenyl-piperazine | A2a + A5b | (S)-3-Methyl-piperazine-1-carboxylic acid tert-butyl ester + Bromo-benzene | 176 | 177 |
| 213 | 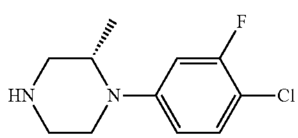 | (2S)-1-(4-chloro-3-fluoro-phenyl)-2-methyl-piperazine | A2a + A5a | (S)-3-Methyl-piperazine-1-carboxylic acid tert-butyl ester + 4-Bromo-1-chloro-2-fluoro-benzene | 229 | 229 |
| 214 | 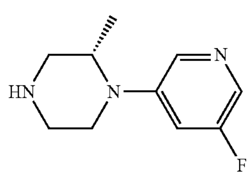 | (2S)-1-(5-fluoro-3-pyridyl)-2-methyl-piperazine | A2a + A5a | (S)-3-Methyl-piperazine-1-carboxylic acid tert-butyl ester + 3-Bromo-5-fluoro-pyridine | 195 | 196 |
| 215 | 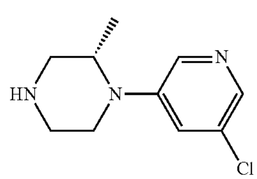 | (2S)-1-(5-chloro-3-pyridyl)-2-methyl-piperazine | A2a + A5a | (S)-3-Methyl-piperazine-1-carboxylic acid tert-butyl ester + 3-Bromo-5-chloro-pyridine | 212 | 212 |
| 216 | 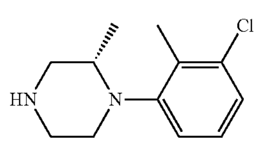 | (2S)-1-(3-chloro-2-methyl-phenyl)-2-methyl-piperazine | A2a + A5a | (S)-3-Methyl-piperazine-1-carboxylic acid tert-butyl ester + 1-Bromo-3-chloro-2-methyl-benzene | 225 | 225 |
| 217 | 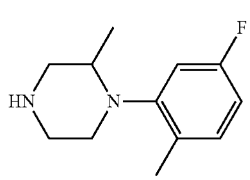 | 1-(5-fluoro-2-methyl-phenyl)-2-methyl-piperazine | A2a + A5b | 3-Methyl-piperazine-1-carboxylic acid tert-butyl ester + 2-Bromo-4-fluoro-1-methyl-benzene | 208 | 209 |

TABLE II-continued

Illustrative intermediate for the synthesis of illustrative compounds of the invention trans:

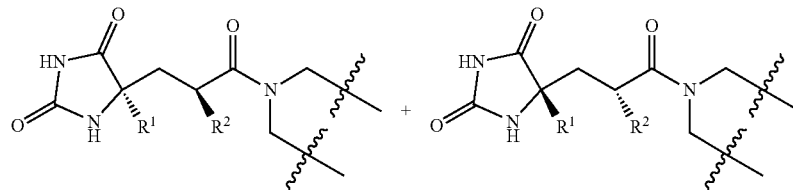

| Int | Structure | Name | Mtd | SM | MW | Ms'd |
|---|---|---|---|---|---|---|
| 218 | 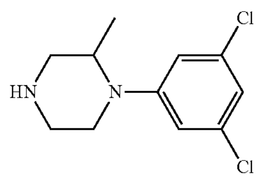 | 1-(3,5-dichlorophenyl)-2-methyl-piperazine | A2a + A5a | 3-Methyl-piperazine-1-carboxylic acid tert-butyl ester + 1-Bromo-3,5-dichloro-benzene | 245 | 245-247 |
| 219 | 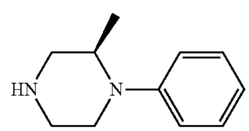 | (2R)-2-methyl-1-phenyl-piperazine | A2a + A5b | (R)-3-Methyl-piperazine-1-carboxylic acid tert-butyl ester + Bromo-benzene | 176 | 177 |
| 220 | 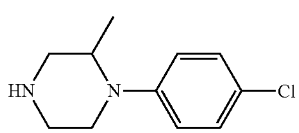 | 1-[4-chlorophenyl)-2-methyl-piperazine | A2a + A5b | 3-Methyl-piperazine-1-carboxylic acid tert-butyl ester + 1-Bromo-4-chloro-benzene | 211 | 211 |
| 221 | 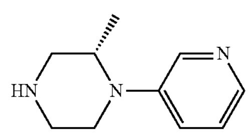 | (2S)-2-methyl-1-(3-pyridyl)piperazine | A2a + A5a | (S)-3-Methyl-piperazine-1-carboxylic acid tert-butyl ester + 3-Bromo-pyridine | 177 | 178 |
| 222 | 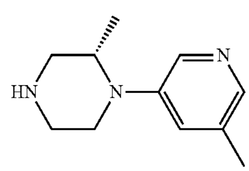 | (2S)-2-methyl-1-(5-methyl-3-pyridyl)piperazine | A2a + A5a | (S)-3-Methyl-piperazine-1-carboxylic acid tert-butyl ester + 3-Bromo-5-methyl-pyridine | 191 | N.A. |
| 223 | 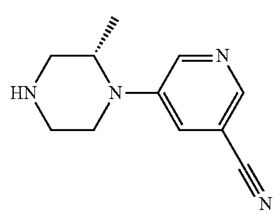 | 5-[(2S)-2-methylpiperazin-1-yl]pyridine-3-carbonitrile | A2a + A5a | (S)-3-Methyl-piperazine-1-carboxylic acid tert-butyl ester + 5-Bromo-nicotinonitrile | 202 | 203 |
| 224 | 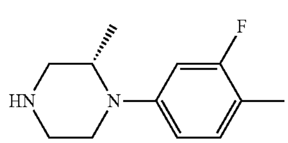 | (2S)-1-(3-fluoro-4-methyl-phenyl)-2-methyl-piperazine | A2a + A5b | (S)-3-Methyl-piperazine-1-carboxylic acid tert-butyl ester + 4-Bromo-2-fluoro-1-methyl-benzene | 208 | 209 |
| 225 | 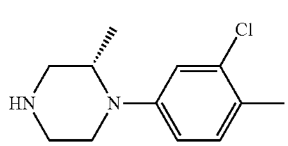 | (2S)-1-(3-chloro-4-methyl-phenyl)-2-methyl-piperazine | A2a + A5b | (S)-3-Methyl-piperazine-1-carboxylic acid tert-butyl ester + 4-Bromo-2-chloro-1-methyl-benzene | 225 | 225-227 |

TABLE II-continued

Illustrative intermediate for the synthesis of illustrative compounds of the invention trans:

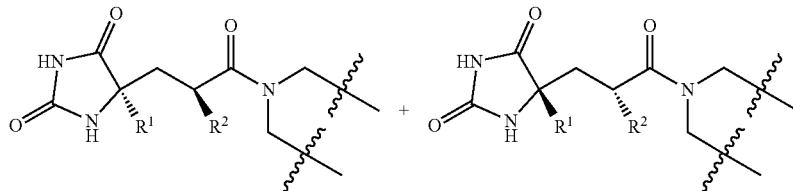

| Int | Structure | Name | Mtd | SM | MW | Ms'd |
|---|---|---|---|---|---|---|
| 226 | 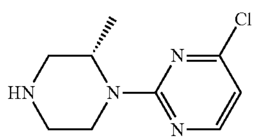 | 4-chloro-2-[(2S)-2-methylpiperazin-1-yl]pyrimidine | A4 + A5a | (S)-3-Methyl-piperazine-1-carboxylic acid tert-butyl ester + 2,4-Dichloro-pyrimidine | 213 | 213 |
| 227 | 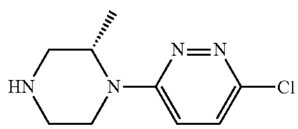 | 3-chloro-6-[(2S)-2-methylpiperazin-1-yl]pyridazine | A4 + A5a | (S)-3-Methyl-piperazine-1-carboxylic acid tert-butyl ester + 3,6-Dichloro-pyridazine | 213 | 213 |
| 228 | 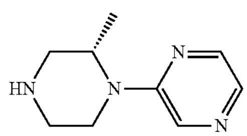 | 2-[(2S)-2-methylpiperazin-1-yl]pyrazine | A2c + A5a | (S)-3-Methyl-piperazine-1-carboxylic acid tert-butyl ester + 2-Chloro-pyrazine | 178 | 179 |
| 229 | 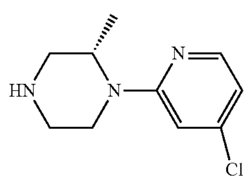 | (2S)-1-(4-chloro-2-pyridyl)-2-methyl-piperazine | A2b + A5a | (S)-3-Methyl-piperazine-1-carboxylic acid tert-butyl ester + 2,4-Dichloro-pyridine | 212 | N.A. |
| 230 | 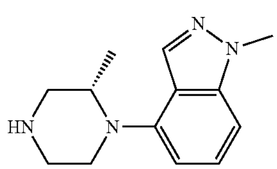 [SMILES: C[C@H]1CNCCN1c1cccc2c1cnn2C] | 1-methyl-4-[(2S)-2-methylpiperazin-1-yl]indazole | A2d + A5b | (S)-3-Methyl-piperazine-1-carboxylic acid tert-butyl ester + 4-Bromo-1-methyl-1H-indazole | 230 | 231 |
| 231 | 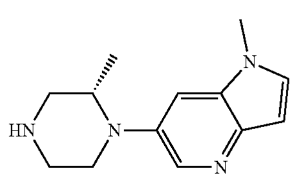 [SMILES: C[C@H]1CNCCN1c1cnc2ccn(C)c2c1] | 1-methyl-6-[(2S)-2-methylpiperazin-1-yl]pyrrolo[3,2-b]pyridine | A2d + A5b | (S)-3-Methyl-piperazine-1-carboxylic acid tert-butyl ester + 6-Bromo-1-methyl-1H-pyrrolo[3,2-b]pyridine | 230 | 231 |
| 232 | 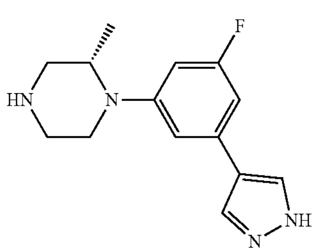 [SMILES: C[C@H]1CNCCN1c1cc(F)cc(-c2cn[nH]c2)c1] | (2S)-1-[3-fluoro-5-(1H-pyrazol-4-yl)phenyl]-2-methyl-piperazine | A2a + A3 + A5b | (S)-3-Methyl-piperazine-1-carboxylic acid tert-butyl ester + 1,3-Dibromo-5-fluoro-benzene | 260 | 261 |

TABLE II-continued

Illustrative intermediate for the synthesis of illustrative compounds of the invention trans:

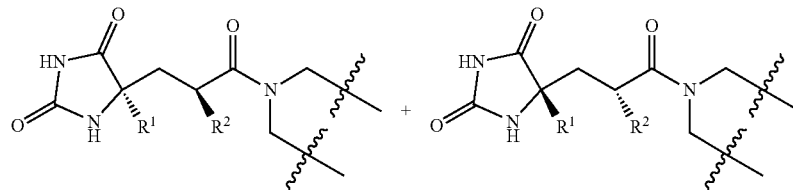

| Int | Structure | Name | Mtd | SM | MW | Ms'd |
|---|---|---|---|---|---|---|
| 233 | 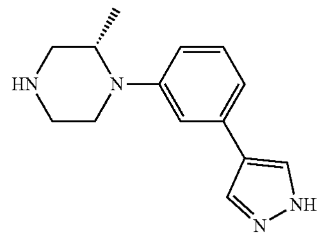 [SMILES: C[C@H]1CNCCN1c1cccc(-c2cn[nH]c2)c1] | (2S)-2-methyl-1-[3-(1H-pyrazol-4-yl)phenyl]piperazine | A2a + A3 + A5b | (S)-3-Methyl-piperazine-1-carboxylic acid tert-butyl ester + 1,3-Dibromo-benzene | 242 | 243 |
| 234 | 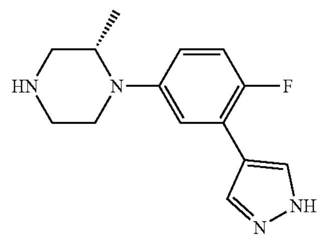 [SMILES: C[C@H]1CNCCN1c1ccc(F)c(-c2cn[nH]c2)c1] | (2S)-1-[4-fluoro-3-(1H-pyrazol-4-yl)phenyl]-2-methyl-piperazine | A2a + A3 + A5a | (S)-3-Methyl-piperazine-1-carboxylic acid tert-butyl ester + 4-Bromo-2-chloro-1-fluoro-benzene | 260 | 261 |
| 235 | 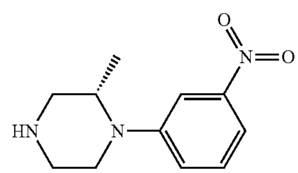 [SMILES: C[C@H]1CNCCN1c1cccc([N+](=O)[O-])c1] | (2S)-2-methyl-1-(3-nitrophenyl)piperazine | A2a + A5b | (S)-3-Methyl-piperazine-1-carboxylic acid tert-butyl ester + 1-Bromo-3-nitro-benzene | 221 | 222 |
| 236 | 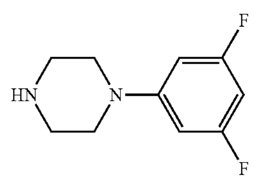 [SMILES: Fc1cc(F)cc(N2CCNCC2)c1] | 1-(3,5-difluorophenyl)piperazine | A2a + A5b | Piperazine-1-carboxylic acid tert-butyl ester + 1-Bromo-3,5-difluoro-benzene | 198 | 199 |
| 237 | 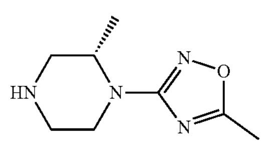 | 5-methyl-3-[(2S)-2-methylpiperazin-1-yl]-1,2,4-oxadiazole | 2.13 + A5a | (S)-3-Methyl-piperazine-1-carboxylic acid tert-butyl ester + BrCN | 182 | N.A. |
| 238 | 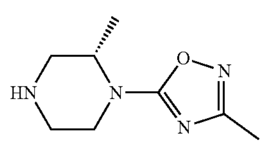 | 3-methyl-5-[(2S)-2-methylpiperazin-1-yl]-1,2,4-oxadiazole | 2.30 | (S)-3-Methyl-piperazine-1-carboxylic acid tert-butyl ester + BrCN | 182 | 183 |
| 239 | 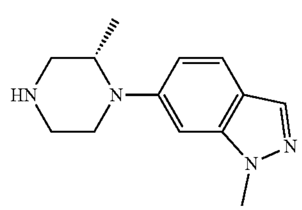 [SMILES: C[C@H]1CNCCN1c1ccc2cnn(C)c2c1] | 1-methyl-6-[(2S)-2-methylpiperazin-1-yl]indazole | A2d + A5c | (S)-3-Methyl-piperazine-1-carboxylic acid tert-butyl ester + 6-Bromo-1-methyl-1H-indazole | 230 | 231 |

TABLE II-continued

Illustrative intermediate for the synthesis of illustrative compounds of the invention trans:

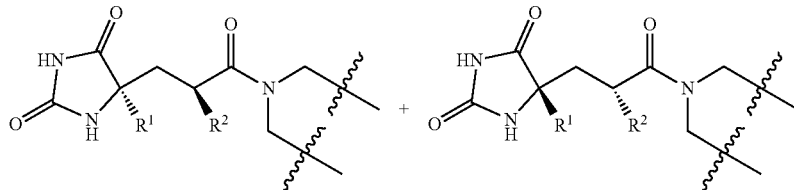

| Int | Structure | Name | Mtd | SM | MW | Ms'd |
|---|---|---|---|---|---|---|
| 240 | 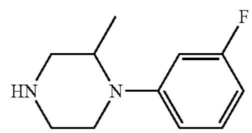 | 1-(3-fluorophenyl)-2-methyl-piperazine | A2a + A5a | 3-Methyl-piperazine-1-carboxylic acid tert-butyl ester + 1-Bromo-3-fluoro-benzene | 194 | 195 |
| 241 | 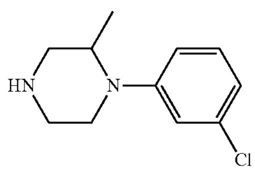 | 1-(3-chlorophenyl)-2-methyl-piperazine | A2a + A5a | 3-Methyl-piperazine-1-carboxylic acid tert-butyl ester + 1-Bromo-3-chloro-benzene | 211 | 211-213 |
| 242 | 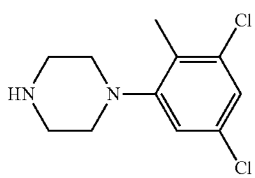 | 1-(3,5-dichloro-2-methyl-phenyl)piperazine | A7 | Piperazine + 1-Bromo-3,5-dichloro-2-methyl-benzene | 245 | 245-247 |
| 243 | 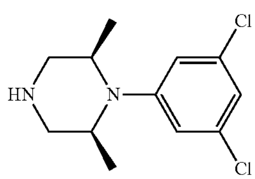 [SMILES: C[C@@H]1CNC[C@H](C)N1c1cc(Cl)cc(Cl)c1] | (2S,6R)-1-(3,5-dichlorophenyl)-2,6-dimethyl-piperazine | A1 + A2a + A5a | cis-2,6-Dimethyl-piperazine + 3,5-dichloro bromobenzene | 259 | 259-261 |
| 244 | 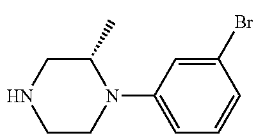 | (2S)-1-(3-bromophenyl)-2-methyl-piperazine | A2a + A5a | (S)-3-Methyl-piperazine-1-carboxylic acid tert-butyl ester + 1,3-Dibromo-benzene | 255 | 255-257 |
| 245 | 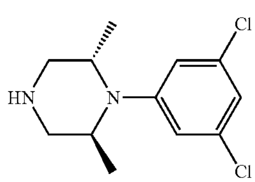 [SMILES: C[C@H]1CNC[C@H](C)N1c1cc(Cl)cc(Cl)c1] | (2S,6S)-1-(3,5-dichlorophenyl)-2,6-dimethyl-piperazine | A2a + A5a | (3S,5S)-3,5-Dimethyl-piperazine-1-carboxylic acid tert-butyl ester + 1-Bromo-3,5-dichloro-benzene | 259 | 259- |
| 246 | 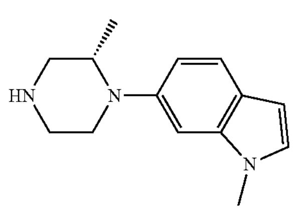 [SMILES: C[C@H]1CNCCN1c1ccc2ccn(C)c2c1] | 1-(benzofuran-5-yl)piperazine | A2e + A5a | Piperazine-1-carboxylic acid tert-butyl ester + 5-Bromo-benzofuran | 202 | N.A. |

TABLE II-continued

Illustrative intermediate for the synthesis of illustrative compounds of the invention trans:

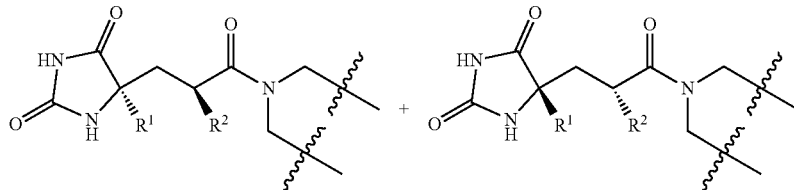

| Int | Structure | Name | Mtd | SM | MW | Ms'd |
|---|---|---|---|---|---|---|
| 247 | 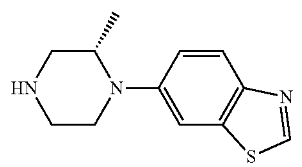 [SMILES: C[C@H]1CNCCN1c1ccc2ncsc2c1] | 5-piperazin-1-yl-1,3-benzothiazole | A2e + A5a | Piperazine-1-carboxylic acid tert-butyl ester + 5-Bromo-benzo thiazole | 219 | N.A. |
| 248 | 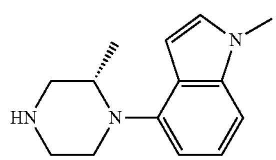 [SMILES: C[C@H]1CNCCN1c1cccc2c1ccn2C] | 5-[(2S)-2-methylpiperazin-1-yl]pyrimidine | A2a + A5b | (S)-3-Methyl-piperazine-1-carboxylic acid tert-butyl ester + 5-Bromo-pyrimidine | 178 | N.A. |
| 249 | 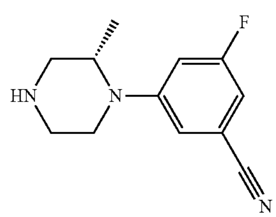 [SMILES: C[C@H]1CNCCN1c1cc(F)cc(C#N)c1] | (2S)-1-(benzofuran-7-yl)-2-methyl-piperazine | A2f + A5a | (S)-3-Methyl-piperazine-1-carboxylic acid tert-butyl ester + 7-Bromo-benzofuran | 216 | 217 |
| 250 | 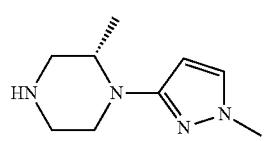 | 3-[(2S)-2-methylpiperazin-1-yl]quinoline | A2f + A5a | (S)-3-Methyl-piperazine-1-carboxylic acid tert-butyl ester + 3-Bromo-quinoline | 227 | 228 |
| 251 | 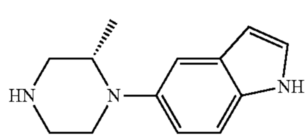 [SMILES: C[C@H]1CNCCN1c1ccc2[nH]ccc2c1] | 1-methyl-5-[(2S)-2-methylpiperazin-1-yl]indole | A2b + A5a | (S)-3-Methyl-piperazine-1-carboxylic acid tert-butyl ester + 5-Bromo-1-methyl-1H-indole | 229 | 230 |
| 252 | 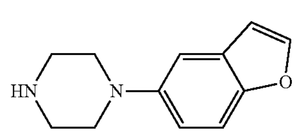 [SMILES: c1cc2cc(N3CCNCC3)ccc2o1] | 1-methyl-6-[(2S)-2-methylpiperazin-1-yl]indole | A2d + A5b | (S)-3-Methyl-piperazine-1-carboxylic acid tert-butyl ester + 6-Bromo-1-methyl-1H-indole | 229 | 230 |
| 253 | 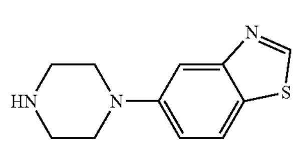 [SMILES: c1nc2cc(N3CCNCC3)ccc2s1] | 6-[(2S)-2-methylpiperazin-1-yl]-1,3-benzothiazole | A2d + A5a | (S)-3-Methyl-piperazine-1-carboxylic acid tert-butyl ester + 6-Bromo-benzothiazole | 233 | 234 |
| 254 | 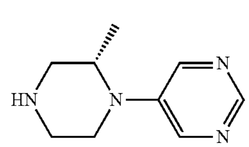 | 1-methyl-4-[(2S)-2-methylpiperazin-1-yl]indole | A2d + A5c | (S)-3-Methyl-piperazine-1-carboxylic acid tert-butyl ester + 4-Bromo-1-methyl-1H-indole | 229 | 230 |

TABLE II-continued

Illustrative intermediate for the synthesis of illustrative compounds of the invention trans:

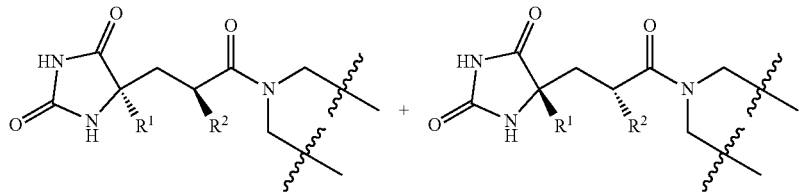

| Int | Structure | Name | Mtd | SM | MW | Ms'd |
|---|---|---|---|---|---|---|
| 255 | 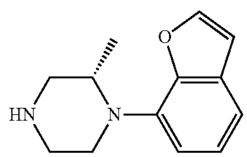 [SMILES: C[C@H]1CNCCN1c1cccc2ccoc12] | 3-fluoro-5-[(2S)-2-methylpiperazin-1-yl]benzonitrile | A2e + A5a | (S)-3-Methyl-piperazine-1-carboxylic acid tert-butyl ester + 3-Bromo-5-fluoro-benzonitrile | 219 | 220 |
| 256 | 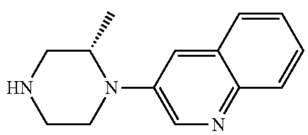 [SMILES: C[C@H]1CNCCN1c1cnc2ccccc2c1] | (2S)-2-methyl-1-(1-methylpyrazol-3-yl)piperazine | A2g + A5a | (S)-3-Methyl-piperazine-1-carboxylic acid tert-butyl ester + 3-Bromo-1-methyl-1H-pyrazole | 180 | 181 |
| 257 | 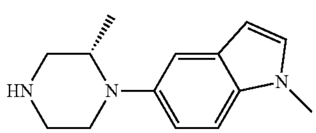 [SMILES: C[C@H]1CNCCN1c1ccc2c(ccn2C)c1] | 5-[(2S)-2-methylpiperazin-1-yl]-1H-indole | A6 | 5-Bromo-1H-indole | 215 | 216 |
| 258 | 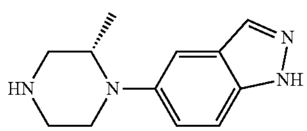 [SMILES: C[C@H]1CNCCN1c1ccc2[nH]ncc2c1] | 5-[(2S)-2-methylpiperazin-1-yl]-1H-indazole | A6 | 5-Bromo-1H-indazole | 216 | N.A. |
| 259 | 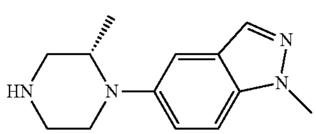 [SMILES: C[C@H]1CNCCN1c1ccc2c(cnn2C)c1] | 1-methyl-5-[(2S)-2-methylpiperazin-1-yl] indazole | A2d + A5c | (S)-3-Methyl-piperazine-1-carboxylic acid tert-butyl ester + 5-Bromo-1-methyl-1H-indazole | 230 | 231 |
| 260 | 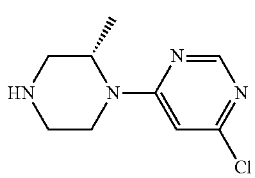 | 4-chloro-6-[(2S)-2-methylpiperazin-1-yl] pyrimidine | A4 + A5a | (S)-3-Methyl-piperazine-1-carboxylic acid tert-butyl ester + 4,6-Dichloro-pyrimidine | 213 | 213 |
| 261 | 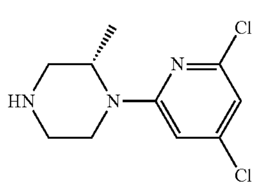 | (2S)-1-(4,6-dichloro-2-pyridyl)-2-methyl-piperazine | A4 + A5a | (S)-3-Methyl-piperazine-1-carboxylic acid tert-butyl ester + 2,4,6-Trichloro-pyridine | 246 | 246 |
| 262 | 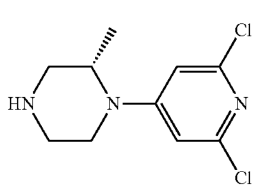 | (2S)-1-(2,6-dichloro-4-pyridyl)-2-methyl-piperazine | A4 + A5a | (S)-3-Methyl-piperazine-1-carboxylic acid tert-butyl ester + 2,4,6-Trichloro-pyridine | 246 | 246 |

TABLE II-continued

Illustrative intermediate for the synthesis of illustrative compounds of the invention trans:

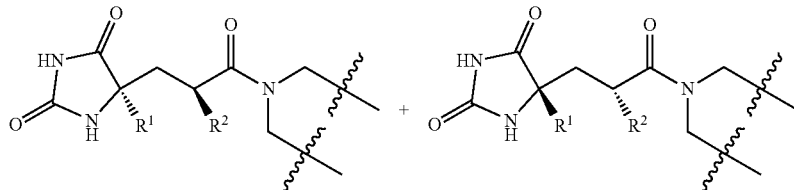

| Int | Structure | Name | Mtd | SM | MW | Ms'd |
|---|---|---|---|---|---|---|
| 263 | 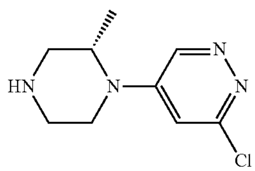 | 3-chloro-5-[(2S)-2-methylpiperazin-1-yl] pyridazine | A4 + A5a | (S)-3-Methyl-piperazine-1-carboxylic acid tert-butyl ester + 3,5-Dichloro-pyridazine | 213 | 213 |
| 264 | 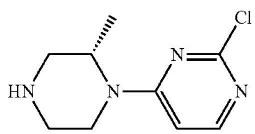 | 2-chloro-4-[(2S)-2-methylpiperazin-1-yl] pyrimidine | A4 + A5a | (S)-3-Methyl-piperazine-1-carboxylic acid tert-butyl ester + 2,4-Dichloro-pyrimidine | 213 | 213 |
| 265 | 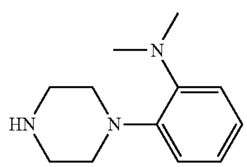 | N,N-dimethyl-2-piperazin-1-yl-aniline | A7 | piperazine + (2-Bromo-phenyl)-dimethyl-amine | 205 | N.A. |
| 266 | 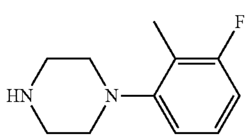 | 1-(3-fluoro-2-methyl-phenyl)piperazine | A7 | piperazine + 1-Bromo-3-fluoro-2-methyl-benzene | 194 | 195 |
| 267 | 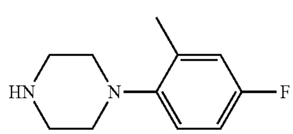 | 1-(4-fluoro-2-methyl-phenyl)piperazine | A7 | piperazine + 1-Bromo-4-fluoro-2-methyl-benzene | 194 | 195 |
| 268 | 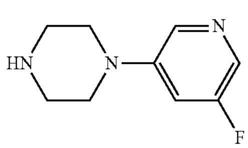 [SMILES: Fc1cncc(N2CCNCC2)c1] | 1-(5-fluoro-3-pyridyl)piperazine | A2a + A5a | Piperazine-1-carboxylic acid tert-butyl ester + 3-Bromo-5-fluoro-pyridine | 181 | N.A. |
| 269 | 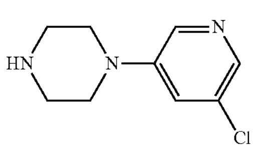 [SMILES: Clc1cncc(N2CCNCC2)c1] | 1-(5-chloro-3-pyridyl)piperazine | A8 | piperazine + 3-Chloro-5-fluoro-pyridine | 198 | 198-200 |
| 270 | 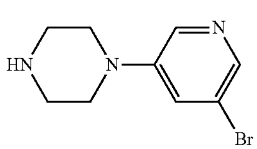 [SMILES: Brc1cncc(N2CCNCC2)c1] | 1-(5-bromo-3-pyridyl)piperazine | A8 | piperazine + 3-Bromo-5-fluoro-pyridine | 242 | 242-244 |

TABLE II-continued

Illustrative intermediate for the synthesis of illustrative compounds of the invention trans:

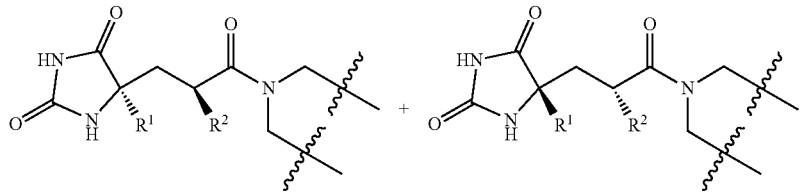

| Int | Structure | Name | Mtd | SM | MW | Ms'd |
|---|---|---|---|---|---|---|
| 271 | 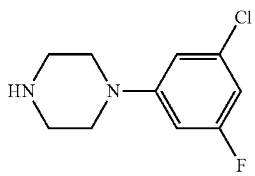 [SMILES: Fc1cc(Cl)cc(N2CCNCC2)c1] | 1-(3-chloro-5-fluoro-phenyl)piperazine | A2a + A5a | Piperazine-1-carboxylic acid tert-butyl ester + 1-Bromo-3-chloro-5-fluoro-benzene | 215 | 215-217 |
| 272 | 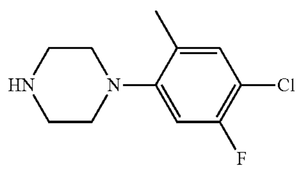 | 1-(4-chloro-5-fluoro-2-methyl-phenyl)piperazine | A7 | Piperazine + 1-Bromo-4-chloro-5-fluoro-2-methyl-benzene | 229 | 229-231 |
| 273 | 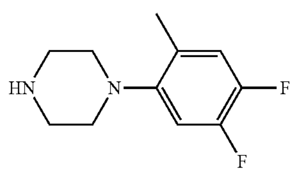 | 1-(4,5-difluoro-2-methyl-phenyl)piperazine | A7 | Piperazine + 1-Bromo-4,5-difluoro-2-methyl-benzene | 212 | 213 |
| 274 | 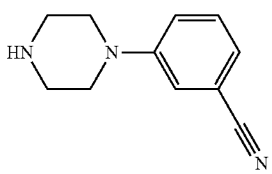 [SMILES: N#Cc1cccc(N2CCNCC2)c1] | 3-piperazin-1-ylbenzonitrile | A8 | Piperazine + 3-Fluoro-benzonitrile | 187 | N.A. |
| 275 | 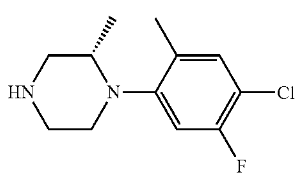 | (2S)-1-(4-chloro-5-fluoro-2-methyl-phenyl)-2-methyl-piperazine | A2a + A5a | (S)-3-Methyl-piperazine-1-carboxylic acid tert-butyl ester + 1-bromo-2-methyl-4-chloro-5-fluoro benzene | 243 | N.A. |
| 276 | 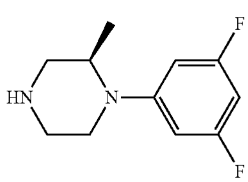 | (2R)-1-(3,5-difluorophenyl)-2-methyl-piperazine | A2a + A5a | (S)-3-Methyl-piperazine-1-carboxylic acid tert-butyl ester + 1-bromo-3,5-difluoro benzene | 212 | 213 |
| 277 | 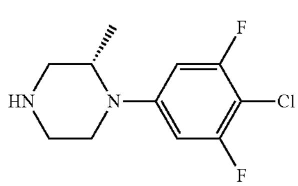 [SMILES: C[C@H]1CNCCN1c1cc(F)c(Cl)c(F)c1] | (2S)-1-(4-chloro-3,5-difluoro-phenyl)-2-methyl-piperazine | A2a + A5b | (S)-3-Methyl-piperazine-1-carboxylic acid tert-butyl ester + 1-bromo-3,5-difluoro-4-chlorobenzene | 247 | N.A. |

TABLE II-continued

Illustrative intermediate for the synthesis of illustrative compounds of the invention trans:

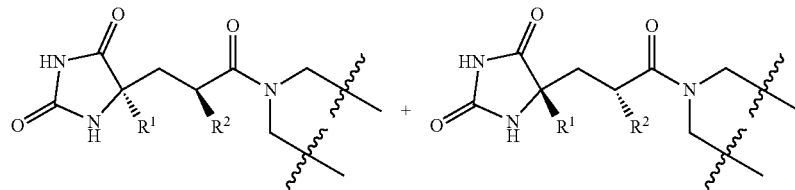

| Int | Structure | Name | Mtd | SM | MW | Ms'd |
|---|---|---|---|---|---|---|
| 278 | 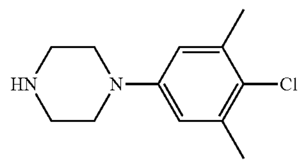 | 1-(4-chloro-3,5-dimethyl-phenyl)piperazine | A2a + A5b | Piperazine-1-carboxylic acid tert-butyl ester + 5-bromo-2-chloro-1,4-dimethyl benzene | 225 | 225-227 |
| 279 | 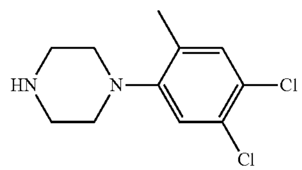 | 1-(4,5-dichloro-2-methyl-phenyl)piperazine | A2a + A5a | Piperazine-1-carboxylic acid tert-butyl ester + 3,4-dichloro-6-bromotoluene | 245 | N.A |
| 280 | 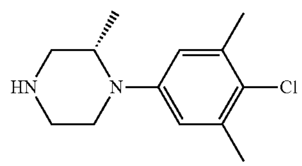 [SMILES: Cc1cc(N2CCNC[C@@H]2C)cc(C)c1Cl] | (2S)-1-(4-chloro-3,5-dimethyl-phenyl)-2-methyl-piperazine | A2a + A5a | Piperazine-1-carboxylic acid tert-butyl ester + 5-bromo-2-chloro-1,3-dimethyl benzene | 239 | 239 |
| 281 | 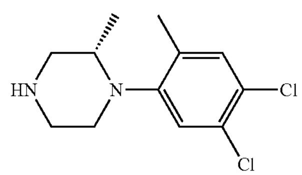 [SMILES: Cc1cc(Cl)c(Cl)cc1N1CCNC[C@@H]1C] | (2S)-1-(4,5-dichloro-2-methyl-phenyl)-2-methyl-piperazine | A2a + A5a | (S)-3-Methyl-piperazine-1-carboxylic acid tert-butyl ester + 3,4-dichloro-6-bromotoluene | 259 | N.A. |
| 282 | 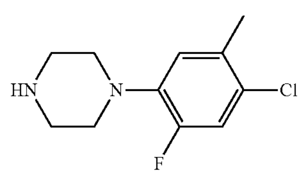 | 1-(4-chloro-2-fluoro-5-methyl-phenyl)piperazine | A2a + A5a | Piperazine-1-carboxylic acid tert-butyl ester + 1-Bromo-4-chloro-2-fluoro-5-methylbenzene | 229 | N.A. |
| 283 | 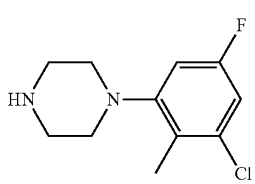 | 1-(3-chloro-5-fluoro-2-methyl-phenyl)piperazine | A2a + A5c | Piperazine-1-carboxylic acid tert-butyl ester + Int 287 | 229 | N.A. |
| 284 | 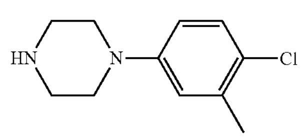 | 1-(4-chloro-3-methyl-phenyl)piperazine | A2a + A5a | Piperazine-1-carboxylic acid tert-butyl ester + 5-bromo-2-chloro toluene | 211 | 211-213 |
| 285 | 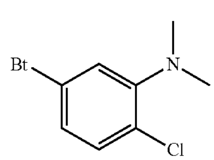 | 5-bromo-2-chloro-N,N-dimethyl-aniline | 2.31 | 1-bromo-4-chloro-3-fluoro-benzene | 235 | 234-236 |

TABLE II-continued

Illustrative intermediate for the synthesis of illustrative compounds of the invention trans:

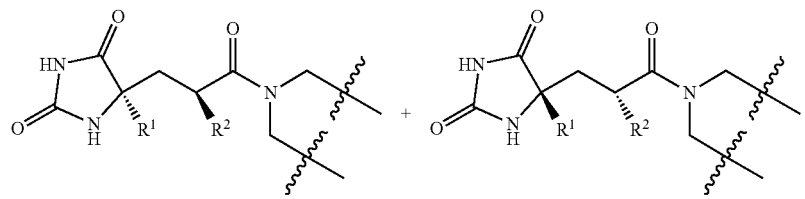

| Int | Structure | Name | Mtd | SM | MW | Ms'd |
|---|---|---|---|---|---|---|
| 286 | 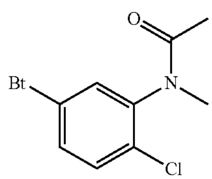 | N-(5-bromo-2-chloro-phenyl)-N-methyl-acetamide | 2.32 | 3-bromo-6-chloroaniline | 263 | 262-264 |
| 287 | 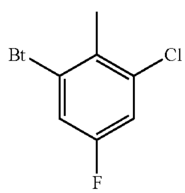 | 1-bromo-3-chloro-5-fluoro-2-methyl-benzene | 2.33 | 2-chloro-4-fluorotoluene | 223 | N.A. |
| 288 | 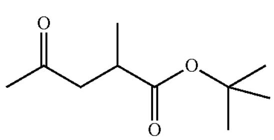 | 2-Methyl-4-oxo-pentanoic acid tert-butyl ester | C1 step ii + step iii | 3-Oxo-butyric acid benzyl ester | 186 | N.A. |
| 289 | 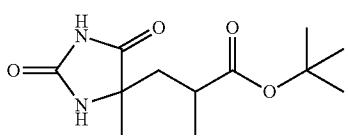 [SMILES: CC(CC1(C)NC(=O)NC1=O)C(=O)OC(C)(C)C] | 2-Methyl-3-(4-methyl-2,5-dioxo-imidazolidin-4-yl)-propionic acid tert-butyl ester | F | Int 288 | 256 | N.A. |
| 290 | 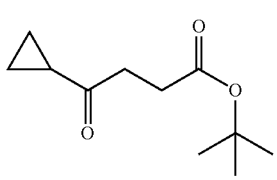 | 4-Cyclopropyl-4-oxo-butyric acid tert-butyl ester | 2.34 | 1-cyclopropyl-ethanone | 198 | N.A. |
| 291 | 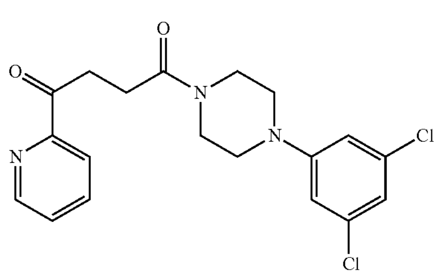 [SMILES: O=C(CCC(=O)N1CCN(c2cc(Cl)cc(Cl)c2)CC1)c1ccccn1] | 1-[4-(3,5-dichlorophenyl)piperazin-1-yl]-4-(2-pyridyl)butane-1,4-dione | H3 | 4-oxo-4-pyridin-2ylbutyric acid + 1-(3,5-dichlorophenyl)piperazine | 392 | 392-394 |

TABLE II-continued

Illustrative intermediate for the synthesis of illustrative compounds of the invention trans:

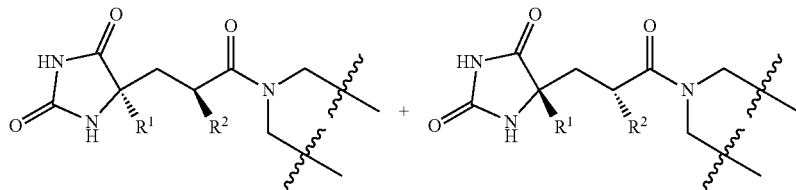

| Int | Structure | Name | Mtd | SM | MW | Ms'd |
|---|---|---|---|---|---|---|
| 292 | 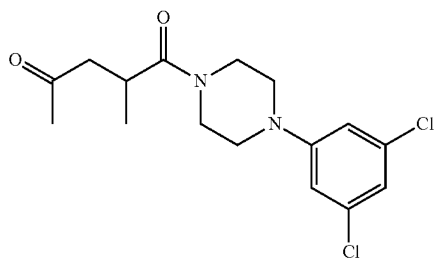 [SMILES: CC(=O)CC(C)C(=O)N1CCN(c2cc(Cl)cc(Cl)c2)CC1] | 1-[4-(3,5-dichlorophenyl)piperazin-1-yl]-2-methyl-pentane-1,4-dione | D2b | Int 001 + acetaldehyde | 343 | 343-345 |
| 293 | 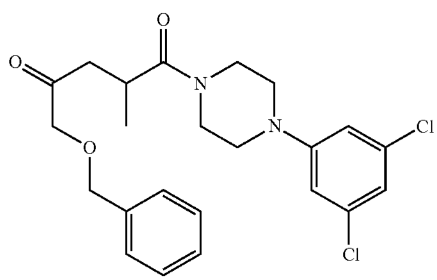 [SMILES: CC(CC(=O)COCc1ccccc1)C(=O)N1CCN(c2cc(Cl)cc(Cl)c2)CC1] | 5-benzyloxy-1-[4-(3,5-dichlorophenyl)piperazin-1-yl]-2-methyl-pentane-1,4-dione | D2b | Int 001 + Benzyloxy-acetaldehyde | 449 | 449-451 |
| 294 | 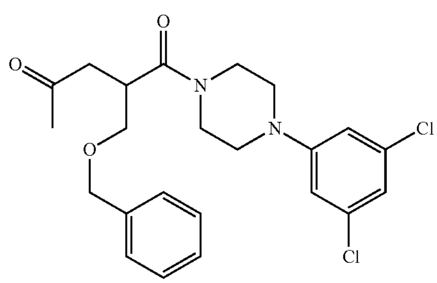 [SMILES: CC(=O)CC(COCc1ccccc1)C(=O)N1CCN(c2cc(Cl)cc(Cl)c2)CC1] | 2-(benzyloxymethyl)-1-[4-(3,5-dichlorophenyl)piperazin-1-yl]pentane-1,4-dione | H2 | Int 138+ 1-(3,5-dichlorophenyl)piperazine | 449 | 449-451 |
| 295 | 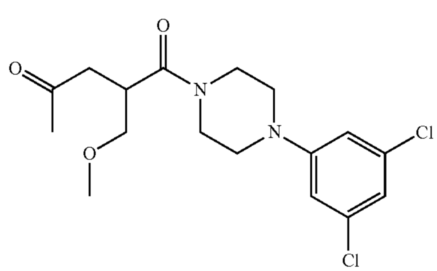 [SMILES: COCC(CC(C)=O)C(=O)N1CCN(c2cc(Cl)cc(Cl)c2)CC1] | 1-[4-(3,5-dichlorophenyl)piperazin-1-yl]-2-(methoxymethyl)pentane-1,4-dione | E | Int 121 + Bromo-methoxy-methane | 373 | 373-375 |

TABLE II-continued

Illustrative intermediate for the synthesis of illustrative compounds of the invention trans:

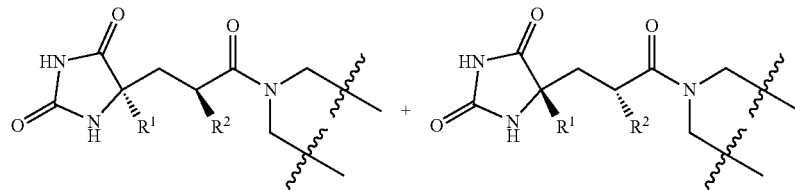

| Int | Structure | Name | Mtd | SM | MW | Ms'd |
|---|---|---|---|---|---|---|
| 296 | 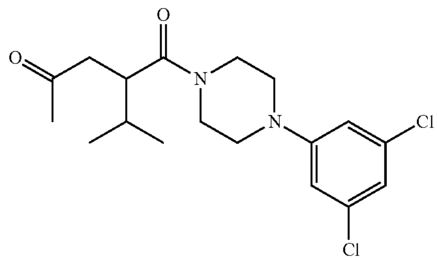 [SMILES: CC(=O)CC(C(=O)N1CCN(c2cc(Cl)cc(Cl)c2)CC1)C(C)C] | 1-[4-(3,5-dichlorophenyl)piperazin-1-yl]-2-isopropyl-pentane-1,4-dione | E | Int 121 + 2-Chloro-propane | 371 | 371-373 |
| 297 | 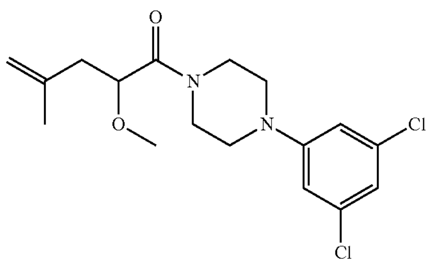 [SMILES: C=C(C)CC(OC)C(=O)N1CCN(c2cc(Cl)cc(Cl)c2)CC1] | 1-[4-(3,5-dichlorophenyl)piperazin-1-yl]-2-methoxy-4-methyl-pent-4-en-1-one | H3 | Int 154+ 1-(3,5-dichlorophenyl)piperazine | 357 | 357-359 |
| 298 | 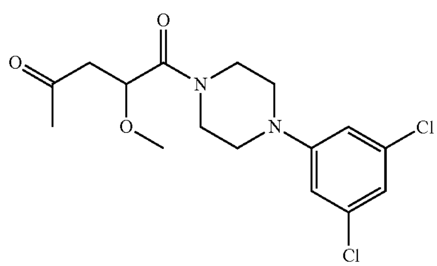 [SMILES: COC(CC(C)=O)C(=O)N1CCN(c2cc(Cl)cc(Cl)c2)CC1] | 1-[4-(3,5-dichlorophenyl)piperazin-1-yl]-2-methoxy-pentane-1,4-dione | D4 | Int 297 | 359 | 359-361 |
| 299 | Trans | 5-2-(benzyloxymethyl)-3-[(3S)-4-(3-chloro-4-fluoro-phenyl)-3-methyl-piperazin-1-yl]-3-oxo-propyl]-5-methyl-imidazolidine-2,4-dione | H2 | Int 135 + Int 198 | 517 | N.A. |
| 300 | 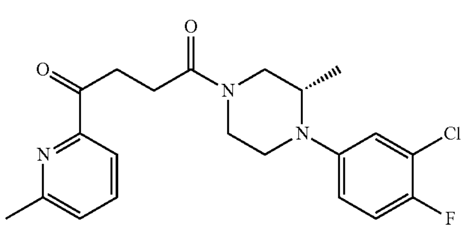 [SMILES: Cc1cccc(C(=O)CCC(=O)N2CCN(c3ccc(F)c(Cl)c3)[C@@H](C)C2)n1] | 1-[(3S)-4-(3-chloro-4-fluoro-phenyl)-3-methyl-piperazin-1-yl]-4-(6-methyl-2-pyridyl)butane-1,4-dione | D2a | Int 006 + 6-Methyl-pyridine-2-carbaldehyde | 404 | 404-406 |

TABLE II-continued

Illustrative intermediate for the synthesis of illustrative compounds of the invention trans:

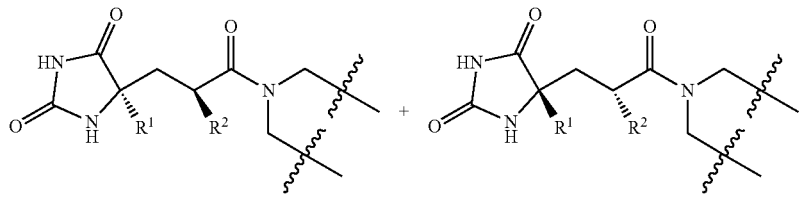

| Int | Structure | Name | Mtd | SM | MW | Ms'd |
|---|---|---|---|---|---|---|
| 301 | 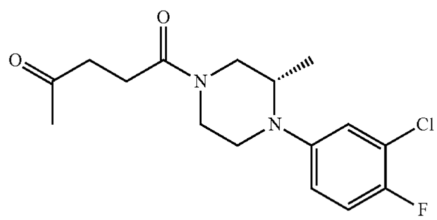 [SMILES: CC(=O)CCC(=O)N1CCN(c2ccc(F)c(Cl)c2)[C@@H](C)C1] | 1-[(3S)-4-(3-chloro-4-fluoro-phenyl)-3-methyl-piperazin-1-yl]pentane-1,4-dione | H2 | levulinic acid + Int 198 | 327 | |
| 302 | 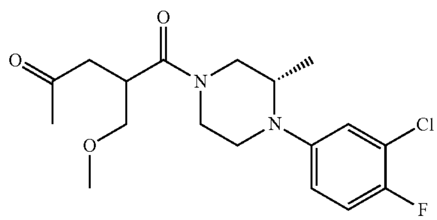 [SMILES: COCC(CC(C)=O)C(=O)N1CCN(c2ccc(F)c(Cl)c2)[C@@H](C)C1] | 1-[(3S)-4-(3-chloro-4-fluoro-phenyl)-3-methyl-piperazin-1-yl]-2-(methoxymethyl)pentane-1,4-dione | E | Int 301 + Bromo-methoxy-methane | 371 | 371-373 |
| 303 | 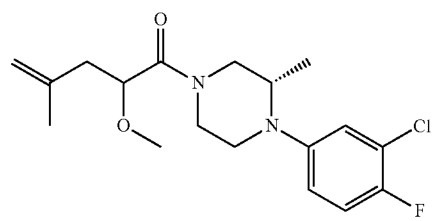 [SMILES: C=C(C)CC(OC)C(=O)N1CCN(c2ccc(F)c(Cl)c2)[C@@H](C)C1] | 1-[(3S)-4-(3-chloro-4-fluoro-phenyl)-3-methyl-piperazin-1-yl]-2-methoxy-4-methyl-pent-4-en-1-one | H3 | Int 154 + Int 198 | 355 | 355-357 |
| 304 | 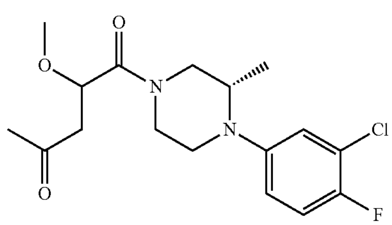 [SMILES: COC(CC(C)=O)C(=O)N1CCN(c2ccc(F)c(Cl)c2)[C@@H](C)C1] | 1-[(3S)-4-(3-chloro-4-fluoro-phenyl)-3-methyl-piperazin-1-yl]-2-methoxy-pentane-1,4-dione | D4 | Int 303 | 357 | N.A. |
| 305 | 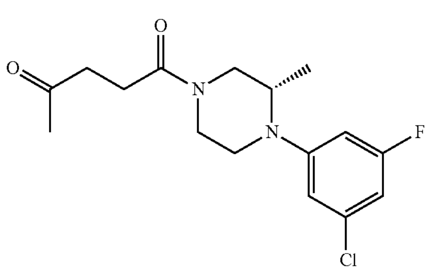 [SMILES: CC(=O)CCC(=O)N1CCN(c2cc(F)cc(Cl)c2)[C@@H](C)C1] | 1-[(3S)-4-(3-chloro-5-fluoro-phenyl)-3-methyl-piperazin-1-yl]pentane-1,4-dione | H2 | levulinic acid + Int 206 | 327 | 327-329 |

TABLE II-continued

Illustrative intermediate for the synthesis of illustrative compounds of the invention trans:

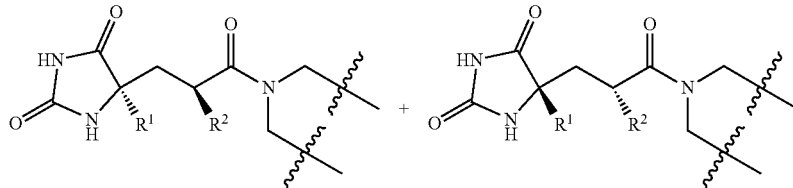

| Int | Structure | Name | Mtd | SM | MW | Ms'd |
|---|---|---|---|---|---|---|
| 306 | 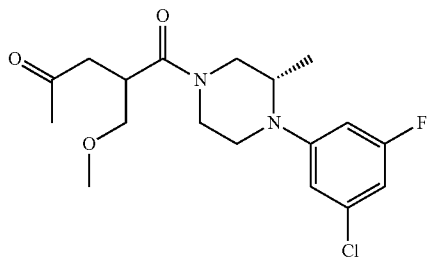 [SMILES: COCC(CC(C)=O)C(=O)N1CCN(c2cc(F)cc(Cl)c2)[C@@H](C)C1] | 1-[(3S)-4-(3-chloro-5-fluoro-phenyl)-3-methyl-piperazin-1-yl]-2-(methoxymethyl) pentane-1,4-dione | E | Int 305 + Bromo-methoxy-methane | 371 | 371-373 |
| 307 | 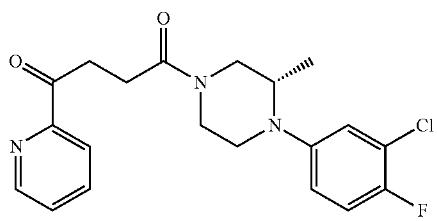 [SMILES: C[C@H]1CN(C(=O)CCC(=O)c2ccccn2)CCN1c1ccc(F)c(Cl)c1] | 1-[(3S)-4-(3-chloro-4-fluoro-phenyl)-3-methyl-piperazin-1-yl]-4-(2-pyridyl)butane-1,4-dione | H3 | 4-oxo-4-pyridin-2ylbutyric acid + Int 198 | 390 | 390-392 |
| 308 | 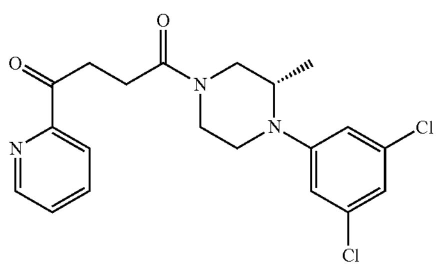 [SMILES: C[C@H]1CN(C(=O)CCC(=O)c2ccccn2)CCN1c1cc(Cl)cc(Cl)c1] | 1-[(3S)-4-(3,5-dichlorophenyl)-3-methyl-piperazin-1-yl]-4-(2-pyridyl)butane-1,4-dione | H3 | 4-oxo-4-pyridin-2ylbutyric acid + Int 197 | 406 | 406-408 |
| 309 | 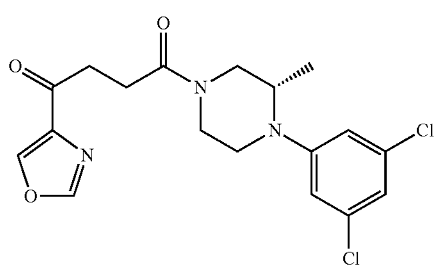 [SMILES: C[C@H]1CN(C(=O)CCC(=O)c2cocn2)CCN1c1cc(Cl)cc(Cl)c1] | 1-[(3S)-4-(3,5-dichlorophenyl)-3-methyl-piperazin-1-yl]-4-oxazol-4-yl-butane-1,4-dione | D2a | Int 008 + Oxazole-4-carbaldehyde | 396 | 396-398 |
| 310 | 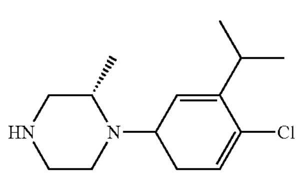 [SMILES: CC(C)C1=CC(N2CCNC[C@@H]2C)CC=C1Cl] | (2S)-1-(4-chloro-3-isopropyl-phenyl)-2-methyl-piperazine | A2a + A5a | (S)-3-Methyl-piperazine-1-carboxylic acid tert-butyl ester + 1-bromo-3-isopropyl-4-chlorobenzene | 253 | 253 |

TABLE II-continued

Illustrative intermediate for the synthesis of illustrative compounds of the invention trans:

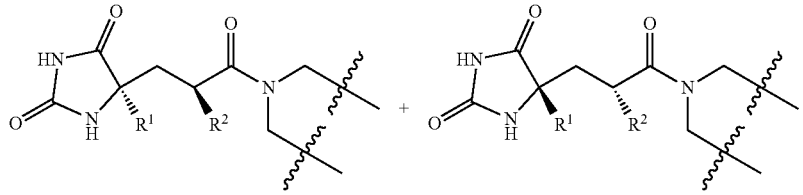

| Int | Structure | Name | Mtd | SM | MW | Ms'd |
|---|---|---|---|---|---|---|
| 311 | 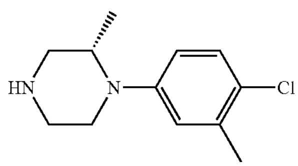 | (2S)-1-(4-chloro-3-methyl-phenyl)-2-methyl-piperazine | A2a + A5b | (S)-3-Methyl-piperazine-1-carboxylic acid tert-butyl ester + 5-bromo-2-chloro toluene | 225 | 225-227 |
| 312 | 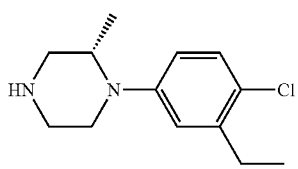 [SMILES: CCc1cc(N2CCNC[C@@H]2C)ccc1Cl] | (2S)-1-(4-chloro-3-ethyl-phenyl)-2-methyl-piperazine | A2a + A5a | (S)-3-Methyl-piperazine-1-carboxylic acid tert-butyl ester + 1-bromo-3-ethyl-4-chloro benzene | 239 | 239 |
| 313 | 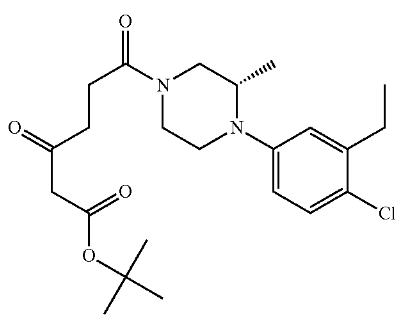 [SMILES: CCc1cc(N2CCN(C(=O)CCC(=O)CC(=O)OC(C)(C)C)C[C@@H]2C)ccc1Cl] | tert-butyl 6-[(3S)-4-(4-chloro-3-ethyl-phenyl)-3-methyl-piperazin-1-yl]-3,6-dioxo-hexanoate | H2 | Int 129 + Int 312 | 437 | 437-439 |
| 314 | 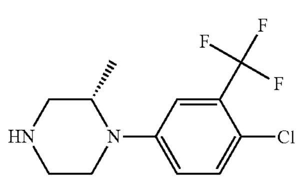 [SMILES: C[C@H]1CNCCN1c1ccc(Cl)c(C(F)(F)F)c1] | (2S)-1-[4-chloro-3-(trifluoromethyl)phenyl]-2-methyl-piperazine | A2a + A5a | (S)-3-Methyl-piperazine-1-carboxylic acid tert-butyl ester + 4-bromo-1-chloro-2-trifluoromethyl benzene | 279 | 279 |
| 315 | 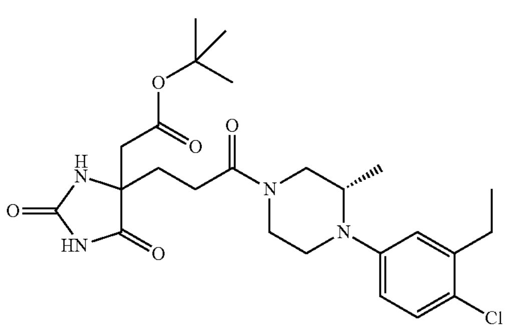 [SMILES: CCc1cc(N2CCN(C(=O)CCC3(CC(=O)OC(C)(C)C)NC(=O)NC3=O)C[C@@H]2C)ccc1Cl] | tert-butyl 2-[4-[3-[(3S)-4-(4-chloro-3-ethyl-phenyl)-3-methyl-piperazin-1-yl]-3-oxo-propyl]-2,5-dioxo-imidazolidin-4-yl]acetate | F | Int 313 | 507 | 507-509 |

TABLE II-continued

Illustrative intermediate for the synthesis of illustrative compounds of the invention trans:

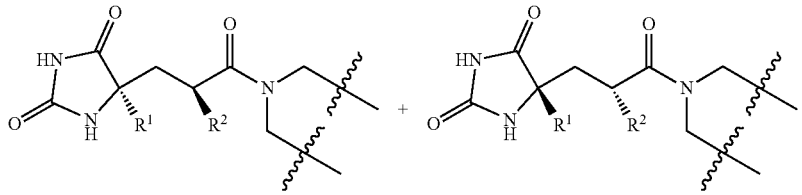

| Int | Structure | Name | Mtd | SM | MW | Ms'd |
|---|---|---|---|---|---|---|
| 316 | 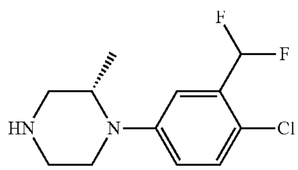 [SMILES: C[C@H]1CNCCN1c1ccc(Cl)c(C(F)F)c1] | (2S)-1-[4-chloro-3-(difluoromethyl)phenyl]-2-methyl-piperazine | A2a + A5a | (S)-3-Methyl-piperazine-1-carboxylic acid tert-butyl ester + 4-bromo-1-chloro-2-(difluoromethyl)benzene (CAS 627527-07-5) | 261 | 261-263 |
| 317 | 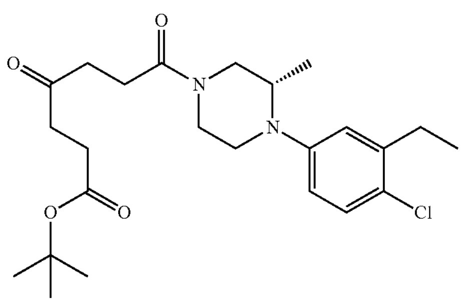 [SMILES: CCc1cc(N2CCN(C(=O)CCC(=O)CCC(=O)OC(C)(C)C)C[C@@H]2C)ccc1Cl] | tert-butyl 7-[(3S)-4-(4-chloro-3-ethyl-phenyl)-3-methyl-piperazin-1-yl]-4,7-dioxo-heptanoate | 2.36 | 1,6-dioxaspiro[4.4]nonane-2,7-dione + Int 313 | 451 | 451-453 |
| 318 | 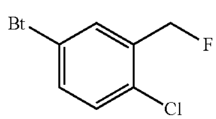 | 4-bromo-1-chloro-2-(fluoromethyl)benzene | 2.37 | 5-bromo-2-chloro-benzaldehyde | 223 | N.A |
| 319 | 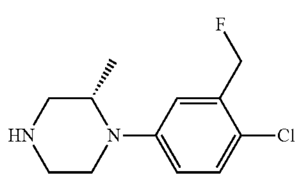 [SMILES: C[C@H]1CNCCN1c1ccc(Cl)c(CF)c1] | (2S)-1-[4-chloro-3-(fluoromethyl)phenyl]-2-methyl-piperazine | A2A + A5b | (S)-3-Methyl-piperazine-1-carboxylic acid tert-butyl ester + 4-bromo-1-chloro-2-(fluoromethyl)benzene Int 318 | 243 | 243 |
| 320 | 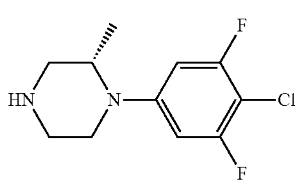 [SMILES: C[C@H]1CNCCN1c1cc(F)c(Cl)c(F)c1] | (2S)-1-(4-chloro-3,5-difluoro-phenyl)-2-methyl-piperazine | A2A + A5b | (S)-3-Methyl-piperazine-1-carboxylic acid tert-butyl ester + 1-bromo-3,5-difluoro-4-chlorobenzene | 247 | N.A. |

TABLE III

Illustrative compounds of the invention
trans:

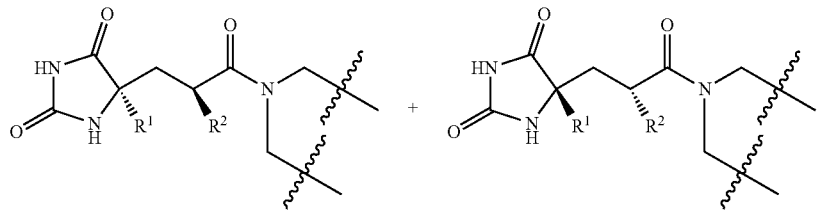

| Cpd | Structure | MW | Ms'd | Mtd | SM |
|---|---|---|---|---|---|
| 001 | 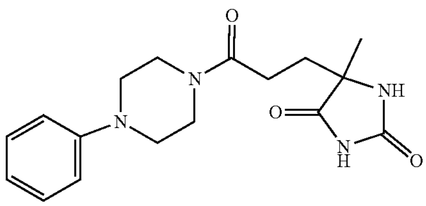 [SMILES: CC1(CCC(=O)N2CCN(c3ccccc3)CC2)NC(=O)NC1=O] | 330 | 331 | H5 | 3-(4-Methyl-2,5-dioxo-imidazolidin-4-yl)propionic acid + 1-Phenyl-piperazine |
| 002 | 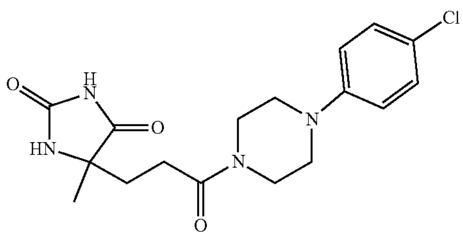 [SMILES: CC1(CCC(=O)N2CCN(c3ccc(Cl)cc3)CC2)NC(=O)NC1=O] | 365 | 365 | H5 | 3-(4-Methyl-2,5-dioxo-imidazolidin-4-yl)propionic acid + 1-(4-Chloro-phenyl)-piperazine |
| 003 | 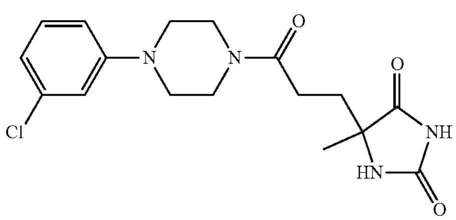 [SMILES: CC1(CCC(=O)N2CCN(c3cccc(Cl)c3)CC2)NC(=O)NC1=O] | 365 | 365-367 | H5 | 3-(4-Methyl-2,5-dioxo-imidazolidin-4-yl)propionic acid + 1-(3-chlorophenyl)piperazine |
| 004 | 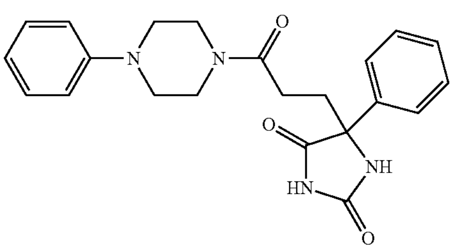 [SMILES: O=C1NC(=O)C(CCC(=O)N2CCN(c3ccccc3)CC2)(c2ccccc2)N1] | 392 | 393 | H5 | 3-(2,5-Dioxo-4-phenyl-imidazolidin-4-yl)propionic acid + 1-Phenyl-piperazine |
| 005 | 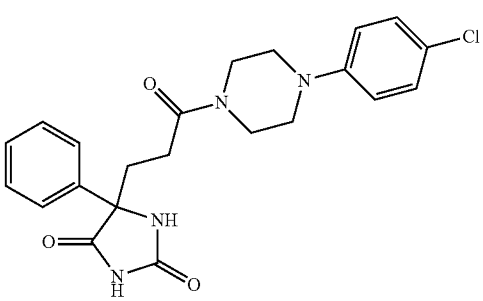 [SMILES: O=C1NC(=O)C(CCC(=O)N2CCN(c3ccc(Cl)cc3)CC2)(c2ccccc2)N1] | 427 | 427-429 | H5 | 3-(2,5-Dioxo-4-phenyl-imidazolidin-4-yl)propionic acid + 1-(4-Chloro-phenyl)-piperazine |

TABLE III-continued

Illustrative compounds of the invention trans:

| Cpd | Structure | MW | Ms'd | Mtd | SM |
|---|---|---|---|---|---|
| 006 | 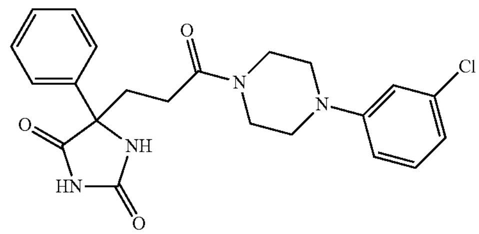 [SMILES: O=C1NC(=O)C(CCC(=O)N2CCN(c3cccc(Cl)c3)CC2)(c2ccccc2)N1] | 427 | 427-429 | H3 | 3-(2,5-Dioxo-4-phenyl-imidazolidin-4-yl)propionic acid + 1-(3-chlorophenyl)piperazine |
| 007 | 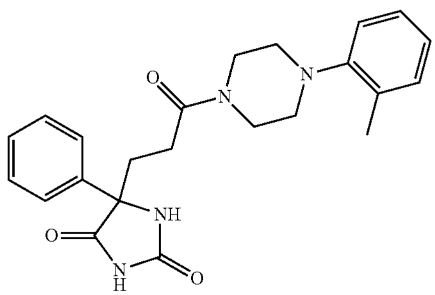 [SMILES: Cc1ccccc1N1CCN(C(=O)CCC2(c3ccccc3)NC(=O)NC2=O)CC1] | 406 | 407 | H1 | 3-(2,5-Dioxo-4-phenyl-imidazolidin-4-yl)propionic acid + 1-(o-tolyl)piperazine dihydrochloride |
| 008 | 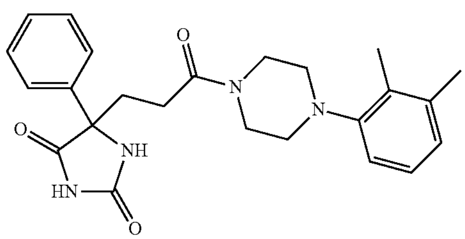 [SMILES: Cc1cccc(N2CCN(C(=O)CCC3(c4ccccc4)NC(=O)NC3=O)CC2)c1C] | 421 | 421 | H1 | 3-(2,5-Dioxo-4-phenyl-imidazolidin-4-yl)propionic acid + 1-(2,3-Dimethylphenyl)piperazine |
| 009 | 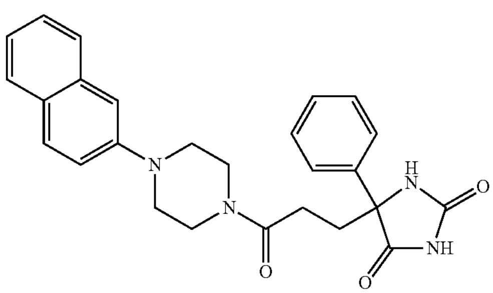 [SMILES: O=C1NC(=O)C(CCC(=O)N2CCN(c3ccc4ccccc4c3)CC2)(c2ccccc2)N1] | 443 | 443 | H1 | 3-(2,5-Dioxo-4-phenyl-imidazolidin-4-yl)propionic acid + 1-(2-naphthyl)piperazine dihydrochloride |

TABLE III-continued

Illustrative compounds of the invention
trans:

| Cpd | Structure | MW | Ms'd | Mtd | SM |
|---|---|---|---|---|---|
| 010 | 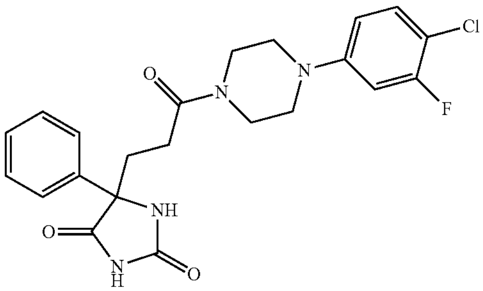 [SMILES: O=C1NC(=O)C(CCC(=O)N2CCN(c3ccc(Cl)c(F)c3)CC2)(c2ccccc2)N1] | 445 | 445 | H1 | 3-(2,5-Dioxo-4-phenyl-imidazolidin-4-yl)propionic acid + 1-(4-Chloro-3-fluorophenyl) piperazine |
| 011 | 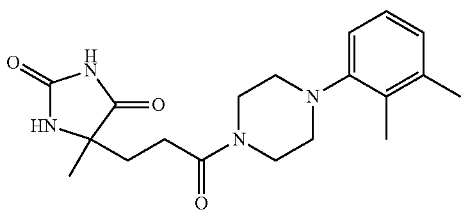 [SMILES: Cc1cccc(N2CCN(C(=O)CCC3(C)NC(=O)NC3=O)CC2)c1C] | 358 | 359 | H1 | 3-(4-Methyl-2,5-dioxo-imidazolidin-4-yl)propionic acid + 1-(2,3-Dimethyl phenyl)piperazine |
| 012 | 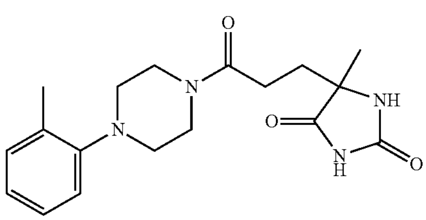 [SMILES: Cc1ccccc1N1CCN(C(=O)CCC2(C)NC(=O)NC2=O)CC1] | 344 | 345 | H1 | 3-(4-Methyl-2,5-dioxo-imidazolidin-4-yl)propionic acid + 1-(o-tolyl)piperazine dihydrochloride |
| 013 | 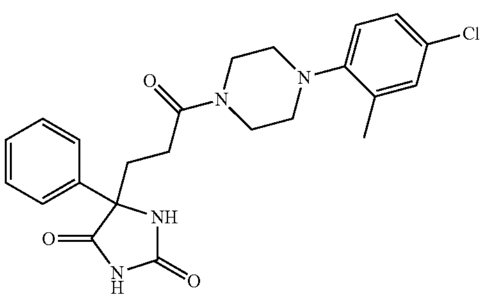 | 441 | 441-443 | H1 | 3-(2,5-Dioxo-4-phenyl-imidazolidin-4-yl)propionic acid + 1-(4-chloro-2-methylphenyl)piperazine hydrochloride |
| 014 | 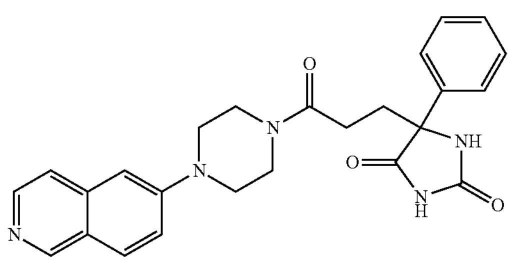 [SMILES: O=C1NC(=O)C(CCC(=O)N2CCN(c3ccc4cnccc4c3)CC2)(c2ccccc2)N1] | 444 | 444 | H1 | 3-(2,5-Dioxo-4-phenyl-imidazolidin-4-yl)propionic acid + 6-(1-piperazinyl)-isoquinoline hydrochloride |

TABLE III-continued

Illustrative compounds of the invention
trans:

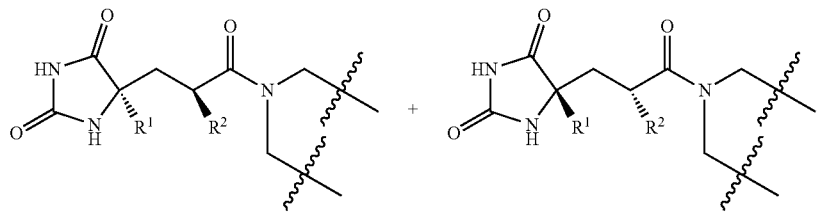

| Cpd | Structure | MW | Ms'd | Mtd | SM |
|---|---|---|---|---|---|
| 015 | 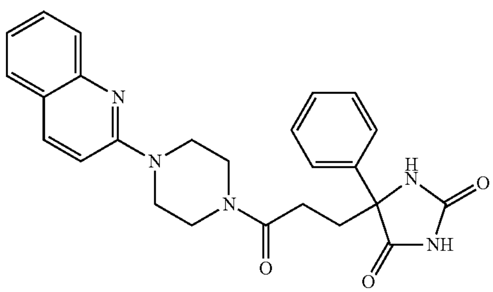 [SMILES: O=C1NC(=O)C(CCC(=O)N2CCN(c3ccc4ccccc4n3)CC2)(c2ccccc2)N1] | 444 | 444 | H1 | 3-(2,5-Dioxo-4-phenyl-imidazolidin-4-yl)propionic acid + 2-piperazin-1-yl-quinoline |
| 016 | 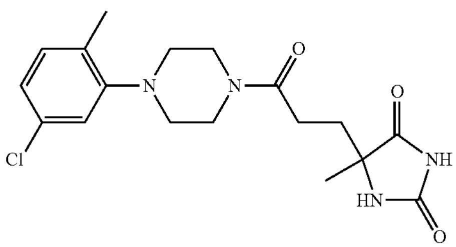 [SMILES: Cc1ccc(Cl)cc1N1CCN(C(=O)CCC2(C)NC(=O)NC2=O)CC1] | 379 | 379-381 | H1 | 3-(4-Methyl-2,5-dioxo-imidazolidin-4-yl)propionic acid + 1-(5-chloro-2-methyl-phenyl)piperazine |
| 017 | 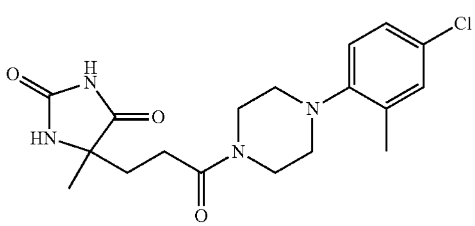 [SMILES: Cc1cc(Cl)ccc1N1CCN(C(=O)CCC2(C)NC(=O)NC2=O)CC1] | 379 | 379-381 | H2 | 3-(4-Methyl-2,5-dioxo-imidazolidin-4-yl)propionic acid + 1-(4-chloro-2-methyl phenyl)piperazine hydrochloride |
| 018 | 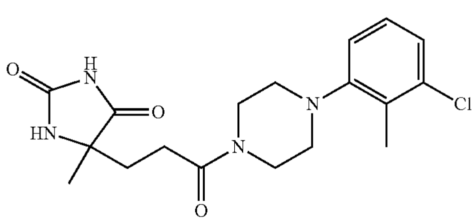 [SMILES: Cc1c(Cl)cccc1N1CCN(C(=O)CCC2(C)NC(=O)NC2=O)CC1] | 379 | 379-381 | H1 | 3-(4-Methyl-2,5-dioxo-imidazolidin-4-yl)propionic acid + 1-(3-chloro-2-methylphenyl)-piperazine |
| 019 | 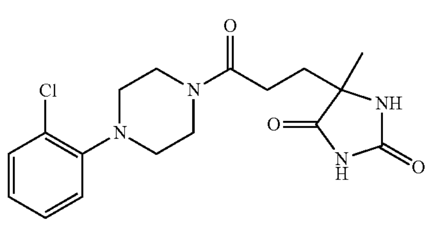 [SMILES: CC1(CCC(=O)N2CCN(c3ccccc3Cl)CC2)NC(=O)NC1=O] | 365 | 365 | H1 | 3-(4-Methyl-2,5-dioxo-imidazolidin-4-yl)propionic acid + 1-(2-chlorophenyl)piperazine hydrochloride |

TABLE III-continued

Illustrative compounds of the invention
trans:

| Cpd | Structure | MW | Ms'd | Mtd | SM |
|---|---|---|---|---|---|
| 020 | 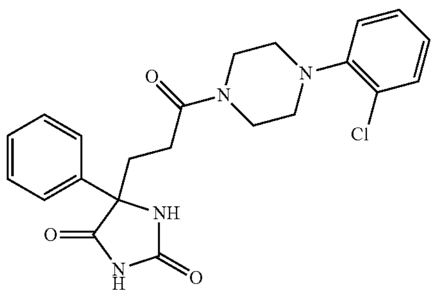 [SMILES: O=C1NC(=O)C(CCC(=O)N2CCN(c3ccccc3Cl)CC2)(c2ccccc2)N1] | 427 | 427 | H1 | 3-(2,5-Dioxo-4-phenyl-imidazolidin-4-yl)propionic acid + 1-(2-chlorophenyl)piperazine hydrochloride |
| 021 | 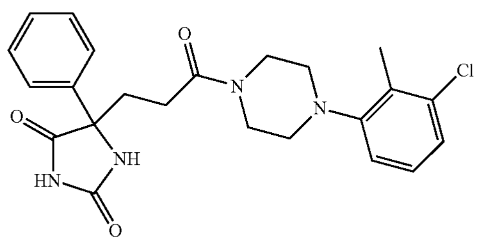 [SMILES: Cc1c(Cl)cccc1N1CCN(C(=O)CCC2(c3ccccc3)NC(=O)NC2=O)CC1] | 441 | 441-443 | H1 | 3-(2,5-Dioxo-4-phenyl-imidazolidin-4-yl)propionic acid + Int 196 |
| 022 | 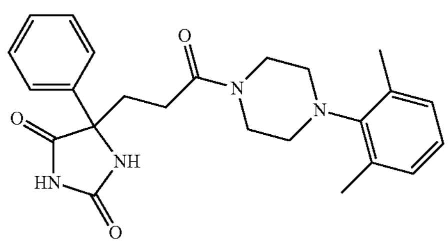 [SMILES: Cc1cccc(C)c1N1CCN(C(=O)CCC2(c3ccccc3)NC(=O)NC2=O)CC1] | 421 | 421 | H1 | 3-(2,5-Dioxo-4-phenyl-imidazolidin-4-yl)propionic acid + 1-(2,6-Dimethyl phenyl)piperazine |
| 023 | 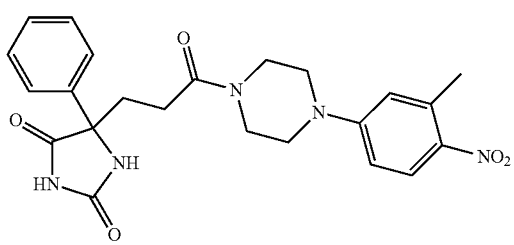 [SMILES: Cc1cc(N2CCN(C(=O)CCC3(c4ccccc4)NC(=O)NC3=O)CC2)ccc1[N+](=O)[O-]] | 451 | 452 | H1 | 3-(2,5-Dioxo-4-phenyl-imidazolidin-4-yl)propionic acid + 1-(3-methyl-4-nitro phenyl)piperazine |
| 024 | 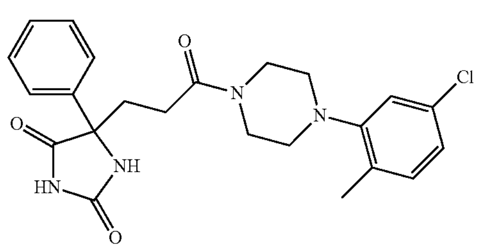 [SMILES: Cc1ccc(Cl)cc1N1CCN(C(=O)CCC2(c3ccccc3)NC(=O)NC2=O)CC1] | 441 | 441-443 | H1 | 3-(2,5-Dioxo-4-phenyl-imidazolidin-4-yl)propionic acid + 1-(5-chloro-2-methyl phenyl)-piperazine |

TABLE III-continued

Illustrative compounds of the invention
trans:

| Cpd | Structure | MW | Ms'd | Mtd | SM |
|---|---|---|---|---|---|
| 025 | 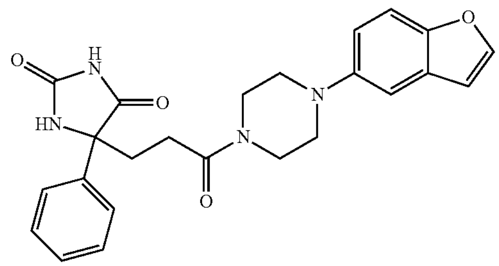 [SMILES: O=C1NC(=O)C(CCC(=O)N2CCN(c3ccc4occc4c3)CC2)(c2ccccc2)N1] | 432 | 433 | H1 | 3-(2,5-Dioxo-4-phenyl-imidazolidin-4-yl)propionic acid + Int 246 |
| 026 | 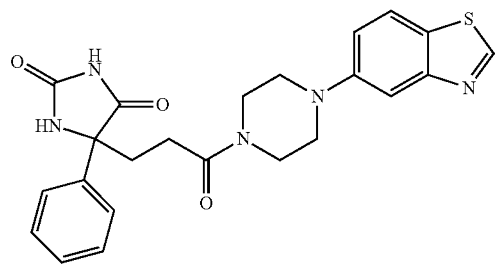 [SMILES: O=C1NC(=O)C(CCC(=O)N2CCN(c3ccc4scnc4c3)CC2)(c2ccccc2)N1] | 450 | 450 | H1 | 3-(2,5-Dioxo-4-phenyl-imidazolidin-4-yl)propionic acid + Int 247 |
| 027 | 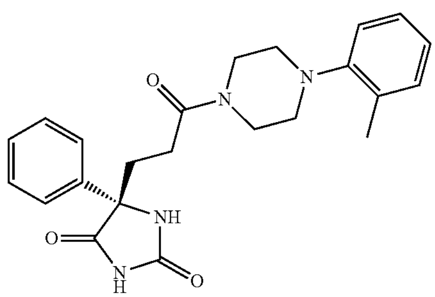 [SMILES: Cc1ccccc1N1CCN(C(=O)CC[C@@]2(c3ccccc3)NC(=O)NC2=O)CC1] | 406 | 407 | 2.9 | Cpd 007 |
| 028 | 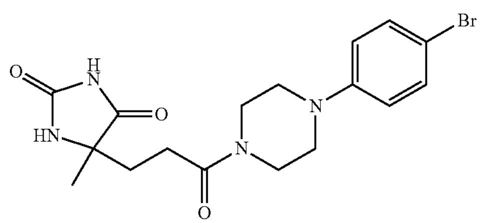 [SMILES: CC1(CCC(=O)N2CCN(c3ccc(Br)cc3)CC2)NC(=O)NC1=O] | 409 | 409-411 | H1 | 3-(4-Methyl-2,5-dioxo-imidazolidin-4-yl)propionic acid + 1-(4-bromophenyl)piperazine |
| 029 | 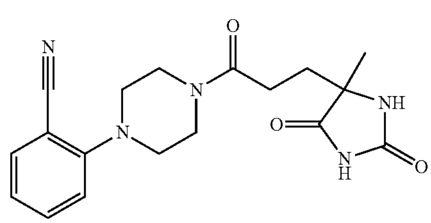 [SMILES: CC1(CCC(=O)N2CCN(c3ccccc3C#N)CC2)NC(=O)NC1=O] | 355 | 356 | H1 | 3-(4-Methyl-2,5-dioxo-imidazolidin-4-yl)propionic acid + 1-(2-cyanophenyl)piperazine |

TABLE III-continued
Illustrative compounds of the invention
trans:
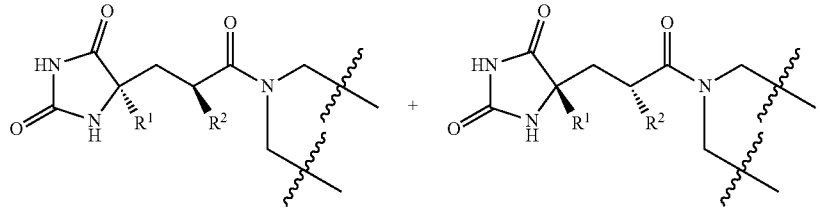
| Cpd | Structure | MW | Ms'd | Mtd | SM |
|---|---|---|---|---|---|
| 030 | 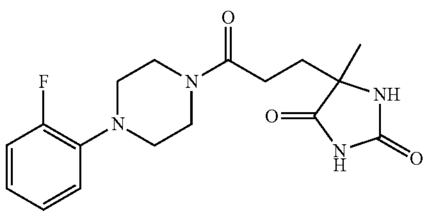 [SMILES: CC1(CCC(=O)N2CCN(c3ccccc3F)CC2)NC(=O)NC1=O] | 348 | 349 | H1 | 3-(4-Methyl-2,5-dioxo-imidazolidin-4-yl)propionic acid + 1-(2-fluorophenyl)piperazine |
| 031 | 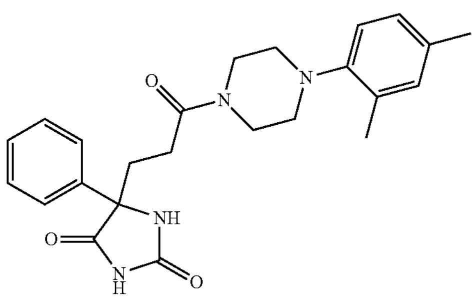 [SMILES: Cc1ccc(N2CCN(C(=O)CCC3(c4ccccc4)NC(=O)NC3=O)CC2)c(C)c1] | 421 | 421 | H1 | 3-(2,5-Dioxo-4-phenyl-imidazolidin-4-yl)propionic acid + 1-(2,4-Dimethylphenyl)piperazine |
| 032 | 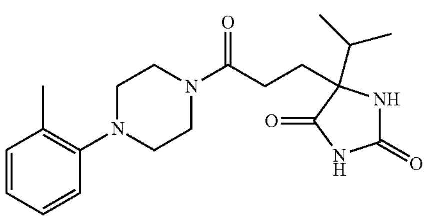 [SMILES: Cc1ccccc1N1CCN(C(=O)CCC2(C(C)C)NC(=O)NC2=O)CC1] | 372 | 373 | F | Int 029 |
| 033 | 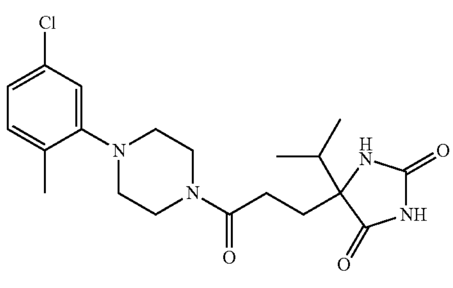 [SMILES: Cc1ccc(Cl)cc1N1CCN(C(=O)CCC2(C(C)C)NC(=O)NC2=O)CC1] | 407 | 407-409 | F | Int 030 |
| 034 | 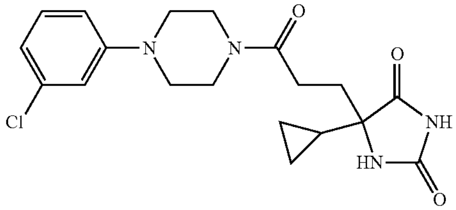 [SMILES: O=C1NC(=O)C(CCC(=O)N2CCN(c3cccc(Cl)c3)CC2)(C2CC2)N1] | 391 | 391-393 | F | Int 031 |

TABLE III-continued

Illustrative compounds of the invention
trans:

| Cpd | Structure | MW | Ms'd | Mtd | SM |
|---|---|---|---|---|---|
| 035 | 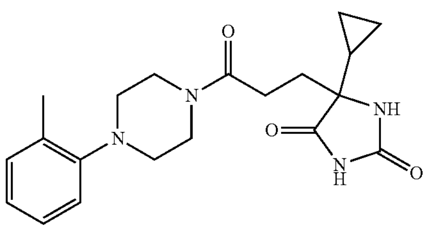 [SMILES: Cc1ccccc1N1CCN(C(=O)CCC2(C3CC3)NC(=O)NC2=O)CC1] | 370 | 371 | F | Int 032 |
| 036 | 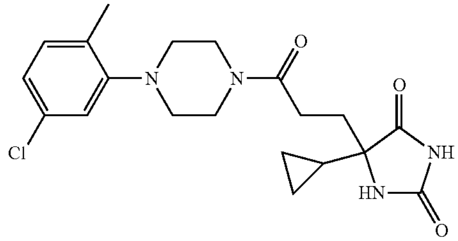 [SMILES: Cc1ccc(Cl)cc1N1CCN(C(=O)CCC2(C3CC3)NC(=O)NC2=O)CC1] | 405 | 405-407 | F | Int 033 |
| 037 | 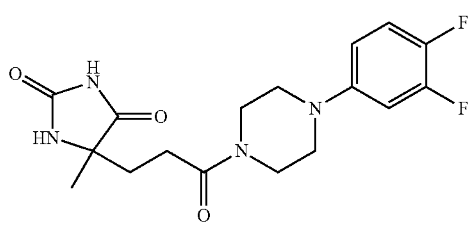 [SMILES: CC1(CCC(=O)N2CCN(c3ccc(F)c(F)c3)CC2)NC(=O)NC1=O] | 366 | 367 | H1 | 3-(4-Methyl-2,5-dioxo-imidazolidin-4-yl)propionic acid + 1-(3,4-difluorophenyl)piperazine |
| 038 | 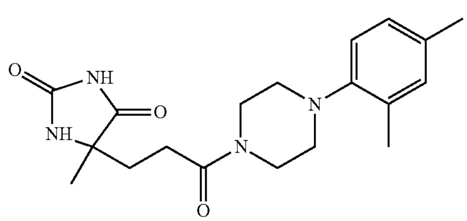 [SMILES: Cc1ccc(N2CCN(C(=O)CCC3(C)NC(=O)NC3=O)CC2)c(C)c1] | 358 | 359 | H1 | 3-(4-Methyl-2,5-dioxo-imidazolidin-4-yl)propionic acid + 1-(2,4-Dimethyl phenyl)piperazine |
| 039 | 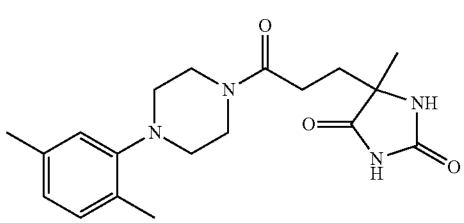 [SMILES: Cc1ccc(C)c(N2CCN(C(=O)CCC3(C)NC(=O)NC3=O)CC2)c1] | 358 | 359 | H1 | 3-(4-Methyl-2,5-dioxo-imidazolidin-4-yl)propionic acid + 1-(2,5-Dimethyl phenyl)piperazine |

TABLE III-continued

Illustrative compounds of the invention
trans:

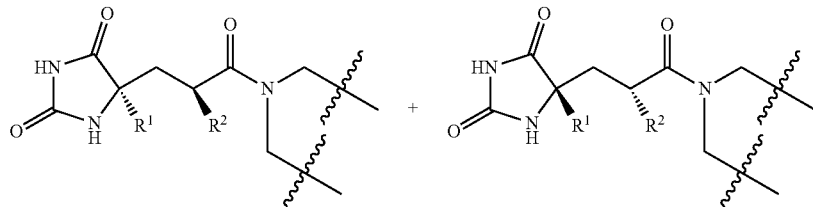

| Cpd | Structure | MW | Ms'd | Mtd | SM |
|---|---|---|---|---|---|
| 040 | 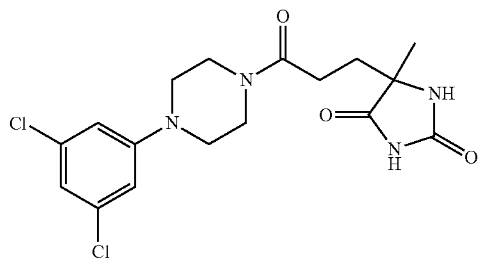 [SMILES: CC1(CCC(=O)N2CCN(c3cc(Cl)cc(Cl)c3)CC2)NC(=O)NC1=O] | 399 | 399-401 | H1 | 3-(4-Methyl-2,5-dioxo-imidazolidin-4-yl)propionic acid + 1-(3,5-dichloro phenyl)piperazine |
| 041 | 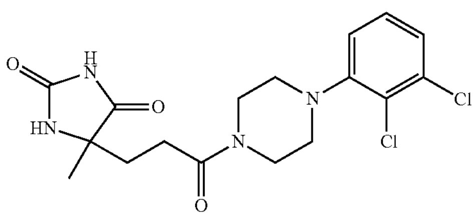 [SMILES: CC1(CCC(=O)N2CCN(c3cccc(Cl)c3Cl)CC2)NC(=O)NC1=O] | 399 | 399-401 | H1 | 3-(4-Methyl-2,5-dioxo-imidazolidin-4-yl)propionic acid + 1-(2,3-dichloro phenyl)-piperazine |
| 042 | 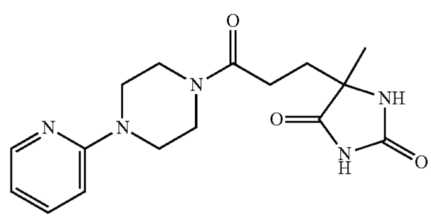 [SMILES: CC1(CCC(=O)N2CCN(c3ccccn3)CC2)NC(=O)NC1=O] | 331 | 332 | H1 | 3-(4-Methyl-2,5-dioxo-imidazolidin-4-yl)propionic acid + 1-(2-pyridyl) piperazine |
| 043 | 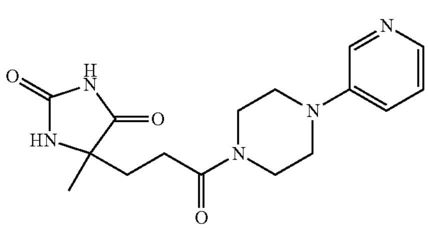 [SMILES: CC1(CCC(=O)N2CCN(c3cccnc3)CC2)NC(=O)NC1=O] | 331 | 332 | H1 | 3-(4-Methyl-2,5-dioxo-imidazolidin-4-yl)propionic acid + 1-Pyridin-3-yl-piperazine |
| 044 | 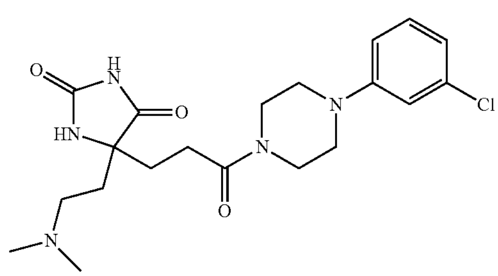 [SMILES: CN(C)CCC1(CCC(=O)N2CCN(c3cccc(Cl)c3)CC2)NC(=O)NC1=O] | 422 | 422-424 | F | Int 109 |

TABLE III-continued

Illustrative compounds of the invention
trans:

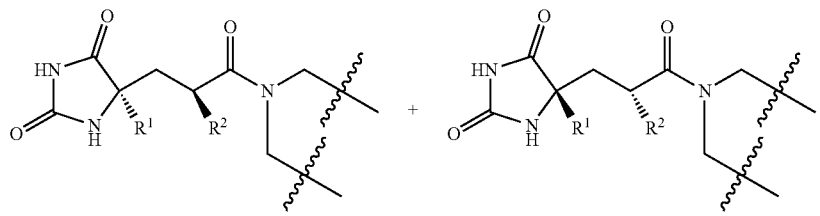

| Cpd | Structure | MW | Ms'd | Mtd | SM |
|---|---|---|---|---|---|
| 045 | 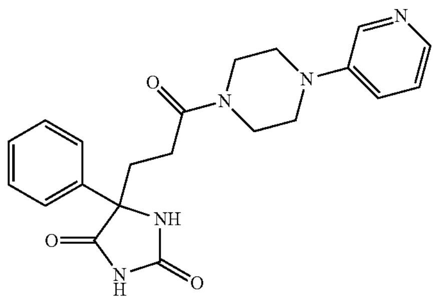 [SMILES: O=C1NC(=O)C(CCC(=O)N2CCN(c3cccnc3)CC2)(c2ccccc2)N1] | 393 | 394 | H1 | 3-(2,5-Dioxo-4-phenyl-imidazolidin-4-yl)propionic acid + 1-Pyridin-3-yl-piperazine |
| 046 | 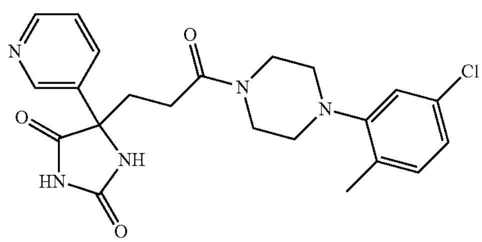 [SMILES: Cc1ccc(Cl)cc1N1CCN(C(=O)CCC2(c3cccnc3)NC(=O)NC2=O)CC1] | 442 | 442-44 | F | Int 025 |
| 047 | 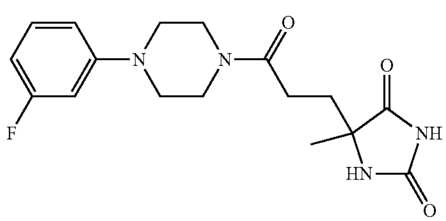 [SMILES: CC1(CCC(=O)N2CCN(c3cccc(F)c3)CC2)NC(=O)NC1=O] | 348 | 349 | H1 | 3-(4-Methyl-2,5-dioxo-imidazolidin-4-yl)propionic acid + 1-(3-fluorophenyl)piperazine |
| 048 | 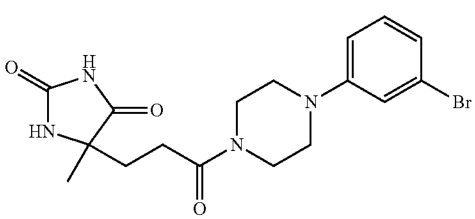 [SMILES: CC1(CCC(=O)N2CCN(c3cccc(Br)c3)CC2)NC(=O)NC1=O] | 409 | 409-411 | H1 | 3-(4-Methyl-2,5-dioxo-imidazolidin-4-yl)propionic acid + 1-(3-bromophenyl)piperazine |
| 049 | 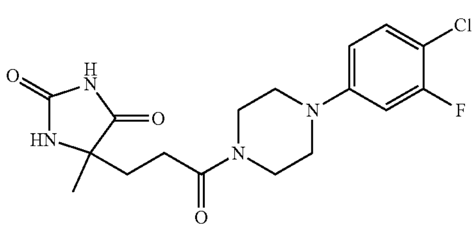 [SMILES: CC1(CCC(=O)N2CCN(c3ccc(Cl)c(F)c3)CC2)NC(=O)NC1=O] | 383 | 383-385 | H1 | 3-(4-Methyl-2,5-dioxo-imidazolidin-4-yl)propionic acid + 1-(4-Chloro-3-fluorophenyl)piperazine |

TABLE III-continued
Illustrative compounds of the invention
trans:
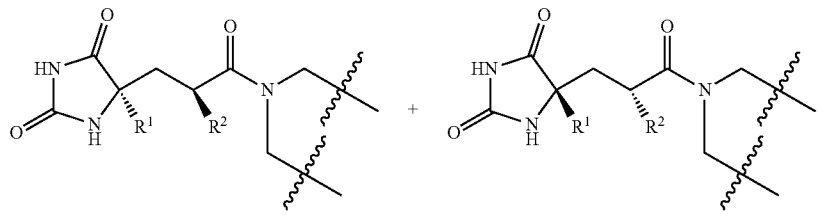
| Cpd | Structure | MW | Ms'd | Mtd | SM |
|---|---|---|---|---|---|
| 050 | | 373 | 375 | H1 | 3-(4-Methyl-2,5-dioxo-imidazolidin-4-yl)propionic acid + Int 265 |
| 051 | | 362 | 363 | H1 | 3-(4-Methyl-2,5-dioxo-imidazolidin-4-yl)propionic acid + Int 204 |
| 052 | | 383 | 383-385 | H1 | 3-(4-Methyl-2,5-dioxo-imidazolidin-4-yl)propionic acid + 1-(3-Chloro-4-fluoro phenyl)piperazine dihydrochloride |
| 053 | | 393 | 393-395 | F | Int 074 |
| 054 | | 427 | 427-429 | F | Int 075 |

TABLE III-continued

Illustrative compounds of the invention
trans:

| Cpd | Structure | MW | Ms'd | Mtd | SM |
|---|---|---|---|---|---|
| 055 | 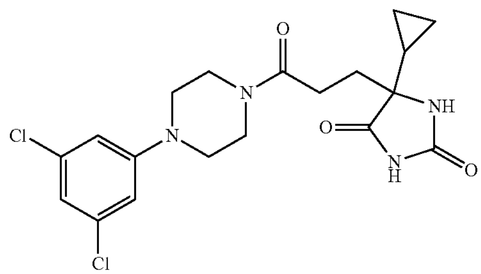 [SMILES: O=C1NC(=O)C(CCC(=O)N2CCN(c3cc(Cl)cc(Cl)c3)CC2)(C2CC2)N1] | 425 | 425-427 | F | Int 045 |
| 056 | 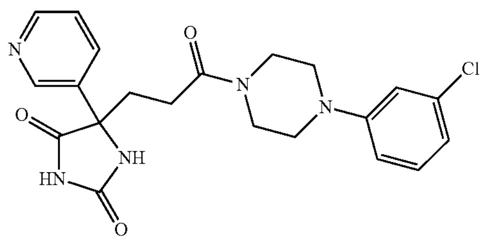 [SMILES: O=C1NC(=O)C(CCC(=O)N2CCN(c3cccc(Cl)c3)CC2)(c2cccnc2)N1] | 428 | 428-430 | F | Int 026 |
| 057 | 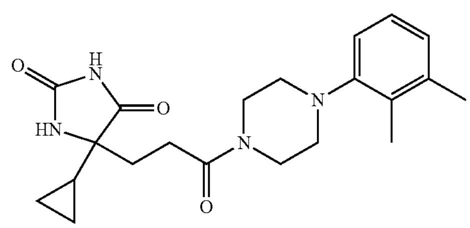 [SMILES: Cc1cccc(N2CCN(C(=O)CCC3(C4CC4)NC(=O)NC3=O)CC2)c1C] | 384 | 385 | F | Int 082 |
| 058 | 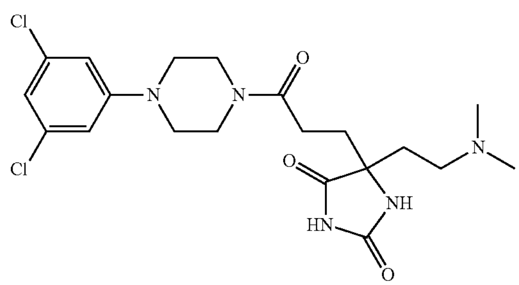 [SMILES: CN(C)CCC1(CCC(=O)N2CCN(c3cc(Cl)cc(Cl)c3)CC2)NC(=O)NC1=O] | 456 | 456-458 | F | Int 086 |
| 059 | 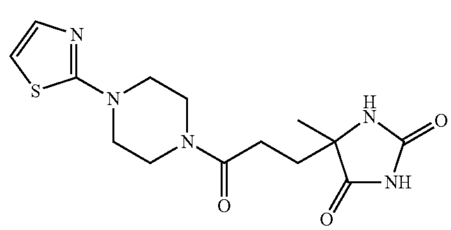 [SMILES: CC1(CCC(=O)N2CCN(c3nccs3)CC2)NC(=O)NC1=O] | 337 | 338 | H3 | 3-(4-Methyl-2,5-dioxo-imidazolidin-4-yl)propionic acid + 1-Thiazol-2-yl-piperazine |

TABLE III-continued
Illustrative compounds of the invention
trans:
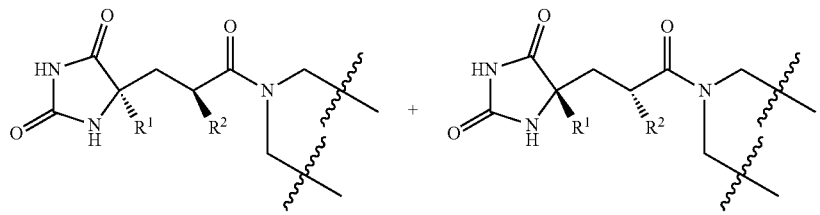
| Cpd | Structure | MW | Ms'd | Mtd | SM |
|---|---|---|---|---|---|
| 060 | 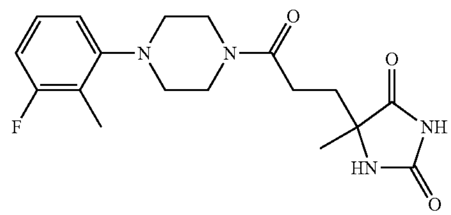 [SMILES: Cc1c(F)cccc1N1CCN(C(=O)CCC2(C)NC(=O)NC2=O)CC1] | 362 | 363 | H1 | 3-(4-Methyl-2,5-dioxo-imidazolidin-4-yl)propionic acid + Int 266 |
| 061 | 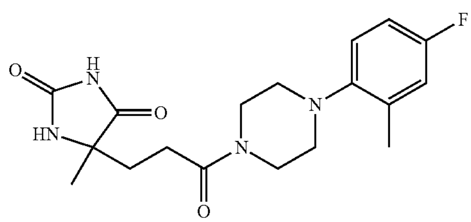 | 362 | 363 | H1 | 3-(4-Methyl-2,5-dioxo-imidazolidin-4-yl)propionic acid + Int 267 |
| 062 | 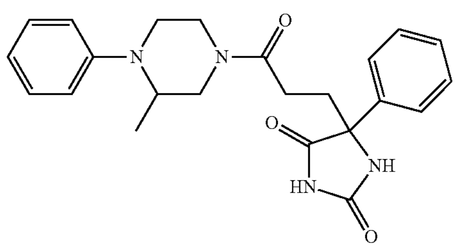 [SMILES: CC1CN(C(=O)CCC2(c3ccccc3)NC(=O)NC2=O)CCN1c1ccccc1] | 406 | 407 | H1 | 3-(2,5-Dioxo-4-phenyl-imidazolidin-4-yl)propionic acid + 2-Methyl-1-phenyl piperazine |
| 063 | 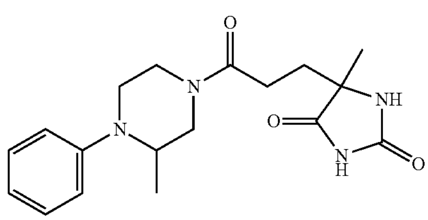 [SMILES: CC1CN(C(=O)CCC2(C)NC(=O)NC2=O)CCN1c1ccccc1] | 344 | 345 | H1 | 3-(4-Methyl-2,5-dioxo-imidazolidin-4-yl)propionic acid + 2-Methyl-1-phenyl piperazine |
| 064 | 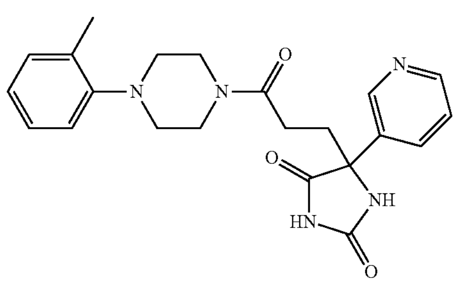 [SMILES: Cc1ccccc1N1CCN(C(=O)CCC2(c3cccnc3)NC(=O)NC2=O)CC1] | 407 | 408 | F | Int 027 |

TABLE III-continued

Illustrative compounds of the invention
trans:

| Cpd | Structure | MW | Ms'd | Mtd | SM |
|---|---|---|---|---|---|
| 065 | 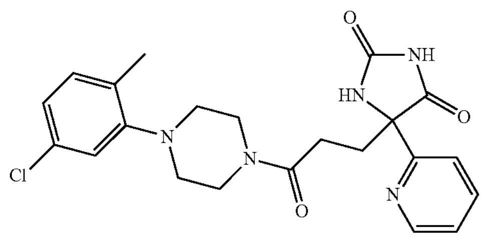 [SMILES: Cc1ccc(Cl)cc1N1CCN(C(=O)CCC2(c3ccccn3)NC(=O)NC2=O)CC1] | 442 | 442-444 | F | Int 028 |
| 066 | 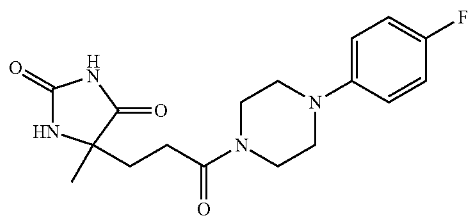 [SMILES: CC1(CCC(=O)N2CCN(c3ccc(F)cc3)CC2)NC(=O)NC1=O] | 348 | 349 | H3 | 3-(4-Methyl-2,5-dioxo-imidazolidin-4-yl)propionic acid + 1-(4-fluorophenyl)piperazine |
| 067 | 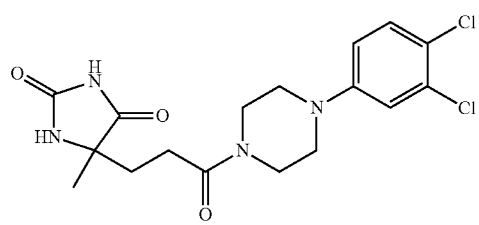 [SMILES: CC1(CCC(=O)N2CCN(c3ccc(Cl)c(Cl)c3)CC2)NC(=O)NC1=O] | 399 | 399-401 | H3 | 3-(4-Methyl-2,5-dioxo-imidazolidin-4-yl)propionic acid + 1-(3,4-dichloro phenyl)piperazine hydrochloride |
| 068 | 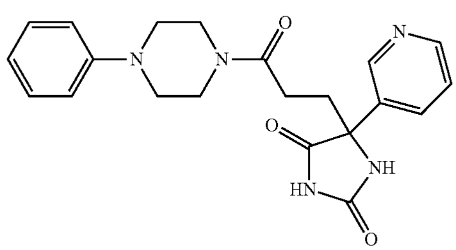 [SMILES: O=C1NC(=O)C(CCC(=O)N2CCN(c3ccccc3)CC2)(c2cccnc2)N1] | 393 | 394 | H1 | Int 132 + 1-Phenyl-piperazine |
| 069 | 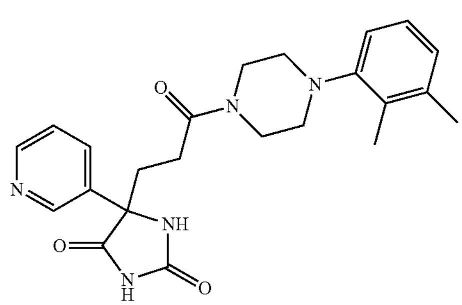 [SMILES: Cc1cccc(N2CCN(C(=O)CCC3(c4cccnc4)NC(=O)NC3=O)CC2)c1C] | 422 | 422 | H1 | Int 132 + 1-(2,3-Dimethyl-phenyl)-piperazine |

TABLE III-continued
Illustrative compounds of the invention
trans:
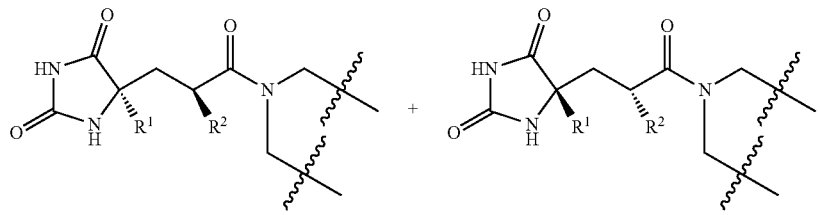
| Cpd | Structure | MW | Ms'd | Mtd | SM |
|---|---|---|---|---|---|
| 070 | | 405 | 405-407 | F | Int 034 |
| 071 | | 419 | 419-421 | F | Int 035 |
| 072 | | 433 | 433-435 | F | Int 111 |
| 073 | | 447 | 393 | F | Int 080 |

TABLE III-continued

Illustrative compounds of the invention
trans:

| Cpd | Structure | MW | Ms'd | Mtd | SM |
|---|---|---|---|---|---|
| 074 | 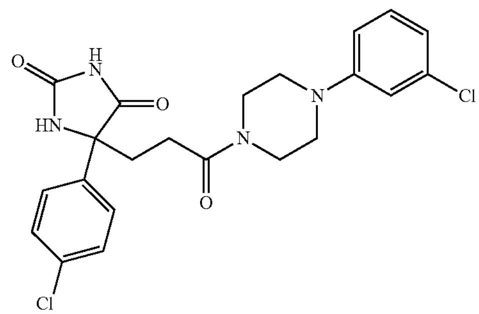 [SMILES: O=C1NC(=O)C(CCC(=O)N2CCN(c3cccc(Cl)c3)CC2)(c2ccc(Cl)cc2)N1] | 461 | 461-463 | H1 | 3-[4-(4-Chloro-phenyl)-2,5-dioxo-imidazolidin-4-yl] propionic acid + 1-(3-chlorophenyl) piperazine |
| 075 | 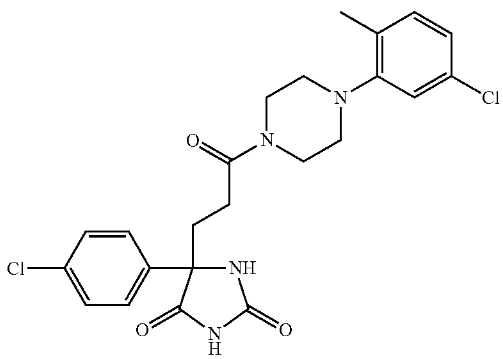 [SMILES: Cc1ccc(Cl)cc1N1CCN(C(=O)CCC2(c3ccc(Cl)cc3)NC(=O)NC2=O)CC1] | 475 | 475-477 | H1 | 3-[4-(4-Chloro-phenyl)-2,5-dioxo-imidazolidin-4-yl]-propionic acid + 1-(5-chloro-2-methylphenyl)-piperazine |
| 076 | 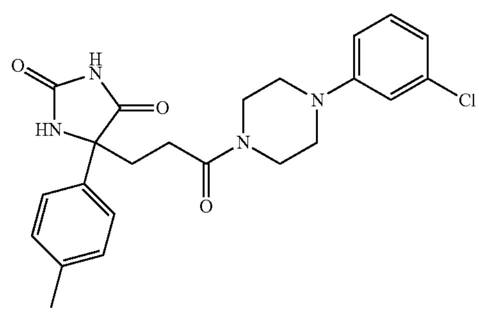 [SMILES: Cc1ccc(C2(CCC(=O)N3CCN(c4cccc(Cl)c4)CC3)NC(=O)NC2=O)cc1] | 441 | 441-443 | H1 | 3-(2,5-Dioxo-4-p-tolyl-imidazolidin-4-yl)propionic acid + 1-(3-chloro phenyl)piperazine |
| 077 | 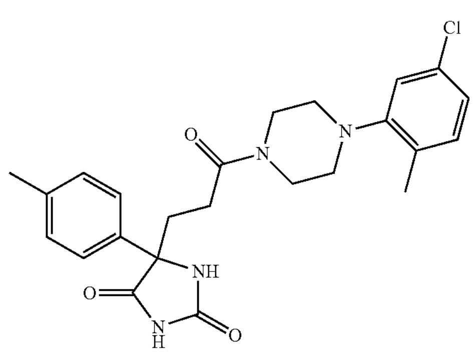 [SMILES: Cc1ccc(C2(CCC(=O)N3CCN(c4cc(Cl)ccc4C)CC3)NC(=O)NC2=O)cc1] | 455 | 455 | H1 | 3-(2,5-Dioxo-4-p-tolyl-imidazolidin-4-yl)-propionic acid + 1-(5-chloro-2-methylphenyl)-piperazine |

TABLE III-continued

Illustrative compounds of the invention
trans:

| Cpd | Structure | MW | Ms'd | Mtd | SM |
|---|---|---|---|---|---|
| 078 | 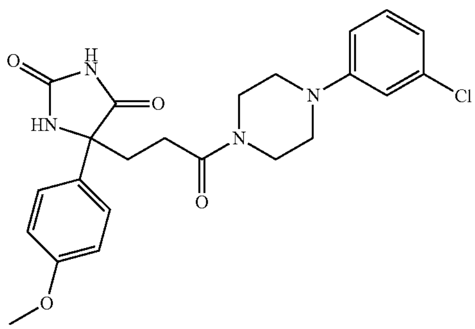 [SMILES: COc1ccc(C2(CCC(=O)N3CCN(c4cccc(Cl)c4)CC3)NC(=O)NC2=O)cc1] | 457 | 457 | H1 | 3-[4-(4-Methoxy-phenyl)-2,5-dioxo-imidazolidin-4-yl]-propionic acid + 1-(3-chlorophenyl) piperazine |
| 079 | 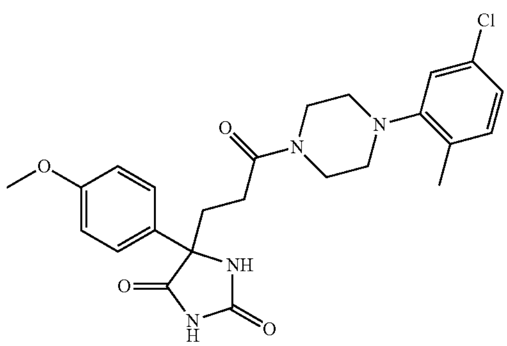 [SMILES: COc1ccc(C2(CCC(=O)N3CCN(c4cc(Cl)ccc4C)CC3)NC(=O)NC2=O)cc1] | 471 | 471-473 | H1 | 3-[4-(4-Methoxy-phenyl)-2,5-dioxo-imidazolidin-4-yl]-propionic acid + 1-(5-chloro-2-methylphenyl)-piperazine |
| 080 | 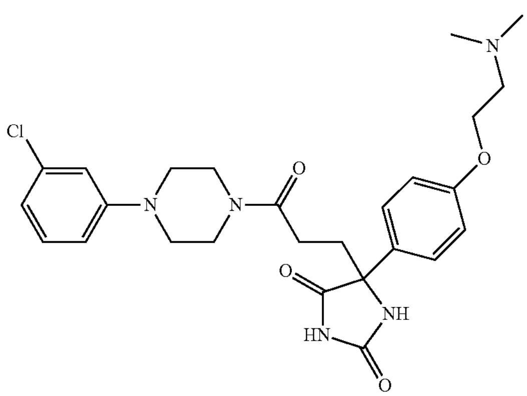 [SMILES: CN(C)CCOc1ccc(C2(CCC(=O)N3CCN(c4cccc(Cl)c4)CC3)NC(=O)NC2=O)cc1] | 514 | 514 | F | Int 088 |

TABLE III-continued
Illustrative compounds of the invention
trans:
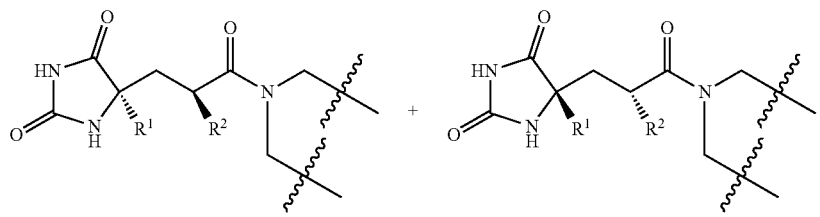
| Cpd | Structure | MW | Ms'd | Mtd | SM |
|---|---|---|---|---|---|
| 081 | 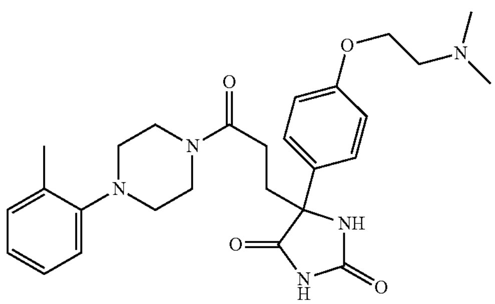 [SMILES: Cc1ccccc1N1CCN(C(=O)CCC2(c3ccc(OCCN(C)C)cc3)NC(=O)NC2=O)CC1] | 494 | 494 | F | Int 089 |
| 082 | 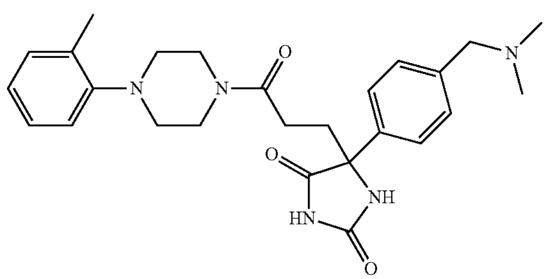 [SMILES: Cc1ccccc1N1CCN(C(=O)CCC2(c3ccc(CN(C)C)cc3)NC(=O)NC2=O)CC1] | 464 | 464 | F | Int 087 |
| 083 | 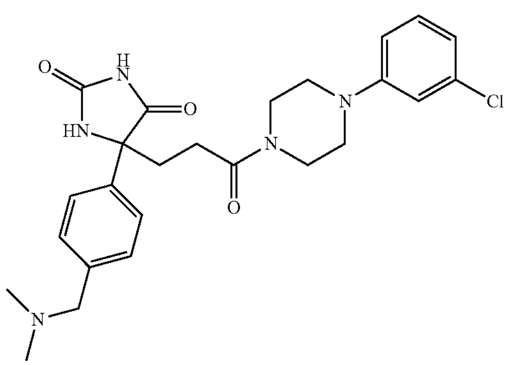 [SMILES: CN(C)Cc1ccc(C2(CCC(=O)N3CCN(c4cccc(Cl)c4)CC3)NC(=O)NC2=O)cc1] | 484 | 484 | F | Int 090 |
| 084 | 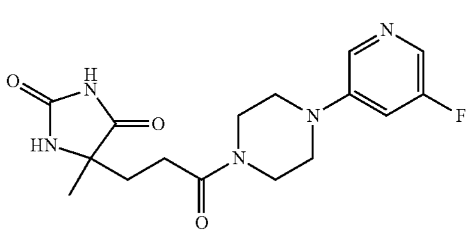 [SMILES: CC1(CCC(=O)N2CCN(c3cncc(F)c3)CC2)NC(=O)NC1=O] | 349 | 350 | H3 | 3-(4-Methyl-2,5-dioxo-imidazolidin-4-yl)propionic acid + Int 268 |

TABLE III-continued

Illustrative compounds of the invention
trans:

| Cpd | Structure | MW | Ms'd | Mtd | SM |
|-----|-----------|----|------|-----|-----|
| 085 | | 366 | 366-368 | H3 | 3-(4-Methyl-2,5-dioxo-imidazolidin-4-yl)propionic acid + Int 269 |
| 086 | | 410 | 410-412 | H3 | 3-(4-Methyl-2,5-dioxo-imidazolidin-4-yl)propionic acid + Int 270 |
| 087 | | 422 | 422 | F | Int 076 |
| 088 | | 422 | 422 | H3 | Int 132 + 1-(2,5-Dimethylphenyl)piperazine |
| 089 | | 384 | 386 | F | Int 077 |

TABLE III-continued

Illustrative compounds of the invention
trans:

| Cpd | Structure | MW | Ms'd | Mtd | SM |
|---|---|---|---|---|---|
| 090 | 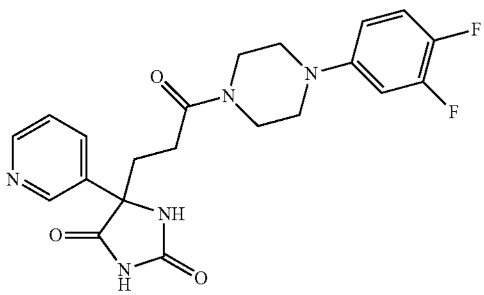 [SMILES: O=C1NC(=O)C(CCC(=O)N2CCN(c3ccc(F)c(F)c3)CC2)(c2cccnc2)N1] | 429 | 430 | H1 | Int 132 + 1-(3,4-difluoro phenyl)piperazine |
| 091 | 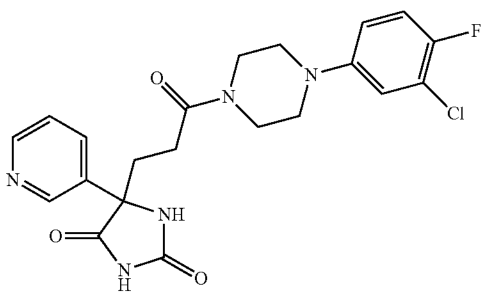 [SMILES: O=C1NC(=O)C(CCC(=O)N2CCN(c3ccc(F)c(Cl)c3)CC2)(c2cccnc2)N1] | 446 | 446-448 | H1 | Int 132 + 1-(3-Chloro-4-fluorophenyl)piperazine dihydrochloride |
| 092 | 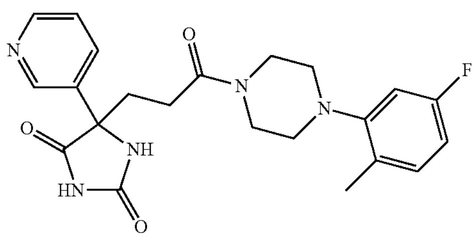 [SMILES: Cc1ccc(F)cc1N1CCN(C(=O)CCC2(c3cccnc3)NC(=O)NC2=O)CC1] | 425 | 426 | H1 | Int 132 + Int 204 |
| 093 | 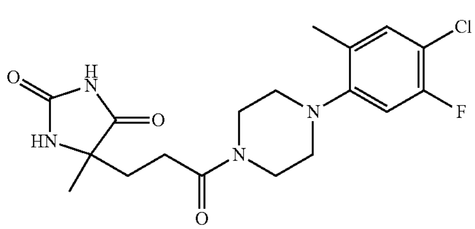 [SMILES: Cc1cc(Cl)c(F)cc1N1CCN(C(=O)CCC2(C)NC(=O)NC2=O)CC1] | 397 | 397 | H1 | 3-(4-Methyl-2,5-dioxo-imidazolidin-4-yl)propionic acid + Int 272 |
| 094 | 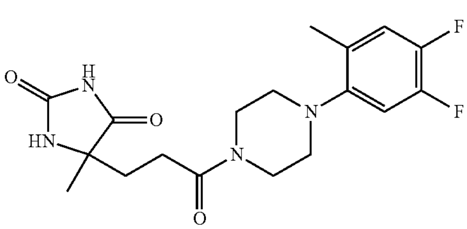 [SMILES: Cc1cc(F)c(F)cc1N1CCN(C(=O)CCC2(C)NC(=O)NC2=O)CC1] | 380 | 381 | H1 | 3-(4-Methyl-2,5-dioxo-imidazolidin-4-yl)propionic acid + Int 273 |

TABLE III-continued
Illustrative compounds of the invention
trans:
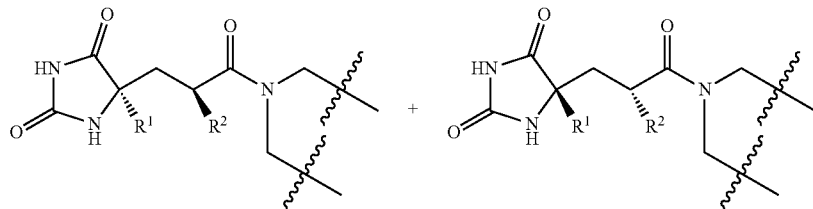
| Cpd | Structure | MW | Ms'd | Mtd | SM |
|---|---|---|---|---|---|
| 095 | 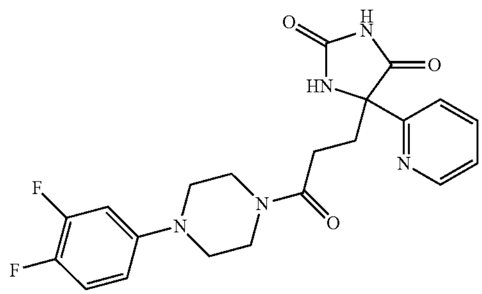 [SMILES: O=C1NC(=O)C(CCC(=O)N2CCN(c3ccc(F)c(F)c3)CC2)(c2ccccn2)N1] | 429 | 430 | F | Int 083 |
| 096 | 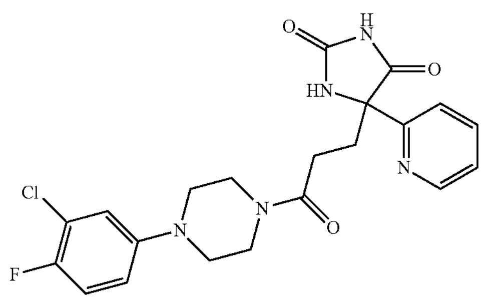 [SMILES: O=C1NC(=O)C(CCC(=O)N2CCN(c3ccc(F)c(Cl)c3)CC2)(c2ccccn2)N1] | 446 | 446-448 | F | Int 084 |
| 097 | 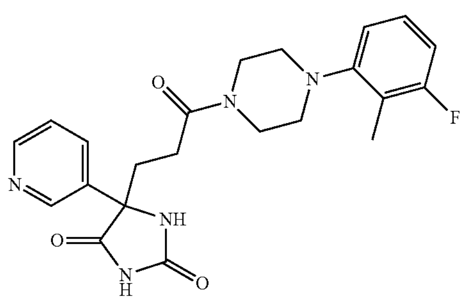 [SMILES: Cc1c(F)cccc1N1CCN(C(=O)CCC2(c3cccnc3)NC(=O)NC2=O)CC1] | 425 | 426 | H3 | Int 132 + 1-(3-fluoro-2-methylphenyl)-piperazine |
| 098 | 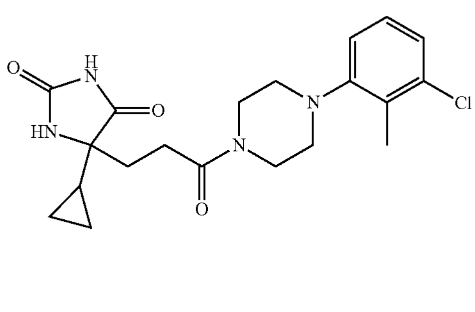 [SMILES: Cc1c(Cl)cccc1N1CCN(C(=O)CCC2(C3CC3)NC(=O)NC2=O)CC1] | 405 | 405-407 | F | Int 036 |

TABLE III-continued
Illustrative compounds of the invention
trans:
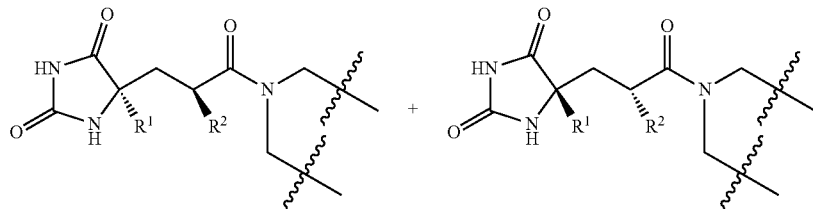
| Cpd | Structure | MW | Ms'd | Mtd | SM |
|---|---|---|---|---|---|
| 099 | 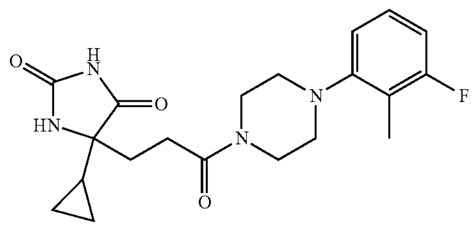 [SMILES: Cc1c(F)cccc1N1CCN(C(=O)CCC2(C3CC3)NC(=O)NC2=O)CC1] | 388 | 389 | F | Int 037 |
| 100 | 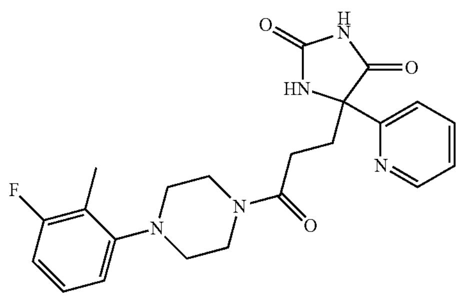 [SMILES: Cc1c(F)cccc1N1CCN(C(=O)CCC2(c3ccccn3)NC(=O)NC2=O)CC1] | 425 | 426 | F | Int 038 |
| 101 | 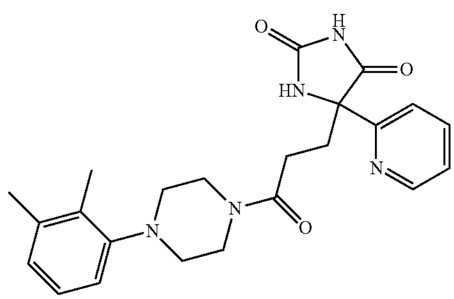 [SMILES: Cc1cccc(N2CCN(C(=O)CCC3(c4ccccn4)NC(=O)NC3=O)CC2)c1C] | 422 | 422 | F | Int 039 |
| 102 | 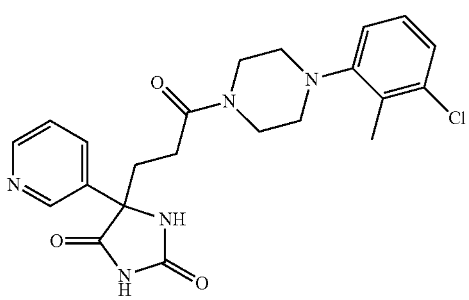 [SMILES: Cc1c(Cl)cccc1N1CCN(C(=O)CCC2(c3cccnc3)NC(=O)NC2=O)CC1] | 442 | 442-444 | H3 | Int 132 + 1-(3-chloro-2-methylphenyl)-piperazine |

TABLE III-continued

Illustrative compounds of the invention
trans:

| Cpd | Structure | MW | Ms'd | Mtd | SM |
|---|---|---|---|---|---|
| 103 | 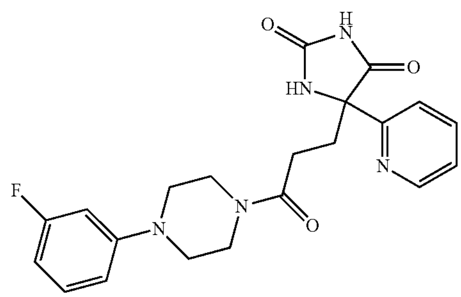 [SMILES: O=C1NC(=O)C(CCC(=O)N2CCN(c3cccc(F)c3)CC2)(c2ccccn2)N1] | 411 | 412 | F | Int 112 |
| 104 | 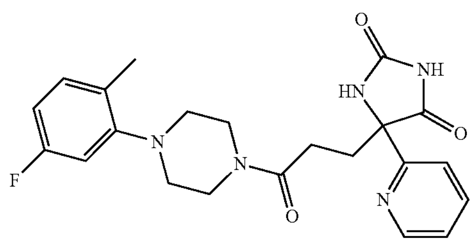 [SMILES: Cc1ccc(F)cc1N1CCN(C(=O)CCC2(c3ccccn3)NC(=O)NC2=O)CC1] | 425 | 426 | F | Int 113 |
| 105 | 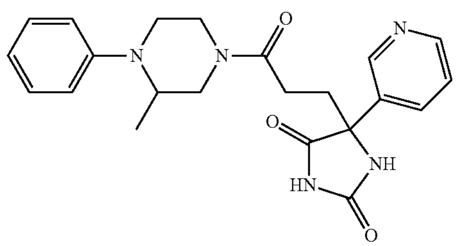 [SMILES: CC1CN(C(=O)CCC2(c3cccnc3)NC(=O)NC2=O)CCN1c1ccccc1] | 407 | 408 | H3 | Int 132 + 2-methyl-1-phenyl piperazine |
| 106 | 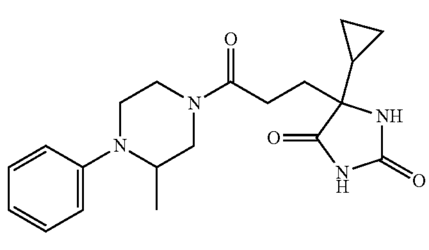 [SMILES: CC1CN(C(=O)CCC2(C3CC3)NC(=O)NC2=O)CCN1c1ccccc1] | 370 | 371 | H1 | Int 162 + 2-methyl-1-phenylpiperazine |
| 107 | 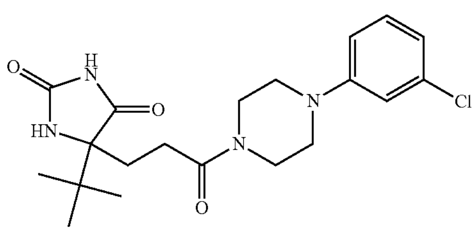 [SMILES: CC(C)(C)C1(CCC(=O)N2CCN(c3cccc(Cl)c3)CC2)NC(=O)NC1=O] | 407 | 407 | F | Int 091 |

TABLE III-continued

Illustrative compounds of the invention
trans:

| Cpd | Structure | MW | Ms'd | Mtd | SM |
|---|---|---|---|---|---|
| 108 | | 421 | 421 | F | Int 092 |
| 109 | | 419 | 419 | F | Int 093 |
| 110 | | 433 | 433 | F | Int 094 |
| 111 | | 462 | 462-464 | H1 | Int 132 + 1-(3,5-dichloro phenyl)piperazine |
| 112 | | 411 | 412 | H1 | Int 132 + 1-(3-fluoro phenyl)piperazine |

TABLE III-continued
Illustrative compounds of the invention
trans:
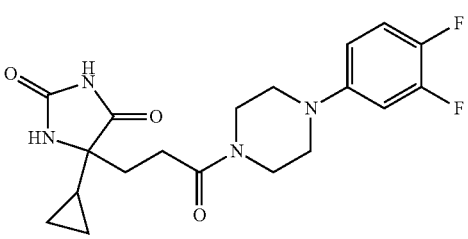 [SMILES: O=C1NC(=O)C(CCC(=O)N2CCN(c3ccc(F)c(F)c3)CC2)(C2CC2)N1]
| Cpd | Structure | MW | Ms'd | Mtd | SM |
|---|---|---|---|---|---|
| 113 | 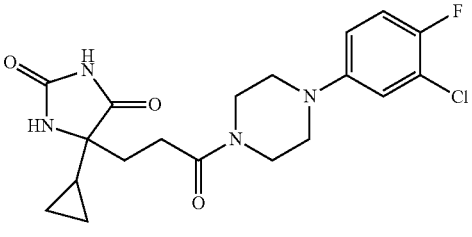 [SMILES: O=C1NC(=O)C(CCC(=O)N2CCN(c3ccc(F)c(Cl)c3)CC2)(C2CC2)N1] | 392 | 393 | H1 | Int 162 + 1-(3,4-difluoro phenyl)piperazine |
| 114 | 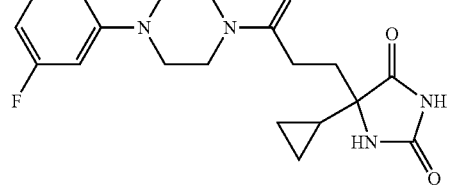 | 409 | 409-411 | H1 | Int 162 + 1-(3-Chloro-4-fluorophenyl) piperazine dihydrochloride |
| 115 | 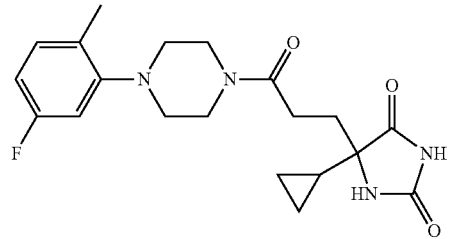 [SMILES: Cc1ccc(F)cc1N1CCN(C(=O)CCC2(C3CC3)NC(=O)NC2=O)CC1] | 374 | 375 | H1 | Int 162 + 1-(3-fluorophenyl) piperazine |
| 116 | 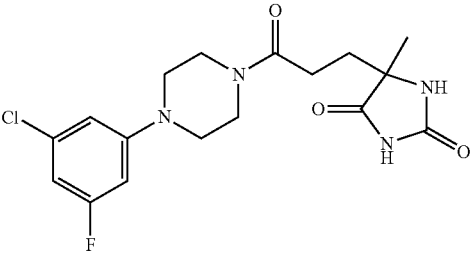 | 388 | 389 | H1 | Int 162 + Int 204 |
| 117 | 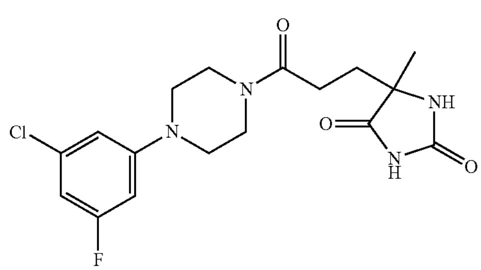 [SMILES: CC1(CCC(=O)N2CCN(c3cc(F)cc(Cl)c3)CC2)NC(=O)NC1=O] | 383 | 383-385 | H3 | 3-(4-Methyl-2,5-dioxo-imidazolidin-4-yl)propionic acid + Int 271 |

TABLE III-continued

Illustrative compounds of the invention trans:

| Cpd | Structure | MW | Ms'd | Mtd | SM |
|---|---|---|---|---|---|
| 118 | 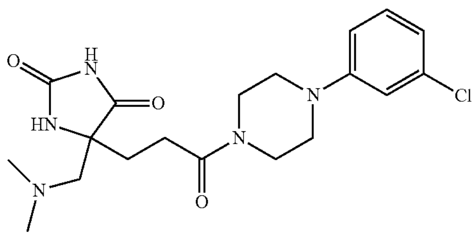 [SMILES: CN(C)CC1(CCC(=O)N2CCN(c3cccc(Cl)c3)CC2)NC(=O)NC1=O] | 408 | 408 | F | Int 013 |
| 119 | 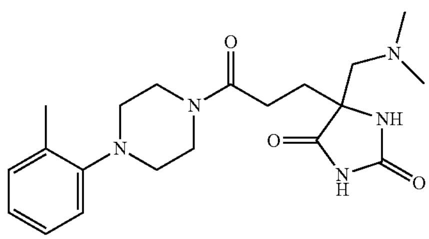 [SMILES: Cc1ccccc1N1CCN(C(=O)CCC2(CN(C)C)NC(=O)NC2=O)CC1] | 387 | 388 | F | Int 015 |
| 120 | 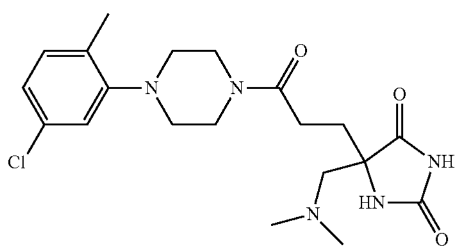 [SMILES: Cc1ccc(Cl)cc1N1CCN(C(=O)CCC2(CN(C)C)NC(=O)NC2=O)CC1] | 422 | 422-424 | F | Int 014 |
| 121 | (trans) | 405 | 405-407 | F | Int 040 |
| 122 | 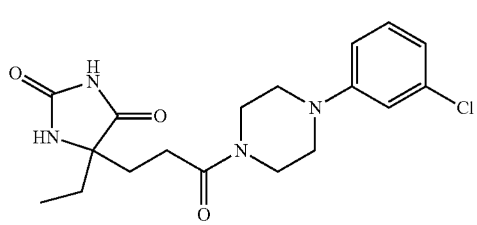 [SMILES: CCC1(CCC(=O)N2CCN(c3cccc(Cl)c3)CC2)NC(=O)NC1=O] | 379 | 379-381 | F | Int 041 |

TABLE III-continued
Illustrative compounds of the invention
trans:
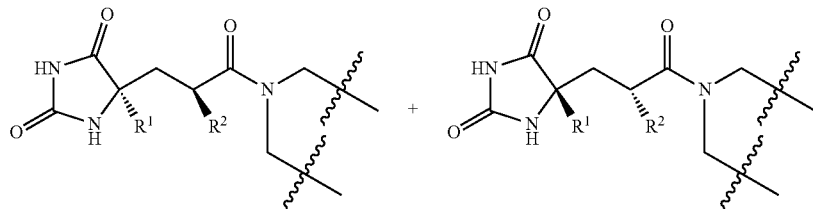
| Cpd | Structure | MW | Ms'd | Mtd | SM |
|---|---|---|---|---|---|
| 123 | 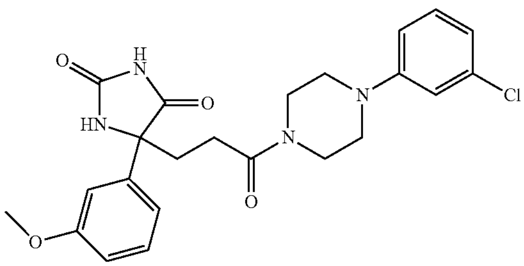 [SMILES: COc1cccc(C2(CCC(=O)N3CCN(c4cccc(Cl)c4)CC3)NC(=O)NC2=O)c1] | 457 | 457-459 | F | Int 042 |
| 124 | 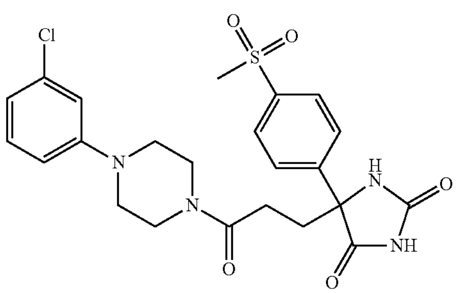 [SMILES: CS(=O)(=O)c1ccc(C2(CCC(=O)N3CCN(c4cccc(Cl)c4)CC3)NC(=O)NC2=O)cc1] | 505 | 505-507 | F | Int 043 |
| 125 | 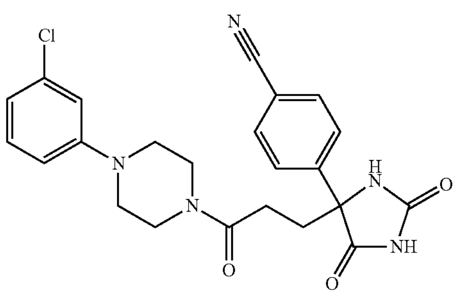 [SMILES: N#Cc1ccc(C2(CCC(=O)N3CCN(c4cccc(Cl)c4)CC3)NC(=O)NC2=O)cc1] | 452 | 452-454 | F | Int 044 |
| 126 | 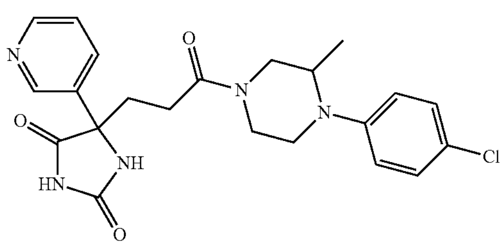 [SMILES: CC1CN(C(=O)CCC2(c3cccnc3)NC(=O)NC2=O)CCN1c1ccc(Cl)cc1] | 442 | 442-444 | H1 | Int 132 + Int 220 |

TABLE III-continued

Illustrative compounds of the invention trans:

| Cpd | Structure | MW | Ms'd | Mtd | SM |
|---|---|---|---|---|---|
| 127 | 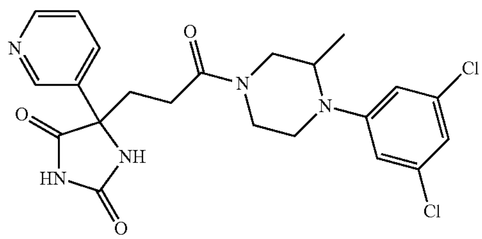 [SMILES: CC1CN(C(=O)CCC2(c3cccnc3)NC(=O)NC2=O)CCN1c1cc(Cl)cc(Cl)c1] | 476 | 476-478 | H1 | Int 132 + Int 218 |
| 128 | 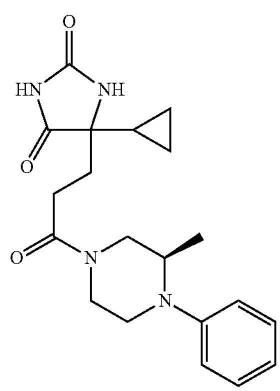 [SMILES: C[C@@H]1CN(C(=O)CCC2(C3CC3)NC(=O)NC2=O)CCN1c1ccccc1] | 370 | 371 | H1 | Int 162 + Int 219 |
| 129 | 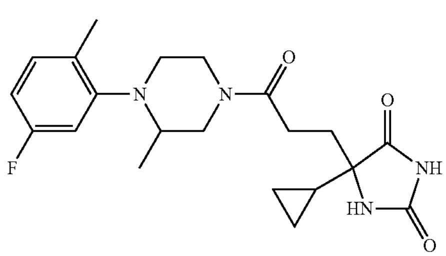 [SMILES: Cc1ccc(F)cc1N1CCN(C(=O)CCC2(C3CC3)NC(=O)NC2=O)CC1C] | 402 | 403 | H1 | Int 162 + Int 217 |
| 130 | 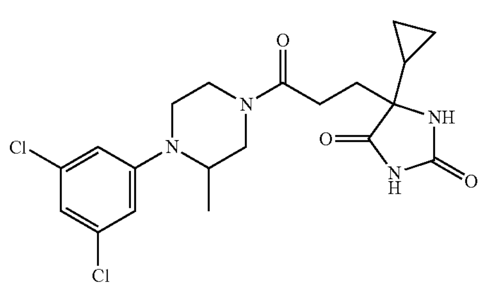 [SMILES: CC1CN(C(=O)CCC2(C3CC3)NC(=O)NC2=O)CCN1c1cc(Cl)cc(Cl)c1] | 439 | 439-441 | H1 | Int 162 + Int 218 |

TABLE III-continued
Illustrative compounds of the invention
trans:
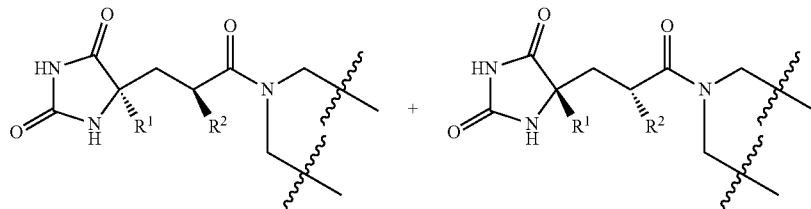
| Cpd | Structure | MW | Ms'd | Mtd | SM |
|-----|-----------|-----|------|-----|-----|
| 131 | 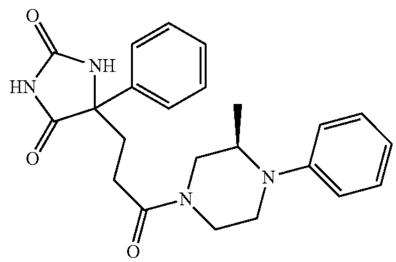 [SMILES: C[C@@H]1CN(C(=O)CCC2(c3ccccc3)NC(=O)NC2=O)CCN1c1ccccc1] | 406 | 407 | H1 | 3-(2,5-Dioxo-4-phenylimidazolidin-4-yl)propanoic acid + Int 219 |
| 132 | 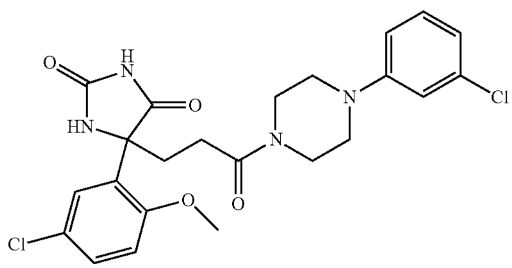 [SMILES: COc1ccc(Cl)cc1C1(CCC(=O)N2CCN(c3cccc(Cl)c3)CC2)NC(=O)NC1=O] | 491 | 491-493 | H1 | 3-[4-(5-Chloro-2-methoxy-phenyl)-2,5-dioxo-imidazolidin-4-yl]-propionic acid + 1-(3-chlorophenyl)piperazine |
| 133 | 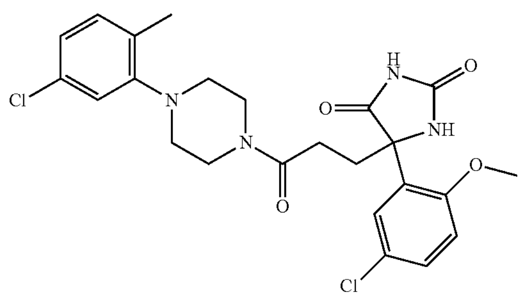 [SMILES: COc1ccc(Cl)cc1C1(CCC(=O)N2CCN(c3cc(Cl)ccc3C)CC2)NC(=O)NC1=O] | 505 | 505-507 | H1 | 3-[4-(5-Chloro-2-methoxy-phenyl)-2,5-dioxo-imidazolidin-4-yl]-propionic acid + 1-(5-chloro-2-methylphenyl)-piperazine |
| 134 | 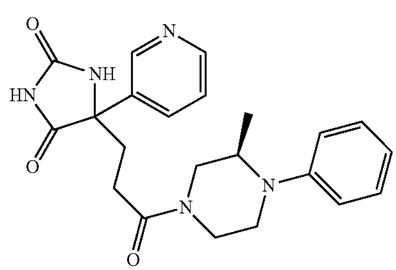 [SMILES: C[C@@H]1CN(C(=O)CCC2(c3cccnc3)NC(=O)NC2=O)CCN1c1ccccc1] | 407 | 408 | H1 | Int 132 + Int 219 |

TABLE III-continued

Illustrative compounds of the invention
trans:

| Cpd | Structure | MW | Ms'd | Mtd | SM |
|---|---|---|---|---|---|
| 135 | 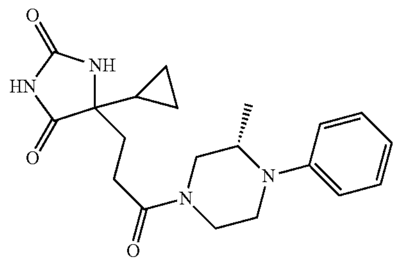 [SMILES: C[C@H]1CN(C(=O)CCC2(C3CC3)NC(=O)NC2=O)CCN1c1ccccc1] | 370 | 371 | H1 | Int 162 + Int 212 |
| 136 | 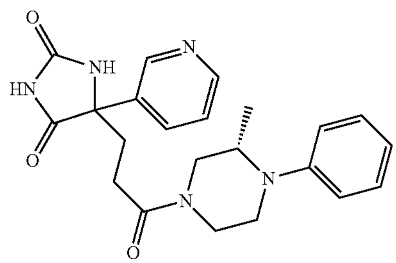 [SMILES: C[C@H]1CN(C(=O)CCC2(c3cccnc3)NC(=O)NC2=O)CCN1c1ccccc1] | 407 | 408 | H1 | Int 132 + Int 212 |
| 137 | 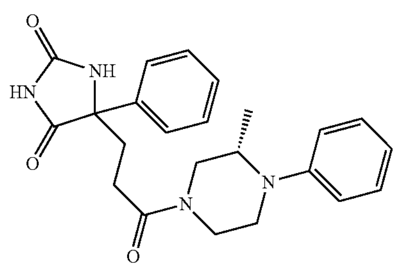 [SMILES: C[C@H]1CN(C(=O)CCC2(c3ccccc3)NC(=O)NC2=O)CCN1c1ccccc1] | 406 | 407 | H1 | 3-(2,5-Dioxo-4-phenyl-imidazolidin-4-yl)propionic acid + Int 212 |
| 138 | 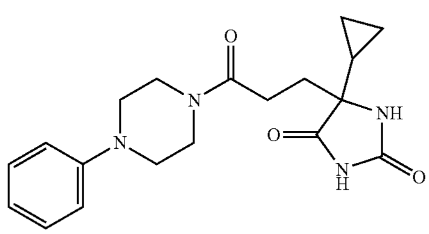 [SMILES: O=C1NC(=O)C(CCC(=O)N2CCN(c3ccccc3)CC2)(C2CC2)N1] | 356 | 357 | H1 | Int 162 + 1-Phenyl-piperazine |
| 139 | 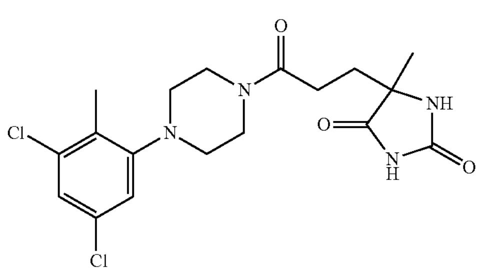 | 413 | 413-415 | H1 | 3-(4-Methyl-2,5-dioxo-imidazolidin-4-yl)propionic acid + Int 242 |

TABLE III-continued

Illustrative compounds of the invention
trans:

| Cpd | Structure | MW | Ms'd | Mtd | SM |
|---|---|---|---|---|---|
| 140 | | 366 | 367 | H1 | 3-(4-Methyl-2,5-dioxo-imidazolidin-4-yl)propionic acid + Int 236 |
| 141 | | 441 | 441 | F | Int 095 |
| 142 | | 439 | 439-441 | H1 | Int 162 + Int 197 |
| 143 | | 379 | 379-381 | H1 | 3-(4-Methyl-2,5-dioxo-imidazolidin-4-yl)propionic acid + Int 205 |
| 144 | | 413 | 413-415 | H1 | 3-(4-Methyl-2,5-dioxo-imidazolidin-4-yl)propionic acid + Int 197 |

TABLE III-continued

Illustrative compounds of the invention
trans:

| Cpd | Structure | MW | Ms'd | Mtd | SM |
|---|---|---|---|---|---|
| 145 | 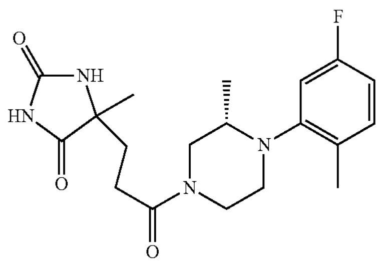 [SMILES: Cc1ccc(F)cc1N1CCN(C(=O)CCC2(C)NC(=O)NC2=O)C[C@@H]1C] | 376 | 377 | H1 | 3-(4-Methyl-2,5-dioxo-imidazolidin-4-yl)propionic acid + Int 208 |
| 146 | 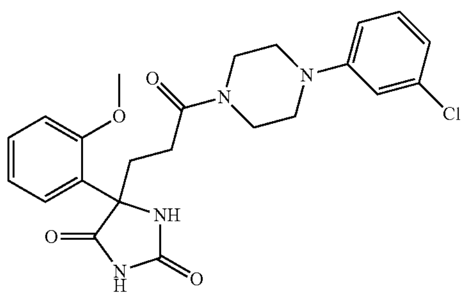 [SMILES: COc1ccccc1C1(CCC(=O)N2CCN(c3cccc(Cl)c3)CC2)NC(=O)NC1=O] | 457 | 457-459 | F | Int 078 |
| 147 | 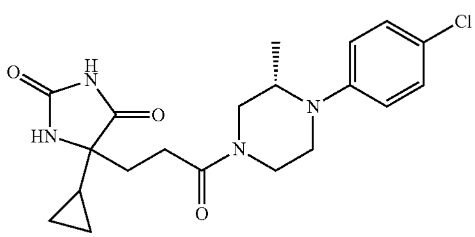 [SMILES: C[C@H]1CN(C(=O)CCC2(C3CC3)NC(=O)NC2=O)CCN1c1ccc(Cl)cc1] | 405 | 405-407 | H1 | Int 162 + Int 205 |
| 148 | 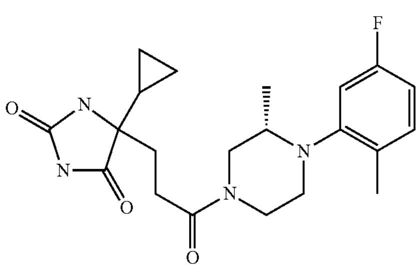 [SMILES: Cc1ccc(F)cc1N1CCN(C(=O)CCC2(C3CC3)NC(=O)NC2=O)C[C@@H]1C] | 402 | 403 | H1 | Int 162 + Int 208 |
| 149 | 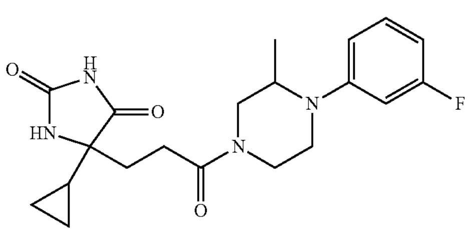 [SMILES: CC1CN(C(=O)CCC2(C3CC3)NC(=O)NC2=O)CCN1c1cccc(F)c1] | 388 | 389 | H1 | Int 162 + Int 240 |

TABLE III-continued
Illustrative compounds of the invention
trans:
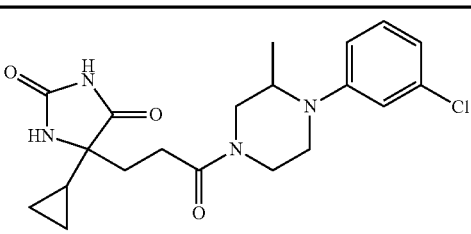
| Cpd | Structure | MW | Ms'd | Mtd | SM |
|---|---|---|---|---|---|
| 150 | 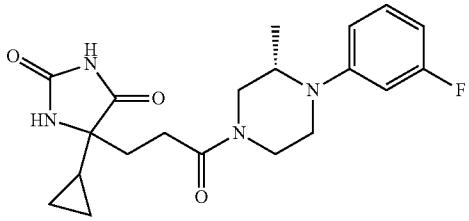 | 405 | 405-407 | H1 | Int 162 + Int 241 |
| 151 | 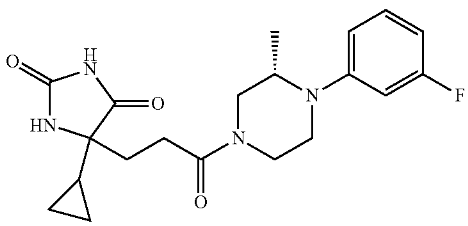 [SMILES: C[C@H]1CN(C(=O)CCC2(C3CC3)NC(=O)NC2=O)CCN1c1cccc(F)c1] | 388 | 389 | H1 | Int 162 + Int 202 |
| 152 | 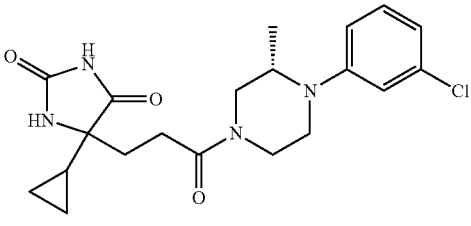 [SMILES: C[C@H]1CN(C(=O)CCC2(C3CC3)NC(=O)NC2=O)CCN1c1cccc(Cl)c1] | 405 | 405-407 | H1 | Int 162 + Int 200 |
| 153 | 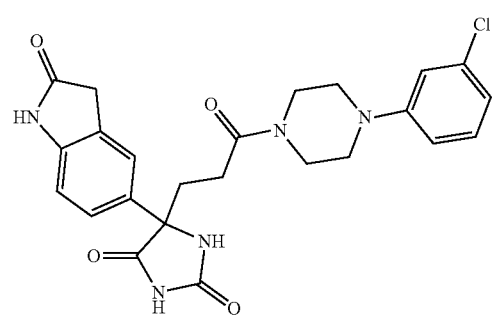 [SMILES: O=C1Cc2cc(C3(CCC(=O)N4CCN(c5cccc(Cl)c5)CC4)NC(=O)NC3=O)ccc2N1] | 482 | 482 | H1 | 3-[2,5-Dioxo-4-(2-oxo-2,3-dihydro-1H-indol-5-yl)-imidazolidin-4-yl]-propionic acid + 1-(3-chlorophenyl)piperazine |
| 154 | 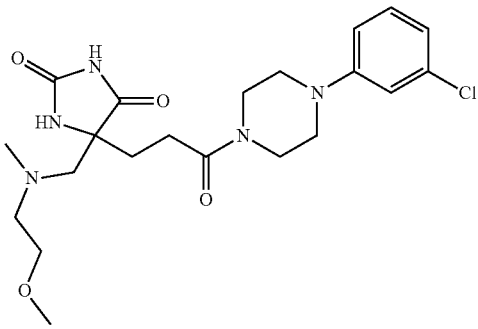 [SMILES: COCCN(C)CC1(CCC(=O)N2CCN(c3cccc(Cl)c3)CC2)NC(=O)NC1=O] | 452 | 452 | F | Int 016 |

TABLE III-continued

Illustrative compounds of the invention trans:

| Cpd | Structure | MW | Ms'd | Mtd | SM |
|---|---|---|---|---|---|
| 155 | 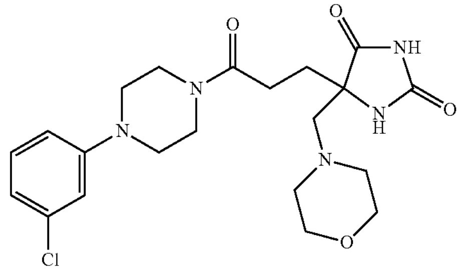 [SMILES: O=C1NC(=O)C(CCC(=O)N2CCN(c3cccc(Cl)c3)CC2)(CN2CCOCC2)N1] | 450 | 450 | F | Int 017 |
| 156 | 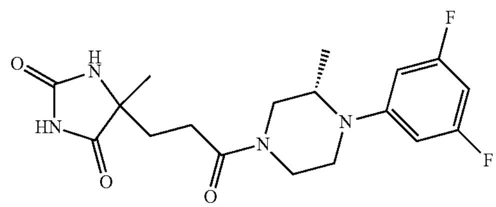 [SMILES: C[C@H]1CN(C(=O)CCC2(C)NC(=O)NC2=O)CCN1c1cc(F)cc(F)c1] | 380 | 381 | H1 | 3-(4-Methyl-2,5-dioxo-imidazolidin-4-yl)propionic acid + Int 207 |
| 157 | 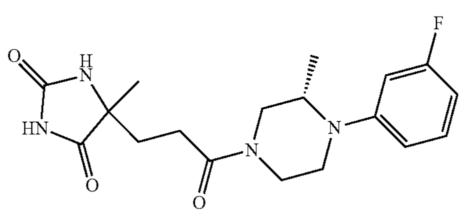 [SMILES: C[C@H]1CN(C(=O)CCC2(C)NC(=O)NC2=O)CCN1c1cccc(F)c1] | 362 | 363 | H1 | 3-(4-Methyl-2,5-dioxo-imidazolidin-4-yl)propionic acid + Int 202 |
| 158 | 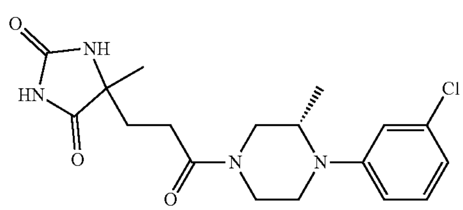 [SMILES: C[C@H]1CN(C(=O)CCC2(C)NC(=O)NC2=O)CCN1c1cccc(Cl)c1] | 379 | 379-381 | H1 | 3-(4-Methyl-2,5-dioxo-imidazolidin-4-yl)propionic acid + Int 200 |
| 159 | 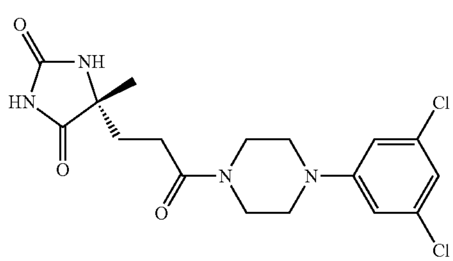 [SMILES: C[C@]1(CCC(=O)N2CCN(c3cc(Cl)cc(Cl)c3)CC2)NC(=O)NC1=O] | 399 | 399-401 | H1 | Int 172 + 1-(3,5-dichlorophenyl)piperazine |

TABLE III-continued
Illustrative compounds of the invention
trans:
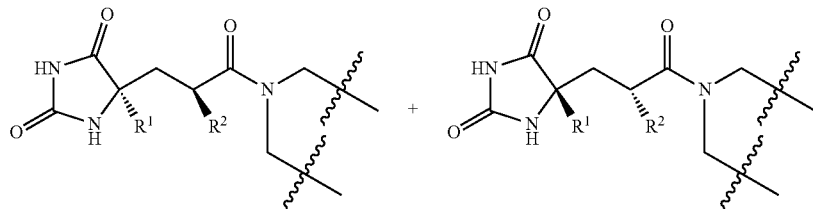
| Cpd | Structure | MW | Ms'd | Mtd | SM |
|---|---|---|---|---|---|
| 160 | | 406 | 407 | H1 | Int 162 + Int 207 |
| 161 | | 406 | 407 | H1 | Int 162 + Int 199 |
| 162 | | 423 | 423-425 | H1 | Int 162 + Int 213 |
| 163 | | 423 | 423-425 | H1 | Int 162 + Int 198 |
| 164 | | 397 | 397 | H1 | 3-(4-Methyl-2,5-dioxo-imidazolidin-4-yl) propionic acid + Int 213 |

TABLE III-continued

Illustrative compounds of the invention
trans:

| Cpd | Structure | MW | Ms'd | Mtd | SM |
|---|---|---|---|---|---|
| 165 | 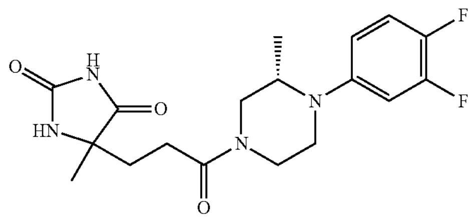 [SMILES: C[C@H]1CN(C(=O)CCC2(C)NC(=O)NC2=O)CCN1c1ccc(F)c(F)c1] | 380 | 381 | H1 | 3-(4-Methyl-2,5-dioxo-imidazolidin-4-yl) propionic acid + Int 199 |
| 166 | 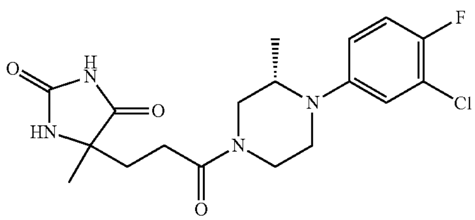 [SMILES: C[C@H]1CN(C(=O)CCC2(C)NC(=O)NC2=O)CCN1c1ccc(F)c(Cl)c1] | 397 | 397 | H1 | 3-(4-Methyl-2,5-dioxo-imidazolidin-4-yl) propionic acid + Int 198 |
| 167 | 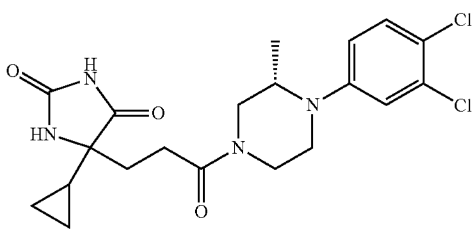 [SMILES: C[C@H]1CN(C(=O)CCC2(C3CC3)NC(=O)NC2=O)CCN1c1ccc(Cl)c(Cl)c1] | 439 | 439-441 | H1 | Int 162 + Int 201 |
| 168 | 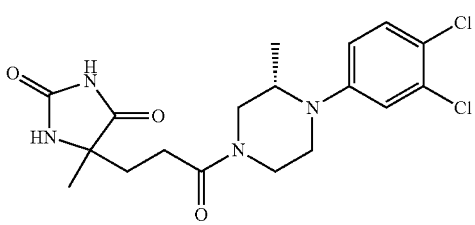 [SMILES: C[C@H]1CN(C(=O)CCC2(C)NC(=O)NC2=O)CCN1c1ccc(Cl)c(Cl)c1] | 413 | 413-415 | H1 | 3-(4-Methyl-2,5-dioxo-imidazolidin-4-yl) propionic acid + Int 201 |
| 169 | 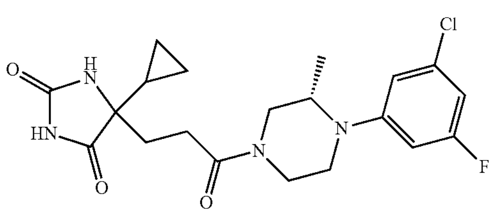 | 423 | 423-425 | H1 | Int 162 + Int 206 |
| 170 | 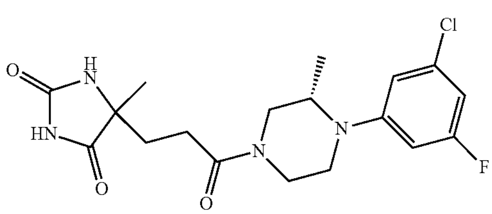 [SMILES: C[C@H]1CN(C(=O)CCC2(C)NC(=O)NC2=O)CCN1c1cc(F)cc(Cl)c1] | 397 | 397-399 | H1 | 3-(4-Methyl-2,5-dioxo-imidazolidin-4-yl)-propionic acid + Int 206 |

TABLE III-continued

Illustrative compounds of the invention
trans:

| Cpd | Structure | MW | Ms'd | Mtd | SM |
|---|---|---|---|---|---|
| 171 | 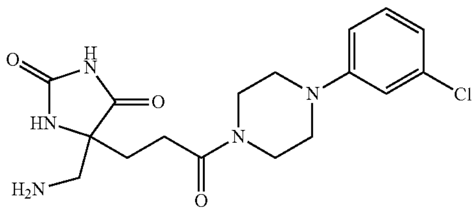 [SMILES: NCC1(CCC(=O)N2CCN(c3cccc(Cl)c3)CC2)NC(=O)NC1=O] | 380 | 380 | I2 | Int 018 |
| 172 | 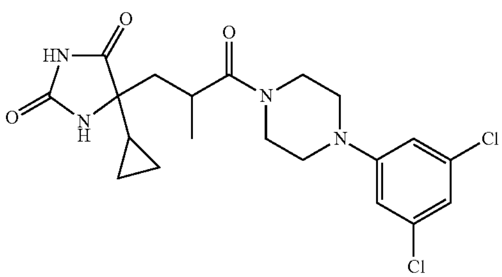 [SMILES: CC(CC1(C2CC2)NC(=O)NC1=O)C(=O)N1CCN(c2cc(Cl)cc(Cl)c2)CC1] | 439 | 439-441 | F | Int 046 |
| 173 | 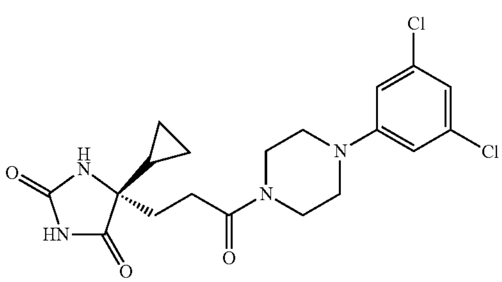 [SMILES: O=C1NC(=O)[C@](CCC(=O)N2CCN(c3cc(Cl)cc(Cl)c3)CC2)(C2CC2)N1] | 425 | 425-427 | H1 | Int 163 + 1-(3,5-dichlorophenyl)piperazine |
| 174 | 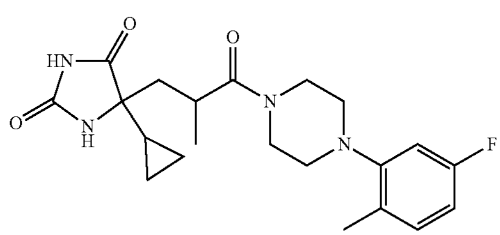 [SMILES: Cc1ccc(F)cc1N1CCN(C(=O)C(C)CC2(C3CC3)NC(=O)NC2=O)CC1] | 402 | 403-404 | F | Int 047 |
| 175 | 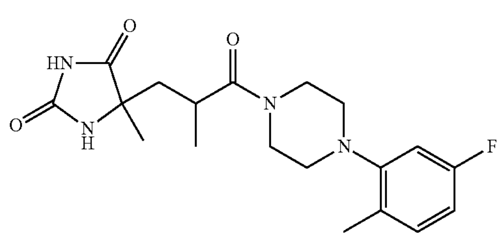 [SMILES: Cc1ccc(F)cc1N1CCN(C(=O)C(C)CC2(C)NC(=O)NC2=O)CC1] | 376 | 377 | F | Int 048 |

TABLE III-continued

Illustrative compounds of the invention
trans:

| Cpd | Structure | MW | Ms'd | Mtd | SM |
|---|---|---|---|---|---|
| 176 | trans | 419 | 419-421 | F | Int 101 |
| 177 | 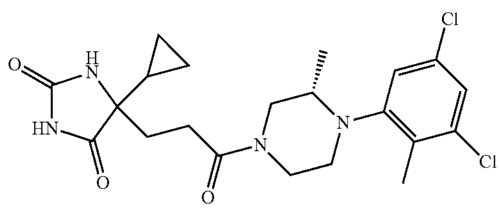 [SMILES: Cc1c(Cl)cc(Cl)cc1N1CCN(C(=O)CCC2(C3CC3)NC(=O)NC2=O)C[C@@H]1C] | 453 | 453-455 | H1 | Int 162 + Int 211 |
| 178 | 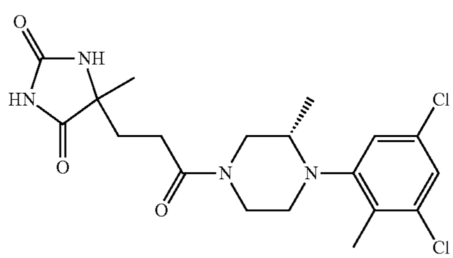 [SMILES: Cc1c(Cl)cc(Cl)cc1N1CCN(C(=O)CCC2(C)NC(=O)NC2=O)C[C@@H]1C] | 427 | 427-429 | H1 | 3-(4-Methyl-2,5-dioxo-imidazolidin-4-yl)propionic acid + Int 211 |
| 179 | trans | 393 | 393-395 | F | Int 102 |
| 180 | 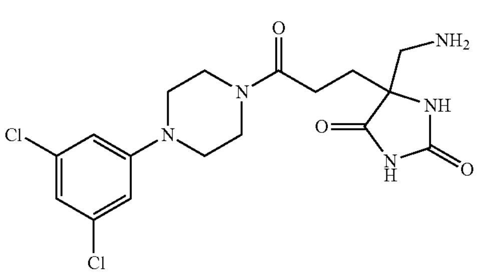 [SMILES: NCC1(CCC(=O)N2CCN(c3cc(Cl)cc(Cl)c3)CC2)NC(=O)NC1=O] | 414 | 414-416 | I2 | Int 019 |

TABLE III-continued
Illustrative compounds of the invention
trans:
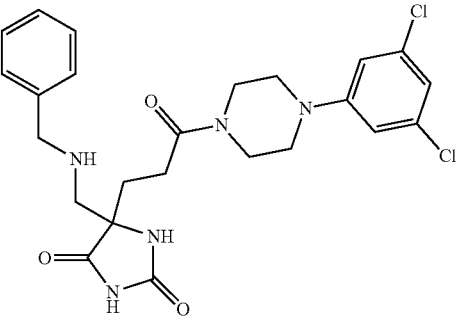 [SMILES: O=C1NC(=O)C(CCC(=O)N2CCN(c3cc(Cl)cc(Cl)c3)CC2)(CNCc2ccccc2)N1]
| Cpd | Structure | MW | Ms'd | Mtd | SM |
|---|---|---|---|---|---|
| 181 | 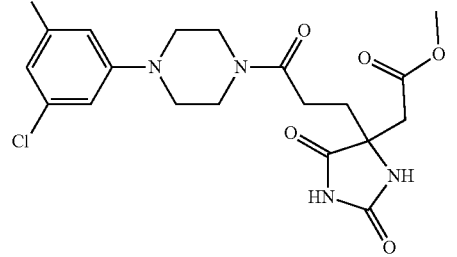 | 504 | 504-506 | I3 | Cpd 180 |
| 182 | 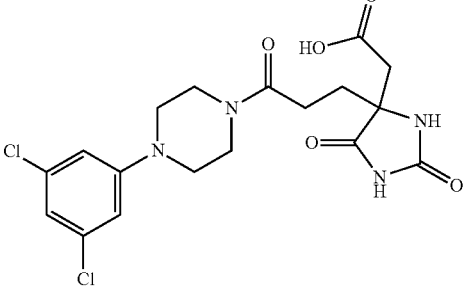 | 457 | 457-459 | 2.1 | Cpd 188 |
| 183 | 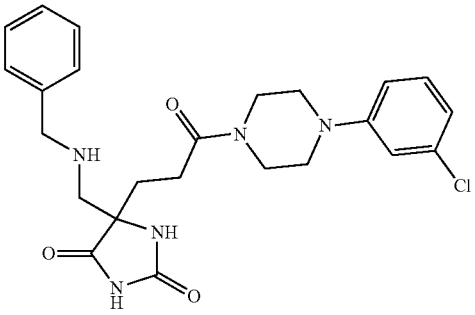 [SMILES: O=C1NC(=O)C(CCC(=O)N2CCN(c3cccc(Cl)c3)CC2)(CNCc2ccccc2)N1] | 443 | 443-445 | 2.1 | Cpd 188 |
| 184 | | 470 | 470 | I3 | Cpd 171 |

TABLE III-continued

Illustrative compounds of the invention trans:

| Cpd | Structure | MW | Ms'd | Mtd | SM |
|---|---|---|---|---|---|
| 185 | 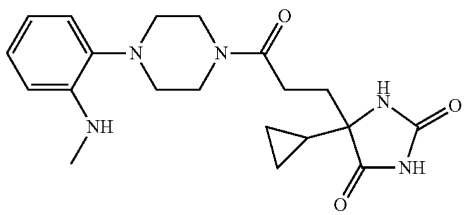 [SMILES: CNc1ccccc1N1CCN(C(=O)CCC2(C3CC3)NC(=O)NC2=O)CC1] | 385 | 386 | H1 | Int 162 + N-methyl-2-piperazin-1-ylaniline |
| 186 | 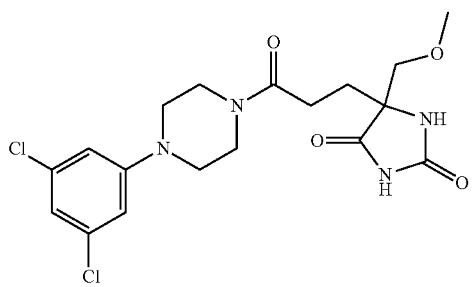 [SMILES: COCC1(CCC(=O)N2CCN(c3cc(Cl)cc(Cl)c3)CC2)NC(=O)NC1=O] | 429 | 429-431 | F | Int 020 |
| 187 | 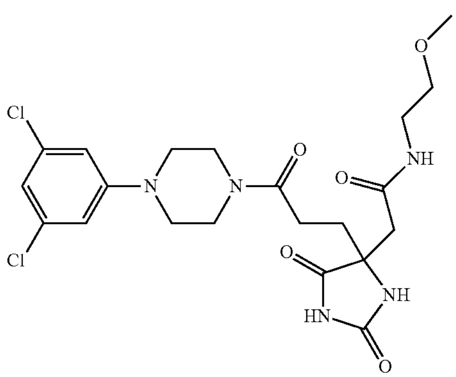 [SMILES: COCCNC(=O)CC1(CCC(=O)N2CCN(c3cc(Cl)cc(Cl)c3)CC2)NC(=O)NC1=O] | 500 | 500-502 | H1 | Cpd 183 + 2-Methoxy-ethylamine |
| 188 | 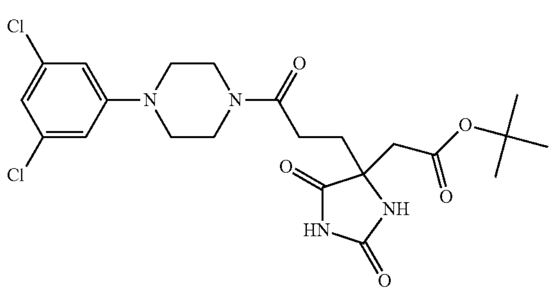 [SMILES: CC(C)(C)OC(=O)CC1(CCC(=O)N2CCN(c3cc(Cl)cc(Cl)c3)CC2)NC(=O)NC1=O] | 499 | 499-501 | 2.2 | succininc anhydride + 1-(3,5-dichloro phenyl)piperazine |

TABLE III-continued
Illustrative compounds of the invention
trans:
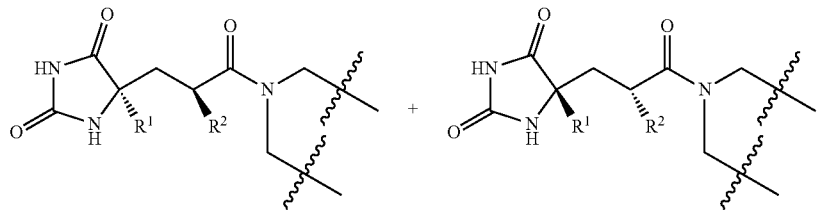
| Cpd | Structure | MW | Ms'd | Mtd | SM |
|-----|-----------|----|----|-----|-----|
| 189 | | 486 | 486-488 | 2.3 | Cpd 182 + 2-Amino-ethanol |
| 190 | trans | 402 | 403 | F | Int 049 |
| 191 | trans | 420 | 421 | H2 | Int 164 + Int 199 |
| 192 | trans | 437 | 437-439 | F | Int 050 |

349                                                                                              350
TABLE III-continued
Illustrative compounds of the invention
trans:
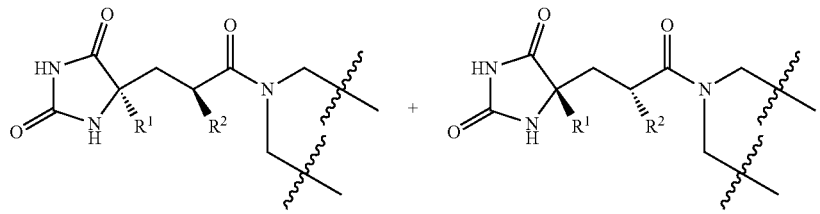
| Cpd | Structure | MW | Ms'd | Mtd | SM |
|---|---|---|---|---|---|
| 193 | trans | 419 | 419-421 | F | Int 051 |
| 194 | trans | 437 | 437-439 | F | Int 052 |
| 195 | 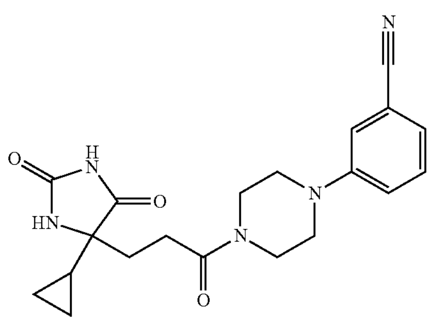 [SMILES: N#Cc1cccc(N2CCN(C(=O)CCC3(C4CC4)NC(=O)NC3=O)CC2)c1] | 381 | 382 | H1 | Int 162 + Int 274 |
| 196 | trans | 454 | 454-456 | I2 | Int 096 |

TABLE III-continued
Illustrative compounds of the invention
trans:
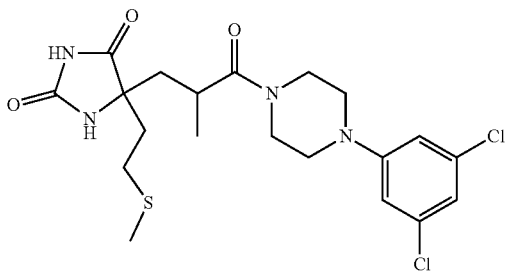 [SMILES: CSCCC1(CC(C)C(=O)N2CCN(c3cc(Cl)cc(Cl)c3)CC2)NC(=O)NC1=O] + 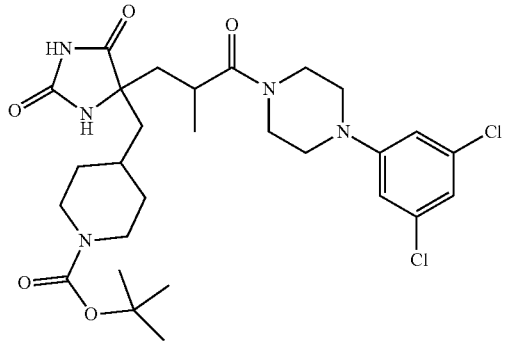 [SMILES: CC(CC1(CC2CCN(C(=O)OC(C)(C)C)CC2)NC(=O)NC1=O)C(=O)N1CCN(c2cc(Cl)cc(Cl)c2)CC1]
| Cpd | Structure | MW | Ms'd | Mtd | SM |
|---|---|---|---|---|---|
| 197 | 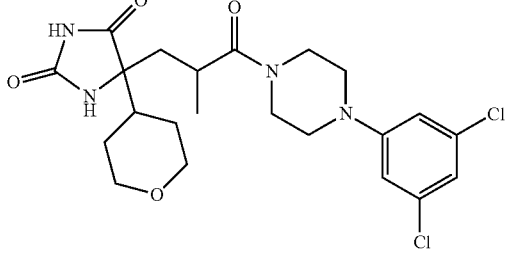 trans | 473 | 473-475 | F | Int 098 |
| 198 | 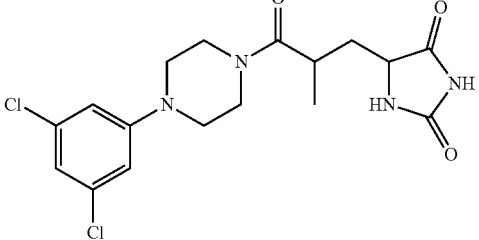 trans | 597 | 596-598 | F | Int 099 |
| 199 |  trans | 483 | 483-485 | F | Int 097 |
| 200 | 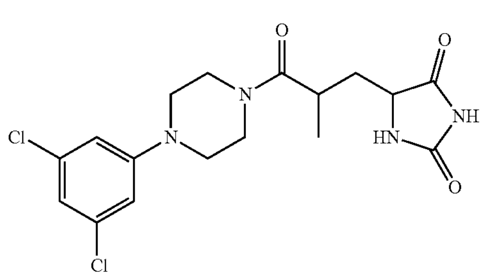 [SMILES: CC(CC1NC(=O)NC1=O)C(=O)N1CCN(c2cc(Cl)cc(Cl)c2)CC1] | 399 | 399-401 | F | Int 055 |

TABLE III-continued
Illustrative compounds of the invention
trans:
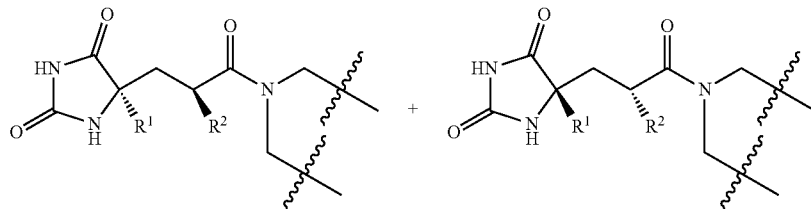
| Cpd | Structure | MW | Ms'd | Mtd | SM |
|---|---|---|---|---|---|
| 201 | 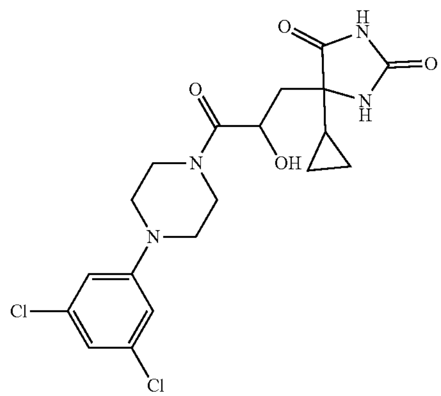 [SMILES: O=C1NC(=O)C(CC(O)C(=O)N2CCN(c3cc(Cl)cc(Cl)c3)CC2)(C2CC2)N1] | 441 | 441-443 | F | Int 053 |
| 202 | 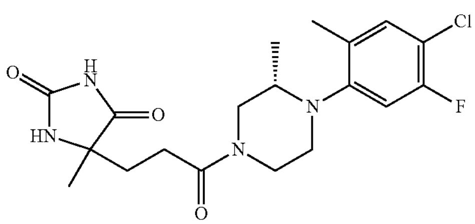 [SMILES: Cc1cc(Cl)c(F)cc1N1CCN(C(=O)CCC2(C)NC(=O)NC2=O)C[C@@H]1C] | 411 | 411 | H2 | 3-(4-Methyl-2,5-dioxo-imidazolidin-4-yl)propionic acid + Int 275 |
| 203 | 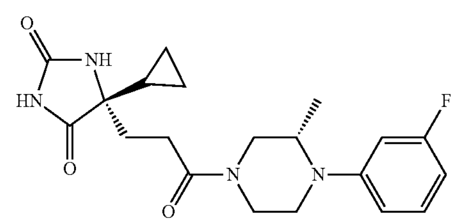 [SMILES: C[C@H]1CN(C(=O)CC[C@@]2(C3CC3)NC(=O)NC2=O)CCN1c1cccc(F)c1] | 388 | 389 | H2 | Int 163 + Int 202 |
| 204 | 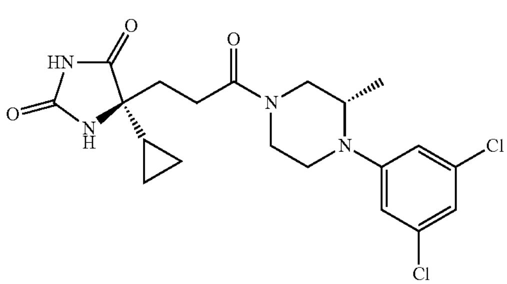 [SMILES: C[C@H]1CN(C(=O)CC[C@@]2(C3CC3)NC(=O)NC2=O)CCN1c1cc(Cl)cc(Cl)c1] | 439 | 439-441 | H3 | Int 163 + Int 197 |

TABLE III-continued

Illustrative compounds of the invention
trans:

| Cpd | Structure | MW | Ms'd | Mtd | SM |
|---|---|---|---|---|---|
| 205 | 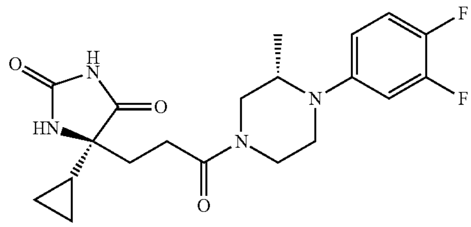 [SMILES: C[C@H]1CN(C(=O)CC[C@@]2(C3CC3)NC(=O)NC2=O)CCN1c1ccc(F)c(F)c1] | 406 | 407 | H2 | Int 163 + Int 199 |
| 206 | 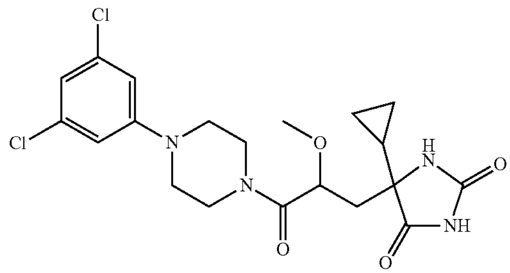 [SMILES: COC(CC1(C2CC2)NC(=O)NC1=O)C(=O)N1CCN(c2cc(Cl)cc(Cl)c2)CC1] | 455 | 455-457 | F | Int 056 |
| 207 | 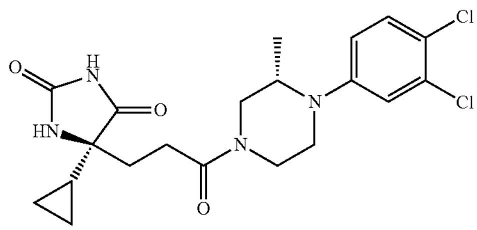 [SMILES: C[C@H]1CN(C(=O)CC[C@@]2(C3CC3)NC(=O)NC2=O)CCN1c1ccc(Cl)c(Cl)c1] | 439 | 439-441 | H2 | Int 163 + (S)-1-(3,4-Dichloro-phenyl)-2-methyl-piperazine |
| 208 | 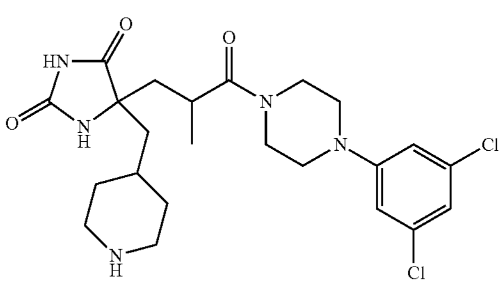 [SMILES: CC(CC1(CC2CCNCC2)NC(=O)NC1=O)C(=O)N1CCN(c2cc(Cl)cc(Cl)c2)CC1] | 496 | 796-798 | I2 | Cpd 198 |
| 209 | 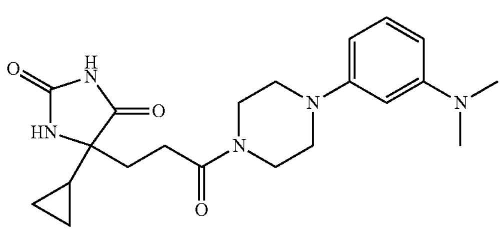 [SMILES: CN(C)c1cccc(N2CCN(C(=O)CCC3(C4CC4)NC(=O)NC3=O)CC2)c1] | 399 | 400 | H1 | Int 162 + N,N-dimethyl-3-piperazine-1-yl aniline trihydrochloride |

TABLE III-continued
Illustrative compounds of the invention
trans:
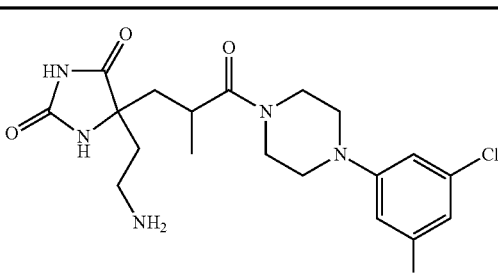
| Cpd | Structure | MW | Ms'd | Mtd | SM |
|---|---|---|---|---|---|
| 210 | 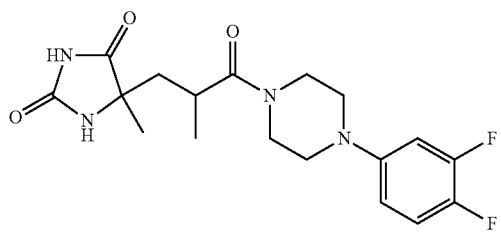 [SMILES: CC(CC1(C)NC(=O)NC1=O)C(=O)N1CCN(c2ccc(F)c(F)c2)CC1]<br>trans | 442 | 442-444 | I2 | Int 100 |
| 211 | 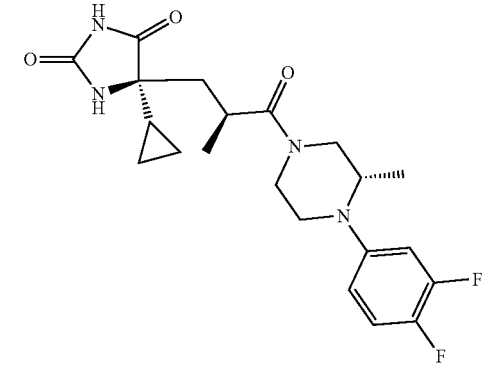 [SMILES: C[C@@H](C[C@@]1(C2CC2)NC(=O)NC1=O)C(=O)N1CCN(c2ccc(F)c(F)c2)[C@@H](C)C1]<br>trans | 380 | 381 | H2 | Int 165 +<br>1-(3,4-difluoro<br>phenyl)piperazine |
| 212 | 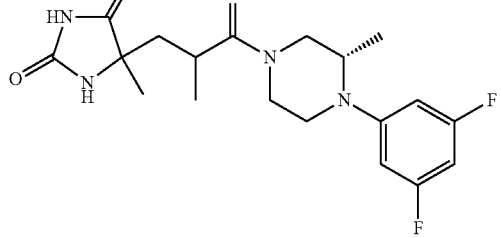 | 420 | 421 | 2.10 | Cpd 191 |
| 213 | <br>trans | 394 | 395 | H2 | Int 165 +<br>Int 207 |

TABLE III-continued
Illustrative compounds of the invention
trans:
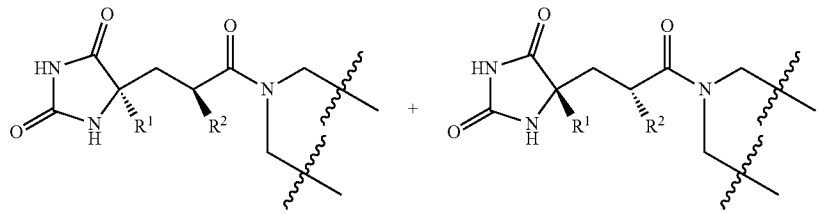
| Cpd | Structure | MW | Ms'd | Mtd | SM |
|---|---|---|---|---|---|
| 214 | trans | 393 | 393-395 | H2 | Int 165 + Int 200 |
| 215 | trans | 376 | 377 | H2 | Int 165 + Int 202 |
| 216 | trans | 390 | 391 | H2 | Int 165 + Int 208 |
| 217 | trans | 358 | 359 | H2 | Int 165 + Int 212 |
| 218 | trans | 505 | 505-507 | 2.4 | Cpd 197 |

TABLE III-continued
Illustrative compounds of the invention
trans:
| Cpd | Structure | MW | Ms'd | Mtd | SM |
|---|---|---|---|---|---|
| 219 | 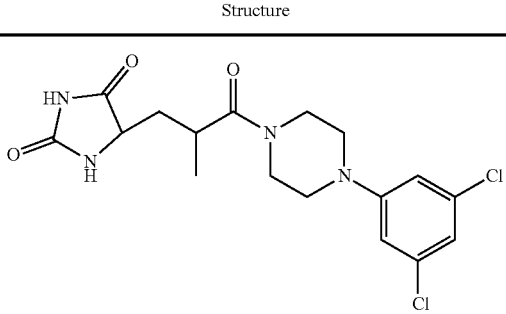 trans | 399 | 399-401 | H2 | Int 151 + 1-(3,5-dichlorophenyl)piperazine |
| 220 | 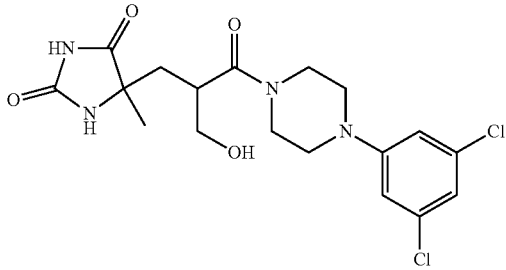 [SMILES: CC1(CC(CO)C(=O)N2CCN(c3cc(Cl)cc(Cl)c3)CC2)NC(=O)NC1=O] trans | 429 | 429-431 | H2 + F + I4 | Int 138 + 1-(3,5-dichlorophenyl)piperazine |
| 221 | 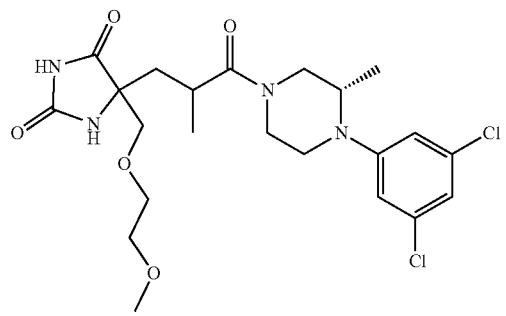 [SMILES: COCCOCC1(CC(C)C(=O)N2CCN(c3cc(Cl)cc(Cl)c3)[C@@H](C)C2)NC(=O)NC1=O] trans | 501 | 501-503 | F | Int 063 |
| 222 | 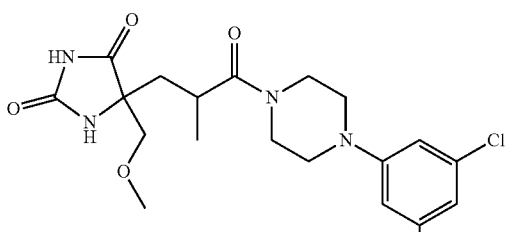 trans | 443 | 443-445 | H2 | Int 156 + 1-(3,5-dichlorophenyl)piperazine |

TABLE III-continued

Illustrative compounds of the invention
trans:

| Cpd | Structure | MW | Ms'd | Mtd | SM |
|---|---|---|---|---|---|
| 223 | | 456 | 456-458 | I1 | Cpd 180 |
| 224 | trans | 410 | 411 | H2 | Int 156 + 1-(3,4-difluoro phenyl)piperazine |
| 225 | trans | 424 | 425 | H2 | Int 156 + Int 207 |
| 226 | trans | 424 | 425 | H2 | Int 156 + Int 199 |

TABLE III-continued
Illustrative compounds of the invention
trans:
| Cpd | Structure | MW | Ms'd | Mtd | SM |
|---|---|---|---|---|---|
| 227 | 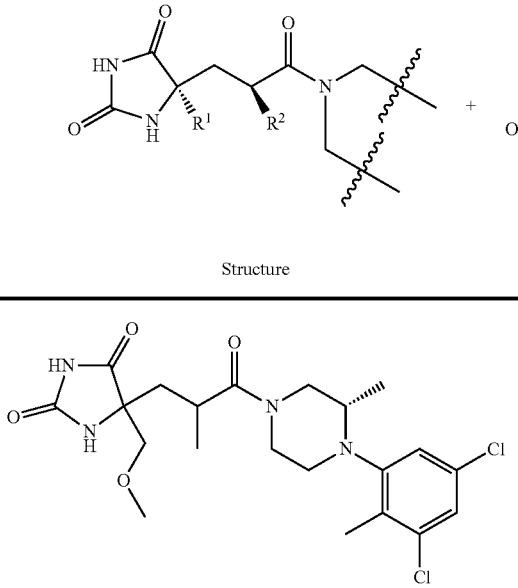 trans | 471 | 471 | H2 | Int 156 + Int 211 |
| 228 | 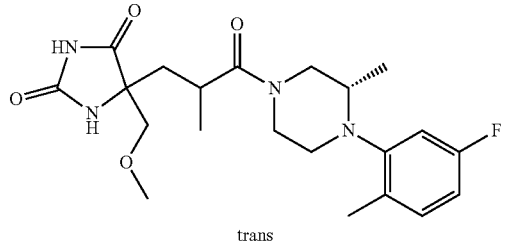 trans | 420 | 421 | H2 | Int 156 + Int 208 |
| 229 | 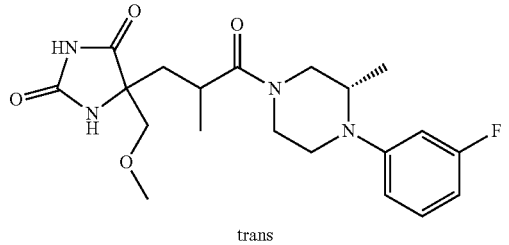 trans | 406 | 407 | H2 | Int 156 + Int 202 |
| 230 | 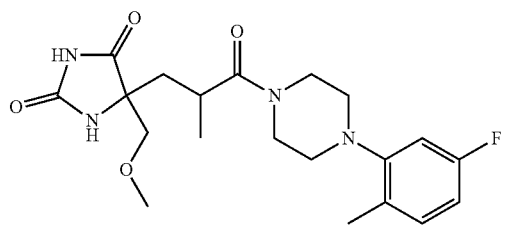 [SMILES: COCC1(CC(C)C(=O)N2CCN(c3cc(F)ccc3C)CC2)NC(=O)NC1=O] trans | 406 | 407 | H2 | Int 156 + Int 204 |

TABLE III-continued
Illustrative compounds of the invention
trans:
| Cpd | Structure | MW | Ms'd | Mtd | SM |
|---|---|---|---|---|---|
| 231 | 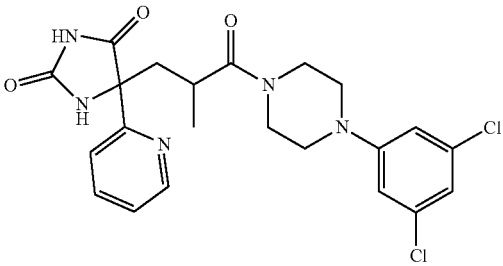 [SMILES: CC(CC1(c2ccccn2)NC(=O)NC1=O)C(=O)N1CCN(c2cc(Cl)cc(Cl)c2)CC1] trans | 476 | 476-478 | H2 | Int 159 + 1-(3,5-dichloro phenyl)piperazine |
| 232 | 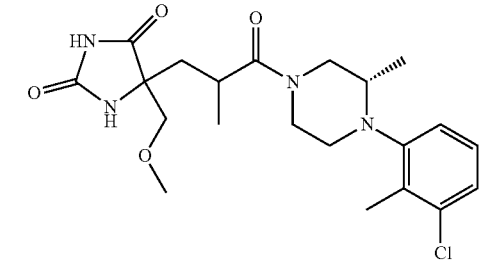 [SMILES: COCC1(CC(C)C(=O)N2CCN(c3cccc(Cl)c3C)[C@@H](C)C2)NC(=O)NC1=O] trans | 437 | 437-439 | H2 | Int 156 + Int 216 |
| 233 | 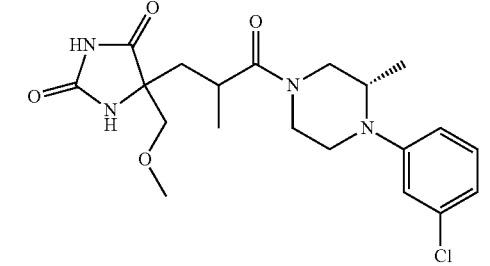 [SMILES: COCC1(CC(C)C(=O)N2CCN(c3cccc(Cl)c3)[C@@H](C)C2)NC(=O)NC1=O] trans | 423 | 423-425 | H2 | Int 156 + Int 200 |
| 234 | 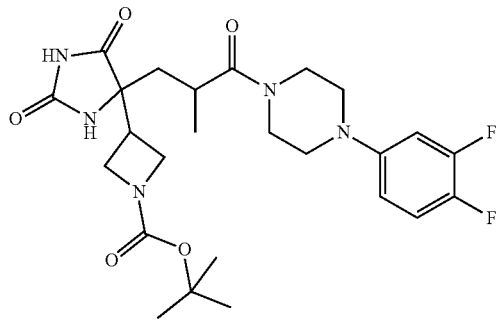 [SMILES: CC(CC1(C2CN(C(=O)OC(C)(C)C)C2)NC(=O)NC1=O)C(=O)N1CCN(c2ccc(F)c(F)c2)CC1] trans | 522 | 522 | F | Int 067 |

TABLE III-continued

Illustrative compounds of the invention
trans:

| Cpd | Structure | MW | Ms'd | Mtd | SM |
|---|---|---|---|---|---|
| 235 | trans | 510 | 510 | F | Int 069 |
| 236 | trans | 427 | 427-429 | F | Int 061 |
| 237 | trans | 407 | 407-409 | H2 | Int 165 + Int 216 |
| 238 | trans | 507 | 507-509 | F | Int 064 |

TABLE III-continued
Illustrative compounds of the invention
trans:
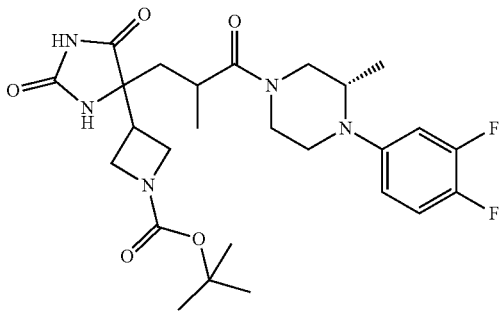 [SMILES: CC(CC1(C2CN(C(=O)OC(C)(C)C)C2)NC(=O)NC1=O)C(=O)N1CCN(c2ccc(F)c(F)c2)[C@@H](C)C1]
| Cpd | Structure | MW | Ms'd | Mtd | SM |
|---|---|---|---|---|---|
| 239 | 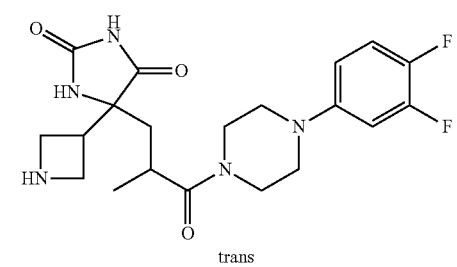 trans | 536 | 536 | F | Int 068 |
| 240 | 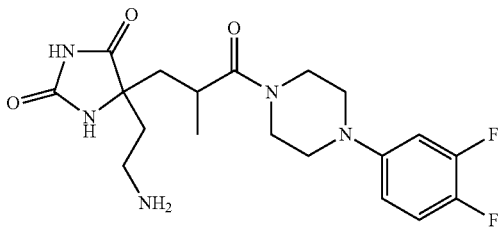 [SMILES: CC(CC1(CCN)NC(=O)NC1=O)C(=O)N1CCN(c2ccc(F)c(F)c2)CC1] trans | 421 | 422 | I2 | Cpd 234 |
| 241 | 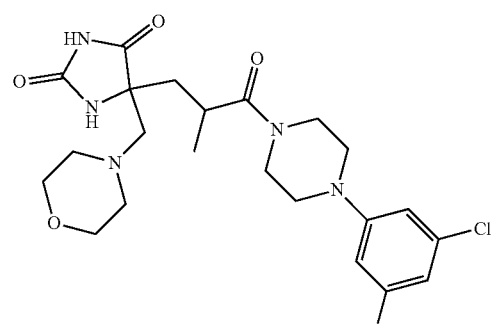 trans | 409 | 410 | I2 | Cpd 235 |
| 242 | trans | 498 | 498-500 | H2 | Int 186 + 1-(3,5-dichloro phenyl)piperazine |

TABLE III-continued
Illustrative compounds of the invention
trans:
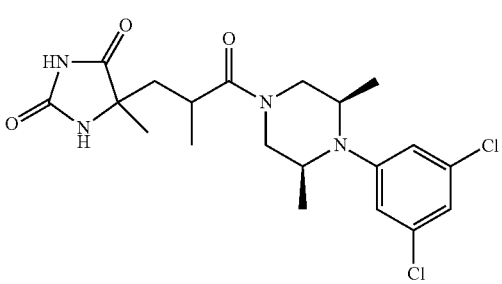 [SMILES: CC(CC1(C)NC(=O)NC1=O)C(=O)N1C[C@@H](C)N(c2cc(Cl)cc(Cl)c2)[C@@H](C)C1]
| Cpd | Structure | MW | Ms'd | Mtd | SM |
|---|---|---|---|---|---|
| 243 | 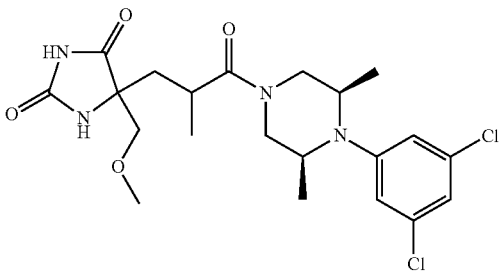 [SMILES: COCC1(CC(C)C(=O)N2C[C@@H](C)N(c3cc(Cl)cc(Cl)c3)[C@@H](C)C2)NC(=O)NC1=O] trans | 441 | 441 | H2 | Int 165 + Int 243 |
| 244 | 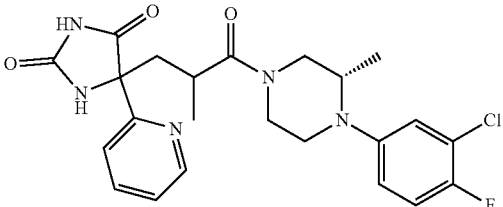 trans | 471 | 471 | H2 | Int 156 + Int 243 |
| 245 | 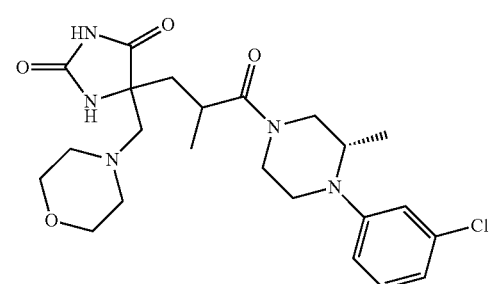 trans | 474 | 474 | H2 | Int 159 + Int 198 |
| 246 | trans | 512 | 512-514 | H2 | Int 186 + Int 197 |

TABLE III-continued

Illustrative compounds of the invention
trans:

| Cpd | Structure | MW | Ms'd | Mtd | SM |
|---|---|---|---|---|---|
| 247 | trans | 435 | 436 | I2 | Cpd 239 |
| 248 | trans | 463 | 464 | I1 | Cpd 240 |
| 249 | trans | 478 | 478 | I1 | Cpd 247 |
| 250 | 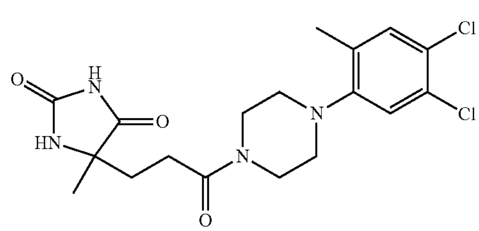 [SMILES: Cc1cc(Cl)c(Cl)cc1N1CCN(C(=O)CCC2(C)NC(=O)NC2=O)CC1] | 413 | 412-414-416 | H2 | 3-(4-Methyl-2,5-dioxo-imidazolidin-4-yl)propionic acid + Int 279 |
| 251 | trans | 380 | 381 | H2 | Int 151 + Int 199 |

TABLE III-continued
Illustrative compounds of the invention
trans:
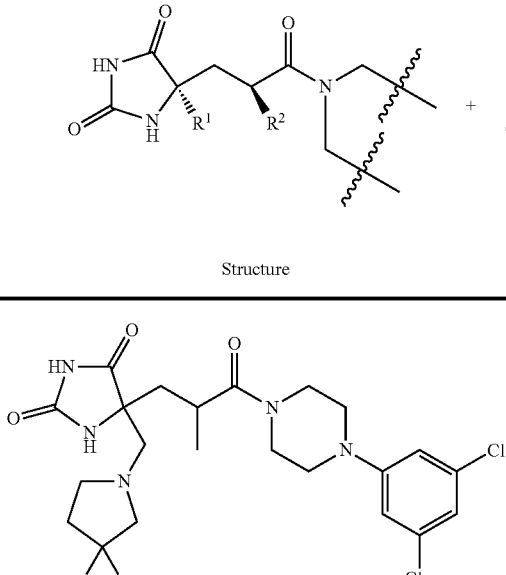
| Cpd | Structure | MW | Ms'd | Mtd | SM |
|---|---|---|---|---|---|
| 252 | 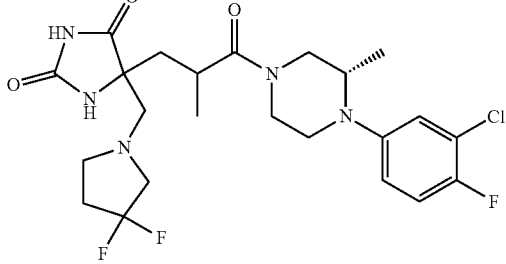 trans | 518 | 518-520 | H2 | Int 145 + 1-(3,5-dichloro phenyl) piperazine |
| 253 | 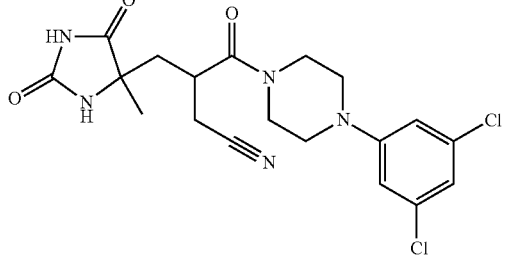 trans | 516 | 516-518 | H2 | Int 145 + Int 198 |
| 254 | 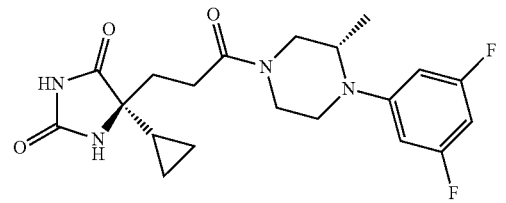 trans | 438 | 438-440 | F | Int 065 |
| 255 | 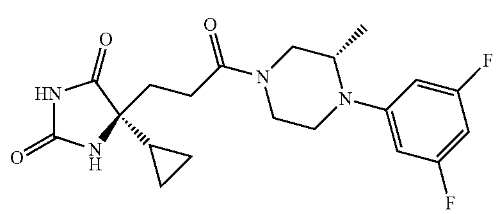 [SMILES: C[C@H]1CN(C(=O)CC[C@@]2(C3CC3)NC(=O)NC2=O)CCN1c1cc(F)cc(F)c1] | 406 | 407 | 2.5 | Int 163 + Int 207 |

TABLE III-continued

Illustrative compounds of the invention
trans:

| Cpd | Structure | MW | Ms'd | Mtd | SM |
|---|---|---|---|---|---|
| 256 | 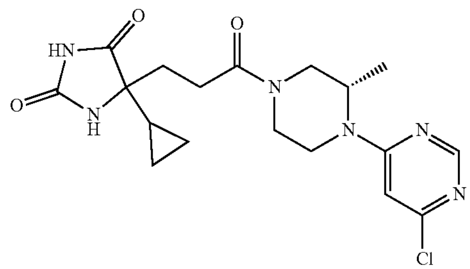 [SMILES: C[C@H]1CN(C(=O)CCC2(C3CC3)NC(=O)NC2=O)CCN1c1cc(Cl)ncn1] | 407 | 407-409 | H2 | Int 162 + Int 260 |
| 257 | 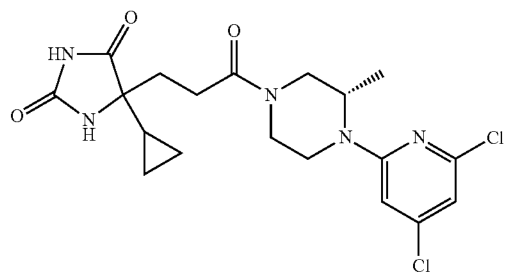 [SMILES: C[C@H]1CN(C(=O)CCC2(C3CC3)NC(=O)NC2=O)CCN1c1cc(Cl)cc(Cl)n1] | 440 | 440-442 | H2 | Int 162 + Int 261 |
| 258 | 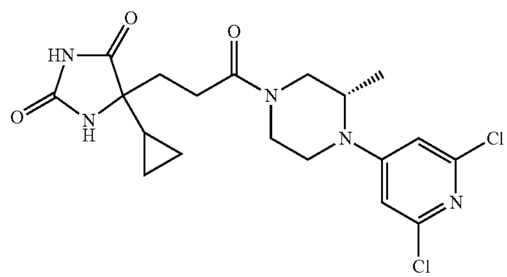 [SMILES: C[C@H]1CN(C(=O)CCC2(C3CC3)NC(=O)NC2=O)CCN1c1cc(Cl)nc(Cl)c1] | 440 | 440-442 | H2 | Int 162 + Int 262 |
| 259 | 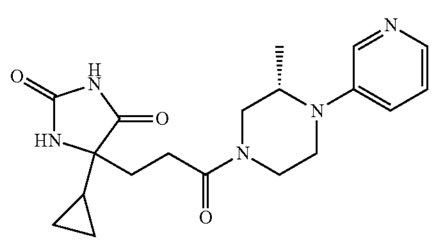 | 371 | 372 | H2 | Int 162 + Int 221 |
| 260 | 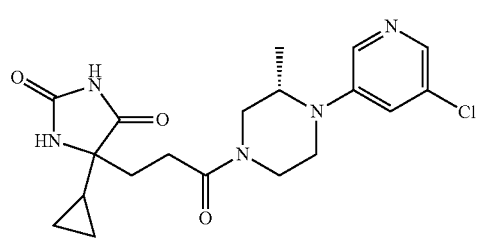 [SMILES: C[C@H]1CN(C(=O)CCC2(C3CC3)NC(=O)NC2=O)CCN1c1cncc(Cl)c1] | 406 | 406-408 | H2 | Int 162 + Int 215 |

TABLE III-continued
Illustrative compounds of the invention
trans:
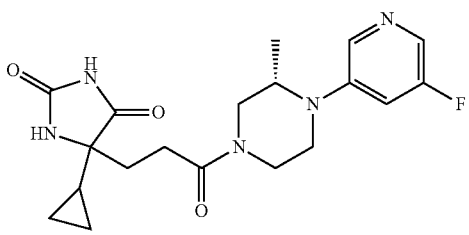 [SMILES: C[C@H]1CN(C(=O)CCC2(C3CC3)NC(=O)NC2=O)CCN1c1cncc(F)c1]
| Cpd | Structure | MW | Ms'd | Mtd | SM |
|---|---|---|---|---|---|
| 261 | 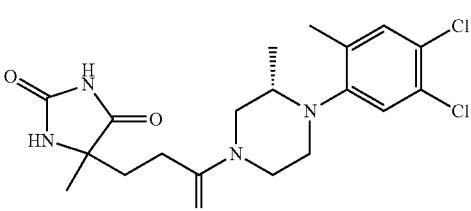 | 389 | 390 | H2 | Int 162 + Int 214 |
| 262 | 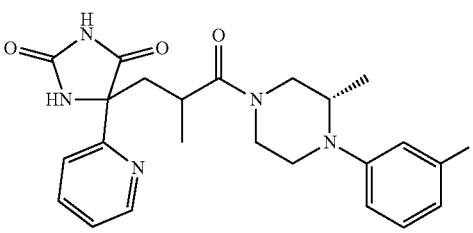 | 427 | 426-428-430 | H2 | 3-(4-Methyl-2,5-dioxo-imidazolidin-4-yl)propionic acid + Int 281 |
| 263 | 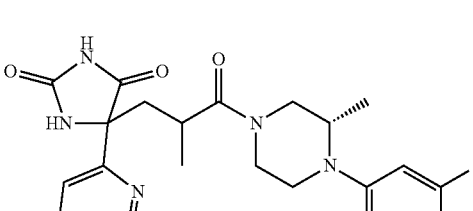  trans | 439 | 440 | H2 | Int 159 + Int 202 |
| 264 | 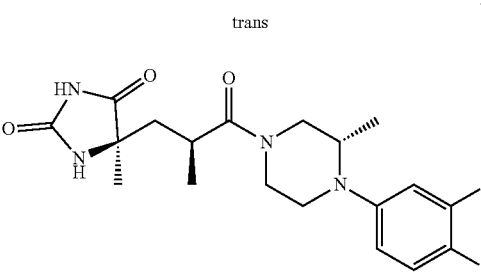  trans | 457 | 458 | H2 | Int 159 + Int 199 |
| 265 | 411 | 411-413 | 2.11 | Cpd 405 |

TABLE III-continued

Illustrative compounds of the invention
trans:

| Cpd | Structure | MW | Ms'd | Mtd | SM |
|---|---|---|---|---|---|
| 266 | trans | 390 | 391 | H2 | Int 169 + Int 202 |
| 267 | 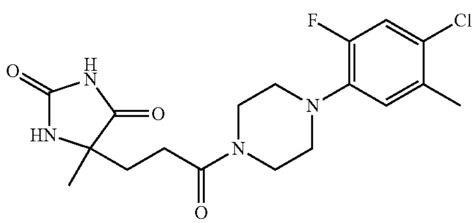 | 397 | 397-399 | H2 | 3-(4-Methyl-2,5-dioxo-imidazolidin-4-yl)propionic acid + Int 282 |
| 268 | trans | 392 | 393 | I4 | Int 062 |
| 269 | trans | 456 | 456-458 | H2 | Int 159 + Int 200 |
| 270 | 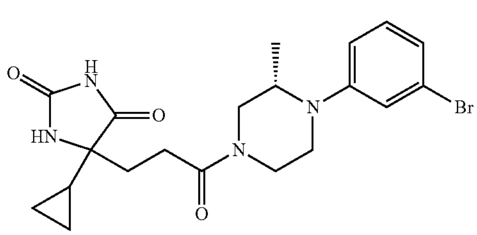 [SMILES: C[C@H]1CN(C(=O)CCC2(C3CC3)NC(=O)NC2=O)CCN1c1cccc(Br)c1] | 449 | 449-451 | H2 | Int 162 + Int 244 |

TABLE III-continued

Illustrative compounds of the invention
trans:

| Cpd | Structure | MW | Ms'd | Mtd | SM |
|---|---|---|---|---|---|
| 271 | trans | 441 | 441 | H2 | Int 165 + Int 245 |
| 272 | trans | 471 | 471 | H2 | Int 156 + Int 245 |
| 273 | | 448 | 449 | I6 | Cpd 270 + Pyridine-3-boronic acid |
| 274 | | 409 | 410 | H2 | Int 162 + Int 257 |
| 275 | trans | 359 | 360 | H2 | Int 165 + Int 221 |

TABLE III-continued
Illustrative compounds of the invention
trans:
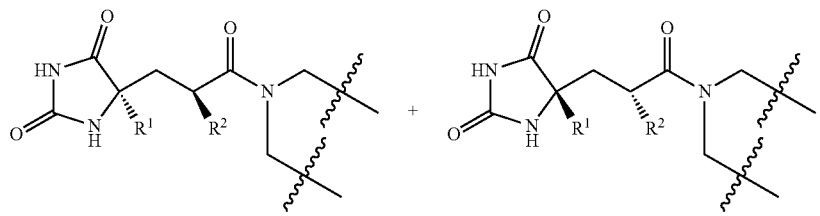
| Cpd | Structure | MW | Ms'd | Mtd | SM |
|---|---|---|---|---|---|
| 276 | trans | 394 | 394-936 | H2 | Int 165 + Int 215 |
| 277 | trans | 377 | 378 | H2 | Int 165 + Int 214 |
| 278 | 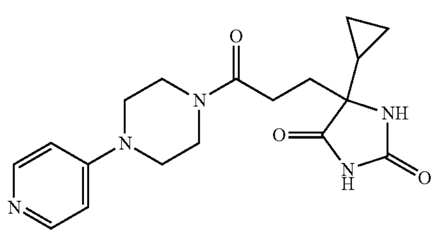 [SMILES: O=C1NC(=O)C(CCC(=O)N2CCN(c3ccncc3)CC2)(C2CC2)N1] | 357 | 358 | H2 | Int 162 + 1-(4-pyridyl)piperazine |
| 279 | trans | 445 | 445-447 | H2 | Int 156 + Int 203 |

TABLE III-continued

Illustrative compounds of the invention
trans:

| Cpd | Structure | MW | Ms'd | Mtd | SM |
|---|---|---|---|---|---|
| 280 | 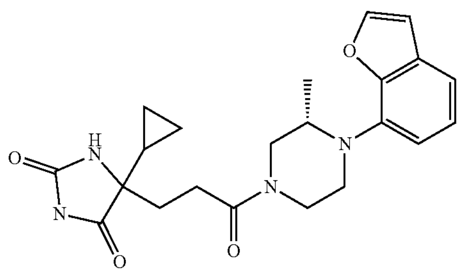 [SMILES: C[C@H]1CN(C(=O)CCC2(C3CC3)NC(=O)NC2=O)CCN1c1cccc2ccoc12] | 410 | 411 | H1 | Int 162 + Int 249 |
| 281 | 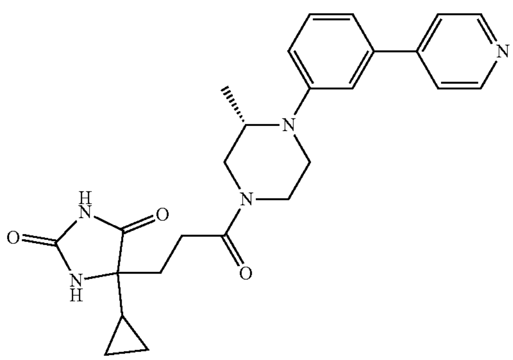 [SMILES: C[C@H]1CN(C(=O)CCC2(C3CC3)NC(=O)NC2=O)CCN1c1cccc(-c2ccncc2)c1] | 448 | 449 | I6 | Cpd 270 + Pyridine-4-boronic acid |
| 282 | 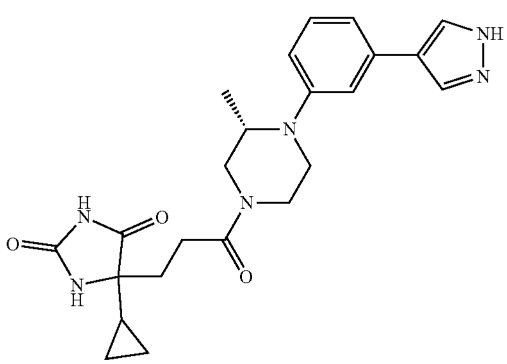 [SMILES: C[C@H]1CN(C(=O)CCC2(C3CC3)NC(=O)NC2=O)CCN1c1cccc(-c2cn[nH]c2)c1] | 437 | 437 | I6 | Cpd 270 + Pyrazole-4-boronic acid |

TABLE III-continued
Illustrative compounds of the invention
trans:
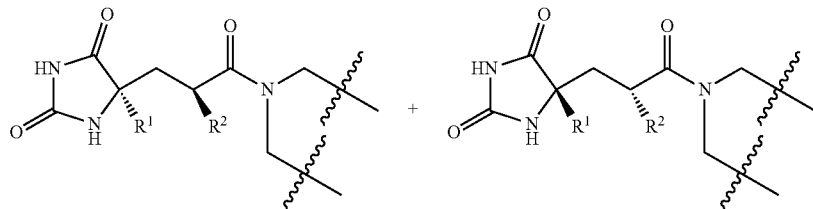
| Cpd | Structure | MW | Ms'd | Mtd | SM |
|---|---|---|---|---|---|
| 283 | 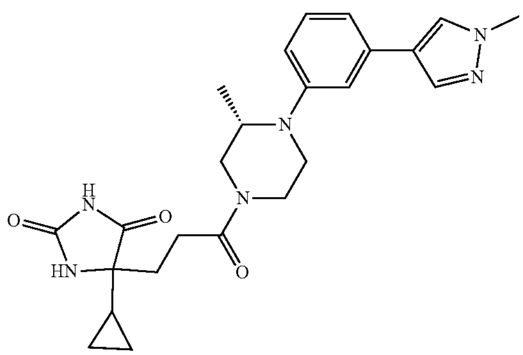 [SMILES: C[C@H]1CN(C(=O)CCC2(C3CC3)NC(=O)NC2=O)CCN1c1cccc(-c2cnn(C)c2)c1] | 451 | 451 | I6 | Cpd 270 + 1-Methyl-1H-pyrazole-4-boronic acid |
| 284 | 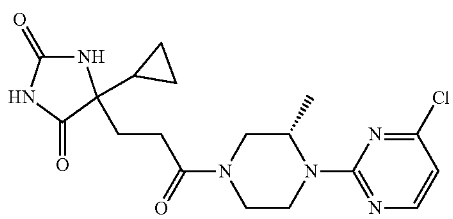 [SMILES: C[C@H]1CN(C(=O)CCC2(C3CC3)NC(=O)NC2=O)CCN1c1nccc(Cl)n1] | 407 | 407-409 | H1 | Int 162 + Int 226 |
| 285 | 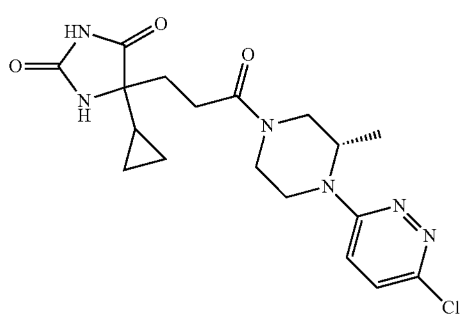 [SMILES: C[C@H]1CN(C(=O)CCC2(C3CC3)NC(=O)NC2=O)CCN1c1ccc(Cl)nn1] | 407 | 407-409 | H1 | Int 162 + Int 227 |
| 286 | 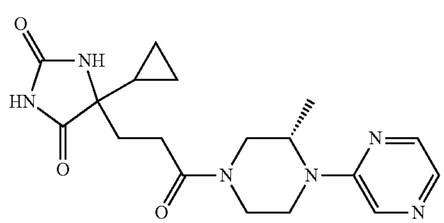 [SMILES: C[C@H]1CN(C(=O)CCC2(C3CC3)NC(=O)NC2=O)CCN1c1cnccn1] | 372 | 373 | H1 | Int 162 + Int 228 |

TABLE III-continued

Illustrative compounds of the invention
trans:

| Cpd | Structure | MW | Ms'd | Mtd | SM |
|---|---|---|---|---|---|
| 287 | 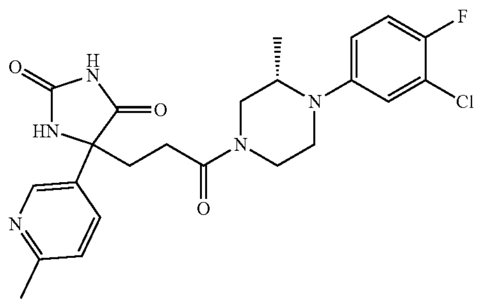 [SMILES: Cc1ccc(C2(CCC(=O)N3CCN(c4ccc(F)c(Cl)c4)[C@@H](C)C3)NC(=O)NC2=O)cn1] | 474 | 474-476 | F | Int 059 |
| 288 | 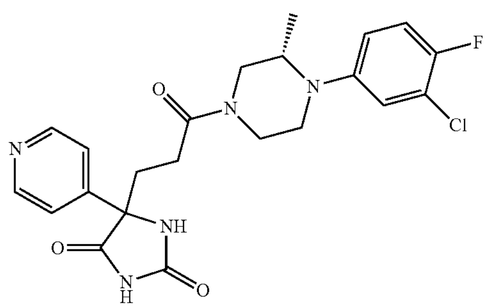 [SMILES: C[C@H]1CN(C(=O)CCC2(c3ccncc3)NC(=O)NC2=O)CCN1c1ccc(F)c(Cl)c1] | 460 | 460-462 | F | Int 060 |
| 289 | 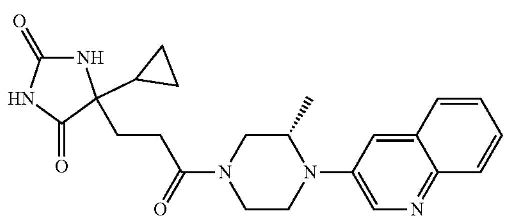 [SMILES: C[C@H]1CN(C(=O)CCC2(C3CC3)NC(=O)NC2=O)CCN1c1cnc2ccccc2c1] | 422 | 422 | H1 | Int 162 + Int 250 |
| 290 | 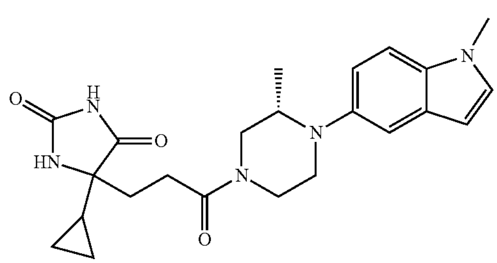 [SMILES: C[C@H]1CN(C(=O)CCC2(C3CC3)NC(=O)NC2=O)CCN1c1ccc2c(ccn2C)c1] | 424 | 425 | H1 | Int 162 + Int 251 |
| 291 | 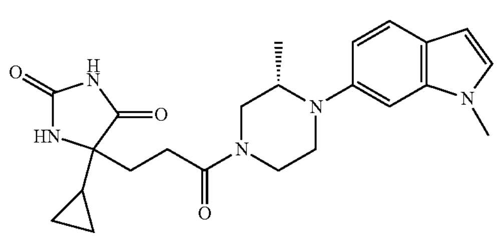 [SMILES: C[C@H]1CN(C(=O)CCC2(C3CC3)NC(=O)NC2=O)CCN1c1ccc2ccn(C)c2c1] | 424 | 425 | H1 | Int 162 + Int 252 |

TABLE III-continued

Illustrative compounds of the invention
trans:

| Cpd | Structure | MW | Ms'd | Mtd | SM |
|---|---|---|---|---|---|
| 292 | trans | 406 | 407 | F | Int 066 |
| 293 | 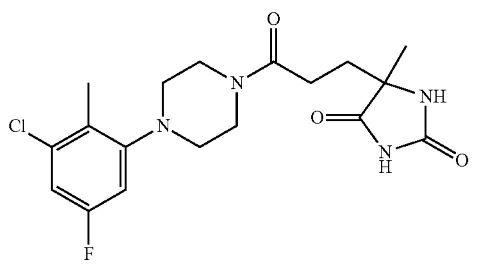 [SMILES: Cc1c(Cl)cc(F)cc1N1CCN(C(=O)CCC2(C)NC(=O)NC2=O)CC1] | 397 | 397-399 | H4 | 3-(4-Methyl-2,5-dioxo-imidazolidin-4-yl)propionic acid + Int 283 |
| 294 | trans | 392 | 393 | F | Int 057 |
| 295 | trans | 427 | 427-429 | F | Int 058 |
| 296 | 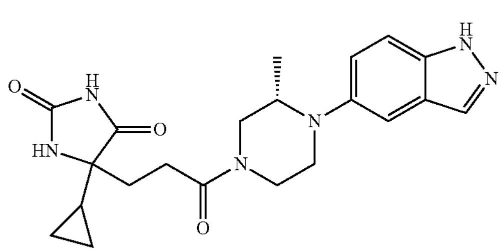 [SMILES: C[C@H]1CN(C(=O)CCC2(C3CC3)NC(=O)NC2=O)CCN1c1ccc2[nH]ncc2c1] | 410 | 411 | H2 | Int 162 + Int 258 |

TABLE III-continued

Illustrative compounds of the invention
trans:

| Cpd | Structure | MW | Ms'd | Mtd | SM |
|---|---|---|---|---|---|
| 297 | 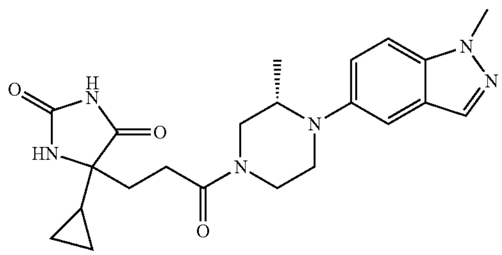 [SMILES: C[C@H]1CN(C(=O)CCC2(C3CC3)NC(=O)NC2=O)CCN1c1ccc2c(cnn2C)c1] | 425 | 425 | H2 | Int 162 + Int 259 |
| 298 | 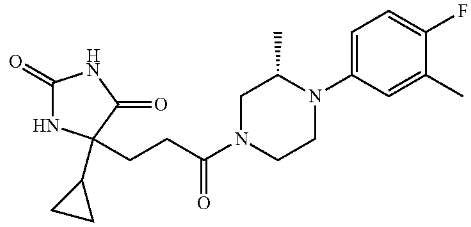 [SMILES: Cc1cc(N2CCN(C(=O)CCC3(C4CC4)NC(=O)NC3=O)C[C@@H]2C)ccc1F] | 402 | 403 | H2 | Int 162 + Int 210 |
| 299 | 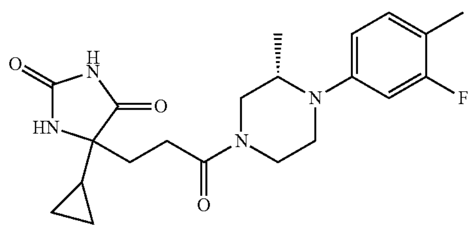 [SMILES: Cc1ccc(N2CCN(C(=O)CCC3(C4CC4)NC(=O)NC3=O)C[C@@H]2C)cc1F] | 402 | 403 | H2 | Int 162 + Int 224 |
| 300 | 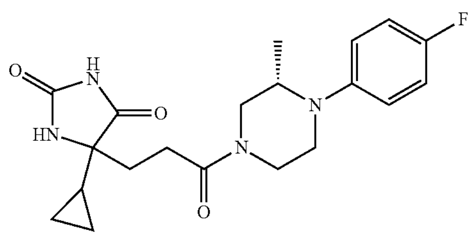 [SMILES: C[C@H]1CN(C(=O)CCC2(C3CC3)NC(=O)NC2=O)CCN1c1ccc(F)cc1] | 388 | 389 | H2 | Int 162 + Int 209 |
| 301 | 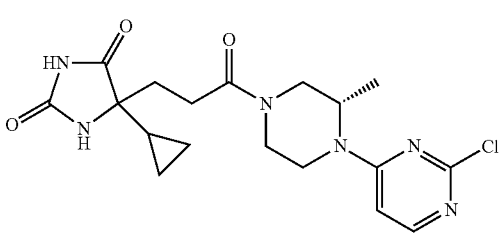 [SMILES: C[C@H]1CN(C(=O)CCC2(C3CC3)NC(=O)NC2=O)CCN1c1ccnc(Cl)n1] | 407 | 407-409 | H2 | Int 162 + Int 264 |

TABLE III-continued
Illustrative compounds of the invention
trans:
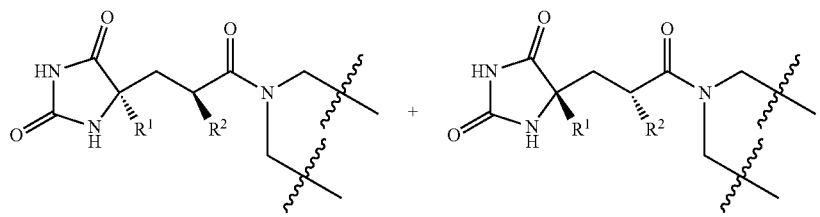
| Cpd | Structure | MW | Ms'd | Mtd | SM |
|---|---|---|---|---|---|
| 302 | | 372 | 373 | 2.35 | Cpd 285 |
| 303 | | 385 | 386 | H2 | Int 162 + Int 222 |
| 304 | | 372 | 373 | H2 | Int 162 + Int 248 |
| 305 | | 428 | 428 | H1 | Int 162 + Int 253 |
| 306 | | 419 | 419-421 | H2 | Int 162 + Int 225 |

TABLE III-continued

Illustrative compounds of the invention
trans:

| Cpd | Structure | MW | Ms'd | Mtd | SM |
|---|---|---|---|---|---|
| 307 | 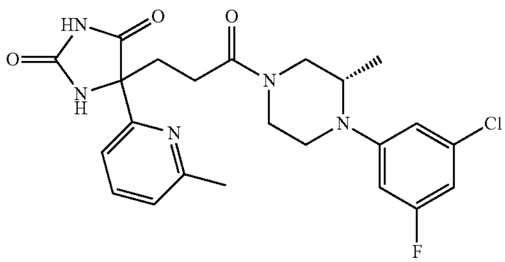 [SMILES: Cc1cccc(C2(CCC(=O)N3CCN(c4cc(F)cc(Cl)c4)[C@@H](C)C3)NC(=O)NC2=O)n1] | 474 | 474-476 | H1 | Int 166 + Int 206 |
| 308 | 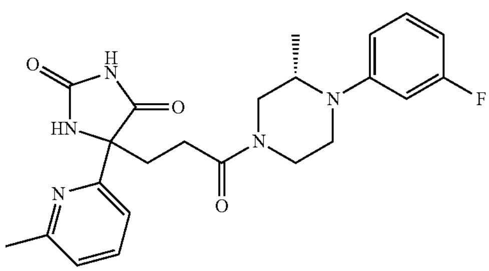 [SMILES: Cc1cccc(C2(CCC(=O)N3CCN(c4cccc(F)c4)[C@@H](C)C3)NC(=O)NC2=O)n1] | 439 | 440 | H1 | Int 166 + Int 202 |
| 309 | 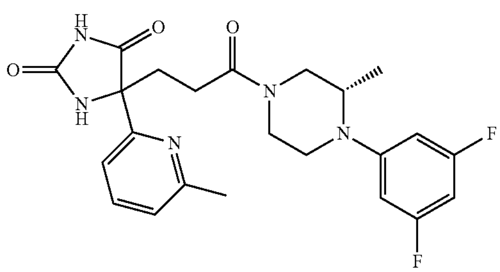 [SMILES: Cc1cccc(C2(CCC(=O)N3CCN(c4cc(F)cc(F)c4)[C@@H](C)C3)NC(=O)NC2=O)n1] | 457 | 458 | H1 | Int 166 + Int 207 |
| 310 | 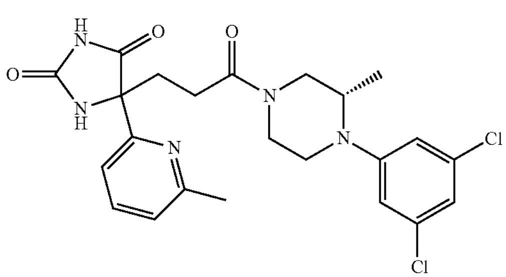 [SMILES: Cc1cccc(C2(CCC(=O)N3CCN(c4cc(Cl)cc(Cl)c4)[C@@H](C)C3)NC(=O)NC2=O)n1] | 490 | 490-492 | H1 | Int 166 + Int 197 |

TABLE III-continued
Illustrative compounds of the invention
trans:
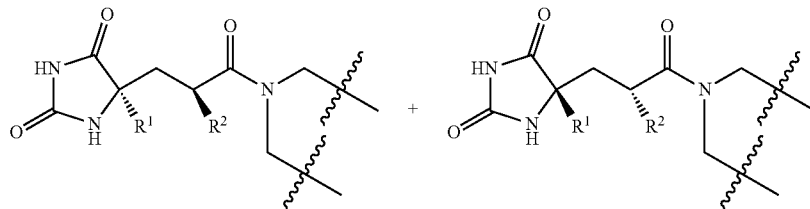
| Cpd | Structure | MW | Ms'd | Mtd | SM |
|---|---|---|---|---|---|
| 311 | 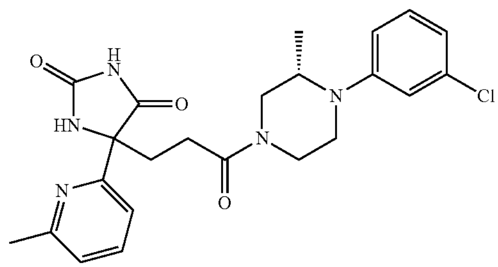 [SMILES: Cc1cccc(C2(CCC(=O)N3CCN(c4cccc(Cl)c4)[C@@H](C)C3)NC(=O)NC2=O)n1] | 456 | 456-458 | H1 | Int 166 + Int 200 |
| 312 | 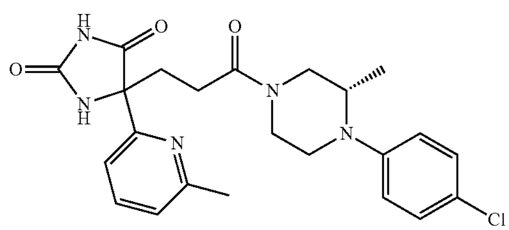 [SMILES: Cc1cccc(C2(CCC(=O)N3CCN(c4ccc(Cl)cc4)[C@@H](C)C3)NC(=O)NC2=O)n1] | 456 | 456-458 | H1 | Int 166 + Int 205 |
| 313 | 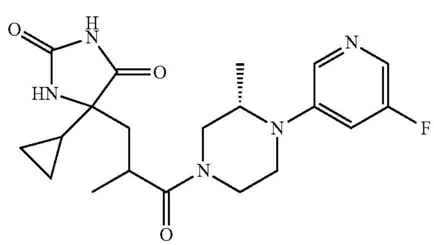 [SMILES: CC(CC1(C2CC2)NC(=O)NC1=O)C(=O)N1CCN(c2cncc(F)c2)[C@@H](C)C1] | 403 | 404 | H2 | Int 164 + Int 214 |
| 314 | 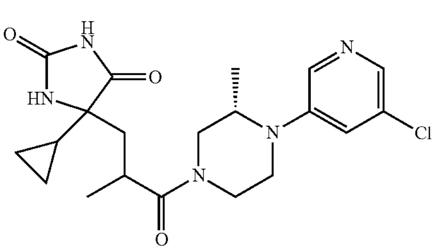 [SMILES: CC(CC1(C2CC2)NC(=O)NC1=O)C(=O)N1CCN(c2cncc(Cl)c2)[C@@H](C)C1] | 420 | 420-422 | H2 | Int 164 + Int 215 |

TABLE III-continued
Illustrative compounds of the invention
trans:
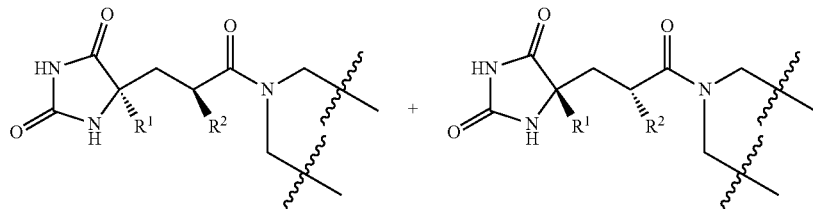
| Cpd | Structure | MW | Ms'd | Mtd | SM |
|---|---|---|---|---|---|
| 315 | 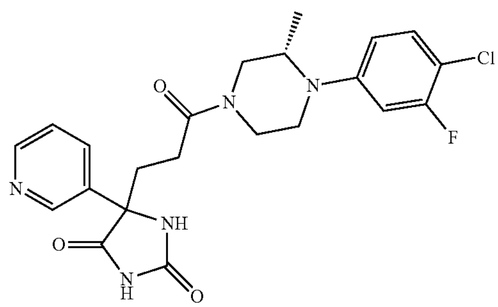 [SMILES: C[C@H]1CN(C(=O)CCC2(c3cccnc3)NC(=O)NC2=O)CCN1c1ccc(Cl)c(F)c1] | 460 | 460-462 | H2 | Int 132 + Int 213 |
| 316 | 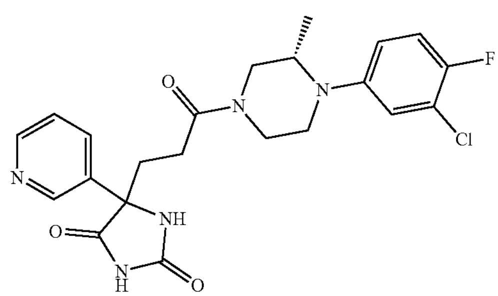 [SMILES: C[C@H]1CN(C(=O)CCC2(c3cccnc3)NC(=O)NC2=O)CCN1c1ccc(F)c(Cl)c1] | 460 | 460-462 | H2 | Int 132 + Int 198 |
| 317 | 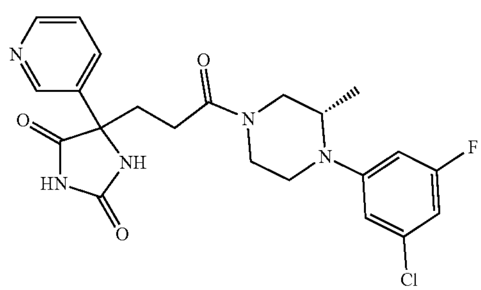 [SMILES: C[C@H]1CN(C(=O)CCC2(c3cccnc3)NC(=O)NC2=O)CCN1c1cc(F)cc(Cl)c1] | 460 | 460-462 | H2 | Int 132 + Int 206 |
| 318 | 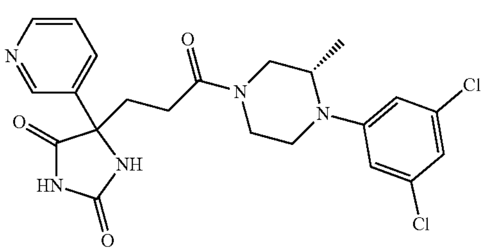 [SMILES: C[C@H]1CN(C(=O)CCC2(c3cccnc3)NC(=O)NC2=O)CCN1c1cc(Cl)cc(Cl)c1] | 476 | 476-478 | H2 | Int 132 + Int 197 |

TABLE III-continued
Illustrative compounds of the invention
trans:
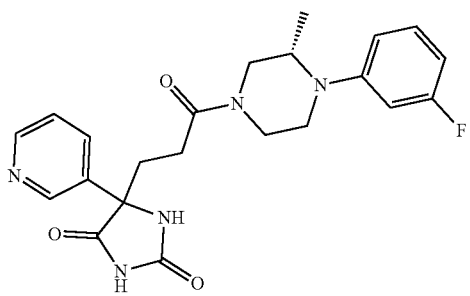 [SMILES: C[C@H]1CN(C(=O)CCC2(c3cccnc3)NC(=O)NC2=O)CCN1c1cccc(F)c1]
| Cpd | Structure | MW | Ms'd | Mtd | SM |
|---|---|---|---|---|---|
| 319 | 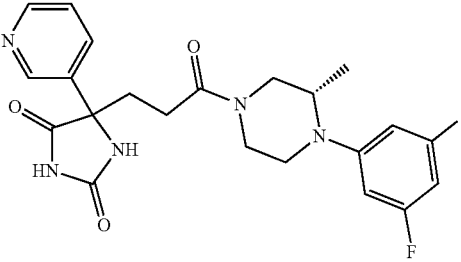 | 425 | 426 | H2 | Int 132 + Int 202 |
| 320 | 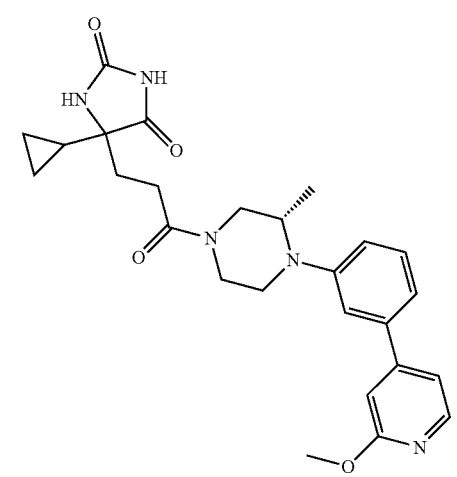 | 443 | 444 | H2 | Int 132 + Int 207 |
| 321 | 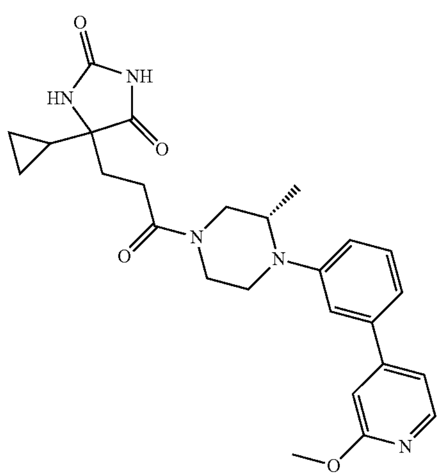 [SMILES: COc1cc(-c2cccc(N3CCN(C(=O)CCC4(C5CC5)NC(=O)NC4=O)C[C@@H]3C)c2)ccn1] | 478 | 479 | I6 | Cpd 270 + 2-Methoxypyridine-4-boronic acid |

TABLE III-continued

Illustrative compounds of the invention
trans:

| Cpd | Structure | MW | Ms'd | Mtd | SM |
|-----|-----------|----|----|-----|-----|
| 322 | 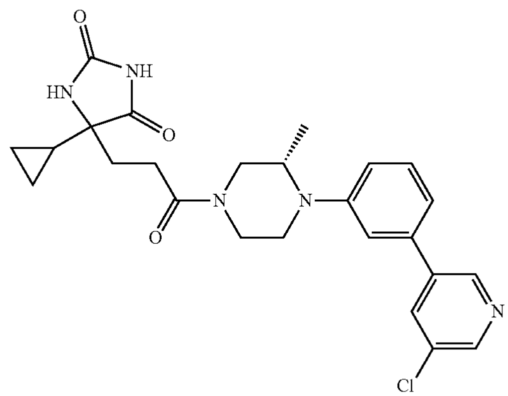 [SMILES: C[C@H]1CN(C(=O)CCC2(C3CC3)NC(=O)NC2=O)CCN1c1cccc(-c2cncc(Cl)c2)c1] | 482 | 482-484 | I6 | Cpd 270 + 5-Chloropyridine-3-boronic acid |
| 323 | 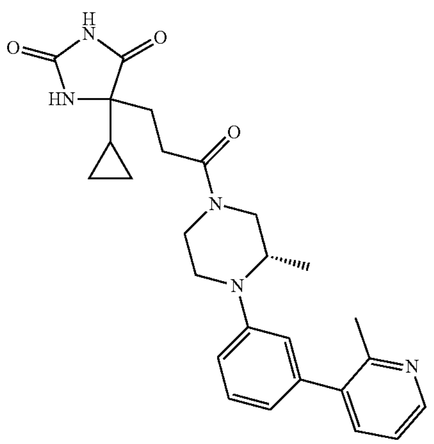 [SMILES: Cc1ncccc1-c1cccc(N2CCN(C(=O)CCC3(C4CC4)NC(=O)NC3=O)C[C@@H]2C)c1] | 462 | 462 | I6 | Cpd 270 + 2-Methyl-3-(4,4,5,5-tetramethyl-[1,3,2]dioxaborolan-2-yl)-pyridine |
| 324 | 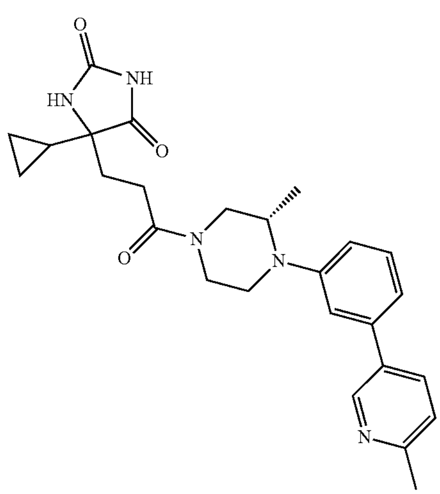 [SMILES: Cc1ccc(-c2cccc(N3CCN(C(=O)CCC4(C5CC5)NC(=O)NC4=O)C[C@@H]3C)c2)cn1] | 462 | 462 | I6 | Cpd 270 + 2-methyl-5-pyridinylboronic acid |

TABLE III-continued
Illustrative compounds of the invention
trans:
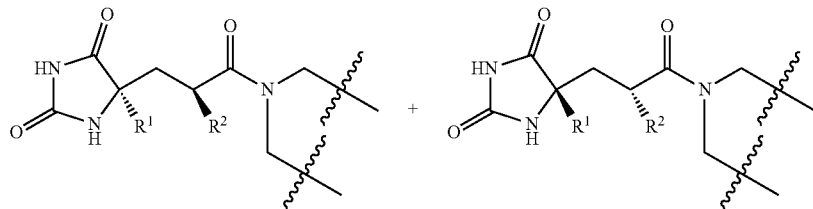
| Cpd | Structure | MW | Ms'd | Mtd | SM |
|---|---|---|---|---|---|
| 325 | 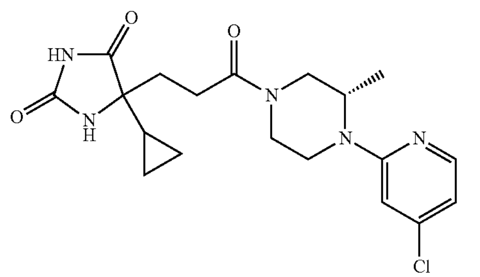 [SMILES: C[C@H]1CN(C(=O)CCC2(C3CC3)NC(=O)NC2=O)CCN1c1cc(Cl)ccn1] | 406 | 406-408 | H2 | Int 162 + Int 229 |
| 326 | 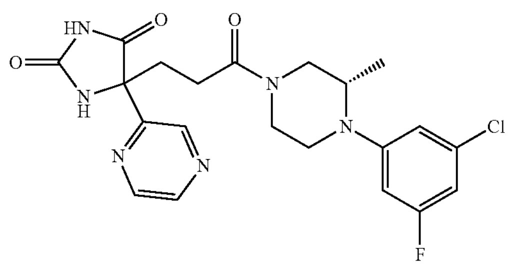 [SMILES: C[C@H]1CN(C(=O)CCC2(c3cnccn3)NC(=O)NC2=O)CCN1c1cc(F)cc(Cl)c1] | 461 | 461-463 | H2 | Int 142 + Int 206 |
| 327 | 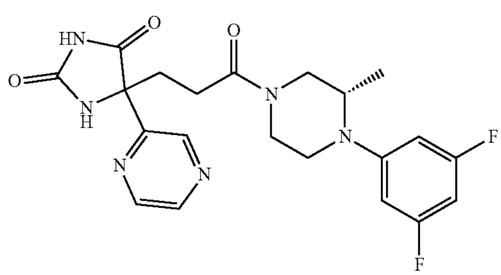 [SMILES: C[C@H]1CN(C(=O)CCC2(c3cnccn3)NC(=O)NC2=O)CCN1c1cc(F)cc(F)c1] | 444 | 445 | H2 | Int 142 + Int 207 |
| 328 | 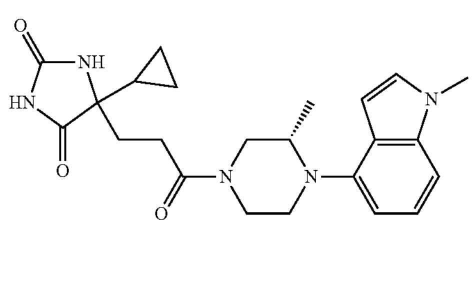 [SMILES: C[C@H]1CN(C(=O)CCC2(C3CC3)NC(=O)NC2=O)CCN1c1cccc2c1ccn2C] | 424 | 424 | H1 | Int 162 + Int 254 |

TABLE III-continued

Illustrative compounds of the invention
trans:

| Cpd | Structure | MW | Ms'd | Mtd | SM |
|---|---|---|---|---|---|
| 329 | 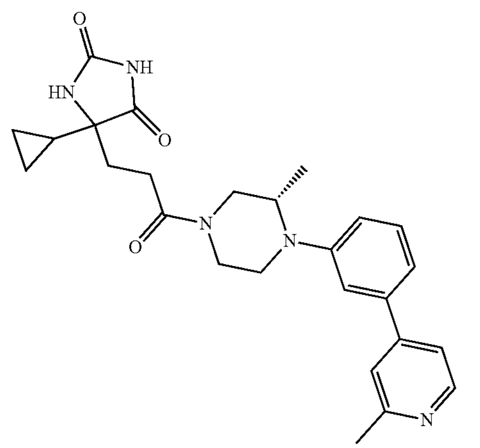 [SMILES: Cc1cc(-c2cccc(N3CCN(C(=O)CCC4(C5CC5)NC(=O)NC4=O)C[C@@H]3C)c2)ccn1] | 462 | 462 | I6 | Cpd 270 + 2-Methyl-4-(4,4,5,5-tetramethyl-[1,3,2]dioxaborolan-2-yl)-pyridine |
| 330 | 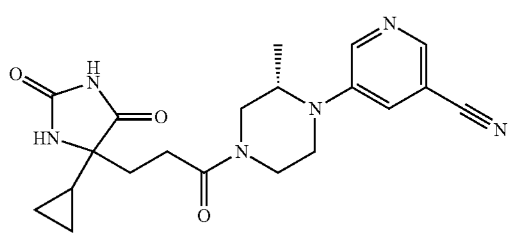 [SMILES: C[C@H]1CN(C(=O)CCC2(C3CC3)NC(=O)NC2=O)CCN1c1cncc(C#N)c1] | 396 | 397 | H2 | Int 162 + Int 223 |
| 331 | 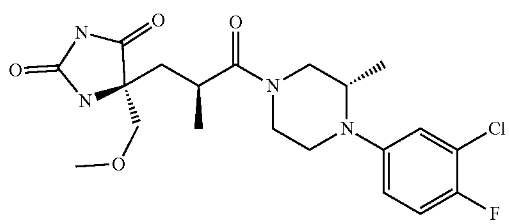 [SMILES: COC[C@]1(C[C@H](C)C(=O)N2CCN(c3ccc(F)c(Cl)c3)[C@@H](C)C2)NC(=O)NC1=O] | 441 | 441-443 | 2.12 | Cpd 406 |
| 332 | 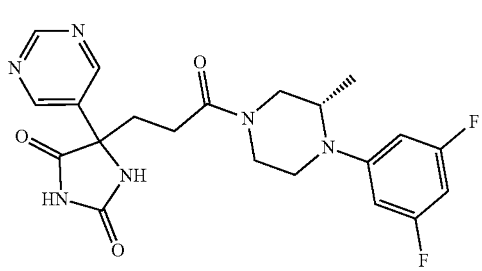 [SMILES: C[C@H]1CN(C(=O)CCC2(c3cncnc3)NC(=O)NC2=O)CCN1c1cc(F)cc(F)c1] | 444 | 445 | H2 | Int 182 + Int 207 |

US 11,718,588 B2

415                                                                                             416

TABLE III-continued

Illustrative compounds of the invention
trans:

| Cpd | Structure | MW | Ms'd | Mtd | SM |
|-----|-----------|----|----|-----|----|
| 333 | 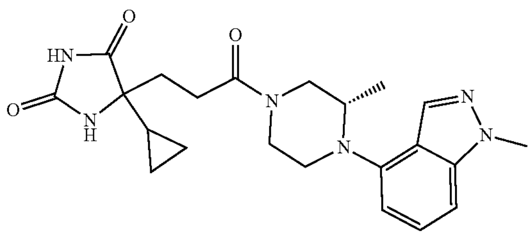 [SMILES: C[C@H]1CN(C(=O)CCC2(C3CC3)NC(=O)NC2=O)CCN1c1cccc2c1cnn2C] | 425 | 425 | H2 | Int 162 + Int 230 |
| 334 | 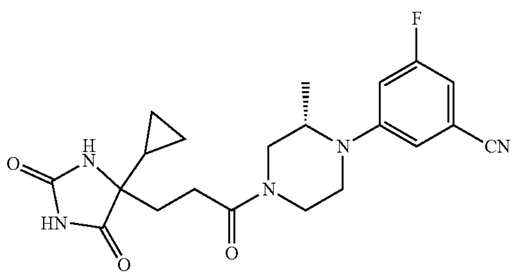 [SMILES: C[C@H]1CN(C(=O)CCC2(C3CC3)NC(=O)NC2=O)CCN1c1cc(F)cc(C#N)c1] | 413 | 414 | H1 | Int 162 + Int 255 |
| 335 | 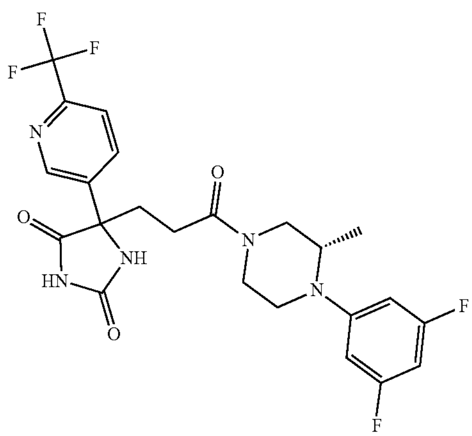 [SMILES: C[C@H]1CN(C(=O)CCC2(c3ccc(C(F)(F)F)nc3)NC(=O)NC2=O)CCN1c1cc(F)cc(F)c1] | 511 | 512 | F | Int 072 |
| 336 | 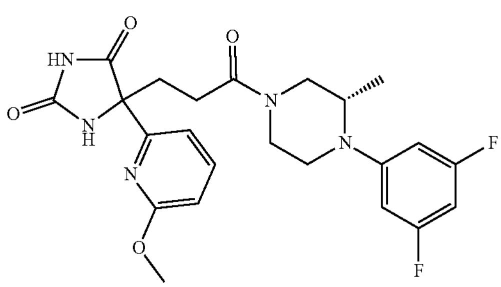 [SMILES: COc1cccc(C2(CCC(=O)N3CCN(c4cc(F)cc(F)c4)[C@@H](C)C3)NC(=O)NC2=O)n1] | 473 | 474 | F | Int 070 |

TABLE III-continued
Illustrative compounds of the invention
trans:
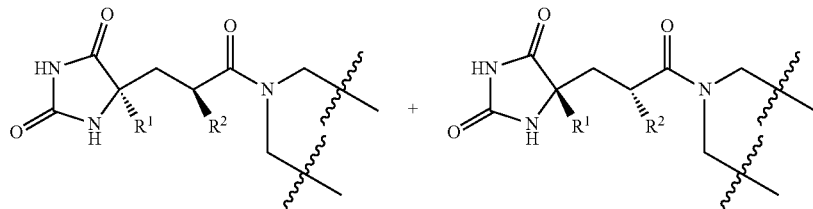
| Cpd | Structure | MW | Ms'd | Mtd | SM |
|---|---|---|---|---|---|
| 337 | 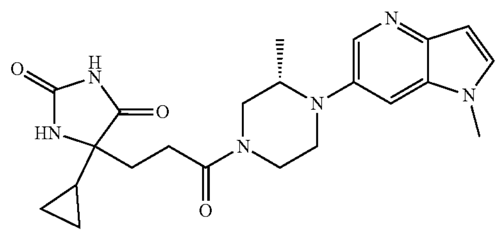 [SMILES: C[C@H]1CN(C(=O)CCC2(C3CC3)NC(=O)NC2=O)CCN1c1cnc2ccn(C)c2c1] | 425 | 425 | H2 | Int 162 + Int 231 |
| 338 | 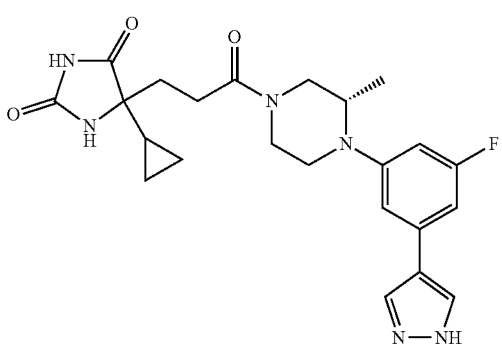 [SMILES: C[C@H]1CN(C(=O)CCC2(C3CC3)NC(=O)NC2=O)CCN1c1cc(F)cc(-c2cn[nH]c2)c1] | 455 | 455 | H2 | Int 162 + Int 232 |
| 339 | 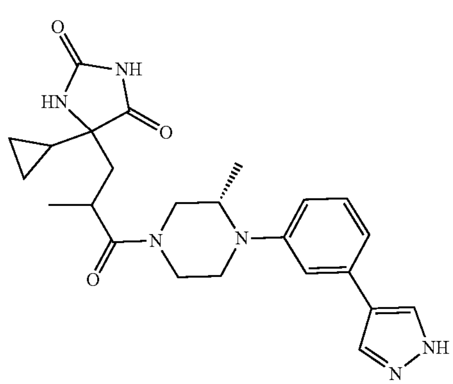 [SMILES: CC(CC1(C2CC2)NC(=O)NC1=O)C(=O)N1CCN(c2cccc(-c3cn[nH]c3)c2)[C@@H](C)C1] | 451 | 451 | H2 | Int 164 + Int 233 |

TABLE III-continued
Illustrative compounds of the invention
trans:
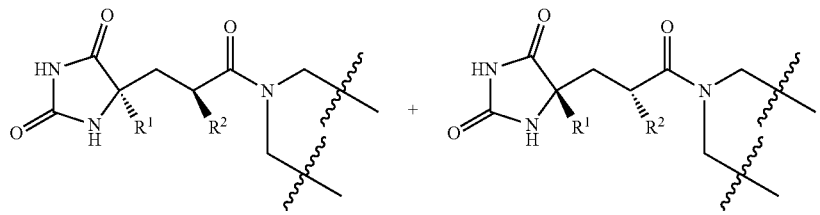
| Cpd | Structure | MW | Ms'd | Mtd | SM |
|---|---|---|---|---|---|
| 340 | 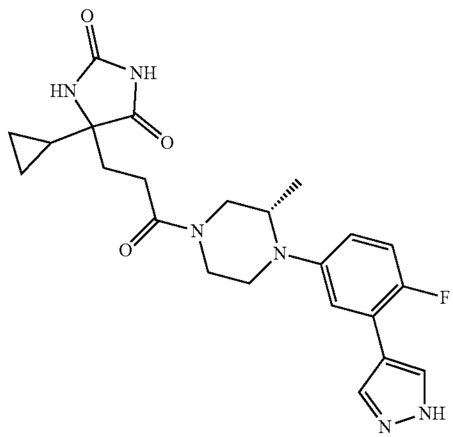 [SMILES: C[C@H]1CN(C(=O)CCC2(C3CC3)NC(=O)NC2=O)CCN1c1ccc(F)c(-c2cn[nH]c2)c1] | 455 | 455 | H2 | Int 162 + Int 234 |
| 341 | 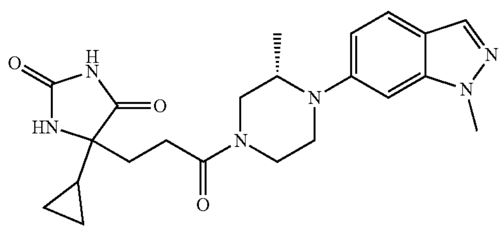 [SMILES: C[C@H]1CN(C(=O)CCC2(C3CC3)NC(=O)NC2=O)CCN1c1ccc2cnn(C)c2c1] | 425 | 425 | H2 | Int 162 + Int 239 |
| 342 | 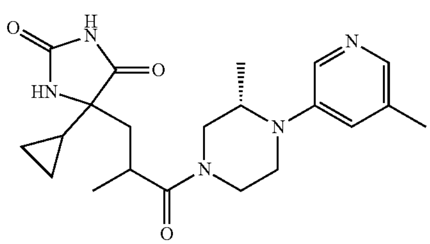 [SMILES: Cc1cncc(N2CCN(C(=O)C(C)CC3(C4CC4)NC(=O)NC3=O)C[C@@H]2C)c1] | 399 | 400 | H2 | Int 164 + Int 222 |
| 343 | 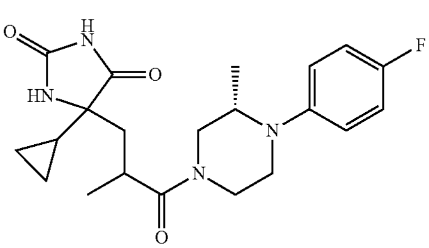 [SMILES: CC(CC1(C2CC2)NC(=O)NC1=O)C(=O)N1CCN(c2ccc(F)cc2)[C@@H](C)C1] | 402 | 403 | H2 | Int 164 + Int 209 |

TABLE III-continued

Illustrative compounds of the invention
trans:

| Cpd | Structure | MW | Ms'd | Mtd | SM |
|---|---|---|---|---|---|
| 344 | 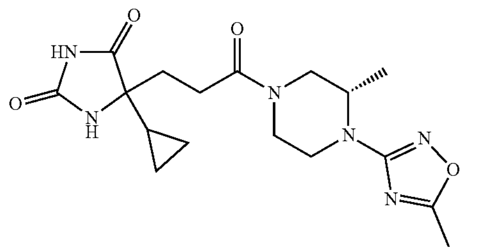 [SMILES: Cc1nc(N2CCN(C(=O)CCC3(C4CC4)NC(=O)NC3=O)C[C@@H]2C)no1] | 376 | 377 | H2 | Int 162 + Int 237 |
| 345 | 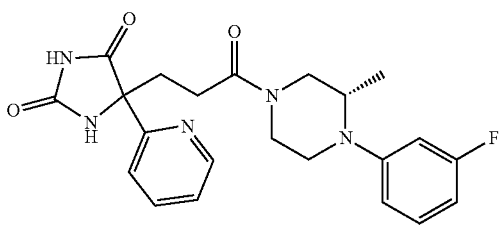 [SMILES: C[C@H]1CN(C(=O)CCC2(c3ccccn3)NC(=O)NC2=O)CCN1c1cccc(F)c1] | 425 | 426 | F | Int 103 |
| 346 | 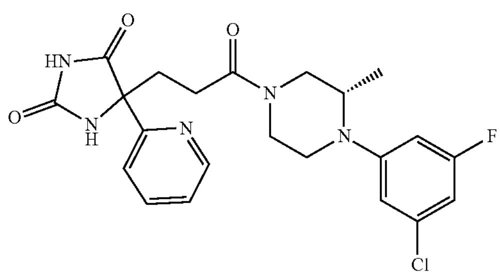 [SMILES: C[C@H]1CN(C(=O)CCC2(c3ccccn3)NC(=O)NC2=O)CCN1c1cc(F)cc(Cl)c1] | 460 | 460-462 | F | Int 104 |
| 347 | 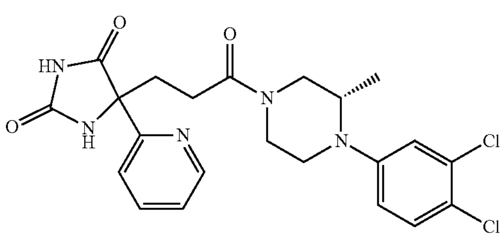 [SMILES: C[C@H]1CN(C(=O)CCC2(c3ccccn3)NC(=O)NC2=O)CCN1c1ccc(Cl)c(Cl)c1] | 476 | 476-478 | F | Int 105 |
| 348 | 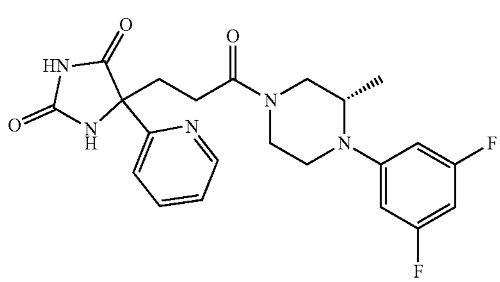 [SMILES: C[C@H]1CN(C(=O)CCC2(c3ccccn3)NC(=O)NC2=O)CCN1c1cc(F)cc(F)c1] | 443 | 444 | F | Int 106 |

TABLE III-continued
Illustrative compounds of the invention
trans:
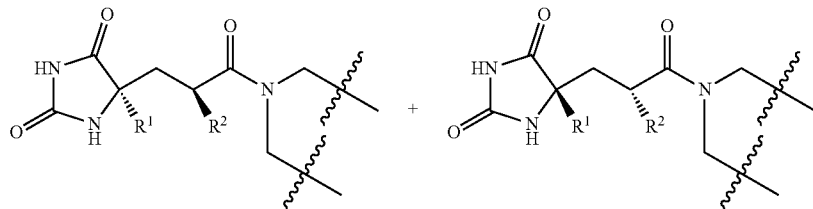
| Cpd | Structure | MW | Ms'd | Mtd | SM |
|---|---|---|---|---|---|
| 349 | 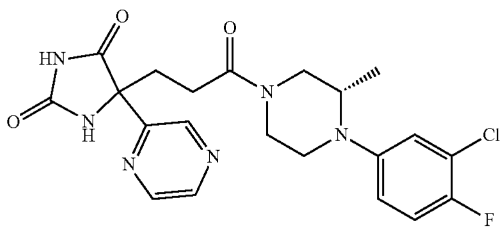 [SMILES: C[C@H]1CN(C(=O)CCC2(c3cnccn3)NC(=O)NC2=O)CCN1c1ccc(F)c(Cl)c1] | 461 | 461-463 | H2 | Int 142 + Int 198 |
| 350 | 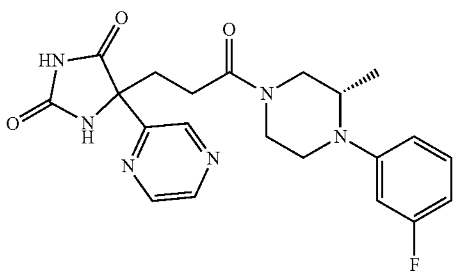 [SMILES: C[C@H]1CN(C(=O)CCC2(c3cnccn3)NC(=O)NC2=O)CCN1c1cccc(F)c1] | 426 | 427 | H2 | Int 142 + Int 202 |
| 351 | 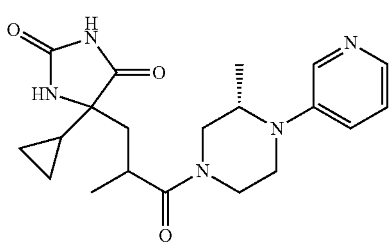 [SMILES: CC(CC1(C2CC2)NC(=O)NC1=O)C(=O)N1CCN(c2cccnc2)[C@@H](C)C1] | 385 | 386 | H2 | Int 164 + Int 221 |
| 352 | 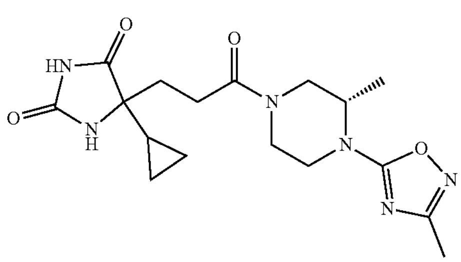 [SMILES: Cc1noc(N2CCN(C(=O)CCC3(C4CC4)NC(=O)NC3=O)C[C@@H]2C)n1] | 376 | 377 | H2 | Int 162 + Int 238 |

TABLE III-continued
Illustrative compounds of the invention
trans:
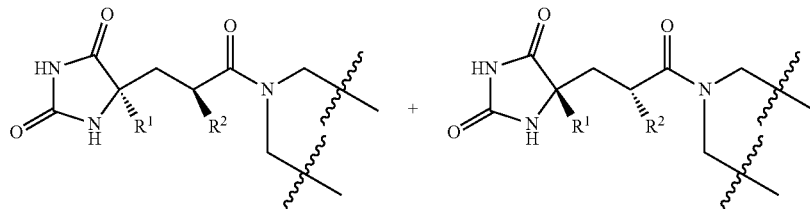
| Cpd | Structure | MW | Ms'd | Mtd | SM |
|---|---|---|---|---|---|
| 353 | 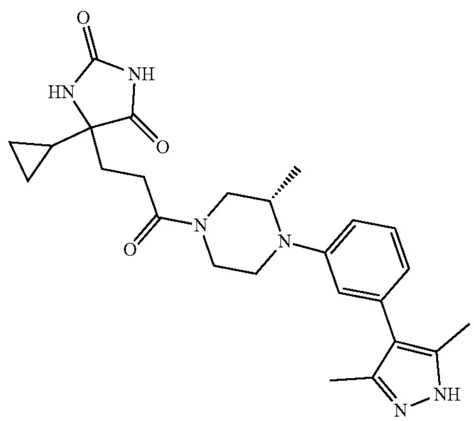 [SMILES: Cc1n[nH]c(C)c1-c1cccc(N2CCN(C(=O)CCC3(C4CC4)NC(=O)NC3=O)C[C@@H]2C)c1] | 465 | 466 | I6 | Cpd 270 + 3,5-dimethylpyrazole-4-boronic acid, pinacol ester |
| 354 | 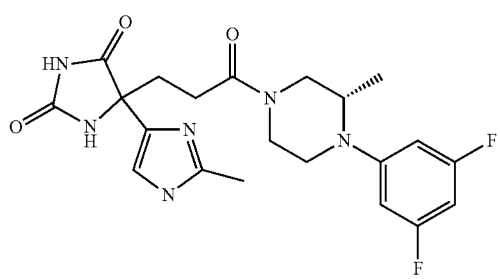 [SMILES: Cc1nc(C2(CCC(=O)N3CCN(c4cc(F)cc(F)c4)[C@@H](C)C3)NC(=O)NC2=O)c[nH]1] | 446 | 447 | F | Int 012 |
| 355 | 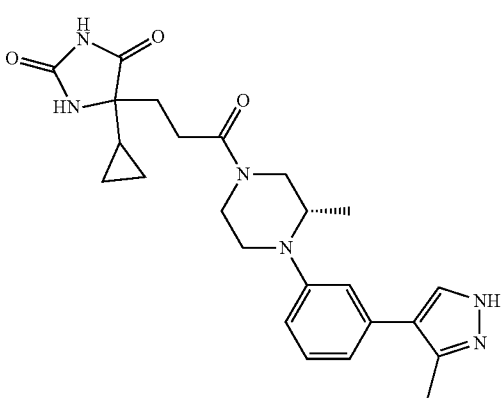 [SMILES: Cc1n[nH]cc1-c1cccc(N2CCN(C(=O)CCC3(C4CC4)NC(=O)NC3=O)C[C@@H]2C)c1] | 451 | 452 | I6 | Cpd 270 + 3-methyl-1H-pyrazole-4-boronic acid pinacol ester |

TABLE III-continued
Illustrative compounds of the invention
trans:
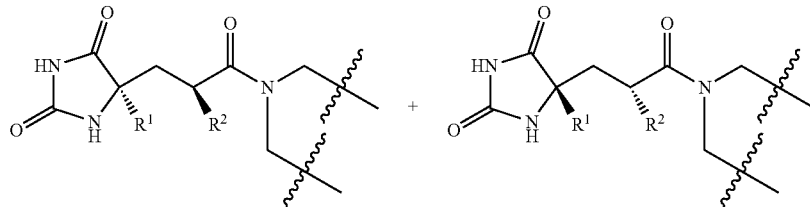
| Cpd | Structure | MW | Ms'd | Mtd | SM |
|---|---|---|---|---|---|
| 356 | | 473 | 474 | F | Int 024 |
| 357 | | 455 | 455 | H2 | Int 163 + Int 232 |
| 358 | | 437 | 438 | I6 | Cpd 270 + 1H-pyrazole-3-boronic acid |
| 359 | | 408 | 408 | H2 | Int 169 + Int 215 |

TABLE III-continued
Illustrative compounds of the invention
trans:
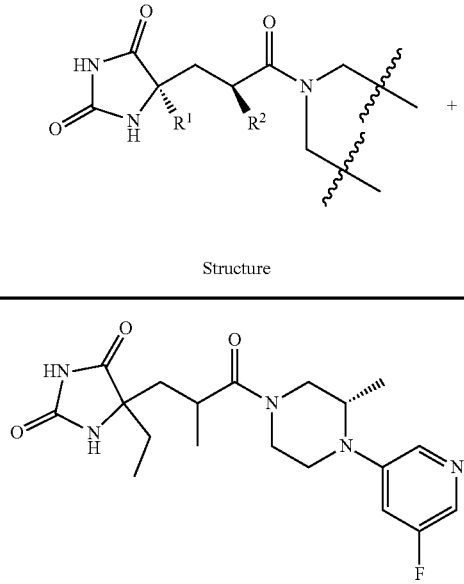
| Cpd | Structure | MW | Ms'd | Mtd | SM |
|---|---|---|---|---|---|
| 360 | 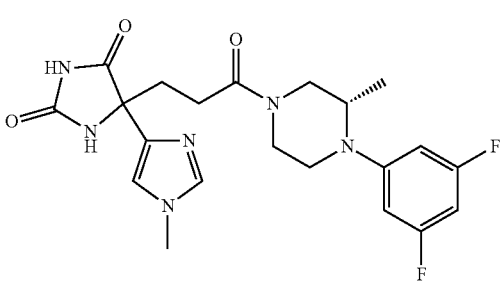 [SMILES: C[C@H]1CN(C(=O)CCC2(c3cn(C)cn3)NC(=O)NC2=O)CCN1c1cc(F)cc(F)c1] trans | 391 | 392 | H2 | Int 169 + Int 214 |
| 361 | 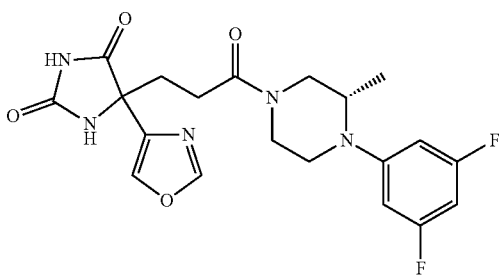 [SMILES: C[C@H]1CN(C(=O)CCC2(c3cocn3)NC(=O)NC2=O)CCN1c1cc(F)cc(F)c1] | 446 | 447 | F | Int 108 |
| 362 | 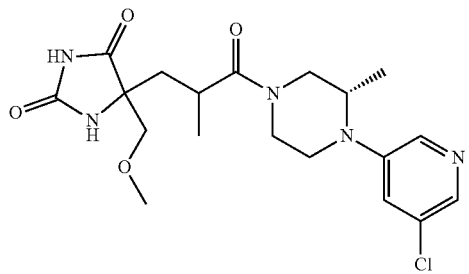 [SMILES: COCC1(CC(C)C(=O)N2CCN(c3cncc(Cl)c3)[C@@H](C)C2)NC(=O)NC1=O] | 433 | 434 | F | Int 107 |
| 363 | trans | 424 | 424 | H2 | Int 156 + Int 215 |

TABLE III-continued
Illustrative compounds of the invention
trans:
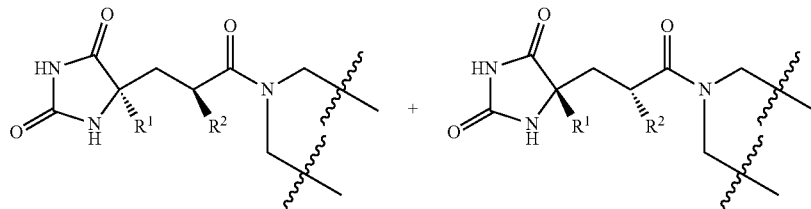
| Cpd | Structure | MW | Ms'd | Mtd | SM |
|---|---|---|---|---|---|
| 364 | trans | 407 | 408 | H2 | Int 156 + Int 214 |
| 365 | trans | 376 | 377 | H2 | Int 165 + Int 209 |
| 366 | trans | 406 | 407 | H2 | Int 156 + Int 209 |
| 367 | 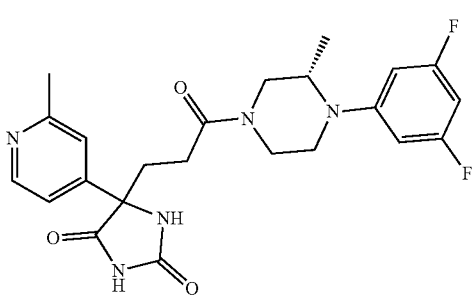 [SMILES: Cc1cc(C2(CCC(=O)N3CCN(c4cc(F)cc(F)c4)[C@@H](C)C3)NC(=O)NC2=O)ccn1] | 457 | 458 | F | Int 073 |

TABLE III-continued
Illustrative compounds of the invention
trans:
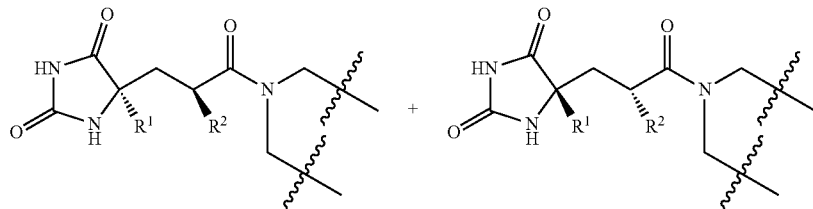
| Cpd | Structure | MW | Ms'd | Mtd | SM |
|---|---|---|---|---|---|
| 368 | 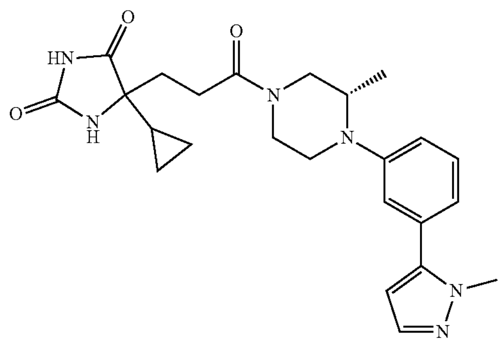 [SMILES: C[C@H]1CN(C(=O)CCC2(C3CC3)NC(=O)NC2=O)CCN1c1cccc(-c2ccnn2C)c1] | 451 | 451 | I6 | Cpd 270 + 1-Methyl-5-(4,4,5,5-tetramethyl-[1,3,2]dioxaborolan-2-yl)-1H-pyrazole |
| 369 | 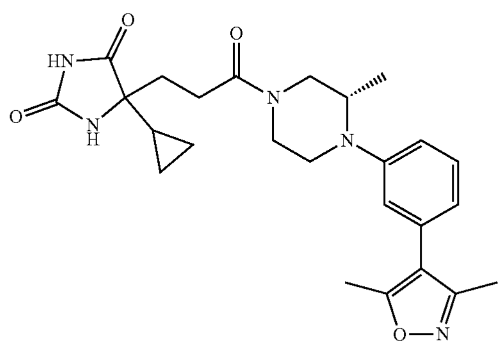 [SMILES: Cc1noc(C)c1-c1cccc(N2CCN(C(=O)CCC3(C4CC4)NC(=O)NC3=O)C[C@@H]2C)c1] | 466 | 466 | I6 | Cpd 270 + 3,5-Dimethyl-4-(4,4,5,5-tetramethyl-[1,3,2]dioxaborolan-2-yl)-isoxazole |
| 370 | 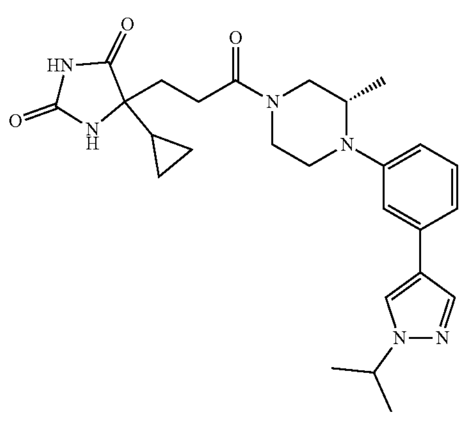 [SMILES: CC(C)n1cc(-c2cccc(N3CCN(C(=O)CCC4(C5CC5)NC(=O)NC4=O)C[C@@H]3C)c2)cn1] | 479 | 479 | I6 | Cpd 270 + 1-Isopropyl-4-(4,4,5,5-tetramethyl-[1,3,2]dioxaborolan-2-yl)-1H-pyrazole |

TABLE III-continued
Illustrative compounds of the invention
trans:
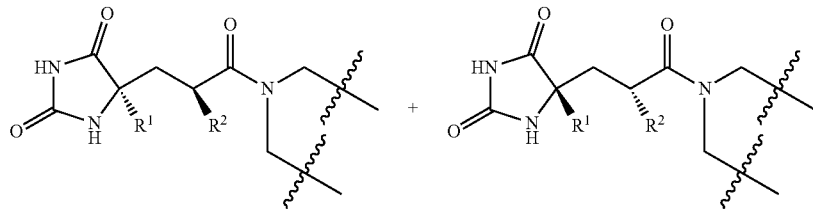
| Cpd | Structure | MW | Ms'd | Mtd | SM |
|---|---|---|---|---|---|
| 371 | trans | 425 | 425 | H2 | Int 165 + Int 233 |
| 372 | 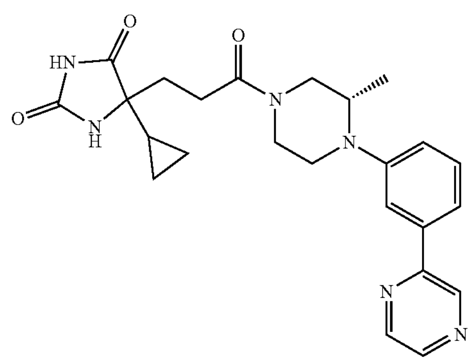 [SMILES: C[C@H]1CN(C(=O)CCC2(C3CC3)NC(=O)NC2=O)CCN1c1cccc(-c2cnccn2)c1] | 449 | 449 | I5 | Cpd 270 + 2-Iodo-pyrazine |
| 373 | 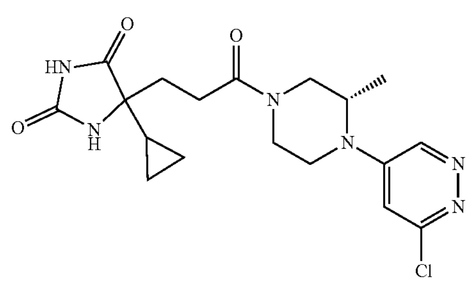 [SMILES: C[C@H]1CN(C(=O)CCC2(C3CC3)NC(=O)NC2=O)CCN1c1cnnc(Cl)c1] | 407 | 407-409 | H2 | Int 162 + Int 263 |
| 374 | 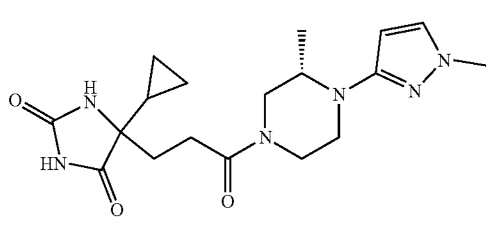 [SMILES: C[C@H]1CN(C(=O)CCC2(C3CC3)NC(=O)NC2=O)CCN1c1ccn(C)n1] | 374 | 375 | H1 | Int 162 + Int 256 |

US 11,718,588 B2
437 438
TABLE III-continued
Illustrative compounds of the invention
trans:
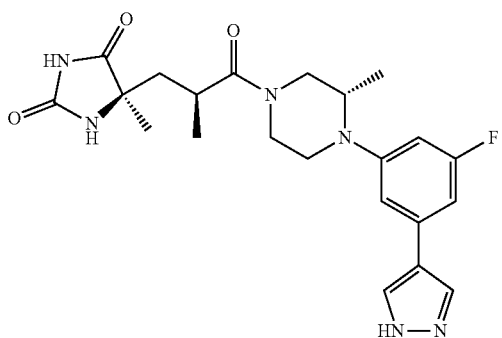 [SMILES: C[C@@H](C[C@@]1(C)NC(=O)NC1=O)C(=O)N1CCN(c2cc(F)cc(-c3cn[nH]c3)c2)[C@@H](C)C1]
| Cpd | Structure | MW | Ms'd | Mtd | SM |
|---|---|---|---|---|---|
| 375 | 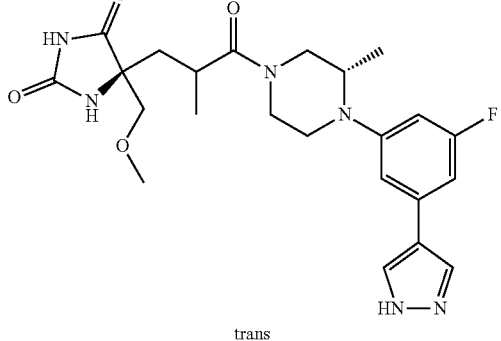 trans | 442 | 443 | H4 | Int 165 + Int 232 |
| 376 | 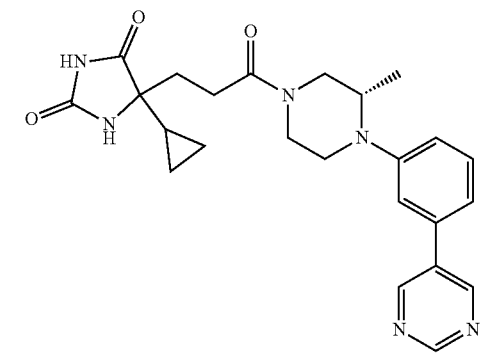 trans | 473 | 473 | H4 | Int 156 + Int 232 |
| 377 | 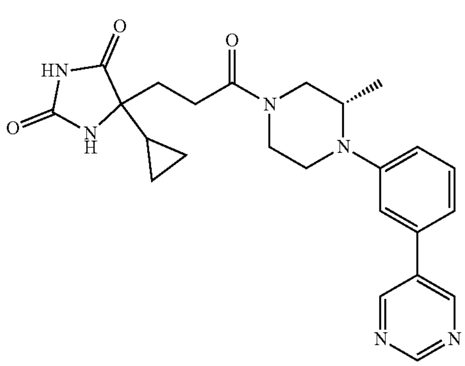 [SMILES: C[C@H]1CN(C(=O)CCC2(C3CC3)NC(=O)NC2=O)CCN1c1cccc(-c2cncnc2)c1] | 449 | 449 | I5 | Cpd 270 + 5-Bromo-pyrimidine |

TABLE III-continued

Illustrative compounds of the invention
trans:

| Cpd | Structure | MW | Ms'd | Mtd | SM |
|-----|-----------|----|------|-----|----|
| 378 | trans | 469 | 469 | H4 | Int 164 + Int 234 |
| 379 | trans | 469 | 469 | H4 | Int 164 + Int 232 |
| 380 | trans | 455 | 455 | H4 | Int 156 + Int 233 |

TABLE III-continued

Illustrative compounds of the invention
trans:

| Cpd | Structure | MW | Ms'd | Mtd | SM |
|---|---|---|---|---|---|
| 381 | 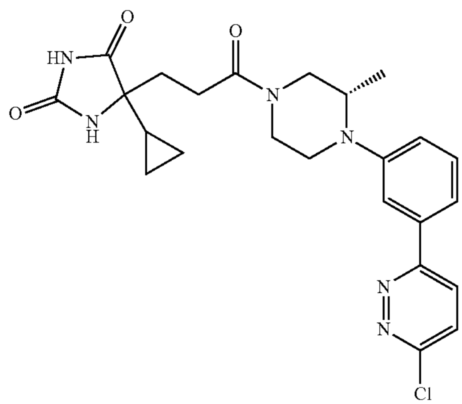 [SMILES: C[C@H]1CN(C(=O)CCC2(C3CC3)NC(=O)NC2=O)CCN1c1cccc(-c2ccc(Cl)nn2)c1] | 483 | 483 | I5 | Cpd 270 + 3-Chloro-6-iodo-pyridazine |
| 382 | 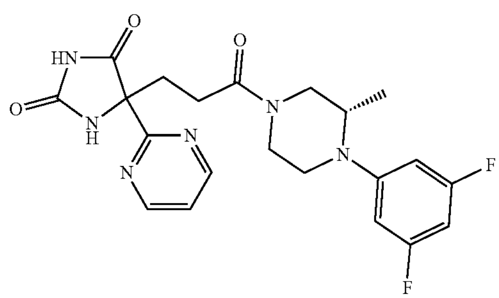 [SMILES: C[C@H]1CN(C(=O)CCC2(c3ncccn3)NC(=O)NC2=O)CCN1c1cc(F)cc(F)c1] | 444 | 445 | H2 | Int 139 + Int 207 |
| 383 | 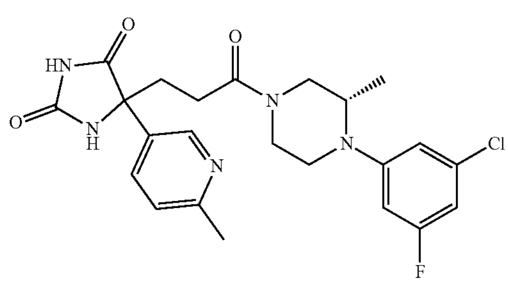 [SMILES: Cc1ccc(C2(CCC(=O)N3CCN(c4cc(F)cc(Cl)c4)[C@@H](C)C3)NC(=O)NC2=O)cn1] | 474 | 474 | H2 | Int 174 + Int 206 |
| 384 | 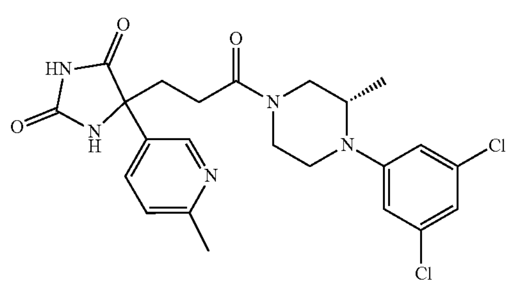 [SMILES: Cc1ccc(C2(CCC(=O)N3CCN(c4cc(Cl)cc(Cl)c4)[C@@H](C)C3)NC(=O)NC2=O)cn1] | 490 | 490-492 | H2 | Int 174 + Int 197 |

TABLE III-continued

Illustrative compounds of the invention
trans:

| Cpd | Structure | MW | Ms'd | Mtd | SM |
|-----|-----------|-----|------|-----|-----|
| 385 | 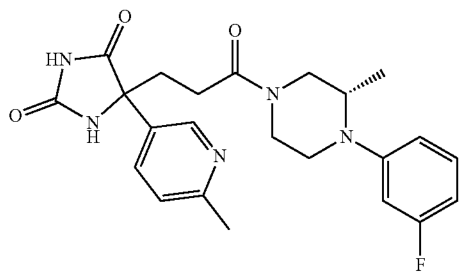 [SMILES: Cc1ccc(C2(CCC(=O)N3CCN(c4cccc(F)c4)[C@@H](C)C3)NC(=O)NC2=O)cn1] | 439 | 440 | H2 | Int 174 + Int 202 |
| 386 | 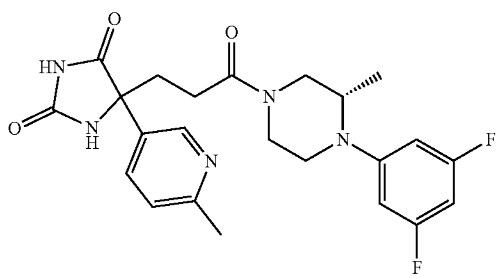 [SMILES: Cc1ccc(C2(CCC(=O)N3CCN(c4cc(F)cc(F)c4)[C@@H](C)C3)NC(=O)NC2=O)cn1] | 457 | 458 | H2 | Int 174 + Int 207 |
| 387 | 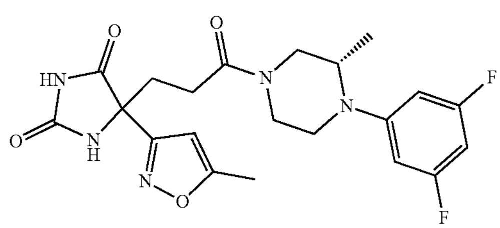 [SMILES: Cc1cc(C2(CCC(=O)N3CCN(c4cc(F)cc(F)c4)[C@@H](C)C3)NC(=O)NC2=O)no1] | 447 | 448 | F | Int 079 |
| 388 | 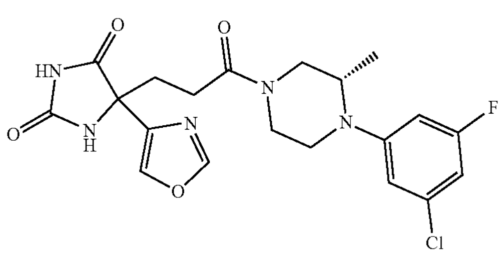 [SMILES: C[C@H]1CN(C(=O)CCC2(c3cocn3)NC(=O)NC2=O)CCN1c1cc(F)cc(Cl)c1] | 450 | 450-452 | F | Int 085 |
| 389 | 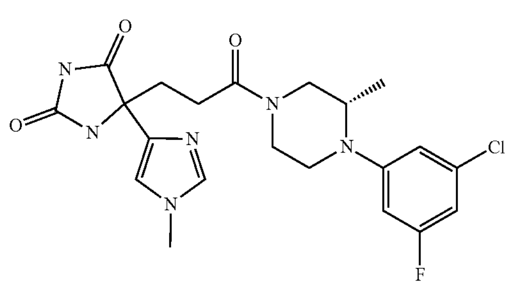 [SMILES: C[C@H]1CN(C(=O)CCC2(c3cn(C)cn3)NC(=O)NC2=O)CCN1c1cc(F)cc(Cl)c1] | 463 | 463-465 | H1 | Int 179 + Int 206 |

TABLE III-continued
Illustrative compounds of the invention
trans:
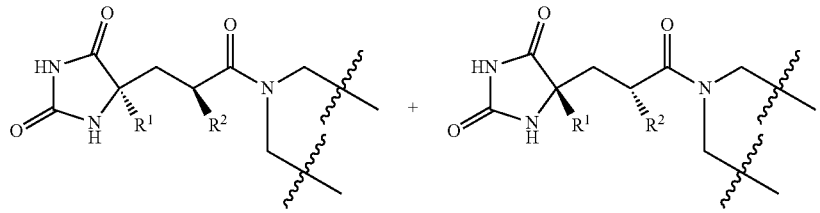
| Cpd | Structure | MW | Ms'd | Mtd | SM |
|---|---|---|---|---|---|
| 390 | 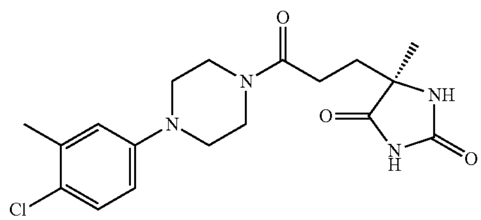 [SMILES: Cc1cc(N2CCN(C(=O)CC[C@@]3(C)NC(=O)NC3=O)CC2)ccc1Cl] | 379 | 379-381 | H2 | Int 172 + Int 284 |
| 391 | 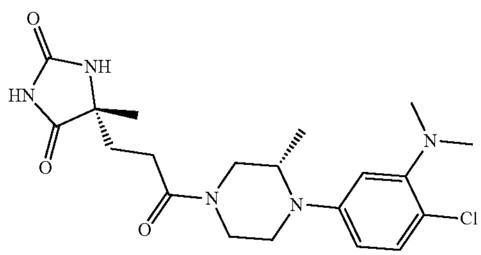 [SMILES: C[C@H]1CN(C(=O)CC[C@@]2(C)NC(=O)NC2=O)CCN1c1ccc(Cl)c(N(C)C)c1] | 422 | 422-424 | H2 | Int 172 + Int 192 |
| 392 | 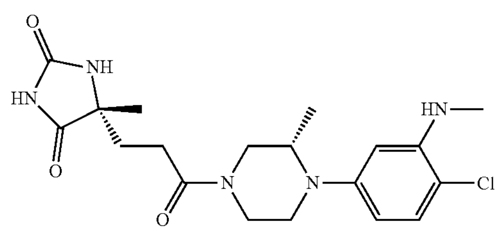 [SMILES: CNc1cc(N2CCN(C(=O)CC[C@@]3(C)NC(=O)NC3=O)C[C@@H]2C)ccc1Cl] | 408 | 408-410 | H2 | Int 172 + Int 193 |
| 393 | 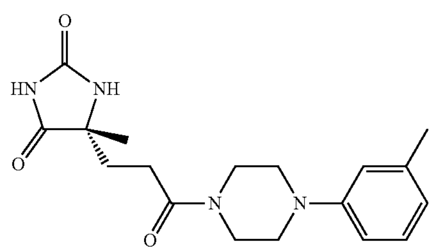 [SMILES: Cc1cccc(N2CCN(C(=O)CC[C@@]3(C)NC(=O)NC3=O)CC2)c1] | 344 | 345 | H2 | Int 172 + Int 194 |
| 394 | 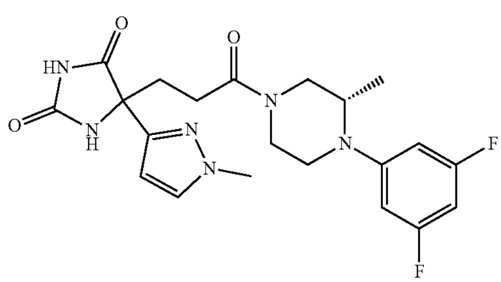 [SMILES: C[C@H]1CN(C(=O)CCC2(c3ccn(C)n3)NC(=O)NC2=O)CCN1c1cc(F)cc(F)c1] | 446 | 447 | F | Int 022 |

TABLE III-continued

Illustrative compounds of the invention
trans:

| Cpd | Structure | MW | Ms'd | Mtd | SM |
|---|---|---|---|---|---|
| 395 | 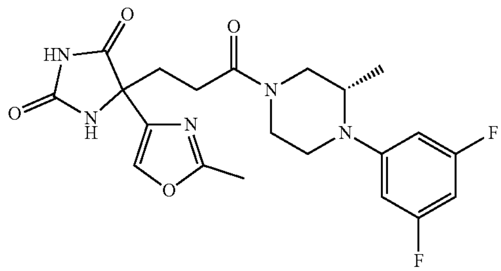 [SMILES: Cc1nc(C2(CCC(=O)N3CCN(c4cc(F)cc(F)c4)[C@@H](C)C3)NC(=O)NC2=O)co1] | 447 | 448 | F | Int 023 |
| 396 | 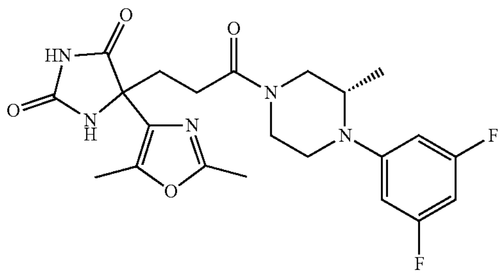 [SMILES: Cc1nc(C2(CCC(=O)N3CCN(c4cc(F)cc(F)c4)[C@@H](C)C3)NC(=O)NC2=O)c(C)o1] | 461 | 462 | F | Int 115 |
| 397 | 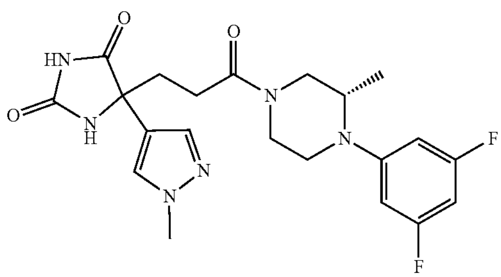 [SMILES: C[C@H]1CN(C(=O)CCC2(c3cnn(C)c3)NC(=O)NC2=O)CCN1c1cc(F)cc(F)c1] | 446 | 447 | F | Int 114 |
| 398 | 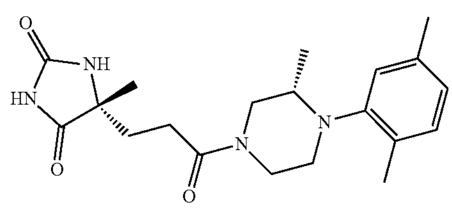 [SMILES: Cc1ccc(C)c(N2CCN(C(=O)CC[C@@]3(C)NC(=O)NC3=O)C[C@@H]2C)c1] | 372 | 373 | H2 | Int 172 + Int 195 |
| 399 | 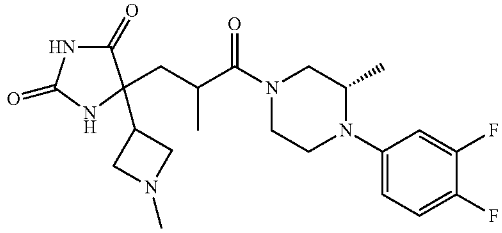 [SMILES: CC(CC1(C2CN(C)C2)NC(=O)NC1=O)C(=O)N1CCN(c2ccc(F)c(F)c2)[C@@H](C)C1] | 450 | 450 | 2.7 | Cpd 247 |

TABLE III-continued
Illustrative compounds of the invention
trans:
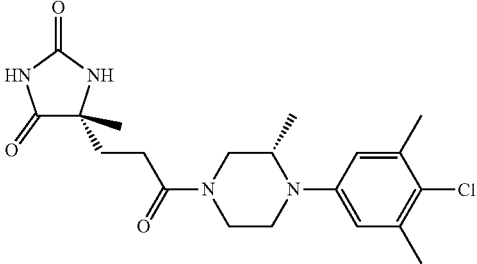 [SMILES: Cc1cc(N2CCN(C(=O)CC[C@@]3(C)NC(=O)NC3=O)C[C@@H]2C)cc(C)c1Cl]
| Cpd | Structure | MW | Ms'd | Mtd | SM |
|---|---|---|---|---|---|
| 400 | 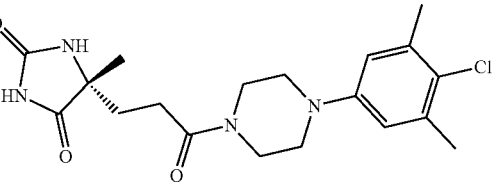 | 407 | 407-409 | H2 | Int 172 + Int 280 |
| 401 | 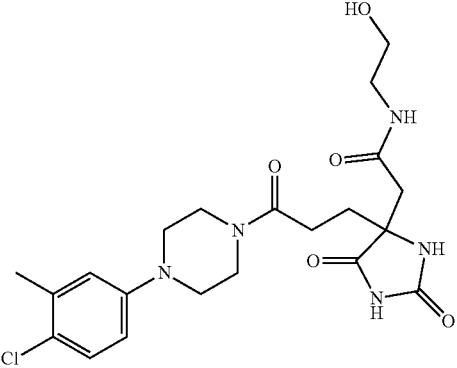 [SMILES: Cc1cc(N2CCN(C(=O)CCC3(CC(=O)NCCO)NC(=O)NC3=O)CC2)ccc1Cl] | 393 | 393-395 | H2 | Int 172 + Int 278 |
| 402 | 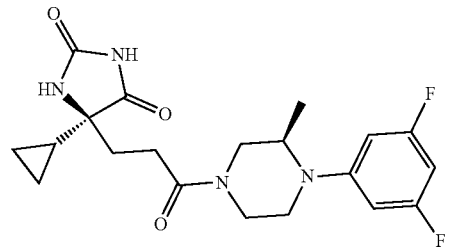 [SMILES: C[C@@H]1CN(C(=O)CC[C@@]2(C3CC3)NC(=O)NC2=O)CCN1c1cc(F)cc(F)c1] | 466 | 466-468 | 2.8 | Int 116 |
| 403 | | 406 | 407 | H1 | Int 163 + Int 276 |

TABLE III-continued
Illustrative compounds of the invention
trans:
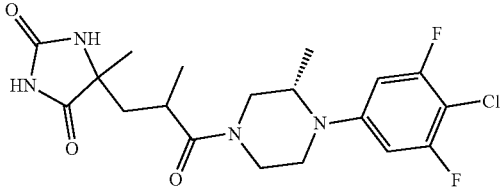 [SMILES: CC(CC1(C)NC(=O)NC1=O)C(=O)N1CCN(c2cc(F)c(Cl)c(F)c2)[C@@H](C)C1]
| Cpd | Structure | MW | Ms'd | Mtd | SM |
|---|---|---|---|---|---|
| 404 | 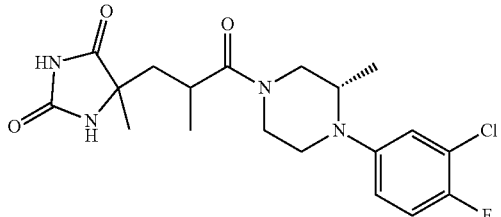 trans | 429 | 429 | H2 | Int 165 + Int 277 |
| 405 | 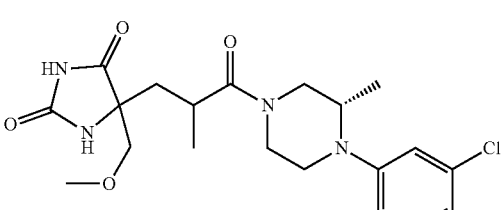 trans | 410 | 411 | H2 | Int 165 + Int 229 |
| 406 | 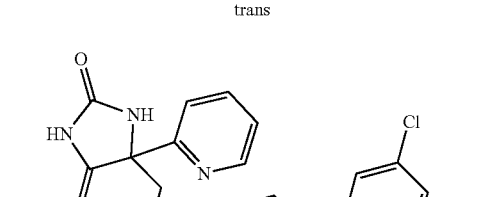 trans | 441 | 441-443 | H2 | Int 156 + Int 229 |
| 407 | 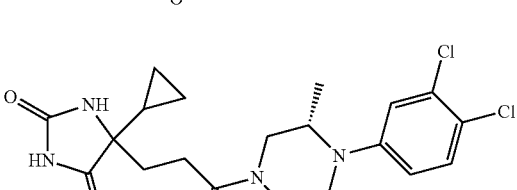 | 462 | 462-464 | F | Int 291 |
| 408 | 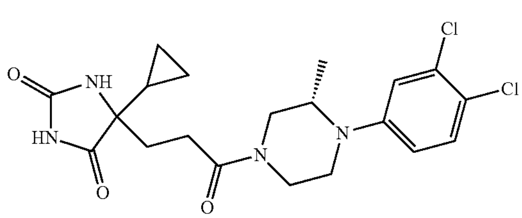 [SMILES: C[C@H]1CN(C(=O)CCC2(C3CC3)NC(=O)NC2=O)CCN1c1ccc(Cl)c(Cl)c1] | 439 | 439-441 | H1 | Int 162 + Int 201 |

TABLE III-continued
Illustrative compounds of the invention
trans:
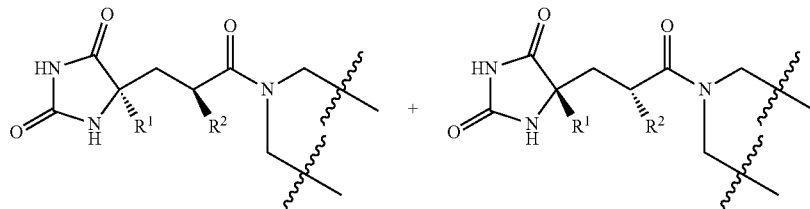
| Cpd | Structure | MW | Ms'd | Mtd | SM |
|---|---|---|---|---|---|
| 409 | trans | 439 | 439.38-441.37 | F | Int 046 |
| 410 | trans | 413 | 413.36-415.36 | F | Int 292 |
| 411 | trans | 437 | 437-439 | F | Int 050 |
| 412 | trans | 419 | 419.45-421.42 | F | Int 051 |

TABLE III-continued
Illustrative compounds of the invention
trans:
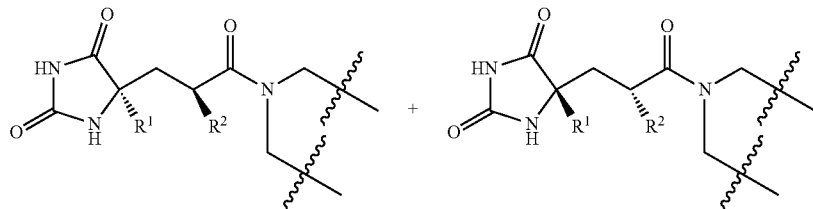
| Cpd | Structure | MW | Ms'd | Mtd | SM |
|---|---|---|---|---|---|
| 413 | trans | 437 | 437-439 | F | Int 052 |
| 414 | 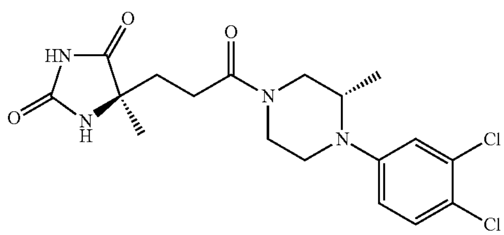 [SMILES: C[C@H]1CN(C(=O)CC[C@@]2(C)NC(=O)NC2=O)CCN1c1ccc(Cl)c(Cl)c1] | 413 | 413-415 | H1 | Int 172 + Int 201 |
| 415 | trans | 519 | 519-521 | F | Int 293 |
| 416 | 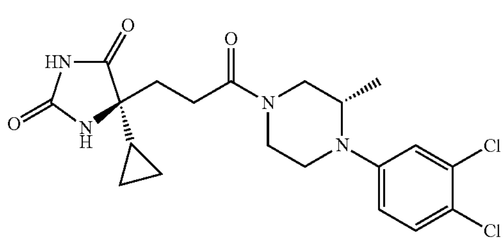 [SMILES: C[C@H]1CN(C(=O)CC[C@@]2(C3CC3)NC(=O)NC2=O)CCN1c1ccc(Cl)c(Cl)c1] | 439 | 439-441 | H2 | Int 163 + Int 201 |

TABLE III-continued
Illustrative compounds of the invention
trans:
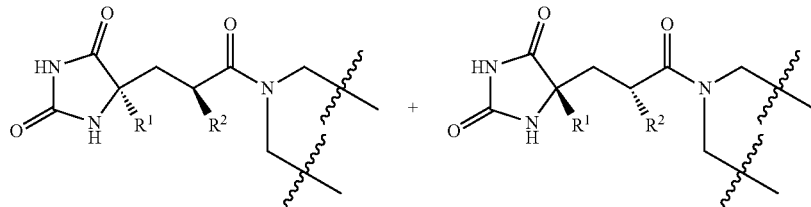
| Cpd | Structure | MW | Ms'd | Mtd | SM |
|---|---|---|---|---|---|
| 417 | trans | 429 | 429-431 | I4 | Cpd 415 |
| 418 | trans | 411 | 411-413 | H2 | Int 165 + Int 206 |
| 419 | trans | 427 | 427-429 | H2 | Int 165 + Int 201 |
| 420 | trans | 427 | 427-429 | H2 | Int 165 + Int 197 |

TABLE III-continued
Illustrative compounds of the invention
trans:
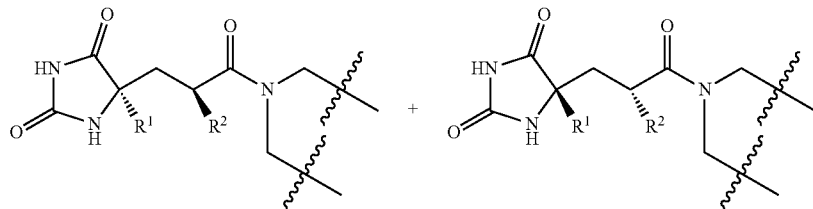
| Cpd | Structure | MW | Ms'd | Mtd | SM |
|---|---|---|---|---|---|
| 421 | trans | 394 | 395 | H2 | Int 165 + Int 199 |
| 422 | trans | 411 | 411-413 | H2 | Int 165 + Int 198 |
| 423 | trans | 441 | 441-443 | H2 | Int 165 + Int 211 |
| 424 | trans | 519 | 519-521 | F | Int 294 |

TABLE III-continued
Illustrative compounds of the invention
trans:
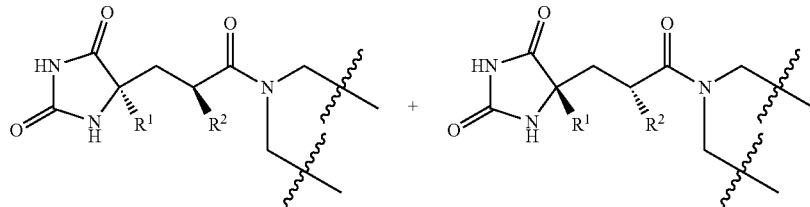
| Cpd | Structure | MW | Ms'd | Mtd | SM |
|---|---|---|---|---|---|
| 425 | trans | 429 | 429-431 | I4 | Cpd 424 |
| 426 | trans | 501 | 501-503 | F | Int 063 |
| 427 | trans | 443 | 443-445 | H2 | Int 156 + 1-(3,5-dichlorophenyl)piperazine |
| 428 | trans | 410 | 411 | H2 | Int 156 + 1-(3,4-difluorophenyl)piperazine |

TABLE III-continued
Illustrative compounds of the invention
trans:
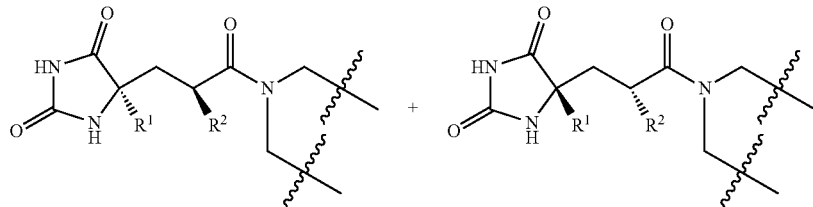
| Cpd | Structure | MW | Ms'd | Mtd | SM |
|---|---|---|---|---|---|
| 429 | trans | 457 | 457-459 | H2 | Int 156 + Int 197 |
| 430 | trans | 471 | 471 | H2 | Int 156 + Int 211 |
| 431 | trans | 441 | 441-443 | H2 | Int 156 + Int 206 |
| 432 | trans | 441 | 441-443 | H2 | Int 156 + Int 198 |

TABLE III-continued
Illustrative compounds of the invention
trans:
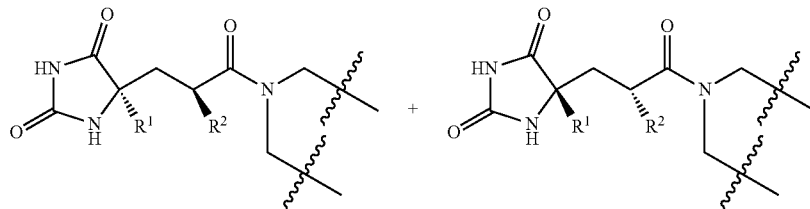
| Cpd | Structure | MW | Ms'd | Mtd | SM |
|---|---|---|---|---|---|
| 433 | trans | 423 | 423-425 | H2 | Int 156 + Int 196 |
| 434 | trans | 476 | 476-478 | H2 | Int 159 + 1-(3,5-dichlorophenyl)piperazine |
| 435 | trans | 427 | 427-429 | F | Int 061 |
| 436 | trans | 443 | 443-445 | F | Int 295 |

TABLE III-continued

Illustrative compounds of the invention
trans:

| Cpd | Structure | MW | Ms'd | Mtd | SM |
|---|---|---|---|---|---|
| 437 | trans | 474 | 474 | H2 | Int 159 + Int 198 |
| 438 | 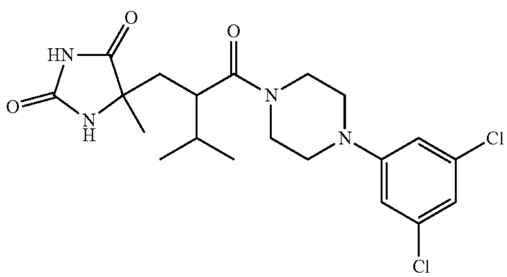 [SMILES: CC(C)C(CC1(C)NC(=O)NC1=O)C(=O)N1CCN(c2cc(Cl)cc(Cl)c2)CC1] | 441 | 441-443 | F | Int 296 |
| 439 | trans | 429 | 429-431 | F | Int 298 |
| 440 | 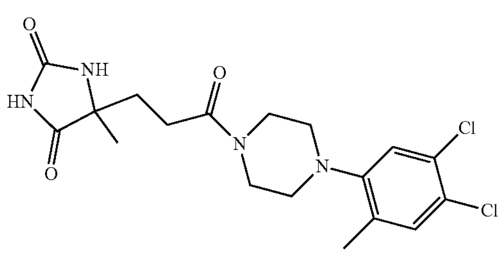 [SMILES: Cc1cc(Cl)c(Cl)cc1N1CCN(C(=O)CCC2(C)NC(=O)NC2=O)CC1] | 413 | 412-414-416 | H2 | 3-(4-Methyl-2,5-dioxo-imidazolidin-4-yl) propionic acid + Int 279 |
| 441 | trans | 397 | 397-399 | H2 | Int 151 + Int 198 |

TABLE III-continued
Illustrative compounds of the invention
trans:
| Cpd | Structure | MW | Ms'd | Mtd | SM |
|---|---|---|---|---|---|
| 442 | 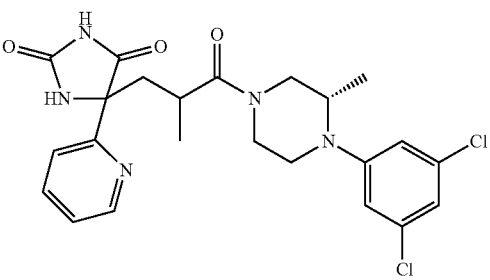 [SMILES: CC(CC1(c2ccccn2)NC(=O)NC1=O)C(=O)N1CCN(c2cc(Cl)cc(Cl)c2)[C@@H](C)C1] trans | 490 | 490-492 | H2 | Int 159 + Int 197 |
| 443 | 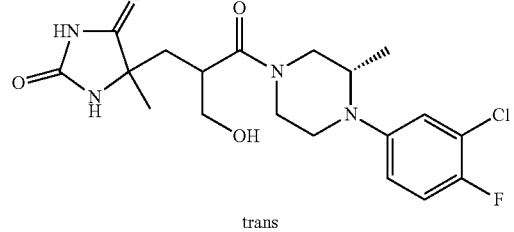 trans | 427 | 427-429 | I4 | Int 299 |
| 444 | 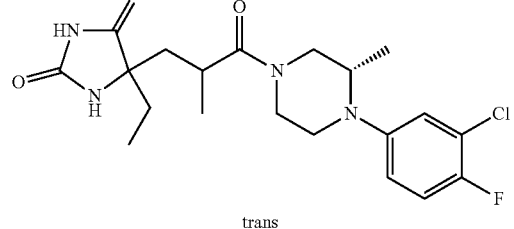 trans | 425 | 425-427 | H2 | Int 169 + Int 198 |
| 445 | 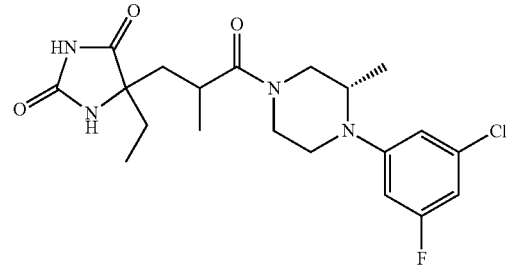 [SMILES: CCC1(CC(C)C(=O)N2CCN(c3cc(F)cc(Cl)c3)[C@@H](C)C2)NC(=O)NC1=O] trans | 425 | 425-427 | H2 | Int 169 + Int 206 |

TABLE III-continued
Illustrative compounds of the invention
trans:
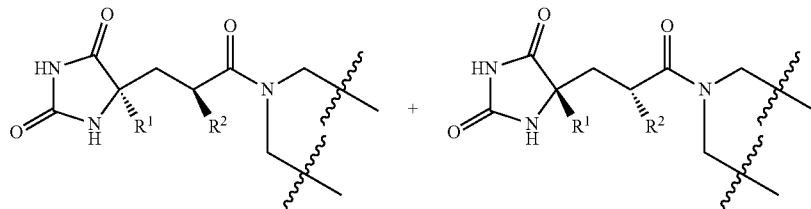
| Cpd | Structure | MW | Ms'd | Mtd | SM |
|---|---|---|---|---|---|
| 446 | trans | 456 | 456-458 | H2 | Int 159 + Int 200 |
| 447 | | 474 | 474-476 | F | Int 300 |
| 448 | trans | 445 | 445-447 | H2 | Int 156 + Int 203 |
| 449 | trans | 441 | 441-443 | F | Int 302 |

TABLE III-continued
Illustrative compounds of the invention
trans:
| Cpd | Structure | MW | Ms'd | Mtd | SM |
|---|---|---|---|---|---|
| 450 | 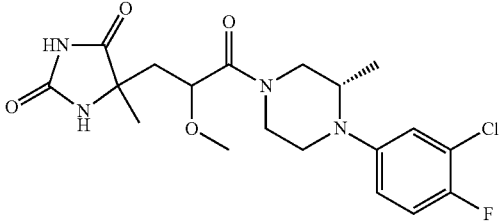 [SMILES: COC(CC1(C)NC(=O)NC1=O)C(=O)N1CCN(c2ccc(F)c(Cl)c2)[C@@H](C)C1] trans | 427 | 427-429 | F | Int 304 |
| 451 | 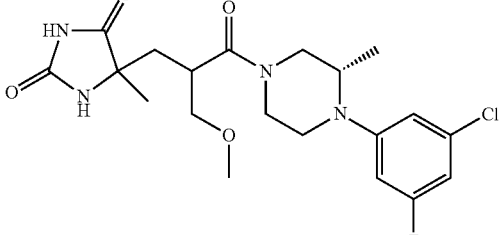 trans | 441 | 441-443 | F | Int 306 |
| 452 | 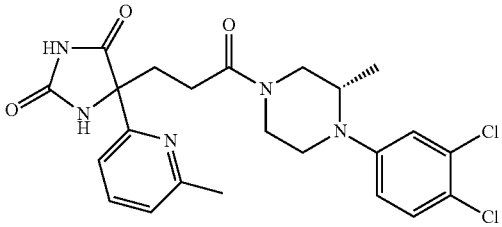 | 490 | 490-492 | H1 | Int 166 + Int 201 |
| 453 | 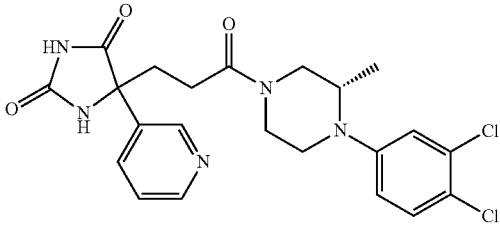 [SMILES: C[C@H]1CN(C(=O)CCC2(c3cccnc3)NC(=O)NC2=O)CCN1c1ccc(Cl)c(Cl)c1] | 476 | 476-478 | H2 | Int 132 + Int 201 |
| 454 | 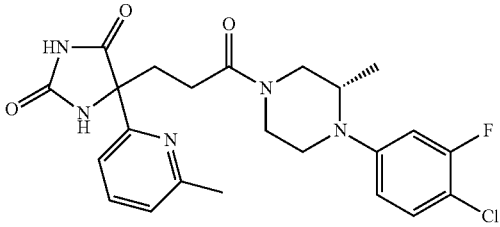 [SMILES: Cc1cccc(C2(CCC(=O)N3CCN(c4ccc(Cl)c(F)c4)[C@@H](C)C3)NC(=O)NC2=O)n1] | 474 | 474-476 | H1 | Int 166 + Int 213 |

TABLE III-continued

Illustrative compounds of the invention trans:

| Cpd | Structure | MW | Ms'd | Mtd | SM |
|---|---|---|---|---|---|
| 455 | 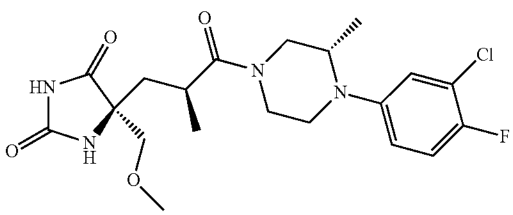 [SMILES: COC[C@]1(C[C@H](C)C(=O)N2CCN(c3ccc(F)c(Cl)c3)[C@@H](C)C2)NC(=O)NC1=O] | 441 | 441-443 | 2.40 | Cpd 432 |
| 456 | 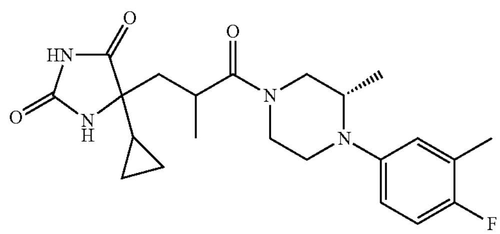 [SMILES: Cc1cc(N2CCN(C(=O)C(C)CC3(C4CC4)NC(=O)NC3=O)C[C@@H]2C)ccc1F] | 417 | 417 | H2 | Int 164 + Int 210 |
| 457 | 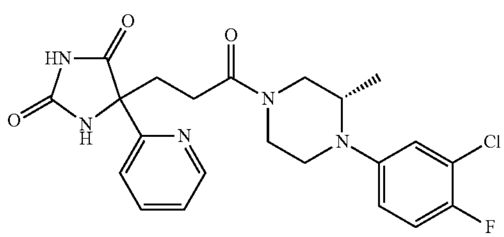 [SMILES: C[C@H]1CN(C(=O)CCC2(c3ccccn3)NC(=O)NC2=O)CCN1c1ccc(F)c(Cl)c1] | 460 | 460-462 | F | Int 307 |
| 458 | 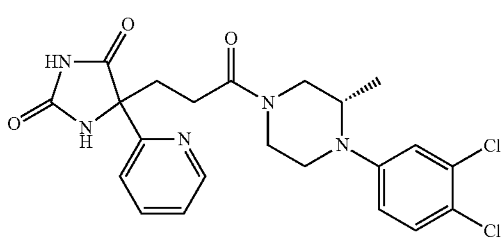 [SMILES: C[C@H]1CN(C(=O)CCC2(c3ccccn3)NC(=O)NC2=O)CCN1c1ccc(Cl)c(Cl)c1] | 476 | 476-478 | F | Int 105 |
| 459 | 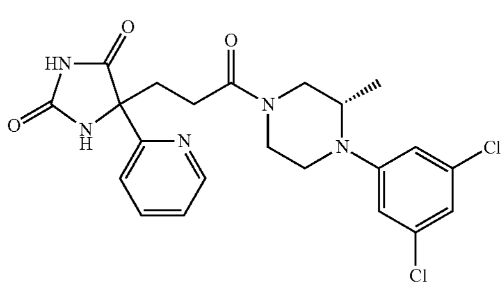 [SMILES: C[C@H]1CN(C(=O)CCC2(c3ccccn3)NC(=O)NC2=O)CCN1c1cc(Cl)cc(Cl)c1] | 476 | 476-478 | F | Int 308 |

TABLE III-continued
Illustrative compounds of the invention
trans:
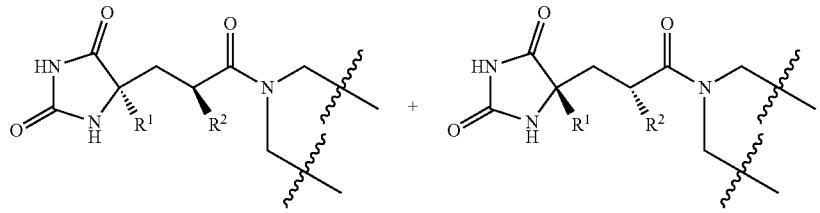
| Cpd | Structure | MW | Ms'd | Mtd | SM |
|---|---|---|---|---|---|
| 460 | 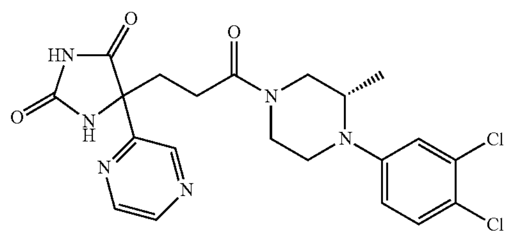 [SMILES: C[C@H]1CN(C(=O)CCC2(c3cnccn3)NC(=O)NC2=O)CCN1c1ccc(Cl)c(Cl)c1] | 477 | 477-479 | H2 | Int 142 + Int 201 |
| 461 | 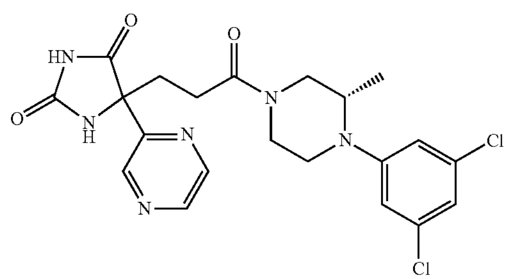 [SMILES: C[C@H]1CN(C(=O)CCC2(c3cnccn3)NC(=O)NC2=O)CCN1c1cc(Cl)cc(Cl)c1] | 477 | 477 | H2 | Int 142 + Int 197 |
| 462 | 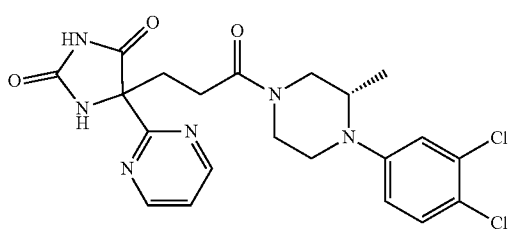 [SMILES: C[C@H]1CN(C(=O)CCC2(c3ncccn3)NC(=O)NC2=O)CCN1c1ccc(Cl)c(Cl)c1] | 477 | 477-479 | H2 | Int 139 + Int 201 |
| 463 | 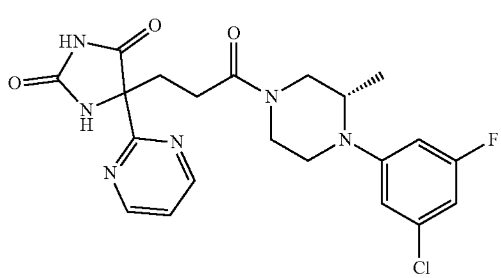 [SMILES: C[C@H]1CN(C(=O)CCC2(c3ncccn3)NC(=O)NC2=O)CCN1c1cc(F)cc(Cl)c1] | 461 | 461-463 | H2 | Int 139 + Int 206 |
| 464 | 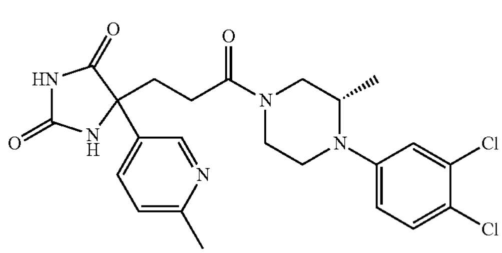 [SMILES: Cc1ccc(C2(CCC(=O)N3CCN(c4ccc(Cl)c(Cl)c4)[C@@H](C)C3)NC(=O)NC2=O)cn1] | 490 | 490-492 | H2 | Int 174 + Int 201 |

TABLE III-continued

Illustrative compounds of the invention
trans:

| Cpd | Structure | MW | Ms'd | Mtd | SM |
|---|---|---|---|---|---|
| 465 | 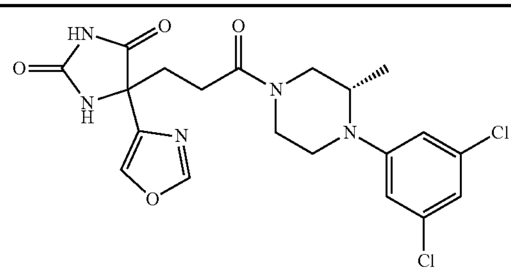 | 466 | 466-468 | F | Int 309 |
| 466 | 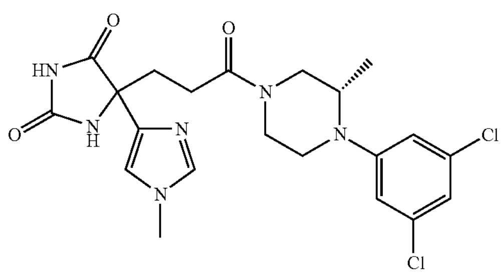 [SMILES: C[C@H]1CN(C(=O)CCC2(c3cn(C)cn3)NC(=O)NC2=O)CCN1c1cc(Cl)cc(Cl)c1] | 479 | 479-481 | H1 | Int 179 + Int 197 |
| 467 | 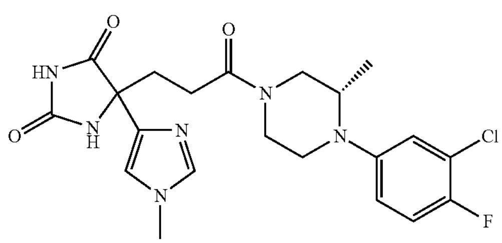 [SMILES: C[C@H]1CN(C(=O)CCC2(c3cn(C)cn3)NC(=O)NC2=O)CCN1c1ccc(F)c(Cl)c1] | 463 | 463-465 | H1 | Int 179 + Int 198 |
| 468 | 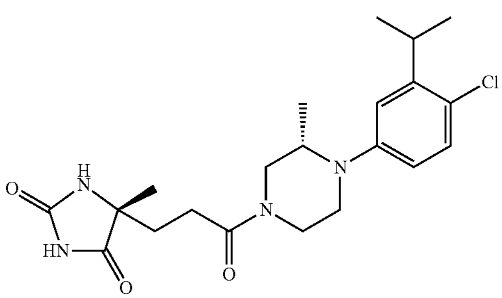 [SMILES: CC(C)c1cc(N2CCN(C(=O)CC[C@@]3(C)NC(=O)NC3=O)C[C@@H]2C)ccc1Cl] | 421 | 421-423 | H2 | Int 172 + Int 310 |
| 469 | 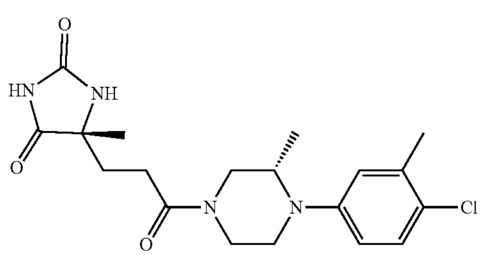 [SMILES: Cc1cc(N2CCN(C(=O)CC[C@@]3(C)NC(=O)NC3=O)C[C@@H]2C)ccc1Cl] | 393 | 393-395 | H2 | Int 172 + Int 311 |

TABLE III-continued

Illustrative compounds of the invention
trans:

| Cpd | Structure | MW | Ms'd | Mtd | SM |
|---|---|---|---|---|---|
| 470 | | 407 | 407-409 | H2 | Int 172 + Int 280 |
| 471 | | 451 | 451-453 | 2.38 | Int 315 |
| 472 | | 447 | 447-449 | H2 | Int 172 + Int 314 |
| 473 | | 484 | 484-486 | H2 | Int 166 + Int 312 |

TABLE III-continued

Illustrative compounds of the invention
trans:

| Cpd | Structure | MW | Ms'd | Mtd | SM |
|---|---|---|---|---|---|
| 474 | 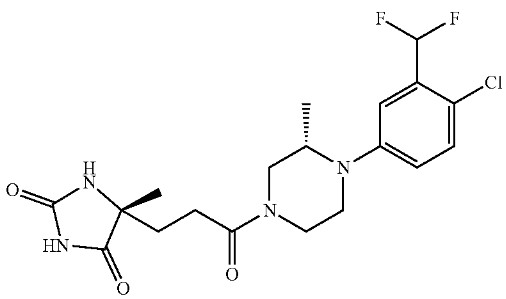 [SMILES: C[C@H]1CN(C(=O)CC[C@@]2(C)NC(=O)NC2=O)CCN1c1ccc(Cl)c(C(F)F)c1] | 429 | 429-431 | H2 | Int 172 + Int 316 |
| 475 | 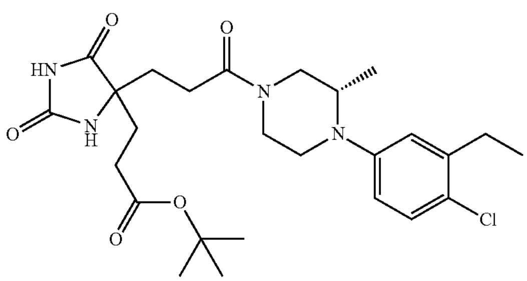 [SMILES: CCc1cc(N2CCN(C(=O)CCC3(CCC(=O)OC(C)(C)C)NC(=O)NC3=O)C[C@@H]2C)ccc1Cl] | 521 | 521-523 | F | Int 317 |
| 476 | 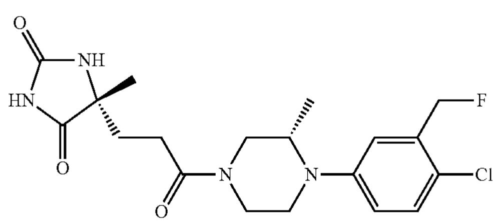 [SMILES: C[C@H]1CN(C(=O)CC[C@@]2(C)NC(=O)NC2=O)CCN1c1ccc(Cl)c(CF)c1] | 411 | 411 | H2 | Int 172 + Int 319 |
| 477 | 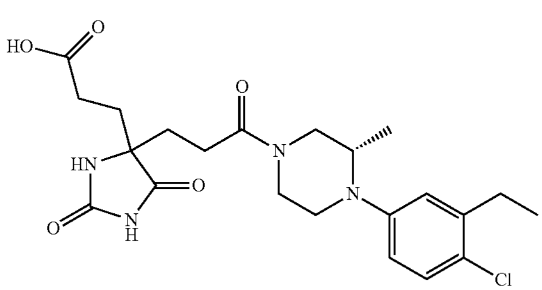 [SMILES: CCc1cc(N2CCN(C(=O)CCC3(CCC(=O)O)NC(=O)NC3=O)C[C@@H]2C)ccc1Cl] | 465 | 465-467 | 2.39 | Cpd 475 |

TABLE III-continued
Illustrative compounds of the invention
trans:
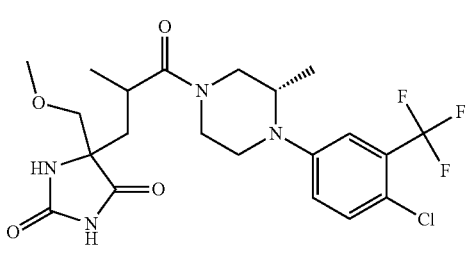 [SMILES: COCC1(CC(C)C(=O)N2CCN(c3ccc(Cl)c(C(F)(F)F)c3)[C@@H](C)C2)NC(=O)NC1=O]
| Cpd | Structure | MW | Ms'd | Mtd | SM |
|---|---|---|---|---|---|
| 478 | 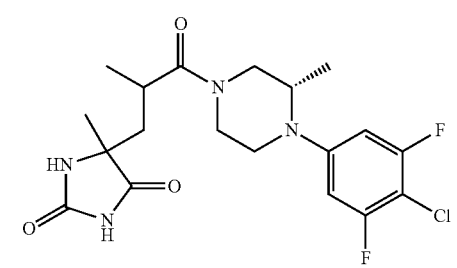 [SMILES: CC(CC1(C)NC(=O)NC1=O)C(=O)N1CCN(c2cc(F)c(Cl)c(F)c2)[C@@H](C)C1] trans | 491 | 491 | H2 | Int 156 + Int 314 |
| 479 | 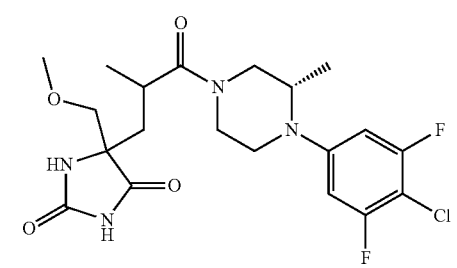 [SMILES: COCC1(CC(C)C(=O)N2CCN(c3cc(F)c(Cl)c(F)c3)[C@@H](C)C2)NC(=O)NC1=O] trans | 429 | 429 | H2 | Int 165 + Int 320 |
| 480 | 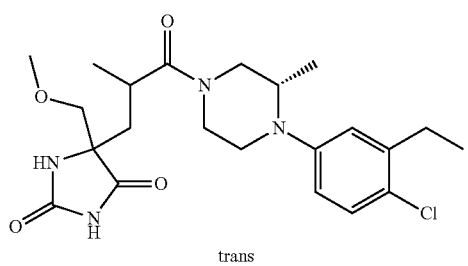 trans | 459 | 459 | H2 | Int 156 + Int 320 |
| 481 | trans | 451 | 451 | H2 | Int 156 + Int 312 |

TABLE IV

NMR of illustrative compounds of the invention

| Cpd | NMR |
|---|---|
| 003 | $^1$H NMR (400 MHz, DMSO-d$_6$) δ ppm 10.61 (1H, s), 7.91 (1H, m), 7.22 (1H, t), 6.97-6.94 (1H, m), 6.90 (1H, dd), 6.80 (1H, dd), 3.60-3.49 (4H, m), 3.24-3.10 (4H, m), 2.42-2.31 (1H, m), 2.27-2.16 (1H, m), 1.82 (2H, t), 1.27 (3H, s) |
| 006 | $^1$H NMR (400 MHz, DMSO-d$_6$) δ ppm 10.81 (1H, s), 8.69 (1H, s), 7.53-7.48 (2H, m), 7.44-7.38 (2H, m), 7.36-7.31 (1H, m), 7.22 (1H, t), 6.96-6.93 −1H, m), 6.89 (1H, dd), 6.80 (1H, dd), 3.58-3.40 (4H, m), 3.21-3.08 (4H, m), 2.40-2.11 (4H, m) |
| 034 | $^1$H NMR (400 MHz, DMSO-d$_6$) δ ppm 10.60 (1H, s), 7.70 (1H, m), 7.22 (1H, t), 6.98-6.94 (1H, m), 6.90 (1H, dd), 6.80 (1H, dd), 3.60-3.49 (4H, m), 3.25-3.10 (4H, m), 2.47-2.36 (1H, m), 2.33-2.21 (1H, m), 2.00-1.89 (2H, m), 1.14-1.05 (1H, m), 0.50-0.41 (1H, m), 0.41-0.27 (2H, m), 0.15-0.06 (1H, m) |
| 049 | $^1$H NMR (400 MHz, DMSO-d$_6$) δ ppm 10.61 (1H, s), 7.91 (1H, m), 7.35 (1H, t), 6.97 (1H, dd), 6.79 (1H, dd), 3.59-3.47 (4H, m), 3.27-3.10 (4H, m), 2.42-2.31 (1H, m), 2.27-2.15 (1H, m), 1.81 (2H, t), 1.27 (3H, s) |
| 052 | $^1$H NMR (400 MHz, CDCl$_3$) δ ppm 8.40 (1H, s), 7.04 (1H, t), 6.92 (1H, dd), 6.79-6.74 (1H, m), 6.15 (1H, s), 3.82-3.68 (2H, m), 3.64-3.54 (2H, m), 3.12-3.03 (4H, m), 2.41-2.35 (2H, m), 2.25-2.08 (2H, m), 1.48 (3H, s) |
| 054 | $^1$H NMR (400 MHz, DMSO-d$_6$) δ ppm 10.63 (1H, s), 7.85 (1H, s), 6.94 (2H, d), 6.87 (1H, t), 3.58-3.46 (4H, m), 3.30-3.16 (4H, m), 2.36-2.25 (1H, m), 2.20-2.09 (1H, m), 1.96-1.75 (3H, m), 0.89 (3H, d), 0.81 (3H, d) |
| 059 | $^1$H NMR (400 MHz, CDCl$_3$) δ ppm 8.56 (1H, s), 7.22 (1H, d), 6.62 (1H, d), 6.30 (1H, s), 3.83-3.75 (1H, m), 3.75-3.67 (1H, m), 3.63-3.50 (4H, m), 3.48-3.42 (2H, m), 2.39 (2H, t), 2.25-2.08 (2H, m), 1.48 (3H, s) |
| 067 | $^1$H NMR (400 MHz, DMSO-d$_6$) δ ppm 10.61 (1H, s), 7.91 (1H, m), 7.41 (1H, d), 7.14 (1H, d), 6.94 (1H, dd), 3.62-3.46 (4H, m), 3.26-3.10 (4H, m), 2.43-2.30 (1H, m), 2.26-2.15 (1H, m), 1.81 (2H, t), 1.27 (3H, s) |
| 088 | $^1$H NMR (400 MHz, DMSO-d$_6$) δ ppm 11.0 (1H, s), 8.80 (1H, s), 8.71 (1H, d), 8.57 (1H, dd), 7.94-7.89 (1H, m), 7.56 (1H, dd), 7.04 (1H, d), 6.82-6.76 (2H, m), 3.60-3.43 (4H, m), 2.84-2.68 (4H, m), 2.42-2.16 (4H, m), 2.23 (3H, s), 2.20 (3H, s) |
| 113 | $^1$H NMR (400 MHz, DMSO-d$_6$) δ ppm 10.60 (1H, s), 7.70 (1H, s), 7.26 (1H, q), 7.02 (1H, ddd), 6.79-6.69 (1H, m), 3.62-3.47 (4H, m), 3.19-3.01 (4H, m), 2.48-2.34 (1H, m), 2.34-2.19 (1H, m), 2.00-1.87 (2H, m), 1.15-1.03 (1H, m), 0.51-0.25 (3H, m), 0.15-0.03 (1H, m) |
| 181 | $^1$H NMR (400 MHz, DMSO-d$_6$) δ ppm 10.59 (1H, s), 7.72 (1H, s), 7.39-7.12 (5H, m), 6.94 (2H, s), 6.88 (1H, s), 3.74-3.62 (2H, m), 3.59-3.42 (4H, m), 3.29-3.12 (4H, m), 2.75-2.67 (2H, m), 2.40-2.27 (1H, m), 2.25-2.20 (2H, m), 1.88-1.69 (2H, m) |
| 188 | $^1$H NMR (400 MHz, DMSO-d$_6$) δ ppm 10.66 (1H, s), 7.92 (1H, s), 6.95 (2H, d), 6.88 (1H, t), 3.59-3.45 (4H, m), 3.30-3.15 (4H, m), 2.77 (1H, d), 2.48 (1H, d), 2.44-2.32 (1H, m), 2.28-2.16 (1H, m), 1.88-1.72 (2H, m), 1.36 (9H, s) |
| 212 | $^1$H NMR (400 MHz, DMSO-d6) δ ppm 10.61 (1H, s), 7.60 (0.4H, s), 7.56 (0.6H, s), 7.25 (1H, q), 7.02-6.91 (1H, m), 6.74-6.65 (1H, m), 4.24-4.16 (0.6H, m), 4.04-3.97 (0.4H, m), 3.97-3.82 (1.4H, m), 3.75-3.67 (0.6H, m), 3.47-3.38 (0.6H, m), 3.37-3.21 (1.4H, m), 3.16-3.08 (0.4H, m), 3.00-2.73 (2.6H, m), 2.42-2.25 (1H, m), 1.70 (1H, dd), 1.10-0.94 (4H, m), 0.90 (3H, dd), 0.47-0.21 (3H, m), 0.12-(−0.03) (1H, m)<br>Rotamers ratio: 6:4 |
| 218 | $^1$H NMR (400 MHz, CDCl$_3$) δ ppm 8.71 (1H, s), 6.83 (1H, t), 6.74 (2H, d), 6.20 (1H, br. s), 3.90-3.77 (1H, m), 3.70-3.49 (3H, m), 3.26-3.08 (5H, m), 3.07-2.94 (1H, m), 2.91 (3H, s), 2.73-2.49 (2H, m), 2.35-2.13 (2H, m), 1.85 (1H, d), 1.13 (3H, d) |
| 223 | $^1$H NMR (400 MHz, DMSO-d$_6$) δ ppm 10.66 (1H, s), 7.91 (1H, t), 7.67 (1H, m), 6.95 (2H, s), 6.88 (1H, s), 3.60-3.42 (4H, m), 3.42-3.10 (6H, m), 2.44-2.28 (1H, m), 2.26-2.12 (1H, m), 1.88-1.74 (5H, m) |
| 241 | $^1$H NMR (400 MHz, DMSO-d$_6$) δ ppm 7.9-7.4 (1H, br. s), 7.26 (1H, q), 7.00 (1H, ddd), 6.77-6.70 (1H, m), 3.72-3.41 (4H, m), 3.20-3.00 (4H, m), 2.72-2.61 (1H, m), 2.55-2.45 (1H, m), 2.43-2.34 (1H, m), 2.23 (1H, dd), 1.70-1.50 (3H, m), 0.96 (3H, d) |
| 255 | $^1$H NMR (400 MHz, DMSO-d$_6$): δ (ppm) 0.06-0.14 (m, 1H), 0.28-0.40 (m, 2H), 0.42-0.49 (m, 1H), 0.91 (d, 1.5H), 0.97 (d, 1.5H), 1.04-1.14 (m, 1H), 1.88-2.03 (m, 2H), 2.20-2.33 (m, 1H), 2.37-2.52 (m, 1H), 2.81-3.05 (m, 2H), 3.21-3.29 (m, 0.5H), 3.40-3.49 (m, 1.5H), 3.65 (d, 0.5H), 3.80 (d, 0.5H), 4.10 (br. s., 1H), 4.17 (d, 0.5H), 4.29 (d, 0.5H), 6.44 (t, 1H), 6.50-6.60 (m, 2H), 7.70 (s, 0.5H), 7.74 (s, 0.5H), 10.61 (br. s., 1H) |
| 281 | $^1$H NMR (400 MHz, DMSO-d$_6$) δ ppm 10.62 (1H, br. s), 8.62 (2H, s), 7.78-7.64 (3H, m), 7.36 (1H, t), 7.24 (1H, s), 7.17 (1H, d), 7.05-6.98 (1H, m), 4.32-4.23 (0.5H, m), 4.20-4.10 (1.5H, m), 3.87-3.78 (0.5H, m), 3.68-3.60 (0.5H, m), 3.54-3.41 (1.5H, m), 3.37-3.30 (0.5H, m), 3.14-2.90 (2H, m), 2.48-2.18 (2H, m), 2.02-1.92 (2H, m), 1.16-1.06 (1H, m), 0.96 (1.5H, d), 0.89 (1.5H, d), 0.50-0.41 (1H, m), 0.41-0.27 (2H, m), 0.15-0.05 (1H, m) |
| 293 | $^1$H NMR (400 MHz, DMSO-d$_6$) δ ppm 10.62 (1H, s), 7.93 (1H, s), 7.11 (1H, dd), 6.89 (1H, dd), 3.63-3.53 (4H, m), 2.88-2.76 (4H, m), 2.42-2.34 (1H, m), 2.26 (3H, s), 2.26-2.16 (1H, m), 1.82 (2H, t), 1.27 (3H, s) |
| 302 | $^1$H NMR (400 MHz, DMSO-d$_6$) δ ppm 10.62 (1H, s), 8.56-8.54 (1H, m), 7.78-7.71 (1H, m), 7.39 (1H, dd), 7.20 (1H, d), 4.66-4.52 (1H, m), 4.37-4.28 (0.5H, m), 4.23 (0.5H, d), 4.18-4.05 (1H, m), 3.90-3.83 (0.5H, m), 3.75-3.67 (0.5H, m), 3.45 (0.5H, dd), 3.32-3.13 (1H, m), 3.12-2.95 (1H, m), 2.91-2.80 (0.5H, m), 2.49-2.21 (2H, m), 2.05-1.88 (2H, m), 1.15-1.05 (1H, m), 1.08 (1.5H, d), 1.00 (1.5H, d), 0.50-0.40 (1H, m), 0.40-0.26 (2H, m), 0.14-0.05 (1H, m) |
| 372 | $^1$H NMR (400 MHz, DMSO-d$_6$) δ ppm 10.62 (1H, s), 9.25 (1H, s), 8.71-8.69 (1H, m), 8.60 (1H, d), 7.76-7.70 (1H, t), 7.65-7.61 (1H, m), 7.53 (1H, d), 7.39 (1H, t), 7.09-7.03 (1H, m), 4.33-4.26 (0.5H, m), 4.20-4.11 (1.5H, m), 3.88-3.80 (0.5H, m), 3.70-3.60 (0.5H, m), 3.55-3.36 (2H, m), 3.14-2.90 (2H, m), 2.48-2.20 (2H, m), 2.05-1.91 (2H, m), 1.17-1.03 (1H, m), 0.97 (1.5H, d), 0.90 (1.5H, d), 0.51-0.41 (1H, m), 0.41-0.27 (2H, m), 0.16-0.05 (1H, m) |

BIOLOGICAL EXAMPLES

Example 3. In Vitro Assays

3.1. hADAMTS-1

The basis for the assay is the cleavage of the substrate 5(6)-Fluorescein-NH-AELQGRPISIAK-5(6)-TAMRA (SEQ ID N°1) by human ADAMTS1

For the dose response (10 point), 4 μL of a dilution series of compound (2 mM highest concentration, 1/5 dilution in DMSO further diluted 1 in 10 in water corresponding to a final highest concentration of 20 μM), is transferred to 384 well Fluotrac 200 plate (Greiner, cat #781076) and incubated at room temperature for 30 min with a 26 μL buffer solution (50 mM MOPS pH7; 50 mM NaCl; 5 mM $CaCl_2$; 0.05% CHAPS; 5 μM $ZnCl_2$) containing hADAMTS1 (0.38 ng/μL, R&D SYSTEMS INC., Cat #2197-AD)) (it will be appreciated by the skilled person that the potency read out is independent of the enzyme concentration).

The reaction is initiated by adding to the assay plate 5(6)-Fluorescein-NH-AELQGRPISIAK-5(6)-TAMRA (SEQ ID N°1) (10 μL, 7 μM, Anaspec) in the same buffer.

Finally, the fluorescence is read on the Envision (Perkin Elmer) after an incubation of 120 min at 37° C. (Excitation 485 nm, Emission 535).

3.2. hADAMTS-4

3.2.1. Protocol 1

The basis for the assay is the cleavage of the substrate TBIS-1 (5-FAM-TEGEARGSVILLK (5TAMRA)K—$NH_2$) (SEQ ID N°2) by human ADAMTS4

For the dose response (10 point), 4 μL of a dilution series of compound (2 mM highest concentration, 1/5 dilution in DMSO further diluted 1 in 10 in water corresponding to a final highest concentration of 20 μM), is transferred to 384 well Fluotrac 200 plate (Greiner, cat #781076) and incubated at room temperature for 30 min with a 26 μL buffer solution (50 mM Hepes pH7.5, 100 mM NaCl, 5 mM $CaCl_2$, 0.1% CHAPS, 5% glycerol) containing hADAMTS4 (0.325 ng/μL) (it will be appreciated by the skilled person that the potency read out is independent of the enzyme concentration).

The reaction is initiated by adding to the assay plate TBIS-1 (10 μL, 4.5 μM, Anaspec) in the same buffer.

Finally, the fluorescence is read on the Envision (Perkin Elmer) after an incubation of 60 min at room temperature (Excitation 485 nm, emission 535).

3.2.2. Protocol 2

The basis for the assay is the cleavage of the substrate TBIS-1 (5 FAM-TEGEARGSVILLK (5TAMRA)K—$NH_2$) (SEQ ID N°2) by human ADAMTS4

For the dose response (10 point), 4 μL of a dilution series of compound (2 mM highest concentration, 1/5 dilution in DMSO further diluted 1 in 10 in water corresponding to a final highest concentration of 20 μM), is transferred to 384 well Fluotrac 200 plate (Greiner, cat #781076) and incubated at room temperature for 30 min with a 26 μL buffer solution (50 mM Hepes pH 7.5, 100 mM NaCl, 5 mM $CaCl_2$, 0.1% CHAPS) containing hADAMTS4 (0.38 ng/μL) (it will be appreciated by the skilled person that the potency read out is independent of the enzyme concentration).

The reaction is initiated by adding to the assay plate TBIS-1 (10 μL, 4.5 μM, Anaspec) in the same buffer.

Finally, the fluorescence is read on the Envision (Perkin Elmer) after an incubation of 180 min at 37° C. (Excitation 485 nm, emission 535).

3.3. Rat ADAMTS-5

The basis for the assay is the cleavage of the substrate TBIS-1 (5 FAM-TEGEARGSVILLK (5TAMRA)K—$NH_2$) (SEQ ID N°2) by rnADAMTS-5 (1-564-6H).

For the dose response (10 point), 4 μL of a dilution series of compound (2 mM highest concentration, 1/5 dilution in DMSO further diluted 1 in 10 in water, corresponding to a final highest concentration of 20 μM), is transferred to 384 well Fluotrac 200 plate (Greiner, cat #781076) and incubated at room temperature for 30 min with a 26 μL buffer solution (50 mM TRIS pH7.5, 100 mM NaCl, 5 mM $CaCl_2$, 0.1% CHAPS) containing rnADAMTS-5 (0.5 ng/μL) (it will be appreciated by the skilled person that the potency read out is independent of the enzyme concentration).

The reaction is initiated by adding to the assay plate TBIS-1 (10 μL, 4.5 μM, Anaspec) in the same buffer.

Finally, the fluorescence is read on the Envision (Perkin Elmer) after an incubation of 120 min at 37° C. (Excitation 485 nm, emission 535).

The $IC_{50}$ measured for illustrative compounds of the invention is reported in Table V below.

TABLE V

Rat ADAMTS-5 potency of illustrative compounds of the invention

| Cpd | $IC_{50}$ (nM) |
|---|---|
| 1 | 730 |
| 2 | 361 |
| 3 | 323 |
| 4 | 66 |
| 5 | 101 |
| 6 | 107 |
| 7 | 272 |
| 8 | 157 |
| 9 | 331 |
| 10 | 41 |
| 11 | 1170 |
| 12 | 1160 |
| 13 | 966 |
| 14 | 784 |
| 15 | >4000 |
| 16 | 329 |
| 17 | >3940 |
| 18 | 930 |
| 19 | >4000 |
| 20 | 1270 |
| 21 | 162 |
| 22 | 3900 |
| 23 | 158 |
| 24 | 132 |
| 27 | 124 |
| 33 | 178 |
| 34 | 41 |
| 35 | 103 |
| 36 | 29 |
| 40 | 234 |
| 46 | 42 |
| 47 | 236 |
| 49 | 141 |
| 51 | 508 |
| 53 | 179 |
| 54 | 91 |
| 55 | 37 |
| 56 | 72 |
| 57 | 117 |

TABLE V-continued

Rat ADAMTS-5 potency of illustrative compounds of the invention

| Cpd | IC$_{50}$ (nM) |
|---|---|
| 64 | 165 |
| 65 | 65 |
| 66 | 1370 |
| 68 | 200 |
| 69 | 185 |
| 70 | 205 |
| 71 | 198 |
| 72 | 282 |
| 73 | 489 |
| 74 | 106 |
| 75 | 141 |
| 76 | 102 |
| 77 | 169 |
| 78 | 96 |
| 79 | 53 |
| 80 | 429 |
| 81 | 827 |
| 82 | 2090 |
| 83 | 436 |
| 84 | 637 |
| 85 | 1110 |
| 86 | 1790 |
| 87 | 113 |
| 88 | 119 |
| 89 | 72 |
| 90 | 70 |
| 91 | 69 |
| 92 | 64 |
| 93 | >4000 |
| 94 | 3020 |
| 95 | 40 |
| 96 | 57 |
| 97 | 148 |
| 98 | 82 |
| 99 | 116 |
| 100 | 163 |
| 101 | 165 |
| 102 | 94 |
| 103 | 24 |
| 104 | 41 |
| 105 | 162 |
| 106 | 222 |
| 107 | 147 |
| 108 | 410 |
| 109 | 182 |
| 110 | 299 |
| 111 | 46 |
| 112 | 39 |
| 113 | 91 |
| 114 | 62 |
| 115 | 38 |
| 116 | 29 |
| 121 | 24 |
| 124 | 37 |
| 135 | 125 |
| 136 | 242 |
| 137 | 249 |
| 138 | 107 |
| 142 | 54 |
| 143 | 314 |
| 144 | 271 |
| 145 | 563 |
| 146 | 133 |
| 147 | 99 |
| 148 | 97 |
| 151 | 83 |
| 152 | 62 |
| 153 | 114 |
| 154 | 507 |
| 156 | 128 |
| 157 | 284 |
| 158 | 389 |
| 159 | 127 |
| 160 | 36 |
| 161 | 37 |
| 162 | 45 |
| 163 | 45 |
| 167 | 10 |
| 168 | 129 |
| 169 | 27 |
| 170 | 244 |
| 172 | 11 |
| 173 | 21 |
| 174 | 17 |
| 175 | 22 |
| 176 | 7 |
| 177 | 40 |
| 178 | 344 |
| 179 | 34 |
| 180 | 241 |
| 181 | 127 |
| 182 | 87 |
| 183 | 266 |
| 184 | 280 |
| 186 | 136 |
| 187 | 396 |
| 188 | 54 |
| 189 | 254 |
| 190 | 15 |
| 191 | 11 |
| 192 | 6 |
| 193 | 7 |
| 194 | 5 |
| 195 | 262 |
| 196 | 104 |
| 197 | 21 |
| 198 | 38 |
| 199 | 48 |
| 200 | 135 |
| 203 | 26 |
| 204 | 11 |
| 205 | 27 |
| 206 | 40 |
| 207 | 6 |
| 208 | 79 |
| 209 | 565 |
| 210 | 105 |
| 211 | 23 |
| 212 | 5 |
| 213 | 21 |
| 214 | 30 |
| 215 | 18 |
| 216 | 250 |
| 217 | 49 |
| 218 | 17 |
| 219 | 29 |
| 233 | 20 |
| 242 | 57 |
| 249 | 34 |
| 255 | 23 |
| 265 | 22 |
| 294 | 128 |
| 295 | 71 |
| 314 | 34 |
| 388 | 74 |
| 405 | 18 |
| 406 | 20 |

3.4. hADAMTS-5

3.4.1. Protocol 1

The basis for the assay is the cleavage of the substrate TBIS-1 (5 FAM-TEGEARGSVILLK (5TAMRA)K—NH$_2$) (SEQ ID N°2) by human ADAMTS-5.

For the dose response (10 point), 4 µL of a dilution series of compound (2 mM highest concentration, 1/5 dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Hepes pH7.5, 100 mM NaCl, 5 mM CaCl$_2$, 0.1% CHAPS, 5% glycerol) containing hADAMTS-5 (0.5 ng/µL) (it will be appreciated by the skilled person that the potency read out is independent of the enzyme concentration).

The reaction is initiated by adding to the assay plate TBIS-1 (10 µL, 4.5 µM, Anaspec) in the same buffer.

Finally, the fluorescence is read on the Envision (Perkin Elmer) after an incubation of 60 min at Room Temperature (Excitation 485 nm, emission 530).

3.4.2. Protocol 2

The basis for the assay is the cleavage of the substrate TBIS-1 (5 FAM-TEGEARGSVILLK (5TAMRA)K—NH$_2$) (SEQ ID N°2) by human ADAMTS-5.

For the dose response (10 point), 4 µL of a dilution series of compound (2 mM highest concentration, 1/5 dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Hepes pH7.5, 100 mM NaCl, 5 mM CaCl$_2$, 0.1% CHAPS 1) containing hADAMTS-5 (1 ng/µL, affinity purified, followed by overnight digestion of 6His tag by thrombin and dialysis) (it will be appreciated by the skilled person that the potency read out is independent of the enzyme concentration).

The reaction is initiated by adding to the assay plate TBIS-1 (10 µL, 4.5 µM, Anaspec) in the same buffer.

Finally, the fluorescence is read on the Envision (Perkin Elmer) after an incubation of 45 min at 37° C. (Excitation 485 nm, emission 530).

The IC$_{50}$ measured for illustrative compounds of the invention is reported in Table VI below.

TABLE VI hADAMTS-5 potency of illustrative compounds of the invention

| Cpd | IC$_{50}$ (nM) |
|---|---|
| 1 | 694 |
| 2 | 274 |
| 3 | 233 |
| 4 | 114 |
| 5 | 78 |
| 6 | 79 |
| 7 | 272 |
| 8 | 142 |
| 9 | 316 |
| 10 | 56 |
| 11 | 988 |
| 12 | 1300 |
| 13 | 836 |
| 14 | 897 |
| 15 | >4000 |
| 16 | 301 |
| 17 | 2840 |
| 18 | 675 |
| 19 | >4000 |
| 20 | 1280 |
| 21 | 166 |
| 22 | >3790 |
| 23 | 157 |
| 24 | 93 |
| 25 | 138 |

TABLE VI-continued hADAMTS-5 potency of illustrative compounds of the invention

| Cpd | IC$_{50}$ (nM) |
|---|---|
| 26 | 706 |
| 27 | 90 |
| 28 | 209 |
| 29 | >12000 |
| 30 | >4000 |
| 31 | 1060 |
| 32 | 385 |
| 33 | 134 |
| 34 | 39 |
| 35 | 99 |
| 36 | 34 |
| 37 | 229 |
| 38 | >4000 |
| 39 | 570 |
| 40 | 186 |
| 41 | 2660 |
| 42 | >3980 |
| 43 | 1530 |
| 44 | 553 |
| 45 | 204 |
| 46 | 35 |
| 47 | 186 |
| 48 | 391 |
| 49 | 127 |
| 50 | >4000 |
| 51 | 282 |
| 52 | 281 |
| 53 | 118 |
| 54 | 61 |
| 55 | 36 |
| 56 | 38 |
| 57 | 93 |
| 58 | >20000 |
| 59 | >20000 |
| 60 | 1160 |
| 61 | 2940 |
| 62 | 293 |
| 63 | 1240 |
| 64 | 125 |
| 65 | 50 |
| 66 | 1310 |
| 67 | 152 |
| 68 | 169 |
| 69 | 178 |
| 70 | 253 |
| 71 | 200 |
| 72 | 264 |
| 73 | 382 |
| 74 | 89 |
| 75 | 73 |
| 76 | 91 |
| 77 | 107 |
| 78 | 79 |
| 79 | 53 |
| 80 | 257 |
| 81 | 681 |
| 82 | 1740 |
| 83 | 423 |
| 84 | 815 |
| 85 | 1270 |
| 86 | 1700 |
| 87 | 137 |
| 88 | 119 |
| 89 | 94 |
| 90 | 85 |
| 91 | 95 |
| 92 | 63 |
| 93 | >4080 |
| 94 | 2130 |
| 95 | 48 |
| 96 | 49 |
| 97 | 168 |
| 98 | 73 |
| 99 | 160 |
| 100 | 185 |

TABLE VI-continued hADAMTS-5 potency of illustrative compounds of the invention

| Cpd | IC$_{50}$ (nM) |
|---|---|
| 101 | 154 |
| 102 | 104 |
| 103 | 28 |
| 104 | 43 |
| 105 | 226 |
| 106 | 233 |
| 107 | 172 |
| 108 | 320 |
| 109 | 261 |
| 110 | 297 |
| 111 | 42 |
| 112 | 40 |
| 113 | 104 |
| 114 | 67 |
| 115 | 36 |
| 116 | 30 |
| 117 | 211 |
| 118 | 563 |
| 119 | 1740 |
| 120 | 690 |
| 121 | 15 |
| 122 | 341 |
| 123 | 95 |
| 124 | 48 |
| 125 | 53 |
| 126 | 106 |
| 127 | 96 |
| 128 | 1170 |
| 129 | 150 |
| 130 | 126 |
| 131 | 1260 |
| 132 | 37 |
| 133 | 108 |
| 134 | 1870 |
| 135 | 167 |
| 136 | 187 |
| 137 | 240 |
| 138 | 101 |
| 139 | 231 |
| 140 | 149 |
| 141 | 119 |
| 142 | 39 |
| 143 | 259 |
| 144 | 227 |
| 145 | 505 |
| 146 | 89 |
| 147 | 62 |
| 148 | 63 |
| 149 | 79 |
| 150 | 95 |
| 151 | 68 |
| 152 | 48 |
| 153 | 84 |
| 154 | 430 |
| 156 | 130 |
| 157 | 275 |
| 158 | 351 |
| 159 | 104 |
| 160 | 29 |
| 407 | 33.5 |

3.4.3. Protocol 3

The basis for the assay is the cleavage of the substrate TBIS-1 (5 FAM-TEGEARGSVILLK (5TAMRA)K—NH$_2$) (SEQ ID N°2) by human ADAMTS-5.

For the dose response (10 point), 4 µL of a dilution series of compound (2 mM highest concentration, 1/5 dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Hepes pH7.5, 100 mM NaCl, 5 mM CaCl$_2$, 0.1% CHAPS) containing hADAMTS-5 (0.63 ng/µL) (it will be appreciated by the skilled person that the potency read out is independent of the enzyme concentration).

The reaction is initiated by adding to the assay plate TBIS-1 (10 µL, 4.5 µM, Anaspec) in the same buffer.

Finally, the fluorescence is read on the Envision (Perkin Elmer) after an incubation of 90 min at 37° C. (Excitation 485 nm, emission 530).

The IC$_{50}$ measured for illustrative compounds of the invention is reported in Table VII below.

TABLE VII hADAMTS-5 potency of illustrative compounds of the invention

| Cpd | IC$_{50}$ (nM) |
|---|---|
| 1 | 1440 |
| 3 | 486 |
| 6 | 86 |
| 12 | 1554 |
| 19 | >4000 |
| 29 | >4000 |
| 30 | >4000 |
| 34 | 73 |
| 40 | 243 |
| 50 | >4000 |
| 51 | 920 |
| 53 | 148 |
| 55 | 69 |
| 75 | 61 |
| 98 | 127 |
| 99 | 534 |
| 102 | 184 |
| 112 | 58 |
| 115 | 106 |
| 116 | 51 |
| 118 | 711 |
| 120 | 1120 |
| 121 | 15 |
| 122 | 590 |
| 124 | 35 |
| 127 | 85 |
| 135 | 233 |
| 136 | 286 |
| 140 | 240 |
| 142 | 25 |
| 143 | 443 |
| 144 | 154 |
| 145 | 838 |
| 146 | 70 |
| 147 | 47 |
| 148 | 76 |
| 151 | 32 |
| 152 | 63 |
| 153 | 63 |
| 154 | 742 |
| 155 | 1250 |
| 156 | 188 |
| 157 | 241 |
| 158 | 364 |
| 159 | 126 |
| 160 | 32 |
| 161 | 54 |
| 162 | 39 |
| 163 | 40 |
| 164 | 236 |
| 165 | 207 |
| 166 | 264 |
| 167 | 19 |
| 168 | 76 |
| 169 | 30 |
| 170 | 170 |
| 171 | 305 |
| 172 | 17 |
| 173 | 22 |
| 174 | 21 |

TABLE VII-continued hADAMTS-5 potency of illustrative compounds of the invention

| Cpd | IC$_{50}$ (nM) |
|---|---|
| 175 | 25 |
| 176 | 16 |
| 177 | 78 |
| 178 | 577 |
| 179 | 94 |
| 180 | 177 |
| 181 | 97 |
| 182 | 104 |
| 183 | 235 |
| 184 | 272 |
| 185 | >4000 |
| 186 | 110 |
| 187 | 456 |
| 188 | 53 |
| 189 | 256 |
| 190 | 22 |
| 191 | 20 |
| 192 | 11 |
| 193 | 23 |
| 194 | 11 |
| 195 | 318 |
| 196 | 102 |
| 197 | 26 |
| 198 | 52 |
| 199 | 62 |
| 200 | 109 |
| 201 | 307 |
| 202 | 724 |
| 203 | 46 |
| 204 | 16 |
| 205 | 26 |
| 206 | 60 |
| 207 | 12 |
| 208 | 126 |
| 209 | 836 |
| 210 | 108 |
| 211 | 48 |
| 212 | 12 |
| 213 | 30 |
| 214 | 61 |
| 215 | 37 |
| 216 | 305 |
| 217 | 59 |
| 218 | 20 |
| 219 | 41 |
| 220 | 18 |
| 221 | 110 |
| 222 | 20 |
| 223 | 70 |
| 224 | 14 |
| 225 | 28 |
| 226 | 22 |
| 227 | 105 |
| 228 | 109 |
| 229 | 31 |
| 230 | 24 |
| 231 | 20 |
| 232 | 47 |
| 233 | 27 |
| 234 | 28 |
| 235 | 16 |
| 236 | 15 |
| 237 | 106 |
| 238 | 141 |
| 239 | 46 |
| 240 | 194 |
| 241 | 232 |
| 242 | 66 |
| 243 | >3890 |
| 244 | 2310 |
| 245 | 17 |
| 246 | 114 |
| 247 | 95 |
| 248 | 49 |
| 249 | 36 |
| 250 | 2150 |
| 251 | 94 |
| 252 | 67 |
| 253 | 35 |
| 254 | 71 |
| 255 | 20 |
| 256 | 1410 |
| 257 | 1570 |
| 258 | 1530 |
| 259 | 224 |
| 260 | 126 |
| 261 | 165 |
| 262 | >4000 |
| 263 | 19 |
| 264 | 19 |
| 265 | 18 |
| 266 | 28 |
| 267 | 3080 |
| 268 | 62 |
| 269 | 19 |
| 270 | 76 |
| 271 | 1300 |
| 272 | 623 |
| 273 | 322 |
| 274 | >4000 |
| 275 | 266 |
| 276 | 115 |
| 277 | 152 |
| 278 | >20000 |
| 279 | 19 |
| 280 | 275 |
| 281 | 189 |
| 282 | 110 |
| 283 | 1080 |
| 284 | >12000 |
| 285 | 892 |
| 286 | >4000 |
| 287 | 52 |
| 288 | 72 |
| 289 | 97 |
| 290 | 2850 |
| 291 | 453 |
| 292 | 48 |
| 293 | 294 |
| 294 | 134 |
| 295 | 115 |
| 296 | >4000 |
| 297 | >3620 |
| 298 | 192 |
| 299 | 114 |
| 300 | 140 |
| 301 | >20000 |
| 302 | 776 |
| 303 | 266 |
| 304 | >4000 |
| 305 | 674 |
| 306 | 67 |
| 307 | 44 |
| 308 | 59 |
| 309 | 31 |
| 310 | 50 |
| 311 | 57 |
| 312 | 40 |
| 313 | 34 |
| 314 | 24 |
| 315 | 42 |
| 316 | 61 |
| 317 | 52 |
| 318 | 59 |
| 319 | 94 |
| 320 | 48 |
| 321 | 199 |
| 322 | 237 |
| 323 | 1240 |
| 324 | 407 |

TABLE VII-continued hADAMTS-5 potency of illustrative compounds of the invention

| Cpd | IC$_{50}$ (nM) |
|---|---|
| 325 | 796 |
| 326 | 52 |
| 327 | 45 |
| 328 | >4000 |
| 329 | 134 |
| 330 | >4000 |
| 331 | 14 |
| 332 | 61 |
| 333 | 3120 |
| 334 | 430 |
| 335 | 78 |
| 336 | 74 |
| 337 | 764 |
| 338 | 60 |
| 339 | 33 |
| 340 | 155 |
| 341 | 264 |
| 342 | 39 |
| 343 | 22 |
| 344 | >20000 |
| 345 | 50 |
| 346 | 37 |
| 347 | 21 |
| 348 | 34 |
| 349 | 62 |
| 350 | 62 |
| 351 | 35 |
| 352 | >20000 |
| 353 | 1640 |
| 354 | >20000 |
| 355 | 200 |
| 356 | 40 |
| 357 | 25 |
| 358 | 953 |
| 359 | 83 |
| 360 | 119 |
| 361 | 51 |
| 362 | 50 |
| 363 | 76 |
| 364 | 92 |
| 365 | 72 |
| 366 | 36 |
| 367 | 44 |
| 368 | 257 |
| 369 | 1080 |
| 370 | 532 |
| 371 | 42 |
| 372 | 2390 |
| 373 | 1530 |
| 374 | 3080 |
| 375 | 30 |
| 376 | 52 |
| 377 | 700 |
| 378 | 22 |
| 379 | 18 |
| 380 | 47 |
| 381 | 1970 |
| 382 | 39 |
| 383 | 43 |
| 384 | 60 |
| 385 | 71 |
| 386 | 48 |
| 387 | 37 |
| 388 | 57 |
| 389 | 40 |
| 391 | >4000 |
| 392 | 567 |
| 394 | 49 |
| 395 | 39 |
| 396 | 53 |
| 397 | 37 |
| 399 | 163 |
| 400 | 383 |
| 401 | 1120 |
| 402 | 732 |
| 403 | 168 |
| 404 | 19 |
| 405 | 22 |
| 406 | 26 |
| 407 | 25 |
| 408 | 19 |
| 409 | 17 |
| 410 | 22 |
| 411 | 11 |
| 412 | 13 |
| 413 | 11 |
| 414 | 40 |
| 415 | 28 |
| 416 | 12 |
| 417 | 22 |
| 418 | 33 |
| 419 | 23 |
| 420 | 32 |
| 421 | 38 |
| 422 | 21 |
| 423 | 58 |
| 424 | 53 |
| 425 | 18 |
| 426 | 110 |
| 427 | 20 |
| 428 | 14 |
| 429 | 53 |
| 430 | 105 |
| 431 | 30 |
| 432 | 26 |
| 433 | 21 |
| 434 | 20 |
| 435 | 15 |
| 436 | 22 |
| 437 | 17 |
| 438 | 56 |
| 439 | 43 |
| 440 | 2150 |
| 441 | 59 |
| 442 | 24 |
| 443 | 32 |
| 444 | 25 |
| 445 | 29 |
| 446 | 19 |
| 447 | 56 |
| 448 | 19 |
| 449 | 40 |
| 450 | 58 |
| 451 | 48 |
| 452 | 23 |
| 453 | 36 |
| 454 | 35 |
| 455 | 14 |
| 456 | 27 |
| 457 | 47 |
| 458 | 21 |
| 459 | 46 |
| 460 | 30 |
| 461 | 39 |
| 462 | 22 |
| 463 | 46 |
| 464 | 26 |
| 465 | 62 |
| 466 | 55 |
| 467 | 42 |
| 468 | >4000 |
| 469 | 215 |
| 470 | 383 |
| 471 | 852 |
| 472 | 899 |
| 474 | 626 |
| 475 | 307 |
| 476 | 175 |
| 477 | 239 |
| 478 | 61 |

TABLE VII-continued hADAMTS-5 potency of illustrative compounds of the invention

| Cpd | IC$_{50}$ (nM) |
|---|---|
| 479 | 19 |
| 480 | 31 |
| 481 | 29 |

3.5. hTACE

The basis for the assay is the cleavage of the substrate 5FAM-LAQAVRSSSRK-5TAMRA (SEQ ID N°3) (Anaspec, custom 34891) by human TACE (R&D SYSTEMS INC., Cat #930-ADB).

For the dose response (10 point), 4 μL of a dilution series of compound (2 mM highest concentration, 1/5 dilution in DMSO further diluted 1 in 10 in water, corresponding to a final highest concentration of 20 μM), is transferred to 384 well Fluotrac 200 plate (Greiner, cat #781076) and incubated at room temperature for 30 min with a 26 μL buffer solution (25 mM Tris pH8.0, 2.5 μM ZnCl$_2$, 0.01% CHAPS) containing TACE (0.05 ng/μL) (it will be appreciated by the skilled person that the potency read out is independent of the enzyme concentration).

The reaction is initiated by adding to the assay plate 5FAM-LAQAVRSSSRK-5TAMRA (5 μL, 5 μM, Anaspec) in the same buffer.

Finally, the fluorescence is read on the Envision (Perkin Elmer) after an incubation of 75 min at room temperature (Excitation 485 nm, Emission 530).

The IC$_{50}$ measured for illustrative compounds of the invention is reported in Table VIII below.

TABLE VIII

TACE potency of illustrative compounds of the invention

| Cpd | IC$_{50}$ (nM) |
|---|---|
| 1 | >20000 |
| 2 | >17500 |
| 3 | >5500 |
| 4 | >5500 |
| 5 | >3330 |
| 6 | 2360 |
| 7 | >2930 |
| 8 | >3220 |
| 9 | 2500 |
| 10 | >2790 |
| 11 | >20000 |
| 12 | >4000 |
| 13 | 1170 |
| 14 | >4000 |
| 16 | 457 |
| 17 | >4000 |
| 18 | >4000 |
| 20 | >4000 |
| 21 | 2060 |
| 24 | 298 |
| 25 | >2000 |
| 26 | >10000 |
| 27 | >2000 |
| 28 | >20000 |
| 32 | >4000 |
| 33 | 429 |
| 34 | >4000 |
| 35 | >4000 |
| 36 | 670 |
| 37 | >20000 |
| 39 | 588 |
| 40 | 2720 |
| 43 | >20000 |
| 44 | >20000 |
| 45 | >20000 |
| 46 | 137 |
| 47 | >20000 |
| 49 | >20000 |
| 51 | >3660 |
| 52 | >20000 |
| 53 | >4000 |
| 54 | 2270 |
| 55 | >3310 |
| 56 | 3190 |
| 57 | >12000 |
| 60 | >20000 |
| 62 | >20000 |
| 63 | >20000 |
| 64 | 3140 |
| 65 | 56 |
| 66 | >20000 |
| 67 | >4000 |
| 70 | >20000 |
| 74 | 1360 |
| 75 | 550 |
| 76 | 1780 |
| 78 | 2660 |
| 79 | 277 |
| 80 | >20000 |
| 83 | 2490 |
| 85 | >4000 |
| 86 | >4000 |
| 87 | 120 |
| 88 | 211 |
| 89 | 984 |
| 90 | >4000 |
| 91 | >4000 |
| 92 | 1050 |
| 93 | >3530 |
| 94 | >4000 |
| 95 | >4000 |
| 96 | 3590 |
| 97 | >4000 |
| 98 | >4000 |
| 99 | >14700 |
| 100 | >4000 |
| 102 | 3400 |
| 103 | 4100 |
| 104 | 461 |
| 105 | >20000 |
| 106 | >20000 |
| 107 | >4000 |
| 109 | 5260 |
| 111 | 963 |
| 112 | >4000 |
| 113 | >20000 |
| 114 | >20000 |
| 115 | >20000 |
| 116 | >4640 |
| 117 | >4000 |
| 118 | >4000 |
| 120 | >4000 |
| 121 | 1100 |
| 122 | >4000 |
| 123 | 1640 |
| 124 | 880 |
| 125 | 1800 |
| 126 | >4000 |
| 127 | >4000 |
| 128 | >20000 |
| 129 | >4000 |
| 130 | >4000 |
| 132 | 348 |
| 133 | 195 |
| 134 | >20000 |

TABLE VIII-continued

TACE potency of illustrative compounds of the invention

| Cpd | IC$_{50}$ (nM) |
|---|---|
| 135 | >20000 |
| 136 | >20000 |
| 137 | >20000 |
| 138 | >20000 |
| 139 | 1320 |
| 140 | >20000 |
| 142 | >4000 |
| 143 | >20000 |
| 144 | >4000 |
| 145 | >4000 |
| 146 | 1580 |
| 147 | >4000 |
| 148 | >4000 |
| 151 | >20000 |
| 152 | >20000 |
| 153 | 2270 |
| 154 | >20000 |
| 155 | >20000 |
| 156 | >20000 |
| 157 | >20000 |
| 158 | >20000 |
| 159 | 1870 |
| 160 | >20000 |
| 161 | >20000 |
| 162 | >20000 |
| 163 | >20000 |
| 164 | >20000 |
| 165 | >20000 |
| 166 | >20000 |
| 167 | >4000 |
| 168 | >20000 |
| 169 | >20000 |
| 170 | n/a |
| 171 | >20000 |
| 172 | 311 |
| 173 | 3140 |
| 174 | 321 |
| 175 | 251 |
| 176 | 1230 |
| 177 | 1990 |
| 179 | 785 |
| 180 | >4000 |
| 181 | 2860 |
| 182 | >4000 |
| 183 | >20000 |
| 186 | 4070 |
| 187 | >20000 |
| 188 | >4000 |
| 189 | >4000 |
| 190 | >20000 |
| 191 | >20000 |
| 192 | >4000 |
| 193 | >20000 |
| 194 | >4000 |
| 196 | >3930 |
| 197 | 134 |
| 198 | 817 |
| 199 | 1050 |
| 200 | 1060 |
| 201 | >20000 |
| 203 | >20000 |
| 204 | 3870 |
| 205 | >20000 |
| 206 | >4000 |
| 207 | >4000 |
| 208 | >4000 |
| 209 | >4000 |
| 210 | 1440 |
| 211 | 3740 |
| 212 | >4000 |
| 213 | >20000 |
| 214 | >4000 |
| 215 | >12000 |
| 216 | >4000 |
| 217 | >4000 |
| 218 | 272 |
| 219 | 441 |
| 220 | 245 |
| 221 | 3200 |
| 222 | 337 |
| 223 | >4000 |
| 224 | >4000 |
| 225 | >20000 |
| 226 | >4000 |
| 227 | >3510 |
| 228 | >4000 |
| 229 | >4000 |
| 230 | 207 |
| 231 | 106 |
| 232 | >4000 |
| 233 | >4000 |
| 234 | >4000 |
| 235 | 1320 |
| 236 | 225 |
| 237 | >4000 |
| 238 | 3160 |
| 239 | >4000 |
| 240 | >20000 |
| 241 | >12000 |
| 242 | 2520 |
| 243 | >19500 |
| 244 | >19500 |
| 245 | 2130 |
| 246 | >19500 |
| 247 | >19600 |
| 248 | >3780 |
| 249 | >19600 |
| 250 | 417 |
| 251 | >12000 |
| 252 | 2690 |
| 253 | >20000 |
| 254 | 1000 |
| 255 | >20000 |
| 256 | >20000 |
| 257 | >4000 |
| 258 | >20000 |
| 259 | >20000 |
| 260 | >20000 |
| 261 | >20000 |
| 262 | >4000 |
| 263 | 2620 |
| 264 | >4000 |
| 265 | >4000 |
| 266 | >4000 |
| 267 | >4000 |
| 268 | >4000 |
| 269 | 840 |
| 270 | >4000 |
| 271 | >20000 |
| 272 | >4000 |
| 273 | >20000 |
| 274 | >20000 |
| 275 | >20000 |
| 276 | >4000 |
| 277 | >4000 |
| 278 | >20000 |
| 279 | 2990 |
| 280 | >20000 |
| 281 | >20000 |
| 282 | >20000 |
| 283 | >20000 |
| 284 | >20000 |
| 285 | >4000 |
| 286 | >20000 |
| 287 | >4000 |
| 288 | >4000 |
| 289 | >4000 |
| 290 | >20000 |
| 291 | >20000 |
| 292 | >4000 |

TABLE VIII-continued

TACE potency of illustrative compounds of the invention

| Cpd | IC$_{50}$ (nM) |
|---|---|
| 294 | >20000 |
| 295 | >20000 |
| 296 | >20000 |
| 297 | >20000 |
| 298 | >20000 |
| 299 | >20000 |
| 300 | >20000 |
| 301 | >20000 |
| 302 | >20000 |
| 303 | >20000 |
| 304 | >20000 |
| 305 | >20000 |
| 306 | >4000 |
| 307 | 3590 |
| 308 | >4000 |
| 309 | >4000 |
| 310 | 1320 |
| 311 | 3070 |
| 312 | 3680 |
| 313 | >20000 |
| 314 | >4000 |
| 315 | >4000 |
| 316 | >4000 |
| 317 | >4000 |
| 318 | 2190 |
| 319 | >4000 |
| 320 | >4000 |
| 321 | >4000 |
| 322 | >4000 |
| 323 | >4000 |
| 324 | >4000 |
| 325 | >20000 |
| 326 | >4000 |
| 327 | >4000 |
| 328 | >20000 |
| 329 | >20000 |
| 330 | >20000 |
| 331 | >4000 |
| 332 | >20000 |
| 333 | >20000 |
| 334 | >20000 |
| 335 | >4000 |
| 336 | >4000 |
| 337 | >20000 |
| 338 | >4000 |
| 339 | >4000 |
| 340 | >4000 |
| 341 | 885 |
| 342 | >4000 |
| 343 | >20000 |
| 344 | >20000 |
| 345 | >4000 |
| 346 | >4000 |
| 347 | 2380 |
| 348 | >4000 |
| 349 | >4000 |
| 350 | >20000 |
| 351 | >20000 |
| 352 | >20000 |
| 353 | >20000 |
| 354 | >20000 |
| 355 | >20000 |
| 356 | >4000 |
| 357 | >4000 |
| 358 | >20000 |
| 359 | >12000 |
| 360 | >20000 |
| 361 | >20000 |
| 362 | >20000 |
| 363 | >12000 |
| 364 | >20000 |
| 365 | >9330 |
| 366 | >4000 |
| 367 | >4000 |
| 368 | >20000 |
| 369 | >20000 |
| 370 | >20000 |
| 371 | >3730 |
| 372 | >20000 |
| 373 | >20000 |
| 374 | >20000 |
| 375 | 1130 |
| 376 | 2430 |
| 377 | >20000 |
| 378 | >4000 |
| 379 | 1490 |
| 380 | >4000 |
| 381 | >20000 |
| 382 | >20000 |
| 383 | >4000 |
| 384 | 2230 |
| 385 | >4000 |
| 386 | >4000 |
| 387 | >4000 |
| 388 | >4000 |
| 389 | >4000 |
| 391 | >4000 |
| 392 | >20000 |
| 394 | >20000 |
| 395 | >20000 |
| 396 | >4000 |
| 397 | >4000 |
| 400 | 2930 |
| 404 | >4000 |
| 405 | >4000 |
| 406 | >4000 |
| 407 | 479 |
| 408 | >4000 |
| 409 | 311 |
| 410 | 170 |
| 411 | >4000 |
| 412 | >20000 |
| 413 | >4000 |
| 414 | >4000 |
| 415 | 396 |
| 416 | >4000 |
| 417 | 479 |
| 418 | >4000 |
| 419 | >4000 |
| 420 | 2980 |
| 421 | >4000 |
| 422 | >4000 |
| 423 | 1470 |
| 424 | >10800 |
| 425 | 245 |
| 426 | 3200 |
| 427 | 337 |
| 428 | >4000 |
| 429 | >3980 |
| 430 | >3510 |
| 431 | >4000 |
| 432 | >4000 |
| 433 | 1250 |
| 434 | 106 |
| 435 | 225 |
| 436 | 368 |
| 437 | 2130 |
| 438 | 1280 |
| 439 | 787 |
| 440 | 417 |
| 441 | >20000 |
| 442 | 789 |
| 443 | >4000 |
| 444 | >4000 |
| 445 | >4000 |
| 446 | 840 |
| 447 | 3620 |
| 448 | 2990 |
| 449 | >20000 |
| 450 | >20000 |

TABLE VIII-continued

TACE potency of illustrative
compounds of the invention

| Cpd | IC$_{50}$ (nM) |
|---|---|
| 451 | >12000 |
| 452 | 1780 |
| 453 | 3180 |
| 454 | 2980 |
| 455 | >4000 |
| 456 | >4000 |
| 457 | >4000 |
| 458 | 2380 |
| 459 | 1740 |
| 460 | >4000 |
| 461 | 2540 |
| 462 | >4000 |
| 463 | >4000 |
| 464 | >4000 |
| 465 | 3500 |
| 466 | 2640 |
| 467 | >4000 |
| 468 | >4000 |
| 469 | >4000 |
| 470 | 2930 |
| 472 | >4000 |
| 474 | >4000 |
| 475 | 2650 |
| 476 | >4000 |
| 477 | >20000 |
| 478 | >4000 |
| 479 | >4000 |
| 480 | >20000 |
| 481 | 3950 |

3.6. hMMP1

Inhibition of the proteases human MMP1 was determined at REACTION BIOLOGY (Reaction Biology Corp. 1 Great Valley Parkway, Suite 2 Malvern, Pa. 19355, USA) in fluorescent based biochemical assays. The protease activities were monitored as a time-course measurement of the increase in fluorescence signal from fluorescently-labeled peptide substrates, and initial linear portion of slope (signal/min) was analyzed.

To determine the IC$_{50}$, a compound is tested starting from 100 nM (highest dilution) with a 1/3 dilution.

The IC$_{50}$ measured for illustrative compounds of the invention is reported in Table IX below.

TABLE IX hMMP-1 potency of illustrative compounds of the invention

| Cpd | IC$_{50}$ (nM) |
|---|---|
| 27 | 30000 |
| 36 | 30000 |
| 40 | >30000 |
| 55 | >30000 |
| 255 | >30000 |

3.7. hMMP2

3.7.1. Protocol 1

The basis for the assay is the cleavage of the substrate 520 MMP fret substrate XV (Anaspec, Catalog #: AS-60582-01) by human MMP2 (R&D SYSTEMS INC. Systems Inc., Cat #902-MP).

For the dose response (10 point), 4 µL of a dilution series of compound (2 mM highest concentration, 1/5 dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Tris pH 7.5, 10 mM, CaCl$_2$, 150 mM NaCl, 0.05% Brij35) containing preactivated MMP2 (0.0125 ng/µL) (it will be appreciated by the skilled person that the potency read out is independent of the enzyme concentration). Human MMP2 is preactivated by incubated the enzyme in the same buffer complemented with 1 mM freshly prepared p-Aminophenylmercuric acetate (AMPA) for 1 hour at 37° C.

The reaction is initiated by adding to the assay plate 520 MMP fret substrate XV (10 µL, 4 µM, Anaspec) in the same buffer.

Finally, the fluorescence is read on the Envision (Perkin Elmer) after an incubation of 30 min at room temperature (Excitation 485 nm, Emission 530).

The IC$_{50}$ measured for illustrative compounds of the invention is reported in Table X below.

TABLE X hMMP-2 potency of illustrative compounds of the invention

| Cpd | IC$_{50}$ (nM) |
|---|---|
| 1 | 1570 |
| 2 | 250 |
| 3 | 1480 |
| 4 | 259 |
| 5 | 44 |
| 6 | 379 |
| 7 | >16700 |
| 8 | >16700 |
| 9 | 271 |
| 10 | 26 |
| 11 | >20000 |
| 12 | >20000 |
| 13 | >20000 |
| 14 | 38 |
| 16 | >16700 |
| 18 | >20000 |
| 20 | >20000 |
| 21 | >20000 |
| 24 | >20000 |
| 25 | 101 |
| 26 | 111 |
| 27 | >10000 |
| 32 | >20000 |
| 33 | >20000 |
| 34 | 220 |
| 35 | >20000 |
| 36 | >20000 |
| 37 | 914 |
| 39 | >20000 |
| 40 | >4000 |
| 44 | 2950 |
| 45 | >4000 |
| 46 | >20000 |
| 47 | 550 |
| 49 | 83 |
| 51 | n/a |
| 52 | 2910 |
| 53 | 3930 |
| 54 | n/a |
| 55 | >20000 |
| 56 | 140 |
| 57 | n/a |
| 60 | >20000 |
| 62 | >20000 |
| 64 | >20000 |
| 65 | >20000 |

3.7.2. Protocol 2

The basis for the assay is the cleavage of the substrate 390 MMP FRET substrate I (Anaspec, Catalog n #: AS-27076) by human MMP2 (R&D SYSTEMS INC., Cat #902-MP).

For the dose response (10 point), 4 μL of a dilution series of compound (2 mM highest concentration, 1/5 dilution in DMSO further diluted 1 in 10 in water, corresponding to a final highest concentration of 20 μM), is transferred to 384 well Fluotrac 200 plate (Greiner, cat #781076) and incubated at room temperature for 30 min with a 26 μL buffer solution (45 mM Tris pH 7.5.9 mM $CaCl_2$, 135 mM NaCl, 0.045% Brij35) containing MMP2 (0.03 ng/μL) (it will be appreciated by the skilled person that the potency read out is independent of the enzyme concentration).

The reaction is initiated by adding to the assay plate 390 MMP FRET substrate I (10 μL, 2.5 μM, Anaspec) in the same buffer.

Finally, the fluorescence is read on the Envision (Perkin Elmer) after an incubation of 30 min at room temperature (Excitation 485 nm, Emission 530).

The $IC_{50}$ measured for illustrative compounds of the invention is reported in Table XI below.

TABLE XI hMMP-2 potency of illustrative compounds of the invention

| Cpd | $IC_{50}$ (nM) |
|---|---|
| 3 | 2560 |
| 5 | 212 |
| 17 | >20000 |
| 28 | 192 |
| 34 | 489 |
| 35 | >20000 |
| 36 | >20000 |
| 40 | >20000 |
| 43 | >20000 |
| 46 | >20000 |
| 47 | 1410 |
| 51 | >20000 |
| 53 | >4000 |
| 54 | >20000 |
| 55 | >20000 |
| 57 | >20000 |
| 60 | >20000 |
| 64 | >20000 |
| 65 | >20000 |
| 66 | >4000 |
| 67 | 794 |
| 70 | 1950 |
| 74 | 1410 |
| 75 | >20000 |
| 76 | 674 |
| 78 | 711 |
| 79 | >20000 |
| 80 | 452 |
| 83 | 407 |
| 85 | >20000 |
| 86 | >20000 |
| 87 | >20000 |
| 88 | >20000 |
| 89 | >20000 |
| 90 | 219 |
| 91 | 745 |
| 92 | >20000 |
| 93 | >20000 |
| 94 | >20000 |
| 95 | 381 |
| 96 | 639 |
| 97 | >20000 |
| 98 | >20000 |
| 99 | >20000 |
| 100 | >20000 |
| 102 | >20000 |
| 103 | 123 |
| 104 | 2560 |
| 105 | 212 |
| 106 | >20000 |
| 107 | 192 |
| 109 | 489 |
| 111 | >20000 |
| 112 | >20000 |
| 113 | >20000 |
| 114 | >20000 |
| 115 | >20000 |
| 116 | 1410 |
| 117 | >20000 |
| 118 | >4000 |
| 120 | >20000 |
| 121 | >20000 |
| 122 | >20000 |
| 123 | >20000 |
| 124 | >20000 |
| 125 | >20000 |
| 126 | >4000 |
| 127 | 794 |
| 128 | 1950 |
| 129 | 1410 |
| 130 | >20000 |
| 132 | 674 |
| 133 | 711 |
| 134 | >20000 |
| 135 | 452 |
| 136 | 407 |
| 137 | >20000 |
| 138 | >20000 |
| 139 | >20000 |
| 140 | >20000 |
| 142 | >20000 |
| 143 | 219 |
| 144 | 745 |
| 145 | >20000 |
| 146 | >20000 |
| 147 | >20000 |
| 148 | 381 |
| 151 | 639 |
| 152 | >20000 |
| 153 | >20000 |
| 154 | >20000 |
| 155 | >20000 |
| 156 | >20000 |
| 157 | 123 |
| 158 | 2560 |
| 159 | 212 |
| 160 | >20000 |
| 161 | 192 |
| 162 | 489 |
| 163 | >20000 |
| 164 | >20000 |
| 165 | >20000 |
| 166 | >20000 |
| 167 | >20000 |
| 168 | 1410 |
| 169 | >20000 |
| 170 | >4000 |
| 171 | >20000 |
| 172 | >20000 |
| 173 | >20000 |
| 174 | >20000 |
| 175 | >20000 |
| 176 | >20000 |
| 177 | >4000 |
| 179 | 794 |
| 180 | 1950 |
| 181 | 1410 |
| 182 | >20000 |
| 183 | 674 |
| 186 | 711 |

TABLE XI-continued hMMP-2 potency of illustrative compounds of the invention

| Cpd | IC$_{50}$ (nM) |
|---|---|
| 187 | >20000 |
| 188 | 452 |
| 189 | 407 |
| 190 | >20000 |
| 191 | >20000 |
| 192 | >20000 |
| 193 | >20000 |
| 194 | 219 |
| 196 | 745 |
| 197 | >20000 |
| 198 | >20000 |
| 199 | >20000 |
| 200 | 381 |
| 201 | 639 |
| 203 | >20000 |
| 204 | >20000 |
| 205 | >20000 |
| 206 | >20000 |
| 207 | >20000 |
| 208 | 123 |
| 209 | 2560 |
| 210 | 212 |
| 211 | >20000 |
| 212 | 192 |
| 213 | 489 |
| 214 | >20000 |
| 215 | >20000 |
| 216 | >20000 |
| 217 | >20000 |
| 218 | >20000 |
| 219 | 1410 |
| 220 | >20000 |
| 221 | >4000 |
| 222 | >20000 |
| 223 | >20000 |
| 224 | >20000 |
| 225 | >20000 |
| 226 | >20000 |
| 227 | >20000 |
| 228 | >4000 |
| 229 | 794 |
| 230 | 1950 |
| 231 | 1410 |
| 232 | >20000 |
| 233 | 674 |
| 234 | 711 |
| 235 | >20000 |
| 236 | 452 |
| 237 | 407 |
| 238 | >20000 |
| 239 | >20000 |
| 240 | >20000 |
| 241 | >20000 |
| 242 | >20000 |
| 243 | 219 |
| 244 | 745 |
| 245 | >20000 |
| 246 | >20000 |
| 247 | >20000 |
| 248 | 381 |
| 249 | 639 |
| 250 | >20000 |
| 251 | >20000 |
| 252 | >20000 |
| 253 | >20000 |
| 254 | >20000 |
| 255 | 123 |
| 256 | 2560 |
| 257 | 212 |
| 258 | >20000 |
| 259 | 192 |
| 260 | 489 |
| 261 | >20000 |
| 262 | >20000 |
| 263 | >20000 |
| 264 | >20000 |
| 265 | >20000 |
| 266 | 1410 |
| 267 | >20000 |
| 268 | >4000 |
| 269 | >20000 |
| 270 | >20000 |
| 271 | >20000 |
| 272 | >20000 |
| 273 | >20000 |
| 274 | >20000 |
| 275 | >4000 |
| 276 | 794 |
| 277 | 1950 |
| 278 | 1410 |
| 279 | >20000 |
| 280 | 674 |
| 281 | 711 |
| 282 | >20000 |
| 283 | 452 |
| 284 | 407 |
| 285 | >20000 |
| 286 | >20000 |
| 287 | >20000 |
| 288 | >20000 |
| 289 | >20000 |
| 290 | 219 |
| 291 | 745 |
| 292 | >20000 |
| 294 | >20000 |
| 295 | >20000 |
| 296 | 381 |
| 297 | 639 |
| 298 | >20000 |
| 299 | >20000 |
| 300 | >20000 |
| 301 | >20000 |
| 302 | >20000 |
| 303 | 123 |
| 304 | 2560 |
| 305 | 212 |
| 306 | >20000 |
| 307 | 192 |
| 308 | 489 |
| 309 | >20000 |
| 310 | >20000 |
| 311 | >20000 |
| 312 | >20000 |
| 313 | >20000 |
| 314 | 1410 |
| 315 | >20000 |
| 316 | >4000 |
| 317 | >20000 |
| 318 | >20000 |
| 319 | >20000 |
| 320 | >20000 |
| 321 | >20000 |
| 322 | >20000 |
| 323 | >4000 |
| 324 | 794 |
| 325 | 1950 |
| 326 | 1410 |
| 327 | >20000 |
| 328 | 674 |
| 329 | 711 |
| 330 | >20000 |
| 331 | 452 |
| 332 | 407 |
| 333 | >20000 |
| 334 | >20000 |
| 335 | >20000 |
| 336 | >20000 |
| 337 | >20000 |
| 338 | 219 |
| 339 | 745 |

TABLE XI-continued hMMP-2 potency of illustrative compounds of the invention

| Cpd | IC$_{50}$ (nM) |
|---|---|
| 340 | >20000 |
| 341 | >20000 |
| 342 | >20000 |
| 343 | 381 |
| 344 | 639 |
| 345 | >20000 |
| 346 | >20000 |
| 347 | >20000 |
| 348 | >20000 |
| 349 | >20000 |
| 350 | 123 |
| 351 | 2560 |
| 352 | 212 |
| 353 | >20000 |
| 354 | 192 |
| 355 | 489 |
| 356 | >20000 |
| 357 | >20000 |
| 358 | >20000 |
| 359 | >20000 |
| 360 | >20000 |
| 361 | 1410 |
| 362 | >20000 |
| 363 | >4000 |
| 364 | >20000 |
| 365 | >20000 |
| 366 | >20000 |
| 367 | >20000 |
| 368 | >20000 |
| 369 | >20000 |
| 370 | >4000 |
| 371 | 794 |
| 372 | 1950 |
| 373 | 1410 |
| 374 | >20000 |
| 375 | 674 |
| 376 | 711 |
| 377 | >20000 |
| 378 | 452 |
| 379 | 407 |
| 380 | >20000 |
| 381 | >20000 |
| 382 | >20000 |
| 383 | >20000 |
| 384 | >20000 |
| 385 | 219 |
| 386 | 745 |
| 387 | >20000 |
| 388 | >20000 |
| 389 | >20000 |
| 391 | 381 |
| 392 | 639 |
| 394 | >20000 |
| 395 | >20000 |
| 396 | >20000 |
| 397 | >20000 |
| 400 | >20000 |
| 404 | 123 |
| 405 | 909 |
| 406 | 581 |
| 407 | >20000 |
| 408 | 1370 |
| 409 | 3020 |
| 410 | >4000 |
| 411 | 547 |
| 412 | 63 |
| 413 | 411 |
| 414 | 2053 |
| 415 | 1390 |
| 416 | 990 |
| 417 | 1070 |
| 418 | 740 |
| 419 | 219 |
| 420 | >14700 |
| 421 | 701 |
| 422 | 879 |
| 423 | >20000 |
| 424 | >20000 |
| 425 | 2820 |
| 426 | >4000 |
| 427 | >4000 |
| 428 | 38 |
| 429 | >12000 |
| 430 | >20000 |
| 431 | 501 |
| 432 | 581 |
| 433 | >4000 |
| 434 | 1620 |
| 435 | 2590 |
| 436 | >4000 |
| 437 | 225 |
| 438 | 3420 |
| 439 | >3890 |
| 440 | >20000 |
| 441 | 1530 |
| 442 | >4000 |
| 443 | 1330 |
| 444 | 1440 |
| 445 | 945 |
| 446 | 119 |
| 447 | >4000 |
| 448 | 2 |
| 449 | 1380 |
| 450 | >3710 |
| 451 | 1100 |
| 452 | 1860 |
| 453 | 1540 |
| 454 | 449 |
| 455 | 209 |
| 456 | 279 |
| 457 | 3110 |
| 458 | 846 |
| 459 | >20000 |
| 460 | 1040 |
| 461 | >20000 |
| 462 | 946 |
| 463 | 2430 |
| 464 | 848 |
| 465 | >20000 |
| 466 | >20000 |
| 467 | 1860 |
| 468 | >20000 |
| 469 | 520 |
| 470 | >4000 |
| 472 | >4000 |
| 474 | 3260 |
| 475 | >4000 |
| 476 | 387 |
| 477 | >20000 |
| 478 | 1020 |
| 479 | 31 |
| 480 | 53 |
| 481 | 3060 |

3.8. hMMP8

Inhibition of the human MMP8 protease is determined at REACTION BIOLOGY (Reaction Biology Corp. 1 Great Valley Parkway, Suite 2 Malvern, Pa. 19355, USA; cat #MMP8) in fluorescence based biochemical assays. The protease activity is monitored as a time-course measurement of the increase in fluorescence signal from fluorescently-labeled peptide substrates, and the slope (signal/min) of the initial linear portion is measured.

The basis for the assay is the cleavage of the substrate 520 MMP FRET Substrate XIV (Anaspec, cat #AS-60581) by human MMP8 (Enzo®, cat #SE-255) in a buffer solution (50 mM HEPES pH 7.5, 10 mM CaCl$_2$, 0.01% Brij-35, 0.1 mg/mL BSA).

A 100% DMSO dilution series of test compound (10 final concentrations starting from 30 µM highest concentration, with 1/3 serial dilutions) is added to MMP8 in buffer solution and incubated at room temperature for 5-15 min (it will be appreciated by the skilled person that the potency read out is independent of the enzyme concentration). The reaction is then initiated by adding 520 MMP FRET Substrate XIV (5 µM final concentration) in the same buffer.

Fluorescence is read at 5 min intervals for 2 h with an Envision (Perkin Elmer) at room temperature (Excitation 485 nm, Emission 520 nm). The slope of the initial linear portion of the fluorescence signal curve is then calculated by using Excel. Percent protease activity is calculated relative to a no inhibitor DMSO control defined as 100% activity. IC$_{50}$ curve fits are performed using Prism software.

3.9. hMMP12

Inhibition of the human MMP12 protease is determined at REACTION BIOLOGY (Reaction Biology Corp. 1 Great Valley Parkway, Suite 2 Malvern, Pa. 19355, USA; cat #MMP12) in fluorescence based biochemical assays. The protease activity is monitored as a time-course measurement of the increase in fluorescence signal from fluorescently-labeled peptide substrates, and the slope (signal/min) of the initial linear portion is measured.

The basis for the assay is the cleavage of the substrate 520 MMP FRET Substrate XIV (Anaspec, cat #AS 60581) by human MMP12 (Enzo®, cat #SE-138) in a buffer solution (50 mM HEPES pH 7.5, 10 mM CaCl2, 0.01% Brij-35, 0.1 mg/mL BSA).

A 100% DMSO dilution series of test compound (10 final concentrations starting from 30 µM highest concentration, with 1/3 serial dilutions) is added to MMP12 in buffer solution and incubated at room temperature for 5-15 min (it will be appreciated by the skilled person that the potency read out is independent of the enzyme concentration). The reaction is then initiated by adding 520 MMP FRET Substrate XIV (5 µM final concentration) in the same buffer.

Fluorescence is read at 5 min intervals for 2 h with an Envision (Perkin Elmer) at room temperature (Excitation 485 nm, Emission 520 nm). The slope of the initial linear portion of the fluorescence signal curve is then calculated by using Excel. Percent protease activity is calculated relative to a no inhibitor DMSO control defined as 100% activity. IC$_{50}$ curve fits are performed using Prism software.

3.10. hMMP13

3.10.1. Protocol 1

The basis for the assay is the cleavage of the substrate 390 MMP FRET Substrate I (Anaspec Cat #AS-27076) by human MMP13 (Chemicon, Cat #CC068).

For the dose response (10 point), 4 µL of a dilution series of compound (20 µM highest concentration, 1/5 dilution in water), is transferred to 384 well Fluotrac 200 plate (Greiner, cat #781076) and incubated at room temperature for 30 min with a 26 µL buffer solution (50 mM Tris pH7.5, 150 mM NaCl, 10 mM CaCl$_2$, 0.05% CHAPS, 5 µM ZnCl$_2$) containing MMP13 (0.01 ng/µL) (it will be appreciated by the skilled person that the potency read out is independent of the enzyme concentration). Human MMP13 is preactivated by incubated the enzyme in the same buffer complemented with 1 mM freshly prepared p-Aminophenylmercuric acetate (AMPA) for 1 hour at 37° C.

The reaction is initiated by adding to the assay plate 390 MMP FRET Substrate I (10 µL, 2.5 µM) in the same buffer.

Finally, the fluorescence is read on the Envision (Perkin Elmer) after an incubation of 45 min at room temperature (Excitation 485 nm, Emission 530).

The IC$_{50}$ measured for illustrative compounds of the invention is reported in Table XII below.

TABLE XII hMMP-13 potency of illustrative compounds of the invention

| Cpd# | IC$_{50}$ (nM) |
|---|---|
| 3 | >4000 |
| 5 | 794 |
| 17 | >20000 |
| 27 | >20000 |
| 28 | 2370 |
| 34 | 3210 |
| 35 | >20000 |
| 36 | >20000 |
| 40 | >20000 |
| 43 | >20000 |
| 46 | n/a |
| 47 | >4000 |
| 53 | >20000 |
| 54 | >20000 |
| 55 | >20000 |
| 57 | n/a |
| 60 | >20000 |
| 64 | >20000 |
| 65 | >20000 |
| 66 | >20000 |
| 67 | >3500 |
| 70 | >4000 |
| 74 | 2660 |
| 75 | >20000 |
| 76 | 2060 |
| 78 | 2100 |
| 79 | >20000 |
| 80 | 3790 |
| 83 | >4000 |
| 85 | >20000 |
| 86 | >20000 |
| 87 | >20000 |
| 88 | >20000 |
| 89 | >20000 |
| 90 | 1210 |
| 91 | 1680 |
| 92 | >20000 |
| 93 | >20000 |
| 94 | >20000 |
| 95 | 2200 |
| 96 | 1060 |
| 97 | >20000 |
| 98 | >20000 |
| 99 | >20000 |
| 100 | >20000 |
| 102 | >20000 |
| 103 | 2000 |
| 104 | >20000 |
| 105 | >20000 |
| 106 | >20000 |
| 107 | >20000 |
| 109 | >4000 |
| 111 | >20000 |
| 112 | 1880 |
| 113 | 3620 |
| 114 | 2580 |
| 115 | >4000 |
| 116 | >20000 |
| 117 | >4000 |
| 118 | >20000 |
| 120 | >20000 |

TABLE XII-continued hMMP-13 potency of illustrative compounds of the invention

| Cpd# | IC$_{50}$ (nM) |
|---|---|
| 121 | 70.6 |
| 122 | >20000 |
| 123 | 919 |
| 124 | 1280 |
| 125 | 2120 |
| 126 | >4000 |
| 127 | >20000 |
| 128 | >20000 |
| 129 | >20000 |
| 130 | >20000 |
| 132 | 3290 |
| 133 | >20000 |
| 134 | >20000 |
| 135 | >20000 |
| 136 | >20000 |
| 137 | >20000 |
| 138 | >4000 |
| 139 | >20000 |
| 140 | >4000 |
| 142 | >20000 |
| 143 | >20000 |
| 144 | >20000 |
| 145 | >20000 |
| 146 | 3880 |
| 147 | >4000 |
| 148 | >20000 |
| 151 | >20000 |
| 152 | >20000 |
| 153 | >4000 |
| 154 | >4000 |
| 155 | >20000 |
| 156 | >20000 |
| 157 | >20000 |
| 158 | >20000 |
| 159 | >20000 |
| 160 | >20000 |
| 161 | >20000 |
| 162 | >4000 |
| 163 | >20000 |
| 164 | >20000 |
| 165 | >20000 |
| 166 | >20000 |
| 167 | >4000 |
| 168 | >20000 |
| 169 | >20000 |
| 170 | >20000 |
| 171 | >4000 |
| 172 | 2740 |
| 173 | >20000 |
| 174 | >20000 |
| 175 | >20000 |
| 176 | >20000 |
| 177 | >20000 |
| 179 | >20000 |
| 180 | >20000 |
| 181 | >20000 |
| 182 | >20000 |
| 183 | >20000 |
| 186 | >20000 |
| 187 | 2610 |
| 188 | 2670 |
| 189 | >20000 |
| 190 | 3060 |
| 191 | 1880 |
| 192 | 865 |
| 193 | 433 |
| 194 | 952 |
| 196 | >20000 |
| 197 | >4000 |
| 198 | 1940 |
| 199 | >20000 |
| 200 | >20000 |
| 201 | >20000 |
| 203 | >20000 |
| 204 | >12000 |
| 205 | >20000 |
| 206 | >4000 |
| 207 | 2880 |
| 208 | >20000 |
| 209 | >20000 |
| 210 | >14700 |
| 211 | 377 |
| 212 | 1040 |
| 213 | >4000 |
| 214 | >3510 |
| 215 | >4000 |
| 216 | >20000 |
| 217 | >4000 |
| 218 | 2220 |
| 219 | >4000 |
| 220 | >4000 |
| 221 | >4000 |
| 222 | >4000 |
| 223 | >20000 |
| 224 | 152 |
| 225 | 3940 |
| 226 | 3270 |
| 227 | >20000 |
| 228 | >4000 |
| 229 | 3850 |
| 230 | >20000 |
| 231 | 766 |
| 232 | >20000 |
| 233 | 1710 |
| 234 | 5.6 |
| 235 | 21.2 |
| 236 | 1220 |
| 242 | >20000 |
| 247 | >20000 |
| 249 | >4000 |
| 250 | >20000 |
| 255 | >20000 |
| 262 | >20000 |
| 405 | 2333 |
| 406 | 2042 |
| 407 | >20000 |
| 408 | >4000 |
| 409 | 2740 |
| 410 | >4000 |
| 411 | 865 |
| 412 | 433 |
| 413 | 952 |
| 414 | >4000 |
| 415 | 1300 |
| 416 | 2880 |
| 417 | 3130 |
| 418 | >4000 |
| 419 | 663 |
| 420 | >14000 |
| 421 | >4000 |
| 422 | 2330 |
| 423 | >20000 |
| 424 | >20000 |
| 425 | >4000 |
| 426 | >4000 |
| 427 | >4000 |
| 428 | 152 |
| 429 | >20000 |
| 430 | >20000 |
| 431 | 3280 |
| 432 | 2040 |
| 433 | >20000 |
| 434 | 766 |
| 435 | 1220 |
| 436 | >4000 |
| 438 | 1850 |
| 439 | >4000 |
| 440 | >20000 |

3.10.2. Protocol 2

The basis for the assay is the cleavage of the substrate 520 MMP-fret substrate XV (Anaspec, Catalog #: AS-60582-01) by human MMP13 (Chemicon, Cat #CC068).

For the dose response (10 point), 4 µL of a dilution series of compound (2 mM highest concentration, 1/5 dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Tris pH7.5, 150 mM NaCl, 10 mM $CaCl_2$, 0.05% CHAPS, 5 µM $ZnCl_2$) containing MMP13 (6.25 $10^{-6}$ µg/µL) (it will be appreciated by the skilled person that the potency read out is independent of the enzyme concentration).

The reaction is initiated by adding to the assay plate 520 MMP-fret substrate XV (10 µL, 4 µM) in the same buffer.

Finally, the fluorescence is read on the Envision (Perkin Elmer) after an incubation of 60 min at room temperature (Excitation 485 nm, Emission 530).

The $IC_{50}$ measured for illustrative compounds of the invention is reported in Table XIII below.

TABLE XIII

| Cpd | $IC_{50}$ (nM) |
|---|---|
| 1 | >20000 |
| 2 | 2370 |
| 3 | >4000 |
| 4 | 2520 |
| 5 | 76.4 |
| 6 | 2150 |
| 7 | >20000 |
| 8 | >20000 |
| 9 | 1480 |
| 10 | 285 |
| 11 | >20000 |
| 12 | >20000 |
| 13 | >20000 |
| 14 | 366 |
| 16 | >20000 |
| 18 | >20000 |
| 20 | >20000 |
| 21 | >20000 | hMMP-13 potency of illustrative compounds of the invention

3.11. hMMP14

The basis for the assay is the cleavage of the substrate 390 MMP FRET Substrate I (Anaspec Cat #AS-27076) by human MMP14 (Biomol, Cat #SE-259).

For the dose response (10 point), 4 µL of a dilution series of compound 2 mM highest concentration, 1/5 dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM MOPS pH7.5 mM $CaCl_2$, 1 µM $ZnCl_2$, 0.1% Brij-35) containing MMP14 (0.05 ng/µL) (it will be appreciated by the skilled person that the potency read out is independent of the enzyme concentration).

The reaction is initiated by adding to the assay plate 390 MMP FRET Substrate I (10 µL, 2.5 µM) in the same buffer.

Finally, the fluorescence is read on the Envision (Perkin Elmer) after an incubation of 60 min at room temperature (Excitation 485 nm, Emission 530).

The $IC_{50}$ measured for illustrative compounds of the invention is reported in Table XIV below.

TABLE XIV hMMP-14 potency of illustrative compounds of the invention

| Cpd | $IC_{50}$ (nM) |
|---|---|
| 27 | >20000 |
| 36 | >20000 |
| 40 | >20000 |
| 51 | >20000 |
| 55 | >20000 |
| 173 | >20000 |
| 192 | 823 |
| 203 | >4000 |
| 204 | >20000 |
| 205 | >4000 |
| 207 | >4000 |
| 210 | >20000 |
| 212 | 378 |
| 214 | 1230 |
| 215 | 2600 |
| 217 | >4000 |
| 218 | 1310 |
| 220 | 3840 |
| 223 | >20000 |
| 226 | 978 |
| 227 | >20000 |
| 228 | >20000 |
| 229 | 682 |
| 230 | >20000 |
| 231 | 549 |
| 232 | >20000 |
| 233 | 384 |
| 234 | 7 |
| 235 | 26 |
| 236 | 1220 |
| 242 | >20000 |
| 247 | >4000 |
| 249 | 1230 |
| 251 | >4000 |
| 255 | 3230 |
| 259 | >20000 |
| 260 | >20000 |
| 261 | >20000 |
| 265 | 2295 |
| 266 | 3640 |
| 270 | >4000 |
| 276 | >20000 |
| 277 | >20000 |
| 282 | >20000 |
| 287 | >4000 |
| 288 | >4000 |
| 295 | 3460 |
| 307 | >20000 |
| 308 | >20000 |
| 309 | >20000 |
| 313 | >20000 |
| 314 | >20000 |
| 316 | >20000 |
| 317 | 823 |
| 319 | >4000 |
| 320 | >20000 |
| 326 | >4000 |
| 327 | >4000 |
| 331 | >20000 |
| 332 | 378 |
| 339 | 1230 |
| 342 | 2600 |
| 346 | >4000 |
| 350 | 1310 |
| 351 | 3840 |
| 357 | >20000 |
| 359 | 978 |
| 365 | >20000 |
| 367 | >20000 |
| 371 | 682 |
| 375 | >20000 |

TABLE XIV-continued hMMP-14 potency of illustrative compounds of the invention

| Cpd | IC$_{50}$ (nM) |
|---|---|
| 388 | 549 |
| 389 | >20000 |
| 391 | 384 |
| 396 | 7 |
| 397 | 26 |
| 400 | 1220 |
| 404 | >20000 |
| 405 | 3817 |
| 406 | 1345 |
| 411 | 547 |
| 414 | 2053 |
| 416 | 990 |
| 418 | 740 |
| 420 | >14700 |
| 421 | 701 |
| 422 | 879 |
| 423 | >20000 |
| 424 | >20000 |
| 425 | 2820 |
| 429 | >12000 |
| 430 | >20000 |
| 431 | 501 |
| 432 | 581 |
| 433 | >4000 |
| 434 | 1620 |
| 435 | 2590 |
| 436 | >4000 |
| 438 | 3420 |
| 439 | >3890 |
| 441 | 1530 |
| 443 | 1330 |
| 444 | 1440 |
| 445 | 945 |
| 447 | >4000 |
| 449 | 1380 |
| 450 | >3710 |
| 451 | 1100 |
| 453 | 1540 |
| 455 | 209 |
| 457 | 3110 |
| 459 | >20000 |
| 464 | 848 |
| 465 | >20000 |
| 466 | >20000 |
| 467 | 1860 |
| 468 | >20000 |
| 469 | 520 |
| 470 | >4000 |
| 472 | >4000 |
| 474 | 3260 |
| 475 | >4000 |
| 476 | 387 |
| 477 | >20000 |
| 478 | 1020 |
| 479 | 31 |
| 480 | 53 |
| 481 | 3060 |

Example 4. Cellular Assays

4.1.1. Mouse Explant Assay

In this assay, quantitation of glycosaminoglycans (GAGs) in the form of aggrecan fragments released from cartilage in culture is used to determine the efficacy of a test compound in preventing cartilage catabolism.

The protocol of mouse cartilage explants is described by Stanton (Stanton et al., 2011). After euthanasia, the femoral head cartilage from the right and left leg of a 3-days-old C57B16 male mouse (Janvier, 7-10 g), were placed in a 48-wells culture plate. Cell culture medium (400 µL) containing human IL1α (1 ng/mL) and test compound (3 µM) were added to the femoral head cartilage.

After 3 days of incubation, the supernatant is harvested and stored at −20° C. until analysis and the cartilages are digested with a papain solution at 60° C. for 24 h. Using the standard curve performed with a dose range of chondroitin sulfate, the concentration of GAG is determined in the supernatant and on the lysate using dimethylmethylene blue solution (reading at a wavelength of 590 nm).

The percentage of GAG release is calculated as follows:

$$GAG\% = \frac{[GAG]_{supernatant}}{[GAG]_{supernatant} + [GAG]_{lysate}}$$

The test compound effect is expressed as percent of inhibition (PIN) using the following formula:

$$PIN = \frac{\text{mean }\%[GAG]_{vehicle+IL1\alpha} - \text{mean }\%[GAG]_{compound+IL1\alpha}}{\text{mean }\%[GAG]_{vehicle+IL1\alpha} - \text{mean }\%[GAG]_{compound}} * 100$$

4.2. Human Explant Assay

In this assay, compounds are tested in human articular cartilage explants in order to evaluate their activity on aggrecan degradation induced by IL1β. AGNx1 is the epitope for aggrecanase-mediated aggrecan degradation; on the other hand, AGNx2 is the epitope for MMP-mediated aggrecan degradation. Therefore quantification of AGNx1 and AGNx2 may be used to evaluate the activity of a test compound.

These studies were conducted in Nordic Bioscience (Herlev Hovedgade 207, DK-2730 Herlev, Denmark).

Human articular cartilage explants are collected from 3 nearby hospitals under an existing ethical committee application.

Full-depth cartilage explants from OA cartilage from different patients are cultured for 21 days in culture medium (DMEM/F12 with 0.5% FCS, 1% PS) containing various (positive control, untreated, and test compound at 0.1, 1 and 10 µM).

The explants from each patient are cultured in a separate 96-well culture plate with 200 µL/well PBS, and the 6 replicates of each treatment are distributed in a diagonal pattern on the plate. At each experimental time point (5, 12 and 19 days), supernatants are harvested from the explants cultures, and new treatment-mediums are added. The supernatants are stored at −20° C. for later biomarker analysis. The human IL1β (Sigma-Aldrich SRP3083) is used at a concentration of 10 ng/mL.

4.3. Results

The AGNx1 and AGNx2 concentrations were determined against a standard curve. Mean and SEM were graphed using the excel software. One-way ANOVA plus Dunnett's multiple comparisons post-hoc test are used for the statistical analysis (Prism 3.03 software).

Example 5. In Vivo Assays

5.1. In Vivo Menisectomized (MNX) Rat Model

5.1.1. In Vivo Efficacy in the Rat MNX Model

In vivo efficacy was studied in a female Lewis meniscectomised rat (MNX) model. The MNX rat model is a wellvalidated disease model of osteoarthritis (Bendele, 2001; Janusz et al., 2002; Pritzker et al., 2006).

5.1.2. Experimental Procedures

5.1.2.1. Surgery and Dosing

Osteoarthritis is induced by meniscectomy at day 0 (D0) in the right leg of each rat by a transection of the medial collateral ligament and 4 mm of ligament are removed. Internal part of the meniscus is transected vertically into two flaps which are pushed to the front and the back of the synovial cavity. Sham animals undergo only anaesthesia, skin and muscle incision then suture. On day 1, rats are randomly assigned to a treatment group (n=20 per group) according to their body weight, in order to have a homogenous distribution. From D2 to D21, rats are dosed per os (po) once daily (qd) or twice a day (bid) with compounds formulated in methylcellulose (MC) 0.5% or in HPβCD 10% pH3.0.

5.1.2.2. Steady-State PK Determination (ssPK)

After at least 7 days of treatment, blood is sampled at 4 time points post administration: 0, 1, 3 and 6 h (and assuming 24 h is equal to the pre-dose sample), in order to determine steady-state plasma exposure.

5.1.2.3. Histology

At sacrifice, the right tibia of each rat is collected and processed for histological analysis. After 48 h of fixation in 4% formaldehyde, tibias are decalcified in Osteosoft for 7 days, and cut into 2 half parts prior to embedding face to face in paraffin. Five series of sections are cut at 200 μm intervals, covering about 1.5 mm of the middle part of the bone. One series of slides is stained with Safranin O and light green for morphological evaluation and OARSI scoring. The other series of slides are mounted with DAPI for chondrocyte density measurement.

The extent of cartilage injury reflecting osteoarthritis in the tibial plateau is evaluated and scored using the OARSI method based on the grading and the staging of cartilage lesion (Pritzker et al, 2006). The OARSI scoring is assessed in a blinded manner by two different readers. For each tibia, one score is attributed as the median of the OARSI score of the 5 sections.

For statistical analysis, medians of groups are compared with a stratified Kruskal-Wallis test followed by Dunnett multiple comparison post hoc test.

Significance levels: ns: not statistically significant; *p<0.05; p<0.01; *p<0.001 versus MNX-vehicle. Statistical analyses are done on all groups of the studies.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Ref 1): Abbaszade, I., Liu, R.-Q., Yang, F., Rosenfeld, S. A., Ross, O. H., Link, J. R., Ellis, D. M., Tortorella, M. D., Pratta, M. A., Hollis, J. M., Wynn, R., Duke, J. L., George, H. J., Hillman, M. C., Murphy, K., Wiswall, B. H., Copeland, R. A., Decicco, C. P., Bruckner, R., Nagase, H., Itoh, Y., Newton, R. C., Magolda, R. L., Trzaskos, J. M., Hollis, G. F., Amer, E. C., Burn, T. C., 1999. Cloning and Characterization of ADAMTS11, an Aggrecanase from the ADAMTS Family. J. Biol. Chem. 274, 23443-23450.

Ref 2): Bendele, A., 2001. Animal models of rheumatoid arthritis. J. Musculoskelet. Neuronal Interact. 1, 377-385.

Ref 3): Botter, S. M., Glasson, S. S., Hopkins, B., Clockaerts, S., Weinans, H., van Leeuwen, J. P. T. M., van Osch, G. J. V. M., 2009. ADAMTS5−/− mice have less subchondral bone changes after induction of osteoarthritis through surgical instability: implications for a link between cartilage and subchondral bone changes. Osteoarthritis Cartilage 17, 636-645. doi:10.1016/j.joca.2008.09.018

Ref 4): Bundgaard, H., 1985. Design of prodrugs. Elsevier.

Ref 5): Chiusaroli, R., Visintin, M., Caselli, G., Rovati, L. C., 2013. Anti-Adamts-5 Antibody, Derivatives and Uses Thereof. WO2013153189 (A1).

Ref 6): Chockalingam, P. S., Sim, W., Rivera-Bermudez, M. A., Zeng, W., Dufield, D. R., Larsson, S., Lohmander, L. S., Flannery, C. R., Glasson, S. S., Georgiadis, K. E., Morris, E. A., 2011. Elevated aggrecanase activity in a rat model of joint injury is attenuated by an aggrecanase specific inhibitor. Osteoarthritis Cartilage 19, 315-323. doi:10.1016/j.joca.2010.12.004

Ref 7): Clegg, D. O., Reda, D. J., Harris, C. L., Klein, M. A., O'Dell, J. R., Hooper, M. M., Bradley, J. D., Bingham, C. O., Weisman, M. H., Jackson, C. G., Lane, N. E., Cush, J. J., Moreland, L. W., Schumacher, H. R., Oddis, C. V., Wolfe, F., Molitor, J. A., Yocum, D. E., Schnitzer, T. J., Furst, D. E., Sawitzke, A. D., Shi, H., Brandt, K. D., Moskowitz, R. W., Williams, H. J., 2006. Glucosamine, Chondroitin Sulfate, and the Two in Combination for Painful Knee Osteoarthritis. N. Engl. J. Med. 354, 795-808. doi:10.1056/NEJMoa052771

Ref 8): Dufour, A., Overall, C. M., 2013. Missing the target: matrix metalloproteinase antitargets in inflammation and cancer. Trends Pharmacol. Sci. 34, 233-242. doi: 10.1016/j.tips.2013.02.004

Ref 9): Georgiadis, D., Yiotakis, A., 2008. Specific targeting of metzincin family members with small-molecule inhibitors: Progress toward a multifarious challenge. Bioorg. Med. Chem. 16, 8781-8794. doi: 10.1016/j.bmc.2008.08.058

Ref 10): Glasson, S. S., Askew, R., Sheppard, B., Carito, B., Blanchet, T., Ma, H.-L., Flannery, C. R., Peluso, D., Kanki, K., Yang, Z., Majumdar, M. K., Morris, E. A., 2005. Deletion of active ADAMTS5 prevents cartilage degradation in a murine model of osteoarthritis. Nature 434, 644-648. doi:10.1038/nature03369

Ref 11): Janusz, M. J., Bendele, A. M., Brown, K. K., Taiwo, Y. O., Hsieh, L., Heitmeyer, S. A., 2002. Induction of osteoarthritis in the rat by surgical tear of the meniscus: Inhibition of joint damage by a matrix metalloproteinase inhibitor. Osteoarthritis Cartilage 10, 785-791. doi: 10.1053/joca.2002.0823

Ref 12): Kato, I., Higashimoto, M., Tamura, O., Ishibashi, H., 2003. Total Synthesis of Mappicine Ketone (Nothapodytine B) by Means of Sulfur-Directed 5-exo-Selective Aryl Radical Cyclization onto Enamides. J. Org. Chem. 68, 7983-7989. doi:10.1021/jo030177m Ref 13): Larsson, S., Lohmander, L. S., Struglics, A., 2014. An ARGS-aggrecan assay for analysis in blood and synovial fluid. Osteoarthritis Cartilage 22, 242-249. doi: 10.1016/j.joca.2013.12.010

Ref 14): Little, C. B., Meeker, C. T., Golub, S. B., Lawlor, K. E., Farmer, P. J., Smith, S. M., Fosang, A. J., 2007. Blocking aggrecanase cleavage in the aggrecan interglobular domain abrogates cartilage erosion and promotes cartilage repair. J. Clin. Invest. 117, 1627-1636. doi: 10.1172/JCI30765

Ref 15): Malfait, A. M., Ritchie, J., Gil, A. S., Austin, J.-S., Hartke, J., Qin, W., Tortorella, M. D., Mogil, J. S., 2010. ADAMTS-5 deficient mice do not develop mechanical allodynia associated with osteoarthritis following medial meniscal destabilization. Osteoarthritis Cartilage 18, 572-580. doi: 10.1016/j.joca.2009.11.013

Ref 16): Mobasheri, A., 2013. The Future of Osteoarthritis Therapeutics: Targeted Pharmacological Therapy. Curr. Rheumatol. Rep. 15. doi:10.1007/s11926-013-0364-9

Ref 17): Pond, M. J., Nuki, G., 1973. Experimentally-induced osteoarthritis in the dog. Ann. Rheum. Dis. 32, 387-388.

Ref 18): Pritzker, K. P. H., Gay, S., Jimenez, S. A., Ostergaard, K., Pelletier, J.-P., Revell, P. A., Salter, D., van den Berg, W. B., 2006. Osteoarthritis cartilage histopathology: grading and staging. Osteoarthritis Cartilage 14, 13-29. doi:10.1016/j.joca.2005.07.014

Ref 19): Shiomi, T., Lemaitre, V., D'Armiento, J., Okada, Y., 2010. Matrix metalloproteinases, a disintegrin and metalloproteinases, and a disintegrin and metalloproteinases with thrombospondin motifs in non-neoplastic diseases. Pathol. Int. 60, 477-496. doi:10.1111/j.1440-1827.2010.02547.x Ref 20): Stanton, H., Golub, S. B., Rogerson, F. M., Last, K., Little, C. B., Fosang, A. J., 2011. Investigating ADAMTS-mediated aggrecanolysis in mouse cartilage. Nat. Protoc. 6, 388-404. doi:10.1038/nprot.2010.179

Ref 21): Stanton, H., Rogerson, F. M., East, C. J., Golub, S. B., Lawlor, K. E., Meeker, C. T., Little, C. B., Last, K., Farmer, P. J., Campbell, I. K., Fourie, A. M., Fosang, A. J., 2005. ADAMTS5 is the major aggrecanase in mouse cartilage in vivo and in vitro. Nature 434, 648-652. doi: 10.103 8/nature03417

Ref 22): Tortorella, M. D., Malfait, A. M., 2008. Will the real aggrecanase(s) step up: evaluating the criteria that define aggrecanase activity in osteoarthritis. Curr. Pharm. Biotechnol. 9, 16-23.

Ref 23): Wieland, H. A., Michaelis, M., Kirschbaum, B. J., Rudolphi, K. A., 2005. Osteoarthritis—an untreatable disease? Nat. Rev. Drug Discov. 4, 331-344. doi:10.1038/nrd1693

Ref 24): Wuts, P. G. M., Greene, T. W., 2012. Greene's Protective Groups in Organic Synthesis, 4 edition, ed. Wiley-Interscience.

The invention claimed is:

1. A compound of formula (II):

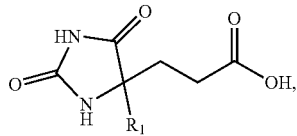

wherein:

$R^1$ is:
  $C_{2-4}$ alkyl optionally substituted with one or more independently selected $R^4$ groups,
  $C_{3-7}$ monocyclic cycloalkyl optionally substituted with one or more independently selected $R^4$ groups,
  4-7 membered monocyclic heterocycloalkyl comprising 1 to 2 heteroatoms independently selected from N, O, and S, optionally substituted with one or more independently selected $C_{1-4}$ alkyl, —C(=O)$C_{1-4}$ alkyl, or —C(=O)O$C_{1-4}$ alkyl,
  phenyl fused to a 5-6 membered monocyclic heterocycloalkyl comprising 1, 2 or 3 heteroatoms independently selected from N, O, and S, which heterocycloalkyl is optionally substituted with one or more =O, or
  imidazolyl, pyrazolyl, oxazolyl, pyridinyl, pyrimidinyl or pyrazinyl, each of which is optionally substituted with one or more independently selected $R^5$ groups;

$R^4$ is:
  halo,
  OH,
  CN,
  $C_{1-4}$ alkyl,
  $C_{1-4}$ alkoxy optionally substituted with one $C_{1-4}$ alkoxy, or phenyl,
  $C_{1-4}$ thioalkoxy,
  4-7-membered monocyclic heterocycloalkyl comprising one or more heteroatoms independently selected from N, S, and O, optionally substituted with one or more independently selected halo, or —C(=O)O$C_{1-4}$ alkyl,
  phenyl,
  —S(=O)$_2C_{1-4}$ alkyl,
  —C(=O)NR$^{7b}$R$^{7c}$,
  —NHC(=O)OR$^{7d}$,
  —NHC(=O)R$^{7e}$, or
  NR$^{8a}$R$^{8b}$;

each $R^5$ is
  halo,
  OH,
  CN,
  $C_{1-4}$ alkyl optionally substituted with one or more independently selected halo, —NR$^{9a}$R$^{9b}$, or —C(=O)NR$^{9c}$R$^{9d}$,
  $C_{1-4}$ alkoxy optionally substituted with one —NR$^{9e}$R$^{9f}$, or
  —S(=O)$_2C_{1-4}$ alkyl;

each $R^6$ is
  halo,
  —CN,
  —NO$_2$,
  —CH$_3$,
  5-10 membered monocyclic or fused bicyclic heteroaryl comprising 1, 2 or 3 heteroatoms independently selected from N, O, and S, optionally substituted with one or more independently selected halo, $C_{1-4}$ alkyl, or $C_{1-4}$ alkoxy, or
  —NR$^{9g}$R$^{9h}$;

each R$^{7a}$, R$^{7b}$, R$^{7c}$, R$^{7d}$, or R$^{7e}$ is
  H, or
  $C_{1-4}$ alkyl optionally substituted with one OH, $C_{1-4}$ alkoxy;

each R$^{8a}$, or R$^{8b}$ is independently selected from
  H, and
  $C_{1-4}$ alkyl optionally substituted with one or more independently selected OH, $C_{1-4}$ alkoxy, or phenyl;

each R$^{9a}$, R$^{9b}$, R$^{9c}$, R$^{9d}$, R$^{9e}$, R$^{9f}$, R$^{9g}$, and R$^{9h}$ is independently selected from H, and $C_{1-4}$ alkyl; or a pharmaceutically acceptable salt, or a solvate, or a pharmaceutically acceptable salt of a solvate thereof.

2. The compound of claim 1, wherein $R^1$ is:
imidazolyl, pyrazolyl, oxazolyl, pyridinyl, pyrimidinyl or pyrazinyl, each of which is, optionally substituted with a $C_1$ alkyl C$_{2-4}$ alkyl, or
C$_3$ monocyclic cycloalkyl.

3. The compound of claim 1, selected from the group consisting of:

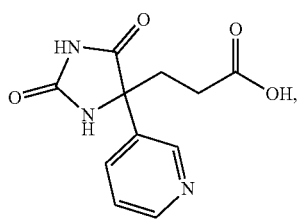
(132)

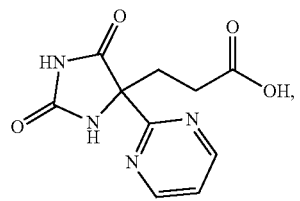
(139)

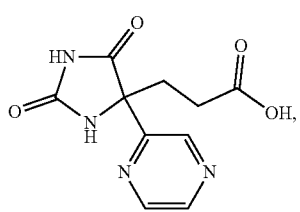
(142)

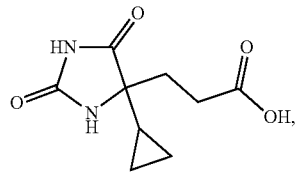
(162)

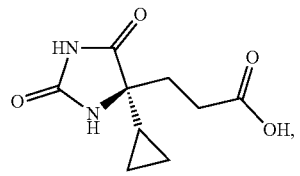
(163)

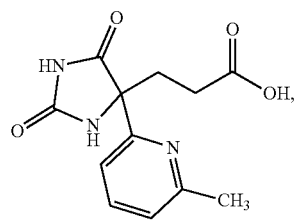
(166)

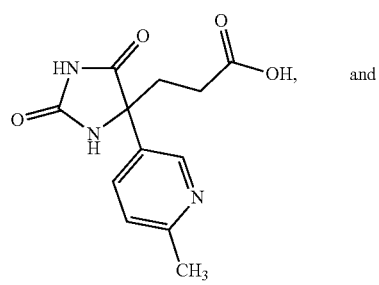
(174)

and

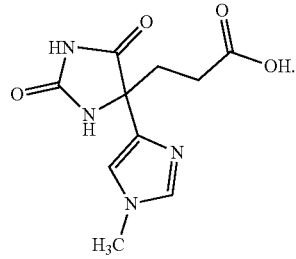
(179)

4. A compound of claim 1, wherein the compound is:

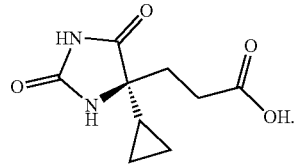
(163)

5. A method of making the compound of formula (II) of claim 1, comprising reacting a compound of formula (I)

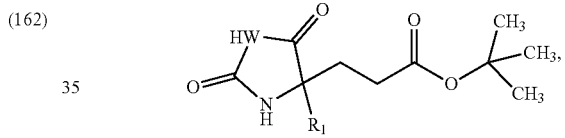
(I)

and producing a compound of formula (II).

6. A method of making a compound of formula (III),

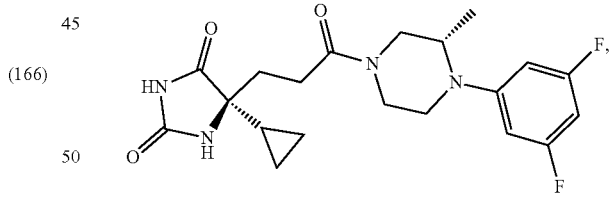
(III)

comprising reacting compound (163),

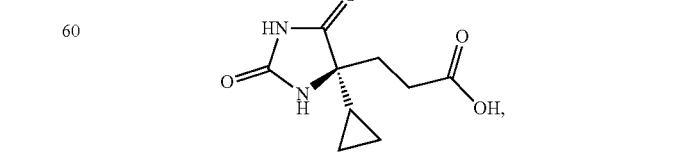
(163)

with (2S)-1-(3,5-difluorophenyl)-2-methyl-piperazine.

7. A method of making compound (173), (173)
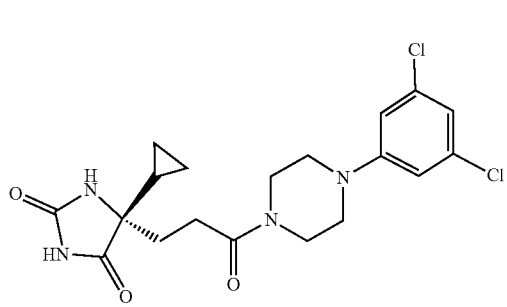

comprising reacting a compound of claim 4 with 1-(3,5-dichlorophenyl) piperazine.

8. A method of making compound (203), (203)
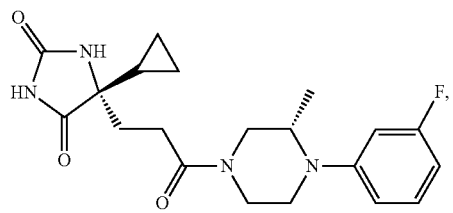

comprising reacting a compound of claim 4 with (2S)-1-(3-fluorophenyl)-2-methyl-piperazine.

9. A method of making compound (204)

(204)
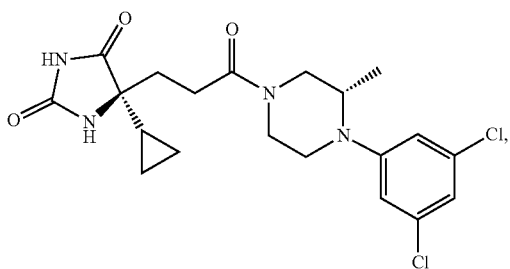

comprising reacting a compound of claim 4 with (2S)-1-(3,5-dichlorophenyl)-2-methyl-piperazine.

10. A method of making compound (205)

(205)
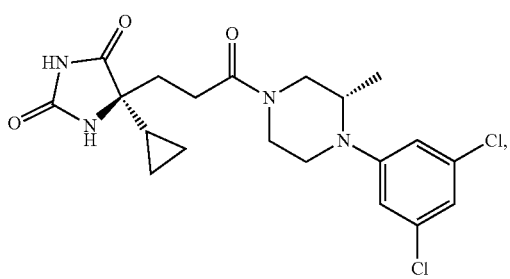

comprising reacting a compound of claim 4 with (2S)-1-(3,4-difluorophenyl)-2-methyl-piperazine.

11. A method of making compound (207)

(207)
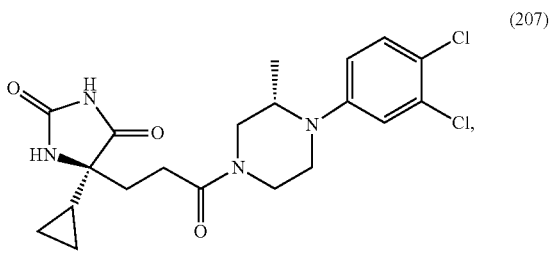 [SMILES: C[C@H]1CN(C(=O)CC[C@@]2(C3CC3)NC(=O)NC2=O)CCN1c1ccc(Cl)c(Cl)c1]

comprising reacting a compound of claim 4 with (S)-1-(3,4-Dichloro-phenyl)-2-methyl-piperazine.

12. A method of making compound (357)

(357)
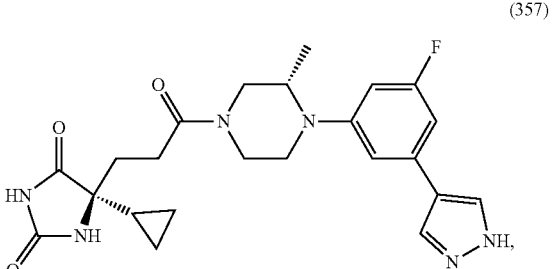

comprising reacting a compound of claim 4 with (2S)-1-[3-fluoro-5-(1H-pyrazol-4-1)phenyl]-2-methyl-piperazine.

13. A method of making compound (403)

(403)
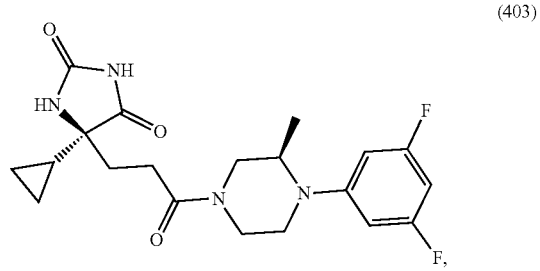 [SMILES: C[C@@H]1CN(C(=O)CC[C@@]2(C3CC3)NC(=O)NC2=O)CCN1c1cc(F)cc(F)c1]

comprising reacting a compound of claim 4 with (2R)-1-(3,5-difluorophenyl)-2-methyl-piperazine.

14. A method of making compound (416)

(416)
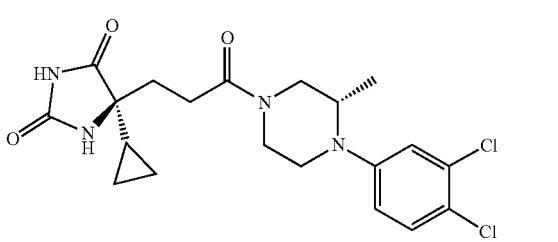

comprising reacting a compound of claim 4 with (2S)-1-(3,4-dichlorophenyl)-2-methyl-piperazine.

15. The compound of claim 1, wherein $R^1$ is ethyl, propyl, isopropyl, and or tertbutyl.

16. The compound of claim 1, wherein $R^1$ is ethyl.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: polypeptide
<220> FEATURE:
<221> NAME/KEY: MOD_RES
<222> LOCATION: (12)..(12)
<223> OTHER INFORMATION: 5(6)-TAMRA_AMIDATION

<400> SEQUENCE: 1

Ala Glu Leu Gln Gly Arg Pro Ile Ser Ile Ala Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: polypeptide
<220> FEATURE:
<221> NAME/KEY: MOD_RES
<222> LOCATION: (1)..(1)
<223> OTHER INFORMATION: 5FAM
<220> FEATURE:
```

```
<221> NAME/KEY: MOD_RES
<222> LOCATION: (1)..(1)
<223> OTHER INFORMATION: 5_FAM

<400> SEQUENCE: 2

Thr Glu Gly Glu Ala Arg Gly Ser Val Ile Leu Leu Lys Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: polypeptide
<220> FEATURE:
<221> NAME/KEY: MOD_RES
<222> LOCATION: (11)..(11)
<223> OTHER INFORMATION: 5-TAMRA_AMIDATION

<400> SEQUENCE: 3

Leu Ala Gln Ala Val Arg Ser Ser Ser Arg Lys
1               5                   10
```